(12) United States Patent
Ichikawa et al.

(10) Patent No.: US 8,026,234 B2
(45) Date of Patent: Sep. 27, 2011

(54) POLO-LIKE KINASE INHIBITORS

(75) Inventors: Takashi Ichikawa, Osaka (JP); Stephen W. Kaldor, Del Mar, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 245 days.

(21) Appl. No.: 12/237,306

(22) Filed: Sep. 24, 2008

(65) Prior Publication Data

US 2009/0281092 A1 Nov. 12, 2009

Related U.S. Application Data

(60) Provisional application No. 60/975,127, filed on Sep. 25, 2007, provisional application No. 61/037,303, filed on Mar. 17, 2008.

(51) Int. Cl.
*C07D 487/04* (2006.01)
*A61K 31/55* (2006.01)

(52) U.S. Cl. ........................................ 514/221; 540/502

(58) Field of Classification Search .................. 540/502; 514/221

See application file for complete search history.

(56) References Cited

U.S. PATENT DOCUMENTS

| | | | |
|---|---|---|---|
| 7,517,873 B2 | 4/2009 | Chen | |
| 2004/0029885 A1 | 2/2004 | Bauer et al. | |
| 2004/0176380 A1 | 9/2004 | Hoffmann et al. | |
| 2006/0025411 A1 | 2/2006 | Hoffmann et al. | |
| 2006/0046989 A1 | 3/2006 | Grauert et al. | |
| 2006/0046990 A1 | 3/2006 | Stadtmueller et al. | |
| 2006/0052383 A1 | 3/2006 | Grauert et al. | |
| 2008/0009482 A1 | 1/2008 | Halsall et al. | |
| 2008/0167289 A1 | 7/2008 | Kay et al. | |
| 2008/0171747 A1 | 7/2008 | Hoffman et al. | |
| 2008/0234255 A1 | 9/2008 | Chen | |

FOREIGN PATENT DOCUMENTS

| | | |
|---|---|---|
| WO | WO/01/19825 | 3/2001 |
| WO | WO/01/19828 | 3/2001 |
| WO | WO/03/020722 | 3/2003 |
| WO | WO/2006/018185 | 2/2006 |
| WO | WO 2007/095188 A2 | 8/2007 |
| WO | WO/2007/135374 | 11/2007 |
| WO | WO 2008/003958 A1 | 1/2008 |
| WO | WO 2008/113711 A1 | 9/2008 |
| WO | WO/2009/023269 | 2/2009 |
| WO | WO/2009/040556 | 4/2009 |
| WO | WO/2009/042806 | 4/2009 |
| WO | WO/2009/153197 | 12/2009 |

OTHER PUBLICATIONS

Michael Kothe et al. "Selectivity-determining Residues in Plk1" Chem Biol Drug Des 2007; 70: 540-546.

Martin Steegmaier, et al. "BI 2536, a Potent and Selective Inhibitor of Polo-like Kinase 1, Inhibits Tumor Growth in Vivo" Current Biology 17, 316-322, Feb. 20, 2007.

Klaus Mross, et al. "Phase I Dose Escalation and Pharmacokinetic Study of BI 2536, a Novel Polo-Like Kinase 1 Inhibitor, in Patients With Advanced Solid Tumors" Journal of Clinical Oncology, vol. 26, No. 34, Dec. 1, 2008.

Patrick Schöffski, "Polo-Like Kinase (PLK) Inhibitors in Preclinical and Early Clinical Development in Oncology" The Oncologist 2009;v14:559-570.

*Primary Examiner* — Bruck Kifle
(74) *Attorney, Agent, or Firm* — David M. Stemerick; Mitchell R. Brunstein

(57) ABSTRACT

Compounds of the following formula are provided for use with kinases:

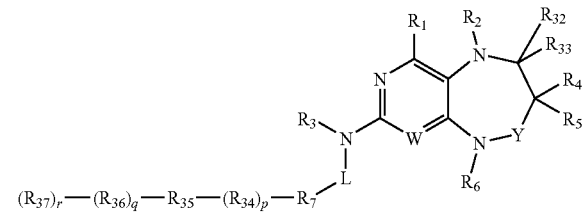

wherein the variables are as defined herein. Also provided are pharmaceutical compositions, kits and articles of manufacture comprising such compounds; methods and intermediates useful for making the compounds; and methods of using said compounds.

2 Claims, 3 Drawing Sheets

FIGURE 1A cDNA sequence encoding human PLK1 [SEQ. ID No. 1]

```
atgagtgctg cagtgactgc agggaagctg gcacgggcac cggccgaccc tgggaaagcc    60
ggggtccccg gagttgcagc tcccggagct ccggcggcgg ctccaccggc gaaagagatc   120
ccggaggtcc tagtggaccc acgcagccgg cggcgctatg tgcggggccg ctttttgggc   180
aagggcggct ttgccaagtg cttcgagatc tcggacgcgg acaccaagga ggtgttcgcg   240
ggcaagattg tgcctaagtc tctgctgctc aagccgcacc agagggagaa gatgtccatg   300
gaaatatcca ttcaccgcag cctcgcccac cagcacgtcg taggattcca cggcttttc    360
gaggacaacg acttcgtgtt cgtggtgttg gagctctgcc gccggaggtc tctcctggag   420
ctgcacaaga ggaggaaagc cctgactgag cctgaggccc gatactacct acggcaaatt   480
gtgcttggct gccagtacct gcaccgaaac cgagttattc atcgagacct caagctgggc   540
aaccttttcc tgaatgaaga tctggaggtg aaaataggg attttggact ggcaaccaaa   600
gtcgaatatg acggggagag gaagaagacc ctgtgtggga ctcctaatta catagctccc   660
gaggtgctga gcaagaaagg gcacagtttc gaggtggatg tgtggtccat gggtgtatc    720
atgtatacct tgttagtggg caaaccacct tttgagactt cttgcctaaa agagacctac   780
ctccggatca agaagaatga atacagtatt cccaagcaca tcaacccgt ggccgcctcc    840
ctcatccaga agatgcttca gacagatccc actgccgcc caaccattaa cgagctgctt   900
aatgacgagt tctttacttc tggctatatc tggcccgtc tccccatcac ctgcctgacc    960
attccaccaa ggttttcgat tgctcccagc agcctggacc cagcaaccga aagccctc    1020
acagtcctca taaaggctt ggagaacccc ctgcctgagc gtccccggga aaaagaagaa   1080
ccagtggttc gagagacagg tgaggtggtc gactgccacc tcagtgacat gctgcagcag   1140
ctgcacagtg tcaatgcctc caagccctcg gagcgtgggc tggtcaggca agaggaggct   1200
gaggatcctg cctgcatccc catcttctgg gtcagcaagt gggtggacta ttcggacaag   1260
tacggccttg ggtatcagct ctgtgataac agcgtggggg tgctcttcaa tgactcaaca   1320
cgcctcatcc tctacaatga tggtgacagc ctgcagtaca tagagcgtga cggcactgag   1380
tcctacctca ccgtgagttc ccatcccaac tccttgatga agaagatcac cctccttaaa   1440
tatttccgca attacatgag cgagcacttg ctgaaggcag gtgccaacat cacgccgcgc   1500
gaaggtgatg agctcgcccg gctgccctac ctacggacct ggttccgcac ccgcagcgcc   1560
atcatcctgc acctcagcaa cggcagcgtg cagatcaact tcttccagga tcacaccaag   1620
ctcatcttgt gcccactgat ggcagccgtg acctacatcg acgagaagcg ggacttccgc   1680
acataccgcc tgagtctcct ggaggagtac ggctgctgca aggagctggc cagccggctc   1740
cgctacgccc gcactatggt ggacaagctg ctgagctcac gctcggccag caaccgtctc   1800
aaggcctcc                                                          1809
```

DNA sequence encoding PCR Primer[SEQ. ID No. 2]

```
agtgctgcag tgactgcagg gaagctg                                        27
```

DNA sequence encoding PCR Primer[SEQ. ID No. 3]

```
ttaggaggcc ttgagacggt tgctggccg                                      29
```

DNA sequence encoding PCR Primer[SEQ. ID No. 4]

```
aaatctagag ccaccatgga ctacaaggac gacgatgaca agagtgctgc agtgactgca    60
gggaagctg                                                            69
```

FIGURE 1B

DNA sequence encoding PCR Primer[SEQ. ID No. 5]

tggcaactag aaggcacagt cgaggct 27

Protein sequence encoding FLAG-tagged PLK1 [SEQ. ID No. 6]

```
Met Asp Tyr Lys Asp Asp Asp Lys Ser Ala Ala Val Thr Ala Gly
                 5                  10                  15
Lys Leu Ala Arg Ala Pro Ala Asp Pro Gly Lys Ala Gly Val Pro Gly
             20                  25                  30
Val Ala Ala Pro Gly Ala Pro Ala Ala Pro Pro Ala Lys Glu Ile
             35                  40                  45
Pro Glu Val Leu Val Asp Pro Arg Ser Arg Arg Arg Tyr Val Arg Gly
     50                  55                  60
Arg Phe Leu Gly Lys Gly Gly Phe Ala Lys Cys Phe Glu Ile Ser Asp
 65                  70                  75                  80
Ala Asp Thr Lys Glu Val Phe Ala Gly Lys Ile Val Pro Lys Ser Leu
             85                  90                  95
Leu Leu Lys Pro His Gln Arg Glu Lys Met Ser Met Glu Ile Ser Ile
             100                 105                 110
His Arg Ser Leu Ala His Gln His Val Val Gly Phe His Gly Phe Phe
         115                 120                 125
Glu Asp Asn Asp Phe Val Phe Val Val Leu Glu Leu Cys Arg Arg Arg
         130                 135                 140
Ser Leu Leu Glu Leu His Lys Arg Arg Lys Ala Leu Thr Glu Pro Glu
145                 150                 155                 160
Ala Arg Tyr Tyr Leu Arg Gln Ile Val Leu Gly Cys Gln Tyr Leu His
             165                 170                 175
Arg Asn Arg Val Ile His Arg Asp Leu Lys Leu Gly Asn Leu Phe Leu
             180                 185                 190
Asn Glu Asp Leu Glu Val Lys Ile Gly Asp Phe Gly Leu Ala Thr Lys
         195                 200                 205
Val Glu Tyr Asp Gly Glu Arg Lys Lys Thr Leu Cys Gly Thr Pro Asn
         210                 215                 220
Tyr Ile Ala Pro Glu Val Leu Ser Lys Lys Gly His Ser Phe Glu Val
225                 230                 235                 240
Asp Val Trp Ser Ile Gly Cys Ile Met Tyr Thr Leu Leu Val Gly Lys
             245                 250                 255
Pro Pro Phe Glu Thr Ser Cys Leu Lys Glu Thr Tyr Leu Arg Ile Lys
             260                 265                 270
Lys Asn Glu Tyr Ser Ile Pro Lys His Ile Asn Pro Val Ala Ala Ser
         275                 280                 285
Leu Ile Gln Lys Met Leu Gln Thr Asp Pro Thr Ala Arg Pro Thr Ile
         290                 295                 300
Asn Glu Leu Leu Asn Asp Glu Phe Phe Thr Ser Gly Tyr Ile Pro Ala
305                 310                 315                 320
Arg Leu Pro Ile Thr Cys Leu Thr Ile Pro Pro Arg Phe Ser Ile Ala
             325                 330                 335
```

FIGURE 1C

```
Pro Ser Ser Leu Asp Pro Ser Asn Arg Lys Pro Leu Thr Val Leu Asn
        340                 345                 350
Lys Gly Leu Glu Asn Pro Leu Pro Glu Arg Pro Arg Glu Lys Glu Glu
        355                 360                 365
Pro Val Val Arg Glu Thr Gly Glu Val Val Asp Cys His Leu Ser Asp
    370                 375                 380
Met Leu Gln Gln Leu His Ser Val Asn Ala Ser Lys Pro Ser Glu Arg
385                 390                 395                 400
Gly Leu Val Arg Gln Glu Glu Ala Glu Asp Pro Ala Cys Ile Pro Ile
                405                 410                 415
Phe Trp Val Ser Lys Trp Val Asp Tyr Ser Asp Lys Tyr Gly Leu Gly
            420                 425                 430
Tyr Gln Leu Cys Asp Asn Ser Val Gly Val Leu Phe Asn Asp Ser Thr
            435                 440                 445
Arg Leu Ile Leu Tyr Asn Asp Gly Asp Ser Leu Gln Tyr Ile Glu Arg
    450                 455                 460
Asp Gly Thr Glu Ser Tyr Leu Thr Val Ser Ser His Pro Asn Ser Leu
465                 470                 475                 480
Met Lys Lys Ile Thr Leu Leu Lys Tyr Phe Arg Asn Tyr Met Ser Glu
                485                 490                 495
His Leu Leu Lys Ala Gly Ala Asn Ile Thr Pro Arg Glu Gly Asp Glu
                500                 505                 510
Leu Ala Arg Leu Pro Tyr Leu Arg Thr Trp Phe Arg Thr Arg Ser Ala
            515                 520                 525
Ile Ile Leu His Leu Ser Asn Gly Ser Val Gln Ile Asn Phe Phe Gln
    530                 535                 540
Asp His Thr Lys Leu Ile Leu Cys Pro Leu Met Ala Ala Val Thr Tyr
545                 550                 555                 560
Ile Asp Glu Lys Arg Asp Phe Arg Thr Tyr Arg Leu Ser Leu Leu Glu
                565                 570                 575
Glu Tyr Gly Cys Cys Lys Glu Leu Ala Ser Arg Leu Arg Tyr Ala Arg
                580                 585                 590
Thr Met Val Asp Lys Leu Leu Ser Ser Arg Ser Ala Ser Asn Arg Leu
            595                 600                 605
Lys Ala Ser
        610
```

POLO-LIKE KINASE INHIBITORS

RELATED APPLICATIONS

This application claims the benefit of U.S. Provisional Application No. 60/975,127, filed Sep. 25, 2007, and U.S. Provisional Application No. 61/037,303, filed Mar. 17, 2008, which is incorporated herein by reference.

FIELD OF THE INVENTION

The present invention relates to compounds that may be used to inhibit kinases, as well as compositions of matter, kits and articles of manufacture comprising these compounds. The invention also relates to methods for inhibiting kinases and treatment methods using compounds according to the present invention. In addition, the invention relates to methods of making the compounds of the present invention, as well as intermediates useful in such methods. In particular, the present invention relates to Polo-like Kinase (PLK) inhibitors, compositions of matter, kits and articles of manufacture comprising these compounds, methods for inhibiting PLK, and methods and intermediates useful for making the inhibitors.

BACKGROUND OF THE INVENTION

The invention relates to inhibitors of enzymes that catalyze phosphoryl transfer and/or that bind ATP/GTP nucleotides, compositions comprising the inhibitors, and methods of using the inhibitors and inhibitor compositions.

Many diseases states are characterized by the uncontrolled proliferation and differentiation of cells. These diseases states encompass a variety of cell types and maladies such as cancer, atherosclerosis, restenosis, and psoriasis. Uncontrolled signaling due to defective control of protein phosphorylation has been implicated in a number of diseases and disease conditions, including, for example, inflammation, cancer, allergy/asthma, diseases and conditions of the immune system, disease and conditions of the central nervous system (CNS), cardiovascular disease, dermatology, and angiogenesis.

The inhibitors and compositions comprising them are useful for treating or modulating disease in which phosphoryl transferases, including kinases, may be involved, symptoms of such disease, or the effect of other physiological events mediated by phosphoryl transferases, including kinases. The invention also provides for methods of making the inhibitor compounds and methods for treating diseases in which one or more phosphoryl transferase, including kinase, activities is involved.

Phosphoryl transferases are a large family of enzymes that transfer phosphorous-containing groups from one substrate to another. By the conventions set forth by the Nomenclature Committee of the International Union of Biochemistry and Molecular Biology (IUBMB) enzymes of this type have Enzyme Commission (EC) numbers starting with 2.7.-.- (See, Bairoch A., The ENZYME database in Nucleic Acids Res. 28:204-305 (2000)). Kinases are a class of enzymes that function in the catalysis of phosphoryl transfer. The protein kinases constitute the largest subfamily of structurally related phosphoryl transferases and are responsible for the control of a wide variety of signal transduction processes within the cell. (See, Hardie, G. and Hanks, S. (1995) The Protein Kinase Facts Book, I and II, Academic Press, San Diego, Calif.). Protein kinases are thought to have evolved from a common ancestral gene due to the conservation of their structure and catalytic function. Almost all kinases contain a similar 250-300 amino acid catalytic domain. The protein kinases may be categorized into families by the substrates they phosphorylate (e.g., protein-tyrosine, protein-serine/threonine, histidine, etc.). Protein kinase sequence motifs have been identified that generally correspond to each of these kinase families (See, for example, Hanks, S. K.; Hunter, T., FASEB J. 9:576-596 (1995); Kinghton et al., Science, 253:407-414 (1991); Hiles et al., Cell 70:419-429 (1992); Kunz et al., Cell, 73:585-596 (1993); Garcia-Bustosi et al., EMBO J., 13:2352-2361 (1994)). Lipid kinases (e.g. PI3K) constitute a separate group of kinases with structural similarity to protein kinases.

Protein and lipid kinases regulate many different cell processes including, but not limited to, proliferation, growth, differentiation, metabolism, cell cycle events, apoptosis, motility, transcription, translation and other signaling processes, by adding phosphate groups to targets such as proteins or lipids. Phosphorylation events catalyzed by kinases act as molecular on/off switches that can modulate or regulate the biological function of the target protein. Phosphorylation of target proteins occurs in response to a variety of extracellular signals (hormones, neurotransmitters, growth and differentiation factors, etc.), cell cycle events, environmental or nutritional stresses, etc. Protein and lipid kinases can function in signaling pathways to activate or inactivate, or modulate the activity of (either directly or indirectly) the targets. These targets may include, for example, metabolic enzymes, regulatory proteins, receptors, cytoskeletal proteins, ion channels or pumps, or transcription factors. Initial interest in protein kinases as pharmacological targets was stimulated by the findings that many viral oncogenes encode structurally modified cellular protein kinases with constitutive enzyme activity. These findings pointed to the potential involvement of oncogene related protein kinases in human proliferatives disorders. Subsequently, deregulated protein kinase activity, resulting from a variety of more subtle mechanisms, has been implicated in the pathophysiology of a number of important human disorders including, for example, cancer, CNS conditions, and immunologically related diseases. The development of selective protein kinase inhibitors that can block the disease pathologies and/or symptoms resulting from aberrant protein kinase activity has therefore generated much interest.

Cancer results from the deregulation of the normal processes that control cell division, differentiation and apoptotic cell death. Protein kinases play a critical role in this regulatory process. A partial non-limiting list of such kinases includes ab1, Aurora-A, Aurora-B, Aurora-C, Akt, bcr-abl, Blk, Brk, Btk, c-Kit, c-Met, c-Src, CDK1, CDK2, CDK4, CDK6, cRaf1, CSF1R, CSK, EGFR, ErbB2, ErbB4, ERK, Fak, fes, FGFR1, FGFR2, FGFR3, FGFR4, FGFR5, Fgr, Flt-4, Flt-1, FER, Frk, Fyn, Hck, IGF-1R, INS-R, Jak, KDR, Lck, Lyn, MEK, p38, PDGFR, PIK, PKC, PLKs, PYK2, Ros, Tie1, Tie2, Trk, Yes and Zap70. In mammalian biology, such protein kinases comprise mitogen activated protein kinase (MAPK) signaling pathways. MAPK signaling pathways are inappropriately activated by a variety of common disease-associated mechanisms such as mutation of ras genes and deregulation of growth factor receptors (Magnuson et al., Seminars in Cancer Biology 5:247-252 (1994)). Therefore the inhibition of protein kinases is an object of the present invention.

Polo-like kinases (PLKs including PLK1, PLK2, PLK3 and PLK4) are serine/threonine protein kinases that have been implicated in human cancer, such as colon, breast and other solid tumors. Polo-like kinases (also referred to as PLKs) are believed to be involved in protein phosphorylation events that regulate the cell cycle. Specifically, PLK1 may play a role in controlling the accurate segregation of chromosomes during mitosis. Misregulation of the cell cycle can lead to cellular proliferation and other abnormalities. In human colon cancer tissue, PLKs have been found to be overexpressed (See, Barr et al in Nat. Rev. Mol. Cell. Biol. 5: 429 (2004); van Vugt et al in Oncogene, 24: 2844 (2005)). PLK1 as an attractive candidate molecule for targeted tumor therapy is reported recently (see Takai et al in Oncogene, 24:287 (2005); McInnes et al in Current Topics in Med. Chem., 5: 181 (2005)).

There is a continued need to find new therapeutic agents to treat human diseases. Protein kinases, specifically but not limited to Polo-like Kinase (PLK), are especially attractive targets for the discovery of new therapeutics due to their important role in hyperproliferative disorders; cancer (e.g., solid tumors, leukemias, lymphomas, non-small cell lung cancers and esophageal carcinomas); inflammatory and autoimmune diseases (e.g., psoriasis, alopecia; multiple sclerosis; colitis, arthritis, Alzheimer's disease, glomerulonephritis and wound healing); chemotherapy agent-induced alopecia and mucositis; cardiovascular diseases (e.g., stenoses, arterioscleroses, restenoses, and hypertrophy); viral, bacterial, fungal and/or parasitic infectious diseases (e.g., cytomegalici infections, herpes, hepatitis B and C, Karposi's sarcoma, HIV diseases); nephrological diseases (e.g., glomerulonephritis); chronic and acute neurodegenerative diseases (e.g., Huntington's disease, amyotrophic lateral sclerosis, Parkinson's disease, AIDS dementia, Alzheimer's disease, ischemias of the brain and neurotraumas); skin diseases (e.g., psoriasis); bone diseases; the protection of proliferating cells (e.g., hair, intestinal, blood and progenitor cells) from DNA damage caused by radiation, UV treatment and/or cytostatic treatment; and other diseases. Certain inhibitors of PLK are disclosed in WO 2007/095188. The present invention provides inhibitors of PLKs, including some having reduced susceptibility to multi-drug resistance.

SUMMARY OF THE INVENTION

The present invention relates to compounds that have activity for inhibiting kinases. The present invention also provides compositions, articles of manufacture and kits comprising these compounds. In addition, the invention relates to methods of making the compounds of the present invention, as well as intermediates useful in such methods.

In one embodiment, a pharmaceutical composition is provided that comprises a kinase inhibitor according to the present invention as an active ingredient. Pharmaceutical compositions according to the invention may optionally comprise 0.001%-100% of one or more inhibitors of this invention. These pharmaceutical compositions may be administered or coadministered by a wide variety of routes, including for example, orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compositions may also be administered or coadministered in slow release dosage forms.

The invention is also directed to kits and other articles of manufacture for treating disease states associated with kinases.

In one embodiment, a kit is provided that comprises a composition comprising at least one kinase inhibitor of the present invention in combination with instructions. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another embodiment, an article of manufacture is provided that comprises a composition comprising at least one kinase inhibitor of the present invention in combination with packaging materials. The packaging material may comprise a container for housing the composition. The container may optionally comprise a label indicating the disease state for which the composition is to be administered, storage information, dosing information and/or instructions regarding how to administer the composition.

Also provided are methods for preparing compounds, compositions and kits according to the present invention. For example, several synthetic schemes are provided herein for synthesizing compounds according to the present invention.

Also provided are methods for using compounds, compositions, kits and articles of manufacture according to the present invention.

In one embodiment, the compounds, compositions, kits and articles of manufacture are used to inhibit kinases. In particular, the compounds, compositions, kits and articles of manufacture can be used to inhibit a PLK.

In another embodiment, the compounds, compositions, kits and articles of manufacture are used to treat a disease state for which kinases possess activity that contributes to the pathology and/or symptomology of the disease state.

In another embodiment, a compound is administered to a subject wherein kinase activity within the subject is altered, preferably reduced.

In another embodiment, a prodrug of a compound is administered to a subject that is converted to the compound in vivo where it inhibits kinase.

In another embodiment, a method of inhibiting kinase is provided that comprises contacting a kinase with a compound according to the present invention.

In another embodiment, a method of inhibiting kinase is provided that comprises causing a compound according to the present invention to be present in a subject in order to inhibit kinase in vivo.

In another embodiment, a method of inhibiting a kinase is provided that comprises administering a first compound to a subject that is converted in vivo to a second compound wherein the second compound inhibits kinase in vivo. It is noted that the compounds of the present invention may be the first or second compounds.

In another embodiment, a therapeutic method is provided that comprises administering a compound according to the present invention.

In another embodiment, a method of treating a condition in a patient that is known to be mediated by kinases, or which is known to be treated by kinase inhibitors, comprising administering to the patient a therapeutically effective amount of a compound according to the present invention.

In another embodiment, a method is provided for treating a disease state for which a kinase possesses activity that contributes to the pathology and/or symptomology of the disease state, the method comprising: causing a compound according to the present invention to be present in a subject in a therapeutically effective amount for the disease state.

In another embodiment, a method is provided for treating a disease state for which a kinase possesses activity that contributes to the pathology and/or symptomology of the disease state, the method comprising: administering a first compound to a subject that is converted in vivo to a second compound such that the second compound is present in the subject in a therapeutically effective amount for the disease state. It is noted that the compounds of the present invention may be the first or second compounds.

In another embodiment, a method is provided for treating a disease state for which a kinase possesses activity that contributes to the pathology and/or symptomology of the disease state, the method comprising: administering a compound according to the present invention to a subject such that the compound is present in the subject in a therapeutically effective amount for the disease state.

In another embodiment, a method is provided for using a compound according to the present invention in order to manufacture a medicament for use in the treatment of a disease state that is known to be mediated by a kinase, or that is known to be treated by kinase inhibitors.

It is noted in regard to all of the above embodiments that the present invention is intended to encompass all pharmaceutically acceptable ionized forms (e.g., salts) and solvates (e.g., hydrates) of the compounds, regardless of whether such ionized forms and solvates are specified since it is well known in the art to administer pharmaceutical agents in an ionized or solvated form. It is also noted that unless a particular stereochemistry is specified, recitation of a compound is intended to encompass all possible stereoisomers (e.g., enantiomers or diastereomers depending on the number of chiral centers, and geometric isomers), independent of whether the compound is present as an individual stereoisomer or a mixture of stereoisomers. Further, unless otherwise specified, recitation of a compound is intended to encompass all possible resonance forms and tautomers. With regard to the claims, the language "compound comprising the formula," "compound having the formula" and "compound of the formula" is intended to encompass the compound and all pharmaceutically acceptable ionized forms and solvates, all possible stereoisomers, and all possible resonance forms and tautomers unless otherwise specifically specified in the particular claim.

It is further noted that prodrugs may also be administered which are altered in vivo and become a compound according to the present invention. The various methods of using the compounds of the present invention are intended, regardless of whether prodrug delivery is specified, to encompass the administration of a prodrug that is converted in vivo to a compound according to the present invention. It is also noted that certain compounds of the present invention may be altered in vivo prior to inhibiting kinase and thus may themselves be prodrugs for another compound. Such prodrugs of another compound may or may not themselves independently have kinase inhibitory activity.

BRIEF DESCRIPTION OF THE FIGURE

FIG. 1 illustrates SEQ. ID Nos. 1-6 referred to in this application.

DEFINITIONS

Unless otherwise stated, the following terms used in the specification and claims shall have the following meanings for the purposes of this Application.

It is noted that, as used in the specification and the appended claims, the singular forms "a," "an" and "the" include plural referents unless the context clearly dictates otherwise. Further, definitions of standard chemistry terms may be found in reference works, including Carey and Sundberg "ADVANCED ORGANIC CHEMISTRY $4^{TH}$ ED." Vols. A (2000) and B (2001), Plenum Press, New York. Also, unless otherwise indicated, conventional methods of mass spectroscopy, NMR, HPLC, protein chemistry, biochemistry, recombinant DNA techniques and pharmacology, within the skill of the art are employed.

"Alicyclic" means a moiety comprising a non-aromatic ring structure. Alicyclic moieties may be saturated or partially unsaturated with one, two or more double or triple bonds. Alicyclic moieties may also optionally comprise heteroatoms such as nitrogen, oxygen and sulfur. The nitrogen atoms can be optionally quaternerized or oxidized and the sulfur atoms can be optionally oxidized. Examples of alicyclic moieties include, but are not limited to moieties with ($C_{3-8}$) rings such as cyclopropyl, cyclohexane, cyclopentane, cyclopentene, cyclopentadiene, cyclohexane, cyclohexene, cyclohexadiene, cycloheptane, cycloheptene, cycloheptadiene, cyclooctane, cyclooctene, and cyclooctadiene. Further examples of alicyclic moieties include tetrahydrofuran, pyrrolidine, piperidine, piperazine, morpholine, and the like.

"Aliphatic" means a moiety characterized by a straight or branched chain arrangement of constituent carbon atoms and may be saturated or partially unsaturated with one, two or more double or triple bonds.

"Alkenyl" means a straight or branched, carbon chain that contains at least one carbon-carbon double bond (—CR=CR'— or —CR=CR'R", wherein R, R' and R" are each independently hydrogen or further substituents). Examples of alkenyl include vinyl, allyl, isopropenyl, pentenyl, hexenyl, heptenyl, 1-propenyl, 2-butenyl, 2-methyl-2-butenyl, and the like. In particular embodiments, "alkenyl," either alone or represented along with another radical, can be a ($C_{2-20}$)alkenyl, a ($C_{2-15}$)alkenyl, a ($C_{2-10}$)alkenyl, a ($C_{2-5}$)alkenyl or a ($C_{2-3}$)alkenyl. Alternatively, "alkenyl," either alone or represented along with another radical, can be a ($C_2$)alkenyl, a ($C_3$)alkenyl or a ($C_4$)alkenyl.

"Alkenylene" means a straight or branched, divalent carbon chain having one or more carbon-carbon double bonds (—CR=CR'—, wherein R and R' are each independently hydrogen or further substituents). Examples of alkenylene include ethene-1,2-diyl, propene-1,3-diyl, methylene-1,1-diyl, and the like. In particular embodiments, "alkenylene," either alone or represented along with another radical, can be a ($C_{2-20}$)alkenylene, a ($C_{2-15}$)alkenylene, a ($C_{2-10}$)alkenylene, a ($C_{2-5}$)alkenylene or a ($C_{2-3}$)alkenylene. Alternatively, "alkenylene," either alone or represented along with another radical, can be a ($C_2$)alkenylene, a ($C_3$)alkenylene or a ($C_4$)alkenylene.

"Alkoxy" means an oxygen moiety having a further alkyl substituent. The alkoxy groups of the present invention can be optionally substituted. When substituted particular groups for alkoxy include substituents independently selected from the group consisting of amino, ($C_{1-4}$)alkoxy, ($C_{1-4}$)alkyl, cyano, ($C_{3-8}$)cycloalkyl, halo, hydroxy, nitro, oxo, and optionally substituted phenyl. An optionally substituted ($C_{1-4}$)alkoxy has from 1 to 6 such substituents.

"Alkyl" represented by itself means a straight or branched, saturated or unsaturated, aliphatic radical having a chain of carbon atoms, optionally with one or more of the carbon atoms being replaced with oxygen (See "oxaalkyl"), a carbonyl group (See "oxoalkyl"), sulfur (See "thioalkyl"), and/or nitrogen (See "azaalkyl"). ($C_X$)alkyl and ($C_{X-Y}$)alkyl are typically used where X and Y indicate the number of carbon atoms in the chain. For example, ($C_{1-6}$)alkyl includes alkyls that have a chain of between 1 and 6 carbons (e.g., methyl, ethyl, propyl, isopropyl, butyl, sec-butyl, isobutyl, tert-butyl, vinyl, allyl, 1-propenyl, isopropenyl, 1-butenyl, 2-butenyl, 3-butenyl, 2-methylallyl, ethynyl, 1-propynyl, 2-propynyl, and the like). Alkyl represented along with another radical (e.g., as in arylalkyl, heteroarylalkyl and the like) means a straight or branched, saturated or unsaturated aliphatic divalent radical having the number of atoms indicated or when no atoms are indicated means a bond (e.g., $(C_{6-10})aryl(C_{1-3})$ alkyl includes, benzyl, phenethyl, 1-phenylethyl, 3-phenylpropyl, 2-thienylmethyl, 2-pyridinylmethyl and the like). In particular embodiments, "alkyl," either alone or represented along with another radical, can be a $(C_{1-20})$alkyl, a $(C_{1-15})$ alkyl, a $(C_{1-10})$alkyl, a $(C_{1-5})$alkyl, a $(C_{1-4})$alkyl or a $(C_{1-3})$ alkyl. Alternatively, "alkyl," either alone or represented along with another radical, can be a $(C_1)$alkyl, a $(C_2)$alkyl or a $(C_3)$alkyl. When substituted particular groups for alkyl include substituents independently selected from the group consisting of amino, $(C_{1-4})$alkoxy, $(C_{1-4})$alkyl, amido, carboxy, cyano, $(C_{3-8})$cycloalkyl, halo, hydroxy, nitro, oxo, an ester of phosphoric $(-OP(O)(OH)_2)$ acid, and optionally substituted phenyl. An optionally substituted $(C_{1-4})$alkyl or $(C_{1-10})$alkyl has from 1 to 6 such substituents.

"Alkylene", unless indicated otherwise, means a straight or branched, saturated or unsaturated, aliphatic, divalent radical. $(C_X)$alkylene and $(C_{X-Y})$alkylene are typically used where X and Y indicate the number of carbon atoms in the chain. For example, $(C_{1-6})$alkylene includes methylene ($-CH_2-$), ethylene ($-CH_2CH_2-$), trimethylene ($-CH_2CH_2CH_2-$), tetramethylene ($-CH_2CH_2CH_2CH_2-$) 2-butenylene ($-CH_2CH=CHCH_2-$), 2-methyltetramethylene ($-CH_2CH(CH_3)CH_2CH_2-$), pentamethylene ($-CH_2CH_2CH_2CH_2CH_2-$) and the like. In particular embodiments, "alkylene," either alone or represented along with another radical, can be a $(C_{1-20})$alkylene, a $(C_{1-15})$alkylene, a $(C_{1-10})$alkylene, a $(C_{1-5})$alkylene or a $(C_{1-3})$alkylene. Alternatively, "alkylene," either alone or represented along with another radical, can be a $(C_1)$alkylene, a $(C_2)$alkylene or a $(C_3)$alkylene.

"Alkylidene" means a straight or branched, saturated or unsaturated, aliphatic radical connected to the parent molecule by a double bond. $(C_X)$alkylidene and $(C_{X-Y})$alkylidene are typically used where X and Y indicate the number of carbon atoms in the chain. For example, $(C_{1-6})$alkylidene includes methylene ($=CH_2$), ethylidene ($=CHCH_3$), isopropylidene ($=C(CH_3)_2$), propylidene ($=CHCH_2CH_3$), allylidene ($=CH-CH=CH_2$), and the like. In particular embodiments, "alkylidene," either alone or represented along with another radical, can be a $(C_{1-20})$alkylidene, a $(C_{1-15})$alkylidene, a $(C_{1-10})$alkylidene, a $(C_{1-5})$alkylidene or a $(C_{1-3})$alkylidene. Alternatively, "alkylidene," either alone or represented along with another radical, can be a $(C_1)$alkylidene, a $(C_2)$alkylidene or a $(C_3)$alkylidene.

"Alkynyl" means a straight or branched, carbon chain that contains at least one carbon-carbon triple bond ($-C\equiv C-$ or $-C\equiv CR$, wherein R is hydrogen or a further substituent). Examples of alkynyl include ethynyl, propargyl, 3-methyl-1-pentynyl, 2-heptynyl and the like. In particular embodiments, "alkynyl," either alone or represented along with another radical, can be a $(C_{2-20})$alkynyl, a $(C_{2-15})$alkynyl, a $(C_{2-10})$alkynyl, a $(C_{2-5})$alkynyl or a $(C_{2-3})$alkynyl. Alternatively, "alkynyl," either alone or represented along with another radical, can be a $(C_2)$alkynyl, a $(C_3)$alkynyl or a $(C_4)$alkynyl.

"Alkynylene" means a straight or branched, divalent carbon chain having one or more carbon-carbon triple bonds ($-CR\equiv CR'-$, wherein R and R' are each independently hydrogen or further substituents). Examples of alkynylene include ethyne-1,2-diyl, propyne-1,3-diyl, and the like. In particular embodiments, "alkynylene," either alone or represented along with another radical, can be a $(C_{2-20})$alkynylene, a $(C_{2-15})$alkynylene, a $(C_{2-10})$alkynylene, a $(C_{2-5})$alkynylene or a $(C_{2-3})$alkynylene. Alternatively, "alkynylene," either alone or represented along with another radical, can be a $(C_2)$alkynylene, a $(C_3)$alkynylene or a $(C_4)$alkynylene.

"Amido" means the radical $-C(=O)-NR-$, $-C(=O)-NRR'$, $-NR-C(=O)-$ and/or $-NR-C(=O)R'$, wherein each R and R' are independently hydrogen or a further substituent. R when attached to nitrogen is typically selected from the group consisting of hydrogen and $(C_{1-4})$alkyl. R' when attached to nitrogen is typically selected from the group consisting of alkyl, cycloalkyl, and heterocycloalkyl, each unsubstituted or substituted. Where R' is a substituted $(C_{1-4})$alkyl typical substituents thereon are $(C_{1-4})$ alkoxy, amido, carboxy, cyano, $(C_{3-8})$cycloalkyl, halo, hydroxy, nitro, oxo, and optionally substituted phenyl. Where R' is a substituted $(C_{3-8})$cycloalkyl typical substituents thereon are $(C_{1-4})$alkoxy, $(C_{1-4})$alkyl, amido, carboxy, cyano, halo, hydroxy, nitro, oxo, and optionally substituted phenyl. Where R' is a substituted hetero$(C_{3-6})$cycloalkyl typical substituents thereon are $(C_{1-4})$alkoxy, $(C_{1-4})$alkyl, amido, carboxy, cyano, $(C_{3-8})$cycloalkyl, halo, hydroxy, nitro, oxo, and optionally substituted phenyl.

"Amino" means a nitrogen moiety having two further substituents where, for example, a hydrogen or carbon atom is attached to the nitrogen. For example, representative amino groups include $-NH_2$, $-NHCH_3$, $-N(CH_3)_2$, $-NH((C_{1-10})alkyl)$, $-N((C_{1-10})alkyl)_2$, $-NH(aryl)$, $-NH(heteroaryl)$, $-N(aryl)_2$, $-N(heteroaryl)_2$, $-NH(cycloalkyl)$, $-NH(heterocycloalkyl)$, and the like and the further substituents on the nitrogen can themselves be substituted or unsubstituted. Where a further substituent is $(C_{1-4})$alkyl typical substituents thereon are $(C_{1-4})$alkoxy, amido, carboxy, cyano, $(C_{3-8})$cycloalkyl, halo, hydroxy, nitro, oxo, and optionally substituted phenyl. Where a further substituent is $(C_{3-8})$cycloalkyl typical substituents thereon are $(C_{1-4})$ alkoxy, $(C_{1-4})$alkyl, amido, carboxy, cyano, halo, hydroxy, nitro, oxo, and optionally substituted phenyl. Where a further substituent is hetero$(C_{3-6})$cycloalkyl typical substituents thereon are $(C_{1-4})$alkoxy, $(C_{1-4})$alkyl, amido, carboxy, cyano, $(C_{3-8})$cycloalkyl, halo, hydroxy, nitro, oxo, and optionally substituted phenyl. Optionally, the two substituents together with the nitrogen may also form a ring. Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Animal" includes humans, non-human mammals (e.g., dogs, cats, rabbits, cattle, horses, sheep, goats, swine, deer, and the like) and non-mammals (e.g., birds, and the like).

"Aromatic" means a moiety wherein the constituent atoms make up an unsaturated, conjugated ring system, either having total number of pi electrons is equal to 4n+2 or having aromatic character or having the maximum number of double bonds. An aromatic ring may be such that the ring atoms are only carbon atoms or may include carbon and non-carbon atoms (See "heteroaryl").

"Aryl" means a monocyclic or polycyclic ring assembly wherein each ring is aromatic or when fused with one or more rings forms an aromatic ring assembly. If one or more ring atoms is not carbon (e.g., N, S), the aryl is a heteroaryl. $(C_X)$aryl and $(C_{X-Y})$aryl are typically used where X and Y indicate the number of carbon atoms in the ring. In particular embodiments, "aryl," either alone or represented along with another radical, can be a $(C_{3-14})$aryl, a $(C_{3-10})$aryl, a $(C_{3-7})$ aryl, a $(C_{8-10})$aryl or a $(C_{5-7})$aryl. Alternatively, "aryl," either alone or represented along with another radical, can be a $(C_5)$aryl, a $(C_6)$aryl, a $(C_7)$aryl, a $(C_8)$aryl, a $(C_9)$aryl or a ($C_{10}$)aryl. Particular aryls are phenyl and naphthyl. When substituted particular groups for aryl include substituents independently selected from the group consisting of amino, optionally substituted ($C_{1-4}$)alkoxy, optionally substituted ($C_{1-4}$)alkyl, amido, carboxy, cyano, ($C_{3-8}$)cycloalkyl, halo, hydroxy, and nitro. An optionally substituted ($C_{4-12}$)aryl has from 1 to 4 such substituents.

"Azaalkyl" means an alkyl, as defined above, except where one or more of the carbon atoms forming the alkyl chain are replaced with substituted or unsubstituted nitrogen atoms (—NR— or —NRR', wherein R and R' are each independently hydrogen or further substituents). For example, a ($C_{1-10}$)azaalkyl refers to a chain comprising between 1 and 10 carbons and one or more nitrogen atoms.

"Bicycloalkyl" means a saturated or partially unsaturated fused, spiro or bridged bicyclic ring assembly. In particular embodiments, "bicycloalkyl," either alone or represented along with another radical, can be a ($C_{4-15}$)bicycloalkyl, a ($C_{4-10}$)bicycloalkyl, a ($C_{6-10}$)bicycloalkyl, ($C_{7-10}$)bicycloalkyl or a ($C_{8-10}$)bicycloalkyl. Alternatively, "bicycloalkyl," either alone or represented along with another radical, can be a ($C_8$)bicycloalkyl, a ($C_9$)bicycloalkyl or a ($C_{10}$) bicycloalkyl.

"Bicycloaryl" means a fused, spiro or bridged bicyclic ring assembly wherein at least one of the rings comprising the assembly is aromatic. ($C_X$)bicycloaryl and ($C_{X-Y}$)bicycloaryl are typically used where X and Y indicate the number of carbon atoms in the bicyclic ring assembly and directly attached to the ring. In particular embodiments, "bicycloaryl," either alone or represented along with another radical, can be a (a ($C_{4-15}$)bicycloaryl, a ($C_{4-10}$)bicycloaryl, a ($C_{6-10}$)bicycloaryl or a ($C_{8-10}$)bicycloaryl. Alternatively, "bicycloalkyl," either alone or represented along with another radical, can be a ($C_8$)bicycloaryl, a ($C_9$)bicycloaryl or a ($C_{10}$) bicycloaryl.

"Bridging ring" and "bridged ring" as used herein refer to a ring that is bonded to another ring to form a compound having a bicyclic or polycyclic structure where two ring atoms that are common to both rings are not directly bound to each other. Non-exclusive examples of common compounds having a bridging ring include borneol, norbornane, 7-oxabicyclo[2.2.1]heptane, and the like. One or both rings of the bicyclic system may also comprise heteroatoms.

"Carbamoyloxy" means the radical —OC(O)NRR', wherein R and R' are each independently hydrogen or further substituents.

"Carbocycle" means a ring consisting of carbon atoms.

"Carbonyl" means the radical —C(=O)— and/or —C(=O)R, wherein R is hydrogen or a further substituent. It is noted that the carbonyl radical may be further substituted with a variety of substituents to form different carbonyl groups including acids, acid halides, aldehydes, amides, esters, and ketones.

"Carbonyloxy" means the radical R—C(=O)O— where the substituent is attached through oxygen and R is hydrogen or further substituents, particularly optionally substituted ($C_{1-4}$)alkyl or optionally substituted phenyl.

"Carboxy" means the radical —C(=O)—O— and/or —C(=O)—OR, wherein R is hydrogen or a further substituent. It is noted that compounds of the invention containing carboxy moieties may include protected derivatives thereof, i.e., where the oxygen is substituted with a protecting group. Suitable protecting groups for carboxy moieties include benzyl, tert-butyl, and the like.

"Cyano" means the radical —CN.

"Cycloalkyl" means a non-aromatic, saturated or partially unsaturated, monocyclic, bicyclic or polycyclic ring assembly. ($C_X$)cycloalkyl and ($C_{X-Y}$)cycloalkyl are typically used where X and Y indicate the number of carbon atoms in the ring assembly. For example, ($C_{3-10}$)cycloalkyl includes cyclopropyl, cyclobutyl, cyclopentyl, cyclohexyl, cyclohexenyl, 2,5-cyclohexadienyl, bicyclo[2.2.2]octyl, adamantan-1-yl, decahydronaphthyl, oxocyclohexyl, dioxocyclohexyl, thiocyclohexyl, 2-oxobicyclo[2.2.1]hept-1-yl, and the like. In particular embodiments, "cycloalkyl," either alone or represented along with another radical, can be a ($C_{3-14}$)cycloalkyl, a ($C_{3-10}$)cycloalkyl, a ($C_{3-7}$)cycloalkyl, a ($C_{8-10}$)cycloalkyl or a ($C_{5-7}$)cycloalkyl. Alternatively, "cycloalkyl," either alone or represented along with another radical, can be a ($C_5$)cycloalkyl, a ($C_6$)cycloalkyl, a ($C_7$)cycloalkyl, a ($C_8$)cycloalkyl, a ($C_9$)cycloalkyl or a ($C_{10}$)cycloalkyl. When substituted particular groups for cycloalkyl include substituents independently selected from the group consisting of amino, optionally substituted ($C_{1-4}$)alkoxy, optionally substituted ($C_{1-4}$)alkyl, amido, carboxy, cyano, halo, hydroxy, nitro, oxo, an ester of phosphoric (—OP(O)(OH)$_2$) acid, and optionally substituted phenyl. An optionally substituted ($C_{3-8}$)alkyl has from 1 to 5 such substituents.

"Cycloalkylene" means a divalent, saturated or partially unsaturated, monocyclic, bicyclic or polycyclic ring assembly. ($C_X$)cycloalkylene and ($C_{X-Y}$)cycloalkylene are typically used where X and Y indicate the number of carbon atoms in the ring assembly. In particular embodiments, "cycloalkylene," either alone or represented along with another radical, can be a ($C_{3-14}$)cycloalkylene, a ($C_{3-10}$)cycloalkylene, a ($C_{3-7}$)cycloalkylene, a ($C_{8-10}$)cycloalkylene or a ($C_{5-7}$)cycloalkylene. Alternatively, "cycloalkylene," either alone or represented along with another radical, can be a ($C_5$)cycloalkylene, a ($C_6$)cycloalkylene, a ($C_7$)cycloalkylene, a ($C_8$) cycloalkylene, a ($C_9$)cycloalkylene or a ($C_{10}$)cycloalkylene.

"Disease," "disorder" and "condition" specifically includes any unhealthy condition of an animal or part thereof and includes an unhealthy condition that may be caused by, or incident to, medical or veterinary therapy applied to that animal, i.e., the "side effects" of such therapy.

"Fused ring" as used herein refers to a ring that is bonded to another ring to form a compound having a bicyclic structure where the ring atoms that are common to both rings are directly bound to each other. Non-exclusive examples of common fused rings include decalin, naphthalene, anthracene, phenanthrene, indole, furan, benzofuran, quinoline, and the like. Compounds having fused ring systems may be saturated, partially saturated, carbocyclics, heterocyclics, aromatics, heteroaromatics, and the like.

"Halo" means fluoro, chloro, bromo or iodo.

"Heteroalkyl" means alkyl, as defined in this Application, provided that one or more of the atoms within the alkyl chain is a heteroatom. In particular embodiments, "heteroalkyl," either alone or represented along with another radical, can be a hetero($C_{1-20}$)alkyl, a hetero($C_{1-15}$)alkyl, a hetero($C_{1-10}$) alkyl, a hetero($C_{1-5}$)alkyl, a hetero($C_{1-3}$)alkyl or a hetero ($C_{1-2}$)alkyl. Alternatively, "heteroalkyl," either alone or represented along with another radical, can be a hetero($C_1$)alkyl, a hetero($C_2$)alkyl or a hetero($C_3$)alkyl.

"Heteroaryl" means a monocyclic, bicyclic or polycyclic aromatic group wherein at least one ring atom is a heteroatom and the remaining ring atoms are carbon. Monocyclic heteroaryl groups include, but are not limited to, cyclic aromatic groups having five or six ring atoms, wherein at least one ring atom is a heteroatom and the remaining ring atoms are carbon. The nitrogen atoms can be optionally quaternerized and the sulfur atoms can be optionally oxidized. Heteroaryl groups of this invention include, but are not limited to, those derived from furan, thiophene, pyrrole, imidazole, isothiazole, isoxazole, oxadiazole, oxazole, 1,2,3-oxadiazole, pyrazine, pyrazole, pyridazine, pyridine, pyrimidine, thiazole, 1,3,4-thiadiazole, triazole and tetrazole. "Heteroaryl" also includes, but is not limited to, bicyclic or tricyclic rings, wherein the heteroaryl ring is fused to one or two rings independently selected from the group consisting of an aryl ring, a cycloalkyl ring, a cycloalkenyl ring, and another monocyclic heteroaryl or heterocycloalkyl ring. These bicyclic or tricyclic heteroaryls include, but are not limited to, those derived from benzo[b]furan, benzo[b]thiophene, benzimidazole, imidazo[4,5-c]pyridine, quinazoline, thieno[2,3-c]pyridine, thieno[3,2-b]pyridine, thieno[2,3-b]pyridine, indolizine, imidazo[1,2a]pyridine, quinoline, isoquinoline, phthalazine, quinoxaline, naphthyridine, quinolizine, indole, isoindole, indazole, indoline, 2-oxoindoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3-c]pyridine, pyrrolo[3,2-c]pyridine, pyrrolo[3,2-b]pyridine, pyrrolo[2,3-d]pyrimidine, pyrrolo[3,2-d]pyrimidine, pyrrolo[2,3-b]pyrazine, pyrazolo[1,5-a]pyridine, pyrrolo[1,2-b]pyridazine, pyrrolo[1,2-c]pyrimidine, pyrrolo[1,2-a]pyrimidine, pyrrolo[1, 2-a]pyrazine, triazo[1,5-a]pyridine, pteridine, purine, carbazole, acridine, phenazine, phenothiazene, phenoxazine, 1,2-dihydropyrrolo[3,2,1-hi]indole, indolizine, pyrido[1,2-a] indole and 2(1H)-pyridinone, benzo[b][1,4]oxazine, benzo [b][1,4]oxazin-3(4H)-one, benzo[d][1,3]dioxole, 2,2-difluorobenzo[d][1,3]dioxole. The bicyclic or tricyclic heteroaryl rings can be attached to the parent molecule through either the heteroaryl group itself or the aryl, cycloalkyl, cycloalkenyl or heterocycloalkyl group to which it is fused. The heteroaryl groups of this invention can be substituted or unsubstituted. In particular embodiments, "heteroaryl," either alone or represented along with another radical, can be a hetero($C_{1-10}$)aryl, hetero($C_{1-13}$)aryl, a hetero($C_{2-13}$)aryl, a hetero($C_{2-6}$)aryl, a hetero($C_{3-9}$)aryl or a hetero($C_{5-9}$)aryl. Alternatively, "heteroaryl," either alone or represented along with another radical, can be a hetero($C_3$)aryl, a hetero($C_4$)aryl, a hetero($C_5$) aryl, a hetero($C_6$)aryl, a hetero($C_7$)aryl, a hetero($C_8$)aryl or a hetero($C_9$)aryl. When substituted particular groups for heteroaryl include substituents independently selected from the group consisting of amino, optionally substituted ($C_{1-4}$) alkoxy, optionally substituted ($C_{1-4}$)alkyl, amido, carboxy, cyano, ($C_{3-8}$)cycloalkyl, halo, hydroxy, and nitro. An optionally substituted hetero($C_{1-10}$)aryl has from 1 to 4 such substituents. It is understood that nitrogen containing heteroaryls may be substituted on nitrogen, particularly with optionally substituted ($C_{1-4}$)alkoxy, optionally substituted ($C_{1-4}$)alkyl, carboxy, and optionally substituted phenyl.

"Heteroatom" refers to an atom that is not a carbon atom. Particular examples of heteroatoms include, but are not limited to, nitrogen, oxygen, and sulfur.

"Heteroatom moiety" includes a moiety where the atom by which the moiety is attached is not a carbon. Examples of heteroatom moieties include —NR—, —N$^+$(O—)=, —O—, —S— or —S(O)$_2$—, wherein R is hydrogen or a further substituent.

"Heterobicycloalkyl" means bicycloalkyl, as defined in this Application, provided that one or more of the atoms within the ring is a heteroatom. For example hetero($C_{9-12}$) bicycloalkyl as used in this application includes, but is not limited to, 3-aza-bicyclo[4.1.0]hept-3-yl, 2-aza-bicyclo [3.1.0]hex-2-yl, 3-aza-bicyclo[3.1.0]hex-3-yl, and the like. In particular embodiments, "heterobicycloalkyl," either alone or represented along with another radical, can be a hetero ($C_{1-14}$)bicycloalkyl, a hetero($C_{4-14}$)bicycloalkyl, a hetero ($C_{4-9}$)bicycloalkyl or a hetero($C_{5-9}$)bicycloalkyl. Alternatively, "heterobicycloalkyl," either alone or represented along with another radical, can be a hetero($C_5$)bicycloalkyl, hetero ($C_6$)bicycloalkyl, hetero($C_7$)bicycloalkyl, hetero($C_8$)bicycloalkyl or a hetero($C_9$)bicycloalkyl.

"Heterobicycloaryl" means bicycloaryl, as defined in this Application, provided that one or more of the atoms within the ring is a heteroatom. For example, hetero($C_{4-12}$)bicycloaryl as used in this Application includes, but is not limited to, 2-amino-4-oxo-3,4-dihydropteridin-6-yl, tetrahydroisoquinolinyl, and the like. In particular embodiments, "heterobicycloaryl," either alone or represented along with another radical, can be a hetero($C_{1-14}$)bicycloaryl, a hetero($C_{4-14}$) bicycloaryl, a hetero($C_{4-9}$)bicycloaryl or a hetero($C_{5-9}$)bicycloaryl. Alternatively, "heterobicycloaryl," either alone or represented along with another radical, can be a hetero($C_5$) bicycloaryl, hetero($C_6$)bicycloaryl, hetero($C_7$)bicycloaryl, hetero($C_8$)bicycloaryl or a hetero($C_9$)bicycloaryl.

"Heterocycloalkyl" means cycloalkyl, as defined in this Application, provided that one or more of the atoms forming the ring is a heteroatom selected, independently from N, O, or S. Non-exclusive examples of heterocycloalkyl include azetidinyl, piperidyl, morpholyl, piperazinyl, pyrrolidinyl, perhydropyrrolizinyl, 1,4-diazaperhydroepinyl, tetrahyrofuranyl, 1,3-dioxanyl, 1,4-dioxanyl and the like. In particular embodiments, "heterocycloalkyl," either alone or represented along with another radical, can be a hetero($C_{1-13}$)cycloalkyl, a hetero($C_{1-9}$)cycloalkyl, a hetero($C_{1-6}$)cycloalkyl, a hetero ($C_{5-9}$)cycloalkyl or a hetero($C_{2-6}$)cycloalkyl or a hetero ($C_{3-6}$)cycloalkyl. Alternatively, "heterocycloalkyl," either alone or represented along with another radical, can be a hetero($C_2$)cycloalkyl, a hetero($C_3$)cycloalkyl, a hetero($C_4$) cycloalkyl, a hetero($C_5$)cycloalkyl, a hetero($C_6$)cycloalkyl, hetero($C_7$)cycloalkyl, hetero($C_8$)cycloalkyl or a hetero($C_9$) cycloalkyl. When substituted particular groups for heterocycloalkyl include substituents independently selected from the group consisting of amino, optionally substituted ($C_{1-4}$) alkoxy, optionally substituted ($C_{1-4}$)alkyl, amido, carboxy, cyano, halo, hydroxy, nitro, oxo, an ester of phosphoric (—OP(O)(OH)$_2$) acid, and optionally substituted phenyl. An optionally substituted hetero($C_{3-6}$)alkyl has from 1 to 5 such substituents. It is understood that nitrogen containing heterocycloalkyls may be substituted on nitrogen, particularly with optionally substituted ($C_{1-4}$)alkoxy, optionally substituted ($C_{1-4}$)alkyl, carboxy, and optionally substituted phenyl.

"Heterocycloalkylene" means cycloalkylene, as defined in this Application, provided that one or more of the ring member carbon atoms is replaced by a heteroatom. In particular embodiments, "heterocycloalkylene," either alone or represented along with another radical, can be a hetero($C_{1-13}$) cycloalkylene, a hetero($C_{1-9}$)cycloalkylene, a hetero($C_{1-6}$) cycloalkylene, a hetero($C_{5-9}$)cycloalkylene or a hetero($C_{2-6}$) cycloalkylene. Alternatively, "heterocycloalkylene," either alone or represented along with another radical, can be a hetero($C_2$)cycloalkylene, a hetero($C_3$)cycloalkylene, a hetero ($C_4$)cycloalkylene, a hetero($C_5$)cycloalkylene, a hetero($C_6$) cycloalkylene, hetero($C_7$)cycloalkylene, hetero($C_8$)cycloalkylene or a hetero($C_9$)cycloalkylene.

"Hydroxy" means the radical —OH.

"IC$_{50}$" means the molar concentration of an inhibitor that produces 50% inhibition of the target enzyme.

"Imino" means the radical —CR(=NR') and/or —C(=NR')—, wherein R and R' are each independently hydrogen or a further substituent, particularly optionally substituted ($C_{1-4}$)alkyl.

"Isomers" means compounds having identical molecular formulae but differing in the nature or sequence of bonding of their atoms or in the arrangement of their atoms in space. Isomers that differ in the arrangement of their atoms in space are termed "stereoisomers." Stereoisomers that are not mirror images of one another are termed "diastereomers" and stereoisomers that are nonsuperimposable mirror images are termed "enantiomers" or sometimes "optical isomers." A carbon atom bonded to four nonidentical substituents is termed a "chiral center." A compound with one chiral center has two enantiomeric forms of opposite chirality. A mixture of the two enantiomeric forms is termed a "racemic mixture." A compound that has more than one chiral center has $2^{n-1}$ enantiomeric pairs, where n is the number of chiral centers. Compounds with more than one chiral center may exist as ether an individual diastereomer or as a mixture of diastereomers, termed a "diastereomeric mixture." When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992).

"Leaving group" means the group with the meaning conventionally associated with it in synthetic organic chemistry, i.e., an atom or group displaceable under reaction (e.g., alkylating) conditions. Examples of leaving groups include, but are not limited to, halo (e.g., F, Cl, Br and I), alkyl (e.g., methyl and ethyl) and sulfonyloxy (e.g., mesyloxy, ethanesulfonyloxy, benzenesulfonyloxy and tosyloxy), thiomethyl, thienyloxy, dihalophosphinoyloxy, tetrahalophosphoxy, benzyloxy, isopropyloxy, acyloxy, and the like.

"Moiety providing X atom separation" and "linker providing X atom separation" between two other moieties mean that the chain of atoms directly linking the two other moieties is X atoms in length. When X is given as a range (e.g., $X_1$-$X_2$), then the chain of atoms is at least $X_1$ and not more than $X_2$ atoms in length. It is understood that the chain of atoms can be formed from a combination of atoms including, for example, carbon, nitrogen, sulfur and oxygen atoms. Further, each atom can optionally be bound to one or more substituents, as valencies allow. In addition, the chain of atoms can form part of a ring. Accordingly, in one embodiment, a moiety providing X atom separation between two other moieties (R and R') can be represented by R-(L)$_X$-R' where each L is independently selected from the group consisting of CR"R''', NR'''', O, S, CO, CS, C=NR''''', SO, SO$_2$, and the like, where any two or more of R", R''', R'''' and R''''' can be taken together to form a substituted or unsubstituted ring. The linker is intended to result in stable compounds. Here the term stable means compounds that are not substantially altered by production, recovery, and storage. Excluded from the term, unless otherwise noted, are peroxides, thioperoxides, ketals, animals, ketenes and the like.

"Nitro" means the radical —NO$_2$.

"Oxaalkyl" means an alkyl, as defined above, except where one or more of the carbon atoms forming the alkyl chain are replaced with oxygen atoms (—O— or —OR, wherein R is hydrogen or a further substituent). For example, an oxa (C$_{1-10}$)alkyl refers to a chain comprising between 1 and 10 carbons and one or more oxygen atoms.

"Oxo" means refers to a carbon atom substituted with a double bonded oxygen, to give a carbonyl group which may, depending on the other substituents attached, be the carbonyl group of an aldehyde, ketone, ester, amide, or acid.

"Oxoalkyl" means an alkyl, as defined above, except where one or more of the carbon atoms forming the alkyl chain are replaced with carbonyl groups (—C(=O)— or —C(=O)—R, wherein R is hydrogen or a further substituent). The carbonyl group may be an aldehyde, ketone, ester, amide, acid, or acid halide. For example, an oxo(C$_{1-10}$)alkyl refers to a chain comprising between 1 and 10 carbon atoms and one or more carbonyl groups.

"Oxy" means the radical —O— or —OR, wherein R is hydrogen or a further substituent. Accordingly, it is noted that the oxy radical may be further substituted with a variety of substituents to form different oxy groups including hydroxy, alkoxy, aryloxy, heteroaryloxy or carbonyloxy.

"Pharmaceutically acceptable" means that which is useful in preparing a pharmaceutical composition that is generally safe, non-toxic and neither biologically nor otherwise undesirable in the amounts used and includes that which is acceptable for veterinary use as well as human pharmaceutical use.

"Pharmaceutically acceptable salts" means salts of compounds of the present invention which are pharmaceutically acceptable. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Optionally substituted phenyl" refers to a phenyl group optionally having 1 to 5 substituents independently selected from the group consisting of amino, optionally substituted C$_{1-4}$ alkyl, optionally substituted)C$_{1-4}$)alkoxy, amido, amino, carboxy, cyano, halogen, hydroxyl, and nitro.

"Oxycarbonyl" means the radical R—O(=O)C— where the substituent is attached through carbon and R is further substituents, particularly optionally substituted (C$_{1-4}$)alkyl.

"Polycyclic ring" includes bicyclic and multi-cyclic rings. The individual rings comprising the polycyclic ring can be fused, spiro or bridging rings.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

"Protected derivatives" means derivatives of inhibitors in which a reactive site or sites are blocked with protecting groups. Protected derivatives are useful in the preparation of inhibitors or in themselves may be active as inhibitors. A comprehensive list of suitable protecting groups can be found in T. W. Greene, *Protecting Groups in Organic Synthesis*, 3rd edition, John Wiley & Sons, Inc. 1999.

"Ring" and "ring assembly" means a carbocyclic or a heterocyclic system and includes aromatic and non-aromatic systems. The system can be monocyclic, bicyclic or polycyclic. In addition, for bicyclic and polycyclic systems, the individual rings comprising the polycyclic ring can be fused, spiro or bridging rings.

"Subject" and "patient" includes humans, non-human mammals (e.g., dogs, cats, rabbits, cattle, horses, sheep, goats, swine, deer, and the like) and non-mammals (e.g., birds, and the like). A particular subject or patient is a human.

"Substituent convertible to hydrogen in vivo" means any group that is convertible to a hydrogen atom by enzymological or chemical means including, but not limited to, hydrolysis and hydrogenolysis. Examples include hydrolyzable groups, such as acyl groups, groups having an oxycarbonyl group, amino acid residues, peptide residues, o-nitrophenylsulfenyl, trimethylsilyl, tetrahydro-pyranyl, diphenylphosphinyl, and the like. Examples of acyl groups include formyl, acetyl, trifluoroacetyl, and the like. Examples of groups having an oxycarbonyl group include ethoxycarbonyl, t-butoxycarbonyl [$(CH_3)_3C-OCO-$], benzyloxycarbonyl, p-methoxybenzyloxycarbonyl, vinyloxycarbonyl, β-(p-toluenesulfonyl)ethoxycarbonyl, and the like. Examples of suitable amino acid residues include amino acid residues per se and amino acid residues that are protected with a protecting group. Suitable amino acid residues include, but are not limited to, residues of Gly (glycine), Ala (alanine; $CH_3CH(NH_2)CO-$), Arg (arginine), Asn (asparagine), Asp (aspartic acid), Cys (cysteine), Glu (glutamic acid), His (histidine), Ile (isoleucine; $(CH_3)_2CHCH_2CH(NH_2)CO-$), Lys (lysine), Met (methionine), Phe (phenylalanine), Pro (proline), Ser (serine), Thr (threonine), Trp (tryptophan), Tyr (tyrosine), Val (valine), Nva (norvaline), Hse (homoserine), 4-Hyp (4-hydroxyproline), 5-Hyl (5-hydroxylysine), Orn (ornithine) and β-Ala. Examples of suitable protecting groups include those typically employed in peptide synthesis, including acyl groups (such as formyl and acetyl), arylmethyloxycarbonyl groups (such as benzyloxycarbonyl and p-nitrobenzyloxycarbonyl), t-butoxycarbonyl groups [$(CH_3)_3C-OCO-$], and the like. Suitable peptide residues include peptide residues comprising two to five, and optionally two to three, of the aforesaid amino acid residues. Examples of such peptide residues include, but are not limited to, residues of such peptides as Ala-Ala [$CH_3CH(NH_2)CO-NHCH(CH_3)CO-$], Gly-Phe, Nva-Nva, Ala-Phe, Gly-Gly, Gly-Gly-Gly, Ala-Met, Met-Met, Leu-Met and Ala-Leu. The residues of these amino acids or peptides can be present in stereochemical configurations of the D-form, the L-form or mixtures thereof. In addition, the amino acid or peptide residue may have an asymmetric carbon atom. Examples of suitable amino acid residues having an asymmetric carbon atom include residues of Ala, Leu, Phe, Trp, Nva, Val, Met, Ser, Lys, Thr and Tyr. Peptide residues having an asymmetric carbon atom include peptide residues having one or more constituent amino acid residues having an asymmetric carbon atom. Examples of suitable amino acid protecting groups include those typically employed in peptide synthesis, including acyl groups (such as formyl and acetyl), arylmethyloxycarbonyl groups (such as benzyloxycarbonyl and p-nitrobenzyloxycarbonyl), t-butoxycarbonyl groups [$(CH_3)_3C-OCO-$], and the like. Other examples of substituents "convertible to hydrogen in vivo" include reductively eliminable hydrogenolyzable groups. Examples of suitable reductively eliminable hydrogenolyzable groups include, but are not limited to, arylsulfonyl groups (such as o-toluenesulfonyl); methyl groups substituted with phenyl or benzyloxy (such as benzyl, trityl and benzyloxymethyl); arylmethoxycarbonyl groups (such as benzyloxycarbonyl and o-methoxybenzyloxycarbonyl); and halogenoethoxycarbonyl groups (such as β,β,β-trichloroethoxycarbonyl and β-iodoethoxycarbonyl).

"Substituted or unsubstituted" means that a given moiety may consist of only hydrogen substituents through available valencies (unsubstituted) or may further comprise one or more non-hydrogen substituents through available valencies (substituted) that are not otherwise specified by the name of the given moiety. For example, isopropyl is an example of an ethylene moiety that is substituted by $-CH_3-$ In general, a non-hydrogen substituent may be any substituent that may be bound to an atom of the given moiety that is specified to be substituted. Examples of substituents include, but are not limited to, aldehyde, alicyclic, aliphatic, $(C_{1-10})$alkyl, alkylene, alkylidene, amido, amino, aminoalkyl, aromatic, aryl, bicycloalkyl, bicycloaryl, carbamoyloxy, carbocyclyl, carboxyl, carbonyl group, carbonyloxy, cycloalkyl, cycloalkylene, ester, halo, heterobicycloalkyl, heterocycloalkylene, heteroaryl, heterobicycloaryl, heterocycloalkyl, oxo, hydroxy, imino, iminoketone, ketone, nitro, oxycarbonyl, oxaalkyl, and oxoalkyl moieties, each of which may optionally also be substituted or unsubstituted. In one particular embodiment, examples of substituents include, but are not limited to, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl. In addition, the substituent is itself optionally substituted by a further substituent. In one particular embodiment, examples of the further substituent include, but are not limited to, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$ cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl.

"Sulfinyl" means the radical —SO— and/or —SO—R, wherein R is hydrogen or a further substituent, particularly (C$_{1-4}$)alkyl and optionally substituted phenyl. It is noted that the sulfinyl radical may be further substituted with a variety of substituents to form different sulfinyl groups including sulfinic acids, sulfinamides, sulfinyl esters, and sulfoxides.

"Sulfonyl" means the radical —SO$_2$— and/or —SO$_2$—R, wherein R is hydrogen or a further substituent, particularly (C$_{1-4}$)alkyl and optionally substituted phenyl. It is noted that the sulfonyl radical may be further substituted with a variety of substituents to form different sulfonyl groups including sulfonic acids, sulfonamides, sulfonate esters, and sulfones.

"Therapeutically effective amount" means that amount which, when administered to an animal for treating a disease, is sufficient to effect such treatment for the disease.

"Thio" denotes replacement of an oxygen by a sulfur and includes, but is not limited to, —SR, —S— and =S containing groups.

"Thioalkyl" means an alkyl, as defined above, except where one or more of the carbon atoms forming the alkyl chain are replaced with sulfur atoms (—S— or —S—R, wherein R is hydrogen or a further substituent). For example, a thio(C$_{1-10}$)alkyl refers to a chain comprising between 1 and 10 carbons and one or more sulfur atoms.

"Thiocarbonyl" means the radical —C(=S)— and/or —C(=S)—R, wherein R is hydrogen or a further substituent. It is noted that the thiocarbonyl radical may be further substituted with a variety of substituents to form different thiocarbonyl groups including thioacids, thioamides, thioesters, and thioketones.

"Treatment" or "treating" or "treat" means any administration of a compound of the present invention and includes:

(1) preventing the disease from occurring in an animal which may be predisposed to the disease but does not yet experience or display the pathology or symptomatology of the disease, (2) inhibiting the disease in an animal that is experiencing or displaying the pathology or symptomatology of the diseased (i.e., arresting further development of the pathology and/or symptomatology), or (3) ameliorating the disease in an animal that is experiencing or displaying the pathology or symptomatology of the diseased (i.e., reversing the pathology and/or symptomatology) and includes all processes providing slowing, interrupting, arresting, controlling, or stopping of the progression of the conditions described herein, but does not necessarily indicate a total elimination of all symptoms or a cure of the disease.

It is noted in regard to all of the definitions provided herein that the definitions should be interpreted as being open ended in the sense that further substituents beyond those specified may be included. Hence, a C$_1$ alkyl indicates that there is one carbon atom but does not indicate what are the substituents on the carbon atom. Hence, a (C$_1$)alkyl comprises methyl (i.e., —CH$_3$) as well as —CRR'R" where R, R', and R" may each independently be hydrogen or a further substituent where the atom attached to the carbon is a heteroatom or cyano. Hence, CF$_3$, CH$_2$OH and CH$_2$CN, for example, are all (C$_1$)alkyls. Similarly, terms such as alkylamino and the like comprise dialkylamino and the like.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C.

DETAILED DESCRIPTION OF THE INVENTION

The present invention relates to compounds that may be used to inhibit kinases and, in particular, Polo-like Kinases (referred to herein as PLKs). The present invention also relates to pharmaceutical compositions, kits and articles of manufacture comprising such compounds. In addition, the present invention relates to methods and intermediates useful for making the compounds. Further, the present invention relates to methods of using said compounds. It is noted that the compounds of the present invention may also possess activity for other members of the same protein family and thus may be used to address disease states associated with these other family members.

Disregulation of PLKs is implicated in such areas as hyperproliferative disorders; cancer (e.g., solid tumors, leukemias, lymphomas, non-small cell lung cancers and esophageal carcinomas); inflammatory and autoimmune diseases (e.g., psoriasis, alopecia; multiple sclerosis; colitis, arthritis, Alzheimer's disease, glomerulonephritis and wound healing); chemotherapy agent-induced alopecia and mucositis; cardiovascular diseases (e.g., stenoses, arteriroscleroses, restenoses, and hypertrophy); viral, bacterial, fungal and/or parasitic infectious diseases (e.g., cytomegalic infections, herpes, hepatitis B and C, Karposi's sarcoma, HIV diseases); nephrological diseases (e.g., glomerulonephritis); chronic and acute neurodegenerative diseases (e.g., Huntington's disease, amyotrophic lateral sclerosis, Parkinson's disease, AIDS dementia, Alzheimer's disease, ischemias of the brain and neurotraumas); skin diseases (e.g., psoriasis); bone diseases; the protection of proliferating cells (e.g., hair, intestinal, blood and progenitor cells) from DNA damage caused by radiation, UV treatment and/or cytostatic treatment.

It is noted that the compounds of the present invention may also possess inhibitory activity for other protein kinase family members and thus may be used to address disease states associated with these other family members.

Polo-Like Kinase Inhibitors

In one embodiment, PLK inhibitors of the present invention comprise:

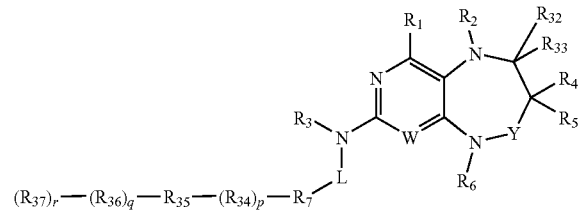

and the pharmaceutically acceptable salts thereof, wherein
W is selected from the group consisting of CR$_8$ and N;
Y is —(CR$_9$R$_{10}$)$_n$—;
n is selected from the group consisting of 1, 2, 3 and 4;
L is absent or a linker providing 1, 2, 3, 4, 5 or 6 atom separation between R$_7$ and the nitrogen to which L is attached, wherein the atoms of the linker providing the separation are selected from the group consisting of carbon, oxygen, nitrogen, and sulfur;
R$_1$ is selected from the group consisting of hydrogen, cyano, thio, hydroxy, carbonyloxy, alkoxy, aryloxy, heteroaryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-3})$alkyl, thiocarbonyl$(C_{1-3})$alkyl, sulfonyl $(C_{1-3})$alkyl, sulfinyl$(C_{1-3})$alkyl, $(C_{1-10})$azaalkyl, imino $(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_2$ is selected from the group consisting of hydrogen, carbonyl, oxycarbonyl sulfonyl, sulfinyl, $(C_{1-10})$alkyl, halo $(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, $(C_{1-10})$azaalkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_2$ and $R_1$ or $R_{14}$ are taken together to form a substituted or unsubstituted ring;

$R_3$ is hydrogen or a substituent convertible in vivo to hydrogen;

$R_4$ is halo;

$R_5$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo $(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_6$ is selected from the group consisting of hydrogen, carbonyl, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl $(C_{1-3})$alkyl, sulfinyl$(C_{1-3})$alkyl, $(C_{1-10})$azaalkyl, imino $(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_7$ is selected from the group consisting of $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_8$ is selected from the group consisting of hydrogen, halo, nitro, cyano, thio, oxy, hydroxy, carbonyloxy, alkoxy, aryloxy, heteroaryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, $(C_{1-10})$azaalkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_9$ and $R_{10}$ are each independently selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy $(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl $(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero $(C_{1-10})$aryl, $(C_{9-12})$bicycloaryl and hetero$(C_{4-12})$bicycloaryl, each substituted or unsubstituted, or $R_9$ and $R_{10}$ are taken together with the carbon to which they are attached to form C=O, C=S, C=NR$_{11}$ or C=CR$_{12}$R$_{13}$;

$R_{11}$ is selected from the group consisting of hydrogen, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl $(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_{12}$ and $R_{13}$ are each independently selected from the group consisting of hydrogen, halo, nitro, cyano, oxycarbonyl, amido, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero $(C_{3-12})$cycloalkyl$(C_{1-10})$alkyl, aryl$(C_{1-10})$alkyl, hetero $(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero $(C_{1-10})$aryl, $(C_{9-12})$bicycloaryl and hetero$(C_{4-12})$bicycloaryl, each substituted or unsubstituted;

$R_{14}$ is selected from the group consisting of $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cycloalkyl$(C_{1-5})$alkyl, hetero$(C_{3-12})$cycloalkyl $(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero($C_{1-10}$)aryl, ($C_{9-12}$)bicycloaryl and hetero($C_{4-12}$)bicycloaryl, each substituted or unsubstituted;

$R_{32}$ and $R_{33}$ are taken together to form X, or $R_{32}$ and $R_{33}$ are each independently selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted; and X is selected from the group consisting of C—$R_{40}$, $NR_{14}$, O, and S or any two $R_2$, $R_5$, $R_6$, $R_9$, $R_{10}$ $R_{32}$ and $R_{33}$ are taken together to form a substituted or unsubstituted ring;

p is selected from the group consisting of 0 and 1;

$R_{34}$ is selected from the group consisting of —$CONJ_{34}$-, —$NJ_{34}$ CO—, —$NJ_{34}$-, —$SO_2NJ_{34}$-, —$NJ_{34}$ $SO_2$—, $J_{34}$ is selected from the group consisting of hydrogen and ($C_{1-4}$)alkyl;

$R_{35}$ is selected from the group consisting of amino, ($C_{4-12}$)aryl, hetero($C_{1-10}$)aryl, ($C_{3-8}$)cycloalkyl, hetero($C_{3-6}$)cycloalkyl, ($C_{7-12}$)bicycloalkyl, hetero($C_{3-12}$)bicycloalkyl, each substituted or unsubstituted;

q is selected from the group consisting of 0 and 1;

$R_{36}$ is selected from the group consisting of is selected from the group consisting ($C_{1-4}$)alkyl, ($C_{1-4}$)azaalkyl, ($C_{3-8}$)cycloalkyl, hetero($C_{3-8}$)cycloalkyl, each substituted or unsubstituted;

r is selected from the group consisting of 0 and 1;

$R_{37}$ is optionally substituted ($C_{3-8}$)cycloalkyl, when $R_{36}$ is selected from the group consisting of optionally substituted ($C_{1-4}$)alkyl and optionally substituted ($C_{1-4}$)azaalkyl;

$R_{37}$ is optionally substituted ($C_{1-4}$)alkyl, when $R_{36}$ is selected from the group consisting of optionally substituted ($C_{3-8}$)cycloalkyl and optionally substituted hetero($C_{3-8}$)cycloalkyl; and $R_{40}$ is selected from the group consisting of dihydrogen, halo, nitro, cyano, ($C_{1-10}$)alkoxy, and ($C_{1-10}$)alkyl.

In a further embodiment, PLK inhibitors of the present invention comprise:

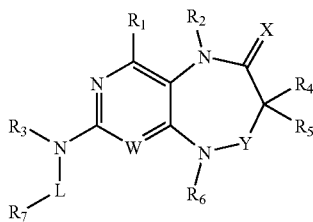

and the pharmaceutically acceptable salts thereof, wherein
W is selected from the group consisting of $CR_8$ and N;
X is selected from the group consisting of $NR_{14}$, O and S;
Y is —$(CR_9R_{10})_n$—;

n is selected from the group consisting of 1, 2, 3 and 4;

L is absent or a linker providing 1, 2, 3, 4, 5 or 6 atom separation between $R_7$ and the nitrogen to which L is attached, wherein the atoms of the linker providing the separation are selected from the group consisting of carbon, oxygen, nitrogen, and sulfur;

$R_1$ is selected from the group consisting of hydrogen, cyano, thio, hydroxy, carbonyloxy, alkoxy, aryloxy, heteroaryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, ($C_{1-10}$)azaalkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_2$ is selected from the group consisting of hydrogen, carbonyl, oxycarbonyl, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, ($C_{1-10}$)azaalkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_2$ and $R_1$ or $R_{14}$ are taken together to form a substituted or unsubstituted ring;

$R_3$ is hydrogen or a substituent convertible in vivo to hydrogen;

$R_4$ is halo;

$R_5$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, ($C_{1-10}$)azaalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_6$ is selected from the group consisting of hydrogen, carbonyl, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, ($C_{1-10}$)azaalkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

R$_7$ is selected from the group consisting of (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted;

R$_8$ is selected from the group consisting of hydrogen, halo, nitro, cyano, thio, oxy, hydroxy, carbonyloxy, alkoxy, aryloxy, heteroaryloxy, carbonyl, oxycarbonyl, amido, amino, (C$_{1-10}$)alkylamino, sulfonamido, imino, sulfonyl, sulfinyl, (C$_{1-10}$)alkyl, halo(C$_{1-10}$)alkyl, hydroxy (C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, (C$_{1-10}$)azaalkyl, imino(C$_{1-3}$)alkyl, (C$_{3-12}$)cycloalkyl(C$_{1-5}$)alkyl, hetero(C$_{3-12}$)cycloalkyl(C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted;

R$_9$ and R$_{10}$ are each independently selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, amido, amino, (C$_{1-10}$)alkylamino, sulfonamido, imino, sulfonyl, sulfinyl, (C$_{1-10}$)alkyl, halo(C$_{1-10}$)alkyl, hydroxy (C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, (C$_{1-10}$)azaalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero (C$_{1-10}$)aryl, (C$_{9-12}$)bicycloaryl and hetero(C$_{4-12}$)bicycloaryl, each substituted or unsubstituted, or R$_9$ and R$_{10}$ are taken together with the carbon to which they are attached to form C=O, C=S, C=NR$_{11}$ or C=CR$_{12}$R$_{13}$;

R$_{11}$ is selected from the group consisting of hydrogen, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted;

R$_{12}$ and R$_{13}$ are each independently selected from the group consisting of hydrogen, halo, nitro, cyano, oxycarbonyl, amido, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, (C$_{1-10}$)oxaalkyl, (C$_{1-10}$)oxoalkyl, imino(C$_{1-10}$)alkyl, (C$_{3-12}$)cycloalkyl(C$_{1-5}$)alkyl, hetero (C$_{3-12}$)cycloalkyl(C$_{1-10}$)alkyl, aryl(C$_{1-10}$)alkyl, hetero (C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero (C$_{1-10}$)aryl, (C$_{9-12}$)bicycloaryl and hetero(C$_{4-12}$)bicycloaryl, each substituted or unsubstituted; and R$_{14}$ is selected from the group consisting of (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, imino(C$_{1-10}$)alkyl, (C$_{3-12}$)cycloalkyl(C$_{1-5}$)alkyl, hetero(C$_{3-12}$)cycloalkyl (C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted, or any two R$_5$, R$_6$, R$_9$ and R$_{10}$ and are taken together to form a substituted or unsubstituted ring.

In another embodiment, PLK inhibitors of the present invention comprise:

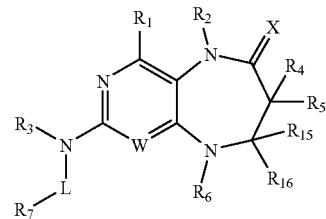

and the pharmaceutically acceptable salts thereof, wherein

R$_{15}$ and R$_{16}$ are each independently selected from the group consisting of hydrogen, cyano, carbonyl, oxycarbonyl, amido, (C$_{1-10}$)alkyl, halo(C$_{1-10}$)alkyl, hydroxy (C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, (C$_{1-10}$)azaalkyl, imino(C$_{1-3}$)alkyl, (C$_{3-12}$)cycloalkyl(C$_{1-5}$)alkyl, hetero(C$_{3-12}$)cycloalkyl(C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted, or R$_{14}$ and R$_{15}$ are taken together with the atom to which they are bound to form a carbonyl or imino group, or any two R$_5$, R$_6$, R$_{15}$ and R$_{16}$ are taken together to form a substituted or unsubstituted ring.

In still another embodiment, PLK inhibitors of the present invention comprise:

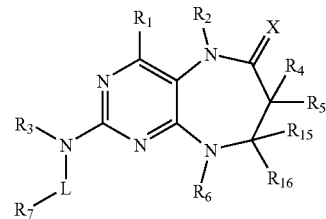

and the pharmaceutically acceptable salts thereof.

In yet another embodiment, PLK inhibitors of the present invention comprise:

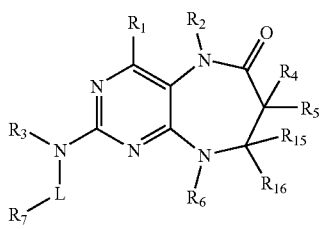

and the pharmaceutically acceptable salts thereof.

In a further embodiment, PLK inhibitors of the present invention comprise:

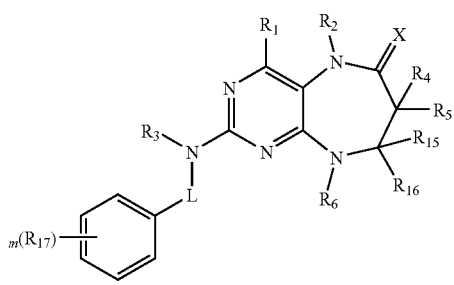

and the pharmaceutically acceptable salts thereof, wherein
m is selected from the group consisting of 0, 1, 2, 3, 4 and 5; and
each $R_{17}$ is independently selected from the group consisting of halo, nitro, cyano, thio, oxy, hydroxy, carbonyloxy, alkoxy, aryloxy, heteroaryloxy, carbamoyloxy, carbonyl, oxycarbonyl, amido, amino, $(C_{1-10})$alkylamino, sulfonamido, carboxyamino, ureido, imino, sulfonyl, aminosulfonyl, sulfinyl, $(C_{1-10})$alkyl, halo$(C_{1-10})$alkyl, hydroxy$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, $(C_{1-10})$azaalkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or two $R_{17}$ are taken together to form a substituted or unsubstituted ring.

In still a further embodiment, PLK inhibitors of the present invention comprise:

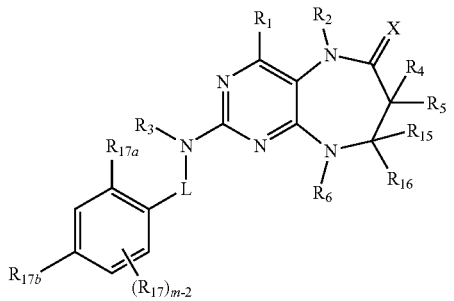

and the pharmaceutically acceptable salts thereof, wherein
m is selected from the group consisting of 2, 3, 4 and 5 (it being understood that m−2 is m as defined here minus 2);
each $R_{17}$ is independently selected from the group consisting of halo, nitro, cyano, thio, oxy, hydroxy, carbonyloxy, alkoxy, aryloxy, heteroaryloxy, carbamoyloxy, carbonyl, oxycarbonyl, amido, amino, $(C_{1-10})$alkylamino, sulfonamido, carboxyamino, ureido, imino, sulfonyl, aminosulfonyl, sulfinyl, $(C_{1-10})$alkyl, halo$(C_{1-10})$alkyl, hydroxy$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, $(C_{1-10})$azaalkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or two $R_{17}$ are taken together to form a substituted or unsubstituted ring; and
$R_{17a}$ and $R_{17b}$ are each independently selected from the group consisting of hydrogen, halo, nitro, cyano, thio, oxy, hydroxy, carbonyloxy, alkoxy, aryloxy, heteroaryloxy, carbamoyloxy, carbonyl, oxycarbonyl, amido, amino, $(C_{1-10})$alkylamino, sulfonamido, carboxyamino, ureido, imino, sulfonyl, aminosulfonyl, sulfinyl, $(C_{1-10})$alkyl, halo$(C_{1-10})$alkyl, hydroxy$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, $(C_{1-10})$azaalkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted.

In yet a further embodiment, PLK inhibitors of the present invention comprise:

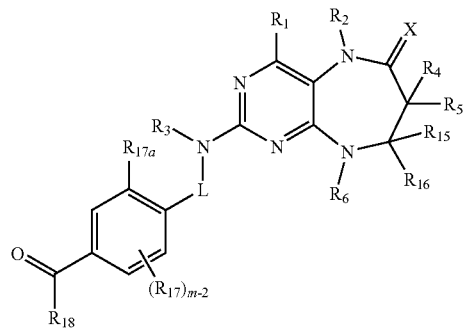

and the pharmaceutically acceptable salts thereof, wherein
m is selected from the group consisting of 2, 3, 4 and 5;
each $R_{17}$ is independently selected from the group consisting of halo, nitro, cyano, thio, oxy, hydroxy, carbonyloxy, alkoxy, aryloxy, heteroaryloxy, carbamoyloxy, carbonyl, oxycarbonyl, amido, amino, $(C_{1-10})$alkylamino, sulfonamido, carboxyamino, ureido, imino, sulfonyl, aminosulfonyl, sulfinyl, $(C_{1-10})$alkyl, halo$(C_{1-10})$alkyl, hydroxy$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, $(C_{1-10})$azaalkyl, imino$(C_{1-3})$alkyl, $(C_{3-12})$cycloalkyl$(C_{1-5})$alkyl, hetero$(C_{3-12})$cycloalkyl$(C_{1-5})$ alkyl, aryl($C_{1-10}$)alkyl, heteroaryl($C_{1-5}$)alkyl, ($C_{9-12}$) bicycloaryl($C_{1-5}$)alkyl, hetero($C_{8-12}$)bicycloaryl($C_{1-5}$) alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$) aryl, hetero($C_{1-10}$)aryl, ($C_{9-12}$)bicycloaryl and hetero ($C_{4-12}$)bicycloaryl, each substituted or unsubstituted, or two $R_{17}$ are taken together to form a substituted or unsubstituted ring; and $R_{17a}$ is selected from the group consisting of hydrogen, halo, nitro, cyano, thio, oxy, hydroxy, carbonyloxy, alkoxy, aryloxy, heteroaryloxy, carbamoyloxy, carbonyl, oxycarbonyl, amido, amino, ($C_{1-10}$)alkylamino, sulfonamido, carboxyamino, ureido, imino, sulfonyl, aminosulfonyl, sulfinyl, ($C_{1-10}$)alkyl, halo($C_{1-10}$)alkyl, hydroxy($C_{1-10}$)alkyl, carbonyl($C_{1-3}$)alkyl, thiocarbonyl ($C_{1-3}$)alkyl, sulfonyl($C_{1-3}$)alkyl, sulfinyl($C_{1-3}$)alkyl, ($C_{1-10}$)azaalkyl, imino($C_{1-3}$)alkyl, ($C_{3-12}$)cycloalkyl ($C_{1-5}$)alkyl, hetero($C_{3-12}$)cycloalkyl($C_{1-5}$)alkyl, aryl ($C_{1-10}$)alkyl, heteroaryl($C_{1-5}$)alkyl, ($C_{9-12}$)bicycloaryl ($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero ($C_{1-10}$)aryl, ($C_{9-12}$)bicycloaryl and hetero($C_{4-12}$)bicycloaryl, each substituted or unsubstituted; and $R_{18}$ is selected from the group consisting of hydrogen, hydroxy, carbonyloxy, alkoxy, aryloxy, heteroaryloxy, carbonyl, oxycarbonyl, amido, amino, ($C_{1-10}$)alkylamino, sulfonamido, imino, sulfonyl, sulfinyl, ($C_{1-10}$) alkyl, halo($C_{1-10}$)alkyl, hydroxy($C_{1-10}$)alkyl, carbonyl ($C_{1-3}$)alkyl, thiocarbonyl($C_{1-3}$)alkyl, sulfonyl($C_{1-3}$) alkyl, sulfinyl($C_{1-3}$)alkyl, ($C_{1-10}$)azaalkyl, imino($C_{1-3}$) alkyl, ($C_{3-12}$)cycloalkyl($C_{1-5}$)alkyl, hetero($C_{3-12}$) cycloalkyl($C_{1-5}$)alkyl, aryl($C_{1-10}$)alkyl, heteroaryl ($C_{1-5}$)alkyl, ($C_{9-12}$)bicycloaryl($C_{1-5}$)alkyl, hetero ($C_{8-12}$)bicycloaryl($C_{1-5}$)alkyl, ($C_{3-12}$)cycloalkyl, hetero ($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted.

In yet a further embodiment, PLK inhibitors of the present invention comprise:

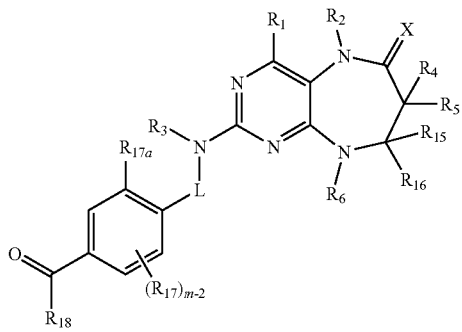

and the pharmaceutically acceptable salts thereof, wherein
X is O;
L is absent;
m is selected from the group consisting of 2 and 3;
$R_{17}$ is halo; and
$R_{17a}$ is selected from the group consisting of hydrogen, halo, and optionally substituted alkoxy; and
$R_{18}$ is amino.

In yet a further embodiment, PLK inhibitors of the present invention comprise:

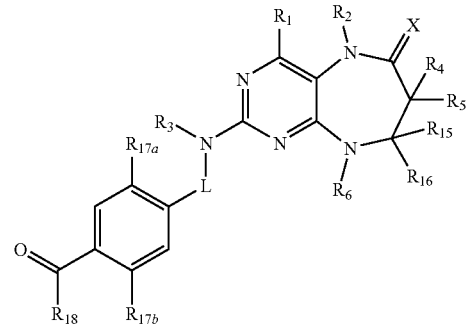

and the pharmaceutically acceptable salts thereof, wherein
X is O;
L is absent;
$R_{17a}$ is selected from the group consisting of hydrogen, halo, and optionally substituted alkoxy;
$R_{17b}$ is selected from the group consisting of hydrogen and halo; and
$R_{18}$ is amino.

In another embodiment, PLK inhibitors of the present invention comprise:

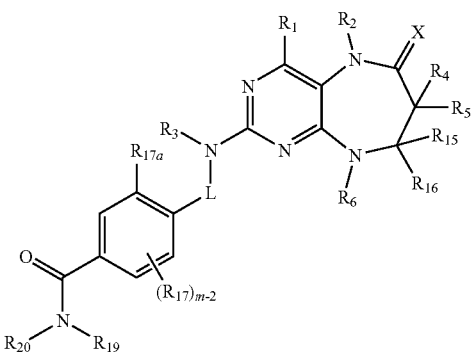

and the pharmaceutically acceptable salts thereof, wherein
m is selected from the group consisting of 2, 3, 4 and 5;
each $R_{17}$ is independently selected from the group consisting of halo, nitro, cyano, thio, oxy, hydroxy, carbonyloxy, alkoxy, aryloxy, heteroaryloxy, carbamoyloxy, carbonyl, oxycarbonyl, amido, amino, ($C_{1-10}$)alkylamino, sulfonamido, carboxyamino, ureido, imino, sulfonyl, aminosulfonyl, sulfinyl, ($C_{1-10}$)alkyl, halo($C_{1-10}$) alkyl, hydroxy($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, ($C_{1-10}$)azaalkyl, imino($C_{1-3}$)alkyl, ($C_{3-12}$) cycloalkyl($C_{1-5}$)alkyl, hetero($C_{3-12}$)cycloalkyl($C_{1-5}$) alkyl, aryl($C_{1-10}$)alkyl, heteroaryl($C_{1-5}$)alkyl, ($C_{9-12}$) bicycloaryl($C_{1-5}$)alkyl, hetero($C_{8-12}$)bicycloaryl($C_{1-5}$) alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$) aryl, hetero($C_{1-10}$)aryl, ($C_{9-12}$)bicycloaryl and hetero ($C_{4-12}$)bicycloaryl, each substituted or unsubstituted, or two $R_{17}$ are taken together to form a substituted or unsubstituted ring; and $R_{17a}$ is selected from the group consisting of hydrogen, halo, nitro, cyano, thio, oxy, hydroxy, carbonyloxy, alkoxy, aryloxy, heteroaryloxy, carbamoyloxy, carbonyl, oxycarbonyl, amido, amino, ($C_{1-10}$)alkylamino, sulfonamido, carboxyamino, ureido, imino, sulfonyl, aminosulfonyl, sulfinyl, $(C_{1-10})$alkyl, halo$(C_{1-10})$alkyl, hydroxy$(C_{1-10})$alkyl, carbonyl$(C_{1-3})$alkyl, thiocarbonyl $(C_{1-3})$alkyl, sulfonyl$(C_{1-3})$alkyl, sulfinyl$(C_{1-3})$alkyl, $(C_{1-10})$azaalkyl, imino$(C_{1-3})$alkyl, $(C_{3-12})$cycloalkyl $(C_{1-5})$alkyl, hetero$(C_{3-12})$cycloalkyl$(C_{1-5})$alkyl, aryl $(C_{1-10})$alkyl, heteroaryl$(C_{1-5})$alkyl, $(C_{9-12})$bicycloaryl $(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted; and $R_{19}$ are $R_{20}$ are each independently selected from the group consisting of hydrogen, oxy, hydroxy, carbonyloxy, alkoxy, aryloxy, heteroaryloxy, carbonyl, oxycarbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, $(C_{1-10})$azaalkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_{19}$ and $R_{20}$ are taken together to form a substituted or unsubstituted ring, or $R_{19}$ is a substituent convertible in vivo into hydroxy.

In still another embodiment, PLK inhibitors of the present invention comprise:

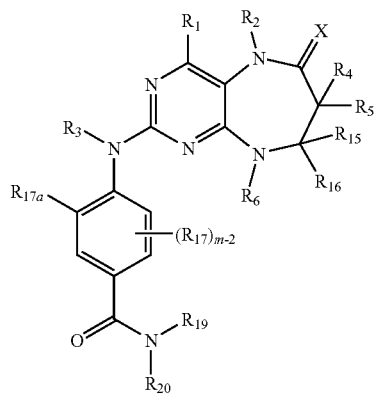

and the pharmaceutically acceptable salts thereof, wherein m is selected from the group consisting of 2, 3, 4 and 5; each $R_{17}$ is independently selected from the group consisting of halo, nitro, cyano, thio, oxy, hydroxy, carbonyloxy, alkoxy, aryloxy, heteroaryloxy, carbamoyloxy, carbonyl, oxycarbonyl, amido, amino, $(C_{1-10})$alkylamino, sulfonamido, carboxyamino, ureido, imino, sulfonyl, aminosulfonyl, sulfinyl, $(C_{1-10})$alkyl, halo$(C_{1-10})$alkyl, hydroxy$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, $(C_{1-10})$azaalkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or two $R_{17}$ are taken together to form a substituted or unsubstituted ring; and $R_{17a}$ is selected from the group consisting of hydrogen, halo, nitro, cyano, thio, oxy, hydroxy, carbonyloxy, alkoxy, aryloxy, heteroaryloxy, carbamoyloxy, carbonyl, oxycarbonyl, amido, amino, $(C_{1-10})$alkylamino, sulfonamido, carboxyamino, ureido, imino, sulfonyl, aminosulfonyl, sulfinyl, $(C_{1-10})$alkyl, halo$(C_{1-10})$alkyl, hydroxy$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, $(C_{1-10})$azaalkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted; and $R_{19}$ are $R_{20}$ are each independently selected from the group consisting of hydrogen, oxy, hydroxy, carbonyloxy, alkoxy, aryloxy, heteroaryloxy, carbonyl, oxycarbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, $(C_{1-10})$azaalkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_{19}$ and $R_{20}$ are taken together to form a substituted or unsubstituted ring, or $R_{19}$ is a substituent convertible in vivo into hydroxy.

In yet another embodiment, PLK inhibitors of the present invention comprise:

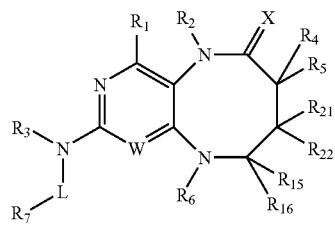

and the pharmaceutically acceptable salts thereof, wherein $R_{15}$ and $R_{16}$ are each independently selected from the group consisting of hydrogen, cyano, carbonyl, oxycarbonyl, amido, $(C_{1-10})$alkyl, halo$(C_{1-10})$alkyl, hydroxy$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, $(C_{1-10})$azaalkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_{15}$ and $R_{16}$ are taken together with the atom to which they are bound to form a carbonyl or imino group; and $R_{21}$ and $R_{22}$ are each independently selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or any two $R_5$, $R_6$, $R_{15}$, $R_{16}$, $R_{21}$ and $R_{22}$ are taken together to form a substituted or unsubstituted ring.

In a further embodiment, PLK inhibitors of the present invention comprise:

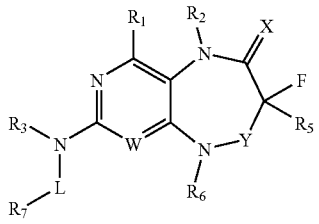

and the pharmaceutically acceptable salts thereof.

In still a further embodiment, PLK inhibitors of the present invention comprise:

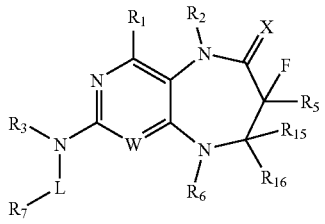

and the pharmaceutically acceptable salts thereof, wherein $R_{15}$ and $R_{16}$ are each independently selected from the group consisting of hydrogen, cyano, carbonyl, oxycarbonyl, amido, $(C_{1-10})$alkyl, halo$(C_{1-10})$alkyl, hydroxy$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, $(C_{1-10})$azaalkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_{15}$ and $R_{16}$ are taken together with the atom to which they are bound to form a carbonyl or imino group, or any two $R_5$, $R_6$, $R_{15}$ and $R_{16}$ are taken together to form a substituted or unsubstituted ring.

In yet a further embodiment, PLK inhibitors of the present invention comprise:

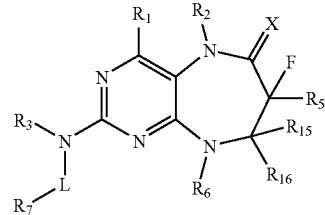

and the pharmaceutically acceptable salts thereof.

In another embodiment, PLK inhibitors of the present invention comprise:

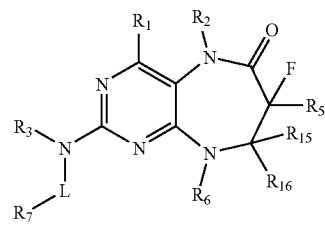

and the pharmaceutically acceptable salts thereof.

In still another embodiment, PLK inhibitors of the present invention comprise:

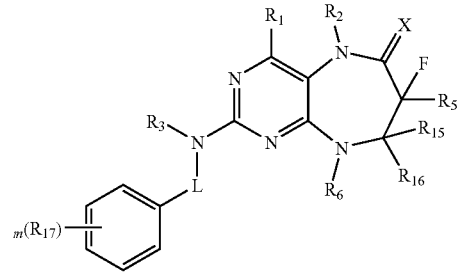

and the pharmaceutically acceptable salts thereof, wherein m is selected from the group consisting of 0, 1, 2, 3, 4 and 5; and each $R_{17}$ is independently selected from the group consisting of halo, nitro, cyano, thio, oxy, hydroxy, carbonyloxy, alkoxy, aryloxy, heteroaryloxy, carbamoyloxy, carbonyl, oxycarbonyl, amido, amino, $(C_{1-10})$alkylamino, sulfonamido, carboxyamino, ureido, imino, sulfonyl, aminosulfonyl, sulfinyl, $(C_{1-10})$alkyl, halo$(C_{1-10})$alkyl, hydroxy$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, $(C_{1-10})$azaalkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or two $R_{17}$ are taken together to form a substituted or unsubstituted ring.

In yet another embodiment, PLK inhibitors of the present invention comprise:

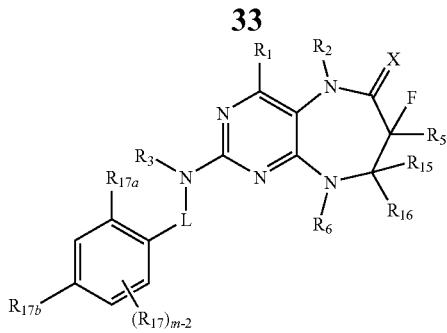

and the pharmaceutically acceptable salts thereof, wherein
m is selected from the group consisting of 2, 3, 4 and 5;
each $R_{17}$ is independently selected from the group consisting of halo, nitro, cyano, thio, oxy, hydroxy, carbonyloxy, alkoxy, aryloxy, heteroaryloxy, carbamoyloxy, carbonyl, oxycarbonyl, amido, amino, $(C_{1-10})$alkylamino, sulfonamido, carboxyamino, ureido, imino, sulfonyl, aminosulfonyl, sulfinyl, $(C_{1-10})$alkyl, halo$(C_{1-10})$alkyl, hydroxy$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, $(C_{1-10})$azaalkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or two $R_{17}$ are taken together to form a substituted or unsubstituted ring; and $R_{17a}$ and $R_{17b}$ are each independently selected from the group consisting of hydrogen, halo, nitro, cyano, thio, oxy, hydroxy, carbonyloxy, alkoxy, aryloxy, heteroaryloxy, carbamoyloxy, carbonyl, oxycarbonyl, amido, amino, $(C_{1-10})$alkylamino, sulfonamido, carboxyamino, ureido, imino, sulfonyl, aminosulfonyl, sulfinyl, $(C_{1-10})$alkyl, halo$(C_{1-10})$alkyl, hydroxy$(C_{1-10})$alkyl, carbonyl $(C_{1-3})$alkyl, thiocarbonyl$(C_{1-3})$alkyl, sulfonyl$(C_{1-3})$ alkyl, sulfinyl$(C_{1-3})$alkyl, $(C_{1-10})$azaalkyl, imino$(C_{1-3})$ alkyl, $(C_{3-12})$cycloalkyl$(C_{1-5})$alkyl, hetero$(C_{3-12})$ cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero $(C_{8-12})$bicycloaryl$(C_{1-5})$alkyl, $(C_{3-12})$cycloalkyl, hetero $(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted.

In a further embodiment, PLK inhibitors of the present invention comprise:

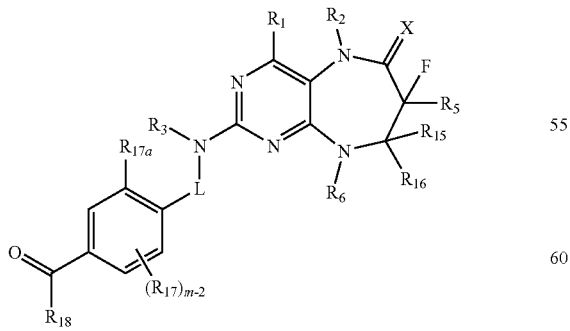

and the pharmaceutically acceptable salts thereof, wherein
m is selected from the group consisting of 2, 3, 4 and 5;
each $R_{17}$ is independently selected from the group consisting of halo, nitro, cyano, thio, oxy, hydroxy, carbonyloxy, alkoxy, aryloxy, heteroaryloxy, carbamoyloxy, carbonyl, oxycarbonyl, amido, amino, $(C_{1-10})$alkylamino, sulfonamido, carboxyamino, ureido, imino, sulfonyl, aminosulfonyl, sulfinyl, $(C_{1-10})$alkyl, halo$(C_{1-10})$ alkyl, hydroxy$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, $(C_{1-10})$azaalkyl, imino$(C_{1-3})$alkyl, $(C_{3-12})$ cycloalkyl$(C_{1-5})$alkyl, hetero$(C_{3-12})$cycloalkyl$(C_{1-5})$ alkyl, aryl$(C_{1-10})$alkyl, heteroaryl$(C_{1-5})$alkyl, $(C_{9-12})$ bicycloaryl$(C_{1-5})$alkyl, hetero$(C_{8-12})$bicycloaryl$(C_{1-5})$ alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$ aryl, hetero$(C_{1-10})$aryl, $(C_{9-12})$bicycloaryl and hetero $(C_{4-12})$bicycloaryl, each substituted or unsubstituted, or two $R_{17}$ are taken together to form a substituted or unsubstituted ring; and $R_{17a}$ is selected from the group consisting of hydrogen, halo, nitro, cyano, thio, oxy, hydroxy, carbonyloxy, alkoxy, aryloxy, heteroaryloxy, carbamoyloxy, carbonyl, oxycarbonyl, amido, amino, $(C_{1-10})$alkylamino, sulfonamido, carboxyamino, ureido, imino, sulfonyl, aminosulfonyl, sulfinyl, $(C_{1-10})$alkyl, halo$(C_{1-10})$alkyl, hydroxy$(C_{1-10})$alkyl, carbonyl$(C_{1-3})$alkyl, thiocarbonyl $(C_{1-3})$alkyl, sulfonyl$(C_{1-3})$alkyl, sulfinyl$(C_{1-3})$alkyl, $(C_{1-10})$azaalkyl, imino$(C_{1-3})$alkyl, $(C_{3-12})$cycloalkyl $(C_{1-5})$alkyl, hetero$(C_{3-12})$cycloalkyl$(C_{1-5})$alkyl, aryl $(C_{1-10})$alkyl, heteroaryl$(C_{1-5})$alkyl, $(C_{9-12})$bicycloaryl $(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero $(C_{1-10})$aryl, $(C_{9-12})$bicycloaryl and hetero$(C_{4-12})$bicycloaryl, each substituted or unsubstituted; and $R_{18}$ is selected from the group consisting of hydrogen, hydroxy, carbonyloxy, alkoxy, aryloxy, heteroaryloxy, carbonyl, oxycarbonyl, amido, amino, $(C_{1-10})$alkylamino, sulfonamido, imino, sulfonyl, sulfinyl, $(C_{1-10})$ alkyl, halo$(C_{1-10})$alkyl, hydroxy$(C_{1-10})$alkyl, carbonyl $(C_{1-3})$alkyl, thiocarbonyl$(C_{1-3})$alkyl, sulfonyl$(C_{1-3})$ alkyl, sulfinyl$(C_{1-3})$alkyl, $(C_{1-10})$azaalkyl, imino$(C_{1-3})$ alkyl, $(C_{3-12})$cycloalkyl$(C_{1-5})$alkyl, hetero$(C_{3-12})$ cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero $(C_{8-12})$bicycloaryl$(C_{1-5})$alkyl, $(C_{3-12})$cycloalkyl, hetero $(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted.

In still a further embodiment, PLK inhibitors of the present invention comprise:

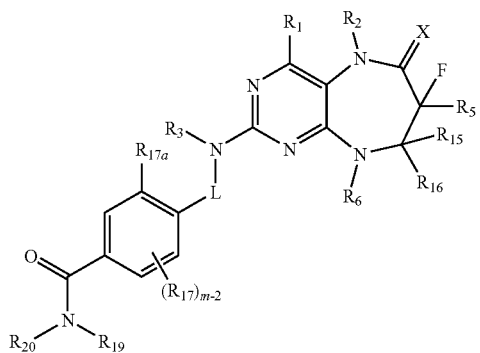

and the pharmaceutically acceptable salts thereof, wherein m is selected from the group consisting of 2, 3, 4 and 5;

each $R_{17}$ is independently selected from the group consisting of halo, nitro, cyano, thio, oxy, hydroxy, carbonyloxy, alkoxy, aryloxy, heteroaryloxy, carbamoyloxy, carbonyl, oxycarbonyl, amido, amino, $(C_{1-10})$alkylamino, sulfonamido, carboxyamino, ureido, imino, sulfonyl, aminosulfonyl, sulfinyl, $(C_{1-10})$alkyl, halo$(C_{1-10})$alkyl, hydroxy$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, $(C_{1-10})$azaalkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or two $R_{17}$ are taken together to form a substituted or unsubstituted ring; and $R_{17a}$ is selected from the group consisting of hydrogen, halo, nitro, cyano, thio, oxy, hydroxy, carbonyloxy, alkoxy, aryloxy, heteroaryloxy, carbamoyloxy, carbonyl, oxycarbonyl, amido, amino, $(C_{1-10})$alkylamino, sulfonamido, carboxyamino, ureido, imino, sulfonyl, aminosulfonyl, sulfinyl, $(C_{1-10})$alkyl, halo$(C_{1-10})$alkyl, hydroxy$(C_{1-10})$alkyl, carbonyl$(C_{1-3})$alkyl, thiocarbonyl $(C_{1-3})$alkyl, sulfonyl$(C_{1-3})$alkyl, sulfinyl$(C_{1-3})$alkyl, $(C_{1-10})$azaalkyl, imino$(C_{1-3})$alkyl, $(C_{3-12})$cycloalkyl $(C_{1-5})$alkyl, hetero$(C_{3-12})$cycloalkyl$(C_{1-5})$alkyl, aryl $(C_{1-10})$alkyl, heteroaryl$(C_{1-5})$alkyl, $(C_{9-12})$bicycloaryl $(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero $(C_{1-10})$aryl, $(C_{9-12})$bicycloaryl and hetero$(C_{4-12})$bicycloaryl, each substituted or unsubstituted; and $R_{19}$ are $R_{20}$ are each independently selected from the group consisting of hydrogen, oxy, hydroxy, carbonyloxy, alkoxy, aryloxy, heteroaryloxy, carbonyl, oxycarbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$alkyl, sulfinyl$(C_{1-3})$alkyl, $(C_{1-10})$azaalkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero $(C_{8-12})$bicycloaryl$(C_{1-5})$alkyl, $(C_{3-12})$cycloalkyl, hetero $(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_{19}$ and $R_{20}$ are taken together to form a substituted or unsubstituted ring, or $R_{19}$ is a substituent convertible in vivo into hydroxy.

In yet a further embodiment, PLK inhibitors of the present invention comprise:

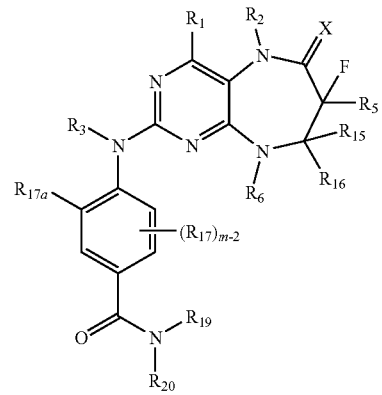

and the pharmaceutically acceptable salts thereof, wherein m is selected from the group consisting of 2, 3, 4 and 5;

each $R_{17}$ is independently selected from the group consisting of halo, nitro, cyano, thio, oxy, hydroxy, carbonyloxy, alkoxy, aryloxy, heteroaryloxy, carbamoyloxy, carbonyl, oxycarbonyl, amido, amino, $(C_{1-10})$alkylamino, sulfonamido, carboxyamino, ureido, imino, sulfonyl, aminosulfonyl, sulfinyl, $(C_{1-10})$alkyl, halo$(C_{1-10})$alkyl, hydroxy$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, $(C_{1-10})$azaalkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero $(C_{4-12})$bicycloaryl, each substituted or unsubstituted, or two $R_{17}$ are taken together to form a substituted or unsubstituted ring; and $R_{17a}$ is selected from the group consisting of hydrogen, halo, nitro, cyano, thio, oxy, hydroxy, carbonyloxy, alkoxy, aryloxy, heteroaryloxy, carbamoyloxy, carbonyl, oxycarbonyl, amido, amino, $(C_{1-10})$alkylamino, sulfonamido, carboxyamino, ureido, imino, sulfonyl, aminosulfonyl, sulfinyl, $(C_{1-10})$alkyl, halo$(C_{1-10})$alkyl, hydroxy$(C_{1-10})$alkyl, carbonyl$(C_{1-3})$alkyl, thiocarbonyl $(C_{1-3})$alkyl, sulfonyl$(C_{1-3})$alkyl, sulfinyl$(C_{1-3})$alkyl, $(C_{1-10})$azaalkyl, imino$(C_{1-3})$alkyl, $(C_{3-12})$cycloalkyl $(C_{1-5})$alkyl, hetero$(C_{3-12})$cycloalkyl$(C_{1-5})$alkyl, aryl $(C_{1-10})$alkyl, heteroaryl$(C_{1-5})$alkyl, $(C_{9-12})$bicycloaryl $(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero $(C_{1-10})$aryl, $(C_{9-12})$bicycloaryl and hetero$(C_{4-12})$bicycloaryl, each substituted or unsubstituted; and $R_{19}$ are $R_{20}$ are each independently selected from the group consisting of hydrogen, oxy, hydroxy, carbonyloxy, alkoxy, aryloxy, heteroaryloxy, carbonyl, oxycarbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$alkyl, sulfinyl$(C_{1-3})$alkyl, $(C_{1-10})$azaalkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero $(C_{8-12})$bicycloaryl$(C_{1-5})$alkyl, $(C_{3-12})$cycloalkyl, hetero $(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero($C_{4-12}$)bicycloaryl, each substituted or unsubstituted, or $R_{19}$ and $R_{20}$ are taken together to form a substituted or unsubstituted ring, or $R_{19}$ is a substituent convertible in vivo into hydroxy.

In another embodiment, PLK inhibitors of the present invention comprise:

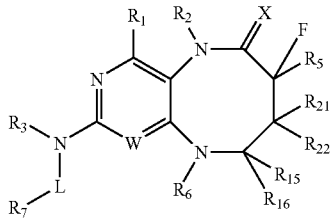

and the pharmaceutically acceptable salts thereof, wherein $R_{15}$ and $R_{16}$ are each independently selected from the group consisting of hydrogen, cyano, carbonyl, oxycarbonyl, amido, ($C_{1-10}$)alkyl, halo($C_{1-10}$)alkyl, hydroxy ($C_{1-10}$)alkyl, carbonyl($C_{1-3}$)alkyl, thiocarbonyl($C_{1-3}$) alkyl, sulfonyl($C_{1-3}$)alkyl, sulfinyl($C_{1-3}$)alkyl, ($C_{1-10}$) azaalkyl, imino($C_{1-3}$)alkyl, ($C_{3-12}$)cycloalkyl($C_{1-5}$) alkyl, hetero($C_{3-12}$)cycloalkyl($C_{1-5}$)alkyl, aryl($C_{1-10}$) alkyl, heteroaryl($C_{1-5}$)alkyl, ($C_{9-12}$)bicycloaryl($C_{1-5}$) alkyl, hetero($C_{8-12}$)bicycloaryl($C_{1-5}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$) bicycloaryl, each substituted or unsubstituted, or $R_{15}$ and $R_{16}$ are taken together with the atom to which they are bound to form a carbonyl or imino group; and $R_{21}$ and $R_{22}$ are each independently selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$) alkyl, ($C_{1-10}$)azaalkyl, imino($C_{1-10}$)alkyl, ($C_{3-12}$)cycloalkyl($C_{1-5}$)alkyl, hetero($C_{3-12}$)cycloalkyl($C_{1-10}$) alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl ($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$) aryl, hetero($C_{1-10}$)aryl, ($C_{9-12}$)bicycloaryl and hetero ($C_{4-12}$)bicycloaryl, each substituted or unsubstituted, or any two $R_5$, $R_6$, $R_{15}$, $R_{16}$, $R_{21}$ and $R_{22}$ are taken together to form a substituted or unsubstituted ring.

In still another embodiment, PLK inhibitors of the present invention comprise:

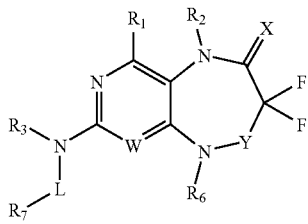

and the pharmaceutically acceptable salts thereof.

In yet another embodiment, PLK inhibitors of the present invention comprise:

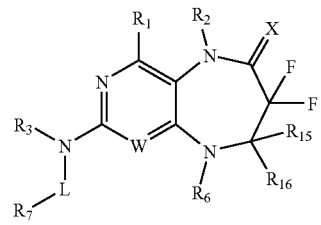

and the pharmaceutically acceptable salts thereof, wherein $R_{15}$ and $R_{16}$ are each independently selected from the group consisting of hydrogen, cyano, carbonyl, oxycarbonyl, amido, ($C_{1-10}$)alkyl, halo($C_{1-10}$)alkyl, hydroxy ($C_{1-10}$)alkyl, carbonyl($C_{1-3}$)alkyl, thiocarbonyl($C_{1-3}$) alkyl, sulfonyl($C_{1-3}$)alkyl, sulfinyl($C_{1-3}$)alkyl, ($C_{1-10}$) azaalkyl, imino($C_{1-3}$)alkyl, ($C_{3-12}$)cycloalkyl($C_{1-5}$) alkyl, hetero($C_{3-12}$)cycloalkyl($C_{1-5}$)alkyl, aryl($C_{1-10}$) alkyl, heteroaryl($C_{1-5}$)alkyl, ($C_{9-12}$)bicycloaryl($C_{1-5}$) alkyl, hetero($C_{8-12}$)bicycloaryl($C_{1-5}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$) bicycloaryl, each substituted or unsubstituted, or $R_{15}$ and $R_{16}$ are taken together with the atom to which they are bound to form a carbonyl or imino group, or any two $R_6$, $R_{15}$ and $R_{16}$ are taken together to form a substituted or unsubstituted ring.

In a further embodiment, PLK inhibitors of the present invention comprise:

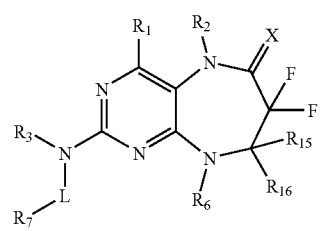

and the pharmaceutically acceptable salts thereof.

In still a further embodiment, PLK inhibitors of the present invention comprise:

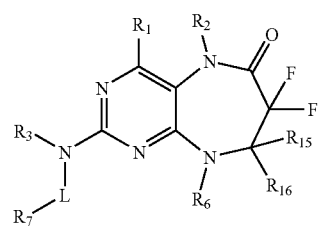

and the pharmaceutically acceptable salts thereof.

In yet a further embodiment, PLK inhibitors of the present invention comprise:

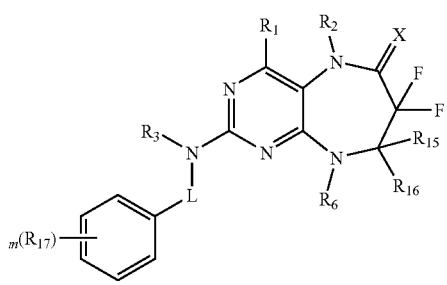

and the pharmaceutically acceptable salts thereof, wherein m is selected from the group consisting of 0, 1, 2, 3, 4 and 5; and each $R_{17}$ is independently selected from the group consisting of halo, nitro, cyano, thio, oxy, hydroxy, carbonyloxy, alkoxy, aryloxy, heteroaryloxy, carbamoyloxy, carbonyl, oxycarbonyl, amido, amino, $(C_{1-10})$alkylamino, sulfonamido, carboxyamino, ureido, imino, sulfonyl, aminosulfonyl, sulfinyl, $(C_{1-10})$alkyl, halo$(C_{1-10})$alkyl, hydroxy$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, $(C_{1-10})$azaalkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or two $R_{17}$ are taken together to form a substituted or unsubstituted ring.

In another embodiment, PLK inhibitors of the present invention comprise:

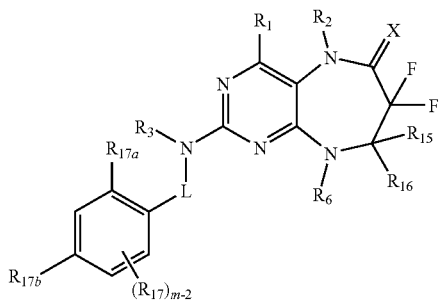

and the pharmaceutically acceptable salts thereof, wherein m is selected from the group consisting of 2, 3, 4 and 5;

each $R_{17}$ is independently selected from the group consisting of halo, nitro, cyano, thio, oxy, hydroxy, carbonyloxy, alkoxy, aryloxy, heteroaryloxy, carbamoyloxy, carbonyl, oxycarbonyl, amido, amino, $(C_{1-10})$alkylamino, sulfonamido, carboxyamino, ureido, imino, sulfonyl, aminosulfonyl, sulfinyl, $(C_{1-10})$alkyl, halo$(C_{1-10})$alkyl, hydroxy$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, $(C_{1-10})$azaalkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or two $R_{17}$ are taken together to form a substituted or unsubstituted ring; and $R_{17a}$ and $R_{17b}$ are each independently selected from the group consisting of hydrogen, halo, nitro, cyano, thio, oxy, hydroxy, carbonyloxy, alkoxy, aryloxy, heteroaryloxy, carbamoyloxy, carbonyl, oxycarbonyl, amido, amino, $(C_{1-10})$alkylamino, sulfonamido, carboxyamino, ureido, imino, sulfonyl, aminosulfonyl, sulfinyl, $(C_{1-10})$alkyl, halo$(C_{1-10})$alkyl, hydroxy$(C_{1-10})$alkyl, carbonyl $(C_{1-3})$alkyl, thiocarbonyl$(C_{1-3})$alkyl, sulfonyl$(C_{1-3})$alkyl, sulfinyl$(C_{1-3})$alkyl, $(C_{1-10})$azaalkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero $(C_{8-12})$bicycloaryl$(C_{1-5})$alkyl, $(C_{3-12})$cycloalkyl, hetero $(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted.

In still another embodiment, PLK inhibitors of the present invention comprise:

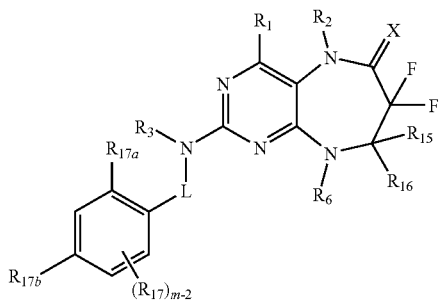

and the pharmaceutically acceptable salts thereof, wherein m is selected from the group consisting of 2, 3, 4 and 5;

each $R_{17}$ is independently selected from the group consisting of halo, nitro, cyano, thio, oxy, hydroxy, carbonyloxy, alkoxy, aryloxy, heteroaryloxy, carbamoyloxy, carbonyl, oxycarbonyl, amido, amino, $(C_{1-10})$alkylamino, sulfonamido, carboxyamino, ureido, imino, sulfonyl, aminosulfonyl, sulfinyl, $(C_{1-10})$alkyl, halo$(C_{1-10})$alkyl, hydroxy$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, $(C_{1-10})$azaalkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or two $R_{17}$ are taken together to form a substituted or unsubstituted ring; and $R_{17a}$ is selected from the group consisting of hydrogen, halo, nitro, cyano, thio, oxy, hydroxy, carbonyloxy, alkoxy, aryloxy, heteroaryloxy, carbamoyloxy, carbonyl, oxycarbonyl, amido, amino, $(C_{1-10})$alkylamino, sulfonamido, carboxyamino, ureido, imino, sulfonyl, aminosulfonyl, sulfinyl, $(C_{1-10})$alkyl, halo$(C_{1-10})$alkyl, hydroxy$(C_{1-10})$alkyl, carbonyl$(C_{1-3})$alkyl, thiocarbonyl $(C_{1-3})$alkyl, sulfonyl$(C_{1-3})$alkyl, sulfinyl$(C_{1-3})$alkyl, ($C_{1-10}$)azaalkyl, imino($C_{1-3}$)alkyl, ($C_{3-12}$)cycloalkyl ($C_{1-5}$)alkyl, hetero($C_{3-12}$)cycloalkyl($C_{1-5}$)alkyl, aryl ($C_{1-10}$)alkyl, heteroaryl($C_{1-5}$)alkyl, ($C_{9-12}$)bicycloaryl ($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero ($C_{1-10}$)aryl, ($C_{9-12}$)bicycloaryl and hetero($C_{4-12}$)bicycloaryl, each substituted or unsubstituted; and $R_{18}$ is selected from the group consisting of hydrogen, hydroxy, carbonyloxy, alkoxy, aryloxy, heteroaryloxy, carbonyl, oxycarbonyl, amido, amino, ($C_{1-10}$)alkylamino, sulfonamido, imino, sulfonyl, sulfinyl, ($C_{1-10}$) alkyl, halo($C_{1-10}$)alkyl, hydroxy($C_{1-10}$)alkyl, carbonyl ($C_{1-3}$)alkyl, thiocarbonyl($C_{1-3}$)alkyl, sulfonyl($C_{1-3}$) alkyl, sulfinyl($C_{1-3}$)alkyl, ($C_{1-10}$)azaalkyl, imino($C_{1-3}$) alkyl, ($C_{3-12}$)cycloalkyl($C_{1-5}$)alkyl, hetero($C_{3-12}$) cycloalkyl($C_{1-5}$)alkyl, aryl($C_{1-10}$)alkyl, heteroaryl ($C_{1-5}$)alkyl, ($C_{9-12}$)bicycloaryl($C_{1-5}$)alkyl, hetero ($C_{8-12}$)bicycloaryl($C_{1-5}$)alkyl, ($C_{3-12}$)cycloalkyl, hetero ($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted.

In still another embodiment, PLK inhibitors of the present invention comprise:

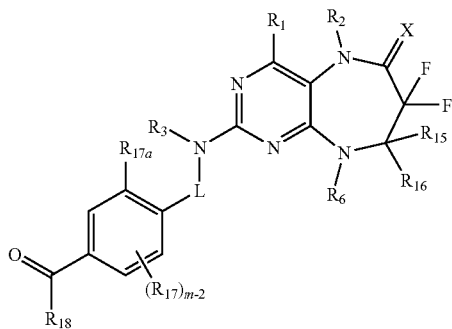

and the pharmaceutically acceptable salts thereof, wherein m is selected from the group consisting of 2 and 3;

$R_{17}$ is halo; and $R_{17a}$ is selected from the group consisting of hydrogen, halo, and optionally substituted alkoxy; and $R_{18}$ is amino.

In still another embodiment, PLK inhibitors of the present invention comprise:

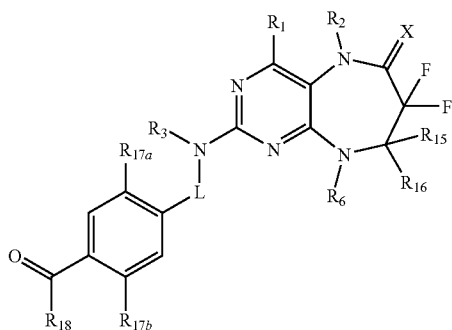

and the pharmaceutically acceptable salts thereof, wherein X is O;

L is absent;

$R_{17a}$ is selected from the group consisting of hydrogen, halo, and optionally substituted alkoxy;

$R_{17b}$ is selected from the group consisting of hydrogen and halo; and $R_{18}$ is amino.

In yet another embodiment, PLK inhibitors of the present invention comprise:

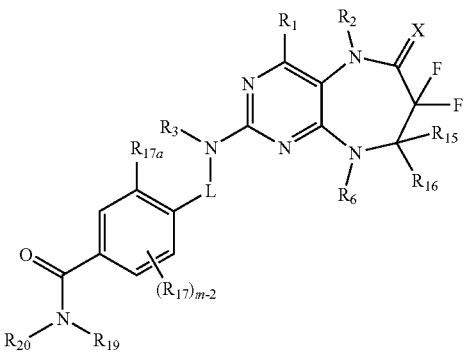

and the pharmaceutically acceptable salts thereof, wherein m is selected from the group consisting of 2, 3, 4 and 5;

each $R_{17}$ is independently selected from the group consisting of halo, nitro, cyano, thio, oxy, hydroxy, carbonyloxy, alkoxy, aryloxy, heteroaryloxy, carbamoyloxy, carbonyl, oxycarbonyl, amido, amino, ($C_{1-10}$)alkylamino, sulfonamido, carboxyamino, ureido, imino, sulfonyl, aminosulfonyl, sulfinyl, ($C_{1-10}$)alkyl, halo($C_{1-10}$) alkyl, hydroxy($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, ($C_{1-10}$)azaalkyl, imino($C_{1-3}$)alkyl, ($C_{3-12}$) cycloalkyl($C_{1-5}$)alkyl, hetero($C_{3-12}$)cycloalkyl($C_{1-5}$) alkyl, aryl($C_{1-10}$)alkyl, heteroaryl($C_{1-5}$)alkyl, ($C_{9-12}$) bicycloaryl($C_{1-5}$)alkyl, hetero($C_{8-12}$)bicycloaryl($C_{1-5}$) alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$) aryl, hetero($C_{1-10}$)aryl, ($C_{9-12}$)bicycloaryl and hetero ($C_{4-12}$)bicycloaryl, each substituted or unsubstituted, or two $R_{17}$ are taken together to form a substituted or unsubstituted ring; and $R_{17a}$ is selected from the group consisting of hydrogen, halo, nitro, cyano, thio, oxy, hydroxy, carbonyloxy, alkoxy, aryloxy, heteroaryloxy, carbamoyloxy, carbonyl, oxycarbonyl, amido, amino, ($C_{1-10}$)alkylamino, sulfonamido, carboxyamino, ureido, imino, sulfonyl, aminosulfonyl, sulfinyl, ($C_{1-10}$)alkyl, halo($C_{1-10}$)alkyl, hydroxy($C_{1-10}$)alkyl, carbonyl($C_{1-3}$)alkyl, thiocarbonyl ($C_{1-3}$)alkyl, sulfonyl($C_{1-3}$)alkyl, sulfinyl($C_{1-3}$)alkyl, ($C_{1-10}$)azaalkyl, imino($C_{1-3}$)alkyl, ($C_{3-12}$)cycloalkyl ($C_{1-5}$)alkyl, hetero($C_{3-12}$)cycloalkyl($C_{1-5}$)alkyl, aryl ($C_{1-10}$)alkyl, heteroaryl($C_{1-5}$)alkyl, ($C_{9-12}$)bicycloaryl ($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero ($C_{1-10}$)aryl, ($C_{9-12}$)bicycloaryl and hetero($C_{4-12}$)bicycloaryl, each substituted or unsubstituted; and $R_{19}$ are $R_{20}$ are each independently selected from the group consisting of hydrogen, oxy, hydroxy, carbonyloxy, alkoxy, aryloxy, heteroaryloxy, carbonyl, oxycarbonyl, amino, ($C_{1-10}$)alkylamino, sulfonamido, imino, sulfonyl, sulfinyl, ($C_{1-10}$)alkyl, halo($C_{1-10}$)alkyl, carbonyl ($C_{1-3}$)alkyl, thiocarbonyl($C_{1-3}$)alkyl, sulfonyl($C_{1-3}$)

alkyl, sulfinyl($C_{1-3}$)alkyl, ($C_{1-10}$)azaalkyl, imino($C_{1-3}$) alkyl, ($C_{3-12}$)cycloalkyl($C_{1-5}$)alkyl, hetero($C_{3-12}$) cycloalkyl($C_{1-5}$)alkyl, aryl($C_{1-10}$)alkyl, heteroaryl ($C_{1-5}$)alkyl, ($C_{9-12}$)bicycloaryl($C_{1-5}$)alkyl, hetero ($C_{8-12}$)bicycloaryl($C_{1-5}$)alkyl, ($C_{3-12}$)cycloalkyl, hetero ($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_{19}$ and $R_{20}$ are taken together to form a substituted or unsubstituted ring, or $R_{19}$ is a substituent convertible in vivo into hydroxy.

In a further embodiment, PLK inhibitors of the present invention comprise:

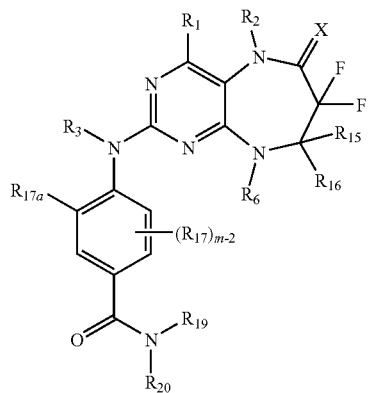

and the pharmaceutically acceptable salts thereof, wherein
m is selected from the group consisting of 2, 3, 4 and 5;
each $R_{17}$ is independently selected from the group consisting of halo, nitro, cyano, thio, oxy, hydroxy, carbonyloxy, alkoxy, aryloxy, heteroaryloxy, carbamoyloxy, carbonyl, oxycarbonyl, amido, amino, ($C_{1-10}$)alkylamino, sulfonamido, carboxyamino, ureido, imino, sulfonyl, aminosulfonyl, sulfinyl, ($C_{1-10}$)alkyl, halo($C_{1-10}$) alkyl, hydroxy($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, ($C_{1-10}$)azaalkyl, imino($C_{1-3}$)alkyl, ($C_{3-12}$) cycloalkyl($C_{1-5}$)alkyl, hetero($C_{3-12}$)cycloalkyl($C_{1-5}$) alkyl, aryl($C_{1-10}$)alkyl, heteroaryl($C_{1-5}$)alkyl, ($C_{9-12}$) bicycloaryl($C_{1-5}$)alkyl, hetero($C_{8-12}$)bicycloaryl($C_{1-5}$) alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$) aryl, hetero($C_{1-10}$)aryl, ($C_{9-12}$)bicycloaryl and hetero ($C_{4-12}$)bicycloaryl, each substituted or unsubstituted, or two $R_{17}$ are taken together to form a substituted or unsubstituted ring; and
$R_{17a}$ is selected from the group consisting of hydrogen, halo, nitro, cyano, thio, oxy, hydroxy, carbonyloxy, alkoxy, aryloxy, heteroaryloxy, carbamoyloxy, carbonyl, oxycarbonyl, amido, amino, ($C_{1-10}$)alkylamino, sulfonamido, carboxyamino, ureido, imino, sulfonyl, aminosulfonyl, sulfinyl, ($C_{1-10}$)alkyl, halo($C_{1-10}$)alkyl, hydroxy($C_{1-10}$)alkyl, carbonyl($C_{1-3}$)alkyl, thiocarbonyl ($C_{1-3}$)alkyl, sulfonyl($C_{1-3}$)alkyl, sulfinyl($C_{1-3}$)alkyl, ($C_{1-10}$)azaalkyl, imino($C_{1-3}$)alkyl, ($C_{3-12}$)cycloalkyl ($C_{1-5}$)alkyl, hetero($C_{3-12}$)cycloalkyl($C_{1-5}$)alkyl, aryl ($C_{1-10}$)alkyl, heteroaryl($C_{1-5}$)alkyl, ($C_{9-12}$)bicycloaryl ($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero ($C_{1-10}$)aryl, ($C_{9-12}$)bicycloaryl and hetero($C_{4-12}$)bicycloaryl, each substituted or unsubstituted; and
$R_{19}$ are $R_{20}$ are each independently selected from the group consisting of hydrogen, oxy, hydroxy, carbonyloxy, alkoxy, aryloxy, heteroaryloxy, carbonyl, oxycarbonyl, amino, ($C_{1-10}$)alkylamino, sulfonamido, imino, sulfonyl, sulfinyl, ($C_{1-10}$)alkyl, halo($C_{1-10}$)alkyl, carbonyl ($C_{1-3}$)alkyl, thiocarbonyl($C_{1-3}$)alkyl, sulfonyl($C_{1-3}$) alkyl, sulfinyl($C_{1-3}$)alkyl, ($C_{1-10}$)azaalkyl, imino($C_{1-3}$) alkyl, ($C_{3-12}$)cycloalkyl($C_{1-5}$)alkyl, hetero($C_{3-12}$) cycloalkyl($C_{1-5}$)alkyl, aryl($C_{1-10}$)alkyl, heteroaryl ($C_{1-5}$)alkyl, ($C_{9-12}$)bicycloaryl($C_{1-5}$)alkyl, hetero ($C_{8-12}$)bicycloaryl($C_{1-5}$)alkyl, ($C_{3-12}$)cycloalkyl, hetero ($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_{19}$ and $R_{20}$ are taken together to form a substituted or unsubstituted ring, or $R_{19}$ is a substituent convertible in vivo into hydroxy.

In still a further embodiment, PLK inhibitors of the present invention comprise:

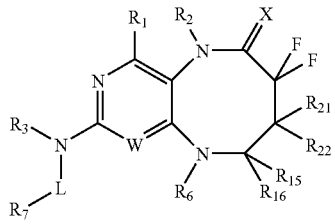

and the pharmaceutically acceptable salts thereof, wherein
$R_{15}$ and $R_{16}$ are each independently selected from the group consisting of hydrogen, cyano, carbonyl, oxycarbonyl, amido, ($C_{1-10}$)alkyl, halo($C_{1-10}$)alkyl, hydroxy ($C_{1-10}$)alkyl, carbonyl($C_{1-3}$)alkyl, thiocarbonyl($C_{1-3}$) alkyl, sulfonyl($C_{1-3}$)alkyl, sulfinyl($C_{1-3}$)alkyl, ($C_{1-10}$) azaalkyl, imino($C_{1-3}$)alkyl, ($C_{3-12}$)cycloalkyl($C_{1-5}$) alkyl, hetero($C_{3-12}$)cycloalkyl($C_{1-5}$)alkyl, aryl($C_{1-10}$) alkyl, heteroaryl($C_{1-5}$)alkyl, ($C_{9-12}$)bicycloaryl($C_{1-5}$) alkyl, hetero($C_{8-12}$)bicycloaryl($C_{1-5}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$) bicycloaryl, each substituted or unsubstituted, or $R_{15}$ and $R_{16}$ are taken together with the atom to which they are bound to form a carbonyl or imino group; and
$R_{21}$ and $R_{22}$ are each independently selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$) alkyl, ($C_{1-10}$)azaalkyl, imino($C_{1-10}$)alkyl, ($C_{3-12}$)cycloalkyl($C_{1-5}$)alkyl, hetero($C_{3-12}$)cycloalkyl($C_{1-10}$) alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl ($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$) aryl, hetero($C_{1-10}$)aryl, ($C_{9-12}$)bicycloaryl and hetero ($C_{4-12}$)bicycloaryl, each substituted or unsubstituted,
or any two $R_6$, $R_{15}$, $R_{16}$, $R_{21}$ and $R_{22}$ are taken together to form a substituted or unsubstituted ring.

In yet a further embodiment, PLK inhibitors of the present invention comprise:

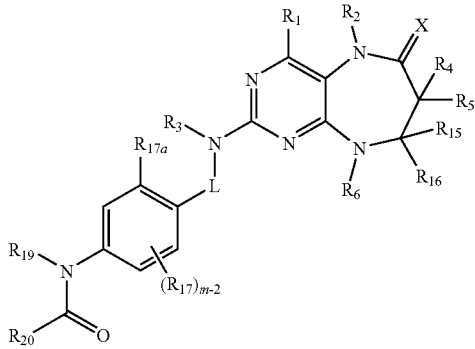

and the pharmaceutically acceptable salts thereof, wherein m is selected from the group consisting of 2, 3, 4 and 5;

$R_{15}$ and $R_{16}$ are each independently selected from the group consisting of hydrogen, cyano, carbonyl, oxycarbonyl, amido, $(C_{1-10})$alkyl, halo$(C_{1-10})$alkyl, hydroxy $(C_{1-10})$alkyl, carbonyl$(C_{1-3})$alkyl, thiocarbonyl$(C_{1-3})$ alkyl, sulfonyl$(C_{1-3})$alkyl, sulfinyl$(C_{1-3})$alkyl, $(C_{1-10})$ azaalkyl, imino$(C_{1-3})$alkyl, $(C_{3-12})$cycloalkyl$(C_{1-5})$ alkyl, hetero$(C_{3-12})$cycloalkyl$(C_{1-5})$alkyl, aryl$(C_{1-10})$ alkyl, heteroaryl$(C_{1-5})$alkyl, $(C_{9-12})$bicycloaryl$(C_{1-5})$ alkyl, hetero$(C_{8-12})$bicycloaryl$(C_{1-5})$alkyl, $(C_{3-12})$ cycloalkyl, hetero$(C_{3-12})$cycloalkyl, $(C_{9-12})$ bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$ bicycloaryl, each substituted or unsubstituted, or $R_{15}$ and $R_{16}$ are taken together with the atom to which they are bound to form a carbonyl or imino group;

each $R_{17}$ is independently selected from the group consisting of halo, nitro, cyano, thio, oxy, hydroxy, carbonyloxy, alkoxy, aryloxy, heteroaryloxy, carbamoyloxy, carbonyl, oxycarbonyl, amido, amino, $(C_{1-10})$alkylamino, sulfonamido, carboxyamino, ureido, imino, sulfonyl, aminosulfonyl, sulfinyl, $(C_{1-10})$alkyl, halo$(C_{1-10})$ alkyl, hydroxy$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, $(C_{1-10})$azaalkyl, imino$(C_{1-3})$alkyl, $(C_{3-12})$ cycloalkyl$(C_{1-5})$alkyl, hetero$(C_{3-12})$cycloalkyl$(C_{1-5})$ alkyl, aryl$(C_{1-10})$alkyl, heteroaryl$(C_{1-5})$alkyl, $(C_{9-12})$ bicycloaryl$(C_{1-5})$alkyl, hetero$(C_{8-12})$bicycloaryl$(C_{1-5})$ alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$ aryl, hetero$(C_{1-10})$aryl, $(C_{9-12})$bicycloaryl and hetero $(C_{4-12})$bicycloaryl, each substituted or unsubstituted, or two $R_{17}$ are taken together to form a substituted or unsubstituted ring;

$R_{17a}$ is selected from the group consisting of hydrogen, halo, nitro, cyano, thio, oxy, hydroxy, carbonyloxy, alkoxy, aryloxy, heteroaryloxy, carbamoyloxy, carbonyl, oxycarbonyl, amido, amino, $(C_{1-10})$alkylamino, sulfonamido, carboxyamino, ureido, imino, sulfonyl, aminosulfonyl, sulfinyl, $(C_{1-10})$alkyl, halo$(C_{1-10})$alkyl, hydroxy$(C_{1-10})$alkyl, carbonyl$(C_{1-3})$alkyl, thiocarbonyl $(C_{1-3})$alkyl, sulfonyl$(C_{1-3})$alkyl, sulfinyl$(C_{1-3})$alkyl, $(C_{1-10})$azaalkyl, imino$(C_{1-3})$alkyl, $(C_{3-12})$cycloalkyl $(C_{1-5})$alkyl, hetero$(C_{3-12})$cycloalkyl$(C_{1-5})$alkyl, aryl $(C_{1-10})$alkyl, heteroaryl$(C_{1-5})$alkyl, $(C_{9-12})$bicycloaryl $(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero $(C_{1-10})$aryl, $(C_{9-12})$bicycloaryl and hetero$(C_{4-12})$bicycloaryl, each substituted or unsubstituted; and $R_{19}$ are $R_{20}$ are each independently selected from the group consisting of hydrogen, oxy, hydroxy, carbonyloxy, alkoxy, aryloxy, heteroaryloxy, carbonyl, oxycarbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$ alkyl, sulfinyl$(C_{1-3})$alkyl, $(C_{1-10})$azaalkyl, imino$(C_{1-3})$ alkyl, $(C_{3-12})$cycloalkyl$(C_{1-5})$alkyl, hetero$(C_{3-12})$ cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero $(C_{8-12})$bicycloaryl$(C_{1-5})$alkyl, $(C_{3-12})$cycloalkyl, hetero $(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_{19}$ and $R_{20}$ are taken together to form a substituted or unsubstituted ring, or $R_{19}$ is a substituent convertible in vivo into hydroxy.

In another embodiment, PLK inhibitors of the present invention comprise:

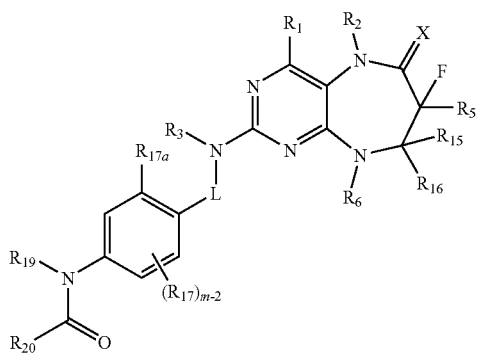

and the pharmaceutically acceptable salts thereof.

In still another embodiment, PLK inhibitors of the present invention comprise:

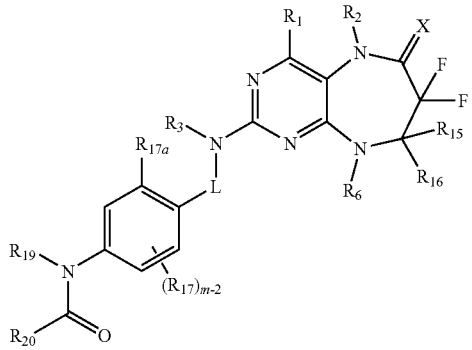

and the pharmaceutically acceptable salts thereof.

It is understood that when p is 0 all of $R_{34}$, $R_{35}$, $R_{36}$, and $R_{37}$ are absent.

In yet a further embodiment, PLK inhibitors of the present invention comprise:

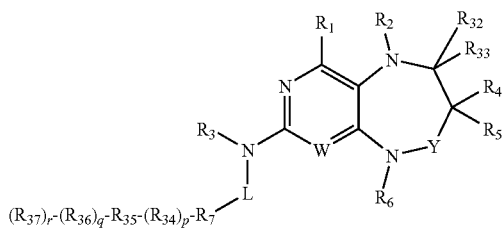

and the pharmaceutically acceptable salts thereof;
Y is —(CR$_9$R$_{10}$)$_n$—;
n is 1;
L is absent;
R$_1$ is selected from the group consisting of hydrogen, alkoxy, and (C$_{1-4}$)alkyl, each substituted or unsubstituted;
R$_2$ is selected from the group consisting of hydrogen and optionally substituted (C$_{1-10}$)alkyl;
R$_4$ is halo;
R$_5$ is selected from the group consisting of hydrogen and halo;
R$_6$ is selected from the group consisting of hydrogen, (C$_{1-4}$)alkyl, and (C$_{3-8}$)cycloalkyl, each substituted or unsubstituted;
R$_7$ is optionally substituted (C$_{4-12}$)aryl;
R$_9$ and R$_{10}$ are each independently selected from the group consisting of hydrogen, halo, and optionally substituted (C$_{1-4}$)alkyl;
X is selected from the group consisting of O and S;
p is selected from the group consisting of 0 and 1;
R$_{34}$ is —CONJ$_{34}$;
J$_{34}$ is selected from the group consisting of hydrogen and (C$_{1-4}$)alkyl;
R$_{35}$ is selected from the group consisting of (C$_{3-8}$)cycloalkyl, hetero(C$_{3-6}$)cycloalkyl, (C$_{7-12}$)bicycloalkyl, hetero(C$_{3-12}$)bicycloalkyl, each substituted or unsubstituted;
q is selected from the group consisting of 0 and 1;
R$_{36}$ is selected from the group consisting of is selected from the group consisting (C$_{1-4}$)alkyl, (C$_{3-8}$)cycloalkyl, hetero(C$_{3-8}$)cycloalkyl, each substituted or unsubstituted;
r is selected from the group consisting of 0 and 1;
R$_{37}$ is optionally substituted (C$_{3-8}$)cycloalkyl, when R$_{36}$ is optionally substituted (C$_{1-4}$)alkyl;
R$_{37}$ is optionally substituted (C$_{1-4}$)alkyl, when R$_{36}$ is selected from the group consisting of optionally substituted (C$_{3-8}$)cycloalkyl and optionally substituted hetero(C$_{3-8}$)cycloalkyl.

In yet a further embodiment, PLK inhibitors of the present invention comprise:

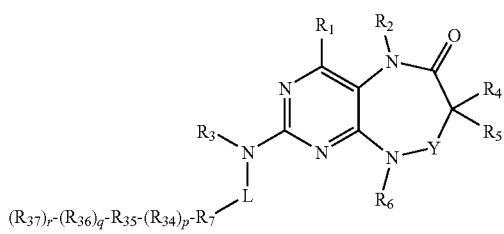

and the pharmaceutically acceptable salts thereof;
Y is —(CR$_9$R$_{10}$)$_n$—;
n is 1;
L is absent;
R$_1$ is selected from the group consisting of hydrogen, alkoxy, and (C$_{1-4}$)alkyl, each substituted or unsubstituted;
R$_2$ is selected from the group consisting of hydrogen and optionally substituted (C$_{1-4}$)alkyl;
R$_4$ is halo;
R$_5$ is selected from the group consisting of hydrogen and halo;
R$_6$ is selected from the group consisting of hydrogen, (C$_{1-4}$)alkyl, and (C$_{3-8}$)cycloalkyl, each substituted or unsubstituted;
R$_7$ is (C$_{4-12}$)aryl, optionally substituted with from 1 to 4 groups independently selected from the group consisting of consisting of (C$_{1-4}$)alkyl, (C$_{1-4}$)alkoxy, cyano, halogen, hydroxyl, nitro, and trifluoromethyl;
R$_9$ and R$_{10}$ are hydrogen;
p is selected from the group consisting of 0 and 1;
R$_{34}$ is —CONJ$_{34}$;
J$_{34}$ is selected from the group consisting of hydrogen and (C$_{1-4}$)alkyl;
R$_{35}$ is selected from the group consisting of (C$_{3-8}$)cycloalkyl, hetero(C$_{3-6}$)cycloalkyl, (C$_{7-12}$)bicycloalkyl, hetero(C$_{3-12}$)bicycloalkyl, each substituted or unsubstituted;
q is selected from the group consisting of 0 and 1;
R$_{36}$ is selected from the group consisting of is selected from the group consisting (C$_{1-4}$)alkyl, (C$_{3-8}$)cycloalkyl, hetero(C$_{3-8}$)cycloalkyl, each substituted or unsubstituted;
r is selected from the group consisting of 0 and 1;
R$_{37}$ is optionally substituted (C$_{3-8}$)cycloalkyl, when R$_{36}$ is optionally substituted (C$_{1-4}$)alkyl;
R$_{37}$ is optionally substituted (C$_{1-4}$)alkyl, when R$_{36}$ is selected from the group consisting of optionally substituted (C$_{3-8}$)cycloalkyl and optionally substituted hetero(C$_{3-8}$)cycloalkyl.

In yet a further embodiment, PLK inhibitors of the present invention comprise:

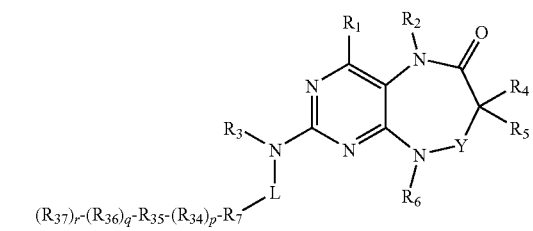

and the pharmaceutically acceptable salts thereof;
Y is —(CR$_9$R$_{10}$)$_n$—;
n is 1;
L is absent;
R$_1$ is selected from the group consisting of hydrogen, alkoxy, and (C$_{1-4}$)alkyl, each substituted or unsubstituted;
R$_2$ is selected from the group consisting of hydrogen and optionally substituted (C$_{1-10}$)alkyl;
R$_4$ is halo;
R$_5$ is selected from the group consisting of hydrogen and halo;
R$_6$ is selected from the group consisting of hydrogen, (C$_{1-4}$)alkyl, and (C$_{3-12}$)cycloalkyl, each substituted or unsubstituted;

$R_7$ is $(C_{4-12})$aryl, optionally substituted with from 1 to 4 groups independently selected from the group consisting of consisting of $(C_{1-4})$alkyl, $(C_{1-4})$alkoxy, cyano, halogen, hydroxyl, nitro, and trifluoromethyl;

$R_9$ and $R_{10}$ are hydrogen;

p is 1;

$R_{34}$ is selected from the group consisting of —CONJ$_{34}$;

$J_{34}$ is selected from the group consisting of hydrogen and $(C_{1-4})$alkyl;

p is 1;

$R_{35}$ is selected from the group consisting of optionally substituted $(C_{3-8})$cycloalkyl;

q is 1;

$R_{36}$ is optionally substituted hetero$(C_{3-8})$cycloalkyl;

r is 1; and $R_{37}$ is optionally substituted $(C_{1-4})$alkyl.

In yet a further embodiment, PLK inhibitors of the present invention comprise:

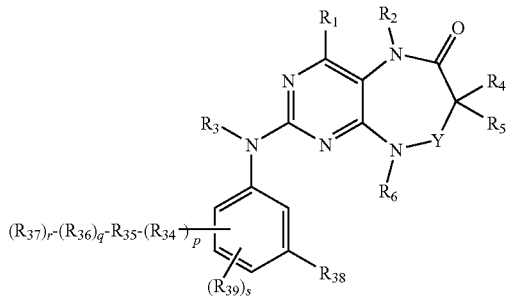

and the pharmaceutically acceptable salts thereof;

Y is —$(CR_9R_{10})_n$—;

n is selected from the group consisting of 1, 2, 3 and 4;

$R_1$ is selected from the group consisting of hydrogen, cyano, thio, hydroxy, carbonyloxy, alkoxy, aryloxy, heteroaryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, $(C_{1-10})$azaalkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-5})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_2$ is selected from the group consisting of hydrogen, carbonyl, oxycarbonyl, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, $(C_{1-10})$azaalkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_2$ and $R_1$ are taken together to form a substituted or unsubstituted ring;

$R_3$ is hydrogen or a substituent convertible in vivo to hydrogen;

$R_4$ is halo;

$R_5$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_6$ is selected from the group consisting of hydrogen, carbonyl, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, $(C_{1-10})$azaalkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_9$ and $R_{10}$ are each independently selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_9$ and $R_{10}$ are taken together with the carbon to which they are attached to form C=O, C=S, C=NR$_{11}$ or C=CR$_{12}$R$_{13}$;

$R_{11}$ is selected from the group consisting of hydrogen, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_{12}$ and $R_{13}$ are each independently selected from the group consisting of hydrogen, halo, nitro, cyano, oxycarbonyl, amido, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

or any two $R_2$, $R_5$, $R_6$, $R_9$, and $R_{10}$ are taken together to form a substituted or unsubstituted ring;

p is selected from the group consisting of 0 and 1;

$R_{34}$ is selected from the group consisting of —$CONJ_{34}$-, —$NJ_{34}CO$—, —$NJ_{34}$-, —$SO_2NJ_{34}$-, —$NJ_{34}SO_2$—, $J_{34}$ is selected from the group consisting of hydrogen and ($C_{1-4}$)alkyl;

$R_{35}$ is selected from the group consisting of amino, ($C_{4-12}$)aryl, hetero($C_{1-10}$)aryl, ($C_{3-8}$)cycloalkyl, hetero($C_{3-6}$)cycloalkyl, ($C_{7-12}$)bicycloalkyl, hetero($C_{3-12}$)bicycloalkyl, each substituted or unsubstituted;

q is selected from the group consisting of 0 and 1;

$R_{36}$ is selected from the group consisting of is selected from the group consisting ($C_{1-4}$)alkyl, ($C_{1-4}$)azaalkyl, ($C_{3-8}$)cycloalkyl, hetero($C_{3-8}$)cycloalkyl, each substituted or unsubstituted;

r is selected from the group consisting of 0 and 1;

$R_{37}$ is optionally substituted ($C_{3-8}$)cycloalkyl, when $R_{36}$ is selected from the group consisting of optionally substituted ($C_{1-4}$)alkyl and optionally substituted ($C_{1-4}$)azaalkyl;

$R_{37}$ is optionally substituted ($C_{1-4}$)alkyl, when $R_{36}$ is selected from the group consisting of optionally substituted ($C_{3-8}$)cycloalkyl and optionally substituted hetero($C_{3-8}$)cycloalkyl;

$R_{38}$ is fluoro or chloro;

s is selected from the group consisting of 0, 1, 2, 3, and 4; and $R_{39}$ is independently selected from the group consisting of amino, optionally substituted ($C_{1-4}$)alkoxy, optionally substituted ($C_{1-4}$)alkyl, amido, carboxy, cyano, ($C_{3-8}$)cycloalkyl, halo, hydroxy, and nitro.

Such compounds are expected to have reduced susceptibility to multi-drug resistant tumors.

In particular, PLK inhibitors of the present invention comprise:

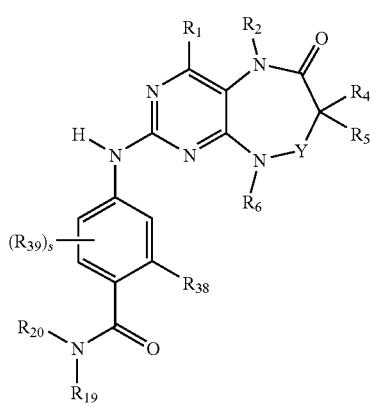

and the pharmaceutically acceptable salts thereof;
n is 1;
Y is —$(CR_9R_{10})_n$—;

$R_1$ is selected from the group consisting of hydrogen, ($C_{1-4}$)alkoxy, and ($C_{1-4}$)alkyl, each substituted or unsubstituted;

$R_2$ is selected from the group consisting of hydrogen and optionally substituted ($C_{1-10}$)alkyl;

$R_4$ is halo;

$R_5$ is selected from the group consisting of hydrogen and halo;

$R_6$ is selected from the group consisting of hydrogen, ($C_{1-10}$)alkyl, and ($C_{3-12}$)cycloalkyl, each substituted or unsubstituted;

$R_9$ and $R_{10}$ are hydrogen;

$R_{19}$ are $R_{20}$ are each independently selected from the group consisting of hydrogen, amino, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_{38}$ is selected from the group consisting of fluoro and chloro;

s is selected from the group consisting of 0, 1, 2, 3, and 4;

each $R_{39}$ is independently selected from the group consisting of hydrogen, halo, nitro, cyano, thio, oxy, hydroxy, carbonyloxy, alkoxy, aryloxy, heteroaryloxy, carbamoyloxy, carbonyl, oxycarbonyl, amido, amino, ($C_{1-10}$)alkylamino, sulfonamido, carboxyamino, ureido, imino, sulfonyl, aminosulfonyl, sulfinyl, ($C_{1-10}$)alkyl, halo($C_{1-10}$)alkyl, hydroxy($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, ($C_{1-10}$)azaalkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or two $R_{17}$ are taken together to form a substituted or unsubstituted ring.

In particular, PLK inhibitors of the present invention comprise:

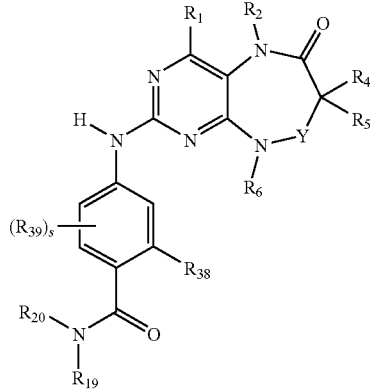

and the pharmaceutically acceptable salts thereof;
n is 1;
Y is —$(CR_9R_{10})_n$—;

$R_1$ is selected from the group consisting of hydrogen, $(C_{1-4})$alkoxy, and $(C_{1-4})$alkyl, each substituted or unsubstituted;

$R_2$ is selected from the group consisting of hydrogen and optionally substituted $(C_{1-10})$alkyl;

$R_4$ is halo;

$R_5$ is selected from the group consisting of hydrogen and halo;

$R_6$ is selected from the group consisting of hydrogen, $(C_{1-10})$alkyl, and $(C_{3-12})$cycloalkyl, each substituted or unsubstituted;

$R_9$ and $R_{10}$ are hydrogen;

$R_{19}$ is hydrogen;

$R_{20}$ optionally substituted hetero$(C_{3-12})$cycloalkyl;

$R_{38}$ is selected from the group consisting of fluoro and chloro;

s is selected from the group consisting of 0, 1, 2, 3, and 4;

each $R_{39}$ is independently selected from the group consisting of hydrogen, halo, nitro, cyano, $(C_{1-4})$alkoxy, $(C_{1-4})$alkyl, each substituted or unsubstituted.

In particular, PLK inhibitors of the present invention comprise:

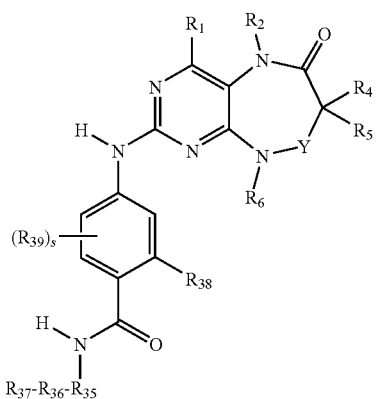

and the pharmaceutically acceptable salts thereof;

n is 1;

Y is $-(CR_9R_{10})_n-$;

$R_1$ is selected from the group consisting of hydrogen, $(C_{1-4})$alkoxy, and $(C_{1-4})$alkyl, each substituted or unsubstituted;

$R_2$ is selected from the group consisting of hydrogen and optionally substituted $(C_{1-10})$alkyl;

$R_4$ is halo;

$R_5$ is selected from the group consisting of hydrogen and halo;

$R_6$ is selected from the group consisting of hydrogen, $(C_{1-10})$alkyl, and $(C_{3-12})$cycloalkyl, each substituted or unsubstituted;

$R_9$ and $R_{10}$ are hydrogen;

$R_{35}$ is selected from the group consisting of $(C_{4-12})$aryl, hetero$(C_{1-10})$aryl, $(C_{3-8})$cycloalkyl, hetero$(C_{3-8})$cycloalkyl, $(C_{7-12})$bicycloalkyl, hetero$(C_{3-12})$bicycloalkyl, each substituted or unsubstituted;

$R_{36}$ is selected from the group consisting of is selected from the group consisting $(C_{1-4})$alkyl, $(C_{1-4})$azaalkyl, $(C_{3-8})$cycloalkyl, hetero$(C_{3-8})$cycloalkyl, each substituted or unsubstituted;

$R_{37}$ is optionally substituted $(C_{3-8})$cycloalkyl, when $R_{36}$ is selected from the group consisting of optionally substituted $(C_{1-4})$alkyl and optionally substituted $(C_{1-4})$azaalkyl;

$R_{37}$ is optionally substituted $(C_{1-4})$alkyl, when $R_{36}$ is selected from the group consisting of optionally substituted $(C_{3-8})$cycloalkyl and optionally substituted hetero$(C_{3-8})$cycloalkyl;

$R_{38}$ is selected from the group consisting of fluoro and chloro;

s is selected from the group consisting of 0, 1, 2, 3, and 4;

each $R_{39}$ is independently selected from the group consisting of hydrogen, halo, nitro, cyano, $(C_{1-4})$alkoxy, $(C_{1-4})$alkyl, aryl$(C_{1-10})$alkyl, and hetero$(C_{1-10})$aryl.

In particular, PLK inhibitors of the present invention comprise:

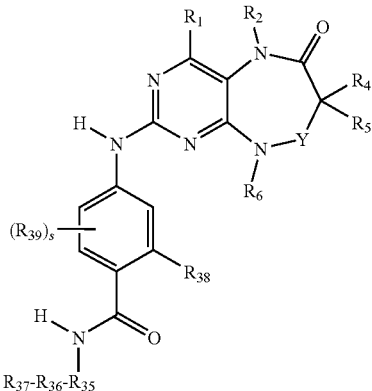

and the pharmaceutically acceptable salts thereof;

n is 1;

Y is $-(CR_9R_{10})_n-$;

$R_1$ is selected from the group consisting of hydrogen, $(C_{1-4})$alkoxy, and $(C_{1-4})$alkyl, each substituted or unsubstituted;

$R_2$ is selected from the group consisting of hydrogen and optionally substituted $(C_{1-10})$alkyl;

$R_4$ is halo;

$R_5$ is selected from the group consisting of hydrogen and halo;

$R_6$ is selected from the group consisting of hydrogen, $(C_{1-10})$alkyl, and $(C_{3-12})$cycloalkyl, each substituted or unsubstituted;

$R_9$ and $R_{10}$ are hydrogen;

$R_{35}$ is selected optionally substituted $(C_{3-8})$cycloalkyl;

$R_{36}$ is optionally substituted hetero$(C_{3-8})$cycloalkyl;

$R_{37}$ is optionally substituted $(C_{1-4})$alkyl;

$R_{38}$ is selected from the group consisting of fluoro and chloro;

s is selected from the group consisting of 0, 1, and 2;

each $R_{39}$ is independently selected from the group consisting of hydrogen, halo, nitro, cyano, $(C_{1-4})$alkoxy, $(C_{1-14})$alkyl, each substituted or unsubstituted.

In a further embodiment, PLK inhibitors of the present invention comprise:

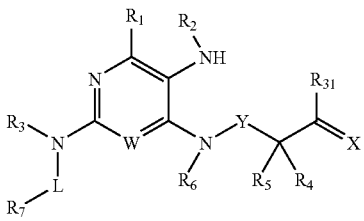

and the pharmaceutically acceptable salts thereof, wherein

W is selected from the group consisting of $CR_8$ and N;

X is selected from the group consisting of $NR_{14}$, O and S;

Y is $—(CR_9R_{10})_n—$;

n is selected from the group consisting of 1, 2, 3 and 4;

L is absent or a linker providing 1, 2, 3, 4, 5 or 6 atom separation between $R_7$ and the nitrogen to which L is attached, wherein the atoms of the linker providing the separation are selected from the group consisting of carbon, oxygen, nitrogen, and sulfur;

$R_1$ is selected from the group consisting of hydrogen, cyano, thio, hydroxy, carbonyloxy, alkoxy, aryloxy, heteroaryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-3})$alkyl, thiocarbonyl$(C_{1-3})$alkyl, sulfonyl $(C_{1-3})$alkyl, sulfinyl$(C_{1-3})$alkyl, $(C_{1-10})$azaalkyl, imino $(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero $(C_{8-12})$bicycloaryl$(C_{1-5})$alkyl, $(C_{3-12})$cycloalkyl, hetero $(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_2$ is selected from the group consisting of hydrogen, carbonyl, oxycarbonyl, sulfonyl, sulfinyl, $(C_{1-10})$alkyl, halo $(C_{1-10})$alkyl, carbonyl$(C_{1-3})$alkyl, thiocarbonyl$(C_{1-3})$ alkyl, sulfonyl$(C_{1-3})$alkyl, sulfinyl$(C_{1-3})$alkyl, $(C_{1-10})$ azaalkyl, imino$(C_{1-3})$alkyl, $(C_{3-12})$cycloalkyl$(C_{1-5})$ alkyl, hetero$(C_{3-12})$cycloalkyl$(C_{1-5})$alkyl, aryl$(C_{1-10})$ alkyl, heteroaryl$(C_{1-5})$alkyl, $(C_{9-12})$bicycloaryl$(C_{1-5})$ alkyl, hetero$(C_{8-12})$bicycloaryl$(C_{1-5})$alkyl, $(C_{3-12})$ cycloalkyl, hetero$(C_{3-12})$cycloalkyl, $(C_{9-12})$ bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$ bicycloaryl, each substituted or unsubstituted, or $R_2$ and $R_1$ or $R_{14}$ are taken together to form a substituted or unsubstituted ring;

$R_3$ is hydrogen or a substituent convertible in vivo to hydrogen;

$R_4$ is halo;

$R_5$ is selected from the group consisting of hydrogen, halo, nitro, cyano, thio, oxy, hydroxy, carbonyloxy, $(C_{1-10})$ alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo $(C_{1-10})$alkyl, hydroxy$(C_{1-10})$alkyl, carbonyl$(C_{1-10})$ alkyl, thiocarbonyl$(C_{1-10})$alkyl, sulfonyl$(C_{1-10})$alkyl, sulfinyl$(C_{1-10})$alkyl, $(C_{1-10})$azaalkyl, imino$(C_{1-10})$alkyl, $(C_{3-12})$cycloalkyl$(C_{1-5})$alkyl, hetero$(C_{3-12})$cycloalkyl $(C_{1-10})$alkyl, aryl$(C_{1-10})$alkyl, hetero$(C_{1-10})$aryl$(C_{1-5})$ alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$ cycloalkyl, $(C_{9-12})$bicycloalkyl, hetero$(C_{3-12})$ bicycloalkyl, $(C_{4-12})$aryl, hetero$(C_{1-10})$aryl, $(C_{9-12})$ bicycloaryl and hetero$(C_{4-12})$bicycloaryl, each substituted or unsubstituted;

$R_6$ is selected from the group consisting of hydrogen, carbonyl, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl $(C_{1-3})$alkyl, sulfinyl$(C_{1-3})$alkyl, $(C_{1-10})$azaalkyl, imino $(C_{1-3})$alkyl, $(C_{3-12})$cycloalkyl$(C_{1-5})$alkyl, hetero$(C_{3-12})$ cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero $(C_{8-12})$bicycloaryl$(C_{1-5})$alkyl, $(C_{3-12})$cycloalkyl, hetero $(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_7$ is selected from the group consisting of $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$ aryl, $(C_{9-12})$bicycloaryl and hetero$(C_{4-12})$bicycloaryl, each substituted or unsubstituted;

$R_8$ is selected from the group consisting of hydrogen, halo, nitro, cyano, thio, oxy, hydroxy, carbonyloxy, alkoxy, aryloxy, heteroaryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy $(C_{1-10})$alkyl, carbonyl$(C_{1-3})$alkyl, thiocarbonyl$(C_{1-3})$ alkyl, sulfonyl$(C_{1-3})$alkyl, sulfinyl$(C_{1-3})$alkyl, $(C_{1-10})$ azaalkyl, imino$(C_{1-3})$alkyl, $(C_{3-12})$cycloalkyl$(C_{1-5})$ alkyl, hetero$(C_{3-12})$cycloalkyl$(C_{1-5})$alkyl, aryl$(C_{1-10})$ alkyl, heteroaryl$(C_{1-5})$alkyl, $(C_{9-12})$bicycloaryl$(C_{1-5})$ alkyl, hetero$(C_{8-12})$bicycloaryl$(C_{1-5})$alkyl, $(C_{3-12})$ cycloalkyl, hetero$(C_{3-12})$cycloalkyl, $(C_{9-12})$ bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$ bicycloaryl, each substituted or unsubstituted;

$R_9$ and $R_{10}$ are each independently selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy $(C_{1-10})$alkyl, carbonyl$(C_{1-10})$alkyl, thiocarbonyl$(C_{1-10})$ alkyl, sulfonyl$(C_{1-10})$alkyl, sulfinyl$(C_{1-10})$alkyl, $(C_{1-10})$ azaalkyl, imino$(C_{1-10})$alkyl, $(C_{3-12})$cycloalkyl$(C_{1-5})$ alkyl, hetero$(C_{3-12})$cycloalkyl$(C_{1-10})$alkyl, aryl$(C_{1-10})$ alkyl, hetero$(C_{1-10})$aryl$(C_{1-5})$alkyl, $(C_{9-12})$bicycloaryl $(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero $(C_{1-10})$aryl, $(C_{9-12})$bicycloaryl and hetero$(C_{4-12})$bicycloaryl, each substituted or unsubstituted, or $R_9$ and $R_{10}$ are taken together with the carbon to which they are attached to form C=O, C=S, C=$NR_{11}$ or C=$CR_{12}R_{13}$;

$R_{11}$ is selected from the group consisting of hydrogen, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$ alkyl, aza$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$ alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl $(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$ bicycloalkyl, $(C_{4-12})$aryl, hetero$(C_{1-10})$aryl, $(C_{9-12})$ bicycloaryl and hetero$(C_{4-12})$bicycloaryl, each substituted or unsubstituted;

R$_{12}$ and R$_{13}$ are each independently selected from the group consisting of hydrogen, halo, nitro, cyano, oxycarbonyl, amido, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, (C$_{1-10}$)oxaalkyl, (C$_{1-10}$)oxoalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted;

R$_{14}$ is selected from the group consisting of (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted; and R$_{31}$ is selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, amido, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, (C$_{1-10}$)oxaalkyl, (C$_{1-10}$)oxoalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted, or any two R$_5$, R$_6$, R$_9$ and R$_{10}$ and are taken together to form a substituted or unsubstituted ring. Particular examples of compounds according to the present invention include, but are not limited to:

4-(9-Cyclopentyl-7,7-difluoro-5-methyl-6-oxo-6,7,8,9-tetrahydro-5H-pyrimido[5,4-b][1,4]diazepin-2-ylamino)-3-methoxybenzoic acid;

4-(9-cyclopentyl-7,7-difluoro-5-methyl-6-oxo-6,7,8,9-tetrahydro-5H-pyrimido[4,5-b][1,4]diazepin-2-ylamino)-N-cyclopropyl-3-methoxybenzamide;

4-(9-Cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide;

4-(9-Cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylazetidin-3-yl)benzamide;

4-(9-cyclopentyl-7,7-difluoro-5-methyl-6-oxo-6,7,8,9-tetrahydro-5H-pyrimido[4,5-b][1,4]diazepin-2-ylamino)-N-(1-(2-hydroxyethyl)piperidin-4-yl)-3-methoxybenzamide;

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(4-methylpiperazin-1-yl)benzamide;

4-(9-cyclopentyl-7,7-difluoro-5-methyl-6-oxo-6,7,8,9-tetrahydro-5H-pyrimido[4,5-b][1,4]diazepin-2-ylamino)-N-(1-ethylpiperidin-4-yl)-3-methoxybenzamide;

(R)-4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(piperidin-3-yl)benzamide;

(S)-4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(piperidin-3-yl)benzamide;

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(piperidin-4-yl)benzamide;

4-(9-cyclopentyl-7,7-difluoro-5-methyl-6-oxo-6,7,8,9-tetrahydro-5H-pyrimido[4,5-b][1,4]diazepin-2-ylamino)-N-(1-(2-(dimethylamino)acetyl)piperidin-4-yl)-3-methoxybenzamide;

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-(2-(pyrrolidin-1-yl)acetyl)piperidin-4-yl)benzamide;

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(pyrrolidin-1-yl)benzamide;

N-(Azepan-4-yl)-4-(9-cyclopentyl-7,7-difluoro-5-methyl-6-oxo-6,7,8,9-tetrahydro-5H-pyrimido[4,5-b][1,4]diazepin-2-ylamino)-3-methoxybenzamide;

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylazepan-4-yl)benzamide;

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-(2-(methylamino)-2-oxoethyl)piperidin-4-yl)benzamide;

9-cyclopentyl-2-(4-(2-(dimethylamino)ethoxy)phenylamino)-7,7-difluoro-5-methyl-8,9-dihydro-5H-pyrimido[4,5-b][1,4]diazepin-6(7H)-one;

6-(9-cyclopentyl-7,7-difluoro-5-methyl-6-oxo-6,7,8,9-tetrahydro-5H-pyrimido[4,5-b][1,4]diazepin-2-ylamino)-2H-benzo[b][1,4]oxazin-3(4H)-one;

9-cyclopentyl-7,7-difluoro-5-methyl-2-(2-oxoindolin-6-ylamino)-8,9-dihydro-5H-pyrimido[4,5-b][1,4]diazepin-6(7H)-one;

2-(1H-Indol-5-ylamino)-9-cyclopentyl-7,7-difluoro-5-methyl-8,9-dihydro-5H-pyrimido[4,5-b][1,4]diazepin-6(7H)-one;

9-Cyclopentyl-7,7-difluoro-5-methyl-2-(3-(1,2,3,6-tetrahydropyridin-4-yl)-1H-indol-5-ylamino)-8,9-dihydro-5H-pyrimido[4,5-b][1,4]diazepin-6(7H)-one;

4-(9-Cyclopentyl-7,7-difluoro-5-methyl-6-oxo-6,7,8,9-tetrahydro-5H-pyrimido[4,5-b][1,4]diazepin-2-ylamino)-3-fluoro-N-(1-methylpiperidin-4-yl)benzamide;

4-(9-Cyclopentyl-7,7-difluoro-5-methyl-6-oxo-6,7,8,9-tetrahydro-5H-pyrimido[4,5-b][1,4]diazepin-2-ylamino)-N-(1-methylpiperidin-4-yl)benzamide;

3-Chloro-4-(9-cyclopentyl-7,7-difluoro-5-methyl-6-oxo-6,7,8,9-tetrahydro-5H-pyrimido[4,5-b][1,4]diazepin-2-ylamino)-N-(1-methylpiperidin-4-yl)benzamide;

4-(9-Cyclopentyl-7,7-difluoro-5-methyl-6-oxo-6,7,8,9-tetrahydro-5H-pyrimido[4,5-b][1,4]diazepin-2-ylamino)-N-(1-methylpiperidin-4-yl)-3-(trifluoromethoxy)-benzamide;

4-(9-Cyclopentyl-7,7-difluoro-5-methyl-6-oxo-6,7,8,9-tetrahydro-5H-pyrimido[4,5-b][1,4]diazepin-2-ylamino)-3-methyl-N-(1-methylpiperidin-4-yl)benzamide;

4-(9-Cyclopentyl-7,7-difluoro-5-methyl-6-oxo-6,7,8,9-tetrahydro-5H-pyrimido[4,5-b][1,4]diazepin-2-ylamino)-3-ethyl-N-(1-methylpiperidin-4-yl)benzamide;

4-(9-Cyclopentyl-7,7-difluoro-5-methyl-6-oxo-6,7,8,9-tetrahydro-5H-pyrimido[4,5-b][1,4]diazepin-2-ylamino)-2-fluoro-N-(1-methylpiperidin-4-yl)benzamide;
4-(9-Cyclopentyl-7,7-difluoro-5-methyl-6-oxo-6,7,8,9-tetrahydro-5H-pyrimido[4,5-b][1,4]diazepin-2-ylamino)-3-ethoxy-N-(1-methylpiperidin-4-yl)benzamide;
4-(9-cyclopentyl-7,7-difluoro-5-methyl-6-oxo-6,7,8,9-tetrahydro-5H-pyrimido[4,5-b][1,4]diazepin-2-ylamino)-N-(1-methylpiperidin-4-yl)-3-(trifluoromethyl)benzamide;
4-(9-Cyclopentyl-7,7-difluoro-5-methyl-6-oxo-6,7,8,9-tetrahydro-5H-pyrimido[4,5-b][1,4]diazepin-2-ylamino)-2-fluoro-5-methoxybenzoic acid;
4-(9-cyclohexyl-7,7-difluoro-5-methyl-6-oxo-6,7,8,9-tetrahydro-5H-pyrimido[4,5-b][1,4]diazepin-2-ylamino)-3-methoxybenzoic acid;
4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide;
4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(4-methylpiperazin-1-yl)benzamide;
4-(9-Cyclohexyl-7,7-difluoro-5-methyl-6-oxo-6,7,8,9-tetrahydro-5H-pyrimido[4,5-b][1,4]diazepin-2-ylamino)-3-methoxy-N-(1-methylazetidin-3-yl)benzamide;
4-(9-cyclohexyl-7,7-difluoro-5-methyl-6-oxo-6,7,8,9-tetrahydro-5H-pyrimido[4,5-b][1,4]diazepin-2-ylamino)-N-(1-ethylpiperidin-4-yl)-3-methoxybenzamide;
(S)-4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(piperidin-3-yl)benzamide;
(R)-4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(piperidin-3-yl)benzamide;
(R)-4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(1-methylpyrrolidin-3-yl)benzamide;
4-(9-cyclohexyl-7,7-difluoro-5-methyl-6-oxo-6,7,8,9-tetrahydro-5H-pyrimido[4,5-b][1,4]diazepin-2-ylamino)-N-((1r,4r)-4-hydroxycyclohexyl)-3-methoxybenzamide;
(1R,4R)-4-(4-(9-cyclopentyl-7,7-difluoro-5-methyl-6-oxo-6,7,8,9-tetrahydro-5H-pyrimido[4,5-b][1,4]diazepin-2-ylamino)-3-methoxybenzamido)cyclohexyl dihydrogen phosphate;
N-(azepan-4-yl)-4-(9-cyclohexyl-7,7-difluoro-5-methyl-6-oxo-6,7,8,9-tetrahydro-5H-pyrimido[4,5-b][1,4]diazepin-2-ylamino)-3-methoxybenzamide;
N-(azetidin-3-yl)-4-(9-cyclohexyl-7,7-difluoro-5-methyl-6-oxo-6,7,8,9-tetrahydro-5H-pyrimido[4,5-b][1,4]diazepin-2-ylamino)-3-methoxybenzamide;
4-(9-cyclohexyl-7,7-difluoro-5-methyl-6-oxo-6,7,8,9-tetrahydro-5H-pyrimido[4,5-b][1,4]diazepin-2-ylamino)-N-(1-(2-hydroxyethyl)piperidin-4-yl)-3-methoxybenzamide;
(R)-4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(quinuclidin-3-yl)benzamide;
(S)-4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(quinuclidin-3-yl)benzamide;
4-(9-cyclohexyl-7,7-difluoro-5-methyl-6-oxo-6,7,8,9-tetrahydro-5H-pyrimido[4,5-b][1,4]diazepin-2-ylamino)-N-((cis)-2-hydroxycyclohexyl)-3-methoxybenzamide;
4-(9-cyclohexyl-7,7-difluoro-5-methyl-6-oxo-6,7,8,9-tetrahydro-5H-pyrimido[4,5-b][1,4]diazepin-2-ylamino)-N-((trans)-2-hydroxycyclohexyl)-3-methoxybenzamide;
4-(9-cyclohexyl-7,7-difluoro-5-methyl-6-oxo-6,7,8,9-tetrahydro-5H-pyrimido[4,5-b][1,4]diazepin-2-ylamino)-N-(4-(dimethylamino)cyclohexyl)-3-methoxybenzamide;
4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(1-(2,2,2-trifluoroethyl)piperidin-4-yl)benzamide;
4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(8-methyl-8-azabicyclo[3.2.1]octan-3-yl)benzamide;
4-(9-cyclohexyl-7,7-difluoro-5-methyl-6-oxo-6,7,8,9-tetrahydro-5H-pyrimido[4,5-b][1,4]diazepin-2-ylamino)-N-(4-cyclopentylpiperazin-1-yl)-3-methoxybenzamide;
4-(9-cyclohexyl-7,7-difluoro-5-methyl-6-oxo-6,7,8,9-tetrahydro-5H-pyrimido[4,5-b][1,4]diazepin-2-ylamino)-N-(2-(dimethylamino)ethyl)-3-methoxybenzamide;
4-(9-cyclohexyl-7,7-difluoro-5-methyl-6-oxo-6,7,8,9-tetrahydro-5H-pyrimido[4,5-b][1,4]diazepin-2-ylamino)-N-(3-(dimethylamino)propyl)-3-methoxybenzamide;
N-(azetidin-3-yl)-4-(9-cyclohexyl-7,7-difluoro-5-methyl-6-oxo-6,7,8,9-tetrahydro-5H-pyrimido[4,5-b][1,4]diazepin-2-ylamino)-3-methoxybenzamide;
4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(2-(pyrrolidin-1-yl)ethyl)benzamide;
9-cyclohexyl-7,7-difluoro-2-(2-methoxy-4-(4-methylpiperazine-1-carbonyl)-phenylamino)-5-methyl-8,9-dihydro-5H-pyrimido[4,5-b][1,4]diazepin-6(7H)-one;
4-(9-cyclohexyl-7,7-difluoro-5-methyl-6-oxo-6,7,8,9-tetrahydro-5H-pyrimido[4,5-b][1,4]diazepin-2-ylamino)-3-methoxybenzamide;
4-(9-cyclohexyl-7,7-difluoro-5-methyl-6-oxo-6,7,8,9-tetrahydro-5H-pyrimido[4,5-b][1,4]diazepin-2-ylamino)-N-(3-(dimethylamino)propyl)-3-methoxybenzamide;
4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-methylbenzamide;
4-(9-cyclohexyl-7,7-difluoro-5-methyl-6-oxo-6,7,8,9-tetrahydro-5H-pyrimido[4,5-b][1,4]diazepin-2-ylamino)-3-methoxy-N',N'-dimethylbenzohydrazide;
(R)-4-(9-cyclohexyl-7,7-difluoro-5-methyl-6-oxo-6,7,8,9-tetrahydro-5H-pyrimido[4,5-b][1,4]diazepin-2-ylamino)-N-(2-hydroxypropyl)-3-methoxybenzamide;
(S)-4-(9-cyclohexyl-7,7-difluoro-5-methyl-6-oxo-6,7,8,9-tetrahydro-5H-pyrimido[4,5-b][1,4]diazepin-2-ylamino)-N-(2-hydroxypropyl)-3-methoxybenzamide;
4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(piperidin-1-yl)benzamide;
4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-morpholinobenzamide;
4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(tetrahydro-2H-pyran-4-yl)benzamide;
4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(pyrrolidin-1-yl)benzamide;
4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(1-(methylsulfonyl)piperidin-4-yl)benzamide;
N-(1-acetylazetidin-3-yl)-4-(9-cyclohexyl-7,7-difluoro-5-methyl-6-oxo-6,7,8,9-tetrahydro-5H-pyrimido[4,5-b][1,4]diazepin-2-ylamino)-3-methoxybenzamide;

4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(piperidin-4-yl)benzamide;
4-(9-cyclohexyl-7,7-difluoro-5-methyl-6-oxo-6,7,8,9-tetrahydro-5H-pyrimido[4,5-b][1,4]diazepin-2-ylamino)-N-(1-(2-(dimethylamino)acetyl)piperidin-4-yl)-3-methoxybenzamide;
(S)-4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(pyrrolidin-3-yl)benzamide;
(R)-4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(pyrrolidin-3-yl)benzamide;
(S)-4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-3-yl)benzamide;
(R)-4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-3-yl)benzamide;
4-(9-cyclohexyl-7,7-difluoro-5-methyl-6-oxo-6,7,8,9-tetrahydro-5H-pyrimido[4,5-b][1,4]diazepin-2-ylamino)-N-cyclopropyl-3-methoxybenzamide;
4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(piperazin-1-yl)benzamide;
4-(9-cyclohexyl-7,7-difluoro-5-methyl-6-oxo-6,7,8,9-tetrahydro-5H-pyrimido[4,5-b][1,4]diazepin-2-ylamino)-N-(4-ethylpiperazin-1-yl)-3-methoxybenzamide;
4-(9-cyclohexyl-7,7-difluoro-5-methyl-6-oxo-6,7,8,9-tetrahydro-5H-pyrimido[4,5-b][1,4]diazepin-2-ylamino)-N-(4-isopropylpiperazin-1-yl)-3-methoxybenzamide;
4-(9-cyclohexyl-7,7-difluoro-5-methyl-6-oxo-6,7,8,9-tetrahydro-5H-pyrimido[4,5-b][1,4]diazepin-2-ylamino)-N-(4-(cyclopropylmethyl)piperazin-1-yl)-3-methoxybenzamidemethoxybenzamide;
4-(9-cyclohexyl-7,7-difluoro-5-methyl-6-oxo-6,7,8,9-tetrahydro-5H-pyrimido[4,5-b][1,4]diazepin-2-ylamino)-N-(4-(2-(dimethylamino)acetyl)piperazin-1-yl)-3-methoxybenzamide;
4-(7,7-difluoro-5-methyl-9-((3R)-3-methylcyclopentyl)-6-oxo-6,7,8,9-tetrahydro-5H-pyrimido[4,5-b][1,4]diazepin-2-ylamino)-3-methoxybenzoic acid;
4-(7,7-difluoro-5-methyl-9-((3R)-3-methylcyclopentyl)-6-oxo-6,7,8,9-tetrahydro-5H-pyrimido[4,5-b][1,4]diazepin-2-ylamino)-3-methoxy-N-(1-methylpiperidin-4-yl)benzamide;
4-(9-cyclopentyl-7-fluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide;
4-(9-cyclopentyl-7-fluoro-5-methyl-6-oxo-7-(trifluoromethyl)-6,7,8,9-tetrahydro-5H-pyrimido[4,5-b][1,4]diazepin-2-ylamino)-3-methoxy-N-(1-methylpiperidin-4-yl)benzamide;
4-(9-Cyclopentyl-7-fluoro-5,7-dimethyl-6-oxo-6,7,8,9-tetrahydro-5H-pyrimido[4,5-b][1,4]diazepin-2-ylamino)-3-methoxy-N-(1-methylpiperidin-4-yl)benzamide;
4-(9-cyclopentyl-7-fluoro-5,7-dimethyl-6-oxo-6,7,8,9-tetrahydro-5H-pyrimido[4,5-b][1,4]diazepin-2-ylamino)-3-methoxy-N-(1-methylpiperidin-4-yl)benzamide;
4-(9-Cyclopentyl-7-fluoro-5,7-dimethyl-6-oxo-6,7,8,9-tetrahydro-5H-pyrimido[4,5-b][1,4]diazepin-2-ylamino)-3-methoxy-N-(1-methylazetidin-3-yl)benzamide;
4-(9-Cyclohexyl-7-fluoro-5,7-dimethyl-6-oxo-6,7,8,9-tetrahydro-5H-pyrimido[4,5-b][1,4]diazepin-2-ylamino)-3-methoxy-N-(1-methylpiperidin-4-yl)benzamide;
4-(9-Cyclohexyl-7-fluoro-5,7-dimethyl-6-oxo-6,7,8,9-tetrahydro-5H-pyrimido[4,5-b][1,4]diazepin-2-ylamino)-3-methoxy-N-(1-methylazetidin-3-yl)benzamide;
(R)-4-(9-cyclopentyl-7-ethyl-7-fluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide;
4-(9-Cyclopentyl-7-ethyl-7-fluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide;
(R)-4-(9-cyclopentyl-7-ethyl-7-fluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide;
(S)-4-(9-cyclopentyl-7-ethyl-7-fluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide;
4-(9-Cyclopentyl-7-ethyl-7-fluoro-5-methyl-6-oxo-6,7,8,9-tetrahydro-5H-pyrimido[4,5-b][1,4]diazepin-2-ylamino)-3-methoxy-N-(1-methylazetidin-3-yl)benzamide;
4-(9-Cyclohexyl-7-ethyl-7-fluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide;
4-(9-Cyclohexyl-7-ethyl-7-fluoro-5-methyl-6-oxo-6,7,8,9-tetrahydro-5H-pyrimido[4,5-b][1,4]diazepin-2-ylamino)-3-methoxy-N-(1-methylazetidin-3-yl)benzamide;
4-(9-cyclopentyl-7-fluoro-5-methyl-6-oxo-7-vinyl-6,7,8,9-tetrahydro-5H-pyrimido[4,5-b][1,4]diazepin-2-ylamino)-3-methoxybenzoic acid;
4-(9-cyclopentyl-7-fluoro-5-methyl-6-oxo-7-vinyl-6,7,8,9-tetrahydro-5H-pyrimido[4,5-b][1,4]diazepin-2-ylamino)-3-methoxy-N-(1-methylpiperidin-4-yl)benzamide;
4-(9-cyclopentyl-7-fluoro-5-methyl-6-oxo-7-vinyl-6,7,8,9-tetrahydro-5H-pyrimido[4,5-b][1,4]diazepin-2-ylamino)-3-methoxy-N-(1-methylazetidin-3-yl)benzamide;
4-(9-cyclopentyl-7-fluoro-5-methyl-6-oxo-7-vinyl-6,7,8,9-tetrahydro-5H-pyrimido[4,5-b][1,4]diazepin-2-ylamino)-3-methoxy-N-(4-methylpiperazin-1-yl)benzamide;
4-(9-cyclopentyl-7-fluoro-5-methyl-6-oxo-7-vinyl-6,7,8,9-tetrahydro-5H-pyrimido[4,5-b][1,4]diazepin-2-ylamino)-3-methoxy-N—((R)-piperidin-3-yl)benzamide;
(R)-4-(9-cyclopentyl-7-fluoro-5-methyl-6-oxo-7-vinyl-6,7,8,9-tetrahydro-5H-pyrimido[4,5-b][1,4]diazepin-2-ylamino)-3-methoxy-N-(1-methylpiperidin-4-yl)benzamide;
(S)-4-(9-cyclopentyl-7-fluoro-5-methyl-6-oxo-7-vinyl-6,7,8,9-tetrahydro-5H-pyrimido[4,5-b][1,4]diazepin-2-ylamino)-3-methoxy-N-(1-methylpiperidin-4-yl)benzamide;
(R)-4-(9-cyclopentyl-7-fluoro-5-methyl-6-oxo-7-vinyl-6,7,8,9-tetrahydro-5H-pyrimido[4,5-b][1,4]diazepin-2-ylamino)-N-(1-ethylpiperidin-4-yl)-3-methoxybenzamide;
(R)-4-(9-cyclopentyl-7-fluoro-5-methyl-6-oxo-7-vinyl-6,7,8,9-tetrahydro-5H-pyrimido[4,5-b][1,4]diazepin-2-ylamino)-N-(1-(2-hydroxyethyl)piperidin-4-yl)-3-methoxybenzamide;
4-((R)-9-cyclopentyl-7-fluoro-5-methyl-6-oxo-7-vinyl-6,7,8,9-tetrahydro-5H-pyrimido[4,5-b][1,4]diazepin-2-ylamino)-3-methoxy-N—((R)-piperidin-3-yl)benzamide;
(R)-4-(9-cyclopentyl-7-fluoro-5-methyl-6-oxo-7-vinyl-6,7,8,9-tetrahydro-5H-pyrimido[4,5-b][1,4]diazepin-2-ylamino)-N-(1-(2-(dimethylamino)acetyl)piperidin-4-yl)-3-methoxybenzamide;

(R)-4-(9-cyclopentyl-7-fluoro-5-methyl-6-oxo-7-vinyl-6,7,8,9-tetrahydro-5H-pyrimido[4,5-b][1,4]diazepin-2-ylamino)-3-methoxy-N-(4-methylpiperazin-1-yl)benzamide;

(S)-4-(9-cyclopentyl-7-fluoro-5-methyl-6-oxo-7-vinyl-6,7,8,9-tetrahydro-5H-pyrimido[4,5-b][1,4]diazepin-2-ylamino)-3-methoxy-N-(4-methylpiperazin-1-yl)benzamide;

(R)-2-(4-(4-(9-cyclopentyl-7-fluoro-5-methyl-6-oxo-7-vinyl-6,7,8,9-tetrahydro-5H-pyrimido[4,5-b][1,4]diazepin-2-ylamino)-3-methoxybenzamido) piperidin-1-yl)ethyl dihydrogen phosphate;

(R)-4-(9-cyclopentyl-7-fluoro-5-methyl-6-oxo-7-vinyl-6,7,8,9-tetrahydro-5H-pyrimido[4,5-b][1,4]diazepin-2-ylamino)-2-fluoro-5-methoxybenzoic acid;

(R)-4-(9-cyclopentyl-7-fluoro-5-methyl-6-oxo-7-vinyl-6,7,8,9-tetrahydro-5H-pyrimido[4,5-b][1,4]diazepin-2-ylamino)-2-fluoro-5-methoxy-N-(1-methylpiperidin-4-yl)benzamide;

N-(1-(2-amino-2-oxoethyl)piperidin-4-yl)-4-(9-cyclopentyl-7,7-difluoro-5-methyl-6-oxo-6,7,8,9-tetrahydro-5H-pyrimido[4,5-b][1,4]diazepin-2-ylamino)-3-methoxybenzamide;

4-(9-cyclopentyl-7,7-difluoro-5-methyl-6-oxo-6,7,8,9-tetrahydro-5H-pyrimido[4,5-b][1,4]diazepin-2-ylamino)-N-(1-(2-(dimethylamino)-2-oxoethyl)piperidin-4-yl)-3-methoxybenzamide;

4-(9-Cyclopentyl-7,7-difluoro-5-methyl-6-oxo-6,7,8,9-tetrahydro-5H-pyrimido[4,5-b][1,4]diazepin-2-ylamino)-2-fluoro-5-methoxy-N-(1-methylpiperidin-4-yl)benzamide;

4-(9-Cyclopentyl-7,7-difluoro-5-methyl-6-oxo-6,7,8,9-tetrahydro-5H-pyrimido[4,5-b][1,4]diazepin-2-ylamino)-2-fluoro-N-(1-(2-hydroxyethyl)piperidin-4-yl)-5-methoxybenzamide;

4-(9-Cyclopentyl-7,7-difluoro-5-methyl-6-oxo-6,7,8,9-tetrahydro-5H-pyrimido[4,5-b][1,4]diazepin-2-ylamino)-N-(1-(2-(dimethylamino)acetyl)piperidin-4-yl)-2-fluoro-5-methoxybenzamide;

(R)-4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxy-N-(piperidin-3-yl)benzamide;

9-Cyclopentyl-7,7-difluoro-2-(5-fluoro-2-methoxyphenylamino)-5-methyl-8,9-dihydro-5H-pyrimido[4,5-b][1,4]diazepin-6(7H)-one;

4-(9-Cyclopentyl-7,7-difluoro-5-methyl-6-oxo-6,7,8,9-tetrahydro-5H-pyrimido[4,5-b][1,4]diazepin-2-ylamino)-3-fluoro-5-methoxybenzoic acid;

4-(9-Cyclopentyl-7,7-difluoro-5-methyl-6-oxo-6,7,8,9-tetrahydro-5H-pyrimido[4,5-b][1,4]diazepin-2-ylamino)-3-fluoro-5-methoxy-N-(1-methylpiperidin-4-yl)benzamide;

4-(9-Cyclopentyl-7,7-difluoro-5-methyl-6-oxo-6,7,8,9-tetrahydro-5H-pyrimido[4,5-b][1,4]diazepin-2-ylamino)-2-fluoro-3-methoxybenzoic acid;

4-(9-Cyclopentyl-7,7-difluoro-5-methyl-6-oxo-6,7,8,9-tetrahydro-5H-pyrimido[4,5-b][1,4]diazepin-2-ylamino)-2-fluoro-3-methoxy-N-(1-methylpiperidin-4-yl)benzamide;

4-(9-cyclohexyl-7,7-difluoro-5-methyl-6-oxo-6,7,8,9-tetrahydro-5H-pyrimido[4,5-b][1,4]diazepin-2-ylamino)-N-(1-isopropylazetidin-3-yl)-3-methoxybenzamide;

4-(9-cyclohexyl-7,7-difluoro-5-methyl-6-oxo-6,7,8,9-tetrahydro-5H-pyrimido[4,5-b][1,4]diazepin-2-ylamino)-N-(1-ethylazetidin-3-yl)-3-methoxybenzamide;

N-(azetidin-3-yl)-4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxybenzamide;

4-(9-cyclopentyl-7,7-difluoro-5-methyl-6-oxo-6,7,8,9-tetrahydro-5H-pyrimido[4,5-b][1,4]diazepin-2-ylamino)-N-(1-ethylazetidin-3-yl)-3-methoxybenzamide;

4-(9-cyclopentyl-7,7-difluoro-5-methyl-6-oxo-6,7,8,9-tetrahydro-5H-pyrimido[4,5-b][1,4]diazepin-2-ylamino)-N-(1-isopropylazetidin-3-yl)-3-methoxybenzamide;

N-(azetidin-3-yl)-4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxybenzamide;

4-(9-cyclopentyl-7,7-difluoro-5-methyl-6-oxo-6,7,8,9-tetrahydro-5H-pyrimido[4,5-b][1,4]diazepin-2-ylamino)-N-(1-ethylazetidin-3-yl)-2-fluoro-5-methoxybenzamide;

4-(9-cyclopentyl-7,7-difluoro-5-methyl-6-oxo-6,7,8,9-tetrahydro-5H-pyrimido[4,5-b][1,4]diazepin-2-ylamino)-2-fluoro-N-(1-isopropylazetidin-3-yl)-5-methoxybenzamide;

4-(9-cyclopentyl-7,7-difluoro-5-methyl-6-oxo-6,7,8,9-tetrahydro-5H-pyrimido[4,5-b][1,4]diazepin-2-ylamino)-N-(1-cyclopentylazetidin-3-yl)-2-fluoro-5-methoxybenzamide;

9-cyclopentyl-2-(4-(4-(cyclopropylmethyl)piperazine-1-carbonyl)-2-methoxyphenylamino)-7,7-difluoro-5-methyl-8,9-dihydro-5H-pyrimido[4,5-b][1,4]diazepin-6(7H)-one;

9-cyclopentyl-2-(4-(4-(cyclopropylmethyl)piperazine-1-carbonyl)-5-fluoro-2-methoxyphenylamino)-7,7-difluoro-5-methyl-8,9-dihydro-5H-pyrimido[4,5-b][1,4]diazepin-6(7H)-one;

9-cyclopentyl-2-(2,2-difluorobenzo[d][1,3]dioxol-4-ylamino)-7,7-difluoro-5-methyl-8,9-dihydro-5H-pyrimido[4,5-b][1,4]diazepin-6(7H)-one;

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(2-(pyrrolidin-1-yl)ethyl)benzamide;

4-(9-cyclopentyl-7,7-difluoro-5-methyl-6-oxo-6,7,8,9-tetrahydro-5H-pyrimido[4,5-b][1,4]diazepin-2-ylamino)-3-methoxybenzamide;

4-(9-cyclopentyl-7,7-difluoro-5-methyl-6-oxo-6,7,8,9-tetrahydro-5H-pyrimido[4,5-b][1,4]diazepin-2-ylamino)-N-(2-(dimethylamino)ethyl)-3-methoxybenzamide;

4-(9-cyclopentyl-7,7-difluoro-5-methyl-6-oxo-6,7,8,9-tetrahydro-5H-pyrimido[4,5-b][1,4]diazepin-2-ylamino)-N-(2-hydroxyethyl)-3-methoxybenzamide;

4-(9-cyclopentyl-7,7-difluoro-5-methyl-6-oxo-6,7,8,9-tetrahydro-5H-pyrimido[4,5-b][1,4]diazepin-2-ylamino)-N-ethyl-3-methoxybenzamide 4-(9-cyclopentyl-7,7-difluoro-5-methyl-6-oxo-6,7,8,9-tetrahydro-5H-pyrimido[4,5-b][1,4]diazepin-2-ylamino)-N-(3-(dimethylamino)propyl)-3-methoxybenzamide;

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-methylbenzamide;

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N',N'-dimethylbenzohydrazide;

(S)-4-(9-cyclopentyl-7,7-difluoro-5-methyl-6-oxo-6,7,8,9-tetrahydro-5H-pyrimido[4,5-b][1,4]diazepin-2-ylamino)-N-(2-hydroxypropyl)-3-methoxybenzamide;

(R)-4-(9-cyclopentyl-7,7-difluoro-5-methyl-6-oxo-6,7,8,9-tetrahydro-5H-pyrimido[4,5-b][1,4]diazepin-2-ylamino)-N-(2-hydroxypropyl)-3-methoxybenzamide;

4-(9-cyclopentyl-7,7-difluoro-5-methyl-6-oxo-6,7,8,9-tetrahydro-5H-pyrimido[4,5-b][1,4]diazepin-2-ylamino)-N-((1S,2S)-2-hydroxycyclohexyl)-3-methoxybenzamide;

4-(9-cyclopentyl-7,7-difluoro-5-methyl-6-oxo-6,7,8,9-tetrahydro-5H-pyrimido[4,5-b][1,4]diazepin-2-ylamino)-N-((1S,2RS)-2-hydroxycyclohexyl)-3-methoxybenzamide;

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(piperidin-1-yl)benzamide;

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-morpholinobenzamide;

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(tetrahydro-2H-pyran-4-yl)benzamide;

4-(9-cyclopentyl-7,7-difluoro-5-methyl-6-oxo-6,7,8,9-tetrahydro-5H-pyrimido[4,5-b][1,4]diazepin-2-ylamino)-N-(4-(dimethylamino)cyclohexyl)-3-methoxybenzamide;

4-(9-cyclopentyl-7,7-difluoro-5-methyl-6-oxo-6,7,8,9-tetrahydro-5H-pyrimido[4,5-b][1,4]diazepin-2-ylamino)-N-(4-(2-hydroxyethyl)piperazin-1-yl)-3-methoxybenzamide;

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(2-oxoazepan-3-yl)benzamide;

(R)-4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(quinuclidin-3-yl)benzamide;

4-(9-cyclopentyl-7,7-difluoro-5-methyl-6-oxo-6,7,8,9-tetrahydro-5H-pyrimido[4,5-b][1,4]diazepin-2-ylamino)-N-(1-isopropylpiperidin-4-yl)-3-methoxybenzamide;

4-(9-cyclopentyl-7,7-difluoro-5-methyl-6-oxo-6,7,8,9-tetrahydro-5H-pyrimido[4,5-b][1,4]diazepin-2-ylamino)-N-(4-(2-hydroxyethyl)piperazin-1-yl)-3-methoxybenzamide;

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-((1R,5S)-8-methyl-8-azabicyclo[3.2.1]octan-3-yl)benzamide;

N-(1-acetylpiperidin-4-yl)-4-(9-cyclopentyl-7,7-difluoro-5-methyl-6-oxo-6,7,8,9-tetrahydro-5H-pyrimido[4,5-b][1,4]diazepin-2-ylamino)-3-methoxybenzamide;

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-(methylsulfonyl)piperidin-4-yl)benzamide;

4-(9-cyclopentyl-7,7-difluoro-5-methyl-6-oxo-6,7,8,9-tetrahydro-5H-pyrimido[4,5-b][1,4]diazepin-2-ylamino)-N-(4-cyclopentylpiperazin-1-yl)-3-methoxybenzamide;

(S)-4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(quinuclidin-3-yl)benzamide; and 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-(2,2,2-trifluoroethyl)piperidin-4-yl)benzamide.

In addition, particular examples of compounds according to the present invention include, but are not limited to:

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(2-(pyrrolidin-1-yl)ethyl)benzamide;

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-(2,2,2-trifluoroethyl)piperidin-4-yl)benzamide;

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-(methylsulfonyl)piperidin-4-yl)benzamide;

4-(9-cyclopentyl-7,7-difluoro-5-methyl-6-oxo-6,7,8,9-tetrahydro-5H-pyrimido[4,5-b][1,4]diazepin-2-ylamino)-N-((1S,2RS)-2-hydroxycyclohexyl)-3-methoxybenzamide;

4-(9-Cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylazetidin-3-yl)benzamide;

(R)-4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(piperidin-3-yl)benzamide;

(S)-4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(piperidin-3-yl)benzamide;

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(piperidin-4-yl)benzamide;

4-(9-cyclopentyl-7,7-difluoro-5-methyl-6-oxo-6,7,8,9-tetrahydro-5H-pyrimido[4,5-b][1,4]diazepin-2-ylamino)-N-(1-(2-(dimethylamino)acetyl)piperidin-4-yl)-3-methoxybenzamide;

4-(9-Cyclopentyl-7,7-difluoro-5-methyl-6-oxo-6,7,8,9-tetrahydro-5H-pyrimido[4,5-b][1,4]diazepin-2-ylamino)-3-fluoro-N-(1-methylpiperidin-4-yl)benzamide 4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide;

4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(4-methylpiperazin-1-yl)benzamide;

4-(9-Cyclohexyl-7,7-difluoro-5-methyl-6-oxo-6,7,8,9-tetrahydro-5H-pyrimido[4,5-b][1,4]diazepin-2-ylamino)-3-methoxy-N-(1-methylazetidin-3-yl)benzamide N-(azetidin-3-yl)-4-(9-cyclohexyl-7,7-difluoro-5-methyl-6-oxo-6,7,8,9-tetrahydro-5H-pyrimido[4,5-b][1,4]diazepin-2-ylamino)-3-methoxybenzamide;

4-(9-cyclohexyl-7,7-difluoro-5-methyl-6-oxo-6,7,8,9-tetrahydro-5H-pyrimido[4,5-b][1,4]diazepin-2-ylamino)-N-(1-(2-hydroxyethyl)piperidin-4-yl)-3-methoxybenzamide;

4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(1-(2,2,2-trifluoroethyl)piperidin-4-yl)benzamide;

(S)-4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(pyrrolidin-3-yl)benzamide;

4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(piperazin-1-yl)benzamide;

4-(9-cyclohexyl-7,7-difluoro-5-methyl-6-oxo-6,7,8,9-tetrahydro-5H-pyrimido[4,5-b][1,4]diazepin-2-ylamino)-N-(4-ethylpiperazin-1-yl)-3-methoxybenzamide;

4-(9-cyclohexyl-7,7-difluoro-5-methyl-6-oxo-6,7,8,9-tetrahydro-5H-pyrimido[4,5-b][1,4]diazepin-2-ylamino)-N-(4-(cyclopropylmethyl)piperazin-1-yl)-3-methoxybenzamidemethoxybenzamide;

4-(9-cyclohexyl-7,7-difluoro-5-methyl-6-oxo-6,7,8,9-tetrahydro-5H-pyrimido[4,5-b][1,4]diazepin-2-ylamino)-N-(4-(2-(dimethylamino)acetyl)piperazin-1-yl)-3-methoxybenzamide;

4-(9-Cyclohexyl-7-fluoro-5,7-dimethyl-6-oxo-6,7,8,9-tetrahydro-5H-pyrimido[4,5-b][1,4]diazepin-2-ylamino)-3-methoxy-N-(1-methylazetidin-3-yl)benzamide;

(R)-4-(9-cyclopentyl-7-fluoro-5-methyl-6-oxo-7-vinyl-6,7,8,9-tetrahydro-5H-pyrimido[4,5-b][1,4]diazepin-2-ylamino)-3-methoxy-N-(4-methylpiperazin-1-yl)benzamide; and 4-(9-Cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide.

Particular examples of compounds according to the present invention also include, but are not limited to:

(R)-4-(9-cyclopentyl-7-ethynyl-7-fluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide;

(R)-4-(9-cyclohexyl-7-ethynyl-7-fluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide;

(R)-4-(9-cyclobutyl-7-ethynyl-7-fluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide;

(R)-4-(9-cyclopentyl-7-ethynyl-7-fluoro-5-methyl-6-oxo-6,7,8,9-tetrahydro-5H-pyrimido[4,5-b][1,4]diazepin-2-ylamino)-3-methoxy-N-(1-methylazetidin-3-yl)benzamide;

4-((R)-9-cyclopentyl-7-ethynyl-7-fluoro-5-methyl-6-oxo-6,7,8,9-tetrahydro-5H-pyrimido[4,5-b][1,4]diazepin-2-ylamino)-3-fluoro-N—((R)-piperidin-3-yl)benzamide;

(R)-4-(9-cyclopentyl-7-ethynyl-7-fluoro-5-methyl-6-oxo-6,7,8,9-tetrahydro-5H-pyrimido[4,5-b][1,4]diazepin-2-ylamino)-N-(1-(2-hydroxyethyl)piperidin-4-yl)-3-methoxybenzamide;

4-((R)-9-cyclopentyl-7-ethynyl-7-fluoro-5-methyl-6-oxo-6,7,8,9-tetrahydro-5H-pyrimido[4,5-b][1,4]diazepin-2-ylamino)-3-methoxy-N—((R)-quinuclidin-3-yl)benzamide;

(R)-4-(9-cyclopentyl-7-fluoro-5-methyl-6-oxo-7-(prop-1-ynyl)-6,7,8,9-tetrahydro-5H-pyrimido[4,5-b][1,4]diazepin-2-ylamino)-3-methoxy-N-(1-methylpiperidin-4-yl)benzamide;

(S)-4-(9-cyclopentyl-7-ethynyl-7-fluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide;

(S)-4-(9-cyclohexyl-7-ethynyl-7-fluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide;

(S)-4-(9-cyclobutyl-7-ethynyl-7-fluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide; and N-(azepan-4-yl)-4-((R)-9-cyclopentyl-7-ethynyl-7-fluoro-5-methyl-6-oxo-6,7,8,9-tetrahydro-5H-pyrimido[4,5-b][1,4]diazepin-2-ylamino)-3-methoxybenzamide.

Further, particular examples of compounds according to the present invention include, but are not limited to:

4-(5-cyclopentyl-7,7-difluoro-6,7-dihydro-5H-imidazo[1,2-d]pyrimido[4,5-b][1,4]diazepin-3-ylamino)-3-methoxy-N-(1-methylpiperidin-4-yl)benzamide;

4-(5-cyclopentyl-7-fluoro-7-methyl-6,7-dihydro-5H-imidazo[1,2-d]pyrimido[4,5-b][1,4]diazepin-3-ylamino)-3-methoxy-N-(1-methylpiperidin-4-yl)benzamide;

4-(6-cyclopentyl-4,4-difluoro-5,6-dihydro-4H-pyrimido[4,5-b][1,2,4]triazolo[4,3-d][1,4]diazepin-8-ylamino)-3-methoxy-N-(1-methylpiperidin-4-yl)benzamide;

4-(6-cyclopentyl-4-fluoro-4-methyl-5,6-dihydro-4H-pyrimido[4,5-b][1,2,4]triazolo[4,3-d][1,4]diazepin-8-ylamino)-3-methoxy-N-(1-methylpiperidin-4-yl)benzamide;

4-(6-cyclopentyl-4,4-difluoro-5,6-dihydro-4H-pyrimido[4,5-b][1,2,4]triazolo[1,5-d][1,4]diazepin-8-ylamino)-3-methoxy-N-(1-methylpiperidin-4-yl)benzamide;

4-(6-cyclopentyl-4-fluoro-4-methyl-5,6-dihydro-4H-pyrimido[4,5-b][1,2,4]triazolo[1,5-d][1,4]diazepin-8-ylamino)-3-methoxy-N-(1-methylpiperidin-4-yl)benzamide;

4-(6-cyclopentyl-4,4-difluoro-5,6-dihydro-4H-pyrimido[4,5-b]tetrazolo[1,5-d][1,4]diazepin-8-ylamino)-3-methoxy-N-(1-methylpiperidin-4-yl)benzamide;

4-(6-cyclopentyl-4-fluoro-4-methyl-5,6-dihydro-4H-pyrimido[4,5-b]tetrazolo[1,5-d][1,4]diazepin-8-ylamino)-3-methoxy-N-(1-methylpiperidin-4-yl)benzamide;

4-(9-cyclopentyl-7,7-difluoro-6-(hydroxyimino)-5-methyl-6,7,8,9-tetrahydro-5H-pyrimido[5,4-b][1,4]diazepin-2-ylamino)-3-methoxy-N-(1-methylpiperidin-4-yl)benzamide;

4-(9-cyclopentyl-7-fluoro-6-(hydroxyimino)-5,7-dimethyl-6,7,8,9-tetrahydro-5H-pyrimido[5,4-b][1,4]diazepin-2-ylamino)-3-methoxy-N-(1-methylpiperidin-4-yl)benzamide;

4-(6-(cyanoimino)-9-cyclopentyl-7,7-difluoro-5-methyl-6,7,8,9-tetrahydro-5H-pyrimido[5,4-b][1,4]diazepin-2-ylamino)-3-methoxy-N-(1-methylpiperidin-4-yl)benzamide;

4-(6-(cyanoimino)-9-cyclopentyl-7-fluoro-5,7-dimethyl-6,7,8,9-tetrahydro-5H-pyrimido[5,4-b][1,4]diazepin-2-ylamino)-3-methoxy-N-(1-methylpiperidin-4-yl)benzamide;

4-(9-cyclopentyl-7,7-difluoro-6-(methoxyimino)-5-methyl-6,7,8,9-tetrahydro-5H-pyrimido[5,4-b][1,4]diazepin-2-ylamino)-3-methoxy-N-(1-methylpiperidin-4-yl)benzamide;

4-(9-cyclopentyl-7-fluoro-6-(methoxyimino)-5,7-dimethyl-6,7,8,9-tetrahydro-5H-pyrimido[5,4-b][1,4]diazepin-2-ylamino)-3-methoxy-N-(1-methylpiperidin-4-yl)benzamide;

4-(9-cyclopentyl-7,7-difluoro-5-methyl-6-(nitroimino)-6,7,8,9-tetrahydro-5H-pyrimido[5,4-b][1,4]diazepin-2-ylamino)-3-methoxy-N-(1-methylpiperidin-4-yl)benzamide; and 4-(9-cyclopentyl-7-fluoro-5,7-dimethyl-6-(nitroimino)-6,7,8,9-tetrahydro-5H-pyrimido[5,4-b][1,4]diazepin-2-ylamino)-3-methoxy-N-(1-methylpiperidin-4-yl)benzamide.

In addition, particular examples of compounds according to the present invention include, but are not limited to:

(4-(9-cyclopentyl-7,7-difluoro-5-methyl-6,7,8,9-tetrahydro-5H-pyrimido[4,5-b][1,4]diazepin-2-ylamino)-3-methoxyphenyl)methanol; and 4-(9-cyclopentyl-7,7-difluoro-5-methyl-6,7,8,9-tetrahydro-5H-pyrimido[4,5-b][1,4]diazepin-2-ylamino)-3-methoxy-N-(1-methylpiperidin-4-yl)benzamide.

Still further, particular examples of compounds according to the present invention include, but are not limited to:

3-(cyclopentyl(2-(2-methoxy-4-(1-methylpiperidin-4-ylcarbamoyl)phenylamino)-5-(methylamino)pyrimidin-4-yl)amino)-2,2-difluoropropanoic acid; and 3-(cyclopentyl(2-(5-fluoro-2-methoxy-4-(1-methylpiperidin-4-ylcarbamoyl)phenylamino)-5-(methylamino)pyrimidin-4-yl)amino)-2,2-difluoropropanoic acid.

In another of its aspects, the present invention relates to methods of making compounds that are useful as PLK inhibitors. In one embodiment, the methods comprise the steps of:

reacting a compound having the formula

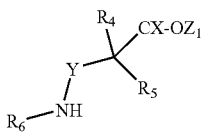

with a compound having the formula

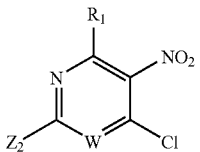

under conditions that form a first reaction product having the formula

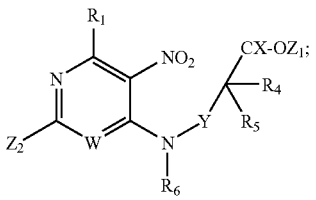

treating the first reaction product under conditions that form a second reaction product having the formula

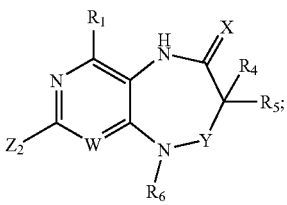

reacting the first reaction product with a compound having the formula

R$_2$—Z$_3$ under conditions that form a second reaction product having the formula

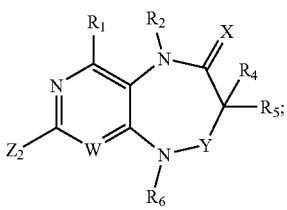

and
reacting the second reaction product with a compound having the formula

R$_7$-L-NR$_3$H under conditions that form a third reaction product having the formula

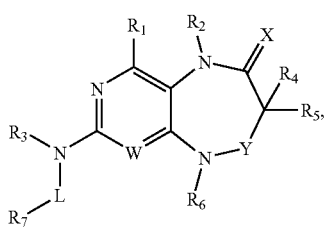

wherein
W is selected from the group consisting of CR$_8$ and N;
X is selected from the group consisting of NR$_{14}$, O and S;
Y is —(CR$_9$R$_{10}$)$_n$—;
n is selected from the group consisting of 1, 2, 3 and 4;
L is absent or a linker providing 1, 2, 3, 4, 5 or 6 atom separation between R$_7$ and the nitrogen to which L is attached, wherein the atoms of the linker providing the separation are selected from the group consisting of carbon, oxygen, nitrogen, and sulfur;
R$_1$ is selected from the group consisting of hydrogen, cyano, thio, hydroxy, carbonyloxy, alkoxy, aryloxy, heteroaryloxy, carbonyl, oxycarbonyl, amido, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-3}$)alkyl, thiocarbonyl(C$_{1-3}$)alkyl, sulfonyl (C$_{1-3}$)alkyl, sulfinyl(C$_{1-3}$)alkyl, (C$_{1-10}$)azaalkyl, imino (C$_{1-3}$)alkyl, (C$_{3-12}$)cycloalkyl(C$_{1-5}$)alkyl, hetero(C$_{3-12}$) cycloalkyl(C$_{1-5}$)alkyl, aryl(C$_{1-10}$)alkyl, heteroaryl (C$_{1-5}$)alkyl, (C$_{9-12}$)bicycloaryl(C$_{1-5}$)alkyl, hetero (C$_{8-12}$)bicycloaryl(C$_{1-5}$)alkyl, (C$_{3-12}$)cycloalkyl, hetero (C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted;
R$_2$ is selected from the group consisting of hydrogen, carbonyl, oxycarbonyl, sulfonyl, sulfinyl, (C$_{1-10}$)alkyl, halo (C$_{1-10}$)alkyl, carbonyl(C$_{1-3}$)alkyl, thiocarbonyl(C$_{1-3}$) alkyl, sulfonyl(C$_{1-3}$)alkyl, sulfinyl(C$_{1-3}$)alkyl, (C$_{1-10}$) azaalkyl, imino(C$_{1-3}$)alkyl, (C$_{3-12}$)cycloalkyl(C$_{1-5}$) alkyl, hetero(C$_{3-12}$)cycloalkyl(C$_{1-5}$)alkyl, aryl(C$_{1-10}$) alkyl, heteroaryl(C$_{1-5}$)alkyl, (C$_{9-12}$)bicycloaryl(C$_{1-5}$) alkyl, hetero(C$_{8-12}$)bicycloaryl(C$_{1-5}$)alkyl, (C$_{3-12}$) cycloalkyl, hetero(C$_{3-12}$)cycloalkyl, (C$_{9-12}$) bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$) bicycloaryl, each substituted or unsubstituted, or R$_2$ and R$_1$ or R$_{14}$ are taken together to form a substituted or unsubstituted ring;
R$_3$ is hydrogen or a substituent convertible in vivo to hydrogen;
R$_4$ is halo;
R$_5$ is selected from the group consisting of hydrogen, halo, nitro, cyano, thio, oxy, hydroxy, carbonyloxy, (C$_{1-10}$) alkoxy, (C$_{4-12}$)aryloxy, hetero(C$_{1-10}$)aryloxy, carbonyl, oxycarbonyl, amido, amino, (C$_{1-10}$)alkylamino, sulfonamido, imino, sulfonyl, sulfinyl, (C$_{1-10}$)alkyl, halo (C$_{1-10}$)alkyl, hydroxy(C$_{1-10}$)alkyl, carbonyl(C$_{1-10}$) alkyl, thiocarbonyl(C$_{1-10}$)alkyl, sulfonyl(C$_{1-10}$)alkyl, sulfinyl(C$_{1-10}$)alkyl, (C$_{1-10}$)azaalkyl, imino(C$_{1-10}$)alkyl, (C$_{3-12}$)cycloalkyl(C$_{1-5}$)alkyl, hetero(C$_{3-12}$)cycloalkyl (C$_{1-10}$)alkyl, aryl(C$_{1-10}$)alkyl, hetero(C$_{1-10}$)aryl(C$_{1-5}$) alkyl, (C$_{9-12}$)bicycloaryl(C$_{1-5}$)alkyl, hetero(C$_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_6$ is selected from the group consisting of hydrogen, carbonyl, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, ($C_{1-10}$)azaalkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_7$ is selected from the group consisting of ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_8$ is selected from the group consisting of hydrogen, halo, nitro, cyano, thio, oxy, hydroxy, carbonyloxy, alkoxy, aryloxy, heteroaryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, ($C_{1-10}$)azaalkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_9$ and $R_{10}$ are each independently selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, ($C_{1-10}$)azaalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_9$ and $R_{10}$ are taken together with the carbon to which they are attached to form C=O, C=S, C=$NR_{11}$ or C=$CR_{12}R_{13}$;

$R_{11}$ is selected from the group consisting of hydrogen, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_{12}$ and $R_{13}$ are each independently selected from the group consisting of hydrogen, halo, nitro, cyano, oxycarbonyl, amido, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_{14}$ is selected from the group consisting of ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

or any two $R_5$, $R_6$, $R_9$ and $R_{10}$ and are taken together to form a substituted or unsubstituted ring; and $Z_1$, $Z_2$ and $Z_3$ are each independently a leaving group.

In another embodiment, the methods comprise the steps of: reacting a compound having the formula

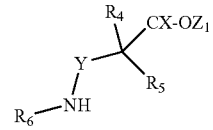

with a compound having the formula

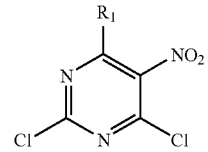

under conditions that form a first reaction product having the formula

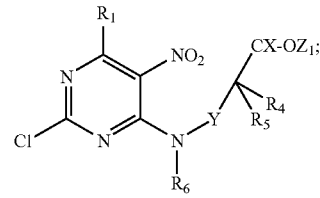

treating the first reaction product under conditions that form a second reaction product having the formula

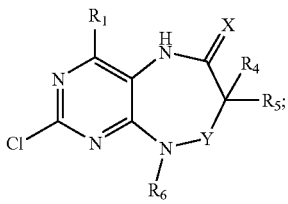

reacting the second reaction product with a compound having the formula

R₂—Z₃ under conditions that form a third reaction product having the formula

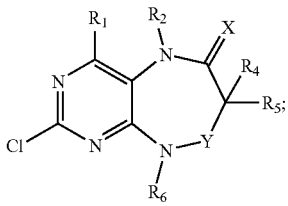

and
reacting the third reaction product with a compound having the formula

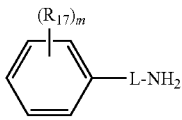

under conditions that form a fourth reaction product having the formula

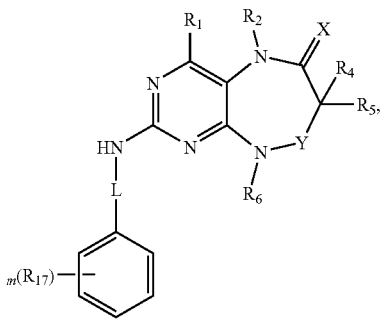

wherein
X is selected from the group consisting of NR₁₄, O and S;
Y is —(CR₉R₁₀)ₙ—;
n is selected from the group consisting of 1, 2, 3 and 4;
L is absent or a linker providing 1, 2, 3, 4, 5 or 6 atom separation between the ring and the nitrogen to which L is attached, wherein the atoms of the linker providing the separation are selected from the group consisting of carbon, oxygen, nitrogen, and sulfur;
R₁ is selected from the group consisting of hydrogen, cyano, thio, hydroxy, carbonyloxy, alkoxy, aryloxy, heteroaryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-3}$)alkyl, thiocarbonyl($C_{1-3}$)alkyl, sulfonyl ($C_{1-3}$)alkyl, sulfinyl($C_{1-3}$)alkyl, ($C_{1-10}$)azaalkyl, imino ($C_{1-3}$)alkyl, ($C_{3-12}$)cycloalkyl($C_{1-5}$)alkyl, hetero($C_{3-12}$) cycloalkyl($C_{1-5}$)alkyl, aryl($C_{1-10}$)alkyl, heteroaryl ($C_{1-5}$)alkyl, ($C_{9-12}$)bicycloaryl($C_{1-5}$)alkyl, hetero ($C_{8-12}$)bicycloaryl($C_{1-5}$)alkyl, ($C_{3-12}$)cycloalkyl, hetero ($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;
R₂ is selected from the group consisting of hydrogen, carbonyl, oxycarbonyl, sulfonyl, sulfinyl, ($C_{1-10}$)alkyl, halo ($C_{1-10}$)alkyl, carbonyl($C_{1-3}$)alkyl, thiocarbonyl($C_{1-3}$) alkyl, sulfonyl($C_{1-3}$)alkyl, sulfinyl($C_{1-3}$)alkyl, ($C_{1-10}$) azaalkyl, imino($C_{1-3}$)alkyl, ($C_{3-12}$)cycloalkyl($C_{1-5}$) alkyl, hetero($C_{3-12}$)cycloalkyl($C_{1-5}$)alkyl, aryl($C_{1-10}$) alkyl, heteroaryl($C_{1-5}$)alkyl, ($C_{9-12}$)bicycloaryl($C_{1-5}$) alkyl, hetero($C_{8-12}$)bicycloaryl($C_{1-5}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$) bicycloaryl, each substituted or unsubstituted, or R₂ and R₁ or R₁₄ are taken together to form a substituted or unsubstituted ring;
R₄ is halo;
R₅ is selected from the group consisting of hydrogen, halo, nitro, cyano, thio, oxy, hydroxy, carbonyloxy, ($C_{1-10}$) alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo ($C_{1-10}$)alkyl, hydroxy($C_{1-10}$)alkyl, carbonyl($C_{1-10}$) alkyl, thiocarbonyl($C_{1-10}$)alkyl, sulfonyl($C_{1-10}$)alkyl, sulfinyl($C_{1-10}$)alkyl, ($C_{1-10}$)azaalkyl, imino($C_{1-10}$)alkyl, ($C_{3-12}$)cycloalkyl($C_{1-5}$)alkyl, hetero($C_{3-12}$)cycloalkyl ($C_{1-10}$)alkyl, aryl($C_{1-10}$)alkyl, hetero($C_{1-10}$)aryl($C_{1-5}$) alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$) cycloalkyl, ($C_{9-12}$)bicycloalkyl, hetero($C_{3-12}$) bicycloalkyl, ($C_{4-12}$)aryl, hetero($C_{1-10}$)aryl, ($C_{9-12}$) bicycloaryl and hetero($C_{4-12}$)bicycloaryl, each substituted or unsubstituted;
R₆ is selected from the group consisting of hydrogen, carbonyl, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl ($C_{1-3}$)alkyl, sulfinyl($C_{1-3}$)alkyl, ($C_{1-10}$)azaalkyl, imino ($C_{1-3}$)alkyl, ($C_{3-12}$)cycloalkyl($C_{1-5}$)alkyl, hetero($C_{3-12}$) cycloalkyl($C_{1-5}$)alkyl, aryl($C_{1-10}$)alkyl, heteroaryl ($C_{1-5}$)alkyl, ($C_{9-12}$)bicycloaryl($C_{1-5}$)alkyl, hetero ($C_{8-12}$)bicycloaryl($C_{1-5}$)alkyl, ($C_{3-12}$)cycloalkyl, hetero ($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;
R₉ and R₁₀ are each independently selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy ($C_{1-10}$)alkyl, carbonyl($C_{1-10}$)alkyl, thiocarbonyl($C_{1-10}$) alkyl, sulfonyl($C_{1-10}$)alkyl, sulfinyl($C_{1-10}$)alkyl, ($C_{1-10}$) azaalkyl, imino($C_{1-10}$)alkyl, ($C_{3-12}$)cycloalkyl($C_{1-5}$) alkyl, hetero($C_{3-12}$)cycloalkyl($C_{1-10}$)alkyl, aryl($C_{1-10}$) alkyl, hetero($C_{1-10}$)aryl($C_{1-5}$)alkyl, ($C_{9-12}$)bicycloaryl ($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_9$ and $R_{10}$ are taken together with the carbon to which they are attached to form C=O, C=S, C=$NR_{11}$ or C=$CR_{12}R_{13}$;

$R_{11}$ is selected from the group consisting of hydrogen, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_{12}$ and $R_{13}$ are each independently selected from the group consisting of hydrogen, halo, nitro, cyano, oxycarbonyl, amido, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted; and $R_{14}$ is selected from the group consisting of ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, m is selected from the group consisting of 0, 1, 2, 3, 4 and 5;

each $R_{17}$ is independently selected from the group consisting of halo, nitro, cyano, thio, oxy, hydroxy, carbonyloxy, alkoxy, aryloxy, heteroaryloxy, carbamoyloxy, carbonyl, oxycarbonyl, amido, amino, ($C_{1-10}$)alkylamino, sulfonamido, carboxyamino, ureido, imino, sulfonyl, aminosulfonyl, sulfinyl, ($C_{1-10}$)alkyl, halo($C_{1-10}$)alkyl, hydroxy($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, ($C_{1-10}$)azaalkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or two $R_{17}$ are taken together to form a substituted or unsubstituted ring; and $Z_1$ and $Z_3$ are each independently a leaving group.

In still another embodiment, the methods comprise the steps of:

treating a compound having the formula

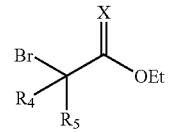

under conditions that form a first reaction product having the formula

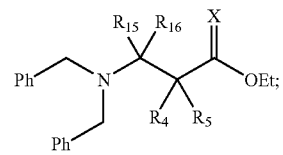

treating the first reaction product under conditions that form a second reaction product having the formula

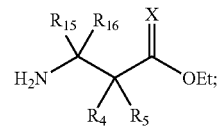

treating the second reaction product under conditions that form a third reaction product having the formula

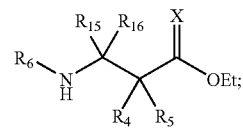

reacting the third reaction product with a compound having the formula

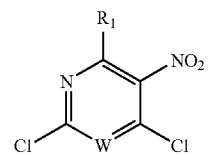

under conditions that form a fourth reaction product having the formula

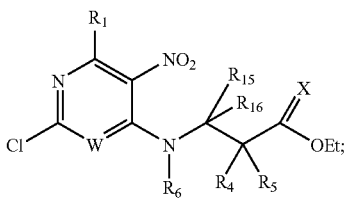

treating the fourth reaction product under conditions that form a fifth reaction product having the formula

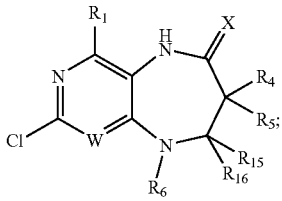

reacting the fifth reaction product with a compound having the formula

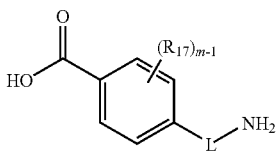

under conditions that form a sixth reaction product having the formula

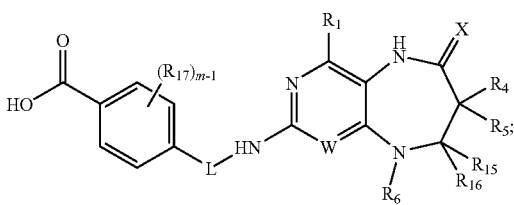

reacting the sixth reaction product with a compound having the formula $R_2—Z_3$ under conditions that form a seventh reaction product having the formula

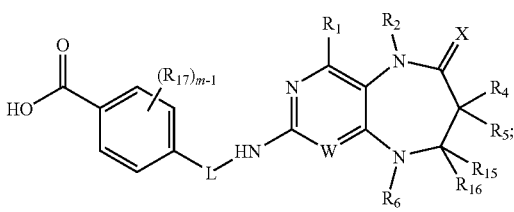

and
reacting the seventh reaction product with a compound having the formula $NHR_{19}R_{20}$ under conditions that form an eighth reaction product having the formula

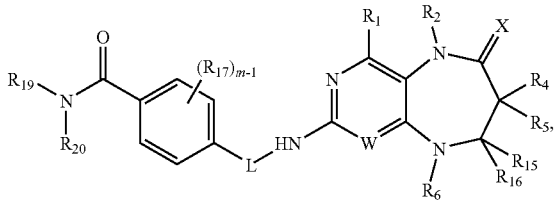

wherein

W is selected from the group consisting of $CR_8$ and N;

X is selected from the group consisting of $NR_{14}$, O and S;

L is absent or a linker providing 1, 2, 3, 4, 5 or 6 atom separation between the ring and the nitrogen to which L is attached, wherein the atoms of the linker providing the separation are selected from the group consisting of carbon, oxygen, nitrogen, and sulfur;

$R_1$ is selected from the group consisting of hydrogen, cyano, thio, hydroxy, carbonyloxy, alkoxy, aryloxy, heteroaryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, $(C_{1-10})$azaalkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_2$ is selected from the group consisting of hydrogen, carbonyl, oxycarbonyl, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, $(C_{1-10})$azaalkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_2$ and $R_1$ or $R_{14}$ are taken together to form a substituted or unsubstituted ring;

$R_4$ is halo;

$R_5$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$ bicycloaryl and hetero($C_{4-12}$)bicycloaryl, each substituted or unsubstituted;

$R_6$ is selected from the group consisting of hydrogen, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, ($C_{1-10}$)azaalkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_8$ is selected from the group consisting of hydrogen, halo, nitro, cyano, thio, oxy, hydroxy, carbonyloxy, alkoxy, aryloxy, heteroaryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, ($C_{1-10}$)azaalkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_{14}$ is selected from the group consisting of ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_{15}$ and $R_{16}$ are each independently selected from the group consisting of hydrogen, cyano, carbonyl, oxycarbonyl, amido, ($C_{1-10}$)alkyl, halo($C_{1-10}$)alkyl, hydroxy($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, ($C_{1-10}$)azaalkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_{14}$ and $R_{15}$ are taken together with the atom to which they are bound to form a carbonyl or imino group;

m is selected from the group consisting of 0, 1, 2, 3, 4 and 5;

each $R_{17}$ is independently selected from the group consisting of halo, nitro, cyano, thio, oxy, hydroxy, carbonyloxy, alkoxy, aryloxy, heteroaryloxy, carbamoyloxy, carbonyl, oxycarbonyl, amido, amino, ($C_{1-10}$)alkylamino, sulfonamido, carboxyamino, ureido, imino, sulfonyl, aminosulfonyl, sulfinyl, ($C_{1-10}$)alkyl, halo($C_{1-10}$)alkyl, hydroxy($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, ($C_{1-10}$)azaalkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or two $R_{17}$ are taken together to form a substituted or unsubstituted ring;

$R_{19}$ are $R_{20}$ are each independently selected from the group consisting of hydrogen, oxy, hydroxy, carbonyloxy, alkoxy, aryloxy, heteroaryloxy, carbonyl, oxycarbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, ($C_{1-10}$)azaalkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_{19}$ and $R_{20}$ are taken together to form a substituted or unsubstituted ring, or $R_{19}$ is a substituent convertible in vivo into hydroxyl; and $Z_3$ is a leaving group.

In yet another embodiment, the methods comprise the steps of:

treating a compound having the formula

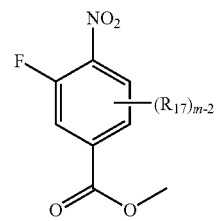

under conditions that form a first reaction product having the formula

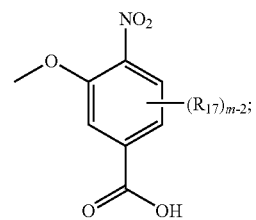

treating the first reaction product under conditions that form a second reaction product having the formula

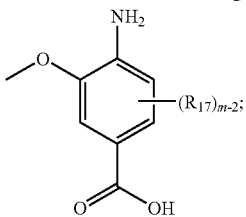

reacting the second reaction product with a compound having the formula

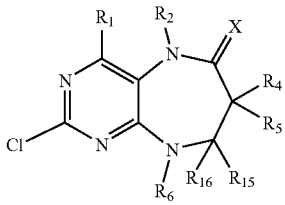

under conditions that form a third reaction product having the formula

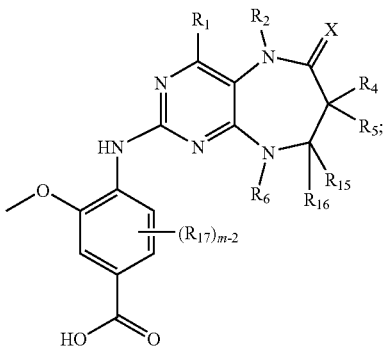

and
reacting the third reaction product with a compound having the formula $NHR_{19}R_{20}$ under conditions that form a fourth reaction product having the formula

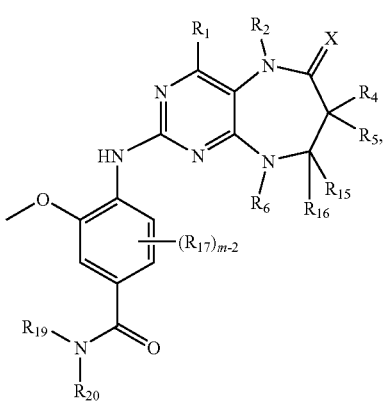

wherein
X is selected from the group consisting of $NR_{14}$, O and S;
$R_1$ is selected from the group consisting of hydrogen, cyano, thio, hydroxy, carbonyloxy, alkoxy, aryloxy, heteroaryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-3})$alkyl, thiocarbonyl$(C_{1-3})$alkyl, sulfonyl $(C_{1-3})$alkyl, sulfinyl$(C_{1-3})$alkyl, $(C_{1-10})$azaalkyl, imino $(C_{1-3})$alkyl, $(C_{3-12})$cycloalkyl$(C_{1-5})$alkyl, hetero$(C_{3-12})$ cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero $(C_{8-12})$bicycloaryl$(C_{1-5})$alkyl, $(C_{3-12})$cycloalkyl, hetero $(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_2$ is selected from the group consisting of hydrogen, carbonyl, oxycarbonyl, sulfonyl, sulfinyl, $(C_{1-10})$alkyl, halo $(C_{1-10})$alkyl, carbonyl$(C_{1-3})$alkyl, thiocarbonyl$(C_{1-3})$ alkyl, sulfonyl$(C_{1-3})$alkyl, sulfinyl$(C_{1-3})$alkyl, $(C_{1-10})$ azaalkyl, imino$(C_{1-3})$alkyl, $(C_{3-12})$cycloalkyl$(C_{1-5})$ alkyl, hetero$(C_{3-12})$cycloalkyl$(C_{1-5})$alkyl, aryl$(C_{1-10})$ alkyl, heteroaryl$(C_{1-5})$alkyl, $(C_{9-12})$bicycloaryl$(C_{1-5})$ alkyl, hetero$(C_{8-12})$bicycloaryl$(C_{1-5})$alkyl, $(C_{3-12})$ cycloalkyl, hetero$(C_{3-12})$cycloalkyl, $(C_{9-12})$ bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$ bicycloaryl, each substituted or unsubstituted, or $R_2$ and $R_1$ or $R_{14}$ are taken together to form a substituted or unsubstituted ring;

$R_4$ is halo;

$R_5$ is selected from the group consisting of hydrogen, halo, nitro, cyano, thio, oxy, hydroxy, carbonyloxy, $(C_{1-10})$ alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo $(C_{1-10})$alkyl, hydroxy$(C_{1-10})$alkyl, carbonyl$(C_{1-10})$ alkyl, thiocarbonyl$(C_{1-10})$alkyl, sulfonyl$(C_{1-10})$alkyl, sulfinyl$(C_{1-10})$alkyl, $(C_{1-10})$azaalkyl, imino$(C_{1-10})$alkyl, $(C_{3-12})$cycloalkyl$(C_{1-5})$alkyl, hetero$(C_{3-12})$cycloalkyl $(C_{1-10})$alkyl, aryl$(C_{1-10})$alkyl, hetero$(C_{1-10})$aryl$(C_{1-5})$ alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$ cycloalkyl, $(C_{9-12})$bicycloalkyl, hetero$(C_{3-12})$ bicycloalkyl, $(C_{4-12})$aryl, hetero$(C_{1-10})$aryl, $(C_{9-12})$ bicycloaryl and hetero$(C_{4-12})$bicycloaryl, each substituted or unsubstituted;

$R_6$ is selected from the group consisting of hydrogen, carbonyl, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl $(C_{1-3})$alkyl, sulfinyl$(C_{1-3})$alkyl, $(C_{1-10})$azaalkyl, imino $(C_{1-3})$alkyl, $(C_{3-12})$cycloalkyl$(C_{1-5})$alkyl, hetero$(C_{3-12})$ cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero $(C_{8-12})$bicycloaryl$(C_{1-5})$alkyl, $(C_{3-12})$cycloalkyl, hetero $(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_{14}$ is selected from the group consisting of $(C_{1-10})$alkyl, halo$(C_{1-10})$alkyl, hydroxy$(C_{1-10})$alkyl, carbonyl$(C_{1-10})$ alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cycloalkyl$(C_{1-5})$alkyl, hetero$(C_{3-12})$cycloalkyl $(C_{1-10})$alkyl, aryl$(C_{1-10})$alkyl, hetero$(C_{1-10})$aryl$(C_{1-5})$ alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$ cycloalkyl, hetero$(C_{3-12})$cycloalkyl, $(C_{9-12})$ bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$ bicycloaryl, each substituted or unsubstituted, R$_{15}$ and R$_{16}$ are each independently selected from the group consisting of hydrogen, cyano, carbonyl, oxycarbonyl, amido, (C$_{1-10}$)alkyl, halo(C$_{1-10}$)alkyl, hydroxy (C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, (C$_{1-10}$)azaalkyl, imino(C$_{1-3}$)alkyl, (C$_{3-12}$)cycloalkyl(C$_{1-5}$)alkyl, hetero(C$_{3-12}$)cycloalkyl(C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted, or R$_{14}$ and R$_{15}$ are taken together with the atom to which they are bound to form a carbonyl or imino group;

m is selected from the group consisting of 2, 3, 4 and 5;

each R$_{17}$ is independently selected from the group consisting of halo, nitro, cyano, thio, oxy, hydroxy, carbonyloxy, alkoxy, aryloxy, heteroaryloxy, carbamoyloxy, carbonyl, oxycarbonyl, amido, amino, (C$_{1-10}$)alkylamino, sulfonamido, carboxyamino, ureido, imino, sulfonyl, aminosulfonyl, sulfinyl, (C$_{1-10}$)alkyl, halo(C$_{1-10}$)alkyl, hydroxy(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, (C$_{1-10}$)azaalkyl, imino(C$_{1-3}$)alkyl, (C$_{3-12}$)cycloalkyl(C$_{1-5}$)alkyl, hetero(C$_{3-12}$)cycloalkyl(C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted, or two R$_{17}$ are taken together to form a substituted or unsubstituted ring; and R$_{19}$ are R$_{20}$ are each independently selected from the group consisting of hydrogen, oxy, hydroxy, carbonyloxy, alkoxy, aryloxy, heteroaryloxy, carbonyl, oxycarbonyl, amino, (C$_{1-10}$)alkylamino, sulfonamido, imino, sulfonyl, sulfinyl, (C$_{1-10}$)alkyl, halo(C$_{1-10}$)alkyl, carbonyl (C$_{1-3}$)alkyl, thiocarbonyl(C$_{1-3}$)alkyl, sulfonyl(C$_{1-3}$)alkyl, sulfinyl(C$_{1-3}$)alkyl, (C$_{1-10}$)azaalkyl, imino(C$_{1-3}$)alkyl, (C$_{3-12}$)cycloalkyl(C$_{1-5}$)alkyl, hetero(C$_{3-12}$)cycloalkyl(C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted, or R$_{19}$ and R$_{20}$ are taken together to form a substituted or unsubstituted ring, or R$_{19}$ is a substituent convertible in vivo into hydroxy.

In a further embodiment, the methods comprise the steps of:

treating a compound having the formula

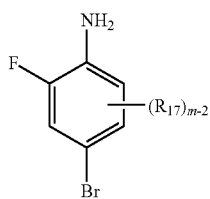

under conditions that form a first reaction product having the formula

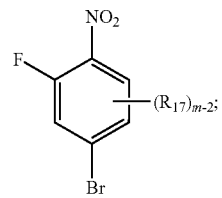

treating the first reaction product under conditions that form a second reaction product having the formula

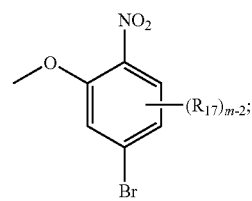

treating the second reaction product under conditions that form a third reaction product having the formula

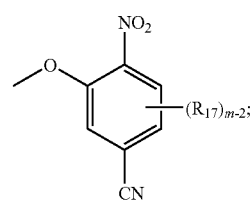

treating the third reaction product under conditions that form a fourth reaction product having the formula

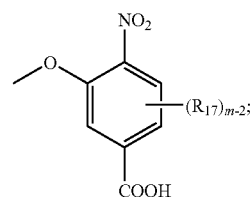

treating the fourth reaction product under conditions that form a fifth reaction product having the formula

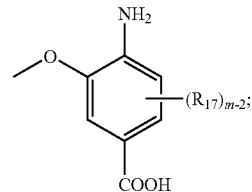

reacting the fifth reaction product with a compound having the formula

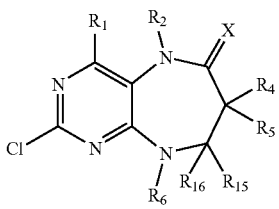

under conditions that form a sixth reaction product having the formula

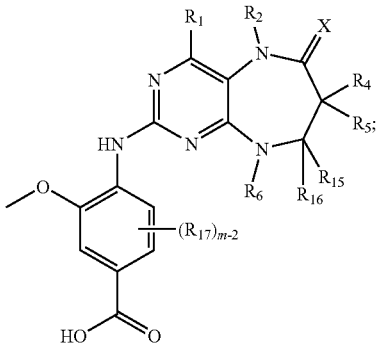

and reacting the sixth reaction product with a compound having the formula

NHR₁₉R₂₀ under conditions that form a seventh reaction product having the formula

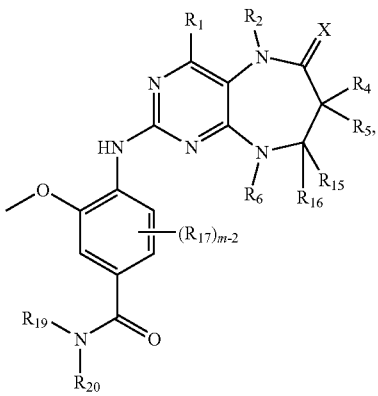

wherein

X is selected from the group consisting of NR$_{14}$, O and S;

R$_1$ is selected from the group consisting of hydrogen, cyano, thio, hydroxy, carbonyloxy, alkoxy, aryloxy, heteroaryloxy, carbonyl, oxycarbonyl, amido, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, (C$_{1-10}$)azaalkyl, imino(C$_{1-3}$)alkyl, (C$_{3-12}$)cycloalkyl(C$_{1-5}$)alkyl, hetero(C$_{3-12}$)cycloalkyl(C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted;

R$_2$ is selected from the group consisting of hydrogen, carbonyl, oxycarbonyl, amino, (C$_{1-10}$)alkylamino, sulfonamido, imino, sulfonyl, sulfinyl, (C$_{1-10}$)alkyl, halo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, (C$_{1-10}$)azaalkyl, imino(C$_{1-3}$)alkyl, (C$_{3-12}$)cycloalkyl(C$_{1-5}$)alkyl, hetero(C$_{3-12}$)cycloalkyl(C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted, or R$_2$ and R$_1$ or R$_{14}$ are taken together to form a substituted or unsubstituted ring;

R$_4$ is halo;

R$_5$ is selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, amido, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, (C$_{1-10}$)azaalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted;

R$_6$ is selected from the group consisting of hydrogen, carbonyl, sulfonyl, sulfinyl, (C$_{1-10}$)alkyl, halo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, (C$_{1-10}$)azaalkyl, imino(C$_{1-3}$)alkyl, (C$_{3-12}$)cycloalkyl(C$_{1-5}$)alkyl, hetero(C$_{3-12}$)cycloalkyl(C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted;

R$_{14}$ is selected from the group consisting of (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted;

R$_{15}$ and R$_{16}$ are each independently selected from the group consisting of hydrogen, cyano, carbonyl, oxycarbonyl, amido, (C$_{1-10}$)alkyl, halo(C$_{1-10}$)alkyl, hydroxy(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, (C$_{1-10}$)azaalkyl, imino(C$_{1-3}$)alkyl, (C$_{3-12}$)cycloalkyl(C$_{1-5}$)alkyl, hetero(C$_{3-12}$)cycloalkyl(C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted, or R$_{14}$ and $R_{15}$ are taken together with the atom to which they are bound to form a carbonyl or imino group;

m is selected from the group consisting of 2, 3, 4 and 5;

each $R_{17}$ is independently selected from the group consisting of halo, nitro, cyano, thio, oxy, hydroxy, carbonyloxy, alkoxy, aryloxy, heteroaryloxy, carbamoyloxy, carbonyl, oxycarbonyl, amido, amino, $(C_{1-10})$alkylamino, sulfonamido, carboxyamino, ureido, imino, sulfonyl, aminosulfonyl, sulfinyl, $(C_{1-10})$alkyl, halo$(C_{1-10})$alkyl, hydroxy$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, $(C_{1-10})$azaalkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or two $R_{17}$ are taken together to form a substituted or unsubstituted ring; and $R_{19}$ are $R_{20}$ are each independently selected from the group consisting of hydrogen, oxy, hydroxy, carbonyloxy, alkoxy, aryloxy, heteroaryloxy, carbonyl, oxycarbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$alkyl, sulfinyl$(C_{1-3})$alkyl, $(C_{1-10})$azaalkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero $(C_{8-12})$bicycloaryl$(C_{1-5})$alkyl, $(C_{3-12})$cycloalkyl, hetero $(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_{19}$ and $R_{20}$ are taken together to form a substituted or unsubstituted ring, or $R_{19}$ is a substituent convertible in vivo into hydroxy.

In still a further embodiment, the methods comprise the steps of:

reacting a compound having the formula

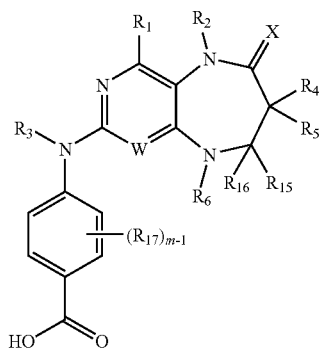

with a compound having the formula

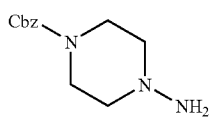

under conditions that form a first reaction product having the formula

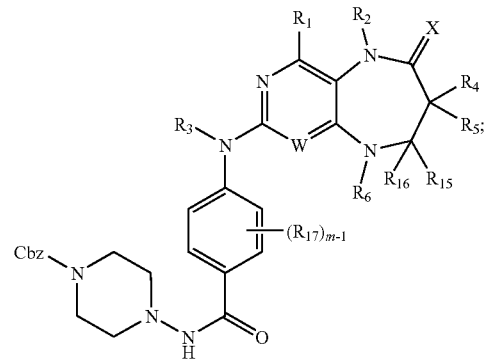

treating the first reaction product under conditions that form a second reaction product having the formula

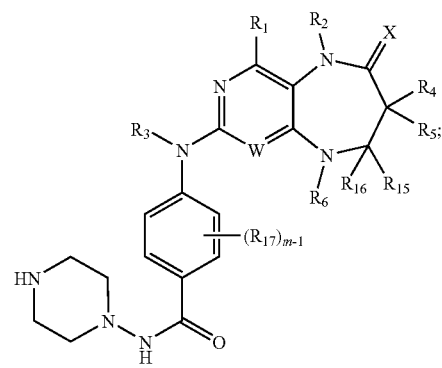

and reacting the second reaction product with a compound having the formula $R_{30}$—Br under conditions that form a third reaction product having the formula

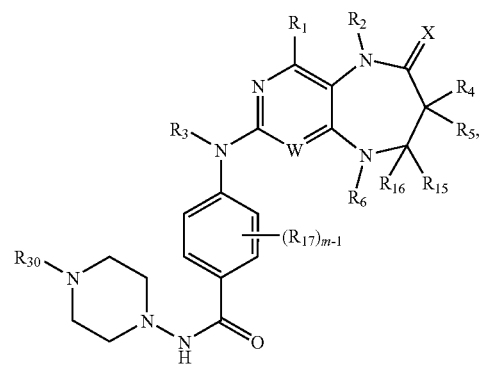

wherein

W is selected from the group consisting of $CR_8$ and N;

X is selected from the group consisting of $NR_{14}$, O and S;

$R_1$ is selected from the group consisting of hydrogen, cyano, thio, hydroxy, carbonyloxy, alkoxy, aryloxy, heteroaryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-3}$)alkyl, thiocarbonyl($C_{1-3}$)alkyl, sulfonyl ($C_{1-3}$)alkyl, sulfinyl($C_{1-3}$)alkyl, ($C_{1-10}$)azaalkyl, imino ($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl ($C_{1-5}$)alkyl, ($C_{9-12}$)bicycloaryl($C_{1-5}$)alkyl, hetero ($C_{8-12}$)bicycloaryl($C_{1-5}$)alkyl, ($C_{3-12}$)cycloalkyl, hetero ($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_2$ is selected from the group consisting of hydrogen, carbonyl, oxycarbonyl, sulfonyl, sulfinyl, ($C_{1-10}$)alkyl, halo ($C_{1-10}$)alkyl, carbonyl($C_{1-3}$)alkyl, thiocarbonyl($C_{1-3}$) alkyl, sulfonyl($C_{1-3}$)alkyl, sulfinyl($C_{1-3}$)alkyl, ($C_{1-10}$) azaalkyl, imino($C_{1-3}$)alkyl, ($C_{3-12}$)cycloalkyl($C_{1-5}$) alkyl, hetero($C_{3-12}$)cycloalkyl($C_{1-5}$)alkyl, aryl($C_{1-10}$) alkyl, heteroaryl($C_{1-5}$)alkyl, ($C_{9-12}$)bicycloaryl($C_{1-5}$) alkyl, hetero($C_{8-12}$)bicycloaryl($C_{1-5}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$) bicycloaryl, each substituted or unsubstituted, or $R_2$ and $R_1$ or $R_{14}$ are taken together to form a substituted or unsubstituted ring;

$R_3$ is hydrogen or a substituent convertible in vivo to hydrogen;

$R_4$ is halo;

$R_5$ is selected from the group consisting of hydrogen, halo, nitro, cyano, thio, oxy, hydroxy, carbonyloxy, ($C_{1-10}$) alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo ($C_{1-10}$)alkyl, hydroxy($C_{1-10}$)alkyl, carbonyl($C_{1-10}$) alkyl, thiocarbonyl($C_{1-10}$)alkyl, sulfonyl($C_{1-10}$)alkyl, sulfinyl($C_{1-10}$)alkyl, ($C_{1-10}$)azaalkyl, imino($C_{1-10}$)alkyl, ($C_{3-12}$)cycloalkyl($C_{1-5}$)alkyl, hetero($C_{3-12}$)cycloalkyl ($C_{1-10}$)alkyl, aryl($C_{1-10}$)alkyl, hetero($C_{1-10}$)aryl($C_{1-5}$) alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$) cycloalkyl, ($C_{9-12}$)bicycloalkyl, hetero($C_{3-12}$) bicycloalkyl, ($C_{4-12}$)aryl, hetero($C_{1-10}$)aryl, ($C_{9-12}$) bicycloaryl and hetero($C_{4-12}$)bicycloaryl, each substituted or unsubstituted;

$R_6$ is selected from the group consisting of hydrogen, carbonyl, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl ($C_{1-3}$)alkyl, sulfinyl($C_{1-3}$)alkyl, ($C_{1-10}$)azaalkyl, imino ($C_{1-3}$)alkyl, ($C_{3-12}$)cycloalkyl($C_{1-5}$)alkyl, hetero($C_{3-12}$) cycloalkyl($C_{1-5}$)alkyl, aryl($C_{1-10}$)alkyl, heteroaryl ($C_{1-5}$)alkyl, ($C_{9-12}$)bicycloaryl($C_{1-5}$)alkyl, hetero ($C_{8-12}$)bicycloaryl($C_{1-5}$)alkyl, ($C_{3-12}$)cycloalkyl, hetero ($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_8$ is selected from the group consisting of hydrogen, halo, nitro, cyano, thio, oxy, hydroxy, carbonyloxy, alkoxy, aryloxy, heteroaryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy ($C_{1-10}$)alkyl, carbonyl($C_{1-3}$)alkyl, thiocarbonyl($C_{1-3}$) alkyl, sulfonyl($C_{1-3}$)alkyl, sulfinyl($C_{1-3}$)alkyl, ($C_{1-10}$) azaalkyl, imino($C_{1-3}$)alkyl, ($C_{3-12}$)cycloalkyl($C_{1-5}$) alkyl, hetero($C_{3-12}$)cycloalkyl($C_{1-5}$)alkyl, aryl($C_{1-10}$) alkyl, heteroaryl($C_{1-5}$)alkyl, ($C_{9-12}$)bicycloaryl($C_{1-5}$) alkyl, hetero($C_{8-12}$)bicycloaryl($C_{1-5}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$) bicycloaryl, each substituted or unsubstituted;

$R_{14}$ is selected from the group consisting of ($C_{1-10}$)alkyl, halo($C_{1-10}$)alkyl, hydroxy($C_{1-10}$)alkyl, carbonyl($C_{1-10}$) alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl ($C_{1-10}$)alkyl, aryl($C_{1-10}$)alkyl, hetero($C_{1-10}$)aryl($C_{1-5}$) alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$) bicycloaryl, each substituted or unsubstituted;

$R_{15}$ and $R_{16}$ are each independently selected from the group consisting of hydrogen, cyano, carbonyl, oxycarbonyl, amido, ($C_{1-10}$)alkyl, halo($C_{1-10}$)alkyl, hydroxy ($C_{1-10}$)alkyl, carbonyl($C_{1-3}$)alkyl, thiocarbonyl($C_{1-3}$) alkyl, sulfonyl($C_{1-3}$)alkyl, sulfinyl($C_{1-3}$)alkyl, ($C_{1-10}$) azaalkyl, imino($C_{1-3}$)alkyl, ($C_{3-12}$)cycloalkyl($C_{1-5}$) alkyl, hetero($C_{3-12}$)cycloalkyl($C_{1-5}$)alkyl, aryl($C_{1-10}$) alkyl, heteroaryl($C_{1-5}$)alkyl, ($C_{9-12}$)bicycloaryl($C_{1-5}$) alkyl, hetero($C_{8-12}$)bicycloaryl($C_{1-5}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$) bicycloaryl, each substituted or unsubstituted, or $R_{14}$ and $R_{15}$ are taken together with the atom to which they are bound to form a carbonyl or imino group;

m is selected from the group consisting of 1, 2, 3, 4 and 5 (it being understood that m−1 is m as defined minus 1);

each $R_{17}$ is independently selected from the group consisting of halo, nitro, cyano, thio, oxy, hydroxy, carbonyloxy, alkoxy, aryloxy, heteroaryloxy, carbamoyloxy, carbonyl, oxycarbonyl, amido, amino, ($C_{1-10}$)alkylamino, sulfonamido, carboxyamino, ureido, imino, sulfonyl, aminosulfonyl, sulfinyl, ($C_{1-10}$)alkyl, halo($C_{1-10}$) alkyl, hydroxy($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, ($C_{1-10}$)azaalkyl, imino($C_{1-3}$)alkyl, ($C_{3-12}$) cycloalkyl($C_{1-5}$)alkyl, hetero($C_{3-12}$)cycloalkyl($C_{1-5}$) alkyl, aryl($C_{1-10}$)alkyl, heteroaryl($C_{1-5}$)alkyl, ($C_{9-12}$) bicycloaryl($C_{1-5}$)alkyl, hetero($C_{8-12}$)bicycloaryl($C_{1-5}$) alkyl, ($C_{3-12}$)cycloalkyl, hetero($C_{3-12}$)cycloalkyl, £ ($C_{9-12}$)bicycloalkyl, hetero($C_{3-12}$)bicycloalkyl, ($C_{4-12}$) aryl, hetero($C_{1-10}$)aryl, ($C_{9-12}$)bicycloaryl and hetero ($C_{4-12}$)bicycloaryl, each substituted or unsubstituted, or two $R_{17}$ are taken together to form a substituted or unsubstituted ring; and $R_{30}$ is selected from the group consisting of hydrogen, oxy, hydroxy, carbonyloxy, ($C_{1-10}$)alkoxy, ($C_{4-12}$)aryloxy, hetero($C_{1-10}$)aryloxy, carbonyl, oxycarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero ($C_{3-12}$)cycloalkyl($C_{1-10}$)alkyl, aryl($C_{1-10}$)alkyl, hetero ($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero ($C_{1-10}$)aryl, ($C_{9-12}$)bicycloaryl and hetero($C_{4-12}$)bicycloaryl, each substituted or unsubstituted, or $R_{30}$ is a substituent convertible in vivo into hydroxy, or $R_{29}$ and $R_{30}$ are taken together to form a substituted or unsubstituted ring.

In yet a further embodiment, the methods comprise the steps of:

reacting a compound having the formula

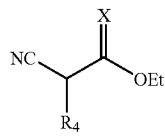

with a compound having the formula

under conditions that form a first reaction product having the formula

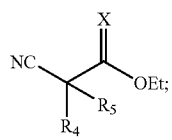

treating the first reaction product under conditions that form a second reaction product having the formula

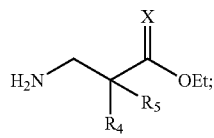

treating the second reaction product under conditions that form a third reaction product having the formula

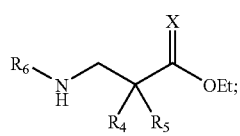

reacting the third reaction product with a compound having the formula

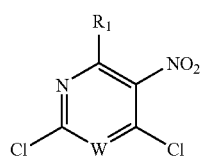

under conditions that form a fourth reaction product having the formula

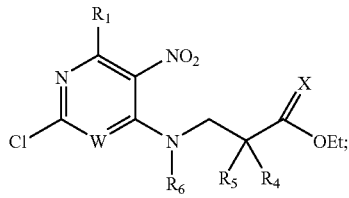

treating the fourth reaction product under conditions that form a fifth reaction product having the formula

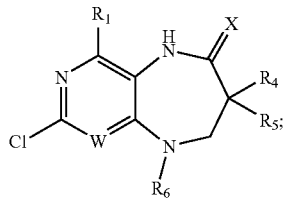

reacting the fifth reaction product with a compound having the formula

under conditions that form a sixth reaction product having the formula

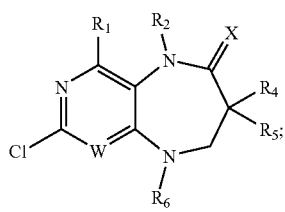

reacting the sixth reaction product with a compound having the formula

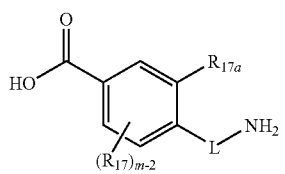

under conditions that form a seventh reaction product having the formula

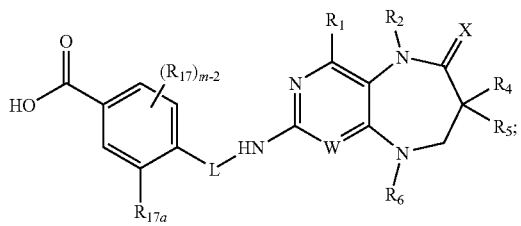

and
reacting the seventh reaction product with a compound having the formula

NHR$_{19}$R$_{20}$ under conditions that form a eighth reaction product having the formula

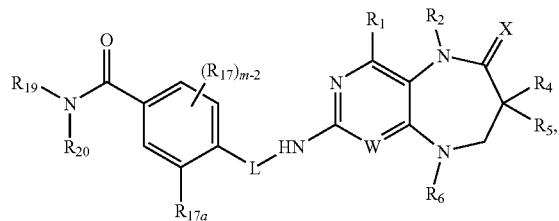

wherein
W is selected from the group consisting of CR$_8$ and N;
X is selected from the group consisting of NR$_{14}$, O and S;
L is absent or a linker providing 1, 2, 3, 4, 5 or 6 atom separation between the ring and the nitrogen to which L is attached, wherein the atoms of the linker providing the separation are selected from the group consisting of carbon, oxygen, nitrogen, and sulfur;
R$_1$ is selected from the group consisting of hydrogen, cyano, thio, hydroxy, carbonyloxy, alkoxy, aryloxy, heteroaryloxy, carbonyl, oxycarbonyl, amido, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-3}$)alkyl, thiocarbonyl(C$_{1-3}$)alkyl, sulfonyl (C$_{1-3}$)alkyl, sulfinyl(C$_{1-3}$)alkyl, (C$_{1-10}$)azaalkyl, imino (C$_{1-3}$)alkyl, (C$_{3-12}$)cycloalkyl(C$_{1-5}$)alkyl, hetero(C$_{3-12}$)cycloalkyl(C$_{1-5}$)alkyl, aryl(C$_{1-10}$)alkyl, heteroaryl (C$_{1-5}$)alkyl, (C$_{9-12}$)bicycloaryl(C$_{1-5}$)alkyl, hetero (C$_{8-12}$)bicycloaryl(C$_{1-5}$)alkyl, (C$_{3-12}$)cycloalkyl, hetero (C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted;
R$_2$ is selected from the group consisting of hydrogen, carbonyl, oxycarbonyl, sulfonyl, sulfinyl, (C$_{1-10}$)alkyl, halo (C$_{1-10}$)alkyl, carbonyl(C$_{1-3}$)alkyl, thiocarbonyl(C$_{1-3}$) alkyl, sulfonyl(C$_{1-3}$)alkyl, sulfinyl(C$_{1-3}$)alkyl, (C$_{1-10}$) azaalkyl, imino(C$_{1-3}$)alkyl, (C$_{3-12}$)cycloalkyl(C$_{1-5}$) alkyl, hetero(C$_{3-12}$)cycloalkyl(C$_{1-5}$)alkyl, aryl(C$_{1-10}$) alkyl, heteroaryl(C$_{1-5}$)alkyl, (C$_{9-12}$)bicycloaryl(C$_{1-5}$) alkyl, hetero(C$_{8-12}$)bicycloaryl(C$_{1-5}$)alkyl, (C$_{3-12}$) cycloalkyl, hetero(C$_{3-12}$)cycloalkyl, (C$_{9-12}$) bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$) bicycloaryl, each substituted or unsubstituted, or R$_2$ and R$_1$ or R$_{14}$ are taken together to form a substituted or unsubstituted ring;
R$_4$ is halo;
R$_5$ is selected from the group consisting of hydrogen, halo, nitro, cyano, thio, oxy, hydroxy, carbonyloxy, (C$_{1-10}$) alkoxy, (C$_{4-12}$)aryloxy, hetero(C$_{1-10}$)aryloxy, carbonyl, oxycarbonyl, amido, amino, (C$_{1-10}$)alkylamino, sulfonamido, imino, sulfonyl, sulfinyl, (C$_{1-10}$)alkyl, halo (C$_{1-10}$)alkyl, hydroxy(C$_{1-10}$)alkyl, carbonyl(C$_{1-10}$) alkyl, thiocarbonyl(C$_{1-10}$)alkyl, sulfonyl(C$_{1-10}$)alkyl, sulfinyl(C$_{1-10}$)alkyl, (C$_{1-10}$)azaalkyl, imino(C$_{1-10}$)alkyl, (C$_{3-12}$)cycloalkyl(C$_{1-5}$)alkyl, hetero(C$_{3-12}$)cycloalkyl (C$_{1-10}$)alkyl, aryl(C$_{1-10}$)alkyl, hetero(C$_{1-10}$)aryl(C$_{1-5}$) alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$) cycloalkyl, (C$_{9-12}$)bicycloalkyl, hetero(C$_{3-12}$) bicycloalkyl, (C$_{4-12}$)aryl, hetero(C$_{1-10}$)aryl, (C$_{9-12}$) bicycloaryl and hetero(C$_{4-12}$)bicycloaryl, each substituted or unsubstituted;
R$_6$ is selected from the group consisting of hydrogen, carbonyl, sulfonyl, sulfinyl, (C$_{1-10}$)alkyl, halo(C$_{1-10}$)alkyl, carbonyl(C$_{1-3}$)alkyl, thiocarbonyl(C$_{1-3}$)alkyl, sulfonyl (C$_{1-3}$)alkyl, sulfinyl(C$_{1-3}$)alkyl, (C$_{1-10}$)azaalkyl, imino (C$_{1-3}$)alkyl, (C$_{3-12}$)cycloalkyl(C$_{1-5}$)alkyl, hetero(C$_{3-12}$) cycloalkyl(C$_{1-5}$)alkyl, aryl(C$_{1-10}$)alkyl, heteroaryl (C$_{1-5}$)alkyl, (C$_{9-12}$)bicycloaryl(C$_{1-5}$)alkyl, hetero (C$_{8-12}$)bicycloaryl(C$_{1-5}$)alkyl, (C$_{3-12}$)cycloalkyl, hetero (C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted;
R$_8$ is selected from the group consisting of hydrogen, halo, nitro, cyano, thio, oxy, hydroxy, carbonyloxy, alkoxy, aryloxy, heteroaryloxy, carbonyl, oxycarbonyl, amido, amino, (C$_{1-10}$)alkylamino, sulfonamido, imino, sulfonyl, sulfinyl, (C$_{1-10}$)alkyl, halo(C$_{1-10}$)alkyl, hydroxy (C$_{1-10}$)alkyl, carbonyl(C$_{1-3}$)alkyl, thiocarbonyl(C$_{1-3}$) alkyl, sulfonyl(C$_{1-3}$)alkyl, sulfinyl(C$_{1-3}$)alkyl, (C$_{1-10}$) azaalkyl, imino(C$_{1-3}$)alkyl, (C$_{3-12}$)cycloalkyl(C$_{1-5}$) alkyl, hetero(C$_{3-12}$)cycloalkyl(C$_{1-5}$)alkyl, aryl(C$_{1-10}$) alkyl, heteroaryl(C$_{1-5}$)alkyl, (C$_{9-12}$)bicycloaryl(C$_{1-5}$) alkyl, hetero(C$_{8-12}$)bicycloaryl(C$_{1-5}$)alkyl, (C$_{3-12}$) cycloalkyl, hetero(C$_{3-12}$)cycloalkyl, (C$_{9-12}$) bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$) bicycloaryl, each substituted or unsubstituted;
R$_{14}$ is selected from the group consisting of (C$_{1-10}$)alkyl, halo(C$_{1-10}$)alkyl, hydroxy(C$_{1-10}$)alkyl, carbonyl(C$_{1-10}$) alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, imino(C$_{1-10}$)alkyl, (C$_{3-12}$)cycloalkyl(C$_{1-5}$)alkyl, hetero(C$_{3-12}$)cycloalkyl (C$_{1-10}$)alkyl, aryl(C$_{1-10}$)alkyl, hetero(C$_{1-10}$)aryl(C$_{1-5}$) alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$) cycloalkyl, hetero(C$_{3-12}$)cycloalkyl, (C$_{9-12}$) bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$) bicycloaryl, each substituted or unsubstituted;
m is selected from the group consisting of 2, 3, 4 and 5;
each R$_{17}$ is independently selected from the group consisting of halo, nitro, cyano, thio, oxy, hydroxy, carbonyloxy, alkoxy, aryloxy, heteroaryloxy, carbamoyloxy, carbonyl, oxycarbonyl, amido, amino, (C$_{1-10}$)alkylamino, sulfonamido, carboxyamino, ureido, imino, sulfonyl, aminosulfonyl, sulfinyl, (C$_{1-10}$)alkyl, halo(C$_{1-10}$) alkyl, hydroxy(C$_{1-10}$)alkyl, carbonyl(C$_{1-3}$)alkyl, thiocarbonyl(C$_{1-3}$)alkyl, sulfonyl(C$_{1-3}$)alkyl, sulfinyl (C$_{1-3}$)alkyl, (C$_{1-10}$)azaalkyl, imino(C$_{1-3}$)alkyl, (C$_{3-12}$) cycloalkyl(C$_{1-5}$)alkyl, hetero(C$_{3-12}$)cycloalkyl(C$_{1-5}$) alkyl, aryl(C$_{1-10}$)alkyl, heteroaryl(C$_{1-5}$)alkyl, (C$_{9-12}$) bicycloaryl(C$_{1-5}$)alkyl, hetero(C$_{8-12}$)bicycloaryl(C$_{1-5}$) alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$) aryl, hetero(C$_{1-10}$)aryl, (C$_{9-12}$)bicycloaryl and hetero (C$_{4-12}$)bicycloaryl, each substituted or unsubstituted, or two R$_{17}$ are taken together to form a substituted or unsubstituted ring;
R$_{17a}$ is selected from the group consisting of hydrogen, halo, nitro, cyano, thio, oxy, hydroxy, carbonyloxy, alkoxy, aryloxy, heteroaryloxy, carbamoyloxy, carbonyl, oxycarbonyl, amido, amino, (C$_{1-10}$)alkylamino, sulfonamido, carboxyamino, ureido, imino, sulfonyl, aminosulfonyl, sulfinyl, $(C_{1-10})$alkyl, halo$(C_{1-10})$alkyl, hydroxy$(C_{1-10})$alkyl, carbonyl$(C_{1-3})$alkyl, thiocarbonyl $(C_{1-3})$alkyl, sulfonyl$(C_{1-3})$alkyl, sulfinyl$(C_{1-3})$alkyl, $(C_{1-10})$azaalkyl, imino$(C_{1-3})$alkyl, $(C_{3-12})$cycloalkyl $(C_{1-5})$alkyl, hetero$(C_{3-12})$cycloalkyl$(C_{1-5})$alkyl, aryl $(C_{1-10})$alkyl, heteroaryl$(C_{1-5})$alkyl, $(C_{9-12})$bicycloaryl $(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_{19}$ are $R_{20}$ are each independently selected from the group consisting of hydrogen, oxy, hydroxy, carbonyloxy, alkoxy, aryloxy, heteroaryloxy, carbonyl, oxycarbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$ alkyl, sulfinyl$(C_{1-3})$alkyl, $(C_{1-10})$azaalkyl, imino$(C_{1-3})$ alkyl, $(C_{3-12})$cycloalkyl$(C_{1-5})$alkyl, hetero$(C_{3-12})$ cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero $(C_{8-12})$bicycloaryl$(C_{1-5})$alkyl, $(C_{3-12})$cycloalkyl, hetero $(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_{19}$ and $R_{20}$ are taken together to form a substituted or unsubstituted ring, or $R_{19}$ is a substituent convertible in vivo into hydroxyl; and $Z_4$ and $Z_5$ are each independently a leaving group.

In another embodiment, the methods comprise the steps of:

treating a compound having the formula

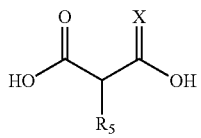

under conditions that form a first reaction product having the formula

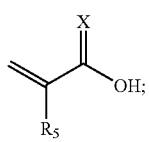

treating the first reaction product under conditions that form a second reaction product having the formula

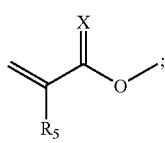

treating the second reaction product under conditions that form a third reaction product having the formula

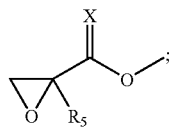

reacting the third reaction product with a compound having the formula $$R_6-NH_2$$

under conditions that form a fourth reaction product having the formula

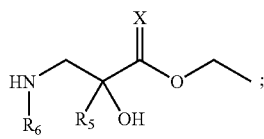

treating the fourth reaction product under conditions that form a fifth reaction product having the formula

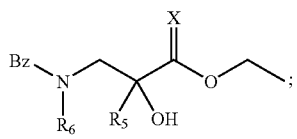

treating the fifth reaction product under conditions that form a sixth reaction product having the formula

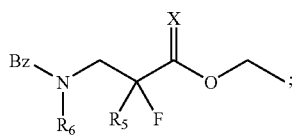

treating the sixth reaction product under conditions that form a seventh reaction product having the formula

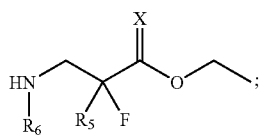

reacting the seventh reaction product with a compound having the formula

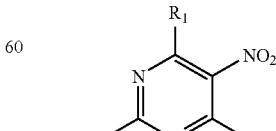

under conditions that form an eighth reaction product having the formula

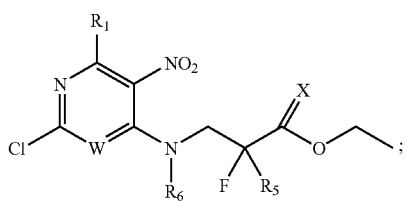

treating the eighth reaction product under conditions that form a ninth reaction product having the formula

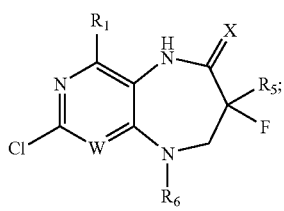

reacting the ninth reaction product with a compound having the formula

R₂—Z₅ under conditions that form a tenth reaction product having the formula

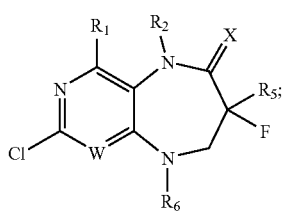

reacting the tenth reaction product with a compound having the formula

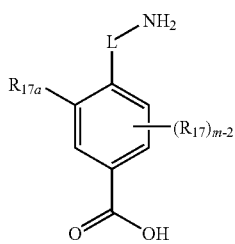

under conditions that form an eleventh reaction product having the formula

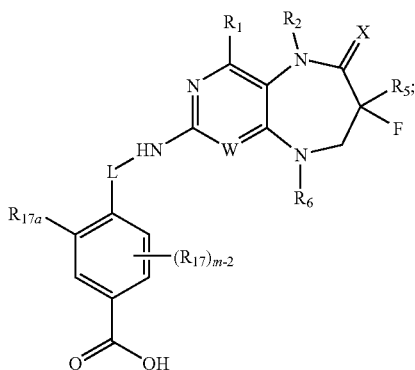

and
reacting the eleventh reaction product with a compound having the formula

NHR₁₉R₂₀ under conditions that form a twelfth reaction product having the formula

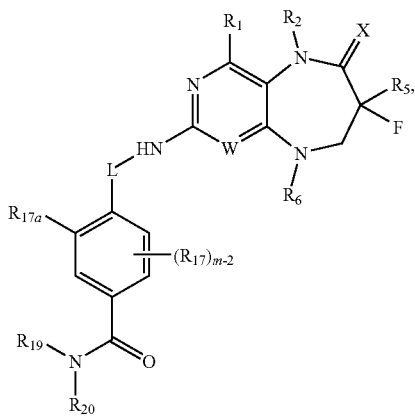

wherein
W is selected from the group consisting of CR₈ and N;
X is selected from the group consisting of NR₁₄, O and S;
L is absent or a linker providing 1, 2, 3, 4, 5 or 6 atom separation between the ring and the nitrogen to which L is attached, wherein the atoms of the linker providing the separation are selected from the group consisting of carbon, oxygen, nitrogen, and sulfur;
R₁ is selected from the group consisting of hydrogen, cyano, thio, hydroxy, carbonyloxy, alkoxy, aryloxy, heteroaryloxy, carbonyl, oxycarbonyl, amido, amino, (C₁₋₁₀)alkylamino, sulfonamido, imino, sulfonyl, sulfinyl, (C₁₋₁₀)alkyl, halo(C₁₋₁₀)alkyl, hydroxy(C₁₋₁₀)alkyl, carbonyl(C₁₋₃)alkyl, thiocarbonyl(C₁₋₃)alkyl, sulfonyl (C₁₋₃)alkyl, sulfinyl(C₁₋₃)alkyl, (C₁₋₁₀)azaalkyl, imino (C₁₋₃)alkyl, (C₃₋₁₂)cycloalkyl(C₁₋₅)alkyl, hetero(C₃₋₁₂) cycloalkyl(C₁₋₅)alkyl, aryl(C₁₋₁₀)alkyl, heteroaryl (C₁₋₅)alkyl, (C₉₋₁₂)bicycloaryl(C₁₋₅)alkyl, hetero (C₈₋₁₂)bicycloaryl(C₁₋₅)alkyl, (C₃₋₁₂)cycloalkyl, hetero (C₃₋₁₂)cycloalkyl, (C₉₋₁₂)bicycloalkyl, hetero(C₃₋₁₂)bicycloalkyl, (C₄₋₁₂)aryl, hetero(C₁₋₁₀)aryl, (C₉₋₁₂)bicycloaryl and hetero(C₄₋₁₂)bicycloaryl, each substituted or unsubstituted;
R₂ is selected from the group consisting of hydrogen, carbonyl, oxycarbonyl, sulfonyl, sulfinyl, (C₁₋₁₀)alkyl, halo ($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, ($C_{1-10}$)azaalkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_2$ and $R_1$ or $R_{14}$ are taken together to form a substituted or unsubstituted ring;

$R_5$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, ($C_{1-10}$)azaalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_6$ is selected from the group consisting of hydrogen, carbonyl, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, ($C_{1-10}$)azaalkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, ($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_8$ is selected from the group consisting of hydrogen, halo, nitro, cyano, thio, oxy, hydroxy, carbonyloxy, alkoxy, aryloxy, heteroaryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, ($C_{1-10}$)azaalkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_{14}$ is selected from the group consisting of ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

m is selected from the group consisting of 2, 3, 4 and 5;

each $R_{17}$ is independently selected from the group consisting of halo, nitro, cyano, thio, oxy, hydroxy, carbonyloxy, alkoxy, aryloxy, heteroaryloxy, carbamoyloxy, carbonyl, oxycarbonyl, amido, amino, ($C_{1-10}$)alkylamino, sulfonamido, carboxyamino, ureido, imino, sulfonyl, aminosulfonyl, sulfinyl, ($C_{1-10}$)alkyl, halo($C_{1-10}$)alkyl, hydroxy($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, ($C_{1-10}$)azaalkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or two $R_{17}$ are taken together to form a substituted or unsubstituted ring;

$R_{17a}$ is selected from the group consisting of hydrogen, halo, nitro, cyano, thio, oxy, hydroxy, carbonyloxy, alkoxy, aryloxy, heteroaryloxy, carbamoyloxy, carbonyl, oxycarbonyl, amido, amino, ($C_{1-10}$)alkylamino, sulfonamido, carboxyamino, ureido, imino, sulfonyl, aminosulfonyl, sulfinyl, ($C_{1-10}$)alkyl, halo($C_{1-10}$)alkyl, hydroxy($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, ($C_{1-10}$)azaalkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_{19}$ are $R_{20}$ are each independently selected from the group consisting of hydrogen, oxy, hydroxy, carbonyloxy, alkoxy, aryloxy, heteroaryloxy, carbonyl, oxycarbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, ($C_{1-10}$)azaalkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_{19}$ and $R_{20}$ are taken together to form a substituted or unsubstituted ring, or $R_{19}$ is a substituent convertible in vivo into hydroxyl; and $Z_5$ is a leaving group.

In still another embodiment, the methods comprise the steps of:

treating a compound having the formula

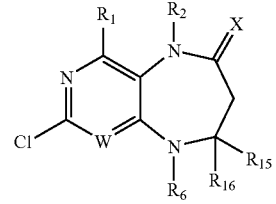

under conditions that form a first reaction product having the formula

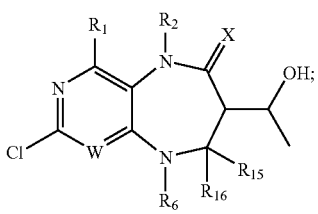

treating the first reaction product under conditions that form a second reaction product having the formula

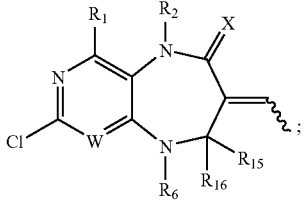

treating the second reaction product under conditions that form a third reaction product having the formula

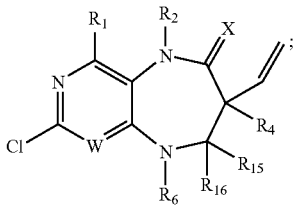

reacting the third reaction product with a compound having the formula

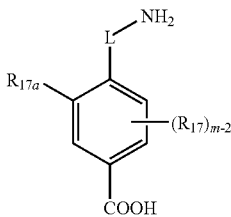

under conditions that form a fourth reaction product having the formula

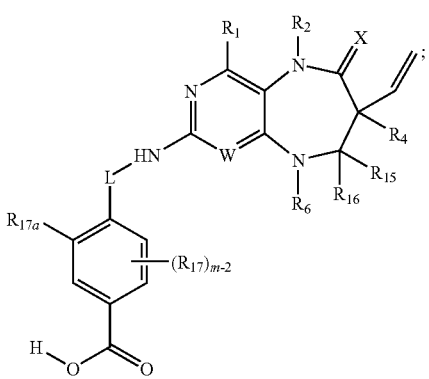

and
reacting the fourth reaction product with a compound having the formula

NHR$_{19}$R$_{20}$ under conditions that form a fifth reaction product having the formula

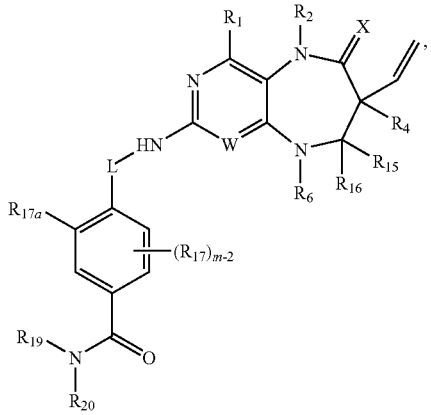

wherein

W is selected from the group consisting of CR$_8$ and N;

X is selected from the group consisting of NR$_{14}$, O and S;

L is absent or a linker providing 1, 2, 3, 4, 5 or 6 atom separation between the ring and the nitrogen to which L is attached, wherein the atoms of the linker providing the separation are selected from the group consisting of carbon, oxygen, nitrogen, and sulfur;

R$_1$ is selected from the group consisting of hydrogen, cyano, thio, hydroxy, carbonyloxy, alkoxy, aryloxy, heteroaryloxy, carbonyl, oxycarbonyl, amido, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, (C$_{1-10}$)azaalkyl, imino(C$_{1-3}$)alkyl, (C$_{3-12}$)cycloalkyl(C$_{1-5}$)alkyl, hetero(C$_{3-12}$)cycloalkyl(C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted;

R$_2$ is selected from the group consisting of hydrogen, carbonyl, oxycarbonyl, sulfonyl, sulfinyl, (C$_{1-10}$)alkyl, halo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, (C$_{1-10}$)azaalkyl, imino(C$_{1-3}$)alkyl, (C$_{3-12}$)cycloalkyl(C$_{1-5}$)alkyl, hetero(C$_{3-12}$)cycloalkyl(C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted, or R$_2$ and R$_1$ or R$_{14}$ are taken together to form a substituted or unsubstituted ring;

R$_4$ is halo;

R$_6$ is selected from the group consisting of hydrogen, carbonyl, sulfonyl, sulfinyl, (C$_{1-10}$)alkyl, halo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, (C$_{1-10}$)azaalkyl, imino(C$_{1-3}$)alkyl, (C$_{3-12}$)cycloalkyl(C$_{1-5}$)alkyl, hetero(C$_{3-12}$)cycloalkyl(C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero ($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_8$ is selected from the group consisting of hydrogen, halo, nitro, cyano, thio, oxy, hydroxy, carbonyloxy, alkoxy, aryloxy, heteroaryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, ($C_{1-10}$)azaalkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_{14}$ is selected from the group consisting of ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_{15}$ and $R_{16}$ are each independently selected from the group consisting of hydrogen, cyano, carbonyl, oxycarbonyl, amido, ($C_{1-10}$)alkyl, halo($C_{1-10}$)alkyl, hydroxy($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, ($C_{1-10}$)azaalkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_{14}$ and $R_{15}$ are taken together with the atom to which they are bound to form a carbonyl or imino group;

m is selected from the group consisting of 2, 3, 4 and 5;

each $R_{17}$ is independently selected from the group consisting of halo, nitro, cyano, thio, oxy, hydroxy, carbonyloxy, alkoxy, aryloxy, heteroaryloxy, carbamoyloxy, carbonyl, oxycarbonyl, amido, amino, ($C_{1-10}$)alkylamino, sulfonamido, carboxyamino, ureido, imino, sulfonyl, aminosulfonyl, sulfinyl, ($C_{1-10}$)alkyl, halo($C_{1-10}$)alkyl, hydroxy($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, ($C_{1-10}$)azaalkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or two $R_{17}$ are taken together to form a substituted or unsubstituted ring;

$R_{17a}$ is selected from the group consisting of hydrogen, halo, nitro, cyano, thio, oxy, hydroxy, carbonyloxy, alkoxy, aryloxy, heteroaryloxy, carbamoyloxy, carbonyl, oxycarbonyl, amido, amino, ($C_{1-10}$)alkylamino, sulfonamido, carboxyamino, ureido, imino, sulfonyl, aminosulfonyl, sulfinyl, ($C_{1-10}$)alkyl, halo($C_{1-10}$)alkyl, hydroxy($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, ($C_{1-10}$)azaalkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted; and $R_{19}$ are $R_{20}$ are each independently selected from the group consisting of hydrogen, oxy, hydroxy, carbonyloxy, alkoxy, aryloxy, heteroaryloxy, carbonyl, oxycarbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, ($C_{1-10}$)azaalkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_{19}$ and $R_{20}$ are taken together to form a substituted or unsubstituted ring, or $R_{19}$ is a substituent convertible in vivo into hydroxy.

In yet another embodiment, the methods comprise the steps of:

treating a compound having the formula

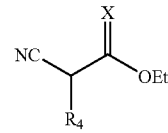

under conditions that form a first reaction product having the formula

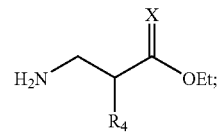

treating the first reaction product under conditions that form a second reaction product having the formula

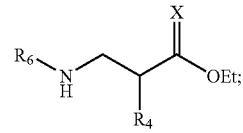

reacting the second reaction product with a compound having the formula

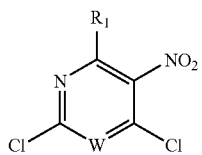

under conditions that form a third reaction product having the formula

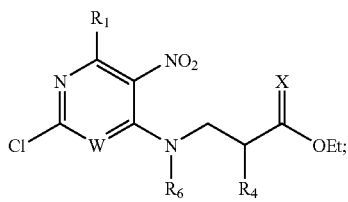

treating the third reaction product under conditions that form a fourth reaction product having the formula

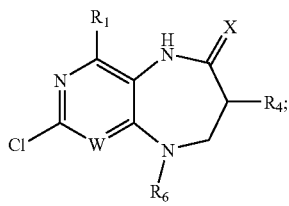

reacting the fourth reaction product with a compound having the formula $R_2-Z_5$ under conditions that form a fifth reaction product having the formula

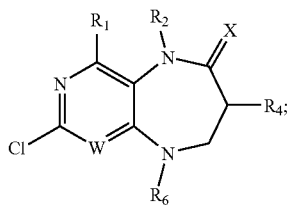

treating the fifth reaction product under conditions that form a sixth reaction product having the formula

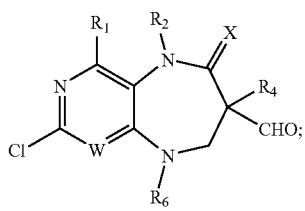

treating the sixth reaction product under conditions that form a seventh reaction product having the formula

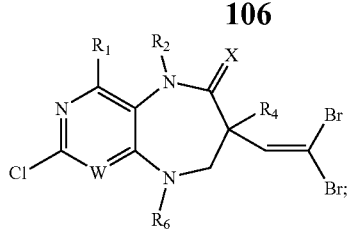

treating the seventh reaction product under conditions that form an eighth reaction product having the formula

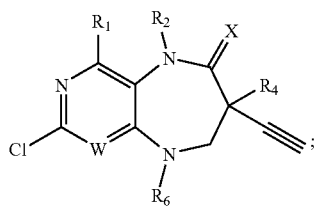

reacting the eighth reaction product with a compound having the formula

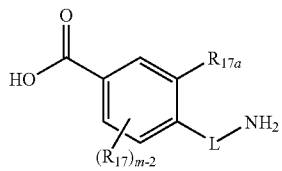

under conditions that form a ninth reaction product having the formula

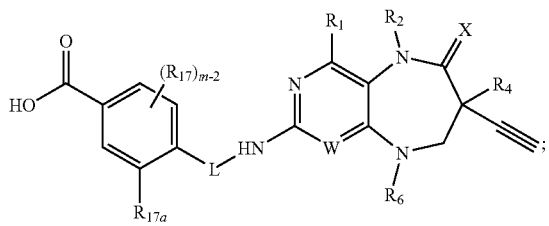

and
reacting the ninth reaction product with a compound having the formula $NHR_{19}R_{20}$ under conditions that form a tenth reaction product having the formula

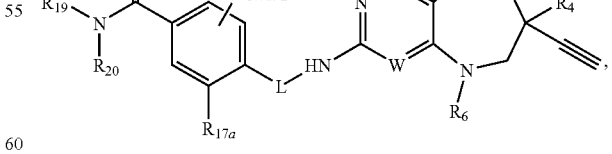

wherein
W is selected from the group consisting of $CR_8$ and N;
X is selected from the group consisting of $NR_{14}$, O and S;
L is absent or a linker providing 1, 2, 3, 4, 5 or 6 atom separation between the ring and the nitrogen to which L is attached, wherein the atoms of the linker providing the separation are selected from the group consisting of carbon, oxygen, nitrogen, and sulfur;

$R_1$ is selected from the group consisting of hydrogen, cyano, thio, hydroxy, carbonyloxy, alkoxy, aryloxy, heteroaryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, $(C_{1-10})$azaalkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_2$ is selected from the group consisting of hydrogen, carbonyl, oxycarbonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, $(C_{1-10})$azaalkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_2$ and $R_1$ or $R_{14}$ are taken together to form a substituted or unsubstituted ring;

$R_4$ is halo;

$R_6$ is selected from the group consisting of hydrogen, carbonyl, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, $(C_{1-10})$azaalkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_8$ is selected from the group consisting of hydrogen, halo, nitro, cyano, thio, oxy, hydroxy, carbonyloxy, alkoxy, aryloxy, heteroaryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, $(C_{1-10})$azaalkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_{14}$ is selected from the group consisting of $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

m is selected from the group consisting of 2, 3, 4 and 5;

each $R_{17}$ is independently selected from the group consisting of halo, nitro, cyano, thio, oxy, hydroxy, carbonyloxy, alkoxy, aryloxy, heteroaryloxy, carbamoyloxy, carbonyl, oxycarbonyl, amido, amino, $(C_{1-10})$alkylamino, sulfonamido, carboxyamino, ureido, imino, sulfonyl, aminosulfonyl, sulfinyl, $(C_{1-10})$alkyl, halo$(C_{1-10})$alkyl, hydroxy$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, $(C_{1-10})$azaalkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or two $R_{17}$ are taken together to form a substituted or unsubstituted ring;

$R_{17a}$ is selected from the group consisting of hydrogen, halo, nitro, cyano, thio, oxy, hydroxy, carbonyloxy, alkoxy, aryloxy, heteroaryloxy, carbamoyloxy, carbonyl, oxycarbonyl, amido, amino, $(C_{1-10})$alkylamino, sulfonamido, carboxyamino, ureido, imino, sulfonyl, aminosulfonyl, sulfinyl, $(C_{1-10})$alkyl, halo$(C_{1-10})$alkyl, hydroxy$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, $(C_{1-10})$azaalkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_{19}$ are $R_{20}$ are each independently selected from the group consisting of hydrogen, oxy, hydroxy, carbonyloxy, alkoxy, aryloxy, heteroaryloxy, carbonyl, oxycarbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, $(C_{1-10})$azaalkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_{19}$ and $R_{20}$ are taken together to form a substituted or unsubstituted ring, or $R_{19}$ is a substituent convertible in vivo into hydroxyl; and $Z_5$ is a leaving group.

In a further embodiment, the methods comprise the steps of:

treating a compound having the formula

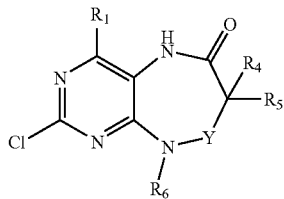

under conditions that form a first reaction product having the formula

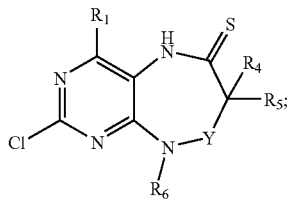

reacting the first reaction product with a compound having the formula

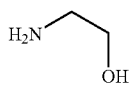

under conditions that form a second reaction product having the formula

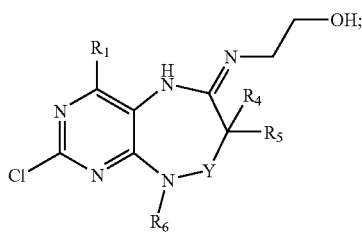

treating the second reaction product under conditions that form a third reaction product having the formula

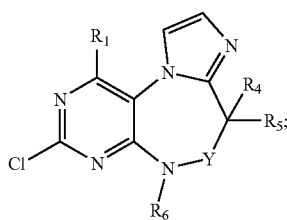

and reacting the third reaction product with a compound having the formula

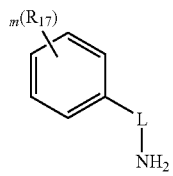

under conditions that form a fourth reaction product having the formula

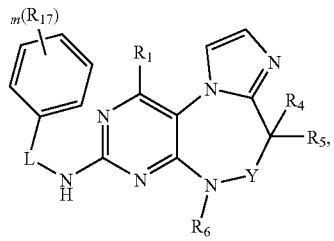

wherein

Y is —(CR$_9$R$_{10}$)$_n$—;

n is selected from the group consisting of 1, 2, 3 and 4;

L is absent or a linker providing 1, 2, 3, 4, 5 or 6 atom separation between the ring and the nitrogen to which L is attached, wherein the atoms of the linker providing the separation are selected from the group consisting of carbon, oxygen, nitrogen, and sulfur;

R$_1$ is selected from the group consisting of hydrogen, cyano, thio, hydroxy, carbonyloxy, alkoxy, aryloxy, heteroaryloxy, carbonyl, oxycarbonyl, amido, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-3}$)alkyl, thiocarbonyl(C$_{1-3}$)alkyl, sulfonyl (C$_{1-3}$)alkyl, sulfinyl(C$_{1-3}$)alkyl, (C$_{1-10}$)azaalkyl, imino (C$_{1-3}$)alkyl, (C$_{3-12}$)cycloalkyl(C$_{1-5}$)alkyl, hetero(C$_{3-12}$) cycloalkyl(C$_{1-5}$)alkyl, aryl(C$_{1-10}$)alkyl, heteroaryl (C$_{1-5}$)alkyl, (C$_{9-12}$)bicycloaryl(C$_{1-5}$)alkyl, hetero (C$_{8-12}$)bicycloaryl(C$_{1-5}$)alkyl, (C$_{3-12}$)cycloalkyl, hetero (C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted;

R$_4$ is halo;

R$_5$ is selected from the group consisting of hydrogen, halo, nitro, cyano, thio, oxy, hydroxy, carbonyloxy, (C$_{1-10}$) alkoxy, (C$_{4-12}$)aryloxy, hetero(C$_{1-10}$)aryloxy, carbonyl, oxycarbonyl, amido, amino, (C$_{1-10}$)alkylamino, sulfonamido, imino, sulfonyl, sulfinyl, (C$_{1-10}$)alkyl, halo (C$_{1-10}$)alkyl, hydroxy(C$_{1-10}$)alkyl, carbonyl(C$_{1-10}$) alkyl, thiocarbonyl(C$_{1-10}$)alkyl, sulfonyl(C$_{1-10}$)alkyl, sulfinyl(C$_{1-10}$)alkyl, (C$_{1-10}$)azaalkyl, imino(C$_{1-10}$)alkyl, (C$_{3-12}$)cycloalkyl(C$_{1-5}$)alkyl, hetero(C$_{3-12}$)cycloalkyl (C$_{1-10}$)alkyl, aryl(C$_{1-10}$)alkyl, hetero(C$_{1-10}$)aryl(C$_{1-5}$) alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$) cycloalkyl, (C$_{9-12}$)bicycloalkyl, hetero(C$_{3-12}$) bicycloalkyl, (C$_{4-12}$)aryl, hetero(C$_{1-10}$)aryl, (C$_{9-12}$) bicycloaryl and hetero(C$_{4-12}$)bicycloaryl, each substituted or unsubstituted;

R$_6$ is selected from the group consisting of hydrogen, carbonyl, amino, (C$_{1-10}$)alkylamino, sulfonamido, imino, sulfonyl, sulfinyl, (C$_{1-10}$)alkyl, halo(C$_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, ($C_{1-10}$)azaalkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_9$ and $R_{10}$ are each independently selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, ($C_{1-10}$)azaalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_9$ and $R_{10}$ are taken together with the carbon to which they are attached to form C=O, C=S, C=$NR_{11}$ or C=$CR_{12}R_{13}$;

$R_{11}$ is selected from the group consisting of hydrogen, oxy, hydroxy, carbonyloxy, ($C_{1-10}$)alkoxy, ($C_{4-12}$)aryloxy, hetero($C_{1-10}$)aryloxy, carbonyl, oxycarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_{12}$ and $R_{13}$ are each independently selected from the group consisting of hydrogen, halo, nitro, cyano, carbonyloxy, oxycarbonyl, amido, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

m is selected from the group consisting of 0, 1, 2, 3, 4 and 5; and each $R_{17}$ is independently selected from the group consisting of halo, nitro, cyano, thio, oxy, hydroxy, carbonyloxy, alkoxy, aryloxy, heteroaryloxy, carbamoyloxy, carbonyl, oxycarbonyl, amido, amino, ($C_{1-10}$)alkylamino, sulfonamido, carboxyamino, ureido, imino, sulfonyl, aminosulfonyl, sulfinyl, ($C_{1-10}$)alkyl, halo($C_{1-10}$)alkyl, hydroxy($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, ($C_{1-10}$)azaalkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or two $R_{17}$ are taken together to form a substituted or unsubstituted ring.

In still another of its aspects, the present invention relates to intermediates that are useful in making PLK inhibitors. In one embodiment, the intermediates comprise

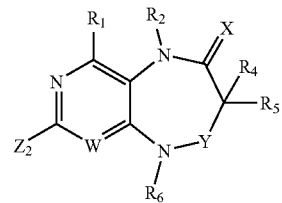

wherein

W is selected from the group consisting of $CR_8$ and N;

X is selected from the group consisting of $NR_{14}$, O and S;

Y is —$(CR_9R_{10})_n$—;

n is selected from the group consisting of 1, 2, 3 and 4;

$R_1$ is selected from the group consisting of hydrogen, cyano, thio, hydroxy, carbonyloxy, alkoxy, aryloxy, heteroaryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, ($C_{1-10}$)azaalkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_2$ is selected from the group consisting of hydrogen, carbonyl, oxycarbonyl, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, ($C_{1-10}$)azaalkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_2$ and $R_1$ or $R_{14}$ are taken together to form a substituted or unsubstituted ring;

$R_4$ is halo;

$R_5$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo ($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, ($C_{1-10}$)azaalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_6$ is selected from the group consisting of hydrogen, carbonyl, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, ($C_{1-10}$)azaalkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_8$ is selected from the group consisting of hydrogen, halo, nitro, cyano, thio, oxy, hydroxy, carbonyloxy, alkoxy, aryloxy, heteroaryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, ($C_{1-10}$)azaalkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_9$ and $R_{10}$ are each independently selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, ($C_{1-10}$)azaalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_9$ and $R_{10}$ are taken together with the carbon to which they are attached to form C=O, C=S, C=N$R_{11}$ or C=C$R_{12}R_{13}$;

$R_{11}$ is selected from the group consisting of hydrogen, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_{12}$ and $R_{13}$ are each independently selected from the group consisting of hydrogen, halo, nitro, cyano, oxycarbonyl, amido, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_{14}$ is selected from the group consisting of ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted; and $Z_2$ is a leaving group.

In another embodiment, the intermediates comprise

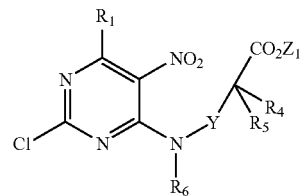

wherein

Y is —(C$R_9R_{10}$)$_n$—;

n is selected from the group consisting of 1, 2, 3 and 4;

$R_1$ is selected from the group consisting of hydrogen, cyano, thio, hydroxy, carbonyloxy, alkoxy, aryloxy, heteroaryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, ($C_{1-10}$)azaalkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_4$ is halo;

$R_5$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)

alkyl, thiocarbonyl($C_{1-10}$)alkyl, sulfonyl($C_{1-10}$)alkyl, sulfinyl($C_{1-10}$)alkyl, ($C_{1-10}$)azaalkyl, imino($C_{1-10}$)alkyl, ($C_{3-12}$)cycloalkyl($C_{1-5}$)alkyl, hetero($C_{3-12}$)cycloalkyl ($C_{1-10}$)alkyl, aryl($C_{1-10}$)alkyl, hetero($C_{1-10}$)aryl($C_{1-5}$) alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$) cycloalkyl, ($C_{9-12}$)bicycloalkyl, hetero($C_{3-12}$) bicycloalkyl, ($C_{4-12}$)aryl, hetero($C_{1-10}$)aryl, ($C_{9-12}$) bicycloaryl and hetero($C_{4-12}$)bicycloaryl, each substituted or unsubstituted;

$R_6$ is selected from the group consisting of hydrogen, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$) alkyl, sulfinyl($C_{1-3}$)alkyl, ($C_{1-10}$)azaalkyl, imino($C_{1-3}$) alkyl, ($C_{3-12}$)cycloalkyl($C_{1-5}$)alkyl, hetero($C_{3-12}$) cycloalkyl($C_{1-5}$)alkyl, aryl($C_{1-10}$)alkyl, heteroaryl ($C_{1-5}$)alkyl, ($C_{9-12}$)bicycloaryl($C_{1-5}$)alkyl, hetero ($C_{8-12}$)bicycloaryl($C_{1-5}$)alkyl, ($C_{3-12}$)cycloalkyl, hetero ($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_9$ and $R_{10}$ are each independently selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy ($C_{1-10}$)alkyl, carbonyl($C_{1-10}$)alkyl, thiocarbonyl($C_{1-10}$) alkyl, sulfonyl($C_{1-10}$)alkyl, sulfinyl($C_{1-10}$)alkyl, ($C_{1-10}$) azaalkyl, imino($C_{1-10}$)alkyl, ($C_{3-12}$)cycloalkyl($C_{1-5}$) alkyl, hetero($C_{3-12}$)cycloalkyl($C_{1-10}$)alkyl, aryl($C_{1-10}$) alkyl, hetero($C_{1-10}$)aryl($C_{1-5}$)alkyl, ($C_{9-12}$)bicycloaryl ($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero ($C_{1-10}$)aryl, ($C_{9-12}$)bicycloaryl and hetero($C_{4-12}$)bicycloaryl, each substituted or unsubstituted, or $R_9$ and $R_{10}$ are taken together with the carbon to which they are attached to form C=O, C=S, C=$NR_{11}$ or C=$CR_{12}R_{13}$;

$R_{11}$ is selected from the group consisting of hydrogen, oxy, hydroxy, carbonyloxy, ($C_{1-10}$)alkoxy, ($C_{4-12}$)aryloxy, hetero($C_{1-10}$)aryloxy, carbonyl, oxycarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero ($C_{3-12}$)cycloalkyl($C_{1-10}$)alkyl, aryl($C_{1-10}$)alkyl, hetero ($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero ($C_{1-10}$)aryl, ($C_{9-12}$)bicycloaryl and hetero($C_{4-12}$)bicycloaryl, each substituted or unsubstituted;

$R_{12}$ and $R_{13}$ are each independently selected from the group consisting of hydrogen, halo, nitro, cyano, oxycarbonyl, amido, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$) alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero ($C_{3-12}$)cycloalkyl($C_{1-10}$)alkyl, aryl($C_{1-10}$)alkyl, hetero ($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero ($C_{1-10}$)aryl, ($C_{9-12}$)bicycloaryl and hetero($C_{4-12}$)bicycloaryl, each substituted or unsubstituted; and $Z_1$ is a leaving group.

In still another embodiment, the intermediates comprise

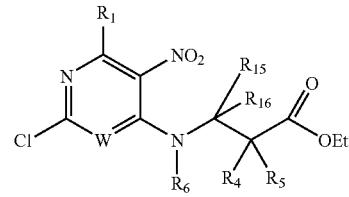

wherein

W is selected from the group consisting of $CR_8$ and N;

$R_1$ is selected from the group consisting of hydrogen, cyano, thio, hydroxy, carbonyloxy, alkoxy, aryloxy, heteroaryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-3}$)alkyl, thiocarbonyl($C_{1-3}$)alkyl, sulfonyl ($C_{1-3}$)alkyl, sulfinyl($C_{1-3}$)alkyl, ($C_{1-10}$)azaalkyl, imino ($C_{1-3}$)alkyl, ($C_{3-12}$)cycloalkyl($C_{1-5}$)alkyl, hetero($C_{3-12}$) cycloalkyl($C_{1-5}$)alkyl, aryl($C_{1-10}$)alkyl, heteroaryl ($C_{1-5}$)alkyl, ($C_{9-12}$)bicycloaryl($C_{1-5}$)alkyl, hetero ($C_{8-12}$)bicycloaryl($C_{1-5}$)alkyl, ($C_{3-12}$)cycloalkyl, hetero ($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_4$ is halo;

$R_5$ is selected from the group consisting of hydrogen, halo, nitro, cyano, thio, oxy, hydroxy, carbonyloxy, ($C_{1-10}$) alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo ($C_{1-10}$)alkyl, hydroxy($C_{1-10}$)alkyl, carbonyl($C_{1-10}$) alkyl, thiocarbonyl($C_{1-10}$)alkyl, sulfonyl($C_{1-10}$)alkyl, sulfinyl($C_{1-10}$)alkyl, ($C_{1-10}$)azaalkyl, imino($C_{1-10}$)alkyl, ($C_{3-12}$)cycloalkyl($C_{1-5}$)alkyl, hetero($C_{3-12}$)cycloalkyl ($C_{1-10}$)alkyl, aryl($C_{1-10}$)alkyl, hetero($C_{1-10}$)aryl($C_{1-5}$) alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$) cycloalkyl, ($C_{9-12}$)bicycloalkyl, hetero($C_{3-12}$) bicycloalkyl, ($C_{4-12}$)aryl, hetero($C_{1-10}$)aryl, ($C_{9-12}$) bicycloaryl and hetero($C_{4-12}$)bicycloaryl, each substituted or unsubstituted;

$R_6$ is selected from the group consisting of hydrogen, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$) alkyl, sulfinyl($C_{1-3}$)alkyl, ($C_{1-10}$)azaalkyl, imino($C_{1-3}$) alkyl, ($C_{3-12}$)cycloalkyl($C_{1-5}$)alkyl, hetero($C_{3-12}$) cycloalkyl($C_{1-5}$)alkyl, aryl($C_{1-10}$)alkyl, heteroaryl ($C_{1-5}$)alkyl, ($C_{9-12}$)bicycloaryl($C_{1-5}$)alkyl, hetero ($C_{8-12}$)bicycloaryl($C_{1-5}$)alkyl, ($C_{3-12}$)cycloalkyl, hetero ($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_8$ is selected from the group consisting of hydrogen, halo, nitro, cyano, thio, oxy, hydroxy, carbonyloxy, alkoxy, aryloxy, heteroaryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy $(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, $(C_{1-10})$azaalkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted; and $R_{15}$ and $R_{16}$ are each independently selected from the group consisting of hydrogen, cyano, carbonyl, oxycarbonyl, amido, $(C_{1-10})$alkyl, halo$(C_{1-10})$alkyl, hydroxy $(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, $(C_{1-10})$azaalkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_{14}$ and $R_{15}$ are taken together with the atom to which they are bound to form a carbonyl or imino group.

In yet another embodiment, the intermediates comprise

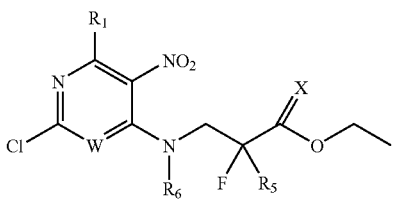

wherein

W is selected from the group consisting of $CR_8$ and N;

X is selected from the group consisting of $NR_{14}$, O and S;

$R_1$ is selected from the group consisting of hydrogen, cyano, thio, hydroxy, carbonyloxy, alkoxy, aryloxy, heteroaryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, $(C_{1-10})$azaalkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_5$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_6$ is selected from the group consisting of hydrogen, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, $(C_{1-10})$azaalkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted; and $R_8$ is selected from the group consisting of hydrogen, halo, nitro, cyano, thio, oxy, hydroxy, carbonyloxy, alkoxy, aryloxy, heteroaryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy $(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, $(C_{1-10})$azaalkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted; and $R_{14}$ is selected from the group consisting of $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted.

In a further embodiment, the intermediates comprise

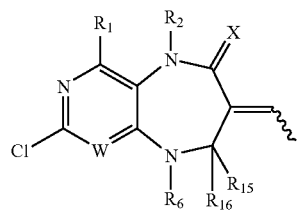

wherein

W is selected from the group consisting of $CR_8$ and N;

X is selected from the group consisting of $NR_{14}$, O and S;

$R_1$ is selected from the group consisting of hydrogen, cyano, thio, hydroxy, carbonyloxy, alkoxy, aryloxy, heteroaryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl($C_{1-3}$)alkyl, thiocarbonyl($C_{1-3}$)alkyl, sulfonyl ($C_{1-3}$)alkyl, sulfinyl($C_{1-3}$)alkyl, ($C_{1-10}$)azaalkyl, imino ($C_{1-3}$)alkyl, ($C_{3-12}$)cycloalkyl($C_{1-5}$)alkyl, hetero($C_{3-12}$) cycloalkyl($C_{1-5}$)alkyl, aryl($C_{1-10}$)alkyl, heteroaryl ($C_{1-5}$)alkyl, ($C_{9-12}$)bicycloaryl($C_{1-5}$)alkyl, hetero ($C_{8-12}$)bicycloaryl($C_{1-5}$)alkyl, ($C_{3-12}$)cycloalkyl, hetero ($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_2$ is selected from the group consisting of hydrogen, carbonyl, oxycarbonyl, sulfonyl, sulfinyl, ($C_{1-10}$)alkyl, halo ($C_{1-10}$)alkyl, carbonyl($C_{1-3}$)alkyl, thiocarbonyl($C_{1-3}$) alkyl, sulfonyl($C_{1-3}$)alkyl, sulfinyl($C_{1-3}$)alkyl, ($C_{1-10}$) azaalkyl, imino($C_{1-3}$)alkyl, ($C_{3-12}$)cycloalkyl($C_{1-5}$) alkyl, hetero($C_{3-12}$)cycloalkyl($C_{1-5}$)alkyl, aryl($C_{1-10}$) alkyl, heteroaryl($C_{1-5}$)alkyl, ($C_{9-12}$)bicycloaryl($C_{1-5}$) alkyl, hetero($C_{8-12}$)bicycloaryl($C_{1-5}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$) bicycloaryl, each substituted or unsubstituted, or $R_2$ and $R_1$ or $R_{14}$ are taken together to form a substituted or unsubstituted ring;

$R_6$ is selected from the group consisting of hydrogen, carbonyl, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl ($C_{1-3}$)alkyl, sulfinyl($C_{1-3}$)alkyl, ($C_{1-10}$)azaalkyl, imino ($C_{1-3}$)alkyl, ($C_{3-12}$)cycloalkyl($C_{1-5}$)alkyl, hetero($C_{3-12}$) cycloalkyl($C_{1-5}$)alkyl, aryl($C_{1-10}$)alkyl, heteroaryl ($C_{1-5}$)alkyl, ($C_{9-12}$)bicycloaryl($C_{1-5}$)alkyl, hetero ($C_{8-12}$)bicycloaryl($C_{1-5}$)alkyl, ($C_{3-12}$)cycloalkyl, hetero ($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_8$ is selected from the group consisting of hydrogen, halo, nitro, cyano, thio, oxy, hydroxy, carbonyloxy, alkoxy, aryloxy, heteroaryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy ($C_{1-10}$)alkyl, carbonyl($C_{1-3}$)alkyl, thiocarbonyl($C_{1-3}$) alkyl, sulfonyl($C_{1-3}$)alkyl, sulfinyl($C_{1-3}$)alkyl, ($C_{1-10}$) azaalkyl, imino($C_{1-3}$)alkyl, ($C_{3-12}$)cycloalkyl($C_{1-5}$) alkyl, hetero($C_{3-12}$)cycloalkyl($C_{1-5}$)alkyl, aryl($C_{1-10}$) alkyl, heteroaryl($C_{1-5}$)alkyl, ($C_{9-12}$)bicycloaryl($C_{1-5}$) alkyl, hetero($C_{8-12}$)bicycloaryl($C_{1-5}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$) bicycloaryl, each substituted or unsubstituted;

$R_{14}$ is selected from the group consisting of ($C_{1-10}$)alkyl, halo($C_{1-10}$)alkyl, hydroxy($C_{1-10}$)alkyl, carbonyl($C_{1-10}$) alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl ($C_{1-10}$)alkyl, aryl($C_{1-10}$)alkyl, hetero($C_{1-10}$)aryl($C_{1-5}$) alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$) bicycloaryl, each substituted or unsubstituted; and $R_{15}$ and $R_{16}$ are each independently selected from the group consisting of hydrogen, cyano, carbonyl, oxycarbonyl, amido, ($C_{1-10}$)alkyl, halo($C_{1-10}$)alkyl, hydroxy ($C_{1-10}$)alkyl, carbonyl($C_{1-3}$)alkyl, thiocarbonyl($C_{1-3}$) alkyl, sulfonyl($C_{1-3}$)alkyl, sulfinyl($C_{1-3}$)alkyl, ($C_{1-10}$) azaalkyl, imino($C_{1-3}$)alkyl, ($C_{3-12}$)cycloalkyl($C_{1-5}$) alkyl, hetero($C_{3-12}$)cycloalkyl($C_{1-5}$)alkyl, aryl($C_{1-10}$) alkyl, heteroaryl($C_{1-5}$)alkyl, ($C_{9-12}$)bicycloaryl($C_{1-5}$) alkyl, hetero($C_{8-12}$)bicycloaryl($C_{1-5}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$) bicycloaryl, each substituted or unsubstituted, or $R_{14}$ and $R_{15}$ are taken together with the atom to which they are bound to form a carbonyl or imino group.

In still a further embodiment, the intermediates comprise

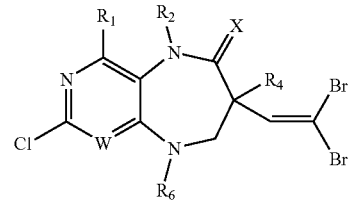

wherein

W is selected from the group consisting of $CR_8$ and N;

X is selected from the group consisting of $NR_{14}$, O and S;

$R_1$ is selected from the group consisting of hydrogen, cyano, thio, hydroxy, carbonyloxy, alkoxy, aryloxy, heteroaryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-3}$)alkyl, thiocarbonyl($C_{1-3}$)alkyl, sulfonyl ($C_{1-3}$)alkyl, sulfinyl($C_{1-3}$)alkyl, ($C_{1-10}$)azaalkyl, imino ($C_{1-3}$)alkyl, ($C_{3-12}$)cycloalkyl($C_{1-5}$)alkyl, hetero($C_{3-12}$) cycloalkyl($C_{1-5}$)alkyl, aryl($C_{1-10}$)alkyl, heteroaryl ($C_{1-5}$)alkyl, ($C_{9-12}$)bicycloaryl($C_{1-5}$)alkyl, hetero ($C_{8-12}$)bicycloaryl($C_{1-5}$)alkyl, ($C_{3-12}$)cycloalkyl, hetero ($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_2$ is selected from the group consisting of hydrogen, carbonyl, oxycarbonyl, sulfonyl, sulfinyl, ($C_{1-10}$)alkyl, halo ($C_{1-10}$)alkyl, carbonyl($C_{1-3}$)alkyl, thiocarbonyl($C_{1-3}$) alkyl, sulfonyl($C_{1-3}$)alkyl, sulfinyl($C_{1-3}$)alkyl, ($C_{1-10}$) azaalkyl, imino($C_{1-3}$)alkyl, ($C_{3-12}$)cycloalkyl($C_{1-5}$) alkyl, hetero($C_{3-12}$)cycloalkyl($C_{1-5}$)alkyl, aryl($C_{1-10}$) alkyl, heteroaryl($C_{1-5}$)alkyl, ($C_{9-12}$)bicycloaryl($C_{1-5}$) alkyl, hetero($C_{8-12}$)bicycloaryl($C_{1-5}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$) bicycloaryl, each substituted or unsubstituted, or $R_2$ and $R_1$ or $R_{14}$ are taken together to form a substituted or unsubstituted ring;

$R_4$ is halo;

$R_6$ is selected from the group consisting of hydrogen, carbonyl, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl ($C_{1-3}$)alkyl, sulfinyl($C_{1-3}$)alkyl, ($C_{1-10}$)azaalkyl, imino ($C_{1-3}$)alkyl, ($C_{3-12}$)cycloalkyl($C_{1-5}$)alkyl, hetero($C_{3-12}$) cycloalkyl($C_{1-5}$)alkyl, aryl($C_{1-10}$)alkyl, heteroaryl ($C_{1-5}$)alkyl, ($C_{9-12}$)bicycloaryl($C_{1-5}$)alkyl, hetero ($C_{8-12}$)bicycloaryl($C_{1-5}$)alkyl, ($C_{3-12}$)cycloalkyl, hetero ($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)

bicycloaryl and hetero($C_{4-12}$)bicycloaryl, each substituted or unsubstituted; and $R_8$ is selected from the group consisting of hydrogen, halo, nitro, cyano, thio, oxy, hydroxy, carbonyloxy, alkoxy, aryloxy, heteroaryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, ($C_{1-10}$)azaalkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted; and $R_{14}$ is selected from the group consisting of ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted.

In yet a further embodiment, the intermediates comprise

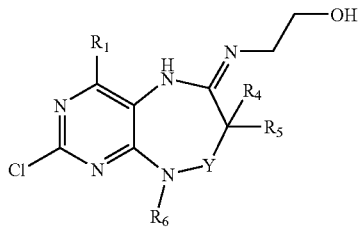

wherein

Y is —($CR_9R_{10}$)$_n$—;

n is selected from the group consisting of 1, 2, 3 and 4;

$R_1$ is selected from the group consisting of hydrogen, cyano, thio, hydroxy, carbonyloxy, alkoxy, aryloxy, heteroaryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, ($C_{1-10}$)azaalkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_4$ is halo;

$R_5$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, ($C_{1-10}$)azaalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_6$ is selected from the group consisting of hydrogen, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, ($C_{1-10}$)azaalkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_9$ and $R_{10}$ are each independently selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, ($C_{1-10}$)azaalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_9$ and $R_{10}$ are taken together with the carbon to which they are attached to form C=O, C=S, C=$NR_{11}$ or C=$CR_{12}R_{13}$;

$R_{11}$ is selected from the group consisting of hydrogen, oxy, hydroxy, carbonyloxy, ($C_{1-10}$)alkoxy, ($C_{4-12}$)aryloxy, hetero($C_{1-10}$)aryloxy, carbonyl, oxycarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted; and $R_{12}$ and $R_{13}$ are each independently selected from the group consisting of hydrogen, halo, nitro, cyano, oxycarbonyl, amido, amino ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted.

In one variation of each of the above embodiments, W is N

In another variation of each of the above embodiments and variations, X is O.

In still another variation of each of the above embodiments and variations, L is a substituted or unsubstituted ($C_{1-3}$)alkyl. In a further variation of each of the above embodiments and variations, L is absent.

In yet another variation of each of the above embodiments and variations, L is —$CHR_{23}$—; and $R_{23}$ is selected from the group consisting of hydrogen, halo, nitro, cyano, thio, oxy, hydroxy, carbonyloxy, alkoxy, aryloxy, heteroaryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, ($C_{1-10}$)azaalkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted.

In a further variation of each of the above embodiments and variations, $R_1$ is hydrogen.

In still a further variation of each of the above embodiments and variations, $R_2$ is selected from the group consisting of hydrogen and a substituted or unsubstituted ($C_{1-3}$)alkyl. In yet a further variation of each of the above embodiments and variations, $R_2$ is methyl.

In another variation of each of the above embodiments and variations, $R_3$ is hydrogen. In still another variation of each of the above embodiments and variations, $R_3$ is a substituent convertible in vivo to hydrogen. In yet another variation of each of the above embodiments and variations, $R_3$ is selected from the group consisting of hydrolyzable groups, groups having an oxycarbonyl group, amino acid residues, peptide residues, o-nitrophenylsulfenyl, trimethylsilyl, tetrahydropyranyl, diphenylphosphinyl, arylsulfonyl groups, methyl groups substituted with phenyl or benzyloxy, arylmethoxycarbonyl groups, and halogenoethoxycarbonyl groups.

In a further variation of each of the above embodiments and variations, $R_4$ is fluoro. In still a further variation of each of the above embodiments and variations, $R_4$ is bromo.

In yet a further variation of each of the above embodiments and variations, $R_5$ is selected from the group consisting of hydrogen, halo, a substituted or unsubstituted ($C_{1-3}$)alkyl and a substituted or unsubstituted ($C_{1-3}$)alkenyl. In another variation of each of the above embodiments and variations, $R_5$ is a substituted or unsubstituted ($C_{1-3}$)alkenyl. In still another variation of each of the above embodiments and variations, $R_5$ is halo. In yet another variation of each of the above embodiments and variations, wherein $R_5$ is fluoro. In a further variation of each of the above embodiments and variations, wherein $R_5$ is bromo.

In still a further variation of each of the above embodiments and variations, $R_6$ is selected from the group consisting of ($C_{1-5}$)alkyl and ($C_{3-12}$)cycloalkyl, each substituted or unsubstituted. In yet a further variation of each of the above embodiments and variations, $R_6$ is selected from the group consisting of isopropyl, cyclopropyl, cyclopentyl and cyclohexyl, each substituted or unsubstituted.

In another variation of each of the above embodiments and variations, $R_6$ is selected from the group consisting of ($C_{1-5}$)alkyl and -$L_1$-$R_{24}$;

$L_1$ is absent or a linker providing 1, 2, 3, 4, 5 or 6 atom separation between $R_{24}$ and the ring to which $L_1$ is attached, wherein the atoms of the linker providing the separation are selected from the group consisting of carbon, oxygen, nitrogen, and sulfur; and $R_{24}$ is selected from the group consisting of ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted.

In still another variation of each of the above embodiments and variations, $R_7$ is a substituted or unsubstituted hetero($C_{1-10}$)aryl.

In a further variation of each of the above embodiments and variations, $R_7$ is

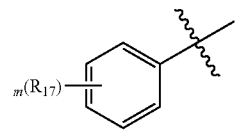

wherein m is selected from the group consisting of 0, 1, 2, 3, 4 and 5; and each $R_{17}$ is independently selected from the group consisting of halo, nitro, cyano, thio, oxy, hydroxy, carbonyloxy, alkoxy, aryloxy, heteroaryloxy, carbamoyloxy, carbonyl, oxycarbonyl, amido, amino, ($C_{1-10}$)alkylamino, sulfonamido, carboxyamino, ureido, imino, sulfonyl, aminosulfonyl, sulfinyl, ($C_{1-10}$)alkyl, halo($C_{1-10}$)alkyl, hydroxy($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, ($C_{1-10}$)azaalkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or two $R_{17}$ are taken together to form a substituted or unsubstituted ring.

In still a further variation of each of the above embodiments and variations, $R_7$ is

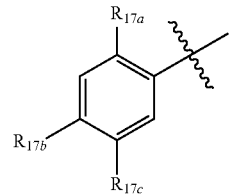

wherein $R_{17a}$, $R_{17b}$ and $R_{17c}$, are each independently selected from the group consisting of hydrogen, halo, nitro, cyano, thio, oxy, hydroxy, carbonyloxy, alkoxy, aryloxy, heteroaryloxy, carbamoyloxy, carbonyl, oxycarbonyl, amido, amino, $(C_{1-10})$alkylamino, sulfonamido, carboxyamino, ureido, imino, sulfonyl, aminosulfonyl, sulfinyl, $(C_{1-10})$alkyl, halo$(C_{1-10})$alkyl, hydroxy$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, $(C_{1-10})$azaalkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted.

In yet another variation of each of the above embodiments and variations, $R_8$ is selected from the group consisting of hydrogen and a substituted or unsubstituted $(C_{1-5})$alkyl.

In a further variation of each of the above embodiments and variations, $R_{15}$ is hydrogen. In still a further variation of each of the above embodiments and variations, $R_{15}$ is a substituted or unsubstituted $(C_{1-3})$alkyl.

In yet a further variation of each of the above embodiments and variations, $R_{16}$ is hydrogen. In another variation of each of the above embodiments and variations, $R_{16}$ is a substituted or unsubstituted $(C_{1-13})$alkyl.

In still another variation of each of the above embodiments and variations, at least one $R_{17}$ is a substituted or unsubstituted alkoxy. In yet another variation of each of the above embodiments and variations, at least one $R_{17}$ is methoxy. In a further variation of each of the above embodiments and variations, at least one $R_{17}$ is a halo. In still a further variation of each of the above embodiments and variations, at least one $R_{17}$ is fluoro.

In yet another variation of each of the above embodiments and variations, at least one $R_{17}$ comprises —C(O)NR$_{25}$R$_{26}$, wherein $R_{25}$ and $R_{26}$ are each independently selected from the group consisting of hydrogen, oxy, hydroxy, carbonyloxy, alkoxy, aryloxy, heteroaryloxy, carbonyl, oxycarbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, $(C_{1-10})$azaalkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_{25}$ and $R_{26}$ are taken together to form a substituted or unsubstituted ring.

In a further variation of each of the above embodiments and variations, at least one $R_{17}$ comprises —C(O)OR$_{27}$, wherein $R_{27}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted.

In still a further variation of each of the above embodiments and variations, m is 2.

In yet a further variation of each of the above embodiments and variations, $R_{17a}$ is selected from the group consisting of hydrogen, halo, alkoxy and $(C_{1-10})$alkyl, each substituted or unsubstituted. In another variation of each of the above embodiments and variations, $R_{17a}$ is a substituted or unsubstituted alkoxy. In still another variation of each of the above embodiments and variations, $R_{17a}$ is methoxy.

In yet another variation of each of the above embodiments and variations, $R_{17b}$ comprises —C(O)NR$_{25}$R$_{26}$, wherein $R_{25}$ and $R_{26}$ are each independently selected from the group consisting of hydrogen, oxy, hydroxy, carbonyloxy, alkoxy, aryloxy, heteroaryloxy, carbonyl, oxycarbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, $(C_{1-10})$azaalkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_{25}$ and $R_{26}$ are taken together to form a substituted or unsubstituted ring.

In a further variation of each of the above embodiments and variations, $R_{17b}$ comprises —C(O)OR$_{27}$, wherein $R_{27}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted.

In another variation of each of the above embodiments and variations, at least one $R_{17c}$ is a halo. In still another variation of each of the above embodiments and variations, at least one $R_{17c}$ is fluoro.

In still a further variation of each of the above embodiments and variations, $R_{18}$ is hydroxy.

In yet a further variation of each of the above embodiments and variations, $R_{19}$ is hydrogen. In another variation of each of the above embodiments and variations, $R_{19}$ is a phosphate.

In still another variation of each of the above embodiments and variations, $R_{20}$ is selected from the group consisting of hydrogen, halo, amino, $(C_{1-10})$alkyl, $(C_{3-12})$cycloalkyl, hetero$(C_{3-12})$cycloalkyl, $(C_{1-10})$azaalkyl, each substituted or unsubstituted.

In yet another variation of each of the above embodiments and variations, $R_{20}$ is selected from the group consisting of $(C_{1-5})$alkyl and -L$_2$-R$_{28}$;

L$_2$ is absent or a linker providing 1, 2, 3, 4, 5 or 6 atom separation between $R_{28}$ and the ring to which L$_2$ is attached, wherein the atoms of the linker providing the separation are selected from the group consisting of carbon, oxygen, nitrogen, and sulfur; and $R_{28}$ is selected from the group consisting of $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$ aryl, ($C_{9-12}$)bicycloaryl and hetero($C_{4-12}$)bicycloaryl, each substituted or unsubstituted.

In a further variation of each of the above embodiments and variations, $R_{20}$ is selected from the group consisting of

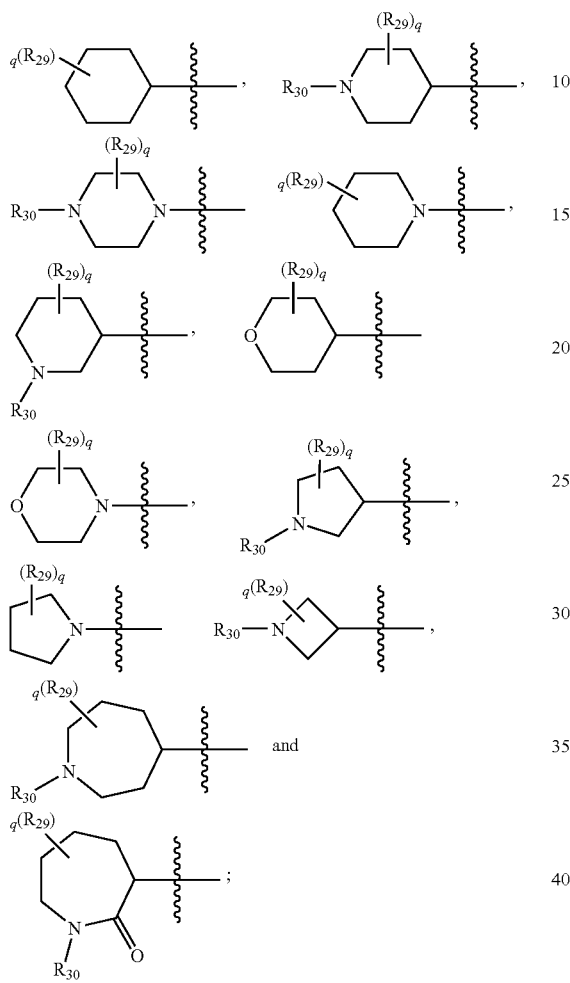

q is selected from the group consisting of 0, 1, 2, 3, 4 and 5; $R_{29}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or two $R_{29}$ are taken together to form a substituted or unsubstituted ring, or $R_{29}$ is a substituent convertible in vivo into hydroxy; and $R_{30}$ is selected from the group consisting of hydrogen, oxy, hydroxy, carbonyloxy, ($C_{1-10}$)alkoxy, ($C_{4-12}$)aryloxy, hetero($C_{1-10}$)aryloxy, carbonyl, oxycarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_{30}$ is a substituent convertible in vivo into hydroxy, or $R_{29}$ and $R_{30}$ are taken together to form a substituted or unsubstituted ring.

In still a further variation of each of the above embodiments and variations, $R_{15}$ and $R_{21}$ are taken together to form a substituted or unsubstituted 5-, 6-, 7- or 8-membered ring. In yet a further variation of each of the above embodiments and variations, $R_{15}$ and $R_{21}$ are taken together to form a substituted or unsubstituted pyrrolidine. In another variation of each of the above embodiments and variations, the ring formed by $R_{15}$ and $R_{21}$ is substituted with one or more substituents independently selected from the group consisting of hydrogen, halo, nitro, cyano, thio, oxy, hydroxy, carbonyloxy, alkoxy, aryloxy, heteroaryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, ($C_{1-10}$)azaalkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted.

In still another variation of each of the above embodiments and variations, $R_{27}$ is hydroxy.

In yet another variation of each of the above embodiments and variations, $R_{31}$ is hydroxy.

In a further variation of each of the above embodiments and variations, $R_{32}$ is selected from the group consisting of hydrogen and ($C_{1-3}$)alkyl. In still a further variation of each of the above embodiments and variations, $R_{32}$ is hydrogen.

In yet a further variation of each of the above embodiments and variations, $R_{33}$ is selected from the group consisting of hydrogen and ($C_{1-3}$)alkyl. In another variation of each of the above embodiments and variations, $R_{33}$ is hydrogen.

In yet another variation of each of the above embodiments and variations, $Z_1$ is halo. In a further variation of each of the above embodiments and variations, $Z_2$ is halo. In still a further variation of each of the above embodiments and variations, $Z_3$ is halo. In yet a further variation of each of the above embodiments and variations, $Z_4$ is halo. In another variation of each of the above embodiments and variations, $Z_5$ is halo. In yet another variation of each of the above embodiments and variations, $R_7$ is an optionally substituted 3-fluoro or 3-chloro-1,4-phenylene. In yet another variation of each of the above embodiments, $R_7$ is a 3-fluoro or 3-chloro-1,4-phenylene optionally substituted with from 1 to 3 groups independently selected from the group consisting of halo, nitro, cyano, optionally substituted ($C_{1-4}$)alkoxy, and optionally substituted ($C_{1-4}$)alkyl.

It is noted that the compounds of the present invention may be in the form of a pharmaceutically acceptable salt, biohydrolyzable ester, biohydrolyzable amide, biohydrolyzable carbamate, solvate, hydrate or prodrug thereof. For example, the compound optionally comprises a substituent that is convertible in vivo to a different substituent such as a hydrogen.

It is further noted that the compound may be present in a mixture of stereoisomers, or the compound may comprise a single stereoisomer.

The present invention also relates to the use of a compound according to any one of above embodiments and variations as a medicament.

In addition, the present invention relates to the use of a compound according to any one of the above embodiments and variations in the manufacture of a medicament for inhibiting a polo-like kinase.

Further, the present invention relates to the use of a compound according to any one of the above embodiments and variations in the manufacture of a medicament for treating a disease state for which a polo-like kinase possess activity that contributes to the pathology and/or symptomology of the disease state.

The present invention also relates to the use of a compound according to any one of the above embodiments and variations in the manufacture of a medicament for treating hyperproliferative disorders; cancer; inflammatory diseases; autoimmune diseases; chemotherapy agent-induced alopecia and mucositis; cardiovascular diseases; viral, bacterial, fungal and/or parasitic infectious diseases; nephrological diseases; chronic and acute neurodegenerative diseases; skin diseases; bone diseases; and the protection of proliferating cells.

The present invention also provides a pharmaceutical composition comprising as an active ingredient a compound according to any one of the above embodiments and variations. In one particular variation, the composition is a solid formulation adapted for oral administration. In another particular variation, the composition is a liquid formulation adapted for oral administration. In yet another particular variation, the composition is a tablet. In still another particular variation, the composition is a liquid formulation adapted for parenteral administration.

In another of its aspects, there is provided a pharmaceutical composition comprising a compound according to any one of the above embodiments and variations, wherein the composition is adapted for administration by a route selected from the group consisting of orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, and intrathecally.

In yet another of its aspects, there is provided a kit comprising a compound of any one of the above embodiments and variations; and instructions which comprise one or more forms of information selected from the group consisting of indicating a disease state for which the composition is to be administered, storage information for the composition, dosing information and instructions regarding how to administer the composition. In one particular variation, the kit comprises the compound in a multiple dose form.

In still another of its aspects, there is provided an article of manufacture comprising a compound of any one of the above embodiments and variations; and packaging materials. In one variation, the packaging material comprises a container for housing the compound. In one particular variation, the container comprises a label indicating one or more members of the group consisting of a disease state for which the compound is to be administered, storage information, dosing information and/or instructions regarding how to administer the compound. In another variation, the article of manufacture comprises the compound in a multiple dose form.

In a further of its aspects, there is provided a therapeutic method comprising administering a compound of any one of the above embodiments and variations to a subject.

In another of its aspects, there is provided a method of inhibiting a kinase comprising contacting the kinase with a compound of any one of the above embodiments and variations.

In yet another of its aspects, there is provided a method of inhibiting a kinase comprising causing a compound of any one of the above embodiments and variations to be present in a subject in order to inhibit the kinase in vivo.

In a further of its aspects, there is provided a method of inhibiting a kinase comprising administering a first compound to a subject that is converted in vivo to a second compound wherein the second compound inhibits the kinase in vivo, the second compound being a compound according to any one of the above embodiments and variations.

In another of its aspects, there is provided a method of treating a disease state for which a kinase possesses activity that contributes to the pathology and/or symptomology of the disease state, the method comprising causing a compound of any one of the above embodiments and variations to be present in a subject in a therapeutically effective amount for the disease state.

In yet another of its aspects, there is provided a method of treating a disease state for which a kinase possesses activity that contributes to the pathology and/or symptomology of the disease state, the method comprising administering a compound of any one of the above embodiments and variations to a subject, wherein the compound is present in the subject in a therapeutically effective amount for the disease state.

In a further of its aspects, there is provided a method of treating a disease state for which a kinase possesses activity that contributes to the pathology and/or symptomology of the disease state, the method comprising administering a first compound to a subject that is converted in vivo to a second compound wherein the second compound inhibits the kinase in vivo, the second compound being a compound according to any one of the above embodiments and variations.

In one variation of each of the above methods the disease state is selected from the group consisting of hyperproliferative disorders; cancer (e.g., solid tumors, leukemias, lymphomas, non-small cell lung cancers and esophageal carcinomas); inflammatory and autoimmune diseases (e.g., psoriasis, alopecia; multiple sclerosis; colitis, arthritis, Alzheimer's disease, glomerulonephritis and wound healing); chemotherapy agent-induced alopecia and mucositis; cardiovascular diseases (e.g., stenoses, arteriosckeroses, restenoses, and hypertrophy); viral, bacterial, fungal and/or parasitic infectious diseases (e.g., cytomegalic infections, herpes, hepatitis B and C, Karposi's sarcoma, HIV diseases); nephrological diseases (e.g., glomerulonephritis); chronic and acute neurodegenerative diseases (e.g., Huntington's disease, amyotrophic lateral sclerosis, Parkinson's disease, AIDS dementia, Alzheimer's disease, ischemias of the brain and neurotraumas); skin diseases (e.g., psoriasis); bone diseases; the protection of proliferating cells (e.g., hair, intestinal, blood and progenitor cells) from DNA damage caused by radiation, UV treatment and/or cytostatic treatment.

In another variation of each of the above methods, the kinase is a protein tyrosine kinase. In still another variation of each of the above methods, the kinase is a Polo-like Kinase (PLK). In yet another variation, the PLK is PLK1, PLK2, PLK3, PLK4, TTK, FAK and/or AIK Salts, Hydrates, and Prodrugs of Kinase Inhibitors It should be recognized that the compounds of the present invention may be present and optionally administered in the form of salts, hydrates and prodrugs that are converted in vivo into the compounds of the present invention. For example, it is within the scope of the present invention to convert the compounds of the present invention into and use them in the form of their pharmaceutically acceptable salts derived from various organic and inorganic acids and bases in accordance with procedures well known in the art.

When the compounds of the present invention possess a free base form, the compounds can be prepared as a pharmaceutically acceptable acid addition salt by reacting the free base form of the compound with a pharmaceutically acceptable inorganic or organic acid, e.g., hydrohalides such as hydrochloride, hydrobromide, hydroiodide; other mineral acids and their corresponding salts such as sulfate, nitrate, phosphate, etc.; and alkyl and monoarylsulfonates such as ethanesulfonate, toluenesulfonate and benzenesulfonate; and other organic acids and their corresponding salts such as acetate, tartrate, maleate, succinate, citrate, benzoate, salicylate and ascorbate. Further acid addition salts of the present invention include, but are not limited to: adipate, alginate, arginate, aspartate, bisulfate, bisulfite, bromide, butyrate, camphorate, camphorsulfonate, caprylate, chloride, chlorobenzoate, cyclopentanepropionate, digluconate, dihydrogenphosphate, dinitrobenzoate, dodecylsulfate, fumarate, galacterate (from mucic acid), galacturonate, glucoheptonate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, iso-butyrate, lactate, lactobionate, malate, malonate, mandelate, metaphosphate, methanesulfonate, methylbenzoate, monohydrogenphosphate, 2-naphthalenesulfonate, nicotinate, nitrate, oxalate, oleate, pamoate, pectinate, persulfate, phenylacetate, 3-phenylpropionate, phosphate, phosphonate and phthalate. It should be recognized that the free base forms will typically differ from their respective salt forms somewhat in physical properties such as solubility in polar solvents, but otherwise the salts are equivalent to their respective free base forms for the purposes of the present invention.

When the compounds of the present invention possess a free acid form, a pharmaceutically acceptable base addition salt can be prepared by reacting the free acid form of the compound with a pharmaceutically acceptable inorganic or organic base. Examples of such bases are alkali metal hydroxides including potassium, sodium and lithium hydroxides; alkaline earth metal hydroxides such as barium and calcium hydroxides; alkali metal alkoxides, e.g., potassium ethanolate and sodium propanolate; and various organic bases such as ammonium hydroxide, piperidine, diethanolamine and N-methylglutamine. Also included are the aluminum salts of the compounds of the present invention. Further base salts of the present invention include, but are not limited to: copper, ferric, ferrous, lithium, magnesium, manganic, manganous, potassium, sodium and zinc salts. Organic base salts include, but are not limited to, salts of primary, secondary and tertiary amines, substituted amines including naturally occurring substituted amines, cyclic amines and basic ion exchange resins, e.g., arginine, betaine, caffeine, chloroprocaine, choline, N,N'-dibenzylethylenediamine (benzathine), dicyclohexylamine, diethanolamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)-methylamine (tromethamine). It should be recognized that the free acid forms will typically differ from their respective salt forms somewhat in physical properties such as solubility in polar solvents, but otherwise the salts are equivalent to their respective free acid forms for the purposes of the present invention.

N-oxides of compounds according to the present invention can be prepared by methods known to those of ordinary skill in the art. For example, N-oxides can be prepared by treating an unoxidized form of the compound with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds can be prepared from the N-oxide of an appropriate starting material.

Prodrug derivatives of compounds according to the present invention can be prepared by modifying substituents of compounds of the present invention that are then converted in vivo to a different substituent. It is noted that in many instances, the prodrugs themselves also fall within the scope of the range of compounds according to the present invention. For example, prodrugs can be prepared by reacting a compound with a carbamoylating agent (e.g., 1,1-acyloxyalkylcarbonochloridate, para-nitrophenyl carbonate, or the like) or an acylating agent. Further examples of methods of making prodrugs are described in Saulnier et al. (1994), Bioorganic and Medicinal Chemistry Letters, Vol. 4, p. 1985.

Protected derivatives of compounds of the present invention can also be made. Examples of techniques applicable to the creation of protecting groups and their removal can be found in T. W. Greene, Protecting Groups in Organic Synthesis, $3^{rd}$ edition, John Wiley & Sons, Inc. 1999.

Compounds of the present invention may also be conveniently prepared, or formed during the process of the invention, as solvates (e.g., hydrates). Hydrates of compounds of the present invention may be conveniently prepared by recrystallization from an aqueous/organic solvent mixture, using organic solvents such as dioxin, tetrahydrofuran or methanol.

A "pharmaceutically acceptable salt", as used herein, is intended to encompass any compound according to the present invention that is utilized in the form of a salt thereof, especially where the salt confers on the compound improved pharmacokinetic properties as compared to the free form of compound or a different salt form of the compound. The pharmaceutically acceptable salt form may also initially confer desirable pharmacokinetic properties on the compound that it did not previously possess, and may even positively affect the pharmacodynamics of the compound with respect to its therapeutic activity in the body. An example of a pharmacokinetic property that may be favorably affected is the manner in which the compound is transported across cell membranes, which in turn may directly and positively affect the absorption, distribution, biotransformation and excretion of the compound. While the route of administration of the pharmaceutical composition is important, and various anatomical, physiological and pathological factors can critically affect bioavailability, the solubility of the compound is usually dependent upon the character of the particular salt form thereof, which it utilized. One of skill in the art will appreciate that an aqueous solution of the compound will provide the most rapid absorption of the compound into the body of a subject being treated, while lipid solutions and suspensions, as well as solid dosage forms, will result in less rapid absorption of the compound.

Compositions Comprising Kinase Inhibitors

A wide variety of compositions and administration methods may be used in conjunction with the compounds of the present invention. Such compositions may include, in addition to the compounds of the present invention, conventional pharmaceutical excipients, and other conventional, pharmaceutically inactive agents. Additionally, the compositions may include active agents in addition to the compounds of the present invention. These additional active agents may include additional compounds according to the invention, and/or one or more other pharmaceutically active agents.

The compositions may be in gaseous, liquid, semi-liquid or solid form, formulated in a manner suitable for the route of administration to be used. For oral administration, capsules and tablets are typically used. For parenteral administration, reconstitution of a lyophilized powder, prepared as described herein, is typically used.

Compositions comprising compounds of the present invention may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds and/or compositions according to the invention may also be administered or coadministered in slow release dosage forms.

The kinase inhibitors and compositions comprising them may be administered or coadministered in any conventional dosage form. Co-administration in the context of this invention is intended to mean the administration of more than one therapeutic agent, one of which includes a kinase inhibitor, in the course of a coordinated treatment to achieve an improved clinical outcome. Such co-administration may also be coextensive, that is, occurring during overlapping periods of time.

Solutions or suspensions used for parenteral, intradermal, subcutaneous, or topical application may optionally include one or more of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; agents for the adjustment of tonicity such as sodium chloride or dextrose, and agents for adjusting the acidity or alkalinity of the composition, such as alkaline or acidifying agents or buffers like carbonates, bicarbonates, phosphates, hydrochloric acid, and organic acids like acetic and citric acid. Parenteral preparations may optionally be enclosed in ampules, disposable syringes or single or multiple dose vials made of glass, plastic or other suitable material.

When compounds according to the present invention exhibit insufficient solubility, methods for solubilizing the compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate. Derivatives of the compounds, such as prodrugs of the compounds may also be used in formulating effective pharmaceutical compositions.

Upon mixing or adding compounds according to the present invention to a composition, a solution, suspension, emulsion or the like may be formed. The form of the resulting composition will depend upon a number of factors, including the intended mode of administration, and the solubility of the compound in the selected carrier or vehicle. The effective concentration needed to ameliorate the disease being treated may be empirically determined.

Compositions according to the present invention are optionally provided for administration to humans and animals in unit dosage forms, such as tablets, capsules, pills, powders, dry powders for inhalers, granules, sterile parenteral solutions or suspensions, and oral solutions or suspensions, and oil-water emulsions containing suitable quantities of the compounds, particularly the pharmaceutically acceptable salts, preferably the sodium salts, thereof. The pharmaceutically therapeutically active compounds and derivatives thereof are typically formulated and administered in unit-dosage forms or multiple-dosage forms. Unit-dose forms, as used herein, refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes individually packaged tablet or capsule. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pint or gallons. Hence, multiple dose form is a multiple of unit-doses that are not segregated in packaging.

In addition to one or more compounds according to the present invention, the composition may comprise: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polyvinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to form a solution or suspension. If desired, the pharmaceutical composition to be administered may also contain minor amounts of auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents. Actual methods of preparing such dosage forms are known in the art, or will be apparent, to those skilled in this art; for example, see Remington's Pharmaceutical Sciences, Mack Publishing Company, Easton, Pa., 15th Edition, 1975. The composition or formulation to be administered will, in any event, contain a sufficient quantity of an inhibitor of the present invention to reduce kinase activity in vivo, thereby treating the disease state of the subject.

Dosage forms or compositions may optionally comprise one or more compounds according to the present invention in the range of 0.005% to 100% (weight/weight) with the balance comprising additional substances such as those described herein. For oral administration, a pharmaceutically acceptable composition may optionally comprise any one or more commonly employed excipients, such as, for example pharmaceutical grades of mannitol, lactose, starch, magnesium stearate, talcum, cellulose derivatives, sodium crosscarmellose, glucose, sucrose, magnesium carbonate, sodium saccharin, talcum. Such compositions include solutions, suspensions, tablets, capsules, powders, dry powders for inhalers and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparing these formulations are known to those skilled in the art. The compositions may optionally contain 0.01%-100% (weight/weight) of one or more kinase inhibitors, optionally 0.1-95%, and optionally 1-95%.

Salts, preferably sodium salts, of the inhibitors may be prepared with carriers that protect the compound against rapid elimination from the body, such as time release formulations or coatings. The formulations may further include other active compounds to obtain desired combinations of properties.

Formulations for Oral Administration

Oral pharmaceutical dosage forms may be as a solid, gel or liquid. Examples of solid dosage forms include, but are not limited to tablets, capsules, granules, and bulk powders. More specific examples of oral tablets include compressed, chewable lozenges and tablets that may be enteric-coated, sugar-coated or film-coated. Examples of capsules include hard or soft gelatin capsules. Granules and powders may be provided in non-effervescent or effervescent forms. Each may be combined with other ingredients known to those skilled in the art.

In certain embodiments, compounds according to the present invention are provided as solid dosage forms, preferably capsules or tablets. The tablets, pills, capsules, troches and the like may optionally contain one or more of the following ingredients, or compounds of a similar nature: a binder; a diluent; a disintegrating agent; a lubricant; a glidant; a sweetening agent; and a flavoring agent.

Examples of binders that may be used include, but are not limited to, microcrystalline cellulose, gum tragacanth, glucose solution, acacia mucilage, gelatin solution, sucrose, and starch paste.

Examples of lubricants that may be used include, but are not limited to, talc, starch, magnesium or calcium stearate, lycopodium and stearic acid.

Examples of diluents that may be used include, but are not limited to, lactose, sucrose, starch, kaolin, salt, mannitol, and dicalcium phosphate.

Examples of glidants that may be used include, but are not limited to, colloidal silicon dioxide.

Examples of disintegrating agents that may be used include, but are not limited to, crosscarmellose sodium, sodium starch glycolate, alginic acid, corn starch, potato starch, bentonite, methylcellulose, agar and carboxymethylcellulose.

Examples of coloring agents that may be used include, but are not limited to, any of the approved certified water-soluble FD and C dyes, mixtures thereof, and water insoluble FD and C dyes suspended on alumina hydrate.

Examples of sweetening agents that may be used include, but are not limited to, sucrose, lactose, mannitol and artificial sweetening agents such as sodium cyclamate and saccharin, and any number of spray-dried flavors.

Examples of flavoring agents that may be used include, but are not limited to, natural flavors extracted from plants such as fruits and synthetic blends of compounds that produce a pleasant sensation, such as, but not limited to peppermint and methyl salicylate.

Examples of wetting agents that may be used include, but are not limited to, propylene glycol monostearate, sorbitan monooleate, diethylene glycol monolaurate, and polyoxyethylene lauryl ether.

Examples of anti-emetic coatings that may be used include, but are not limited to, fatty acids, fats, waxes, shellac, ammoniated shellac and cellulose acetate phthalates.

Examples of film coatings that may be used include, but are not limited to, hydroxyethylcellulose, sodium carboxymethylcellulose, polyethylene glycol 4000 and cellulose acetate phthalate.

If oral administration is desired, the salt of the compound may optionally be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it may optionally additionally comprise a liquid carrier such as a fatty oil. In addition, dosage unit forms may optionally additionally comprise various other materials that modify the physical form of the dosage unit, for example, coatings of sugar and other enteric agents.

Compounds according to the present invention may also be administered as a component of an elixir, suspension, syrup, wafer, sprinkle, chewing gum or the like. A syrup may optionally comprise, in addition to the active compounds, sucrose as a sweetening agent and certain preservatives, dyes and colorings and flavors.

The compounds of the present invention may also be mixed with other active materials that do not impair the desired action, or with materials that supplement the desired action, such as antacids, H2 blockers, and diuretics. For example, if a compound is used for treating asthma or hypertension, it may be used with other bronchodilators and antihypertensive agents, respectively.

Examples of pharmaceutically acceptable carriers that may be included in tablets comprising compounds of the present invention include, but are not limited to binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets may be compressed tablets to which different layers of pharmaceutically acceptable substances are applied. Film-coated tablets may be compressed tablets that have been coated with polymers or other suitable coating. Multiple compressed tablets may be compressed tablets made by more than one compression cycle utilizing the pharmaceutically acceptable substances previously mentioned. Coloring agents may also be used in tablets. Flavoring and sweetening agents may be used in tablets, and are especially useful in the formation of chewable tablets and lozenges.

Examples of liquid oral dosage forms that may be used include, but are not limited to, aqueous solutions, emulsions, suspensions, solutions and/or suspensions reconstituted from non-effervescent granules and effervescent preparations reconstituted from effervescent granules.

Examples of aqueous solutions that may be used include, but are not limited to, elixirs and syrups. As used herein, elixirs refer to clear, sweetened, hydroalcoholic preparations. Examples of pharmaceutically acceptable carriers that may be used in elixirs include, but are not limited to solvents. Particular examples of solvents that may be used include glycerin, sorbitol, ethyl alcohol and syrup. As used herein, syrups refer to concentrated aqueous solutions of a sugar, for example, sucrose. Syrups may optionally further comprise a preservative.

Emulsions refer to two-phase systems in which one liquid is dispersed in the form of small globules throughout another liquid. Emulsions may optionally be oil-in-water or water-in-oil emulsions. Examples of pharmaceutically acceptable carriers that may be used in emulsions include, but are not limited to non-aqueous liquids, emulsifying agents and preservatives.

Examples of pharmaceutically acceptable substances that may be used in non-effervescent granules, to be reconstituted into a liquid oral dosage form, include diluents, sweeteners and wetting agents.

Examples of pharmaceutically acceptable substances that may be used in effervescent granules, to be reconstituted into a liquid oral dosage form, include organic acids and a source of carbon dioxide.

Coloring and flavoring agents may optionally be used in all of the above dosage forms.

Particular examples of preservatives that may be used include glycerin, methyl and propylparaben, benzoic add, sodium benzoate and alcohol.

Particular examples of non-aqueous liquids that may be used in emulsions include mineral oil and cottonseed oil.

Particular examples of emulsifying agents that may be used include gelatin, acacia, tragacanth, bentonite, and surfactants such as polyoxyethylene sorbitan monooleate.

Particular examples of suspending agents that may be used include sodium carboxymethylcellulose, pectin, tragacanth, Veegum and acacia. Diluents include lactose and sucrose. Sweetening agents include sucrose, syrups, glycerin and artificial sweetening agents such as sodium cyclamate and saccharin.

Particular examples of wetting agents that may be used include propylene glycol monostearate, sorbitan monooleate, diethylene glycol monolaurate, and polyoxyethylene lauryl ether.

Particular examples of organic acids that may be used include citric and tartaric acid.

Sources of carbon dioxide that may be used in effervescent compositions include sodium bicarbonate and sodium carbonate. Coloring agents include any of the approved certified water soluble FD and C dyes, and mixtures thereof.

Particular examples of flavoring agents that may be used include natural flavors extracted from plants such fruits, and synthetic blends of compounds that produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. Re 28,819 and 4,358,603.

Injectables, Solutions, and Emulsions

The present invention is also directed to compositions designed to administer the compounds of the present invention by parenteral administration, generally characterized by subcutaneous, intramuscular or intravenous injection. Injectables may be prepared in any conventional form, for example as liquid solutions or suspensions, solid forms suitable for solution or suspension in liquid prior to injection, or as emulsions.

Examples of excipients that may be used in conjunction with injectables according to the present invention include, but are not limited to water, saline, dextrose, glycerol or ethanol. The injectable compositions may also optionally comprise minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) is also contemplated herein. The percentage of active compound contained in such parenteral compositions is highly dependent on the specific nature thereof, as well as the activity of the compound and the needs of the subject.

Parenteral administration of the formulations includes intravenous, subcutaneous and intramuscular administrations. Preparations for parenteral administration include sterile solutions ready for injection, sterile dry soluble products, such as the lyophilized powders described herein, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

When administered intravenously, examples of suitable carriers include, but are not limited to physiological saline or phosphate buffered saline (PBS), and solutions containing thickening and solubilizing agents, such as glucose, polyethylene glycol, and polypropylene glycol and mixtures thereof.

Examples of pharmaceutically acceptable carriers that may optionally be used in parenteral preparations include, but are not limited to aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles that may optionally be used include Sodium Chloride Injection, Ringers Injection, Isotonic Dextrose Injection, Sterile Water Injection, Dextrose and Lactated Ringers Injection.

Examples of nonaqueous parenteral vehicles that may optionally be used include fixed oils of vegetable origin, cottonseed oil, corn oil, sesame oil and peanut oil.

Antimicrobial agents in bacteriostatic or fungistatic concentrations may be added to parenteral preparations, particularly when the preparations are packaged in multiple-dose containers and thus designed to be stored and multiple aliquots to be removed. Examples of antimicrobial agents that may be used include phenols or cresols, mercurials, benzyl alcohol, chlorobutanol, methyl and propyl p-hydroxybenzoic acid esters, thimerosal, benzalkonium chloride and benzethonium chloride.

Examples of isotonic agents that may be used include sodium chloride and dextrose. Examples of buffers that may be used include phosphate and citrate. Examples of antioxidants that may be used include sodium bisulfate. Examples of local anesthetics that may be used include procaine hydrochloride. Examples of suspending and dispersing agents that may be used include sodium carboxymethylcellulose, hydroxypropyl methylcellulose and polyvinylpyrrolidone. Examples of emulsifying agents that may be used include Polysorbate 80 (TWEEN 80). A sequestering or chelating agent of metal ions include EDTA.

Pharmaceutical carriers may also optionally include ethyl alcohol, polyethylene glycol and propylene glycol for water miscible vehicles and sodium hydroxide, hydrochloric acid, citric acid or lactic acid for pH adjustment.

The concentration of an inhibitor in the parenteral formulation may be adjusted so that an injection administers a pharmaceutically effective amount sufficient to produce the desired pharmacological effect. The exact concentration of an inhibitor and/or dosage to be used will ultimately depend on the age, weight and condition of the patient or animal as is known in the art.

Unit-dose parenteral preparations may be packaged in an ampoule, a vial or a syringe with a needle. All preparations for parenteral administration should be sterile, as is known and practiced in the art.

Injectables may be designed for local and systemic administration. Typically a therapeutically effective dosage is formulated to contain a concentration of at least about 0.1% w/w up to about 90% w/w or more, preferably more than 1% w/w of the kinase inhibitor to the treated tissue(s). The inhibitor may be administered at once, or may be divided into a number of smaller doses to be administered at intervals of time. It is understood that the precise dosage and duration of treatment will be a function of the location of where the composition is parenterally administered, the carrier and other variables that may be determined empirically using known testing protocols or by extrapolation from in vivo or in vitro test data. It is to be noted that concentrations and dosage values may also vary with the age of the individual treated. It is to be further understood that for any particular subject, specific dosage regimens may need to be adjusted over time according to the individual need and the professional judgment of the person administering or supervising the administration of the formulations. Hence, the concentration ranges set forth herein are intended to be exemplary and are not intended to limit the scope or practice of the claimed formulations.

The kinase inhibitor may optionally be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the disease state and may be empirically determined.

Lyophilized Powders

The compounds of the present invention may also be prepared as lyophilized powders, which can be reconstituted for administration as solutions, emulsions and other mixtures. The lyophilized powders may also be formulated as solids or gels.

Sterile, lyophilized powder may be prepared by dissolving the compound in a sodium phosphate buffer solution containing dextrose or other suitable excipient. Subsequent sterile filtration of the solution followed by lyophilization under standard conditions known to those of skill in the art provides the desired formulation. Briefly, the lyophilized powder may optionally be prepared by dissolving dextrose, sorbitol, fructose, corn syrup, xylitol, glycerin, glucose, sucrose or other suitable agent, about 1-20%, preferably about 5 to 15%, in a suitable buffer, such as citrate, sodium or potassium phosphate or other such buffer known to those of skill in the art at, typically, about neutral pH. Then, a kinase inhibitor is added to the resulting mixture, preferably above room temperature, more preferably at about 30-35° C., and stirred until it dissolves. The resulting mixture is diluted by adding more buffer to a desired concentration. The resulting mixture is sterile filtered or treated to remove particulates and to insure sterility, and apportioned into vials for lyophilization. Each vial may contain a single dosage or multiple dosages of the inhibitor.

Topical Administration

The compounds of the present invention may also be administered as topical mixtures. Topical mixtures may be used for local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The kinase inhibitors may be formulated as aerosols for topical application, such as by inhalation (see, U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns, preferably less than 10 microns.

The inhibitors may also be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the kinase inhibitor alone or in combination with other pharmaceutically acceptable excipients can also be administered.

Formulations for Other Routes of Administration

Depending upon the disease state being treated, other routes of administration, such as topical application, transdermal patches, and rectal administration, may also be used. For example, pharmaceutical dosage forms for rectal administration are rectal suppositories, capsules and tablets for systemic effect. Rectal suppositories are used herein mean solid bodies for insertion into the rectum that melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax, (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm. Tablets and capsules for rectal administration may be manufactured using the same pharmaceutically acceptable substance and by the same methods as for formulations for oral administration.

Examples of Formulations

The following are particular examples of oral, intravenous and tablet formulations that may optionally be used with compounds of the present invention. It is noted that these formulations may be varied depending on the particular compound being used and the indication for which the formulation is going to be used.

| ORAL FORMULATION | |
|---|---|
| Compound of the Present Invention | 10-100 mg |
| Citric Acid Monohydrate | 105 mg |
| Sodium Hydroxide | 18 mg |
| Flavoring | |
| Water | q.s. to 100 mL |

| INTRAVENOUS FORMULATION | |
|---|---|
| Compound of the Present Invention | 0.1-10 mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |

| TABLET FORMULATION | |
|---|---|
| Compound of the Present Invention | 1% |
| Microcrystalline Cellulose | 73% |
| Stearic Acid | 25% |
| Colloidal Silica | 1%. |

Kits Comprising Kinase Inhibitors

The invention is also directed to kits and other articles of manufacture for treating diseases associated with kinases. It is noted that diseases are intended to cover all conditions for which the kinase possesses activity that contributes to the pathology and/or symptomology of the condition.

In one embodiment, a kit is provided that comprises a composition comprising at least one inhibitor of the present invention in combination with instructions. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another embodiment, an article of manufacture is provided that comprises a composition comprising at least one inhibitor of the present invention in combination with packaging materials. The packaging material may comprise a container for housing the composition. The container may optionally comprise a label indicating the disease state for which the composition is to be administered, storage information, dosing information and/or instructions regarding how to administer the composition. The kit may also optionally comprise additional components, such as syringes for administration of the composition. The kit may comprise the composition in single or multiple dose forms.

It is noted that the packaging material used in kits and articles of manufacture according to the present invention may form a plurality of divided containers such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container that is employed will depend on the exact dosage form involved, for example a conventional cardboard box would not generally be used to hold a liquid suspension. It is feasible that more than one container can be used together in a single package to market a single dosage form. For example, tablets may be contained in a bottle that is in turn contained within a box. Typically the kit includes directions for the administration of the separate components. The kit form is particularly advantageous when the separate components are preferably administered in different dosage forms (e.g., oral, topical, transdermal and parenteral), are administered at different dosage intervals, or when titration of the individual components of the combination is desired by the prescribing physician.

One particular example of a kit according to the present invention is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

Another specific embodiment of a kit is a dispenser designed to dispense the daily doses one at a time in the order of their intended use. Preferably, the dispenser is equipped with a memory-aid, so as to further facilitate compliance with the regimen. An example of such a memory-aid is a mechanical counter that indicates the number of daily doses that has been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

Dosage, Host and Safety

The compounds of the present invention are stable and can be used safely. In particular, the compounds of the present invention are useful as PLK inhibitors for a variety of subjects (e.g., humans, non-human mammals and non-mammals). The optimal dose may vary depending upon such conditions as, for example, the type of subject, the body weight of the subject, the route of administration, and specific properties of the particular compound being used. In general, the daily dose for oral administration to an adult (body weight of about 60 kg) is about 1 to 1000 mg, about 3 to 300 mg, or about 10 to 200 mg. It will be appreciated that the daily dose can be given in a single administration or in multiple (e.g., 2 or 3) portions a day.

Combination Therapies

A wide variety of therapeutic agents may have a therapeutic additive or synergistic effect with kinase inhibitors according to the present invention. Combination therapies that comprise one or more compounds of the present invention with one or more other therapeutic agents can be used, for example, to: 1) enhance the therapeutic effect(s) of the one or more compounds of the present invention and/or the one or more other therapeutic agents; 2) reduce the side effects exhibited by the one or more compounds of the present invention and/or the one or more other therapeutic agents; and/or 3) reduce the effective dose of the one or more compounds of the present invention and/or the one or more other therapeutic agents. For example, such other therapeutic agents may additively or synergistically combine with the kinase inhibitors to inhibit undesirable cell growth, such as inappropriate cell growth resulting in undesirable benign conditions or tumor growth.

In one embodiment, a method is provided for treating a cell proliferative disease state comprising treating cells with a compound according to the present invention in combination with an anti-proliferative agent, wherein the cells are treated with the compound according to the present invention before, at the same time, and/or after the cells are treated with the anti-proliferative agent, referred to herein as combination therapy. It is noted that treatment of one agent before another is referred to herein as sequential therapy, even if the agents are also administered together. It is noted that combination therapy is intended to cover when agents are administered before or after each other (sequential therapy) as well as when the agents are administered at the same time.

Examples of therapeutic agents that may be used in combination with kinase inhibitors include, but are not limited to, anticancer agents, alkylating agents, antibiotic agents, antimetabolic agents, hormonal agents, plant-derived agents, and biologic agents.

Alkylating agents are polyfunctional compounds that have the ability to substitute alkyl groups for hydrogen ions. Examples of alkylating agents include, but are not limited to, bischloroethylamines (nitrogen mustards, e.g. chlorambucil, cyclophosphamide, ifosfamide, mechlorethamine, melphalan, uracil mustard), aziridines (e.g. thiotepa), alkyl alkone sulfonates (e.g. busulfan), nitrosoureas (e.g. carmustine, lomustine, streptozocin), nonclassic alkylating agents (altretamine, dacarbazine, and procarbazine), platinum compounds (carboplastin and cisplatin). These compounds react with phosphate, amino, hydroxyl, sulfihydryl, carboxyl, and imidazole groups. Under physiological conditions, these drugs ionize and produce positively charged ion that attach to susceptible nucleic acids and proteins, leading to cell cycle arrest and/or cell death. Combination therapy including a kinase inhibitor and an alkylating agent may have therapeutic synergistic effects on cancer and reduce sides affects associated with these chemotherapeutic agents.

Antibiotic agents are a group of drugs that produced in a manner similar to antibiotics as a modification of natural products. Examples of antibiotic agents include, but are not limited to, anthracyclines (e.g. doxorubicin, daunorubicin, epirubicin, idarubicin and anthracenedione), mitomycin C, bleomycin, dactinomycin, plicatomycin. These antibiotic agents interferes with cell growth by targeting different cellular components. For example, anthracyclines are generally believed to interfere with the action of DNA topoisomerase II in the regions of transcriptionally active DNA, which leads to DNA strand scissions. Bleomycin is generally believed to chelate iron and forms an activated complex, which then binds to bases of DNA, causing strand scissions and cell death. Combination therapy including a kinase inhibitor and an antibiotic agent may have therapeutic synergistic effects on cancer and reduce sides affects associated with these chemotherapeutic agents.

Antimetabolic agents are a group of drugs that interfere with metabolic processes vital to the physiology and proliferation of cancer cells. Actively proliferating cancer cells require continuous synthesis of large quantities of nucleic acids, proteins, lipids, and other vital cellular constituents. Many of the antimetabolites inhibit the synthesis of purine or pyrimidine nucleosides or inhibit the enzymes of DNA replication. Some antimetabolites also interfere with the synthesis of ribonucleosides and RNA and/or amino acid metabolism and protein synthesis as well. By interfering with the synthesis of vital cellular constituents, antimetabolites can delay or arrest the growth of cancer cells. Examples of antimetabolic agents include, but are not limited to, fluorouracil (5-FU), floxuridine (5-FUdR), methotrexate, leucovorin, hydroxyurea, thioguanine (6-TG), mercaptopurine (6-MP), cytarabine, pentostatin, fludarabine phosphate, cladribine (2-CDA), asparaginase, and gemcitabine. Combination therapy including a kinase inhibitor and a antimetabolic agent may have therapeutic synergistic effects on cancer and reduce sides affects associated with these chemotherapeutic agents.

Hormonal agents are a group of drug that regulate the growth and development of their target organs. Most of the hormonal agents are sex steroids and their derivatives and analogs thereof, such as estrogens, androgens, and progestins. These hormonal agents may serve as antagonists of receptors for the sex steroids to down regulate receptor expression and transcription of vital genes. Examples of such hormonal agents are synthetic estrogens (e.g. diethylstibestrol), antiestrogens (e.g. tamoxifen, toremifene, fluoxymesterol and raloxifene), antiandrogens (bicalutamide, nilutamide, flutamide), aromatase inhibitors (e.g., aminoglutethimide, anastrozole and tetrazole), ketoconazole, goserelin acetate, leuprolide, megestrol acetate and mifepristone. Combination therapy including a kinase inhibitor and a hormonal agent may have therapeutic synergistic effects on cancer and reduce sides affects associated with these chemotherapeutic agents.

Plant-derived agents are a group of drugs that are derived from plants or modified based on the molecular structure of the agents. Examples of plant-derived agents include, but are not limited to, vinca alkaloids (e.g., vincristine, vinblastine, vindesine, vinzolidine and vinorelbine), podophyllotoxins (e.g., etoposide (VP-16) and teniposide (VM-26)), taxanes (e.g., paclitaxel and docetaxel). These plant-derived agents generally act as antimitotic agents that bind to tubulin and inhibit mitosis. Podophyllotoxins such as etoposide are believed to interfere with DNA synthesis by interacting with topoisomerase II, leading to DNA strand scission. Combination therapy including a kinase inhibitor and a plant-derived agent may have therapeutic synergistic effects on cancer and reduce sides affects associated with these chemotherapeutic agents.

Biologic agents are a group of biomolecules that elicit cancer/tumor regression when used alone or in combination with chemotherapy and/or radiotherapy. Examples of biologic agents include, but are not limited to, immuno-modulating proteins such as cytokines, monoclonal antibodies against tumor antigens, tumor suppressor genes, and cancer vaccines. Combination therapy including a kinase inhibitor and a biologic agent may have therapeutic synergistic effects on cancer, enhance the patient's immune responses to tumorigenic signals, and reduce potential sides affects associated with this chemotherapeutic agent.

Cytokines possess profound immunomodulatory activity. Some cytokines such as interleukin-2 (IL-2, aldesleukin) and interferon have demonstrated antitumor activity and have been approved for the treatment of patients with metastatic renal cell carcinoma and metastatic malignant melanoma. IL-2 is a T-cell growth factor that is central to T-cell-mediated immune responses. The selective antitumor effects of IL-2 on some patients are believed to be the result of a cell-mediated immune response that discriminate between self and nonself. Examples of interleukins that may be used in conjunction with a kinase inhibitor include, but are not limited to, interleukin 2 (IL-2), and interleukin 4 (IL-4), interleukin 12 (IL-12).

Interferon include more than 23 related subtypes with overlapping activities, all of the IFN subtypes within the scope of the present invention. IFN has demonstrated activity against many solid and hematologic malignancies, the later appearing to be particularly sensitive.

Other cytokines that may be used in conjunction with a kinase inhibitor include those cytokines that exert profound effects on hematopoiesis and immune functions. Examples of such cytokines include, but are not limited to erythropoietin, granulocyte-CSF (filgrastin), and granulocyte, macrophage-CSF (sargramostim). These cytokines may be used in conjunction with a kinase inhibitor to reduce chemotherapy-induced myelopoietic toxicity.

Other immuno-modulating agents other than cytokines may also be used in conjunction with a kinase inhibitor to inhibit abnormal cell growth. Examples of such immuno-modulating agents include, but are not limited to bacillus Calmette-Guerin, levamisole, and octreotide, a long-acting octapeptide that mimics the effects of the naturally occurring hormone somatostatin.

Monoclonal antibodies against tumor antigens are antibodies elicited against antigens expressed by tumors, preferably tumor-specific antigens. For example, monoclonal antibody HERCEPTIN® (Trastruzumab) is raised against human epidermal growth factor receptor2 (HER2) that is overexpressed in some breast tumors including metastatic breast cancer. Overexpression of HER2 protein is associated with more aggressive disease and poorer prognosis in the clinic. HERCEPTIN® is used as a single agent for the treatment of patients with metastatic breast cancer whose tumors over express the HER2 protein. Combination therapy including a kinase inhibitor and HERCEPTIN® may have therapeutic synergistic effects on tumors, especially on metastatic cancers.

Another example of monoclonal antibodies against tumor antigens is RITUXAN® (Rituximab) that is raised against CD20 on lymphoma cells and selectively deplete normal and malignant CD20⁺ pre-B and mature B cells. RITUXAN® is used as single agent for the treatment of patients with relapsed or refractory low-grade or follicular, CD20+, B cell non-Hodgkin's lymphoma. Combination therapy including a kinase inhibitor and RITUXAN® may have therapeutic synergistic effects not only on lymphoma, but also on other forms or types of malignant tumors.

Tumor suppressor genes are genes that function to inhibit the cell growth and division cycles, thus preventing the development of neoplasia. Mutations in tumor suppressor genes cause the cell to ignore one or more of the components of the network of inhibitory signals, overcoming the cell cycle check points and resulting in a higher rate of controlled cell growth-cancer. Examples of the tumor suppressor genes include, but are not limited to, DPC-4, NF-1, NF-2, RB, p53, WT1, BRCA1 and BRCA2.

DPC-4 is involved in pancreatic cancer and participates in a cytoplasmic pathway that inhibits cell division. NF-1 codes for a protein that inhibits Ras, a cytoplasmic inhibitory protein. NF-1 is involved in neurofibroma and pheochromocytomas of the nervous system and myeloid leukemia. NF-2 encodes a nuclear protein that is involved in meningioma, schwanoma, and ependymoma of the nervous system. RB codes for the pRB protein, a nuclear protein that is a major inhibitor of cell cycle. RB is involved in retinoblastoma as well as bone, bladder, small cell lung and breast cancer. P53 codes for p53 protein that regulates cell division and can induce apoptosis. Mutation and/or inaction of p53 is found in a wide ranges of cancers. WT1 is involved in Wilms tumor of the kidneys. BRCA1 is involved in breast and ovarian cancer, and BRCA2 is involved in breast cancer. The tumor suppressor gene can be transferred into the tumor cells where it exerts its tumor suppressing functions. Combination therapy including a kinase inhibitor and a tumor suppressor may have therapeutic synergistic effects on patients suffering from various forms of cancers.

Cancer vaccines are a group of agents that induce the body's specific immune response to tumors. Most of cancer vaccines under research and development and clinical trials are tumor-associated antigens (TAAs). TAA are structures (i.e. proteins, enzymes or carbohydrates) which are present on tumor cells and relatively absent or diminished on normal cells. By virtue of being fairly unique to the tumor cell, TAAs provide targets for the immune system to recognize and cause their destruction. Example of TAAs include, but are not limited to gangliosides (GM2), prostate specific antigen (PSA), alpha-fetoprotein (AFP), carcinoembryonic antigen (CEA) (produced by colon cancers and other adenocarcinomas, e.g. breast, lung, gastric, and pancreas cancers), melanoma associated antigens (MART-1, gp100, MAGE 1,3 tyrosinase), papillomavirus E6 and E7 fragments, whole cells or portions/lysates of antologous tumor cells and allogeneic tumor cells.

An adjuvant may be used to augment the immune response to TAAs. Examples of adjuvants include, but are not limited to, bacillus Calmette-Guerin (BCG), endotoxin lipopolysaccharides, keyhole limpet hemocyanin (GKLH), interleukin-2 (IL-2), granulocyte-macrophage colony-stimulating factor (GM-CSF) and cytoxan, a chemotherapeutic agent which is believe to reduce tumor-induced suppression when given in low doses.

EXAMPLES

Preparation of Kinase Inhibitors

Various methods may be developed for synthesizing compounds according to the present invention. Representative methods for synthesizing these compounds are provided in the Examples. It is noted, however, that the compounds of the present invention may also be synthesized by other synthetic routes that others may devise.

It will be readily recognized that certain compounds according to the present invention have atoms with linkages to other atoms that confer a particular stereochemistry to the compound (e.g., chiral centers). It is recognized that synthesis of compounds according to the present invention may result in the creation of mixtures of different stereoisomers (i.e., enantiomers and diastereomers). Unless a particular stereochemistry is specified, recitation of a compound is intended to encompass all of the different possible stereoisomers.

Various methods for separating mixtures of different stereoisomers are known in the art. For example, a racemic mixture of a compound may be reacted with an optically active resolving agent to form a pair of diastereoisomeric compounds. The diastereomers may then be separated in order to recover the optically pure enantiomers. Dissociable complexes may also be used to resolve enantiomers (e.g., crystalline diastereoisomeric salts). Diastereomers typically have sufficiently distinct physical properties (e.g., melting points, boiling points, solubilities, reactivity, etc.) and can be readily separated by taking advantage of these dissimilarities. For example, diastereomers can typically be separated by chromatography or by separation/resolution techniques based upon differences in solubility. A more detailed description of techniques that can be used to resolve stereoisomers of compounds from their racemic mixture can be found in Jean Jacques Andre Collet, Samuel H. Wilen, Enantiomers, Racemates and Resolutions, John Wiley & Sons, Inc. (1981).

Compounds according to the present invention can also be prepared as a pharmaceutically acceptable acid addition salt by reacting the free base form of the compound with a pharmaceutically acceptable inorganic or organic acid. Alternatively, a pharmaceutically acceptable base addition salt of a compound can be prepared by reacting the free acid form of the compound with a pharmaceutically acceptable inorganic or organic base. Inorganic and organic acids and bases suitable for the preparation of the pharmaceutically acceptable salts of compounds are set forth in the definitions section of this Application. Alternatively, the salt forms of the compounds can be prepared using salts of the starting materials or intermediates.

The free acid or free base forms of the compounds can be prepared from the corresponding base addition salt or acid addition salt form. For example, a compound in an acid addition salt form can be converted to the corresponding free base by treating with a suitable base (e.g., ammonium hydroxide solution, sodium hydroxide, and the like). A compound in a base addition salt form can be converted to the corresponding free acid by treating with a suitable acid (e.g., hydrochloric acid, etc).

The N-oxides of compounds according to the present invention can be prepared by methods known to those of ordinary skill in the art. For example, N-oxides can be prepared by treating an unoxidized form of the compound with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds can be prepared from the N-oxide of an appropriate starting material.

Compounds in an unoxidized form can be prepared from N-oxides of compounds by treating with a reducing agent (e.g., sulfur, sulfur dioxide, triphenyl phosphine, lithium borohydride, sodium borohydride, phosphorus trichloride, tribromide, or the like) in an suitable inert organic solvent (e.g., acetonitrile, ethanol, aqueous dioxane, or the like) at 0 to 80° C.

Prodrug derivatives of the compounds can be prepared by methods known to those of ordinary skill in the art (e.g., for further details see Saulnier et al. (1994), Bioorganic and Medicinal Chemistry Letters, Vol. 4, p. 1985). For example, appropriate prodrugs can be prepared by reacting a non-derivatized compound with a suitable carbamylating agent (e.g., 1,1-acyloxyalkylcarbonochloridate, para-nitrophenyl carbonate, or the like).

Protected derivatives of the compounds can be made by methods known to those of ordinary skill in the art. A detailed description of the techniques applicable to the creation of protecting groups and their removal can be found in T. W. Greene, Protecting Groups in Organic Synthesis, $3^{rd}$ edition, John Wiley & Sons, Inc. 1999.

Compounds according to the present invention may be conveniently prepared, or formed during the process of the invention, as solvates (e.g., hydrates). Hydrates of compounds of the present invention may be conveniently prepared by recrystallization from an aqueous/organic solvent mixture, using organic solvents such as dioxin, tetrahydrofuran or methanol.

Compounds according to the present invention can also be prepared as their individual stereoisomers by reacting a racemic mixture of the compound with an optically active resolving agent to form a pair of diastereoisomeric compounds, separating the diastereomers and recovering the optically pure enantiomer. While resolution of enantiomers can be carried out using covalent diastereomeric derivatives of compounds, dissociable complexes are preferred (e.g., crystalline diastereoisomeric salts). Diastereomers have distinct physical properties (e.g., melting points, boiling points, solubilities, reactivity, etc.) and can be readily separated by taking advantage of these dissimilarities. The diastereomers can be separated by chromatography or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques Andre Collet, Samuel H. Wilen, Enantiomers, Racemates and Resolutions, John Wiley & Sons, Inc. (1981).

As used herein the symbols and conventions used in these processes, schemes and examples are consistent with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

| | |
|---|---|
| µL (microliters) | Ac (acetyl) |
| atm (atmosphere) | ATP (Adenosine Triphophatase) |
| BOC (tert-butyloxycarbonyl) | BOP (bis(2-oxo-3-oxazolidinyl)phosphinic chloride) |
| BSA (Bovine Serum Albumin) | CBZ (benzyloxycarbonyl) |
| CDI (1,1-carbonyldiimidazole) | DCC (dicyclohexylcarbodiimide) |
| DCE (dichloroethane) | DCM (dichloromethane) |
| DMAP (4-dimethylaminopyridine) | DME (1,2-dimethoxyethane) |
| DMF (N,N-dimethylformamide) | DMPU (N,N'-dimethylpropyleneurea) |
| DMSO (dimethylsulfoxide) | EDCI (ethylcarbodiimide hydrochloride) |

| | |
|---|---|
| EDTA (Ethylenediaminetetraacetic acid) | Et (ethyl) |
| Et$_2$O (diethyl ether) | EtOAc (ethyl acetate) |
| FMOC (9-fluorenylmethoxycarbonyl) | g (grams) |
| h (hours) | HOAc or AcOH (acetic acid) |
| HOBT (1-hydroxybenzotriazole) | HOSu (N-hydroxysuccinimide) |
| HPLC (high pressure liquid chromatography) | Hz (Hertz) |
| i.v. (intravenous) | IBCF (isobutyl chloroformate) |
| i-PrOH (isopropanol) | L (liters) |
| M (molar) | mCPBA (meta-chloroperbenzoic acid) |
| Me (methyl) | MeOH (methanol) |
| mg (milligrams) | MHz (megahertz) |
| min (minutes) | mL (milliliters) |
| mM (millimolar) | mmol (millimoles) |
| mol (moles) | MOPS (Morpholinepropanesulfonic acid) |
| mp (melting point) | NaOAc (sodium acetate) |
| OMe (methoxy) | psi (pounds per square inch) |
| RP (reverse phase) | RT (ambient temperature) |
| SPA (Scintillation Proximity Assay) | TBAF (tetra-n-butylammonium fluoride) |
| TBS (t-butyldimethylsilyl) | tBu (tert-butyl) |
| TEA (triethylamine) | TFA (trifluoroacetic acid) |
| TFAA (trifluoroacetic anhydride) | THF (tetrahydrofuran) |
| TIPS (triisopropylsilyl) | TLC (thin layer chromatography) |
| TMS (trimethylsilyl) | TMSE (2-(trimethylsilyl)ethyl) |
| Tr (retention time) | |

All references to ether or Et$_2$O are to diethyl ether; and brine refers to a saturated aqueous solution of NaCl. Unless otherwise indicated, all temperatures are expressed in ° C. (degrees Centigrade). All reactions are conducted under an inert atmosphere at RT unless otherwise noted.

$^1$H NMR spectra were recorded on a Bruker Avance 400. Chemical shifts are expressed in parts per million (ppm). Coupling constants are in units of Hertz (Hz). Splitting patterns describe apparent multiplicities and are designated as s (singlet), d (doublet), t (triplet), q (quartet), m (multiplet), br (broad).

Low-resolution mass spectra (MS) and compound purity data were acquired on a Waters ZQ LC/MS single quadrupole system equipped with electrospray ionization (ESI) source, UV detector (220 and 254 nm), and evaporative light scattering detector (ELSD). Thin-layer chromatography was performed on 0.25 mm E. Merck silica gel plates (60F-254), visualized with UV light, 5% ethanolic phosphomolybdic acid, Ninhydrin or p-anisaldehyde solution. Flash column chromatography was performed on silica gel (230-400 mesh, Merck).

The starting materials and reagents used in preparing these compounds are either available from commercial suppliers such as the Aldrich Chemical Company (Milwaukee, Wis.), Bachem (Torrance, Calif.), Sigma (St. Louis, Mo.), or may be prepared by methods well known to a person of ordinary skill in the art, following procedures described in such standard references as Fieser and Fieser's Reagents for Organic Synthesis, vols. 1-17, John Wiley and Sons, New York, N.Y., 1991; Rodd's Chemistry of Carbon Compounds, vols. 1-5 and supps., Elsevier Science Publishers, 1989; Organic Reactions, vols. 1-40, John Wiley and Sons, New York, N.Y., 1991; March J.: Advanced Organic Chemistry, 4th ed., John Wiley and Sons, New York, N.Y.; and Larock: Comprehensive Organic Transformations, VCH Publishers, New York, 1989. The entire disclosures of all documents cited throughout this application are incorporated herein by reference.

Synthetic Schemes for Compounds of the Present Invention

Compounds according to the present invention may be synthesized according to the reaction schemes shown below. Other reaction schemes could be readily devised by those skilled in the art. It should also be appreciated that a variety of different solvents, temperatures and other reaction conditions can be varied to optimize the yields of the reactions.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

General synthetic routes for producing compounds of the present invention are shown in the following schemes.

Scheme 1:

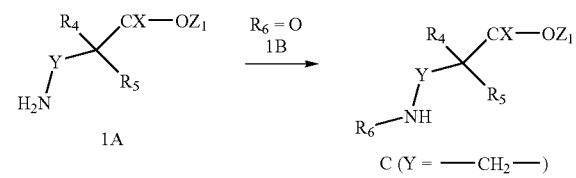

Referring to Scheme 1, Compound C is obtained by reductive amination of Compound 1B by Compound 1A using, for example, sodium triacetoxyborohydride or sodium cyanoborohydride. In particular embodiments, $Z_1$ is Me or Et; $R_6$ is cyclopentyl, isopropyl or a 2-6 membered alkyl bridge to $R_2$ or $R_3$ of Y; and $R_2$ and $R_3$ of Y are each independently H, Me, Et or a 2-6 membered alkyl bridge. In other particular embodiments, Compound 1B is cyclopentanone, cyclohexanone or ketone.

Scheme 2:

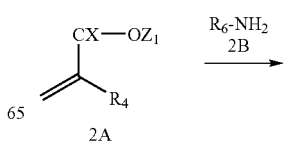

151

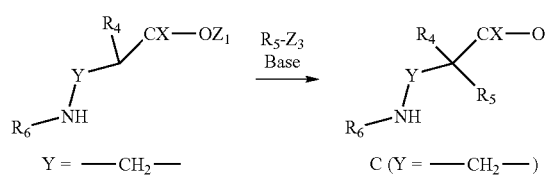

Referring to Scheme 2, Compound C is prepared by Michael addition of Compound 2A (i.e., ethyl acrylate) with Compound 2B (i.e., cyclopropylamine or cyclopentylamine) followed by alkylation with $R_5$—$Z_3$.

Scheme 3:

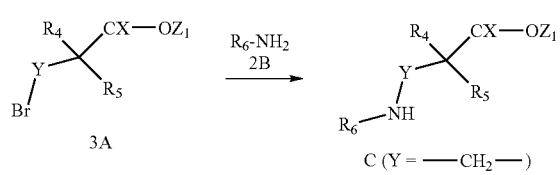

Referring to Scheme 3, Compound 3A is converted to Compound C using Compound 3B (i.e., cyclopropylamine or cyclopentylamine) in the presence of base (i.e., $K_2CO_3$) and sodium iodide.

Scheme 4:

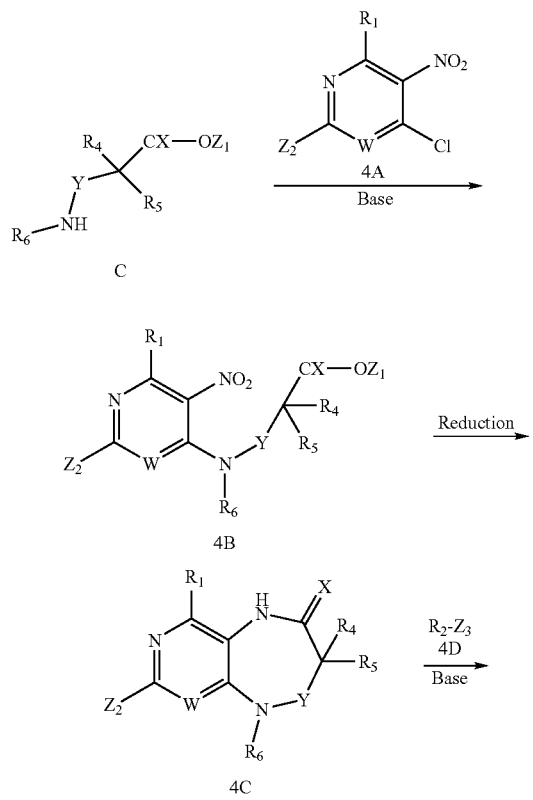

152

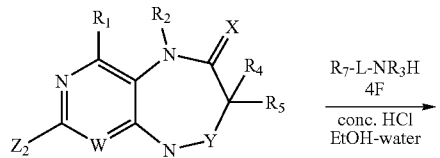

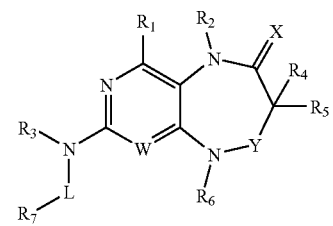

Referring to Scheme 4, Compound C is treated with Compound 4A in the presence of base (i.e., $K_2CO_3$ or diisopropylethylamine) to give Compound 4B. Compound 4B is transformed by reduction using reduced iron and subsequent cyclization reaction to afford Compound 4C. Compound 4E is prepared by N-alkylation of Compound 4C with Compound 4D (e.g., alkyl halide (e.g., iodomethane)). Compound 4E is treated with Compound 4F in the presence of a catalytic amount of acid (i.e., conc. HCl or pyridinium chloride) (about 0.1 to 10 equivalents) to obtain Compound 4G. Compound 4F is one that either has $R_7$ as desired in the end product or gives rise to $R_7$ as desired in the end product.

Scheme 5:

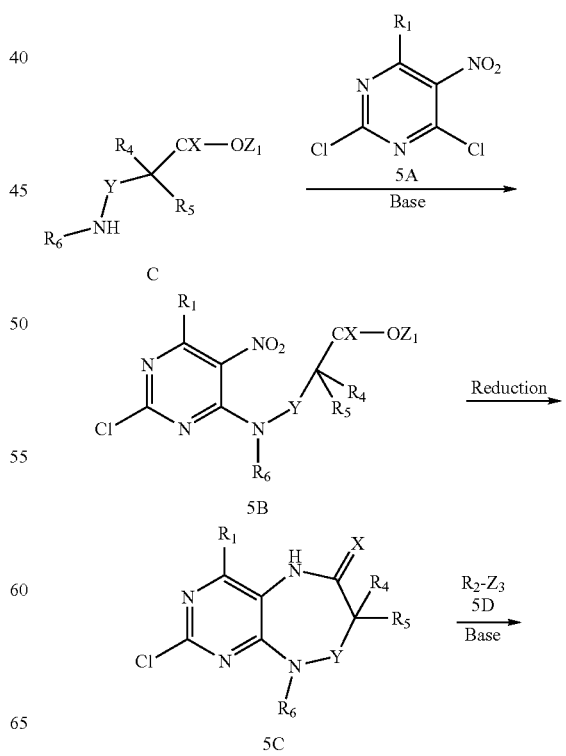

153
-continued

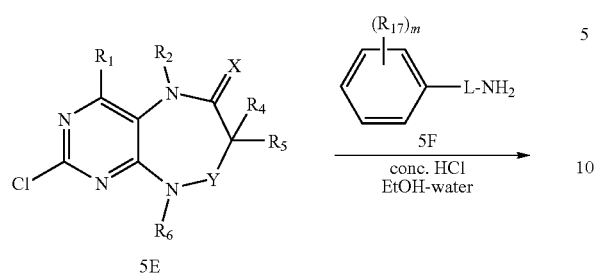
5E

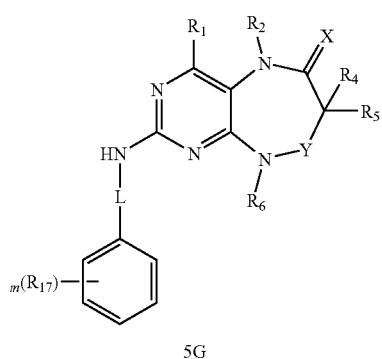
5G

Referring to Scheme 5, Compound C is treated with Compound 5A in the presence of base (i.e., $K_2CO_3$ or diisopropylethylamine) to give Compound 5B. Compound 5B is transformed by reduction using reduced iron and subsequent cyclization reaction to afford Compound 5C. Compound 5E is prepared by N-alkylation of Compound 5C with alkyl halide 5D (i.e., iodomethane). Compound 5E is treated with aniline or benzylamine (Compound 5F, $L=CHR_{14}$) in the presence of a catalytic amount of acid (i.e., conc. HCl or pyridinium chloride) to obtain Compound 5G.

Scheme 6:

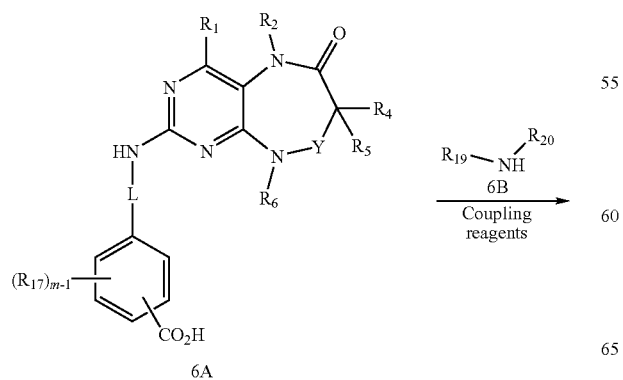
6A

154
-continued

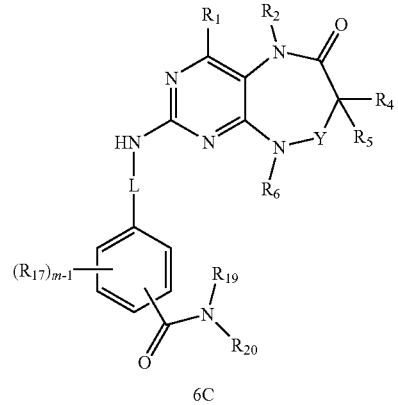
6C

Coupling reaction of Compound 6A with amine (Compound 6B, i.e., methylamine or 1-methylpiperidin-4-amine) using appropriate coupling reagents (i.e., HATU, TBTU, etc.) is carried out to give Compound 6C.

Scheme 7:

a)

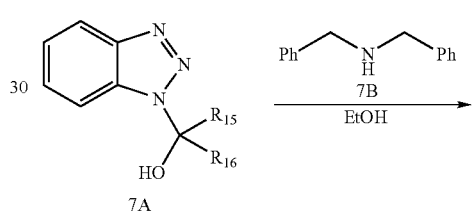

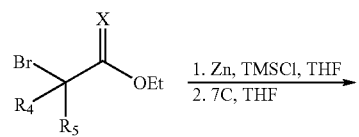
7C b)

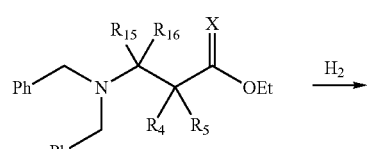

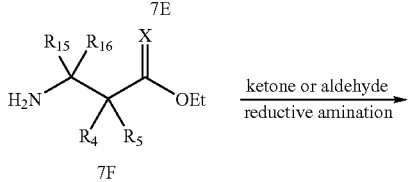

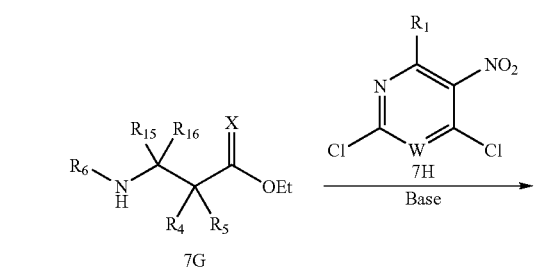

7G

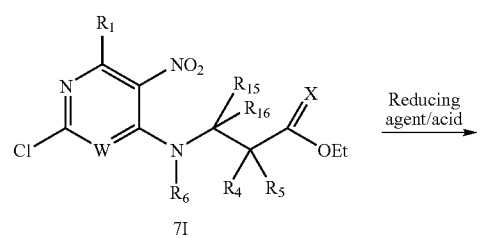

7I

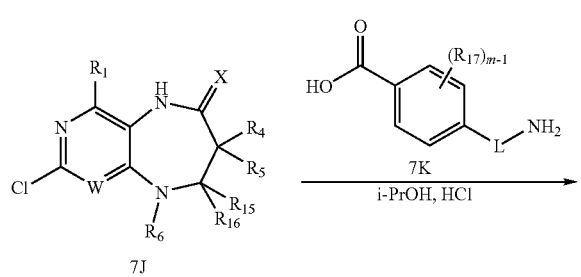

7J

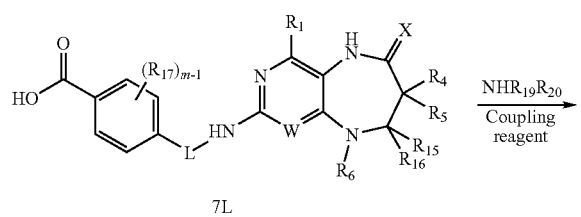

7L

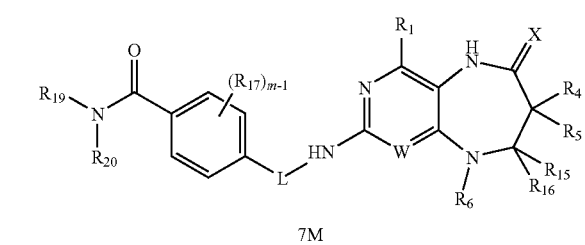

7M

R5 = halo
7N

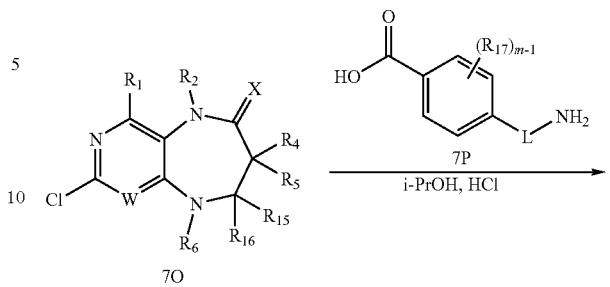

7O

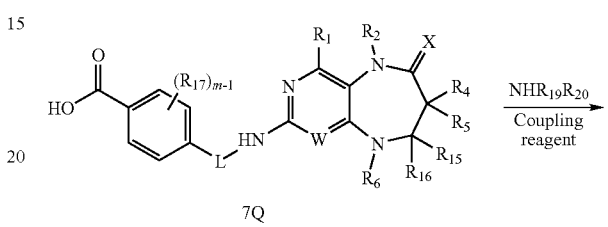

7Q

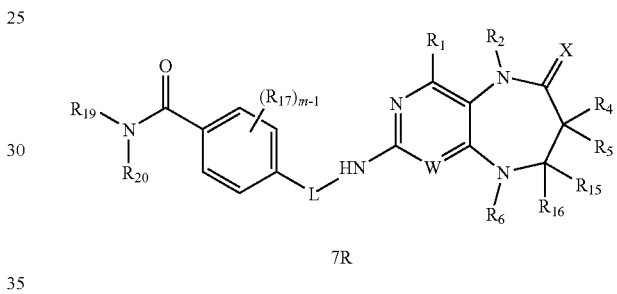

7R

Referring to Scheme 7, Compound 7A is treated with dibenzyl amine (7B) in ethanol to get 7C. Reformatsky reaction of ethyl α-bromo acetate (7D) with 7C in presence of Zinc dust, trimethyl silyl chloride to yield Compound 7E, which is subjected to hydrogenation in the presence of a palladium catalyst (i.e., Pd(OH)$_2$ on Carbon) to yield 7F. Reductive amination of Compound 7F with aldehyde or ketone (i.e., cyclopentanone or cyclohexanone) in presence of sodium triacetoxy borohydride and sodium acetate to afford 7G. Compound 7G is subjected to SNAr reaction with substituted pyrimidine 7H (i.e., 2,4-dichloro 5-nitro pyrimidine) in presence of base (i.e., K$_2$CO$_3$) to afford Compound 7I, which on reductive cyclization using a metal/acid catalyst (i.e., Fe/HCl or Sn/HCl) to obtain Compound 7J. Compound 7J is refluxed with Compound 7K (i.e., 4-amino 3-methoxy benzoic acid) in presence of an acid catalyst (i.e., conc.HCl or TsOH) to get Compound 7L, which is coupled with an amine (i.e., methylamine or 1-methylpiperidin-4-amine) to obtain Compound 7M.

Compound 7N is subjected to N-alkylation using an alkylating agent (i.e., methyl iodide) to afford Compound 7O. Compound 7O is refluxed with Compound 7P (i.e., 4-amino-3-methoxy benzoic acid) in presence of a acid catalyst (i.e., conc.HCl or TsOH) to yield Compound 7Q, which is subjected to an amine (i.e., methylamine or 1-methylpiperidin-4-amine) using appropriate coupling reagents (i.e., HATU, TBTU etc.) to give the Compound 7R.

Scheme 8:

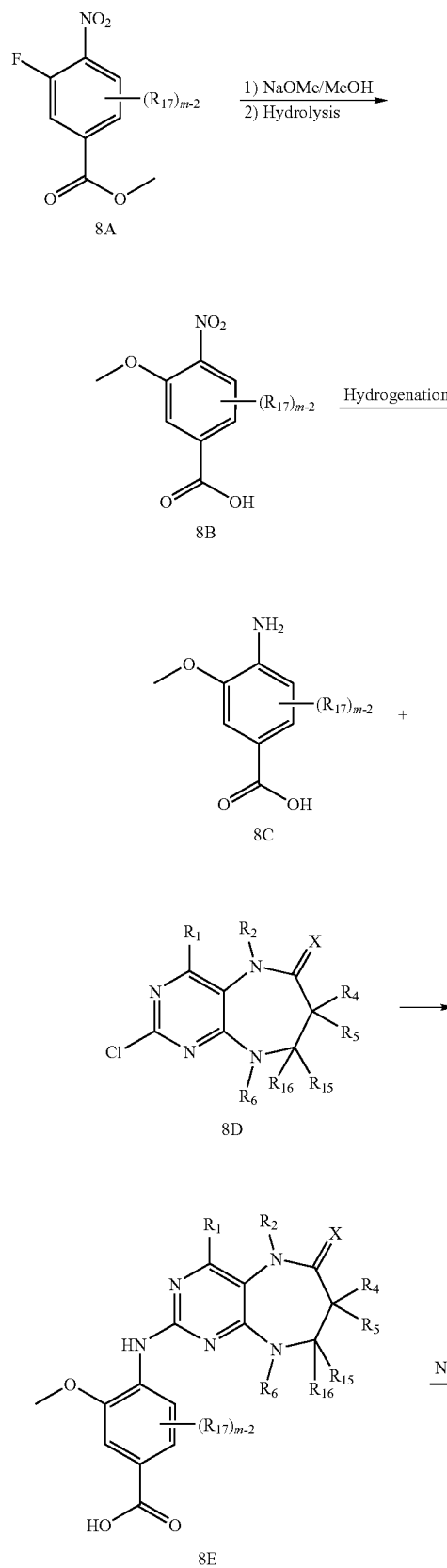

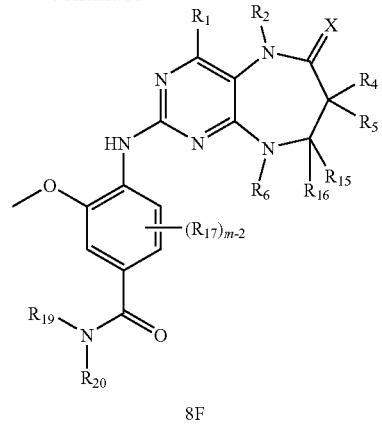

Referring to Scheme 8, Compound 8A is treated with a base (i.e., sodium methoxide) in methanol to afford Compound 8B, which is hydrogenated in presence of a catalyst (i.e., Pd/C) to yield Compound 8C. Compound 8D is refluxed with Compound 8C in presence of acid catalyst (i.e., conc.HCl or TsOH) to give Compound 8E. Compound 8E is condensed with an amine (i.e., methylamine or 1-methylpiperidin-4-amine) using appropriate coupling reagents (i.e., HATU, TBTU etc.) to give the Compound 8F.

Scheme 9:

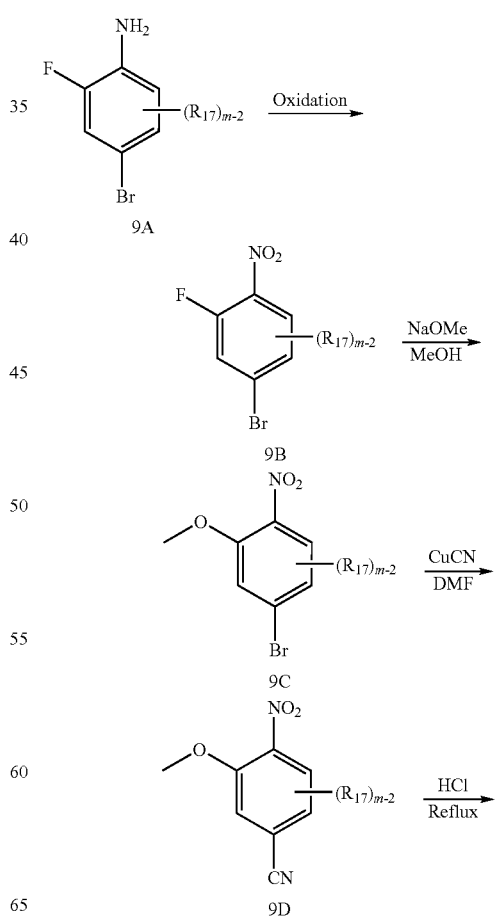

-continued

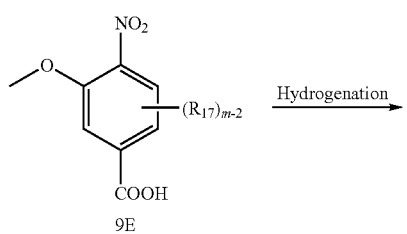
9E

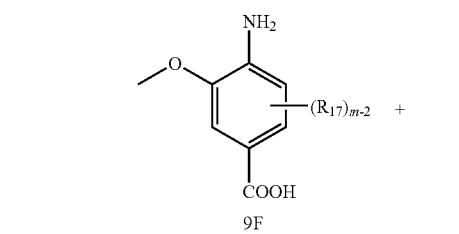
9F +

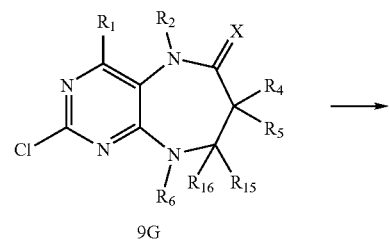
9G

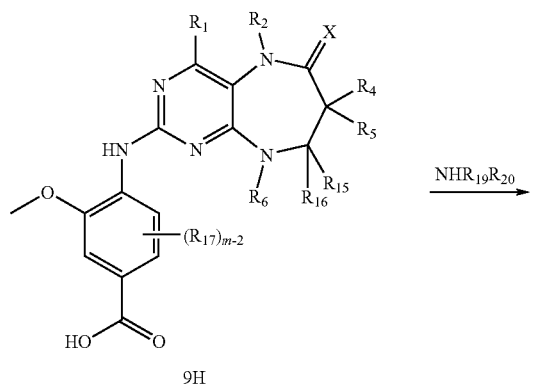
9H

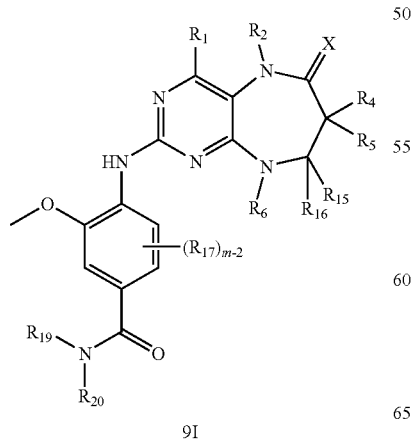
9I

Referring to Scheme 9, Compound 9A is treated with an oxidation agent (e.g., sodium perborate in acetic acid) to afford Compound 9B, which is converted to its methyl ether using a base (i.e., NaOMe) in methanol to give Compound 9C. Compound 9C is subjected to a nucleophilic substitution reaction in presence of CuCN to yield Compound 9D, which is hydrolyzed to its acid 9E in presence of strong acid (i.e., conc.HCl). Compound 9E is hydrogenated in presence of a catalyst (i.e., Pd/C) and acetic acid in alcohol such as methanol to yield Compound 9F. Compound 9F is refluxed with Compound 9G in presence of acid catalyst (i.e., conc.HCl or TsOH) to give Compound 9H. Compound 9H is treated with an amine (i.e., methylamine or 1-methylpiperidin-4-amine) using appropriate coupling reagents (i.e., HATU, TBTU etc.) to give the Compound 9I.

Scheme 10:

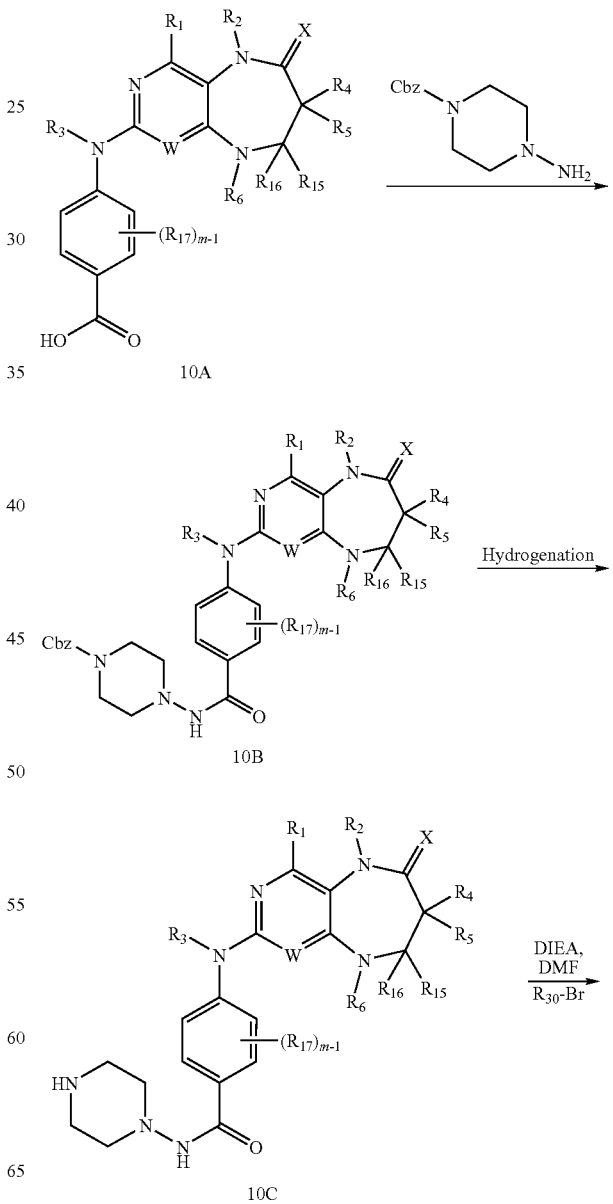

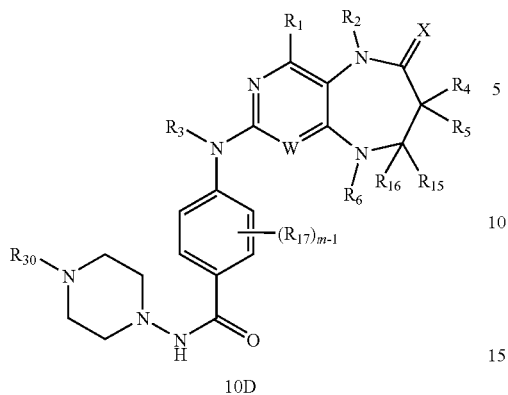

10D

Referring to Scheme 10, Compound 10A is coupled with a piperazine derivative (i.e., benzyl 4-aminopiperazine-1-carboxylate) using appropriate coupling reagents (i.e., HATU, TBTU etc.) to give the Compound 10B. Compound 10B is subjected to hydrogenation for Cbz group deprotection in presence of a catalyst (i.e., Pd—C) in alcohol to get Compound 10C. Compound 10C is alkylated using an alkyl halide (i.e., ethyl bromide or isopropyl bromide) in presence of a base such as diisopropyl ethyl amide to yield Compound 10D.

Scheme 11:

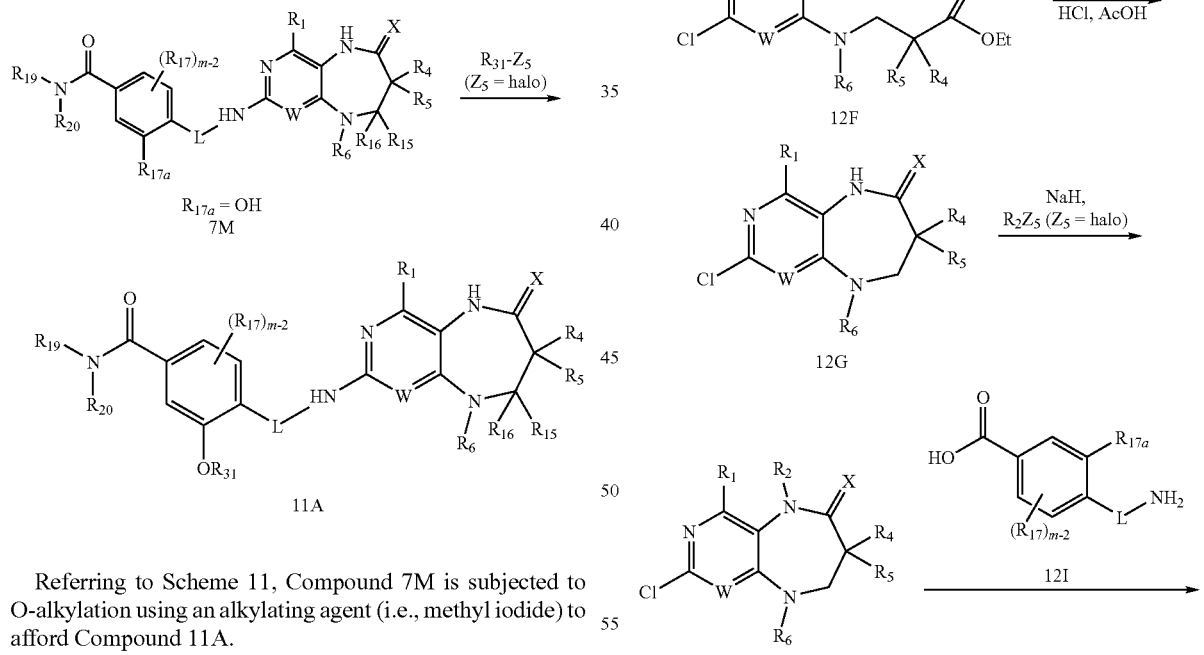

Referring to Scheme 11, Compound 7M is subjected to O-alkylation using an alkylating agent (i.e., methyl iodide) to afford Compound 11A.

Scheme 12:

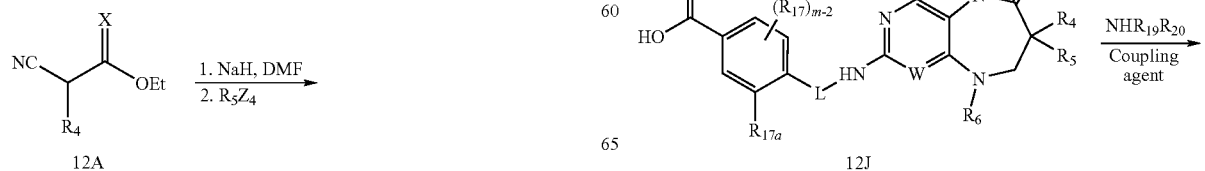

-continued

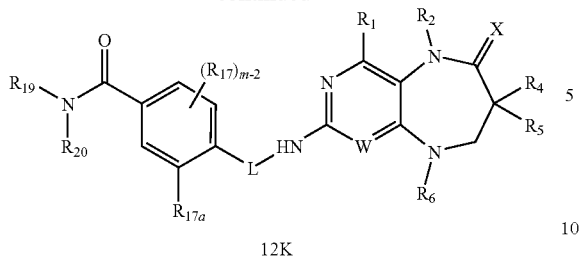

12K

Referring to Scheme 12, Compound 12A is alkylated with an alkylylating agent (i.e., iodomethane) in presence of a strong base (i.e., 60% NaH in mineral oil) to get Compound 12B, which is reduced to its amine 12C by means of hydrogenation in presence of a catalyst (i.e., Rh—$Al_2O_3$) in basic medium $NH_3$ in ethanol. Compound 12C is subjected to reductive amination with an aldehyde or a ketone (i.e., cyclopentanone or cyclohexanone) in presence of sodium triacetoxy borohydride and sodium acetate to afford 12D. Compound 12D is subjected to SNAr reaction with 12E (i.e., 2,4-dichloro 5-nitro pyrimidine) in presence of a base (i.e., $K_2CO_3$) to afford Compound 12F, which on reductive cyclization using a metal/acid catalyst in acetic acid (i.e., Fe/HCl or Sn/HCl) to obtain Compound 12G. Compound 12G is alkylated with an alkyl halide (i.e., iodomethane) to obtain Compound 12H. Compound 12H is refluxed with Compound 12I in presence of an acid catalyst (i.e., conc.HCl or TsOH) in isopropanol to get Compound 12J, which is coupled with an amine (i.e., methylamine or 1-methylpiperidin-4-amine) using appropriate coupling reagents (i.e., HATU, TBTU etc.) to give the Compound 12K.

Scheme 13:

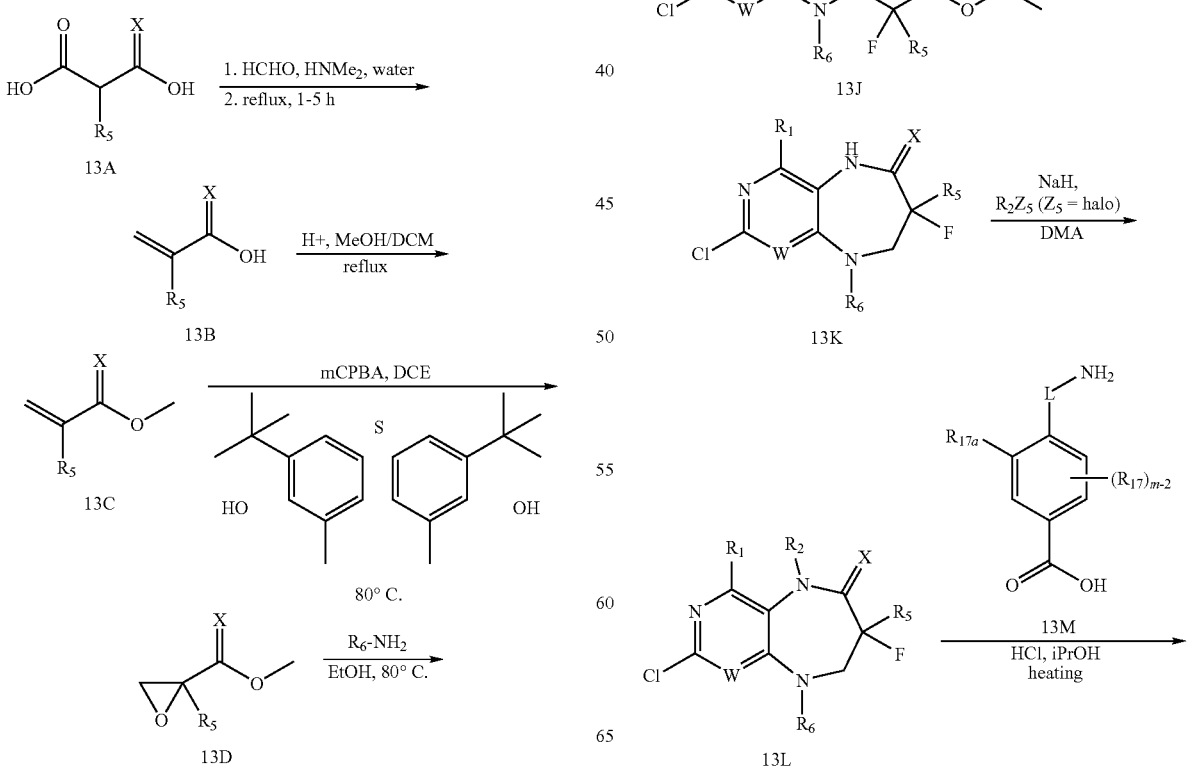

-continued

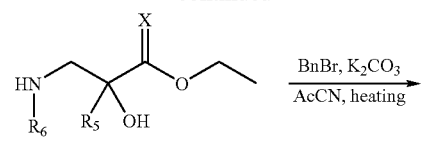

13E

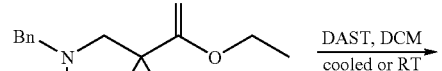

13F

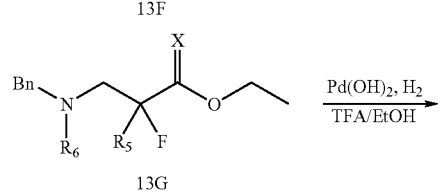

13G

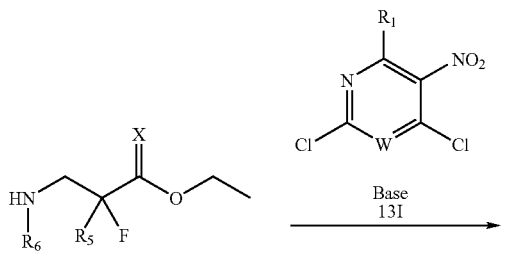

13H, 13I

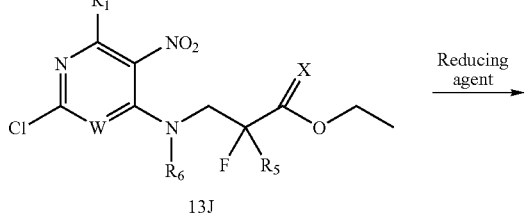

13J

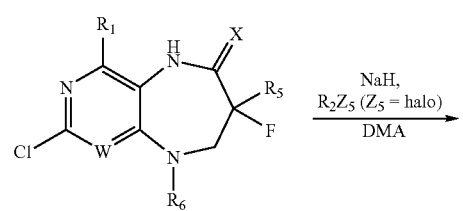

13K 13L, 13M

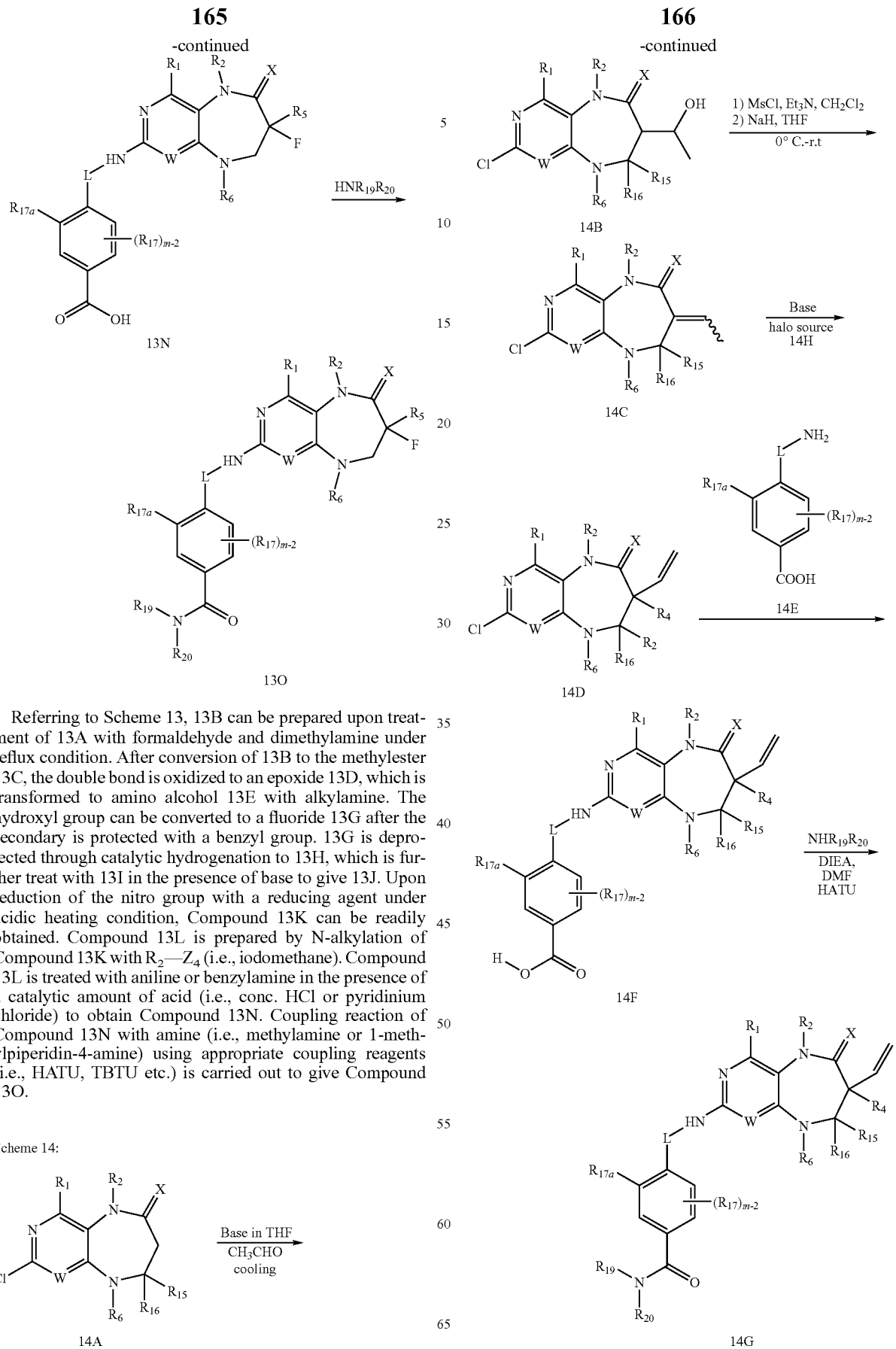

Referring to Scheme 13, 13B can be prepared upon treatment of 13A with formaldehyde and dimethylamine under reflux condition. After conversion of 13B to the methylester 13C, the double bond is oxidized to an epoxide 13D, which is transformed to amino alcohol 13E with alkylamine. The hydroxyl group can be converted to a fluoride 13G after the secondary is protected with a benzyl group. 13G is deprotected through catalytic hydrogenation to 13H, which is further treat with 13I in the presence of base to give 13J. Upon reduction of the nitro group with a reducing agent under acidic heating condition, Compound 13K can be readily obtained. Compound 13L is prepared by N-alkylation of Compound 13K with $R_2$—$Z_4$ (i.e., iodomethane). Compound 13L is treated with aniline or benzylamine in the presence of a catalytic amount of acid (i.e., conc. HCl or pyridinium chloride) to obtain Compound 13N. Coupling reaction of Compound 13N with amine (i.e., methylamine or 1-methylpiperidin-4-amine) using appropriate coupling reagents (i.e., HATU, TBTU etc.) is carried out to give Compound 13O.

Scheme 14:

Referring to Scheme 14, Compound 14A is treated with acetaldehyde in the presence of base (i.e. LDA) to give 14B. The hydroxyl group on 14B is then mesylated at low temperature followed by base treatment (i.e. NaH) to yield the eliminated product Compound 14C. Under the cooling condition, Compound 14C is further reacted with halogen source 14H (e.g., N-fluorobenzenesulfonamide) in the presence of base such as LDA to give vinyl fluoro compound 14D. Compound 14D is refluxed with Compound 14E in presence of an acid catalyst (i.e., conc.HCl or TsOH) in isopropanol to get Compound 14F, which is coupled with an amine (i.e., methylamine or 1-methylpiperidin-4-amine) using appropriate coupling reagents (i.e., HATU, TBTU etc.) to give the Compound 14G.

Scheme 15:

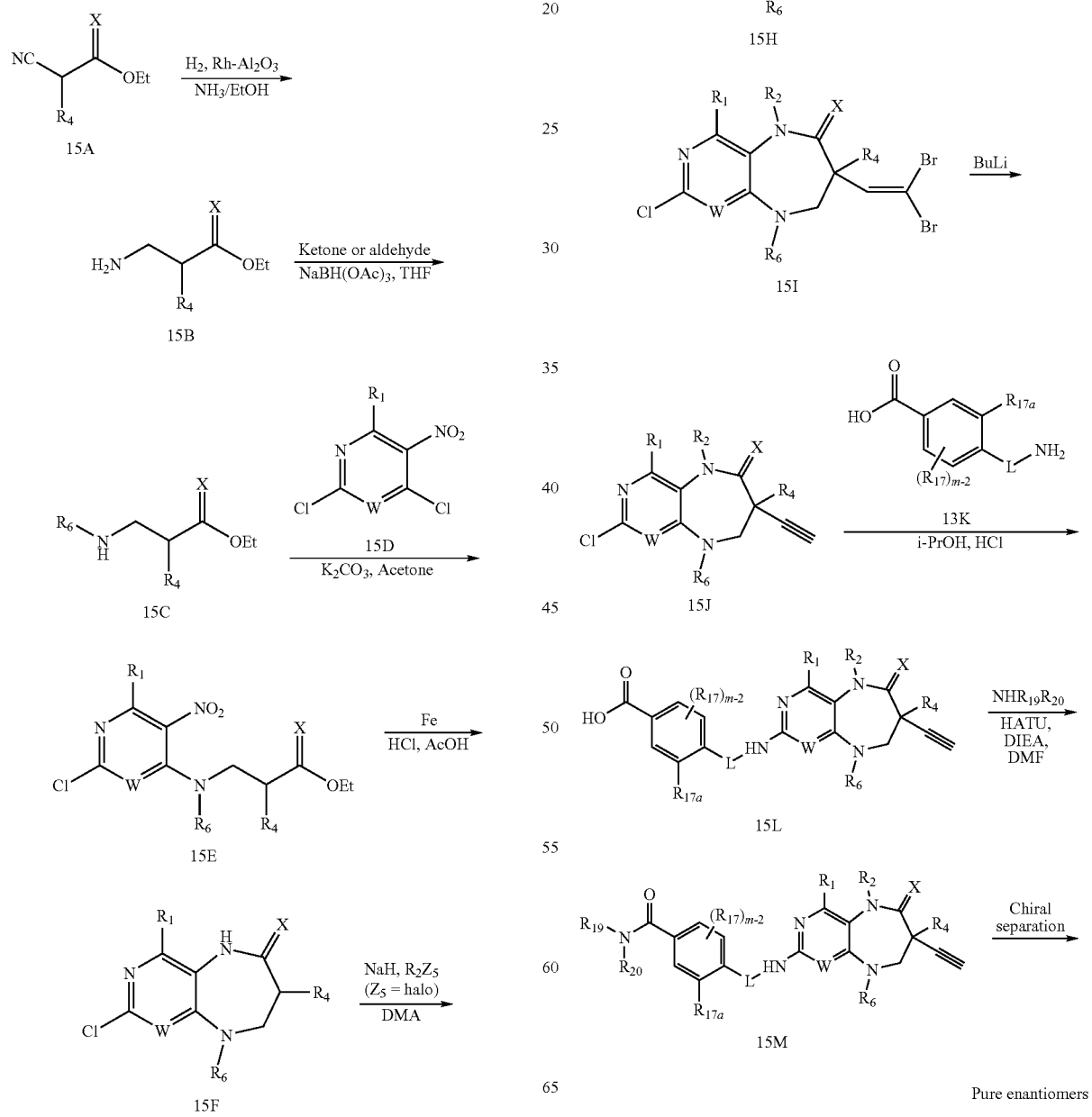

Referring to Scheme 15, hydrogenation of compound 15A in presence of a catalyst (i.e., Rh—Al$_2$O$_3$ using basic medium such as NH$_3$/ethanol to give the compound 15B. Reductive amination of compound 15B with aldehyde or ketone (i.e., cyclopentanone or cyclohexanone) in presence of sodium triacetoxy borohydride to afford 15C. Compound 15C is subjected to SNAr reaction with 15D (i.e., 2,4-dichloro 5-nitro pyrimidine) in presence of a base (i.e., K$_2$CO$_3$) to afford compound 15E, which on reductive cyclization using a metal/acid catalyst in acetic acid (i.e., Fe/HCl or Sn/HCl) to obtain compound 15F. Compound 15F is N-alkylated using a base (i.e., NaH or t-BuOK) and alkyl halide (i.e., iodomethane) in DMA to afford compound 15G. Compound 15G is reacted with oxalyl chloride in presence of a base (i.e., BuLi) to yield the compound 15H, which is further reacted with CBr$_4$/PPh$_3$ to afford compound 15I. Compound 15I is reacted with a strong base (i.e., BuLi) to yield compound 15J. Compound 15J is refluxed with compound 15K in presence of an acid catalyst (i.e., conc.HCl or TsOH) to get compound 15L, which is coupled with an amine (i.e., methylamine or 1-methylpiperidin-4-amine) using appropriate coupling reagents (i.e., HATU, TBTU etc.) to give the compound 15M. Final compound 15M is subjected to chiral separation to get the pure enantiomers.

Scheme 16:

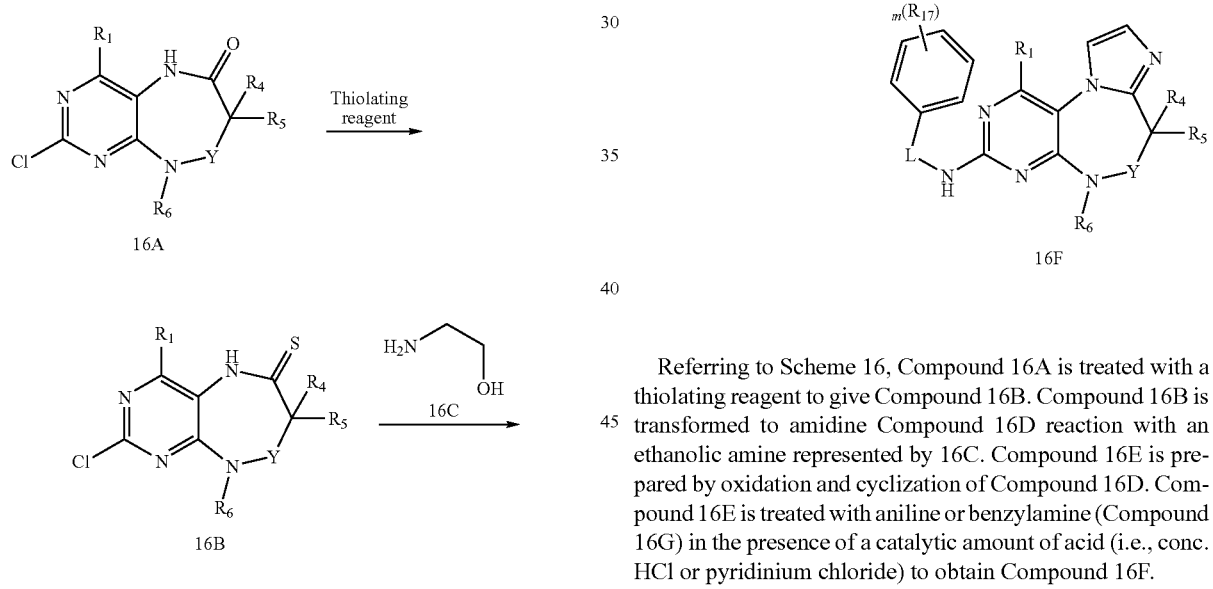

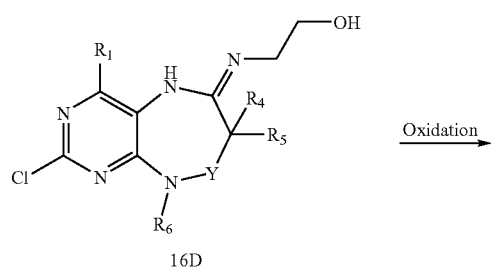

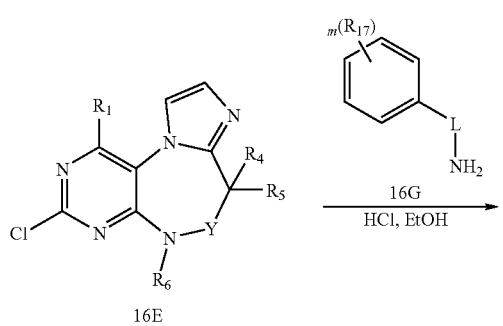

Referring to Scheme 16, Compound 16A is treated with a thiolating reagent to give Compound 16B. Compound 16B is transformed to amidine Compound 16D reaction with an ethanolic amine represented by 16C. Compound 16E is prepared by oxidation and cyclization of Compound 16D. Compound 16E is treated with aniline or benzylamine (Compound 16G) in the presence of a catalytic amount of acid (i.e., conc. HCl or pyridinium chloride) to obtain Compound 16F.

Scheme 17:

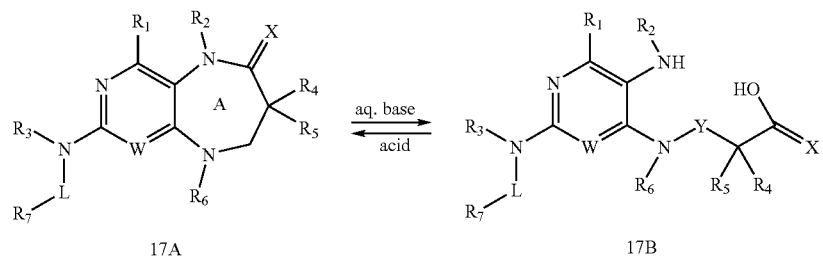

Bicyclic compounds 17A can be subjected to a ring opening reaction in order to form compounds 17B. In particular, exposing compound 17A to a base, such as NaOH, opens ring A to form compound 17B. Conversely, exposing compound 17B to an acid will form compound 17A. Accordingly, it will be appreciated that compounds of the present invention can be formulated with a base, to force the equilibrium to the right, or with an acid, to force the equilibrium to the left. Additionally, the equilibrium can be affected in vivo by, for example, exposing compound 17B to acid in the gut.

Chiral components can be separated and purified using any of a variety of techniques known to those skilled in the art. For example, chiral components can be purified using supercritical fluid chromatography (SFC). In one particular variation, chiral analytical SFC/MS analyses are conducted using a Berger analytical SFC system (AutoChem, Newark, Del.) which consists of a Berger SFC dual pump fluid control module with a Berger FCM 1100/1200 supercritical fluid pump and FCM 1200 modifier fluid pump, a Berger TCM 2000 oven, and an Alcott 718 autosampler. The integrated system can be controlled by BI-SFC Chemstation software version 3.4. Detection can be accomplished with a Watrers ZQ 2000 detector operated in positive mode with an ESI interface and a scan range from 200-800 Da with 0.5 second per scan. Chromatographic separations can be performed on a ChiralPak AD-H, ChiralPak AS-H, ChiralCel OD-H, or ChiralCel OJ-H column (5μ, 4.6×250 mm; Chiral Technologies, Inc. West Chester, Pa.) with 10 to 40% methanol as the modifier and with or without ammonium acetate (10 mM). Any of a variety of flow rates can be utilized including, for example, 1.5 or 3.5 mL/min with an inlet pressure set at 100 bar. Additionally, a variety of sample injection conditions can be used including, for example, sample injections of either 5 or 10 μL in methanol at 0.1 mg/mL in concentration.

In another variation, preparative chiral separations are performed using a Berger MultiGram II SFC purification system. For example, samples can be loaded onto a ChiralPak AD column (21×250 mm, 10μ). In particular variations, the flow rate for separation can be 70 mL/min, the injection volume up to 2 mL, and the inlet pressure set at 130 bar. Stacked injections can be applied to increase the efficiency.

In each of the above reaction procedures or schemes, the various substituents may be selected from among the various substituents otherwise taught herein.

Descriptions of the syntheses of particular compounds according to the present invention based on the above reaction scheme are set forth herein.

Examples of Kinase Inhibitors

The present invention is further exemplified, but not limited by, the following examples that describe the synthesis of particular compounds according to the invention.

Compound 1: 4-(9-Cyclopentyl-7,7-difluoro-5-methyl-6-oxo-6,7,8,9-tetrahydro-5H-pyrimido[5,4-b][1,4]diazepin-2-ylamino)-3-methoxybenzoic acid

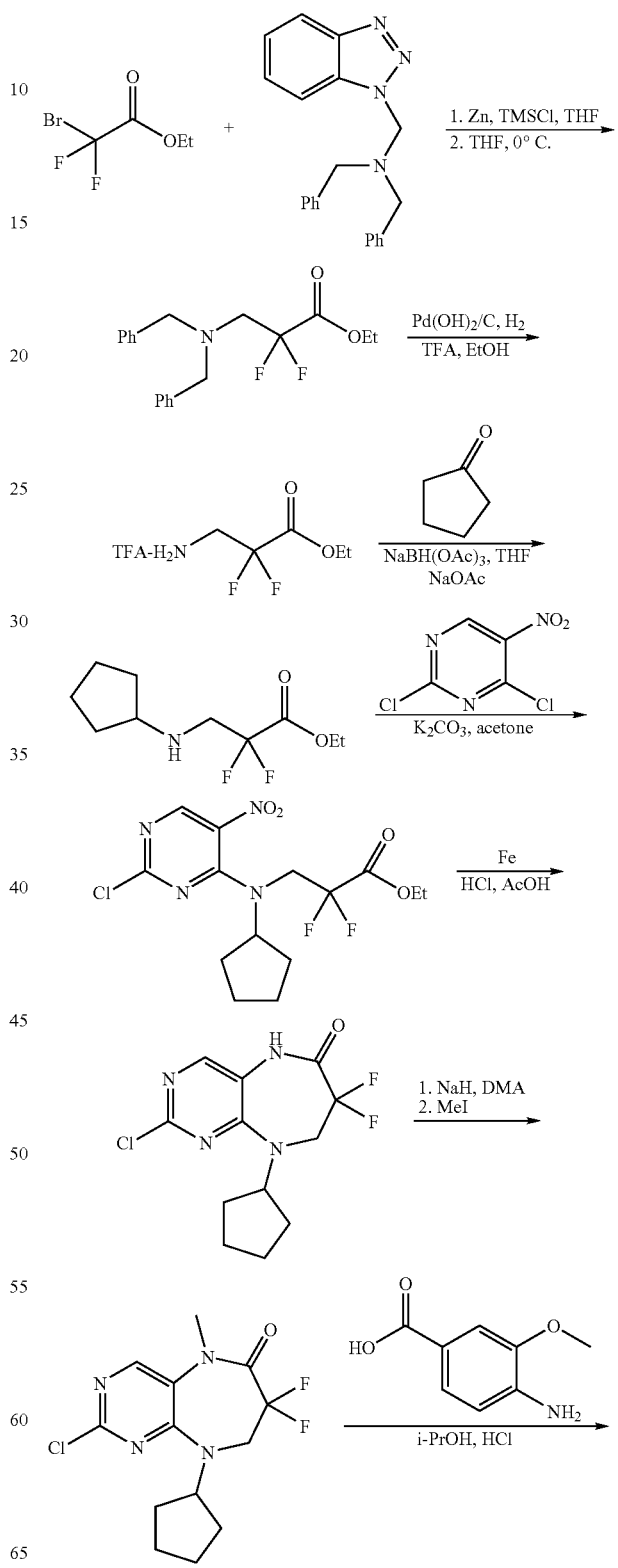

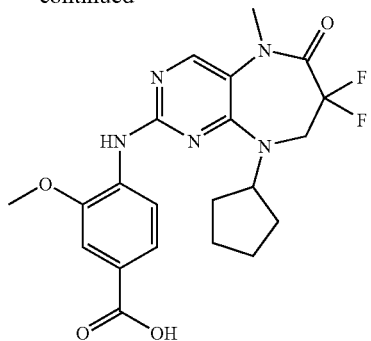

N-(Dibenzylaminomethyl)benzotriazole: 1H-Benzotriazole-1-methanol (51.0 g, 0.342 mol) was weighed into a round bottom flask and solubilized in EtOH (800 mL). Dibenzylamine (67.5 g, 0.342 mol) was added slowly (over 5 min) to the rapidly stirred solution. Formation of a white precipitate was observed shortly after starting addition. The solution was abandoned to stir for 24 h. At this time the reaction is judged complete by NMR (product fragments on LCMS to show only benzotriazole). The majority of the solvent was removed by rotovap and diethyl ether (1 L) was added to the residue with vigorous stirring. This mixture was filtered, the filtrand washed with ether and dried under vacuum to yield the desired product as a fluffy white solid (112 g, quat. yield). $^1$H NMR (400 MHz, chloroform-d) δ ppm 3.80 (s, 4H) 5.48 (s, 2H) 7.21 (d, J=8.34 Hz, 1H) 7.34-7.43 (m, 11H) 7.49 (d, 1H) 8.09 (d, J=7.83 Hz, 1H).

Ethyl 3-(dibenzylamino)-2,2-difluoropropanoate: To a suspension of zinc dust (2.7 g, 41.6 mmol) in dry THF (75 mL), stirred under argon atmosphere, was added chlorotrimethylsilane (2.63 mL, 20.8 mmol) followed, 10 min later, by ethyl dibromo-fluoroacetate (3.92 g, 20.8 mmol). After 10 min a slight exotherm was detected. The reaction was left to activate for 1 hour, whereupon it was cooled in an ice bath and a solution of N-(Dibenzylaminomethyl)benzotriazole (6.83 g, 20.8 mmol) in THF (50 mL) was added dropwise (over 30 minutes) and then the reaction mixture was allowed to warm to room temperature. After 18 h at r.t., NaHCO3 (sat., 50 mL) was added, let stir for 20 minutes, the reaction was filtered on Celite, and the filter pad was washed with EtOAc. The layers were separated and the aqueous phase was extracted with EtOAc (3×50 mL). The organic layers were combined and washed with 1N HCl (70 mL), brine (70 mL), then dried over MgSO$_4$. After evaporation of the solvent, the residue was poured into rapidly stirring ether (100 mL); the solid formed was removed by filtration and discarded. The ether was evaporated from the filtrate to yield a dark yellow syrup. This crude residue was purified on silica gel column chromatographically (0-10% EtOAc:Hexanes) to yield the desired product as a clear liquid (3.6 g, 50% yield). $^1$H NMR in CDCl$_3$: (400 MHz) δ ppm 1.18 (t, J=7.07 Hz, 3H) 3.14 (t, J=13.26 Hz, 2H) 3.69 (s, 4H) 4.14 (q, J=7.16 Hz, 2H) 7.14-7.33 (m, 10H). [M+H] calc'd for C$_{19}$H$_{21}$F$_2$NO$_2$, 334. found 334.

Ethyl 3-amino-2,2-difluoropropanoate-TFA salt: In a round bottom flask, Ethyl 3-(dibenzylamino)-2,2-difluoropropanoate (1.72 g, 5.2 mmol) was solubilized in EtOH (25 mL) and TFA added (0.4 mL, 5.5 mmol). Under an atmosphere of nitrogen Pd(OH)$_2$/C (170 mg of 20% Pd by wt. wet) was added. The reaction mixture was repeatedly purged with nitrogen and then left under hydrogen overnight. At this point the reaction was deemed complete by LCMS, filtered through a pad of Celite, the pad washed with EtOH and the filtrate concentrated without heating to yield a foggy syrup which starts to crystallize upon standing (1.31 g, 94% yield). $^1$H NMR (400 MHz, DMSO-d$_6$) δ ppm 1.29 (t, J=7.20 Hz, 3H) 3.72 (t, J=16.17 Hz, 2H) 4.34 (q, J=7.24 Hz, 2H). [M+H] calc'd for C$_5$H$_9$F$_2$NO$_2$, 154. found 154.

Ethyl 3-(cyclopentylamino)-2,2-difluoropropanoate: To a round bottom flask was added Ethyl 3-amino-2,2-difluoropropanoate (1.31 g, 4.9 mmol), THF (50 mL), cyclopentanone (0.46 mL, 5.1 mmol), and NaOAc (400 mg, 4.9 mmol). To this mixture was added sodium triacetoxyborohydride (1.6 g, 7.3 mmol) portionwise over 15 minutes. The reaction was left to stir overnight. It was then added slowly to a stirring solution of ice (30 mL), NaHCO$_3$ (sat., 10 mL), and EtOAc (100 mL) cooled in an ice-salt bath. The layers were then separated and the aqueous pH further adjusted to 11 using 25% NaOH while cooling in the bath. The aqueous layer was washed with EtOAc (2×50 mL), the organic extracts combined, washed with cold NaHCO$_3$, (sat. 20 mL×2) brine (20 mL), dried over MgSO$_4$, filtered and concentrated to yield the desired product as a clear syrup (960 mg, 89%). $^1$H NMR (400 MHz, DMSO-d$_6$) δ ppm 1.25 (t, J=7.07 Hz, 2H) 1.34-1.74 (m, 8H) 3.00 (q, 1H) 3.11 (t, J=14.15 Hz, 2H) 4.27 (q, J=7.07 Hz, 2H). [M+H] calc'd for C$_{10}$H$_{17}$F$_2$NO$_2$, 222. found 222.

Ethyl 3-((2-chloro-5-nitropyrimidin-4-yl)(cyclopentyl)amino)-2,2-difluoropropanoate: Compound Ethyl 3-(cyclopentylamino)-2,2-difluoropropanoate (396 mg, 1.79 mmol) was solubilized in acetone (40 mL, dry). The solution was cooled in an ice salt bath under a nitrogen atmosphere and K$_2$CO$_3$ (495 mg, 3.58 mmol) added. To this, a solution of 2,4-dichloro-5-nitropyrimidine (378 mg, 1.97 mmol) in acetone (10 mL, dry) was added dropwise. Upon completion of addition the reaction mixture abandoned and allowed to slowly warm to room temperature and stir overnight. The mixture was then filtered through paper, the filter pad washed with acetone, and the filtrate concentrated. The concentrate was then solubilized in EtOAc (10 mL). Hexanes (70 mL) were then added and the solution was put on the rotovap to slowly concentrate. Yellow crystals form and are collected by filtration to yield 360 mg of the desired product Ethyl 3-((2-chloro-5-nitropyrimidin-4-yl)(cyclopentyl)amino)-2,2-difluoropropanoate (53%). The filtrate was found to contain a 1:1:1 mixture of the product, dichloronitropyrimidine, and the 2-addition product. This material was concentrated and set aside for future use. $^1$H NMR (400 MHz, DMSO-d$_6$) δ ppm 1.22 (t, J=7.20 Hz, 3H) 1.36-1.98 (m, 8H) 3.64 (q, 1H) 4.25 (q, J=7.24 Hz, 2H) 4.35 (t, J=13.77 Hz, 2H) 8.94 (s, 1H). [M+H] calc'd for C$_{14}$H$_{17}$F$_2$N$_4$O$_4$, 379. found 379.

2-Chloro-9-cyclopentyl-7,7-difluoro-8,9-dihydro-5H-pyrimido[5,4-b][1,4]diazepin-6(7H)-one: Compound ethyl 3-((2-chloro-5-nitropyrimidin-4-yl)(cyclopentyl)amino)-2,2-difluoropropanoate (1.0 g, 2.7 mmol) was dissolved in AcOH (10 mL) and then cooled in an ice bath. Iron powder (296 mg, 5.3 mmol) was added followed by the slow addition of HCl (1.5 mL, conc.). After 10 minutes the reaction was transferred to a heat bath and left to stir at 60° C. for 5 hours. The reaction was then cooled, the stir bar and unreacted iron removed by filtration through paper, and the solvent volume reduced by about 75% on a rotovap. The mixture was then diluted with ice water (15 mL) and EtOAc (20 mL), the layers separated, the aqueous layer washed with EtOAc (2×30 mL), the organic extracts combined, washed with sat. NaHCO$_3$ (20 mL), brine (20 mL), dried over MgSO$_4$, filtered and concentrated to yield a brown syrup. Trituration with EtOAc (15 mL) and ether (100 mL) was used to coax out a light yellow solid (535 mg, 65% yield). $^1$H NMR (400 MHz, DMSO-d$_6$) δ ppm 1.41-1.96 (m, 8H) 3.98 (t, J=11.49 Hz, 2H) 4.87 (q, 1H) 8.12 (s, 1H) 11.06 (br. s., 1H). [M+H] calc'd for $C_{12}H_{13}ClF_2N_4O$, 303. found 303.

2-Chloro-9-cyclopentyl-7,7-difluoro-5-methyl-8,9-dihydro-5H-pyrimido[5,4-b][1,4]diazepin-6(7H)-one: 2-Chloro-9-cyclopentyl-7,7-difluoro-8,9-dihydro-5H-pyrimido[5,4-b][1,4]diazepin-6(7H)-one (2.4 g, 7.95 mmol) was dissolved in DMA (20 mL) and cooled in an ice bath. Sodium hydride (348 mg of 65% in mineral oil, 8.75 mmol) was added slowly and left to stir for 10 minutes. Methyl iodide (0.546 mL, 8.75 mmol) was then added and then after 10 minutes the solution removed from the bath. After 30 minutes the reaction was deemed complete by LCMS, poured into ice water (300 mL), the solution acidified with 1N HCl, the product filtered off as a yellow solid (2.36 g, 94% yield). $^1$H NMR (400 MHz, DMSO-$d_6$) δ ppm 1.38-2.00 (m, 8H) 3.34 (s, 3H) 4.15 (t, J=13.26 Hz, 2H) 4.80 (q, 1H) 8.35 (s, 1H). [M+H] calc'd for $C_{13}H_{15}ClF_2N_4O$, 317. found 317.

4-(9-Cyclopentyl-7,7-difluoro-5-methyl-6-oxo-6,7,8,9-tetrahydro-5H-pyrimido[5,4-b][1,4]diazepin-2-ylamino)-3-methoxybenzoic acid: 2-Chloro-9-cyclopentyl-7,7-difluoro-5-methyl-8,9-dihydro-5H-pyrimido[5,4-b][1,4]diazepin-6(7H)-one (2.77 g, 8.8 mmol), 4-amino-3-methoxy benzoic acid (1.61 g, 9.6 mmol), i-PrOH (30 mL) and conc. HCl (30 drops) were heated to 95° C. for 18 hours. A this time the reaction was cooled to room temperature and filtered to reveal the product as a tan solid (2.74 g, 70% yield). $^1$H NMR (400 MHz, DMSO-$d_6$): δ ppm 1.50-2.01 (m, 8H) 3.32 (s, 3H) 3.89 (s, 3H) 4.04 (t, J=14.15 Hz, 2H) 4.75 (q, 1H) 7.50 (d, J=8.34 Hz, 1H) 7.52 (s, 1H) 7.90 (s, 1H) 8.19 (d, J=8.34 Hz, 1H) 8.25 (s, 1H). [M+H] calc'd for $C_{21}H_{23}F_2N_5O_4$, 447. found 447.

General Procedure for Amide Bond Synthesis

To a mixture of carboxylic acid (0.2 mmol), amine (0.3 mmol), DIEA (0.054 mL, 0.3 mmol) in 3 mL of anhydrous DMF was added HATU (114 mg, 0.3 mmol). After 30 minutes the reaction mixture was either directly purified by HPLC or diluted with ethyl acetate, washed with water and brine, then organic layer dried over $Na_2SO_4$ and purified on HPLC. The TFA salt obtained was then converted to its free base by washing with sat. $NaHCO_3$ solution.

Compound 2: 4-(9-cyclopentyl-7,7-difluoro-5-methyl-6-oxo-6,7,8,9-tetrahydro-5H-pyrimido[4,5-b][1,4]diazepin-2-ylamino)-N-cyclopropyl-3-methoxybenzamide

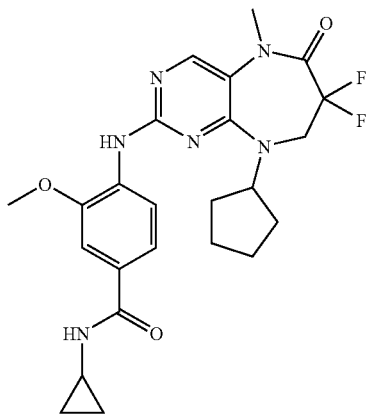

The title compound was synthesized from 4-(9-Cyclopentyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and 1-propylamine. The final compound was purified by reverse phase HPLC and basified to give the free base. $^1$H NMR (400 MHz, DMSO-$d_6$) δ ppm 0.57 (dd, J=3.66, 2.40 Hz, 2H) 0.70 (dd, J=6.95, 2.15 Hz, 2H) 1.50-1.77 (m, 6H) 1.88-1.97 (m, 2H) 2.82 (td, J=7.33, 3.54 Hz, 1H) 3.17 (s, 3H) 3.92 (s, 3H) 3.99-4.08 (m, 3H) 4.75 (d, J=8.84 Hz, 1H) 7.40-7.51 (m, 2H) 7.96 (s, 1H) 8.26 (d, J=8.34 Hz, 1H) 8.35 (d, J=4.04 Hz, 1H). [M+H] $C_{24}H_{28}F_2N_6O_3$ calc'd for, 487. found 487.

Compound 3: 4-(9-Cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide

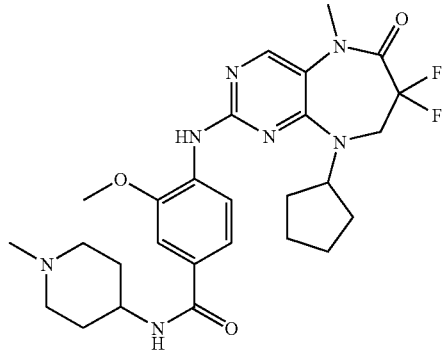

The title compound was synthesized from 4-(9-Cyclopentyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and 1-methylpiperidin-4-amine. The final compound was purified by reverse phase HPLC and basified to give the free base. $^1$H NMR (400 MHz, DMSO-$d_6$) δ ppm 1.46-1.78 (m, 10H) 1.98 (m, 4H) 2.18 (s, 3H) 2.79 (d, J=11.4 Hz, 2H) 3.33 (s, 3H) 3.74 (m, 1H) 3.94 (s, 3H) 4.04 (t, J=14.0 Hz, 2H) 4.75 (q, J=7.9 Hz, 1H) 7.50 (s, 1H) 7.47 (d, J=1.5 Hz, 1H) 7.94 (s, 1H) 8.09 (d, J=7.8 Hz, 1H) 8.27 (d, J=8.1 Hz, 1H) 8.26 (s, 1H). [M+H] calc'd for $C_{27}H_{35}F_2N_7O_3$, 544. found 544.

Compound 4: 4-(9-Cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylazetidin-3-yl)benzamide

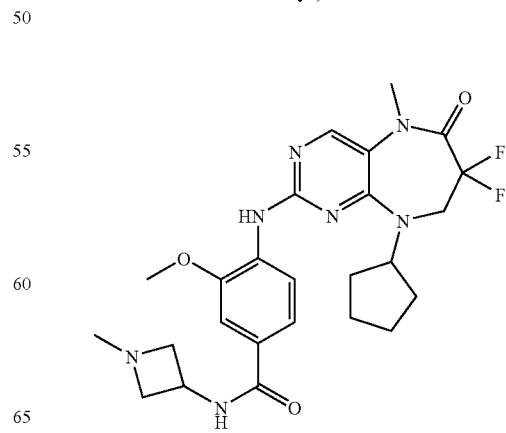

The title compound was synthesized from 4-(9-Cyclopentyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and 1-methylazetidin-3-amine hydrochloride. The final compound was purified by reverse phase HPLC and basified to give the free base. $^1$H NMR (400 MHz, DMSO-$d_6$) δ ppm 1.58-1.71 (m, 7H) 1.90 (m, 3H) 2.42 (s, 3H) 3.32 (s, 3H) 3.76 (t, J=7.2 Hz, 2H) 3.94 (s, 3H) 4.05 (t, J=13.8 Hz, 2H) 4.38-4.60 (m, 1H) 4.76 (d, J=7.8 Hz, 1H) 7.35-7.59 (m, 2H) 7.99 (s, 1H) 8.26 (s, 1H) 8.29 (d, J=8.3 Hz, 1H) 8.72 (d, J=6.6 Hz, 1H). Melting point: 157-162° C. [M+H] calc'd for $C_{25}H_{31}F_2N_7O_3$, 516. found 516.

Compound 5: 4-(9-cyclopentyl-7,7-difluoro-5-methyl-6-oxo-6,7,8,9-tetrahydro-5H-pyrimido[4,5-b][1,4]diazepin-2-ylamino)-N-(1-(2-hydroxyethyl)piperidin-4-yl)-3-methoxybenzamide

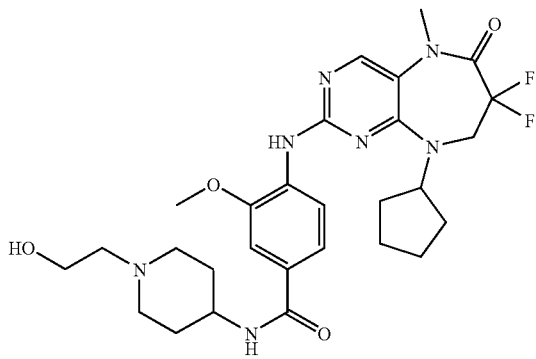

The title compound was synthesized from 4-(9-Cyclopentyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and 4-amino piperidine 1-ethanol. The final compound was purified by reverse phase HPLC and basified to give the free base. $^1$H NMR (400 MHz, DMSO-$d_6$) δ ppm 1.44-2.07 (m, 12H) 2.38 (t, J=6.32 Hz, 2H) 2.89 (d, J=11.37 Hz, 2H) 3.27-3.34 (s, 3H) 3.49 (q, J=6.06 Hz, 2H) 3.65-3.83 (m, 1H) 3.93 (s, 2H) 3.97-4.14 (m, 2H) 4.37 (t, J=5.31 Hz, 1H) 4.76 (t, J=7.83 Hz, 1H) 7.48 (d, J=8.0 Hz, 1H), 7.49 (br. s., 1H) 7.96 (s, 1H) 8.12 (d, J=7.83 Hz, 1H)), 8.26 (s, 1H) 8.27 (d, J=8.0 Hz, 1H). [M+H] calculated for $C_{28}H_{37}F_2N_7O_4$, 574. found 574.

Compound 6: 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(4-methylpiperazin-1-yl)benzamide

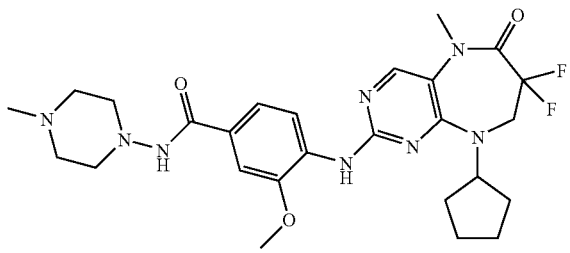

The title compound was synthesized from 4-(9-Cyclopentyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and 4-methylpiperazin-1-amine. The final compound was purified by reverse phase HPLC and basified to give the free base. $^1$H NMR (400 MHz, DMSO-$d_6$) δ ppm 1.59-1.64 (m, 4H) 1.67-1.75 (m, 2H) 1.89-1.97 (m, 2H) 2.79 (d, J=4.6 Hz, 3H) 3.11-3.30 (m, 6H) 3.32 (s, 3H) 3.44 (d, J=12.6 Hz, 2H) 3.93 (s, 3H) 4.09 (t, J=13.9 Hz, 2H) 4.76-4.81 (m, 1H) 7.46 (d, J=8.3 Hz, 1H) 7.48 (s, 3H) 8.24 (d, J=8.34 Hz, 1H) 8.27 (s, 1H) 9.79 (s, 1H). Melting point: 168-174° C. [M+H] calc'd for $C_{26}H_{34}F_2N_8O_3$, 545. found 545.

Compound 7: 4-(9-cyclopentyl-7,7-difluoro-5-methyl-6-oxo-6,7,8,9-tetrahydro-5H-pyrimido[4,5-b][1,4]diazepin-2-ylamino)-N-(1-ethylpiperidin-4-yl)-3-methoxybenzamide

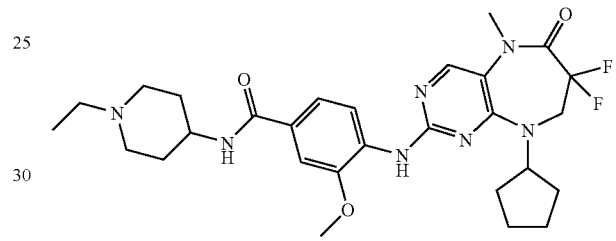

The title compound was synthesized from 4-(9-Cyclopentyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and 4-ethylpiperidin-1-amine. The final compound was purified by reverse phase HPLC and basified to give the free base. $^1$H NMR (400 MHz, DMSO-$d_6$) δ ppm 1.26 (t, J=7.2 Hz, 3H) 1.58-1.72 (m, 6H) 1.87-2.04 (m, 6H) 2.96-3.06 (br. s., 4H) 3.32 (s, 3H) 3.47 (d, 2H) 3.94 (s, 3H) 4.03 (m, 1H) 4.16 (t, J=13.4 Hz, 2H) 4.78-4.88 (m, 3H) 7.55 (dd, J=8.3, 1.8 Hz, 3H) 7.59 (d, J=1.5 Hz, 1H) 8.13 (d, J=8.6 Hz, 1H) 8.30 (s, 1H) 8.54 (d, J=7.3 Hz, 1H). [M+H] calc'd for $C_{28}H_{37}F_2N_7O_3$, 558. found 558.

Compound 8: (R)-4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(piperidin-3-yl)benzamide

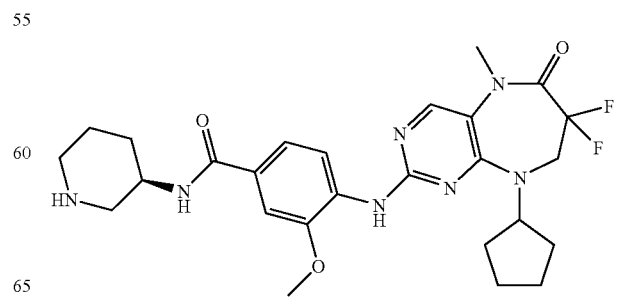

The title compound was synthesized from 4-(9-Cyclopentyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and (R)-tert-butyl 3-aminopiperidine-1-carboxylate, where Boc was removed using TFA in DCM. The final compound was purified by reverse phase HPLC and basified to give the free base. $^1$H NMR (400 MHz, DMSO-$d_6$) δ ppm 1.41-1.52 (m, 2H) 1.52-1.77 (m, 7H) 1.85-1.99 (m, 3H) 2.45 (t, J=9.9 Hz, 2H) 2.85 (d, J=12.4 Hz, 1H) 3.01 (dd, J=11.8, 3.4 Hz, 1H) 3.32 (s, 3H) 3.85 (m, 1H) 3.94 (s, 3H) 4.05 (t, J=14.0 Hz, 3H) 4.76 (quin, J=8.2 Hz, 1H) 7.47 (dd, J=1.8 Hz, 1H) 7.49 (s, 1H) 7.97 (s, 1H) 8.04 (d, J=7.8 Hz, 1H) 8.26 (s, 1H) 8.28 (d, 1H). [M+H] calc'd for $C_{26}H_{33}F_2N_7O_3$, 530. found 530.

Compound 9: (S)-4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(piperidin-3-yl)benzamide

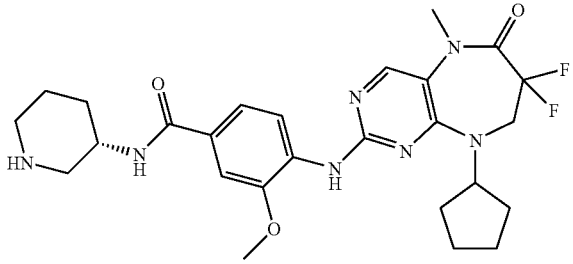

The title compound was synthesized from 4-(9-Cyclopentyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and (S)-tert-butyl 3-aminopiperidine-1-carboxylate, where Boc was removed using TFA in DCM. The final compound was purified by reverse phase HPLC and basified to give the free base. $^1$H NMR (400 MHz, DMSO-$d_6$) δ ppm 1.41-1.52 (m, 2H) 1.52-1.77 (m, 7H) 1.85-1.99 (m, 3H) 2.45 (t, J=9.9 Hz, 2H) 2.85 (d, J=12.4 Hz, 1H) 3.01 (dd, J=11.8, 3.4 Hz, 1H) 3.32 (s, 3H) 3.85 (m, 1H) 3.94 (s, 3H) 4.05 (t, J=14.0 Hz, 3H) 4.76 (quin, J=8.2 Hz, 1H) 7.47 (dd, J=1.8 Hz, 1H) 7.49 (s, 1H) 7.97 (s, 1H) 8.04 (d, J=7.8 Hz, 1H) 8.26 (s, 1H) 8.28 (d, 1H). [M+H] calc'd for $C_{26}H_{33}F_2N_7O_3$, 530. found 530.

Compound 10: 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(piperidin-4-yl)benzamide

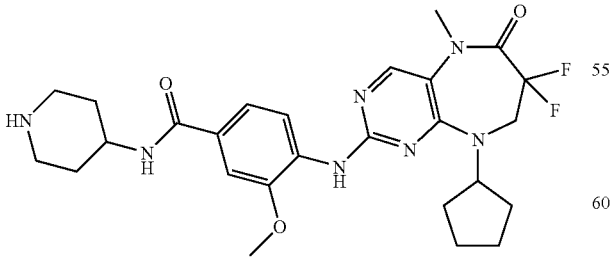

The title compound was synthesized from 4-(9-Cyclopentyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and tert-butyl 4-aminopiperidine-1-carboxylate, where Boc was removed using TFA in DCM. The final compound was purified by reverse phase HPLC and basified to give the free base. $^1$H NMR (400 MHz, DMSO-$d_6$) δ ppm 1.43 (qd, J=11.9, 3.8 Hz, 2H) 1.54-1.66 (m, 5H) 1.66-1.77 (m, 4H) 1.98 (br. s, 2H) 2.52 (d, J=1.8 Hz, 2H) 2.98 (d, J=11.9 Hz, 2H) 3.79-3.87 (m, 1H) 3.93 (s, 3H) 4.04 (t, J=14.2 Hz, 2H) 4.76 (quin, J=8.1 Hz, 1H) 7.48 (d, 1H) 7.50 (s, 1H) 7.96 (s, 1H) 8.13 (d, J=8.1 Hz, 1H) 8.26 (d, J=8.1 Hz, 1H) 8.26 (s, 1H). [M+H] calc'd for $C_{26}H_{33}F_2N_7O_3$, 530. found 530.

Compound 11: 4-(9-cyclopentyl-7,7-difluoro-5-methyl-6-oxo-6,7,8,9-tetrahydro-5H-pyrimido[4,5-b][1,4]diazepin-2-ylamino)-N-(1-(2-(dimethylamino)acetyl)piperidin-4-yl)-3-methoxybenzamide

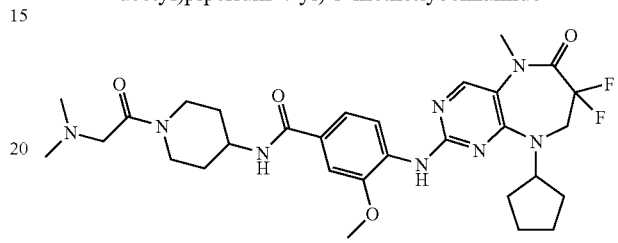

The title compound was synthesized from 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(piperidin-4-yl)benzamide in accordance with scheme 6 using 2-(dimethylamino)acetyl chloride. $^1$H NMR (400 MHz, DMSO-$d_6$) δ ppm 1.38 (dd, J=13.1, 4.0 Hz, 1H) 1.58 (m, 5H) 1.71 (m, 2H) 1.83 (m, 2H) 1.93 (m, 2H) 2.21 (s, 5H) 2.52 (d, J=1.8 Hz, 1H) 2.63-2.73 (m, 1H) 3.05 (t, J=12.1 Hz, 2H) 3.17-3.24 (m, 1H) 3.32 (s, 5H) 3.93 (s, 3H) 4.05 (t, J=14.2 Hz, 3H) 4.36 (d, J=12.6 Hz, 1H) 4.77 (q, J=8.3 Hz, 1H) 7.48 (dd, 1H) 7.50 (s, 1H) 7.97 (s, 1H) 8.17 (d, J=7.8 Hz, 1H) 8.26 (s, 1H) 8.29 (d, 1H). [M+H] calc'd for $C_{30}H_{40}F_2N_8O_4$, 615. found 615.

Compound 12: 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-(2-(pyrrolidin-1-yl)acetyl)piperidin-4-yl)benzamide

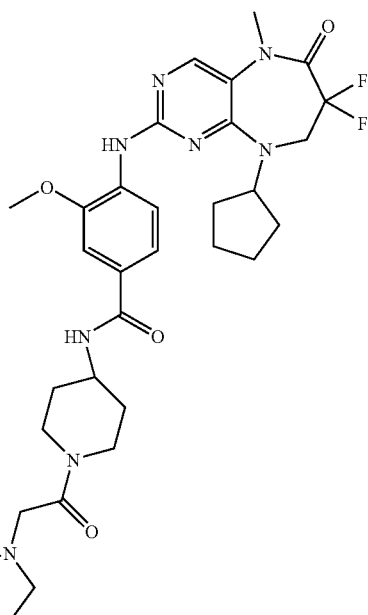

The title compound was synthesized from (R)-4-(9-cyclohexyl-7-fluoro-7-vinyl-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and 1-Boc-4-aminopiperidine. Further, after washing with water (10 ml), t-butoxycarbonyl (Boc) protection group was removed using 40% TFA in dichloromethane (6 ml). The resulting product was further acylated using 2-(pyrrolidin-1-yl)acetyl chloride. The title product using preparative HPLC and neutralized with bicarbonate. $^1$H NMR (400 MHz, DMF) δ ppm 1.53-2.30 (m, 18H) 2.79-3.01 (m, 2H) 3.21-3.47 (m, 5H) 4.17 (s, 3H) 4.21-4.41 (m, 6H) 4.59 (d, J=12.13 Hz, 1H) 5.00 (t, J=8.34 Hz, 1H) 7.71 (d, J=1.77 Hz, 2H) 8.21 (s, 1H) 8.40 (d, J=7.83 Hz, 1H) 8.50 (s, 2H). [M+H] calc'd for $C_{32}H_{42}F_2N_8O_4$, 641. found 641.

Compound 13: 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(pyrrolidin-1-yl)benzamide

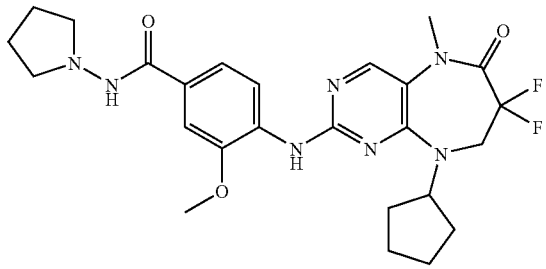

The title compound was synthesized from 4-(9-Cyclopentyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and pyrrolidin-1-amine. The final compound was purified by reverse phase HPLC and basified to give the free base. $^1$H NMR (400 MHz, CHLOROFORM-d) δ ppm 1.43-1.75 (m, 6H) 1.90-2.02 (m, 2H) 2.67-3.03 (m, 4H) 3.57 (s, 3H) 3.95 (s, 3H) 4.05 (t, 2H) 4.73-4.81 (m, 1H) 7.48-7.54 (m, 2H) 8.00 (s, 1H) 8.20 (d, 1H) 8.27 (s, 1H) 8.30 (d, 1H). [M+H] calc'd for $C_{25}H_{31}F_2N_7O_3$, 516. found 516.

Compound 14: N-(Azepan-4-yl)-4-(9-cyclopentyl-7,7-difluoro-5-methyl-6-oxo-6,7,8,9-tetrahydro-5H-pyrimido[4,5-b][1,4]diazepin-2-ylamino)-3-methoxybenzamide

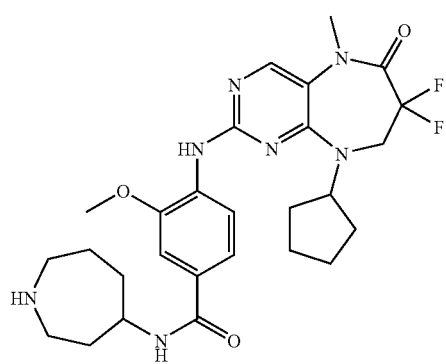

The title compound was synthesized from 4-(9-Cyclopentyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and tert-butyl 4-aminoazepane-1-carboxylate, where Boc was removed using TFA in DCM. The final compound was purified by reverse phase HPLC and basified to give the free base. $^1$H NMR (400 MHz, DMSO-d$_6$) δ ppm 1.41-1.65 (m, 4H) 1.65-1.83 (m, 3H) 1.83-1.99 (m, 4H) 2.07 (m., 2H) 3.16 (s, 3H) 3.32 (s, 3H) 3.93 (s, 3H) 4.07 (t, J=13.8 Hz, 3H) 4.78 (t, J=8.1 Hz, 1H) 7.41-7.54 (m, 2H) 8.14-8.29 (m, 2H) 8.31 (d, J=7.6 Hz, 1H) 8.55 (br. s., 2H). [M+H] calc'd for $C_{27}H_{35}F_2N_7O_3$, 544. found 544.

Compound 15: 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylazepan-4-yl)benzamide

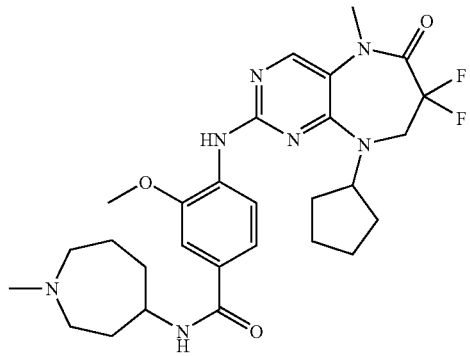

The title compound was synthesized by methylating N-(Azepan-4-yl)-4-(9-cyclopentyl-7,7-difluoro-5-methyl-6-oxo-6,7,8,9-tetrahydro-5H-pyrimido[4,5-b][1,4]diazepin-2-ylamino)-3-methoxybenzamide using methyl iodide. The final compound was purified by reverse phase HPLC and basified to give the free base. $^1$H NMR (400 MHz, DMSO-d$_6$) δ ppm 1.58-1.93 (m, 17H) 2.28 (br. s., 3H) 2.33 (br. s., 1H) 3.93 (s, 3H) 4.05 (t, J=14.0 Hz, 3H) 4.75 (d, J=7.1 Hz, 1H) 7.37-7.53 (m, 2H) 7.96 (s, 1H) 8.15 (d, J=7.8 Hz, 1H) 8.26 (t, J=4.0 Hz, 2H). [M+H] calc'd for $C_{28}H_{37}F_2N_7O_3$, 558. found 558.

Compound 16: 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-(2-(methylamino)-2-oxoethyl)piperidin-4-yl)benzamide

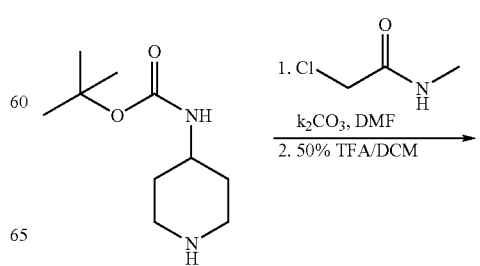

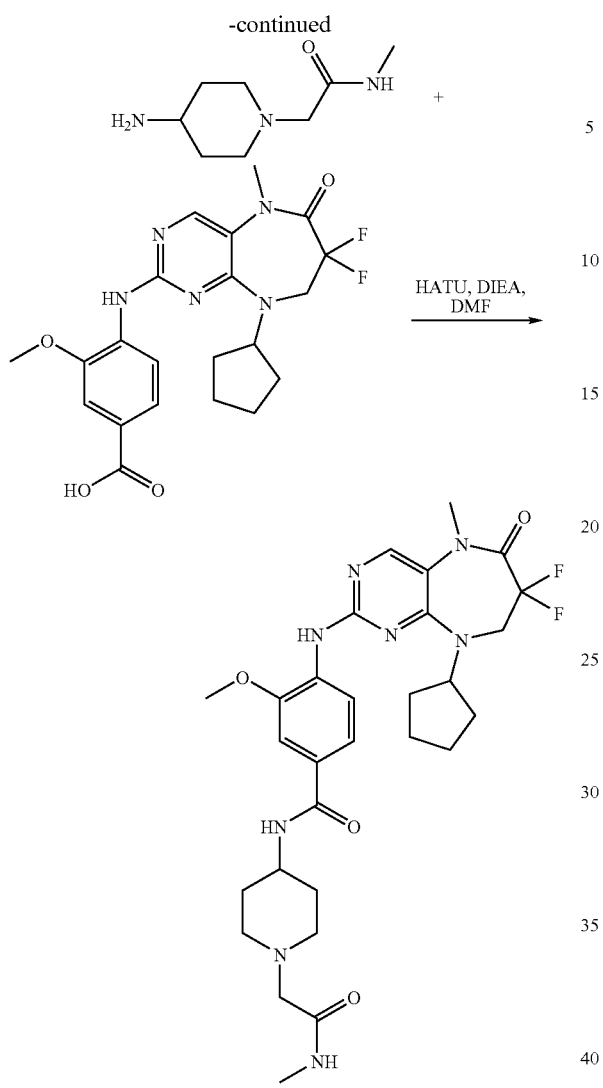

2-(4-aminopiperidin-1-yl)-N-methylacetamide: To a solution of 2.0 g (10 mmoles) of piperidine, which as dissolved in DMF, anhydrous, 100 mL, was added 2.8 g (20 mmoles) $K_2CO_3$, and 1.2 g (11 mmoles) 2-chloro-N-methylacetamide. After stirring at 50° C. for overnight, the mixture was diluted with 500 mL of EtOAc, washed with brine (3×500 mL), dried over $Na_2SO_4$, and solvent was evaporated in vacuum. The resulting residue was treated with 50% TFA/DCM and was stirred at r.t. for 2 hrs, and solvent was evaporated in vacuum. The resulting mixture was purified by prep HPLC to give yellow oil, yield 1.5 g (88%). [M+H] calc'd for $C_8H_{17}N_3O$, 172. found 172.

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-(2-(methylamino)-2-oxoethyl)piperidin-4-yl)benzamide: The title compound was synthesized from 4-(9-Cyclopentyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and 2-(4-aminopiperidin-1-yl)-N-methylacetamide. The final compound was purified by reverse phase HPLC and basified to give the free base. $^1$H NMR (400 MHz, DMSO-$d_6$) δ ppm 1.51-1.86 (m, 11H) 1.95 (d, J=4.29 Hz, 2H) 2.15 (t, J=10.61 Hz, 2H) 2.62 (s, 3H) 2.81 (d, J=11.37 Hz, 2H) 2.90 (s, 2H) 3.33 (s, 3H) 3.94 (s, 3H) 4.05 (t, J=14.02 Hz, 2H) 4.77 (t, J=8.46 Hz, 1H) 7.43-7.53 (m, 2H) 7.57-7.69 (m, 1H) 7.97 (s, 1H) 8.14 (d, J=7.58 Hz, 1H) 8.20-8.35 (m, 2H) [M+H] calc'd for $C_{29}H_{38}F_2N_8O_4$, 601. found 601.

Compound 17: 9-cyclopentyl-2-(4-(2-(dimethylamino)ethoxy)phenylamino)-7,7-difluoro-5-methyl-8,9-dihydro-5H-pyrimido[4,5-b][1,4]diazepin-6(7H)-one

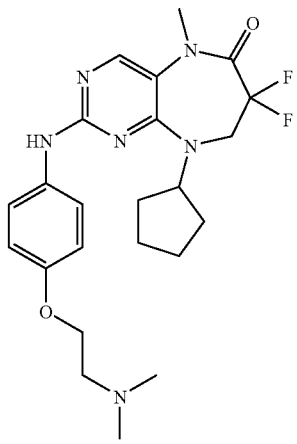

The title compound was synthesized using an analogous procedure to that described in connection with 4-(9-Cyclopentyl-7,7-difluoro-5-methyl-6-oxo-6,7,8,9-tetrahydro-5H-pyrimido[5,4-b][1,4]diazepin-2-ylamino)-3-methoxybenzoic acid from 2-Chloro-9-cyclopentyl-7,7-difluoro-5-methyl-8,9-dihydro-5H-pyrimido[5,4-b][1,4]diazepin-6(7H)-one and 4-(2-(dimethylamino)ethoxy)aniline. $^1$H NMR (400 MHz, DMSO-$d_6$) δ ppm 1.44-1.79 (m, 6H) 1.93 (br. s, 2H) 2.20 (s, 6H) 2.59 (t, J=5.81 Hz, 2H) 3.32 (s, Hz, 3H) 3.88-4.10 (m, 4H) 4.68 (t, J=8.34 Hz, 1H) 6.85 (d, J=8.84 Hz, 2H) 7.55 (d, J=9.09 Hz, 2H) 8.18 (s, 1H) 9.20 (s, 1H). [M+H] calc'd for $C_{23}H_{30}F_2N_6O_2$, 461. found 461.

Compound 18: 6-(9-cyclopentyl-7,7-difluoro-5-methyl-6-oxo-6,7,8,9-tetrahydro-5H-pyrimido[4,5-b][1,4]diazepin-2-ylamino)-2H-benzo[b][1,4]oxazin-3(4H)-one

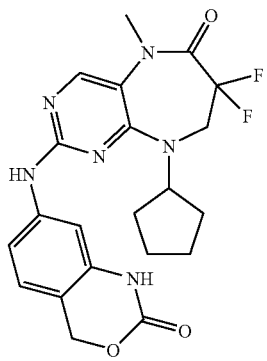

The title compound was synthesized using an analogous procedure to that described in connection with 4-(9-Cyclopentyl-7,7-difluoro-5-methyl-6-oxo-6,7,8,9-tetrahydro-5H-pyrimido[5,4-b][1,4]diazepin-2-ylamino)-3-methoxybenzoic acid from 2-Chloro-9-cyclopentyl-7,7-difluoro-5-methyl-8,9-dihydro-5H-pyrimido[5,4-b][1,4]diazepin-6 (7H)-one and 6-amino-2H-benzo[b][1,4]oxazin-3(4H)-one. $^1$H NMR (400 MHz, DMSO-d$_6$) δ ppm 1.48-1.80 (m, 6H) 1.95 (br. s, 2H) 3.40 (s, 3H) 4.01 (t, J=14.15 Hz, 2H) 4.52 (s, 2H) 4.72 (t, J=8.08 Hz, 1H) 6.77 (d, J=8.34 Hz, 1H) 7.20 (dd, J=8.59, 2.02 Hz, 1H) 7.46 (d, J=2.27 Hz, 1H) 8.20 (s, 1H) 9.35 (s, 1H) 10.54 (br. s., 1H) [M+H] calc'd for C$_{21}$H$_{22}$F$_2$N$_6$O$_3$, 445. found 445.

Compound 19: 9-cyclopentyl-7,7-difluoro-5-methyl-2-(2-oxoindolin-6-ylamino)-8,9-dihydro-5H-pyrimido[4,5-b][1,4]diazepin-6(7H)-one

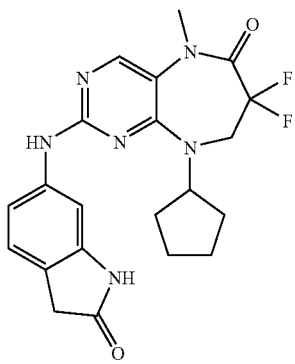

The title compound was synthesized using an analogous procedure to that described in connection with 4-(9-Cyclopentyl-7,7-difluoro-5-methyl-6-oxo-6,7,8,9-tetrahydro-5H-pyrimido[5,4-b][1,4]diazepin-2-ylamino)-3-methoxybenzoic acid from 2-Chloro-9-cyclopentyl-7,7-difluoro-5-methyl-8,9-dihydro-5H-pyrimido[5,4-b][1,4]diazepin-6 (7H)-one and 6-aminoindolin-2-one. $^1$H NMR (400 MHz, CHLOROFORM-d) δ ppm 1.45-1.86 (m, 6H) 1.92-2.16 (m, 2H) 3.39 (s, 3H) 3.54 (s, 2H) 3.87 (t, J=13.39 Hz, 2H) 4.74 (quin, J=8.27 Hz, 1H) 6.81 (d, J=8.34 Hz, 1H) 7.00 (br. s., 1H) 7.26 (s, 1H) 7.50 (br. s., 1H) 7.58 (s, 1H) 7.97 (s, 1H). [M+H] calc'd for C$_{21}$H$_{22}$F$_2$N$_6$O$_2$, 429. found 429.

General Procedure for Buchwald Reaction

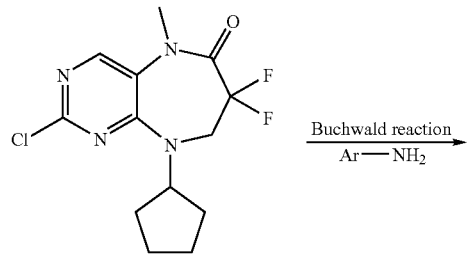

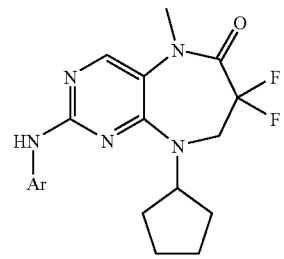

Compounds 20-30 were prepared as follows. A mixture of the 2-Chloro-9-cyclopentyl-7,7-difluoro-5-methyl-8,9-dihydro-5H-pyrimido[5,4-b][1,4]diazepin-6(7H)-one (1 equiv.), the aniline (1.5 equiv.), the catalyst Pd(OAc)$_2$ (0.1 equiv.), the ligand XANPHOS (0.2 equiv.) and Cs$_2$CO$_3$ (4 equiv.) were dissolved in dioxane and N,N-dimethyl acetamide (1: 1, 0.5 M). The reaction mixture was subjected to microwave reaction at 160° C. for 30 min. It was then poured to ice water, filtered through celite. The aqueous filtrate was acidified with HCl, extracted three times with ethyl acetate. The organic extracts were concentrated to a light yellow solid, which was purified on HPLC. When having carboxylic acid on the anilines, the products obtained from Buchwald reactions were directly used for next step amide bond formation reaction using HATU.

Compound 20: 2-(1H-Indol-5-ylamino)-9-cyclopentyl-7,7-difluoro-5-methyl-8,9-dihydro-5H-pyrimido [4,5-b][1,4]diazepin-6(7H)-one

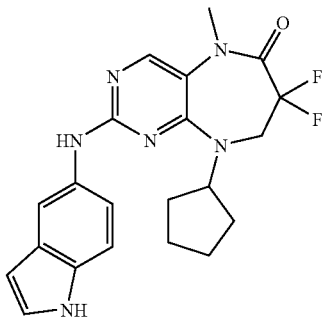

The title compound was prepared using Buchwald reaction from 2-Chloro-9-cyclopentyl-7,7-difluoro-5-methyl-8,9-dihydro-5H-pyrimido[5,4-b][1,4]diazepin-6(7H)-one and 5-aminoindole. $^1$H NMR (400 MHz, DMSO-d$_6$) δ ppm 1.55 (m, 4H) 1.69 (m, 2H) 1.97 (m, 2H) 3.3 (s, 3H) 3.99 (t, J=14.3 Hz, 2H) 4.75 (t, J=8.0 Hz, 1H) 6.29 (br. s., 1H) 7.18-7.41 (m, 3H) 7.96 (s, 1H) 8.18 (s, 1H) 9.16 (s, 1H) 10.91 (br. s., 1H). [M+H] calc'd for C$_{21}$H$_{22}$F$_2$N$_6$O, 413. found 413.

Compound 21: 9-Cyclopentyl-7,7-difluoro-5-methyl-2-(3-(1,2,3,6-tetrahydropyridin-4-yl)-1H-indol-5-ylamino)-8,9-dihydro-5H-pyrimido[4,5-b][1,4]diazepin-6(7H)-one

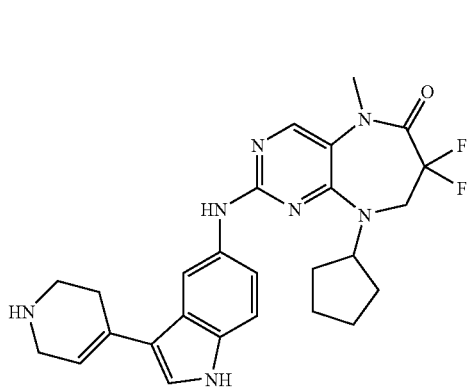

The title compound was prepared using Buchwald reaction from 2-Chloro-9-cyclopentyl-7,7-difluoro-5-methyl-8,9-dihydro-5H-pyrimido[5,4-b][1,4]diazepin-6(7H)-one and 3-(1,2,3,6-tetrahydropyridin-4-yl)-1H-indol-5-amine. $^1$H NMR (400 MHz, DMSO-$d_6$) δ ppm 1.10-1.31 (m, 4H) 1.65 (m, 8H) 2.02 (m, 3H) 2.98 (br. s., 2H) 3.46 (s, 3H) 4.02-4.25 (m, 2H) 4.88 (br. s., 2H) 6.26 (s, 1H), 6.65 (d, J=8 Hz, 1H), 7.10 (s, 1H), 7.98 (s, 1H) 8.34 (d, J=8.0 Hz, 1H) 8.45 (s, 1H). [M+H] calc'd for $C_{26}H_{29}F_2N_7O$, 494. found 494.

Compound 22: 4-(9-Cyclopentyl-7,7-difluoro-5-methyl-6-oxo-6,7,8,9-tetrahydro-5H-pyrimido[4,5-b][1,4]diazepin-2-ylamino)-3-fluoro-N-(1-methylpiperidin-4-yl)benzamide

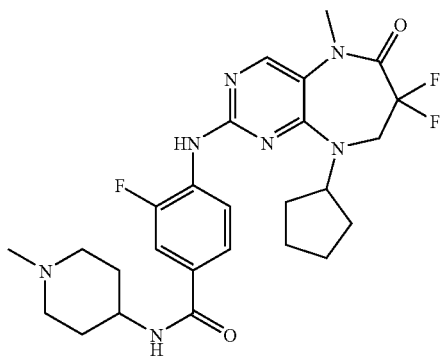

The title compound was synthesized from 4-(9-cyclopentyl-7,7-difluoro-5-methyl-6-oxo-6,7,8,9-tetrahydro-5H-pyrimido[4,5-b][1,4]diazepin-2-ylamino)-3-fluorobenzoic acid as described in the General procedure for amide bond synthesis using HATU and 1-methylpiperidin-4-amine. The final compound was purified by reverse phase HPLC and basified to give the free base $^1$H NMR (400 MHz, DMSO-$d_6$) δ ppm 1.50-1.75 (m, 12H) 1.99 (m, 3H) 2.19 (s, 3H) 2.79 (m, 2H) 3.74 (m, 1H) 4.01 (t, J=14.0 Hz, 2H) 4.68 (m, 1H) 7.67 (d, J=8.6 Hz, 1H) 7.72 (d, J=12.4 Hz, 1H) 7.99 (t, J=8.2 Hz, 1H) 8.20 (d, J=7.3 Hz, 1H) 8.23 (s, 1H) 9.08 (s, 1H). [M+H] calc'd for $C_{26}H_{32}F_3N_7O_2$, 532. found 532.

Compound 23: 4-(9-Cyclopentyl-7,7-difluoro-5-methyl-6-oxo-6,7,8,9-tetrahydro-5H-pyrimido[4,5-b][1,4]diazepin-2-ylamino)-N-(1-methylpiperidin-4-yl)benzamide

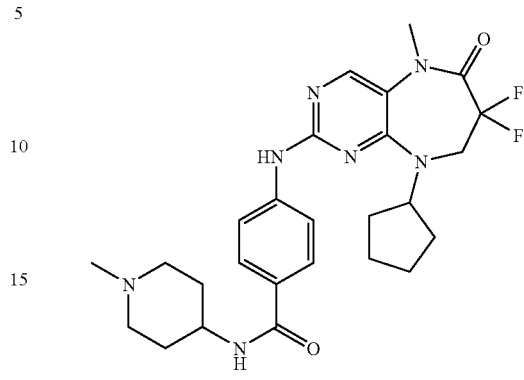

The title compound was synthesized from 4-(9-cyclopentyl-7,7-difluoro-5-methyl-6-oxo-6,7,8,9-tetrahydro-5H-pyrimido[4,5-b][1,4]diazepin-2-ylamino)-benzoic acid as described in the General procedure for amide bond synthesis using HATU and 1-methylpiperidin-4-amine. The final compound was purified by reverse phase HPLC and basified to give the free base $^1$H NMR (400 MHz, DMSO-$d_6$) δ ppm 1.43-1.66 (m, 6H) 1.72 (m, 4H) 1.92-1.99 (m, 5H) 2.15 (s, 3H) 2.76 (d, J=11.4 Hz, 2H) 3.71 (m, 1H) 4.04 (t, J=14.2 Hz, 2H) 4.78 (t, J=7.8 Hz, 1H) 7.77 (s, 4H) 8.03 (d, J=7.6 Hz, 1H) 8.27 (s, 1H) 9.67 (s, 1H). Melting point: 234-235ºC. [M+H] calc'd for $C_{26}H_{33}F_2N_7O_2$, 514. found 514.

Compound 24: 3-Chloro-4-(9-cyclopentyl-7,7-difluoro-5-methyl-6-oxo-6,7,8,9-tetrahydro-5H-pyrimido[4,5-b][1,4]diazepin-2-ylamino)-N-(1-methylpiperidin-4-yl)benzamide

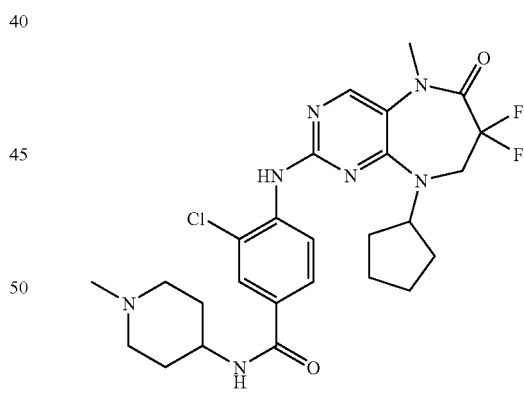

The title compound was synthesized from 4-(9-cyclopentyl-7,7-difluoro-5-methyl-6-oxo-6,7,8,9-tetrahydro-5H-pyrimido[4,5-b][1,4]diazepin-2-ylamino)-3-chlorobenzoic acid as described in the General procedure for amide bond synthesis using HATU and 1-methylpiperidin-4-amine. The final compound was purified by reverse phase HPLC and basified to give the free base $^1$H NMR (400 MHz, DMSO-$d_6$) δ ppm 1.44-1.77 (m, 15H) 2.23 (s, 3H) 2.84 (m, 2H) 3.96-4.07 (t, J=12 Hz, 2H) 4.66 (m, 1H) 7.80 (dd, J=8.5, 1.9 Hz, 1H) 8.00 (d, J=1.8 Hz, 1H) 8.08 (d, J=8.6 Hz, 1H) 8.19-8.33 (m, 2H) 8.58 (s, 1H). [M+H] calc'd for $C_{26}H_{32}ClF_2N_7O_2$, 548. found 548.

Compound 25: 4-(9-Cyclopentyl-7,7-difluoro-5-methyl-6-oxo-6,7,8,9-tetrahydro-5H-pyrimido[4,5-b][1,4]diazepin-2-ylamino)-N-(1-methylpiperidin-4-yl)-3-(trifluoromethoxy)-benzamide

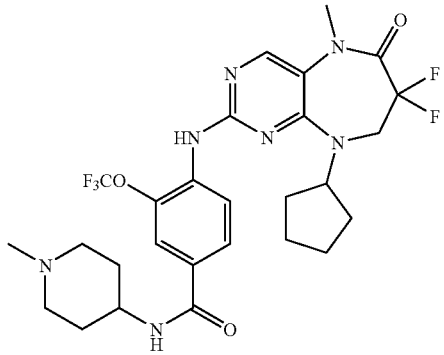

The title compound was synthesized from 4-(9-cyclopentyl-7,7-difluoro-5-methyl-6-oxo-6,7,8,9-tetrahydro-5H-pyrimido[4,5-b][1,4]diazepin-2-ylamino)-3-trifluoromethylbenzoic acid as described in the General procedure for amide bond synthesis using HATU and 1-methylpiperidin-4-amine. The final compound was purified by reverse phase HPLC and basified to give the free base $^1$H NMR (400 MHz, DMSO-$d_6$) δ ppm 1.53-2.11 (m, 17H) 2.23 (s, 3H) 2.84 (m, 2H) 4.02 (t, J=14.0 Hz, 2H) 4.66 (d, J=8.1 Hz, 1H) 7.77-7.92 (m, 2H) 8.13 (d, J=8.6 Hz, 1H) 8.24 (s, 1H) 9.01 (s, 1H). [M+H] calc'd for $C_{27}H_{32}F_5N_7O_3$, 598. found 598.

Compound 26: 4-(9-Cyclopentyl-7,7-difluoro-5-methyl-6-oxo-6,7,8,9-tetrahydro-5H-pyrimido[4,5-b][1,4]diazepin-2-ylamino)-3-methyl-N-(1-methylpiperidin-4-yl)benzamide

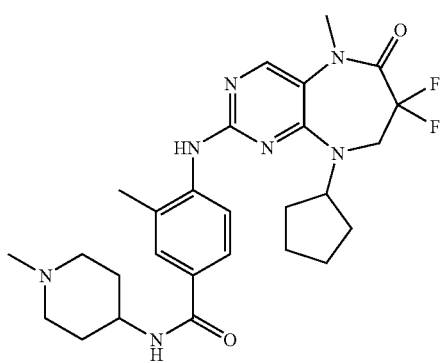

The title compound was synthesized from 4-(9-cyclopentyl-7,7-difluoro-5-methyl-6-oxo-6,7,8,9-tetrahydro-5H-pyrimido[4,5-b][1,4]diazepin-2-ylamino)-3-methylbenzoic acid as described in the General procedure for amide bond synthesis using HATU and 1-methylpiperidin-4-amine. The final compound was purified by reverse phase HPLC and basified to give the free base $^1$H NMR (400 MHz, DMSO-$d_6$) δ ppm 1.42-2.04 (m, 16H) 2.10-2.22 (m, 3H) 2.29 (s, 3H) 2.77 (d, J=11.1 Hz, 2H) 3.72 (dd, J=7.3, 4.0 Hz, 1H) 3.98 (t, J=14.0 Hz, 2H) 4.60 (t, J=8.2 Hz, 1H) 7.64 (d, J=8.3 Hz, 1H) 7.68-7.80 (m, 2H) 8.08 (d, J=7.8 Hz, 1H) 8.19 (s, 1H) 8.60 (s, 1H). [M+H] calc'd for $C_{27}H_{35}F_2N_7O_2$, 528. found 528.

Compound 27: 4-(9-Cyclopentyl-7,7-difluoro-5-methyl-6-oxo-6,7,8,9-tetrahydro-5H-pyrimido[4,5-b][1,4]diazepin-2-ylamino)-3-ethyl-N-(1-methylpiperidin-4-yl)benzamide

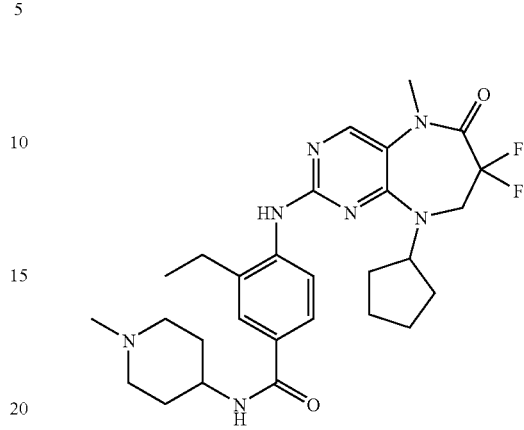

The title compound was synthesized from 4-(9-cyclopentyl-7,7-difluoro-5-methyl-6-oxo-6,7,8,9-tetrahydro-5H-pyrimido[4,5-b][1,4]diazepin-2-ylamino)-3-ethylbenzoic acid as described in the General procedure for amide bond synthesis using HATU and 1-methylpiperidin-4-amine. The final compound was purified by reverse phase HPLC and basified to give the free base $^1$H NMR (400 MHz, DMSO-$d_6$) δ ppm 1.14 (t, J=8.0 Hz, 3H) 1.23-1.69 (m, 11H) 1.77 (m, 4H) 1.99 (m, 2H) 2.20 (s, 3H) 2.69 (q, J=7.3 Hz, 2H) 3.75 (s, 1H) 3.97 (t, J=14.2 Hz, 2H) 4.54 (t, J=8.1 Hz, 1H) 7.57-7.81 (m, 3H) 8.12 (d, J=7.8 Hz, 1H) 8.17 (s, 1H) 8.61 (s, 1H). [M+H] calc'd for $C_{28}H_{37}F_2N_7O_2$, 542. found 542.

Compound 28: 4-(9-Cyclopentyl-7,7-difluoro-5-methyl-6-oxo-6,7,8,9-tetrahydro-5H-pyrimido[4,5-b][1,4]diazepin-2-ylamino)-2-fluoro-N-(1-methylpiperidin-4-yl)benzamide

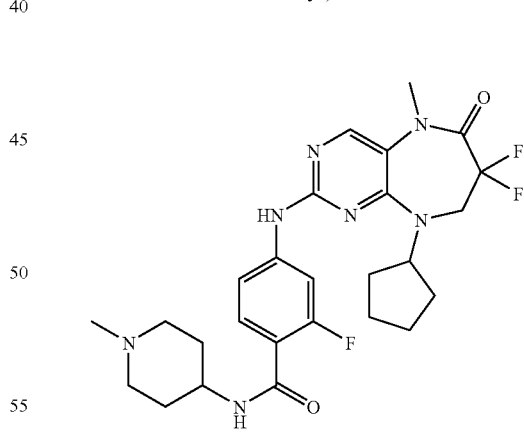

The title compound was synthesized from 4-(9-cyclopentyl-7,7-difluoro-5-methyl-6-oxo-6,7,8,9-tetrahydro-5H-pyrimido[4,5-b][1,4]diazepin-2-ylamino)-2-fluorobenzoic acid as described in the General procedure for amide bond synthesis using HATU and 1-methylpiperidin-4-amine. The final compound was purified by reverse phase HPLC and basified to give the free base $^1$H NMR (400 MHz, DMSO-$d_6$) δ ppm 1.44-1.74 (m, 11H) 1.86-2.09 (m, 5H) 2.15 (s, 3H) 2.63-2.81 (m, 2H) 3.57-3.79 (m, 1H) 3.94-4.16 (m, 2H) 4.81 (t, J=8.1 Hz, 1H) 7.32-7.46 (m, 1H) 7.51 (t, J=8.6 Hz, 1H) 7.85 (br. s., 1H) 7.88 (dd, J=4.3, 2.3 Hz, 1H) 8.30 (s, 1H) 9.88 (s, 1H). [M+H] calc'd for $C_{26}H_{32}F_3N_7O_2$, 532. found 532.

Compound 29: 4-(9-Cyclopentyl-7,7-difluoro-5-methyl-6-oxo-6,7,8,9-tetrahydro-5H-pyrimido[4,5-b][1,4]diazepin-2-ylamino)-3-ethoxy-N-(1-methylpiperidin-4-yl)benzamide

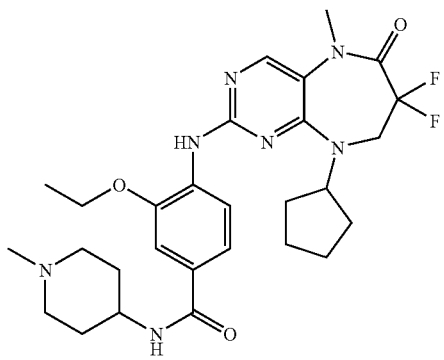

The title compound was synthesized from 4-(9-cyclopentyl-7,7-difluoro-5-methyl-6-oxo-6,7,8,9-tetrahydro-5H-pyrimido[4,5-b][1,4]diazepin-2-ylamino)-3-ethoxybenzoic acid as described in the General procedure for amide bond synthesis using HATU and 1-methylpiperidin-4-amine. The final compound was purified by reverse phase HPLC and basified to give the free base. $^1$H NMR (400 MHz, DMSO-$d_6$) δ ppm 1.41 (t, J=6.7 Hz, 3H) 1.60 (m, 6H) 1.74 (m, 4H) 1.95 (m, 4H) 2.18 (s, 3H) 2.79 (d, J=10.6 Hz, 2H) 3.73 (m, 1H) 4.05 (t, J=13.9 Hz, 2H) 4.19 (d, J=7.1 Hz, 2H) 4.74 (m, 1H) 7.40-7.59 (m, 2H) 7.91 (s, 1H) 8.11 (d, J=7.6 Hz, 1H) 8.26 (m, 2H). [M+H] calc'd for $C_{28}H_{37}F_2N_7O_3$, 558. found 558.

Compound 30: 4-(9-cyclopentyl-7,7-difluoro-5-methyl-6-oxo-6,7,8,9-tetrahydro-5H-pyrimido[4,5-b][1,4]diazepin-2-ylamino)-N-(1-methylpiperidin-4-yl)-3-(trifluoromethyl)benzamide

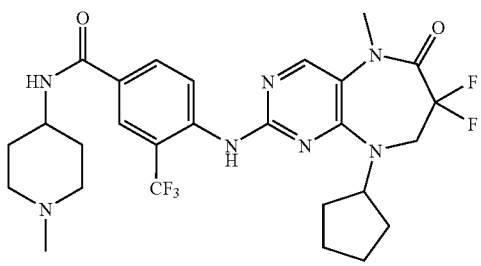

The title compound was synthesized from 4-(9-cyclopentyl-7,7-difluoro-5-methyl-6-oxo-6,7,8,9-tetrahydro-5H-pyrimido[4,5-b][1,4]diazepin-2-ylamino)-3-(trifluoromethyl)benzoic acid as described in the General procedure for amide bond synthesis using HATU and 1-methylpiperidin-4-amine. The final compound was purified by reverse phase HPLC and basified to give the free base. $^1$H NMR (400 MHz, CHLOROFORM-d) δ ppm 1.34-1.67 (m, 9H) 1.70-1.85 (m, 3H) 2.13 (br. s., 1H) 2.27 (s, 3H) 2.84-2.93 (m, 1H) 3.32 (s, 3H) 3.74-3.86 (m, 1H) 4.00 (t, J=14.0 Hz, 1H) 4.50 (quin, 1H) 7.96 (d, J=8.6 Hz, 1H) 8.12 (dd, 1H) 8.20 (s, 1H) 8.21 (s, 1H) 8.48 (d, J=7.8 Hz, 1H) 8.52 (s, 1H). [M+H] calc'd for $C_{27}H_{32}F_5N_7O_2$, 582. found 582.

Compound 31: 4-(9-Cyclopentyl-7,7-difluoro-5-methyl-6-oxo-6,7,8,9-tetrahydro-5H-pyrimido[4,5-b][1,4]diazepin-2-ylamino)-2-fluoro-5-methoxybenzoic acid

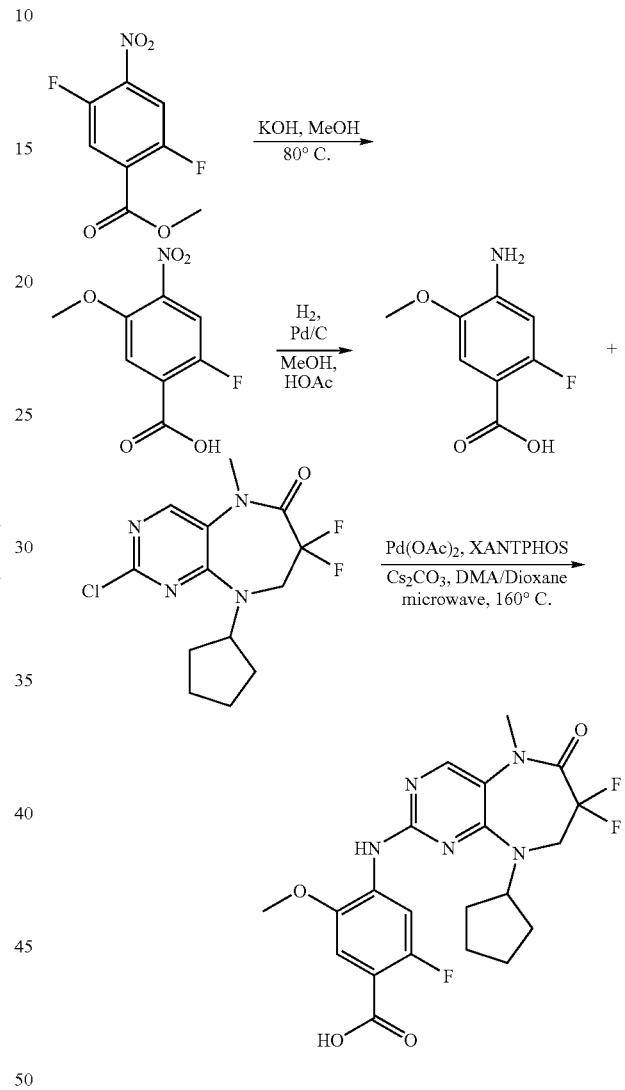

2-Fluoro-5-methoxy-4-nitrobenzoic acid: To a solution of methyl-2,5-difluoro-4-nitrobenzoate (10 g, 46 mmol) in methanol (100 mL) was added potassium hydroxide (7.73 g, 184 mmol) in two batches. The reaction mixture was stirred in an oil bath at 80° C. for 1 h. It was then concentrated, acidified with HCl. Solid was filtered, washed with water and dried to give the product as light yellow powder (10 g, quantitative yield). $^1$H NMR (400 MHz, DMSO-$d_6$) δ ppm 3.95 (s, 3H) 7.66 (d, J=4 Hz, 1H) 8.01 (d, J=8 Hz, 1H). [M+H] calc'd for $C_8H_6FNO_5$, 216. found 216.

4-Amino-2-fluoro-5-methoxybenzoic acid: A solution of 2-fluoro-5-methoxy-4-nitrobenzoic acid (10 g, 46 mmol), HOAc (50 mL) and MeOH (50 mL) was hydrogenated using a hydrogen balloon overnight. The solution was then filtered through celite and concentrated to a residue, which was triturated with ether and ethyl acetate. The solid was filtered and dried to give the product as light yellow powder (8.3 g, 98%).

¹H NMR (400 MHz, DMSO-d₆) δ ppm 3.76 (s, 3H) 5.88 (br s, 2H) 6.36 (d, J=16 Hz, 1H) 7.13 (d, J=8 Hz, 1H) 12.32 (br s, 1H). [M+H] calc'd for $C_8H_8FNO_3$, 186. found 186.

4-(9-Cyclopentyl-7,7-difluoro-5-methyl-6-oxo-6,7,8,9-tetrahydro-5H-pyrimido[4,5-b][1,4]diazepin-2-ylamino)-2-fluoro-5-methoxybenzoic acid: Eleven batches of same scale reactions were carried out as follows: A mixture of the chloropyrimidine (1.1 g, 3.48 mmol), 4-amino-2-fluoro-5-methoxybenzoic acid (676 mg, 3.65 mmol), the catalyst Pd(OAc)₂ (78 mg, 0.35 mmol), the ligand XANTPHOS (405 mg, 0.7 mmol) and $Cs_2CO_3$ (4.5 g, 13.9 mmol) were dissolved in dioxane and N,N-dimethyl acetamide (1:3, 5 mL/15 mL, 0.2 M). The reaction mixture was subjected to microwave reaction at 160° C. for 15 min. All of the eleven batches of reaction mixtures were combined and poured to ice water, filtered through celite. The aqueous filtrate was acidified with HCl carefully and stirred at rt. for 2 h. After which, solid was filtered, washed with water. The dark solid was then dissolved in minimum amount of methanol, triturated with ethyl acetate and ether and concentrated to a slurry which was filtered and washed by ether to give a light tan solid (8.5 g). The filtrate was then concentrated and triturated again to give a second batch of solid (2.5 g). The final filtrate was purified by prep-HPLC to give another 500 mg of product. The total yield was 11.5 g (65%). ¹H NMR (400 MHz, DMSO-d₆) δ ppm 1.61 (m, 3H) 1.73 (m, 2H) 1.84-2.04 (m, 3H) 3.34 (s, 2H) 3.85-3.99 (m, 3H) 4.12 (t, J=13.8 Hz, 2H) 4.84 (d, J=8.1 Hz, 2H) 7.38 (d, J=6.8 Hz, 1H) 8.27 (d, J=13.6 Hz, 1H) 8.33 (s, 1H). [M+H] calc'd for $C_{21}H_{22}F_3N_5O_4$, 466. found 466.

Compound 32: 4-(9-cyclohexyl-7,7-difluoro-5-methyl-6-oxo-6,7,8,9-tetrahydro-5H-pyrimido[4,5-b][1,4]diazepin-2-ylamino)-3-methoxybenzoic acid

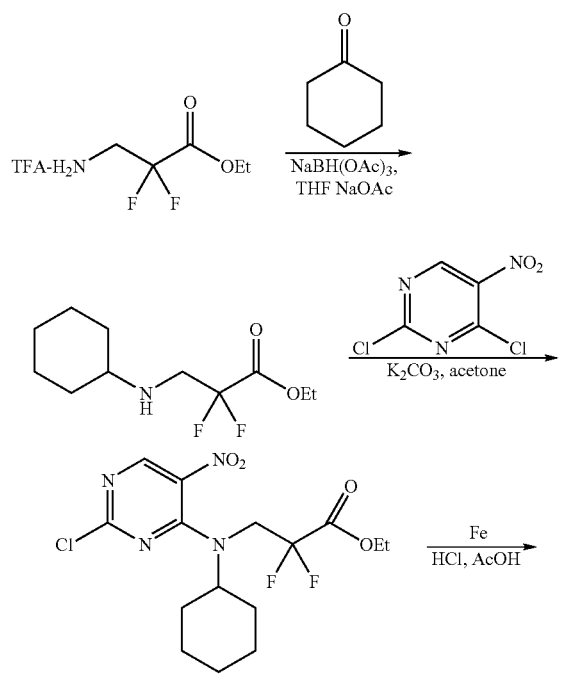

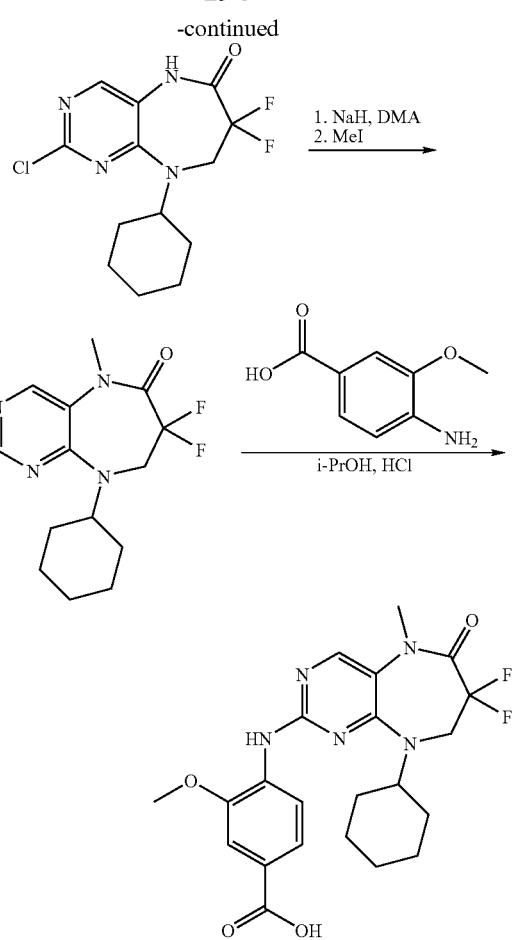

Ethyl 3-(cyclohexylamino)-2,2-difluoropropanoate: To a round bottom flask was added 4 (13.35 g, 50 mmol), THF (150 mL), cyclohexanone (5.89 g, 60 mmol), and NaOAc (4.51 g, 55 mmol). To this mixture was added sodium triacetoxyborohydride (15.90 g, 75 mmol) portion wise over 15 minutes. The reaction was left to stir for 14 hrs. It was then cooled in an ice bath and sodium bicarbonate solution was added (100 mL, sat.) followed by EtOAc (200 ml). At this time the layers were separated and washed the organic layer with more sat.NaHCO₃ (until aqueous layer PH is basic ~9). The aqueous layer was extracted with EtOAc (2×150 mL), the organic extracts combined, washed with brine (100 mL), dried over $Na_2SO_4$, filtered and concentrated to yield the desired product as a cloudy syrup (9.94 g, 90%). ¹H NMR (400 MHz, DMSO-d₆) δ ppm 0.90-1.77 (m, 10H) 2.32 (m, 1H) 3.17 (t, J=16.0 Hz, 2H) 3.81 (s, 1H).

Ethyl 4-((2-chloro-5-nitropyrimidin-4-yl)(cyclohexyl)amino)-3,3-difluoro-2-oxobutanoate: In a round bottom flask, ethyl 3-(cyclohexylamino)-2,2-difluoropropanoate (11.05 g, 50 mmol) was dissolved in acetone (100 mL), and added $K_2CO_3$ (13.8 g, 100 mmol) to it. Cooled the round bottom flask to 0° C. in an ice bath. After 20 min, added 2,4-dichloro 5-nitropyrimidine (9.70 g, 50 mmol) in acetone (25 mL) dropwise and continued stirring for another 30 min at 0° C., then allowed to warm up to room temperature, continued for 12 hrs. Then evaporated the acetone washed with water and extracted into EtOAc (300 mL) dried over $Na_2SO_4$ and evaporated. The crude gummy solid was purified on Combiflash (ISCO) using hexane-EtOAc as solvent system to obtain the desired compound (11.85 g, 60%). ¹H NMR (400

MHz, DMSO-$d_6$) δ ppm 1.02-1.31 (m, 3H) 1.42-1.68 (m, 3H) 1.75 (d, J=9.09 Hz, 4H) 3.33 (m, 1H) 3.80 (s, 3H) 4.40 (t, J=14.02 Hz, 2H) 8.92 (s, 1H). MS (ES) [M+H] calculated for $C_{15}H_{19}ClF_2N_4O_4$, 393. found 393.

2-Chloro-9-cyclohexyl-7,7-difluoro-8,9-dihydro-5H-pyrimido[5,4-b][1,4]diazepin-6(7H)-one: In a round bottom flask compound ethyl 4-((2-chloro-5-nitropyrimidin-4-yl)(cyclohexyl)amino)-3,3-difluoro-2-oxobutanoate (11.85 g, 31.35 mmol) was dissolved in acetic acid (30 mL), and added iron powder (3.51 g, 62.7 mmol) to it. Then cooled the round bottom flask to 0° C. in an ice bath. After 10 min, added conc.HCl (12 mL) dropwise using addition funnel and continued the reaction at 60° C. on a preheated oil bath until starting material disappear. It was then concentrated in vacuo, diluted with EtOAc, basified with 10% NaOH solution at 0° C. The whole was filtered through celite, washed with EtOAc. The filtrate was then separated. The organic layer was dried over $Na_2SO_4$. The solution was concentrated in vacuo followed by precipitation from ether to afford the desired compound (6.0 g, 62% yield) as yellow solid. $^1$H NMR (400 MHz, DMSO-$d_6$) δ ppm 0.96-1.85 (m, 10H) 4.02 (t, J=11.37 Hz, 2H) 4.47 (m, 1H) 8.11 (s, 1H) 11.02 (br. s., 1H). [M+H] calc'd for $C_{13}H_{15}ClF_2N_4O$, 317. found 317.

2-Chloro-9-cyclohexyl-7,7-difluoro-5-methyl-8,9-dihydro-5H-pyrimido[5,4-b][1,4]diazepin-6(7H)-one: To a solution of compound 2-Chloro-9-cyclohexyl-7,7-difluoro-8,9-dihydro-5H-pyrimido[5,4-b][1,4]diazepin-6(7H)-one (6.0 g, 18.98 mmol) in 30 mL of DMA was added sodium hydride (60% dispersion in mineral oil, 1.138 g, 28.47 mmol) at 0° C., followed by the dropwise addition of methyl iodide (1.42 mL, 22.78 mmol). The reaction mixture was warmed up to rt and stirred for 1 h. The whole was poured into ice-water, extracted with ethyl acetate. The organic layer was washed with brine and dried over $Na_2SO_4$. The solution was concentrated in vacuo followed by precipitation from ether/EtOA to afford the desired compound (3.0 g, 47.9% yield) as white solid. $^1$H NMR (400 MHz, DMSO-$d_6$) δ ppm 0.97-1.85 (m, 10H) 3.33 (s, 3H) 4.15 (t, J=12.88 Hz, 2H) 4.44 (m, 1H) 8.31 (s, 1H). [M+H] calc'd for $C_{14}H_{17}ClF_2N_4O$, 331. found 331.

4-(9-cyclohexyl-7,7-difluoro-5-methyl-6-oxo-6,7,8,9-tetrahydro-5H-pyrimido[4,5-b][1,4]diazepin-2-ylamino)-3-methoxybenzoic acid: 2-Chloro-9-cyclohexyl-7,7-difluoro-5-methyl-8,9-dihydro-5H-pyrimido[5,4-b][1,4]diazepin-6(7H)-one (2.77 g, 8.8 mmol), 4-amino-3-methoxy benzoic acid (1.61 g, 9.6 mmol), i-PrOH (30 mL) and conc. HCl (30 drops) were heated to 95° C. for 18 hours. A this time the reaction was cooled to room temperature and filtered to reveal the product as a tan solid (2.74 g, 70% yield). $^1$H NMR (400 MHz, DMSO-$d_6$) δ ppm 1.21 (d, J=12.13 Hz, 1H) 1.23-1.42 (m, 2H) 1.53-1.78 (m, 5H) 1.82 (d, J=12.63 Hz, 2H) 3.32 (s, 3H) 3.94 (s, 3H) 4.26 (t, J=12.38 Hz, 2H) 4.52 (t, J=11.62 Hz, 1H) 7.47-7.65 (m, 2H) 8.13 (d, J=8.08 Hz, 1H) 8.28-8.45 (m, 1H) 9.43 (br. s., 1H). [M+H] calc'd for $C_{22}H_{25}F_2N_5O_4$, 462. found 462.

Compound 33: 4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide

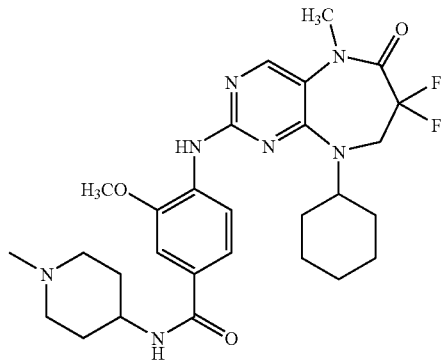

The title compound was synthesized from 4-(9-cyclohexyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and 1-amino 4-methylpiperidine. The final compound was purified by reverse phase HPLC and basified to give the free base. $^1$H NMR (400 MHz, DMSO-$d_6$) δ ppm 1.19-1.26 (m, 2H) 1.39 (m, 2H) 1.50-1.71 (m, 5H) 1.78-1.85 (m, 6H) 1.96 (t, J=10.9 Hz, 2H) 2.18 (s, 3H) 2.79 (d, J=10.6 Hz, 2H) 3.94 (s, 3H) 4.05 (t, J=13.2 Hz, 2H) 4.46 (m., 1H) 7.48 (d, J=8.3 Hz, 1H) 7.51 (br. s., 1H) 7.89 (s, 1H) 8.10 (d, J=7.6 Hz, 1H) 8.21 (s, 1H) 8.26 (d, J=8.1 Hz, 1H). [M+H] calc'd for $C_{28}H_{37}F_2N_7O_3$, 558. found 558.

Compound 34: 4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(4-methylpiperazin-1-yl)benzamide

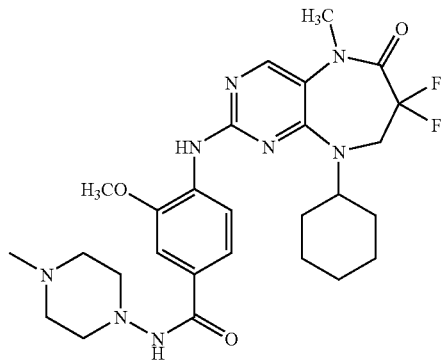

The title compound was synthesized from 4-(9-cyclohexyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and 1-amino 4-methylpiperazine. The final compound was purified by reverse phase HPLC and basified to give the free base. $^1$H NMR (400 MHz, DMSO-$d_6$) δ ppm 1.20-1.85 (m, 10H) 2.18 (s, 3H) 2.93 (br. s., 3H) 3.22-3.47 (m, 7H) 3.93 (s, 3H) 4.06 (t, J=13.39 Hz, 2H)

4.46 (m, 1H) 7.44 (br. s., 1H) 7.42 (d, J=8.84 Hz, 1H) 7.90 (s, 1H) 8.21 (s, 1H) 8.27 (d, J=8.08 Hz, 1H) 9.40 (s, 1H). [M+H] calculated for $C_{27}H_{36}F_2N_8O_3$, 559. found 559.

Compound 35: 4-(9-Cyclohexyl-7,7-difluoro-5-methyl-6-oxo-6,7,8,9-tetrahydro-5H-pyrimido[4,5-b][1,4]diazepin-2-ylamino)-3-methoxy-N-(1-methylazetidin-3-yl)benzamide

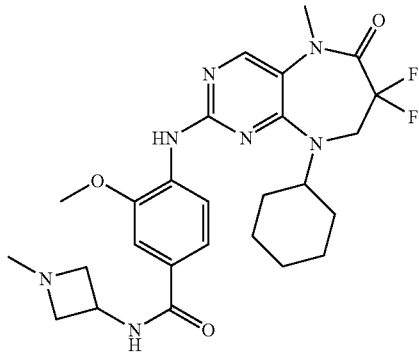

The title compound was synthesized from 4-(9-cyclohexyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and 1-methylazetidin-3-amine hydrochloride. The final compound was purified by reverse phase HPLC and basified to give the free base. $^1$H NMR (400 MHz, DMSO-$d_6$) δ ppm 1.18-1.82 (m, 12H) 2.32 (s, 3H) 3.10 (s, 3H) 3.62 (s, 2H) 3.95 (s, 3H) 4.06 (t, J=13.4 Hz, 2H) 4.47 (m, 1H) 4.45 (d, J=6.8 Hz, 1H) 7.49 (d, J=8.1 Hz, 1H) 7.53 (s, 1H) 7.90 (s., 1H) 8.21 (s, 1H) 8.28 (d, J=8.1 Hz, 1H) 8.65 (d, J=5.8 Hz, 1H). [M+H] calc'd for $C_{26}H_{33}F_2N_7O_3$, 530. found 530.

Compound 36: 4-(9-cyclohexyl-7,7-difluoro-5-methyl-6-oxo-6,7,8,9-tetrahydro-5H-pyrimido[4,5-b][1,4]diazepin-2-ylamino)-N-(1-ethylpiperidin-4-yl)-3-methoxybenzamide

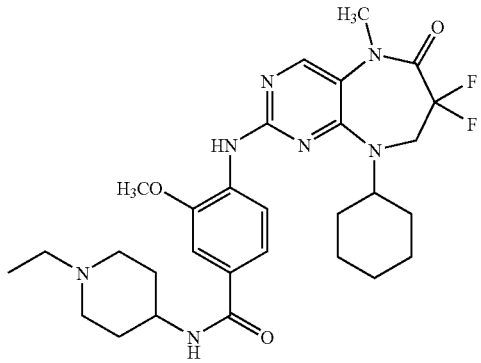

The title compound was synthesized from 4-(9-cyclohexyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and 1-(3-aminopropyl)pyrrolidin-2-one. The final compound was purified by reverse phase HPLC and basified to give the free base. $^1$H NMR (400 MHz, DMSO-$d_6$) δ ppm $^1$H NMR (400 MHz, DMSO-$d_6$) δ ppm 1.00 (t, J=7.07 Hz, 3H) 1.17 (m, 2H) 1.35-1.80 (m, 12H) 2.32 (q, J=7.07 Hz, 2H) 2.87 (br. d., 2H) 3.33 (s, 3H) 3.76 (m, 1H) 3.94 (s, 3H) 4.06 (t, J=13.64 Hz, 2H) 4.46 (m, 1H) 7.47 (d, J=8.59 Hz, 1H) 7.50 (s, 1H) 8.14 (d, 1H) 8.21 (s, 1H) 8.26 (d, J=8.34 Hz, 1H). [M+H] calculated for $C_{29}H_{39}F_2N_7O_3$, 572. found 572.

Compound 37: (S)-4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(piperidin-3-yl)benzamide

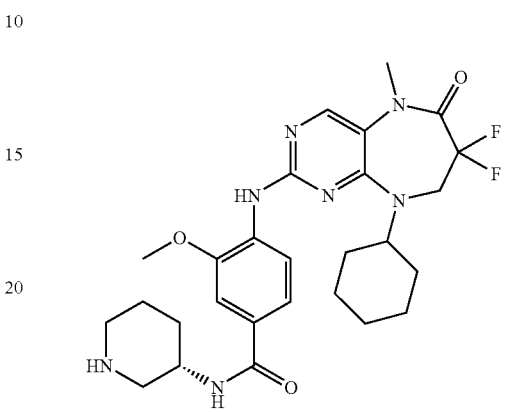

The title compound was synthesized from 4-(9-cyclohexyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and (S)-1-Boc-3-aminopiperidine. The final compound was purified by reverse phase HPLC and basified to give the free base. Further, after washing with water (10 ml), t-butoxycarbonyl (Boc) protection group was removed using 40% TFA in dichloromethane (6 ml) and purified the product using preparative HPLC. $^1$H NMR (400 MHz, DMSO-$d_6$) δ ppm 1.08-1.95 (m., 14H) 2.40 (t, J=7.38 Hz, 2H) 2.80 (br. s., 1H) 2.96 (br. s., 1H) 3.33 (s, 3H) 3.81 (br. s., 1H) 3.94 (s, 3H) 4.06 (t, J=13.64 Hz, 2H) 4.45 (m, 1H) 7.34-7.55 (m, 2H) 7.90 (s, 1H) 8.03 (d, J=7.58 Hz, 1H) 8.21 (s, 1H) 8.26 (d, J=8.34 Hz, 1H). [M+H] calculated for $C_{27}H_{35}F_2N_7O_3$, 544. found 544.

Compound 38: (R)-4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(piperidin-3-yl)benzamide

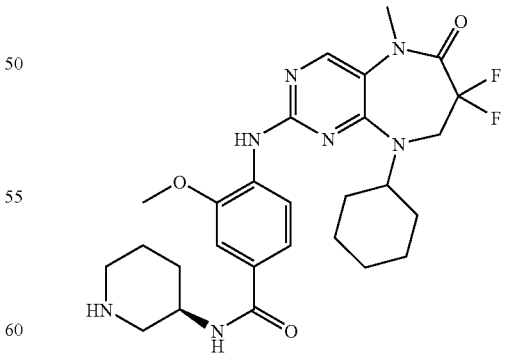

The title compound was synthesized from 4-(9-cyclohexyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and (R)-1-Boc-3-aminopiperidine. The final compound was purified by reverse phase HPLC and basified to give the free base. Further, after washing with water (10 ml), t-butoxycarbonyl (Boc) protection group was removed using 40% TFA in dichloromethane (6 ml) and purified the product using preparative HPLC. $^1$H NMR (400 MHz, DMSO-d$_6$) δ ppm 1.15-1.95 (m., 14H) 2.52 (t, J=7.38 Hz, 2H) 2.92 (br. d., 1H) 3.07 (br. d., 1H) 3.39 (s, 3H) 3.81 (br. s., 1H) 3.94 (s, 3H) 4.06 (t, J=13.64 Hz, 2H) 4.45 (m, 1H) 7.34-7.55 (m, 2H) 7.90 (s, 1H) 8.03 (d, J=7.58 Hz, 1H) 8.21 (s, 1H) 8.26 (d, J=8.34 Hz, 1H). [M+H] calculated for C$_{27}$H$_{35}$F$_2$N$_7$O$_3$, 544. found 544.

Compound 39: (R)-4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(1-methylpyrrolidin-3-yl)benzamide

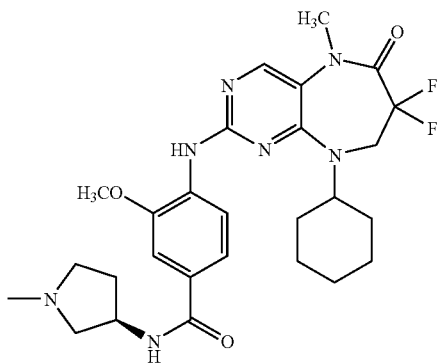

The title compound was synthesized from 4-(9-cyclohexyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and 1-methyl-3-(R)-amino pyrrolidine dihydrochloride. The final compound was purified by reverse phase HPLC and basified to give the free base. $^1$H NMR (400 MHz, DMSO-d$_6$) δ ppm 1.15-1.90 (m, 12H) 2.18 (m, 1H) 2.26 (s, 3H) 2.32-2.56 (m, 2H) 2.60-2.68 (m, 2H) 3.34 (s, 3H) 3.95 (s, 3H) 4.07 (t, J=13.52 Hz, 2H) 4.34-4.54 (m, 2H) 7.51 (d, J=8.0 Hz, 1H), 7.54 (br. s., 1H) 7.90 (s, 1H), 8.21 (s, 1H) 8.27 (d, J=8.0 Hz, 1H) 8.40 (br. s., 1H). Melting point: 98-99° C. [M+H] calculated for C$_{27}$H$_{35}$F$_2$N$_7$O$_3$, 544. found 544.

Compound 40: 4-(9-cyclohexyl-7,7-difluoro-5-methyl-6-oxo-6,7,8,9-tetrahydro-5H-pyrimido[4,5-b][1,4]diazepin-2-ylamino)-N-((1r,4r)-4-hydroxycyclohexyl)-3-methoxybenzamide

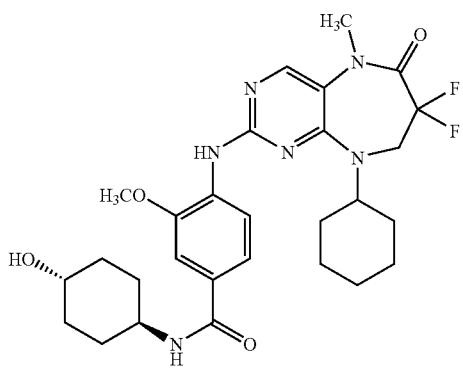

The title compound was synthesized from 4-(9-cyclohexyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and trans-4-aminocyclohexanol. The final compound was purified by reverse phase HPLC and basified to give the free base. $^1$H NMR (400 MHz, DMSO-d$_6$) δ ppm 1.12-1.69 (m, 12H) 1.83 (br. m., 6H) 3.34 (s, 3H) 3.72 (m, 1H) 3.94 (s, 3H) 4.06 (t, J=13.14 Hz, 2H) 4.45 (m, 1H) 4.59 (br s., 1H) 7.47 (d, J=8.0 Hz, 1H), 7.51 (br. s., 1H) 7.89 (s, 1H), 8.10 (br d., 1H) 8.21 (s, 1H) 8.25 (d, J=8.3 Hz, 1H). [M+H] calculated for C$_{28}$H$_{36}$F$_2$N$_6$O$_4$, 559. found 559.

Compound 41: (1R,4R)-4-(4-(9-cyclopentyl-7,7-difluoro-5-methyl-6-oxo-6,7,8,9-tetrahydro-5H-pyrimido[4,5-b][1,4]diazepin-2-ylamino)-3-methoxybenzamido)cyclohexyl dihydrogen phosphate

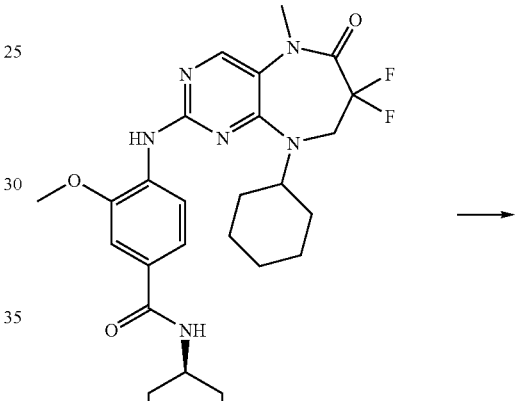

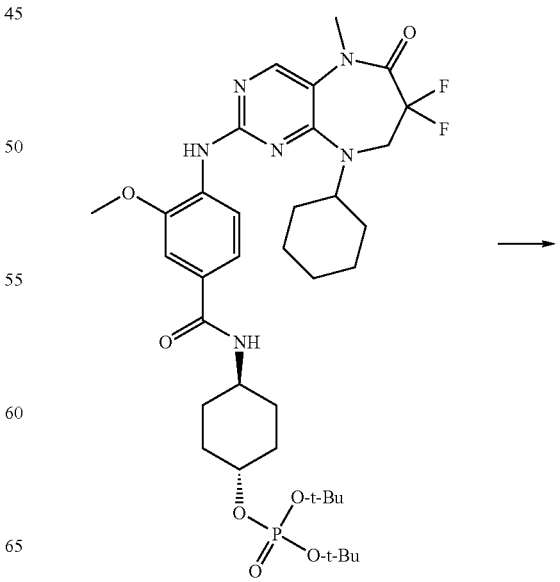

-continued

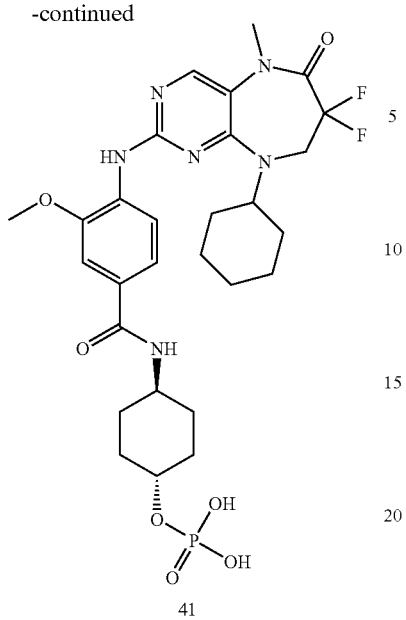

41

Di-tert-butyl (1R,4R)-4-(4-(9-cyclohexyl-7,7-difluoro-5-methyl-6-oxo-6,7,8,9-tetrahydro-5H-pyrimido[4,5-b][1,4]diazepin-2-ylamino)-3-methoxybenzamido) cyclohexyl phosphate: 4-(9-cyclohexyl-7,7-difluoro-5-methyl-6-oxo-6,7,8,9-tetrahydro-5H-pyrimido[4,5-b][1,4]diazepin-2-ylamino)-N-((1r,4r)-4-hydroxycyclohexyl)-3-methoxybenzamide (214 mg, 0.383 mmol) was suspended in DMA (4 mL) and treated with tetrazole (3% wt in water, 4.50 mL, 1.53 mmol) and di-tert-butyl diethylphosphoramidite (0.23 mL, 0.827 mmol). The reaction mixture was stirred at ambient temperature for 16 h, cooled to −10° C. and treated with hydrogen peroxide (30% aqueous, 0.3 mL). It was then stirred at room temperature for 16 h and another portion of hydrogen peroxide was added (30%, 0.3 mL) and stirred for 3 h. A solution of $Na_2S_2O_5$ (500 mg) in water (5 mL) was then added slowly at 0° C., the reaction mixture was stirred for 2 h and poured dropwise into a mixture of $NaHCO_3$ (sat. aq., 25 mL) and water (25 mL) with stirring. The resulting precipitate was stirred vigorously until a fine suspension resulted and the precipitate was filtered and purified by HPLC (acetonitrile-water, buffered with 10 mM $NH_4HCO_3$) to afford the title compound as a white solid (42.0 mg, 15%). [M+H] calc'd for $C_{36}H_{53}F_2N_6O_7P$, 751. found 751.5.

(1R,4R)-4-(4-(9-cyclohexyl-7,7-difluoro-5-methyl-6-oxo-6,7,8,9-tetrahydro-5H-pyrimido[4,5-b][1,4]diazepin-2-ylamino)-3-methoxybenzamido)cyclohexyl dihydrogen phosphate: Di-tert-butyl (1r,4r)-4-(4-(9-cyclohexyl-7,7-difluoro-5-methyl-6-oxo-6,7,8,9-tetrahydro-5H-pyrimido[4,5-b][1,4]diazepin-2-ylamino)-3-methoxybenzamido)cyclohexyl phosphate (42.0 mg, 0.0560 mmol) was dissolved in dichloromethane (1 mL) and methanol (0.2 mL) and treated with HCl (4N, dioxane, 1 mL). The reaction mixture was stirred for 4 h and concentrated in vacuo. The crude material was suspended in acetonitrile, stirred vigorously for 20 min and the resulting fine solid was filtered, and dried in vacuum to afford the title compound a white solid (23.0 mg, 64%). $^1$H NMR (400 MHz, DMSO-$d_6$) δ ppm 1.10-1.37 (m, 3H) 1.37-1.53 (m, 4H) 1.56-1.69 (m, 3H) 1.68-1.77 (m, 2H) 1.77-1.95 (m, 4H) 1.98-2.07 (m, 2H) 3.31 (s, 3H) 3.71-3.83 (m, 1H) 3.94 (s, 3H) 3.98-4.11 (m, 1H) 4.20 (t, J=12.88 Hz, 2H) 4.43-4.54 (m, 1H) 7.50 (dd, J=8.34, 1.77 Hz, 1H) 7.56 (d, J=1.52 Hz, 1H) 8.06 (d, J=8.34 Hz, 1H) 8.20 (d, J=7.58 Hz, 1H) 8.26 (s, 1H). [M+H] calc'd for $C_{28}H_{37}F_2N_6O_7P$, 639. found 639.

Compound 42: N-(azepan-4-yl)-4-(9-cyclohexyl-7,7-difluoro-5-methyl-6-oxo-6,7,8,9-tetrahydro-5H-pyrimido[4,5-b][1,4]diazepin-2-ylamino)-3-methoxybenzamide

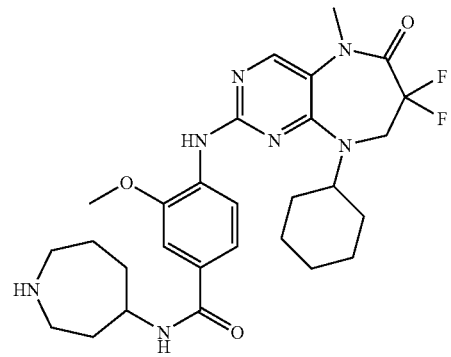

The title compound was synthesized from 4-(9-cyclohexyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and 1-N—Boc-hexahydro azepine 4-amine. The final compound was purified by reverse phase HPLC and basified to give the free base. Further, after washing with water (10 ml), t-butoxycarbonyl (Boc) protection group was removed using 40% TFA in dichloromethane (6 ml) and purified the product using preparative HPLC. $^1$H NMR (400 MHz, DMSO-$d_6$) δ ppm 1.10-2.05 (m, 16H) 2.88 (d, J=3.28 Hz, 1H) 3.01 (br. s., 2H) 3.31 (s, 3H) 3.34 (br. s., 1H) 3.94 (s, 3H) 4.06 (t, J=13.26 Hz, 3H) 4.46 (m, 1H) 7.47 (d, J=8.1 Hz, 1H) 7.50 (s, 1H) 7.91 (s, 1H) 8.21 (s, 1H) 8.23-8.30 (m, 2H). [M+H] calculated for $C_{28}H_{37}F_2N_7O_3$, 558. found 558.

Compound 43: N-(azetidin-3-yl)-4-(9-cyclohexyl-7,7-difluoro-5-methyl-6-oxo-6,7,8,9-tetrahydro-5H-pyrimido[4,5-b][1,4]diazepin-2-ylamino)-3-methoxybenzamide

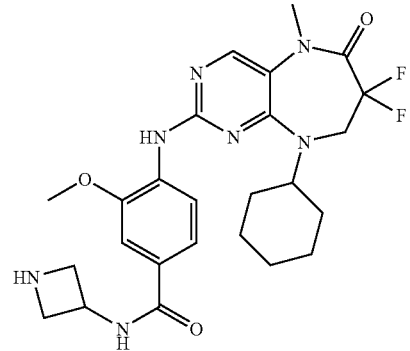

The title compound was synthesized from 4-(9-cyclohexyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and 1-N—Boc 3-amino azetidine. The final compound was purified by reverse phase HPLC and basified to give the free base. Further, after washing with water (10 ml), t-butoxycarbonyl (Boc) protection group was removed using 40% TFA in dichloromethane (6 ml) and purified the product using preparative HPLC. $^1$H NMR (400 MHz, DMSO-$d_6$) δ ppm 1.22-1.85 (m, 10H) 3.32 (s, 3H) 3.35-3.41 (m, 1H) 3.79 (br. s., 2H) 3.95 (s, 3H)

4.01-4.11 (m, 4H) 4.47 (m, 1H) 7.45-7.58 (m, 2H) 7.93 (s, 1H) 8.22 (s, 1H) 8.30 (d, J=8.1 Hz, 1H) 8.86 (br. d., 1H). [M+H] calculated for $C_{25}H_{31}F_2N_7O_3$, 516. found 516.

Compound 44: 4-(9-cyclohexyl-7,7-difluoro-5-methyl-6-oxo-6,7,8,9-tetrahydro-5H-pyrimido[4,5-b][1,4]diazepin-2-ylamino)-N-(1-(2-hydroxyethyl)piperidin-4-yl)-3-methoxybenzamide

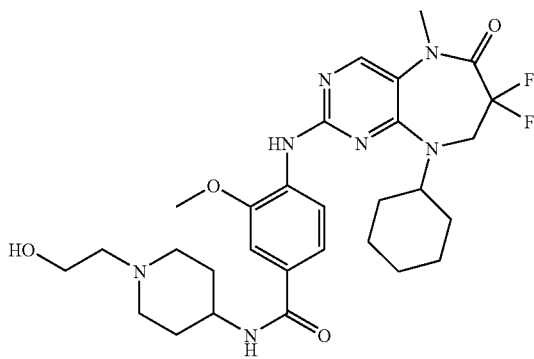

The title compound was synthesized from 4-(9-cyclohexyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and 2-(4-aminopiperidin-1-yl)ethanol. The final compound was purified by reverse phase HPLC and basified to give the free base. $^1$H NMR (400 MHz, DMSO-$d_6$) δ ppm 1.20 (m, 1H) 1.39 (m, 3H) 1.54-1.90 (m, 10H) 2.02 (t, J=10.99 Hz, 2H) 2.38 (t, J=6.32 Hz, 2H) 2.89 (d, J=10.86 Hz, 2H) 3.31 (s, 3H) 3.49 (br. s., 2H) 3.74 (m, 1H) 3.94 (s, 3H) 4.06 (t, J=13.39 Hz, 2H) 4.45 (m, 2H) 7.47 (d, J=8.0 Hz, 1H) 7.51 (s, 1H) 7.90 (s, 1H) 8.14 (d, J=8.0 Hz, 1H) 8.21 (s, 1H) 8.26 (d, J=8.0 Hz, 1H). [M+H] calculated for $C_{29}H_{39}F_2N_7O_4$, 588. found 588.

Compound 45: (R)-4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(quinuclidin-3-yl)benzamide

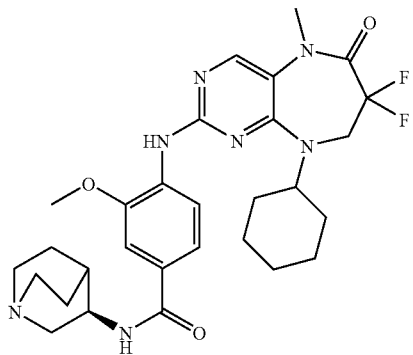

The title compound was synthesized from 4-(9-cyclohexyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and (R)-(+)-3-aminoquinuclidine. The final compound was purified by reverse phase HPLC and basified to give the free base. $^1$H NMR (400 MHz, DMSO-$d_6$) δ ppm 1.10-1.43 (m, 3H) 1.57-1.92 (m, 12H) 2.69 (d, J=6.57 Hz, 2H) 2.71 (m, 3H) 2.89 (m, 1H) 3.13 (m, 1H) 3.31 (s, 3H) 3.95 (s, 3H) 3.97-4.16 (m, 2H) 4.45 (m, 1H) 7.47 (d, J=8.0 Hz, 1H) 7.49 (s, 1H) 7.93 (s, 1H) 8.14 (d, 1H) 8.21 (s, 1H) 8.26 (d, J=8.0 Hz, 1H). [M+H] calculated for $C_{29}H_{37}F_2N_7O_3$, 570. found 570.

Compound 46: (S)-4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(quinuclidin-3-yl)benzamide

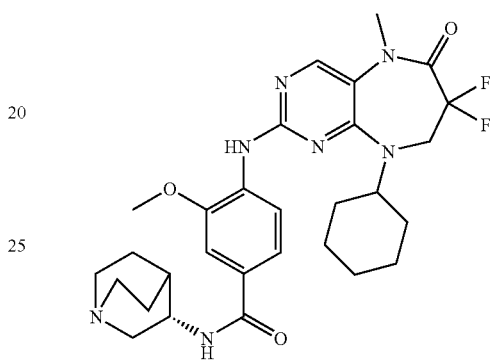

The title compound was synthesized from 4-(9-cyclohexyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and (S)-(−)-3-aminoquinuclidine. The final compound was purified by reverse phase HPLC and basified to give the free base. $^1$H NMR (400 MHz, DMSO-$d_6$) δ ppm 1.10-1.42 (m, 3H) 1.57-1.92 (m, 12H) 2.71-89 (m, 4H) 2.96 (m, 1H) 3.13 (m, 1H) 3.31 (s, 3H) 3.95 (s, 3H) 3.97-4.10 (m, 2H) 4.45 (m, 1H) 7.47 (d, J=8.0 Hz, 1H) 7.50 (s, 1H) 7.93 (s, 1H) 8.19 (d, 1H) 8.21 (s, 1H) 8.26 (d, J=8.0 Hz, 1H). [M+H] calculated for $C_{29}H_{37}F_2N_7O_3$, 570. found 570.

Compound 47: 4-(9-cyclohexyl-7,7-difluoro-5-methyl-6-oxo-6,7,8,9-tetrahydro-5H-pyrimido[4,5-b][1,4]diazepin-2-ylamino)-N-((cis)-2-hydroxycyclohexyl)-3-methoxybenzamide

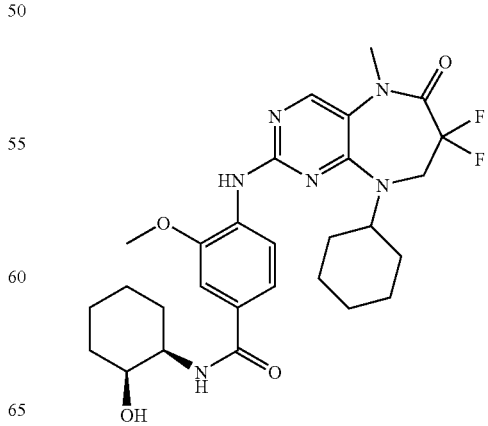

The title compound was synthesized from 4-(9-cyclohexyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and cis-(±)-2-aminocyclohexanol. The final compound was purified by reverse phase HPLC and basified to give the free base. $^1$H NMR (400 MHz, DMSO-$d_6$) δ ppm 1.13-1.93 (m, 18H) 3.31 (s, 3H) 3.73-3.91 (m, 2H) 3.95 (s, 3H) 4.06 (t, J=13.39 Hz, 2H) 4.47 (m, 1H) 4.70 (br. s., 1H) 7.47 (d, J=8.0 Hz, 1H) 7.53 (s, 1H) 7.79 (d, J=7.83 Hz, 1H) 7.90 (s, 1H) 8.21 (s, 1H) 8.27 (d, J=8.34 Hz, 1H). [M+H] calculated for $C_{28}H_{36}F_2N_6O_4$, 559. found 559.

Compound 48: 4-(9-cyclohexyl-7,7-difluoro-5-methyl-6-oxo-6,7,8,9-tetrahydro-5H-pyrimido[4,5-b][1,4]diazepin-2-ylamino)-N-((trans)-2-hydroxycyclohexyl)-3-methoxybenzamide

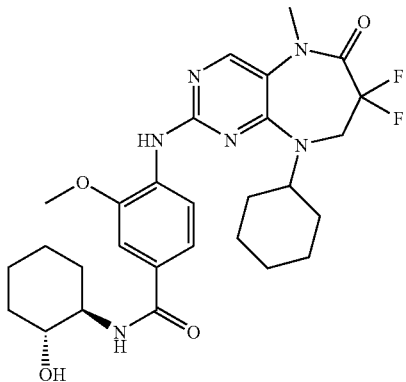

The title compound was synthesized from 4-(9-cyclohexyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and trans-(±)-2-aminocyclohexanol. The final compound was purified by reverse phase HPLC and basified to give the free base. $^1$H NMR (400 MHz, DMSO-$d_6$) δ ppm 1.11-1.93 (m, 18H) 3.32 (s, 1H) 3.45 (m, 1H) 3.64 (m, 1H) 3.95 (s, 3H) 4.07 (t, J=13.39 Hz, 2H) 4.48 (m, 1H) 4.64 (br. s., 1H) 7.49 (d, J=8.0 Hz, 1H) 7.55 (s, 1H) 7.90 (s, 1H) 8.03 (d, J=8.08 Hz, 1H) 8.22 (s, 1H) 8.28 (d, J=8.34 Hz, 1H). [M+H] calculated for $C_{28}H_{36}F_2N_6O_4$, 559. found 559.

Compound 49: 4-(9-cyclohexyl-7,7-difluoro-5-methyl-6-oxo-6,7,8,9-tetrahydro-5H-pyrimido[4,5-b][1,4]diazepin-2-ylamino)-N-(4-(dimethylamino)cyclohexyl)-3-methoxybenzamide

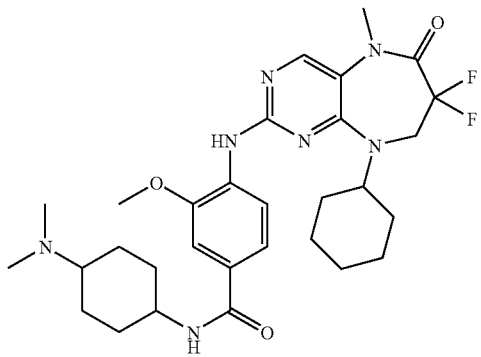

The title compound was synthesized from 4-(9-cyclohexyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and N1,N1-dimethylcyclohexane 1,4-diamine. The final compound was purified by reverse phase HPLC and basified to give the free base. $^1$H NMR (400 MHz, DMSO-$d_6$) δ ppm 1.11-1.96 (m, 18H) 2.17 (s, 6H) 3.31 (s, 3H) 3.73 (m, 1H) 3.92 9m, 1H) 3.94 (s, 3H) 4.06 (t, J=13.52 Hz, 2H) 4.46 (m, 1H) 7.42-7.59 (m, 2H) 7.89 (s, 1H) 8.11 (m, 1H) 8.21 (s, 1H) 8.26 (d, J=8.34 Hz, 1H). Melting point: 208-214° C. [M+H] calculated for $C_{30}H_{41}F_2N_7O_3$, 586. found 586.

Compound 50: 4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(1-(2,2,2-trifluoroethyl)piperidin-4-yl)benzamide

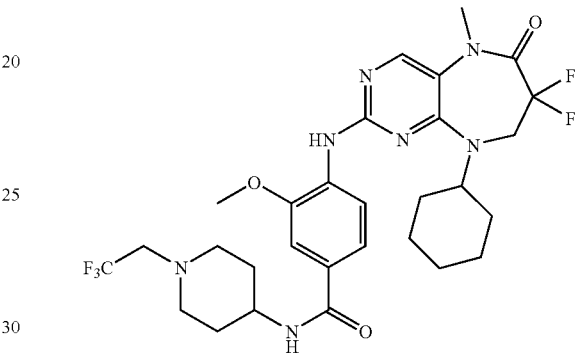

The title compound was synthesized from 4-(9-cyclohexyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and 1-N-(2,2,2-trifluoroethyl)piperidin-4-amine. The final compound was purified by reverse phase HPLC and basified to give the free base. $^1$H NMR (400 MHz, DMSO-$d_6$) δ ppm 1.15-1.44 (m, 4H) 1.55-1.89 (m, 10H) 2.42 (t, J=8.0 Hz, 2H) 2.94 (br. d., 2H) 3.17 (q, J=10.11 Hz, 2H) 3.31 (s, 3H) 3.78 (m, 1H) 3.94 (s, 3H) 4.06 (t, J=13.39 Hz, 2H) 7.47 (d, J=8.0 Hz, 1H) 7.50 (s, 1H) 7.91 (s, 1H) 8.15 (d, J=8.02 Hz, 1H) 8.21 (s, 1H) 8.27 (d, J=8.34 Hz, 1H). Melting point: 213-215° C. [M+H] calculated for $C_{29}H_{36}F_5N_7O_3$, 626. found 626.

Compound 51: 4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(8-methyl-8-azabicyclo[3.2.1]octan-3-yl)benzamide

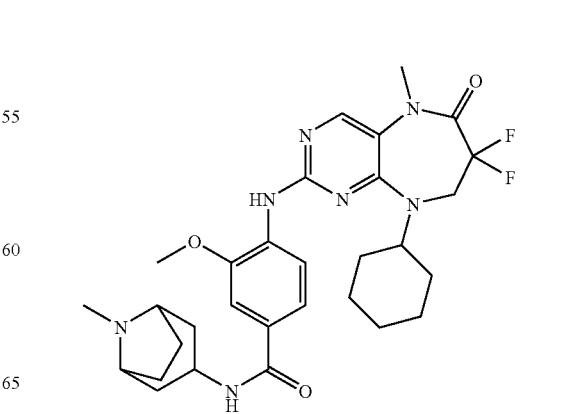

The title compound was synthesized from 4-(9-cyclohexyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and 8-methyl-8-azabicyclo[3.2.1]octan-3-amine dihydrochloride. The final compound was purified by reverse phase HPLC and basified to give the free base. $^1$H NMR (400 MHz, DMSO-$d_6$) δ ppm 1.13-1.45 (m, 4H) 1.37-1.85 (m, 12H) 1.99 (s, 2H) 2.29 (br. s., 2H) 3.31 (s, 3H) 3.93 (s, 3H) 3.97-4.22 (m, 3H) 4.45 (m, 1H) 7.47 (d, J=8.0 Hz, 1H) 7.49 (s, 1H) 7.90 (s, 1H) 8.15 (d, 1H) 8.20 (s, 1H) 8.25 (d, J=8.34 Hz, 1H). [M+H] calculated for $C_{30}H_{39}F_2N_7O_3$, 584. found 584.

Compound 52: 4-(9-cyclohexyl-7,7-difluoro-5-methyl-6-oxo-6,7,8,9-tetrahydro-5H-pyrimido[4,5-b][1,4]diazepin-2-ylamino)-N-(4-cyclopentylpiperazin-1-yl)-3-methoxybenzamide

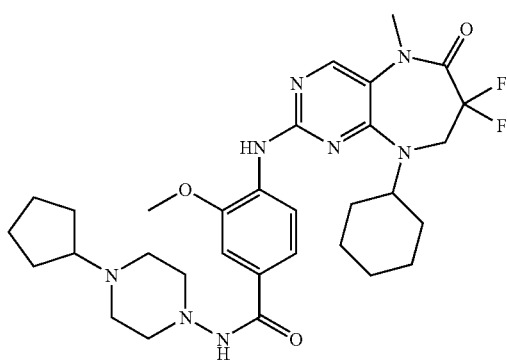

The title compound was synthesized from 4-(9-cyclohexyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and 1-N-cyclopentyl piperazine-4-amine. The final compound was purified by reverse phase HPLC and basified to give the free base. $^1$H NMR (400 MHz, DMSO-$d_6$) δ ppm 1.11-1.92 (m, 18H) 2.93 (br. s., 4H) 3.31 (s, 3H) 3.93 (s, 3H) 4.06 (t, J=13.39 Hz, 2H) 4.44 (m, 1H) 7.41 (d, J=8.0 Hz, 1H) 7.43 (s, 1H) 7.90 (s, 1H) 8.21 (s, 1H) 8.27 (d, J=8.34 Hz, 1H) 9.37 (s, 1H). Melting point: 98-99° C. [M+H] calculated for $C_{31}H_{42}F_2N_8O_3$, 613. found 613.

Compound 53: 4-(9-cyclohexyl-7,7-difluoro-5-methyl-6-oxo-6,7,8,9-tetrahydro-5H-pyrimido[4,5-b][1,4]diazepin-2-ylamino)-N-(2-(dimethylamino)ethyl)-3-methoxybenzamide

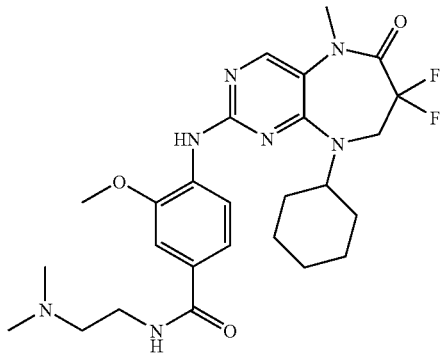

The title compound was synthesized from 4-(9-cyclohexyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and N,N-dimethylethylenediamine. The final compound was purified by reverse phase HPLC and basified to give the free base. $^1$H NMR (400 MHz, DMSO-$d_6$) δ ppm 1.13-1.27 (m, 2H) 1.27-1.51 (m, 2H) 1.51-1.86 (m, 6H) 2.17 (s, 6H) 2.39 (t, J=7.8 Hz, 2H) 3.31 (s, 3H) 3.38 (m, 2H) 3.93 (s, 3H) 4.06 (t, J=13.39 Hz, 2H) 4.46 (m, 1H) 7.48 (d, J=8.0 Hz, 1H) 7.52 (s, 1H) 7.91 (s, 1H) 8.21 (s, 1H) 8.28 (d, J=8.34 Hz, 1H) 8.35 (br. s., 1H). [M+H] calculated for $C_{26}H_{35}F_2N_7O_3$, 532. found 532.

Compound 54: 4-(9-cyclohexyl-7,7-difluoro-5-methyl-6-oxo-6,7,8,9-tetrahydro-5H-pyrimido[4,5-b][1,4]diazepin-2-ylamino)-N-(3-(dimethylamino)propyl)-3-methoxybenzamide

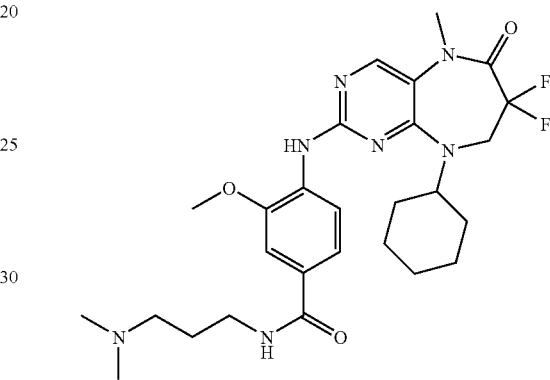

The title compound was synthesized from 4-(9-cyclohexyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and N,N-dimethyl-1,3-propanediamine. The final compound was purified by reverse phase HPLC and basified to give the free base. $^1$H NMR (400 MHz, DMSO-$d_6$) δ ppm 1.14-1.49 (m, 3H) 1.53-1.87 (m., 9H) 2.13 (s, 6H) 2.25 (t, J=6.44 Hz, 2H) 3.29 (m, 2H) 3.31 (s, 3H) 3.93 (s, 3H) 4.06 (t, J=13.26 Hz, 2H) 4.46 (m, 1H) 7.46 (d, J=8.0 Hz, 1H) 7.51 (s, 1H) 7.90 (s, 1H) 8.21 (s, 1H) 8.27 (d, J=8.08 Hz, 1H) 8.48 (br. s., 1H). [M+H] calculated for $C_{27}H_{37}F_2N_7O_3$, 546. found 546.

Compound 55: N-(azetidin-3-yl)-4-(9-cyclohexyl-7,7-difluoro-5-methyl-6-oxo-6,7,8,9-tetrahydro-5H-pyrimido[4,5-b][1,4]diazepin-2-ylamino)-3-methoxybenzamide

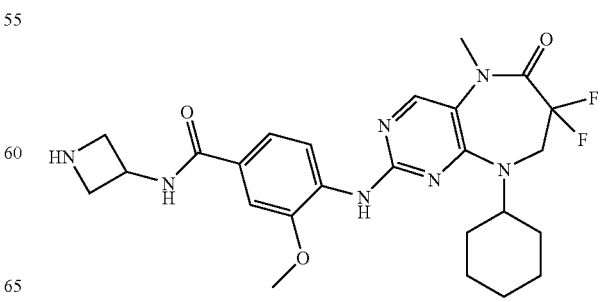

The title compound was synthesized from 4-(9-cyclohexyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and 1-N—Boc 3-amino azetidine. The final compound was purified by reverse phase HPLC and basified to give the free base. Further, after washing with water (10 ml), t-butoxycarbonyl (Boc) protection group was removed using 40% TFA in dichloromethane (6 ml) and the final compound was purified by reverse phase HPLC and basified to give the free base. $^1$H NMR (400 MHz, DMSO-$d_6$) δ ppm 1.13-1.28 (m, 1H) 1.33-1.46 (m, 2H) 1.59-1.66 (m, 2H) 1.75-1.87 (m, 4H) 3.32 (s, 3H) 3.67-3.80 (m, 4H) 3.95 (s, 3H) 4.07 (t, 2H) 4.4-4.5 (m, 1H) 4.65-4.83 (m, 1H) 7.50 (d, J=8.3 Hz, 1H) 7.54 (d, J=1.5 Hz, 1H) 7.93 (s, 1H) 8.21 (s, 1H) 8.29 (d, J=8.1 Hz, 1H) 8.81 (d, J=6.8 Hz, 1H). [M+H] calc'd for $C_{25}H_{31}F_2N_7O_3$ 516. found 516.

Compound 56: 4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(2-(pyrrolidin-1-yl)ethyl)benzamide

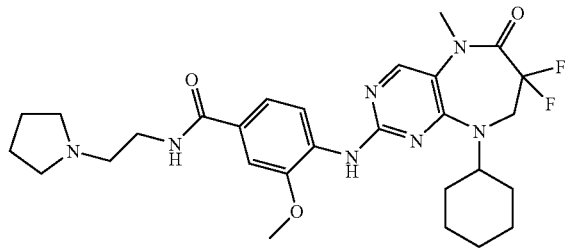

The title compound was synthesized from 4-(9-cyclohexyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and 2-(pyrrolidin-1-yl)ethanamine. The final compound was purified by reverse phase HPLC and basified to give the free base. $^1$H NMR (400 MHz, DMSO-$d_6$) δ ppm 1.22 (m, 1H) 1.38 (m, 2H) 1.65 (t, J=13.1 Hz, 3H) 1.79-1.92 (m, 6H) 2.03 (m, 2H) 3.08 (m, 2H) 3.33 (s, 3H) 3.35 (d, J=5.8 Hz, 2H) 3.61 (m, 4H) 3.96 (s, 3H) 4.12 (t, J=13.0 Hz, 2H) 4.40-4.58 (m, 1H) 7.53 (d, J=8.6 Hz, 1H) 7.56 (s, 1H) 8.22 (s, 1H) 8.24 (d, J=1.3 Hz, 1H) 8.29 (d, J=7.8 Hz, 1H) 8.7 (dd, J=10.1, 1.3 Hz, 1H). [M+H] calc'd for $C_{28}H_{37}F_2N_7O_3$ 558. found 558.

Compound 57: 9-cyclohexyl-7,7-difluoro-2-(2-methoxy-4-(4-methylpiperazine-1-carbonyl)-phenylamino)-5-methyl-8,9-dihydro-5H-pyrimido[4,5-b][1,4]diazepin-6(7H)-one

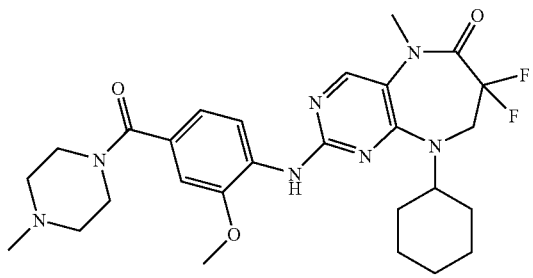

The title compound was synthesized from 4-(9-cyclohexyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and N-methylpiperazine. The final compound was purified by reverse phase HPLC and basified to give the free base. $^1$H NMR (400 MHz, DMSO-$d_6$) δ ppm 1.27-1.35 (m, 2H) 1.54-1.67 (m, 3H) 1.72-1.84 (m, 5H) 2.83 (s, 3H) 3.31 (d, J=3.2 Hz, 3H) 3.91 (d, J=4.6 Hz, 3H) 3.95-4.33 (m, 10H) 4.39-4.54 (m, 1H) 7.06 (dd, J=8.1, 2.0 Hz, 1H) 7.13 (d, J=110 Hz, 1H) 8.10-8.18 (m, 1H) 8.22 (d, J=3.0 Hz, 1H). [M+H] calc'd for $C_{27}H_{35}F_2N_7O_3$ 544. found 544.

Compound 58: 4-(9-cyclohexyl-7,7-difluoro-5-methyl-6-oxo-6,7,8,9-tetrahydro-5H-pyrimido[4,5-b][1,4]diazepin-2-ylamino)-3-methoxybenzamide

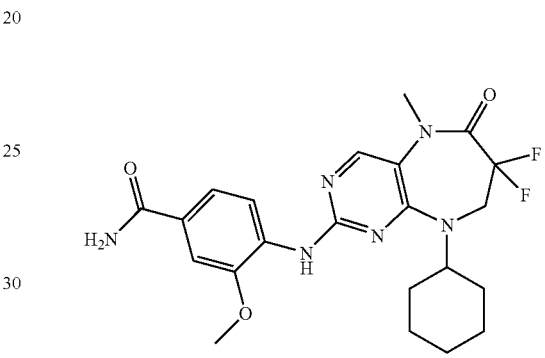

The title compound was synthesized from 4-(9-cyclohexyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and ammonium chloride. The final compound was purified by reverse phase HPLC and basified to give the free base. $^1$H NMR (400 MHz, DMSO-$d_6$) δ ppm 1.10-1.41 (m, 3H) 1.54-1.86 (m, 7H) 3.32 (s, 3H) 3.93 (s, 3H) 4.17 (t, J=12.5 Hz, 2H) 4.44-4.55 (m, 1H) 7.33 (s, 1H) 7.55 (d, J=8.3 Hz, 1H) 7.59 (s, 1H) 7.99 (s, 1H) 8.13 (d, J=8.1 Hz, 1H) 8.24 (s, 1H) 8.61 (s, 1H). [M+H] calc'd for $C_{22}H_{26}F_2N_6O_3$ 461. found 461.

Compound 59: 4-(9-cyclohexyl-7,7-difluoro-5-methyl-6-oxo-6,7,8,9-tetrahydro-5H-pyrimido[4,5-b][1,4]diazepin-2-ylamino)-N-(3-(dimethylamino)propyl)-3-methoxybenzamide

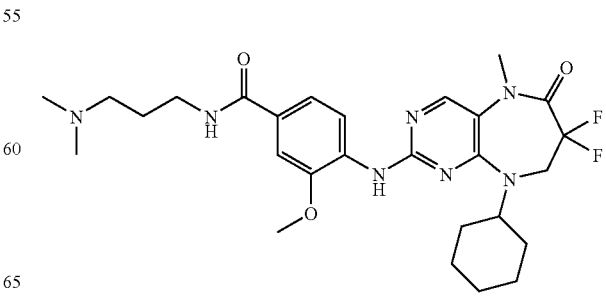

The title compound was synthesized from 4-(9-cyclohexyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and N,N-dimethyl-1,3-propanediamine. The final compound was purified by reverse phase HPLC and basified to give the free base. $^1$H NMR (400 MHz, DMSO-$d_6$) δ ppm 1.16-1.30 (m, 2H) 1.43-1.57 (m, 3H) 1.58-1.80 (m, 2H) 2.67 (m, 6H) 2.91-3.01 (m, 2H) 3.20 (br.s., 3H) 3.22 (m, 2H) 3.82 (s, 3H) 4.02 (t, J=13.0 Hz, 2H) 4.36 (quin., 1H) 7.39 (d, J=6.1 Hz, 1H) 7.43 (br. s., 1H) 8.09 (d, J=8.8 Hz, 1H) 8.10-8.13 (m, 1H) 8.31 (br. s., 1H) 8.50 (br. s., 1H). [M+H] calc'd for $C_{27}H_{37}F_2N_7O_3$ 546. found 546.

Compound 60: 4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-methylbenzamide

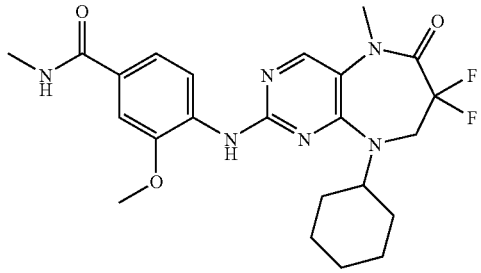

The title compound was synthesized from 4-(9-cyclohexyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and methylamine. The final compound was purified by reverse phase HPLC and basified to give the free base. $^1$H NMR (400 MHz, DMSO-$d_6$) δ ppm 1.13-1.42 (m, 2H) 1.52-1.91 (m, 8H) 2.80 (d, 3H) 3.94 (s, 3H) 4.16 (t, 2H) 4.49 (quin, 1H) 7.50 (d, 1H) 7.55 (s, 1H) 8.14 (d, J=8.1 Hz, 1H) 8.24 (d, J=2.0 Hz, 1H) 8.42 (d, J=4.3 Hz, 1H) 8.58 (br. s., 1H). [M+H] calc'd for $C_{23}H_{28}F_2N_6O_3$ 475. found 475.

Compound 61: 4-(9-cyclohexyl-7,7-difluoro-5-methyl-6-oxo-6,7,8,9-tetrahydro-5H-pyrimido[4,5-b][1,4]diazepin-2-ylamino)-3-methoxy-N',N'-dimethylbenzohydrazide

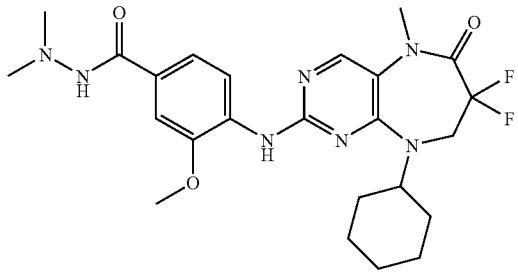

The title compound was synthesized from 4-(9-cyclohexyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and N,N-dimethyl-hydrazine. The final compound was purified by reverse phase HPLC and basified to give the free base. $^1$H NMR (400 MHz, DMSO-$d_6$) δ ppm 1.15-1.43 (m, 2H) 1.53-1.92 (m, 8H) 2.92 (s, 6H) 3.32 (s, 3H) 3.96 (s, 3H) 4.14 (t, J=13.0 Hz, 2H) 4.42-4.52 (m, 1H) 7.44-7.52 (m, 2H) 8.20-8.27 (m, 2H) 8.49 (br. s., 1H). [M+H] calc'd for $C_{24}H_{31}F_2N_7O_3$ 504. found 504.

Compound 62: (R)-4-(9-cyclohexyl-7,7-difluoro-5-methyl-6-oxo-6,7,8,9-tetrahydro-5H-pyrimido[4,5-b][1,4]diazepin-2-ylamino)-N-(2-hydroxypropyl)-3-methoxybenzamide

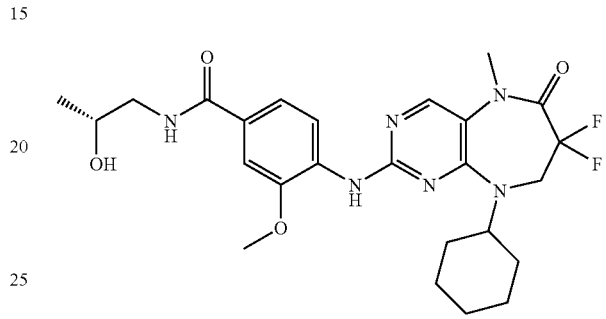

The title compound was synthesized from 4-(9-cyclohexyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and (S)-1-aminopropan-2-ol. The final compound was purified by reverse phase HPLC and basified to give the free base. $^1$H NMR (400 MHz, DMSO-$d_6$) δ ppm 1.07 (d, J=6.1 Hz, 3H) 1.12-1.41 (m, 3H) 1.55-1.87 (m, 8H) 1.70-1.88 (m, 4H) 3.21 (q, J=6.3 Hz, 1H) 3.32 (s, 3H) 3.77 (m, 1H) 3.94 (s, 3H) 4.16 (t, J=13.0 Hz, 2H) 4.49 (quin., J=12.1 Hz, 1H) 7.53 (d, J=8.6 Hz, 1H) 7.58 (s, 1H) 8.14 (d, J=8.3 Hz, 1H) 8.23 (s, 1H) 8.41-8.47 (m, 1H) 8.51-8.57 (m, 1H). [M+H] calc'd for $C_{25}H_{32}F_2N_6O_4$ 519. found 519.

Compound 63: (S)-4-(9-cyclohexyl-7,7-difluoro-5-methyl-6-oxo-6,7,8,9-tetrahydro-5H-pyrimido[4,5-b][1,4]diazepin-2-ylamino)-N-(2-hydroxypropyl)-3-methoxybenzamide

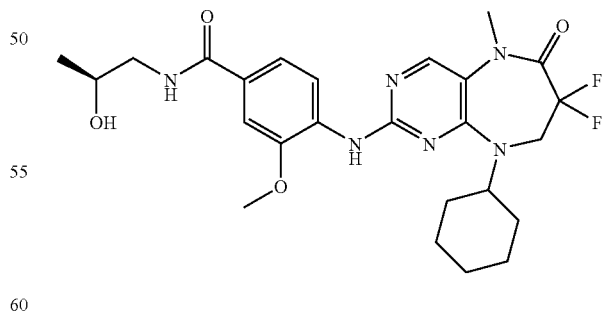

The title compound was synthesized from 4-(9-cyclohexyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and (R)-1-aminopropan-2-ol. The final compound was purified by reverse phase HPLC and basified to give the free base. $^1$H NMR (400 MHz, DMSO-$d_6$)

δ ppm 1.07 (d, J=6.1 Hz, 3H) 1.12-1.41 (m, 3H) 1.55-1.87 (m, 8H) 1.70-1.88 (m, 4H) 3.21 (q, J=6.3 Hz, 1H) 3.32 (s, 3H) 3.77 (m, 1H) 3.94 (s, 3H) 4.16 (t, J=13.0 Hz, 2H) 4.49 (quin., J=12.1 Hz, 1H) 7.53 (d, J=8.6 Hz, 1H) 7.58 (s, 1H) 8.14 (d, J=8.3 Hz, 1H) 8.23 (s, 1H) 8.41-8.47 (m, 1H) 8.51-8.57 (m, 1H). [M+H] calc'd for $C_{25}H_{32}F_2N_6O_4$ 519. found 519.

Compound 64: 4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(piperidin-1-yl)benzamide

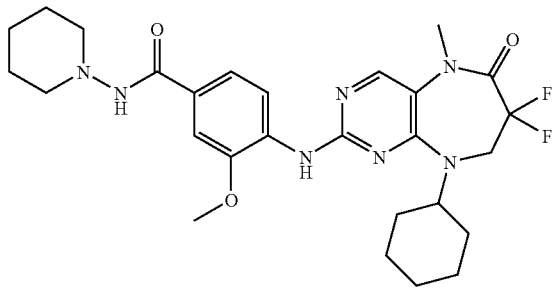

The title compound was synthesized from 4-(9-cyclohexyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and piperidin-1-amine. The final compound was purified by reverse phase HPLC and basified to give the free base. $^1$H NMR (400 MHz, DMSO-d$_6$) δ ppm 1.15-1.90 (m, 16H) 3.16 (br. s., 6H) 3.32 (s, 3H) 3.96 (s, 3H) 4.14 (t, 2H) 4.48 (quin, 1H) 7.47 (d, 1H) 7.49 (s, 1H) 8.22 (d, 1H) 8.24 (s, 1H) 8.47 (br. s., 1H). [M+H] calc'd for $C_{27}H_{35}F_2N_7O_3$ 544. found 544.

Compound 65: 4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-morpholinobenzamide

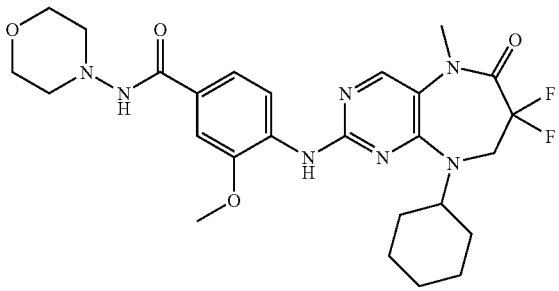

The title compound was synthesized from 4-(9-cyclohexyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and morpholin-4-amine. The final compound was purified by reverse phase HPLC and basified to give the free base. $^1$H NMR (400 MHz, DMSO-d$_6$) δ ppm 1.12-1.41 (m, 2H) 1.59-1.86 (m, 8H) 2.94 (br. s., 4H) 3.31 (s, 3H) 3.67 (br. s., 4H) 3.94 (s, 3H) 4.16 (t, 2H) 4.38- 4.54 (m, 1H) 7.45 (d, J=8.7 Hz, 1H) 7.48 (s, 1H) 8.14 (d, 1H) 8.23 (s, 1H) 8.57 (br. s., 1H) 9.57 (s, 1H). [M+H] calc'd for $C_{26}H_{33}F_2N_7O_4$ 546. found 546.

Compound 66: 4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(tetrahydro-2H-pyran-4-yl)benzamide

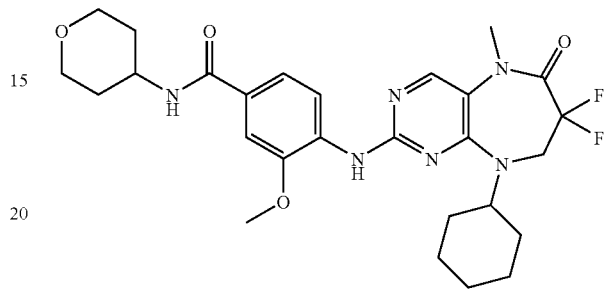

The title compound was synthesized from 4-(9-cyclohexyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and tetrahydro-2H-pyran-4-amine. The final compound was purified by reverse phase HPLC and basified to give the free base. $^1$H NMR (400 MHz, DMSO-d$_6$) δ ppm 1.08-1.43 (m, 3H) 1.49-1.90 (m, 11H) 3.19-3.32 (m, 3H) 3.32-3.46 (m, 2H) 3.84-3.92 (m, 2H) 3.94 (d, J=9.0 Hz, 3H) 3.97-4.08 (m, 1H) 4.07-4.23 (m, 2H) 4.38-4.58 (m, 1H) 7.42-7.61 (m, 2H) 8.06-8.17 (m, 1H) 8.24 (br. s., 2H) 8.62 (br. s., 1H). [M+H] calc'd for $C_{27}H_{34}F_2N_6O_4$ 545. found 545.

Compound 67: 4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(pyrrolidin-1-yl)benzamide

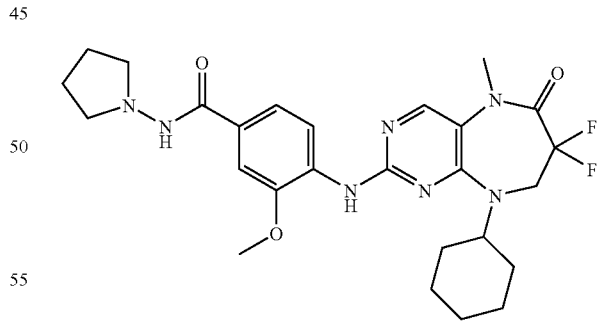

The title compound was synthesized from 4-(9-cyclohexyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and pyrrolidin-1-amine. The final compound was purified by reverse phase HPLC and basified to give the free base. $^1$H NMR (400 MHz, DMSO-d$_6$) δ ppm 1.12-1.45 (m, 3H) 1.55-1.90 (m, 7H) 2.02 (br. s., 4H) 3.33 (s, 3H) 3.52 (br. s., 4H) 3.97 (s, 3H) 4.14 (t, 2H) 4.49

(quin, 1H) 7.48 (d, 1H) 7.52 (s, 1H) 8.26 (s, 1H) 8.31 (d, 1H) 8.42 (s, 1H). [M+H] calc'd for $C_{26}H_{33}F_2N_7O_3$ 530. found 530.

Compound 68: 4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(1-(methylsulfonyl)piperidin-4-yl)benzamide

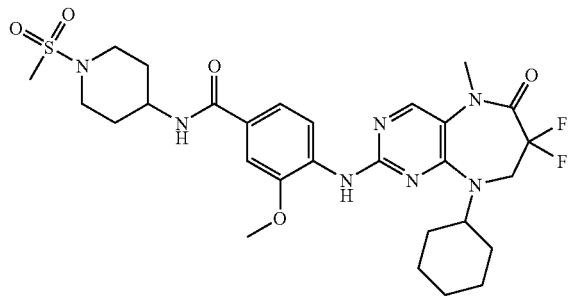

The title compound was synthesized from 4-(9-cyclohexyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and 1-(methylsulfonyl)piperidin-4-amine. The final compound was purified by reverse phase HPLC and basified to give the free base. $^1$H NMR (400 MHz, DMSO-$d_6$) δ ppm 1.03-1.35 (m, 3H) 1.47-1.90 (m, 11H) 2.75-2.80 (m, 1H) 2.82 (s, 3H) 3.25 (s, 3H) 3.79-3.86 (m, 1H) 3.88 (s, 3H) 4.08 (t, 1H) 4.36-4.47 (m, 1H) 7.43 (dd, J=8.6, 1.77 Hz, 1H) 7.47 (d, J=1.8 Hz, 1H) 8.09 (d, J=8.3 Hz, 1H) 8.16 (s, 1H) 8.22 (d, 1H) 8.41 (br. s., 1H). [M+H] calc'd for $C_{28}H_{37}F_2N_7O_5S$ 622. found 622

Compound 69: N-(1-acetylazetidin-3-yl)-4-(9-cyclohexyl-7,7-difluoro-5-methyl-6-oxo-6,7,8,9-tetrahydro-5H-pyrimido[4,5-b][1,4]diazepin-2-ylamino)-3-methoxybenzamide

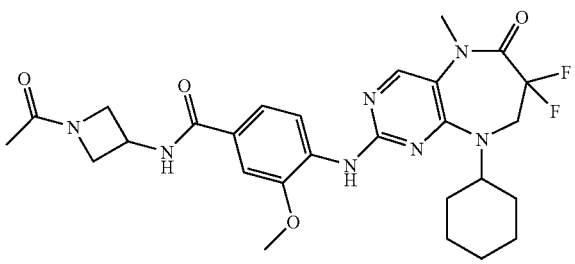

The title compound was synthesized from 4-(9-cyclohexyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and 1-(3-aminoazetidin-1-yl)ethanone. The final compound was purified by reverse phase HPLC and basified to give the free base. $^1$H NMR (400 MHz, DMSO-$d_6$) δ ppm 1.20 (t, J=12.4 Hz, 1H) 1.34-1.45 (bq, 2H) 1.57-1.68 (m, 3H) 1.78 (s, 3H) 1.84 (m, 3H) 3.32 (s, 3H) 3.88 (m, 1H) 3.95 (s, 3H) 4.03-4.12 (m, 4H) 4.42 (t, J=8.2 Hz, 1H) 4.45-4.51 (m, 1H) 4.68 (q, J=6.8 Hz, 3H) 7.51 (dd, J=8.3, 1.8 Hz, 1H) 7.54 (d, J=1.5 Hz, 1H) 7.93 (s, 1H) 8.22 (s, 1H) 8.30 (d, J=8.3 Hz, 1H) 8.89 (d, J=6.8 Hz, 1H). [M+H] calc'd for $C_{27}H_{33}F_2N_7O_4$ 558. found 558.

Compound 70: 4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(piperidin-4-yl)benzamide

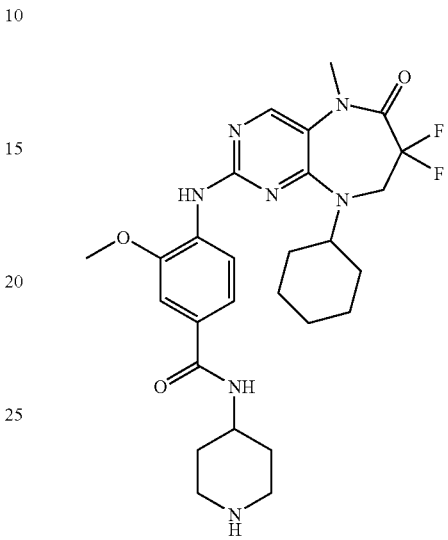

The title compound was synthesized from 4-(9-cyclohexyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and 1-N—Boc 4-amino piperidine. Further, after washing with water (10 ml), t-butoxycarbonyl (Boc) protection group was removed using 40% TFA in dichloromethane (6 ml). The final compound was purified by reverse phase HPLC and basified to give the free base. $^1$H NMR (400 MHz, DMSO-$d_6$) δ ppm 1.11-1.27 (m, 1H) 1.30-1.51 (m, 4H) 1.52-1.69 (m, 3H) 1.69-1.90 (m, 6H) 2.41-2.59 (m, 2H) 2.97 (d, J=12.38 Hz, 2H) 3.31 (s, 3H) 3.73-3.89 (m, 1H) 3.94 (s, 3H) 4.06 (t, J=13.52 Hz, 2H) 4.38-4.52 (m, 1H) 7.48 (dd, J=8.34, 1.77 Hz, 1H) 7.51 (d, J=1.77 Hz, 1H) 7.90 (s, 1H) 8.14 (d, J=7.83 Hz, 1H) 8.21 (s, 1H) 8.26 (d, J=8.34 Hz, 1H). [M+H] calc'd for $C_{27}H_{35}F_2N_7O_3$ 544. found 544.

Compound 71: 4-(9-cyclohexyl-7,7-difluoro-5-methyl-6-oxo-6,7,8,9-tetrahydro-5H-pyrimido[4,5-b][1,4]diazepin-2-ylamino)-N-(1-(2-(dimethylamino)acetyl)piperidin-4-yl)-3-methoxybenzamide

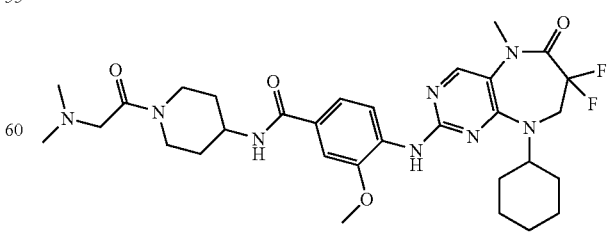

The title compound was synthesized from 4-(9-cyclohexyl-7,7-difluoro-5-methyl-6-oxo-6,7,8,9-tetrahydro-5H- pyrimido[4,5-b][1,4]diazepin-2-ylamino)-3-methoxy-N-(piperidin-4-yl)benzamide and 2-(dimethylamino)acetyl chloride. The final compound was purified by reverse phase HPLC and basified to give the free base. $^1$H NMR (400 MHz, DMSO-d$_6$) δ ppm 1.14-1.25 (m, 1H) 1.33-1.46 (m, 3H) 1.48-1.65 (m, 3H) 1.72-1.90 (m, 6H) 2.35 (s, 6H) 2.72 (t, J=12.2 Hz, 1H) 2.72 (t, 1H) 3.10 (t, J=11.8 Hz, 1H) 3.31 (s, 3H) 3.47 (d, 1H) 3.94 (s, 3H) 4.06 (t, J=13.5 Hz, 2H) 3.97-4.12 (m, 2H) 4.35 (d, 1H) 4.46 (br. s., 1H) 7.47 (dd, J=8.4, 1.6 Hz, 1H) 7.50 (d, J=1.7 Hz, 1H) 7.91 (s, 1H) 8.19 (d, J=8.1 Hz, 1H) 8.21 (s, 1H) 8.27 (d, J=8.3 Hz, 1H). Melting point: 190-191° C. [M+H] calc'd for C$_{31}$H$_{42}$F$_2$N$_8$O$_4$ 629. found 629.

Compound 72: (S)-4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(pyrrolidin-3-yl)benzamide

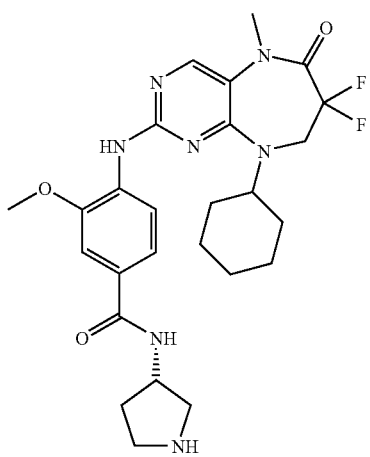

The title compound was synthesized from 4-(9-cyclohexyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and (S)-1-N—Boc 3-amino pyrrolidine. The final compound was purified by reverse phase HPLC and basified to give the free base. Further, after washing with water (10 ml), t-butoxycarbonyl (Boc) protection group was removed using 40% TFA in dichloromethane (6 ml). The final compound was purified by reverse phase HPLC and basified to give the free base. $^1$H NMR (400 MHz, DMSO-d$_6$) δ ppm 1.09-1.28 (m, 1H) 1.30-1.47 (m, 2H) 1.51-1.72 (m, 4H) 1.73-1.88 (m, 4H) 1.90-2.06 (m, 1H) 2.64 (dd, J=11.24, 4.93 Hz, 1H) 2.75 (ddd, J=10.67, 7.89, 6.44 Hz, 1H) 2.82-3.03 (m, 2H) 3.31 (s, 3H) 3.94 (s, 3H) 4.06 (t, J=13.52 Hz, 2H) 4.23-4.37 (m, 1H) 4.39-4.53 (m, 1H) 7.44-7.50 (m, 1H) 7.51 (d, J=1.52 Hz, 1H) 7.90 (s, 1H) 8.21 (s, 1H) 8.23 (d, J=7.07 Hz, 1H) 8.26 (d, J=8.34 Hz, 1H). Melting point: 258-263° C. [M+H] calc'd for C$_{26}$H$_{33}$F$_2$N$_7$O$_3$ 530. found 530.

Compound 73: (R)-4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(pyrrolidin-3-yl)benzamide

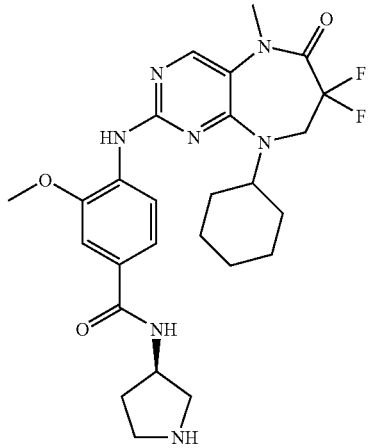

The title compound was synthesized from 4-(9-cyclohexyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and (R)-1-N—Boc 3-amino pyrrolidine. The final compound was purified by reverse phase HPLC and basified to give the free base. Further, after washing with water (10 ml), t-butoxycarbonyl (Boc) protection group was removed using 40% TFA in dichloromethane (6 ml). The final compound was purified by reverse phase HPLC and basified to give the free base. $^1$H NMR (400 MHz, DMSO-d$_6$) δ ppm 1.11-1.27 (m, 1H) 1.28-1.47 (m, 2H) 1.52-1.71 (m, 4H) 1.71-1.89 (m, 4H) 1.89-2.04 (m, 1H) 2.64 (dd, J=11.12, 5.05 Hz, 1H) 2.75 (ddd, J=10.74, 7.96, 6.32 Hz, 1H) 2.83-3.03 (m, 2H) 3.31 (s, 3H) 3.94 (s, 3H) 4.06 (t, J=13.52 Hz, 2H) 4.22-4.36 (m, 1H) 4.38-4.54 (m, 1H) 7.47 (dd, J=8.46, 1.64 Hz, 1H) 7.51 (d, J=1.52 Hz, 1H) 7.90 (s, 1H) 8.21 (s, 1H) 8.23 (d, J=7.07 Hz, 1H) 8.26 (d, J=8.34 Hz, 1H). Melting point: 195-198° C. [M+H] calc'd for C$_{26}$H$_{33}$F$_2$N$_7$O$_3$ 530. found 530.

Compound 74: (S)-4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-3-yl)benzamide

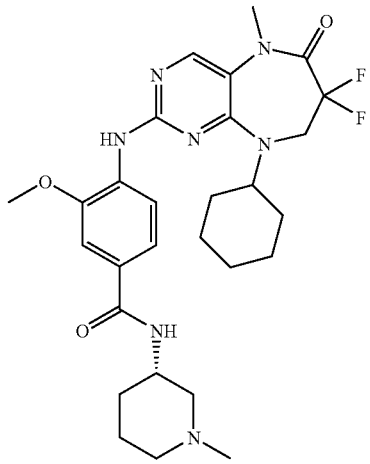

The title compound was synthesized from 4-(9-cyclohexyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and (S)-1-methylpiperidin-3-amine. The final compound was purified by reverse phase HPLC and basified to give the free base. $^1$H NMR (400 MHz, DMSO-d$_6$) δ ppm 1.17-1.26 (m, 2H) 1.29-1.46 (m, 3H) 1.55-1.73 (m, 5H) 1.75-1.90 (m, 6H) 2.23 (br s, 3H) 2.64-2.78 (m, 1H) 2.79-2.95 (m, 1H) 3.31 (s, 3H) 3.90-4.01 (m, 1H) 3.94 (s, 3H) 4.07 (t, J=12.63 Hz, 2H) 4.37-4.53 (m, 1H) 7.47 (dd, J=8.46, 1.64 Hz, 1H) 7.51 (d, J=1.77 Hz, 1H) 7.91 (s, 1H) 8.10 (d, J=7.33 Hz, 1H) 8.21 (s, 1H) 8.27 (d, J=8.34 Hz, 1H). [M+H] calc'd for C$_{28}$H$_{37}$F$_2$N$_7$O$_3$ 558. found 558.

Compound 75: (R)-4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-3-yl)benzamide

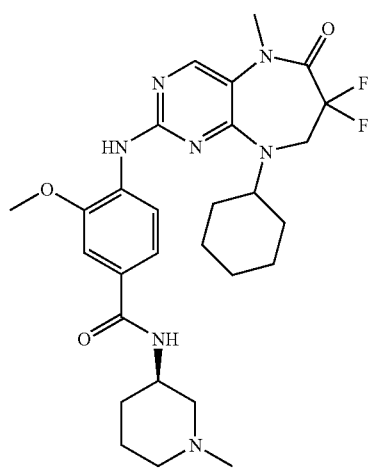

The title compound was synthesized from 4-(9-cyclohexyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and (R)-1-methylpiperidin-3-amine. The final compound was purified by reverse phase HPLC and basified to give the free base. $^1$H NMR (400 MHz, DMSO-d$_6$) δ ppm 1.15-1.26 (m, 2H) 1.29-1.46 (m, 3H) 1.55-1.73 (m, 5H) 1.75-1.90 (m, 6H) 2.17 (s, 3H) 2.63-2.69 (m, 1H) 2.78-2.84 (m, 1H) 3.31 (s, 3H) 3.90-4.01 (m, 1H) 3.94 (s, 3H) 4.06 (t, J=12.63 Hz, 2H) 4.41-4.51 (m, 1H) 7.47 (dd, J=8.46, 1.64 Hz, 1H) 7.51 (d, J=1.77 Hz, 1H) 7.91 (s, 1H) 8.09 (d, J=8.08 Hz, 1H) 8.21 (s, 1H) 8.27 (d, J=8.32 Hz, 1H). [M+H] calc'd for C$_{28}$H$_{37}$F$_2$N$_7$O$_3$ 558. found 558.

Compound 76: 4-(9-cyclohexyl-7,7-difluoro-5-methyl-6-oxo-6,7,8,9-tetrahydro-5H-pyrimido[4,5-b][1,4]diazepin-2-ylamino)-N-cyclopropyl-3-methoxybenzamide

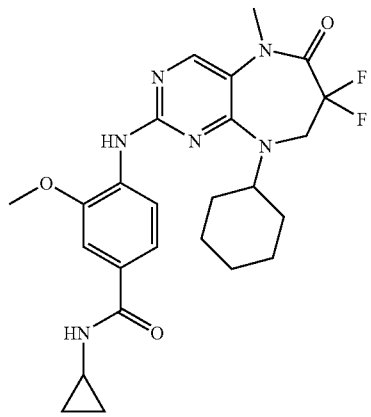

The title compound was synthesized from 4-(9-cyclohexyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and cyclopropylamine. The final compound was purified by reverse phase HPLC and basified to give the free base. $^1$H NMR (400 MHz, DMSO-d$_6$) δ ppm 0.50-0.61 (m, 2H) 0.70 (dd, J=7.07, 2.27 Hz, 2H) 1.31-1.48 (m, 2H) 1.51-1.70 (m, 4H) 1.71-1.91 (m, 4H) 2.81 (dt, J=7.14, 3.63 Hz, 1H) 3.17 (s, 3H) 3.93 (s, 3H) 4.03 (q, J=7.07 Hz, 2H) 4.46 (t, J=11.62 Hz, 1H) 7.40-7.55 (m, 2H) 7.90 (s, 1H) 8.21 (s, 1H) 8.26 (d, J=8.34 Hz, 1H) 8.37 (d, J=3.79 Hz, 1H). [M+H] C$_{25}$H$_{30}$F$_2$N$_6$O$_3$ calc'd for, 501. found 501.

Compound 77: 4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(piperazin-1-yl)benzamide

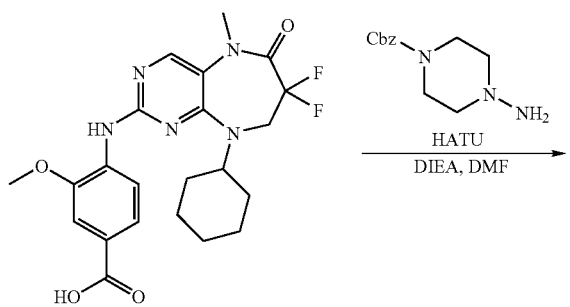

221
-continued

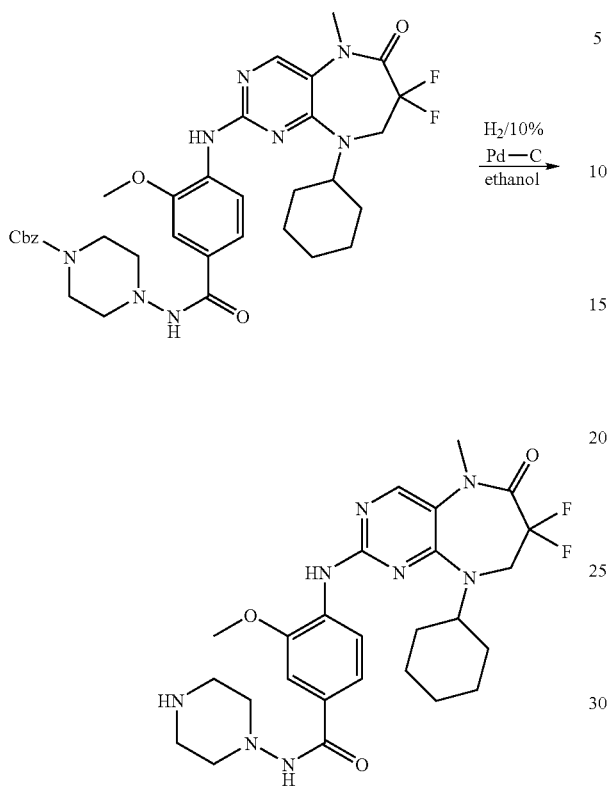

Benzyl 4-(4-(9-cyclohexyl-7,7-difluoro-5-methyl-6-oxo-6,7,8,9-tetrahydro-5H-pyrimido[4,5-b][1,4]diazepin-2-ylamino)-3-methoxybenzamido)piperazine-1-carboxylate: The title compound was synthesized from 4-(9-cyclohexyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and benzyl 4-aminopiperazine 1-carboxylate.

4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(piperazin-1-yl)benzamide: Benzyl 4-(4-(9-cyclohexyl-7,7-difluoro-5-methyl-6-oxo-6,7,8,9-tetrahydro-5H-pyrimido[4,5-b][1,4]diazepin-2-ylamino)-3-methoxybenzamido)piperazine-1-carboxylate (850 mg, 1.25 mmols) was dissolved in ethanol (15 mL), added 10% Pd—C (170 mg, 20% wt) under inert atmosphere and hydrogenated using a balloon for 8 hrs. Then filtered the solution through celite bed and evaporated to give the product (630 mg). $^1$H NMR (400 MHz, DMSO-$d_6$) δ ppm 1.12-1.89 (m, 10H) 2.70-2.85 (m, 8H) 3.31 (s, 3H) 3.93 (s, 3H) 4.06 (t, J=13.26 Hz, 2H) 4.46 (m, 1H) 7.42 (d, J=8.0 Hz, 1H) 7.44 (s, 1H) 7.90 (s, 1H) 8.21 (s, 1H) 8.26 (d, J=8.08 Hz, 1H) 9.38 (s, 1H). [M+H] calculated for $C_{26}H_{34}F_2N_8O_3$, 545. found 545.

222

Compound 78: 4-(9-cyclohexyl-7,7-difluoro-5-methyl-6-oxo-6,7,8,9-tetrahydro-5H-pyrimido[4,5-b][1,4]diazepin-2-ylamino)-N-(4-ethylpiperazin-1-yl)-3-methoxybenzamide

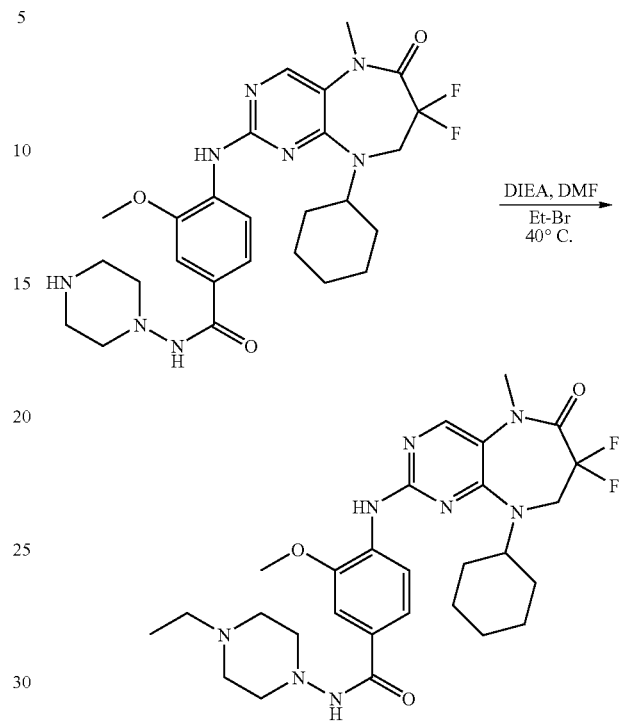

4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(piperazin-1-yl)benzamide (108 mg, 0.2 mmols), ethyl bromide (33 mg, 0.3 mmols) and N,N-diisopropylethylamine (106 μL, 0.3 mmols) were mixed in a screw cap vial (5 mL) in DMF (2 mL) heated at 40° C. for 5-8 hrs, then purified to provide the title compound (76.9 mg). $^1$H NMR (400 MHz, DMSO-$d_6$) δ ppm 0.99 (t, J=7.1 Hz, 3H) 1.14-1.89 (m, 10H) 2.33 (q, J=6.99 Hz, 2H) 2.48 (m, 4H) 2.93 (t, J=4.55 Hz, 4H) 3.31 (s, 3H) 3.93 (s, 3H) 4.06 (t, J=13.22 Hz, 2H) 4.45 (m, 1H). 7.41 (d, J=8.0 Hz, 1H) 7.43 (s, 1H) 7.90 (s, 1H) 8.20 (s, 1H) 8.26 (d, J=8.08 Hz, 1H) 9.38 (s, 1H) [M+H] calculated for $C_{28}H_{38}F_2N_8O_3$, 572. found 572.

Compound 79: 4-(9-cyclohexyl-7,7-difluoro-5-methyl-6-oxo-6,7,8,9-tetrahydro-5H-pyrimido[4,5-b][1,4]diazepin-2-ylamino)-N-(4-isopropylpiperazin-1-yl)-3-methoxybenzamide

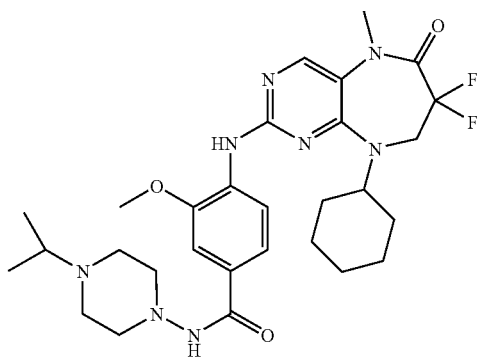

The title compound was synthesized using a procedure that is analogous to that described in connection with 4-(9-cyclohexyl-7,7-difluoro-5-methyl-6-oxo-6,7,8,9-tetrahydro-5H-pyrimido[4,5-b][1,4]diazepin-2-ylamino)-N-(4-isopropylpiperazin-1-yl)-3-methoxybenzamide except that isopropyl bromide. $^1$H NMR (400 MHz, DMSO-d$_6$) δ ppm 0.98 (d, J=6.32 Hz, 6H) 1.16-1.89 (m, 10H) 2.66 (dt, J=12.95, 6.54 Hz, 1H) 2.53 (m, 4H) 2.92 (t, J=4.42 Hz, 4H) 3.31 (s, 3H) 3.94 (s, 3H) 4.06 (t, J=13.26 Hz, 2H) 4.46 (m, 1H). 7.41 (d, J=8.0 Hz, 1H) 7.44 (s, 1H) 7.91 (s, 1H) 8.21 (s, 1H) 8.27 (d, J=8.34 Hz, 1H) 9.35 (s, 1H). [M+H] calculated for C$_{29}$H$_{40}$F$_2$N$_8$O$_3$, 587. found 587.

Compound 80: 4-(9-cyclohexyl-7,7-difluoro-5-methyl-6-oxo-6,7,8,9-tetrahydro-5H-pyrimido[4,5-b][1,4]diazepin-2-ylamino)-N-(4-(cyclopropylmethyl)piperazin-1-yl)-3-methoxybenzamidemethoxybenzamide

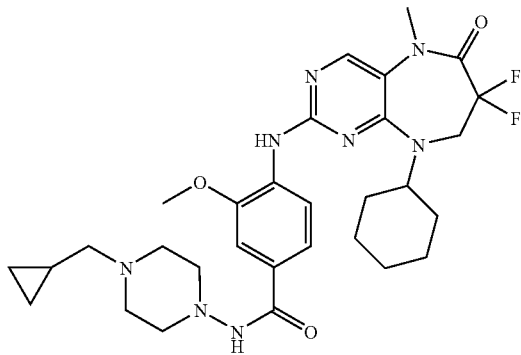

The title compound was synthesized using a procedure that is analogous to that described in connection with 4-(9-cyclohexyl-7,7-difluoro-5-methyl-6-oxo-6,7,8,9-tetrahydro-5H-pyrimido[4,5-b][1,4]diazepin-2-ylamino)-N-(4-isopropylpiperazin-1-yl)-3-methoxybenzamide except that (bromomethyl)cyclopropane. $^1$H NMR (400 MHz, DMSO-d$_6$) δ ppm 0.08 (q, J=4.88 Hz, 2H) 0.38-0.58 (m, 2H) 0.70-0.93 (m, 1H) 1.14-1.89 (m, 10H) 2.19 (d, J=6.32 Hz, 2H) 2.52 (m, 4H) 2.95 (m, 4H) 3.31 (s, 3H) 3.94 (s, 3H) 4.06 (t, J=13.39 Hz, 2H) 4.46 (m, 1H) 7.42 (d, J=8.0 Hz, 1H) 7.44 (s, 1H) 7.91 (s, 1H) 8.21 (s, 1H) 8.27 (d, J=8.34 Hz, 1H) 9.39 (s, 1H). [M+H] calculated for C$_{30}$H$_{40}$F$_2$N$_8$O$_3$, 599. found 599.

Compound 81: 4-(9-cyclohexyl-7,7-difluoro-5-methyl-6-oxo-6,7,8,9-tetrahydro-5H-pyrimido[4,5-b][1,4]diazepin-2-ylamino)-N-(4-(2-(dimethylamino)acetyl)piperazin-1-yl)-3-methoxybenzamide

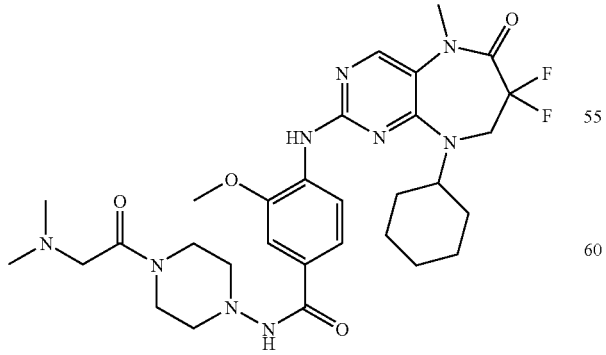

The title compound was synthesized from 4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(piperazin-1-yl)benzamide using a procedure that is analogous to that described in connection with amide formation except that N,N-dimethylglycine. $^1$H NMR (400 MHz, DMSO-d$_6$) δ ppm 1.12-1.89 (m, 10H) 2.19 (s, 6H) 2.89 (br. s., 2H) 2.94 (br. s., 2H) 3.31 (s, 3H) 3.54 (br. s., 2H) 3.63 (br. s., 2H) 3.93 (s, 3H) 4.06 (t, J=13.39 Hz, 2H) 4.46 (m, 1H) 7.42 (d, J=8.0 Hz, 1H) 7.44 (s, 1H) 7.91 (s, 1H) 8.21 (s, 1H) 8.28 (d, J=8.33 Hz, 1H) 9.52 (s, 1H). [M+H] calculated for C$_{30}$H$_{41}$F$_2$N$_9$O$_4$, 630. found 630.

Compound 82: 4-(7,7-difluoro-5-methyl-9-((3R)-3-methylcyclopentyl)-6-oxo-6,7,8,9-tetrahydro-5H-pyrimido[4,5-b][1,4]diazepin-2-ylamino)-3-methoxybenzoic acid

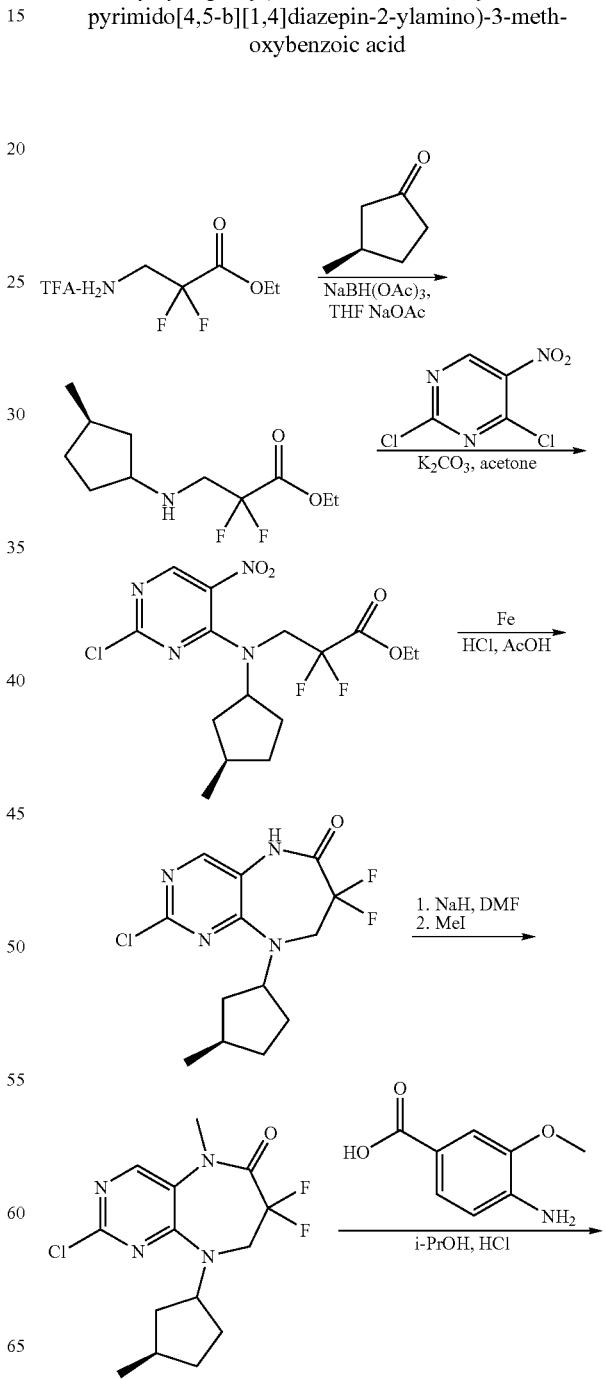

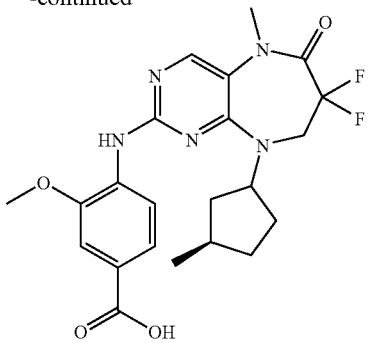

Ethyl 4-((2-chloro-5-nitropyrimidin-4-yl)((3R)-3-methylcyclopentyl)amino)-3,3-difluoro-2-oxobutanoate: Ethyl 3-((2-chloro-5-nitropyrimidin-4-yl)((3R)-3-methylcyclopentyl)amino)-2,2-difluoropropanoate was obtained through reductive amination of ethyl 4-amino-3,3-difluoro-2-oxobutanoate and (R)-3-methylcyclopentanone. The resulting product was further reacted with 2,4-dichloronitropyrimidine to yield ethyl 4-((2-chloro-5-nitropyrimidin-4-yl)((3R)-3-methylcyclopentyl)amino)-3,3-difluoro-2-oxobutanoate. The product crashed out and was collected. $^1$H NMR (400 MHz, DMSO-d$_6$) δ ppm 0.87-1.03 (m, 3H) 1.16-1.34 (m, 4H) 1.47-2.18 (m, 6H) 3.62-3.81 (m, 1H) 4.25 (q, J=7.07 Hz, 4H) 8.94 (s, 1H). m/z 393.

2-chloro-7,7-difluoro-9-((3R)-3-methylcyclopentyl)-8,9-dihydro-5H-pyrimido[4,5-b][1,4]diazepin-6(7H)-one: Compound ethyl 4-((2-chloro-5-nitropyrimidin-4-yl)((3R)-3-methylcyclopentyl)amino)-3,3-difluoro-2-oxobutanoate was dissolved in AcOH and then cooled in an ice bath (sometimes this crystallizes out upon cooling). Iron powder (2 equivalents) was added followed by the slow addition of HCl (15 mL, conc.). After 10 minutes the reaction was transferred to a heat bath and left to stir at 60° C. for 5 hours. The reaction was then cooled, the stir bar and unreacted iron removed with a magnet (or by filtration through paper), and the solvent volume reduced by about 75% on a rotovap. The mixture was then diluted with ice water (150 mL) and EtOAc (1500 mL), the layers separated, the aqueous layer washed with EtOAc (2×150 mL), the organic extracts combined, washed with sat. NaHCO$_3$ (100 mL), brine (100 mL), dried over MgSO$_4$, filtered and concentrated to yield a brown syrup. Trituration with EtOAc (15 mL) and ether (100 mL) to coax out a tannish solid. $^1$H NMR (400 MHz, DMSO-d$_6$) δ ppm 0.91-2.29 (m, 10H) 3.80-4.20 (m, 2H) 4.81-5.07 (m, 1H) 8.12 (s, 1H) 11.07 (br. s., 1H). m/z 317.

2-chloro-7,7-difluoro-5-methyl-9-((3R)-3-methylcyclopentyl)-8,9-dihydro-5H-pyrimido[4,5-b][1,4]diazepin-6(7H)-one: 2-Chloro-7,7-difluoro-9-((3R)-3-methylcyclopentyl)-8,9-dihydro-5H-pyrimido[4,5-b][1,4]diazepin-6(7H)-one was methylated on 5-position using sodium hydride and methyl iodide. After 30 minutes the reaction was deemed complete by LCMS, poured into ice, the solution acidified with 1N HCl, the product filtered off as a tan solid. $^1$H NMR (400 MHz, DMSO-d$_6$) δ ppm 0.91-2.22 (m, 10H) 3.34 (s, 3H) 4.04-4.35 (m, 2H) 4.72-5.04 (m, 1H) 8.35 (s, 1H). m/z 331.2 (M+H)$^+$.

4-(7,7-difluoro-5-methyl-9-((3R)-3-methylcyclopentyl)-6-oxo-6,7,8,9-tetrahydro-5H-pyrimido[4,5-b][1,4]diazepin-2-ylamino)-3-methoxybenzoic acid: 2-Chloro-7,7-difluoro-5-methyl-9-((3R)-3-methylcyclopentyl)-8,9-dihydro-5H-pyrimido[4,5-b][1,4]diazepin-6(7H)-one (500 mg, 1.51 mmol) and 4-amino-3-methoxybenzoic acid (316.0 mg, 1.89 mmol) were weighed into a flask. 4-Methylbenzenesulfonic acid monohydrate (230.0 mg, 1.21 mmol) was weighed into a separate flask and dissolved in dioxane (15 ml). The toxic acid solution was then added to the flask containing the two starting materials. The reaction was stirred at 85° C. for 48 hours followed by 100° C. for an additional 48 hours. The dark brown mixture was cooled to room temperature and filtered through paper. The solids were washed with ethyl acetate (15 ml). m/z 462.4 (M+H)$^+$.

Compound 83: 4-(7,7-difluoro-5-methyl-9-((3R)-3-methylcyclopentyl)-6-oxo-6,7,8,9-tetrahydro-5H-pyrimido[4,5-b][1,4]diazepin-2-ylamino)-3-methoxy-N-(1-methylpiperidin-4-yl)benzamide

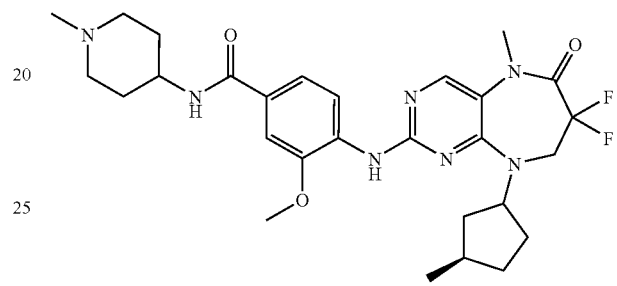

To a mixture of the 4-(7,7-difluoro-5-methyl-9-((3R)-3-methylcyclopentyl)-6-oxo-6,7,8,9-tetrahydro-5H-pyrimido[4,5-b][1,4]diazepin-2-ylamino)-3-methoxybenzoic acid, 1-methylpiperidin-4-amine (1.1 equivalent) and DIEA (3-6 equivalent) in 20 mL of anhydrous DMF, was added HATU (1.5 to 2 equivalent). The reaction mixture was stirred for 30 min. The reaction mixture was then diluted with ethyl acetate, washed with water and brine. The organic layer dried over Na$_2$SO$_4$ followed by HPLC purification. $^1$H NMR (400 MHz, DMSO-d$_6$) δ ppm 0.96-1.06 (m, 3H) 1.06-2.12 (m, 13H) 2.16 (s, 3H) 2.77 (d, J=11.87 Hz, 2H) 3.32 (br. s., 3H) 3.65-3.80 (m, 1H) 3.93 (s, 3H) 3.97-4.12 (m, 2H) 4.73-4.96 (m, 1H) 7.44-7.52 (m, 2H) 7.97 (d, J=6.06 Hz, 1H) 8.12 (d, J=7.83 Hz, 1H) 8.25 (d, 2H). [M+H] calc'd for C$_{28}$H$_{37}$F$_2$N$_7$O$_3$ 558. found 558.

Compound 84: 4-(9-cyclopentyl-7-fluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide

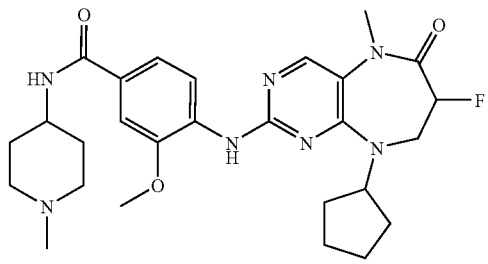

The title compound was synthesized using an analogous procedure to that described in connection with Compound 3 except that 2-fluoro-beta-alaninate was used as the starting material. The final product was purified on reversed phase HPLC as TFA salt. $^1$H NMR (400 MHz, DMSO-$d_6$) δ ppm 1.55-1.87 (m, 11H) 1.91-2.08 (m, 3H) 2.18 (s, 3H) 2.79 (d, J=11.4 Hz, 2H) 3.24 (s, 3H) 3.61-3.83 (m, 3H) 3.94 (s, 3H) 4.77 (quin., J=8.3 Hz, 1H) 5.52 (qd, 1H) 7.47 (dd, J=1.8 Hz, 1H) 7.49 (s, 1H) 7.86 (s, 1H) 8.11 (d, J=7.8 Hz, 1H) 8.16 (s, 1H) 8.33 (d, J=8.34 Hz, 1H). [M+H] calc'd for $C_{27}H_{36}FN_7O_3$ 526. found 526.

Compound 85: 4-(9-cyclopentyl-7-fluoro-5-methyl-6-oxo-7-(trifluoromethyl)-6,7,8,9-tetrahydro-5H-pyrimido[4,5-b][1,4]diazepin-2-ylamino)-3-methoxy-N-(1-methylpiperidin-4-yl)benzamide

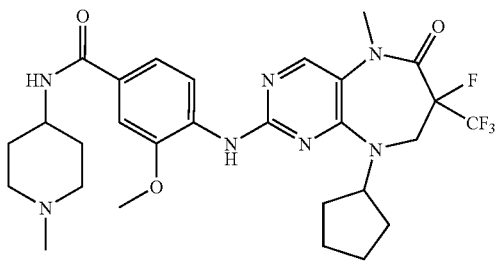

The title compound was synthesized using the analogous procedure to that described in connection with Compound 3 except that 2-(aminomethyl)-2,3,3,3-tetrafluoropropanoic acid was used as the starting material. The final product was purified on reversed phase HPLC as TFA salt. $^1$H NMR (400 MHz, DMSO-$d_6$) δ ppm 1.46-1.76 (m, 10H) 1.83-2.09 (m, 4H) 2.19 (s, 3H) 2.80 (d, J=11.9 Hz, 2H) 3.32 (s, 3H) 3.69-3.81 (m, 1H) 3.89 (t, 1H) 3.94 (s, 3H) 4.15-4.35 (q, 1H) 4.72 (quin., J=8.1 Hz, 1H) 7.48 (dd, J=1.77 Hz, 1H) 7.50 (s, 1H) 8.00 (s, 1H) 8.10 (d, J=7.8 Hz, 1H) 8.26 (d, J=8.3 Hz, 1H) 8.32 (s, 1H). [M+H] calc'd for $C_{28}H_{35}F_4N_7O_3$ 594. found 594.

Compound 86: 4-(9-cyclopentyl-7-fluoro-5,7-dimethyl-6-oxo-6,7,8,9-tetrahydro-5H-pyrimido[4,5-b][1,4]diazepin-2-ylamino)-3-methoxy-N-(1-methylpiperidin-4-yl)benzamide

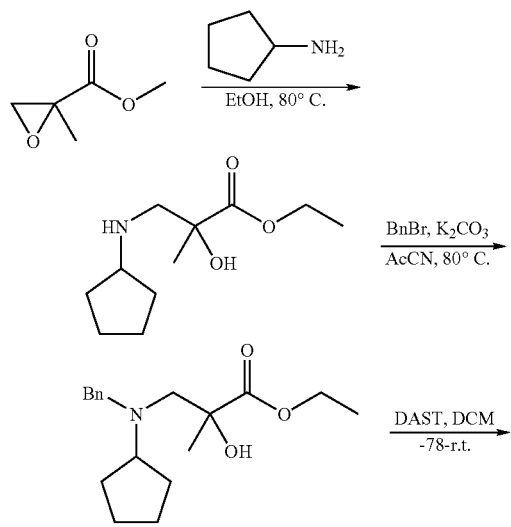

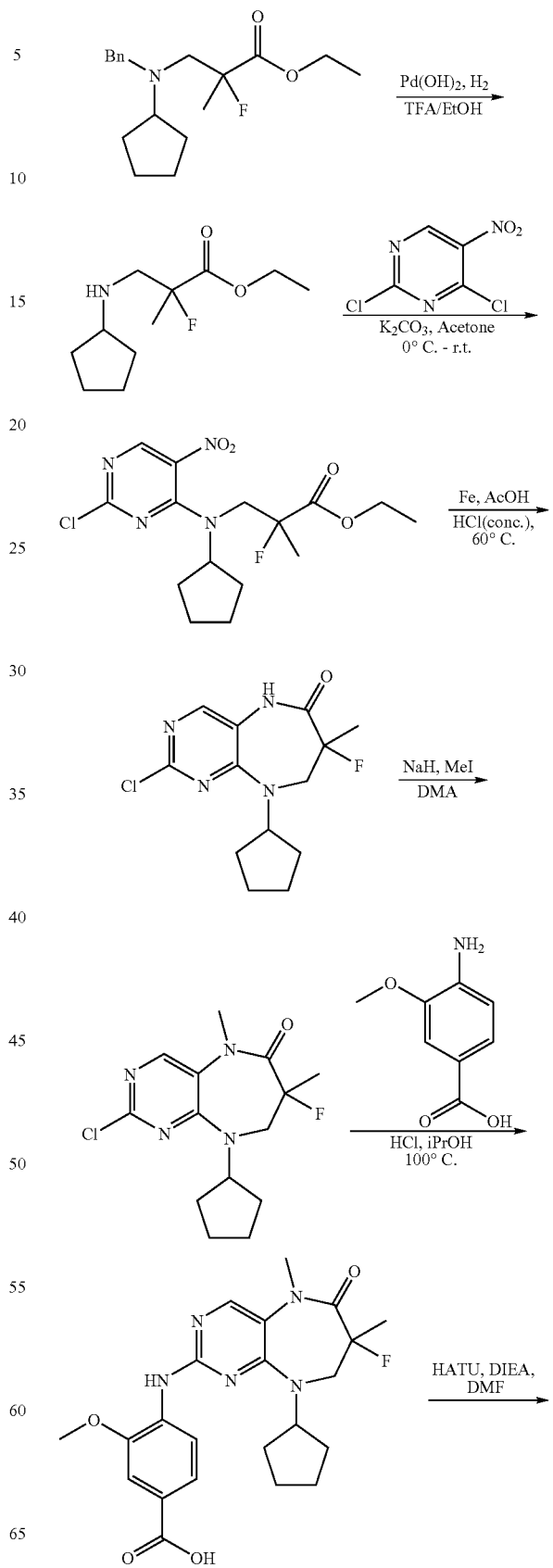

-continued

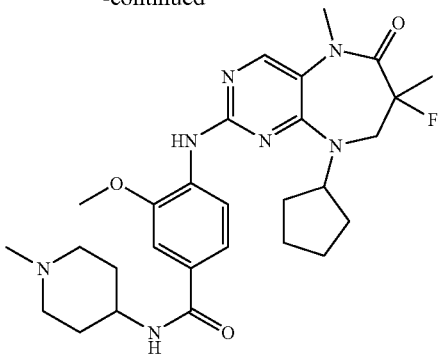

Ethyl 3-(cyclopentylamino)-2-hydroxy-2-methylpropanoate: A mixture of methyl 2-methylglycidate (3.18 g, 27 mmol) and cyclopentylamine (4 mL, 41 mmol) in ethanol (50 mL) was heated at 80° C. for 3 d. The reaction mixture was then concentrated, diluted to EtOAc, washed by NaHCO$_3$, brine and water. Organic layer was dried, concentrated to give a residue which is used for next step without further purification (3.9 g, 60%). [M+H] calc'd for $C_{11}H_{21}NO_3$, 216. found 216.

Ethyl 3-(benzyl(cyclopentyl)amino)-2-hydroxy-2-methylpropanoate: To ethyl 3-(cyclopentylamino)-2-hydroxy-2-methylpropanoate (3.9 g, 18 mmol) in 50 ml of acetonitrile at room temperature, was added benzyl bromide (3.2 ml, 27.2 mmol) dropwise, followed by K$_2$CO$_3$ (7.5 g, 54.3 mmol). The reaction mixture was heated at 80° C. for 18 h. It was then diluted to EtOAc, washed by brine and water. Organic extract dried and concentrated to a residue, which was purified on silica gel column chromatographically (Hex/EtOAc=100:1 to 10:1) to give 4.2 g product (77%). [M+H] calc'd for $C_{18}H_{27}NO_3$, 306. found 306.

Ethyl 3-(benzyl(cyclopentyl)amino)-2-fluoro-2-methylpropanoate: To ethyl 3-(benzyl(cyclopentyl)amino)-2-hydroxy-2-methylpropanoate (4.2 g, 14 mmol) in 50 ml of dichlormethane at −78° C., was added DAST (2.7 ml, 21 mmol) dropwise. The reaction mixture was gradually warmed up to room temperature and stirred for 2 h. It was then diluted to dichloromethane, washed by NaHCO$_3$, brine and water. Organic extract dried and concentrated to a residue, which was purified on silica gel column chromatographically (Hex/EtOAc=40:1 to 20:1) to give 3.5 g product (83%) as light yellow liquid. [M+H] calc'd for $C_{18}H_{26}FNO_2$, 308. found 308.

Ethyl 3-(cyclopentylamino)-2-fluoro-2-methylpropanoate: A solution of ethyl 3-(benzyl(cyclopentyl)amino)-2-fluoro-2-methylpropanoate (3.5 g, 11.4 mmol) in ethanol (30 mL) was hydrogenated with Pd(OH)$_2$ (20%, 400 mg, 0.57 mmol) in presence of TFA (11.4 mmol) at atmospheric pressure for 20 h. The reaction mixture was filtered through celite. The filtrate was concentrated and diluted to EtOAc/H$_2$O, aqueous layer was basified to pH=11-12 by 1N NaOH. The organic layer was then dried and concentrated to give the product (2.1 g, 85%) as light yellow liquid. [M+H] calc'd for $C_{11}H_{20}FNO_2$, 218. found 218.

Ethyl 3-((2-chloro-5-nitropyrimidin-4-yl)(cyclopentyl) amino)-2-fluoro-2-methylpropanoate: To a solution of 2,4-dichloro-5-nitropyrimidine (2.14 g, 11.0 mmol) in anhydrous acetone (30 ml) at 0° C., was added dropwise a solution of compound ethyl 3-(cyclopentylamino)-2-fluoro-2-methylpropanoate (2 g, 9.22 mmol) in acetone (10 mL) over 10 min. After which, potassium carbonate (3.8 g, 27.7 mmol) was added and the whole was stirred at rt for 18 h. After evaporation in vacuo, the residue was partitioned between ethyl acetate (200 ml) and water (200 ml). The organic layer was washed with NaHCO$_3$, brine and water, dried over Na$_2$SO$_4$ and concentrated in vacuo to give a red residue which was used directly for next step. [M+H] calc'd for $C_{15}H_{20}ClFN_4O_4$, 375. found 375.

2-Chloro-9-cyclopentyl-7-fluoro-7-methyl-8,9-dihydro-5H-pyrimido[4,5-b][1,4]diazepin-6(7H)-one: To a suspension of ethyl 3-((2-chloro-5-nitropyrimidin-4-yl)(cyclopentyl)amino)-2-fluoro-2-methylpropanoate (3.4 g, 9 mmol), reduced iron (1.2 g, 23 mmol) in acetic acid (20 ml) was added dropwise concentrated hydrochloric acid (2 ml) at 0° C. The reaction mixture was stirred at 60° C. for 18 h. It was then concentrated in vacuo, diluted to EtOAc, basified with 10% NaOH solution at 0° C. The whole was filtered through celite, washed with EtOAc. The filtrate was then separated. The organic layer was dried over Na$_2$SO$_4$. The solution was concentrated in vacuo followed by precipitation from ether to afford the product (620 mg, 23% yield) as white solid. $^1$H NMR (400 MHz, DMSO-d$_6$) δ ppm 1.42-1.67 (m, 7H) 1.72 (d, J=4.0 Hz, 2H) 1.77-1.91 (m, 2H) 3.58-3.77 (m, 2H) 5.01 (t, J=8.2 Hz, 1H) 7.97 (s, 1H) 10.36 (s, 1H). [M+H] calc'd for $C_{13}H_{16}ClFN_4O$, 299. found 299.

2-Chloro-9-cyclopentyl-7-fluoro-5,7-dimethyl-8,9-dihydro-5H-pyrimido[4,5-b][1,4]diazepin-6(7H)-one: To a solution of 2-chloro-9-cyclopentyl-7-fluoro-7-methyl-8,9-dihydro-5H-pyrimido[4,5-b][1,4]diazepin-6(7H)-one (3 mmol) in 10 mL of DMA was added sodium hydride (60% dispersion in mineral oil, 124 mg, 3.1 mmol) at 0° C., followed by the dropwise addition of methyl iodide (0.193 mL, 3.1 mmol). The reaction mixture was warmed up to rt and stirred for 1 h. The whole was poured into ice-water, extracted with ethyl acetate. The organic layer was washed with brine and dried over Na$_2$SO$_4$. The solution was concentrated in vacuo and used for next step reaction. [M+H] calc'd for $C_{14}H_{18}ClFN_4O$, 313. found 313.

4-(9-cyclopentyl-7-fluoro-5,7-dimethyl-6-oxo-6,7,8,9-tetrahydro-5H-pyrimido[4,5-b][1,4]diazepin-2-ylamino)-3-methoxybenzoic acid: A mixture of 2-chloro-9-cyclopentyl-7-fluoro-5,7-dimethyl-8,9-dihydro-5H-pyrimido[4,5-b][1,4]diazepin-6(7H)-one (obtained above), 4-amino-3-methoxybenzoic acid (585 mg, 3.5 mmol), isopropanol (10 ml), water (5 mL) and concentrated hydrochloric acid (10 drops) was stirred at 100° C. for 20 h. Solid was filtered to give the product as white solid (396 mg). [M+H] calc'd for $C_{22}H_{26}FN_5O_4$, 444. found 444.

Compound 87: 4-(9-cyclopentyl-7-fluoro-5,7-dimethyl-6-oxo-6,7,8,9-tetrahydro-5H-pyrimido[4,5-b][1,4]diazepin-2-ylamino)-3-methoxy-N-(1-methylpiperidin-4-yl)benzamide

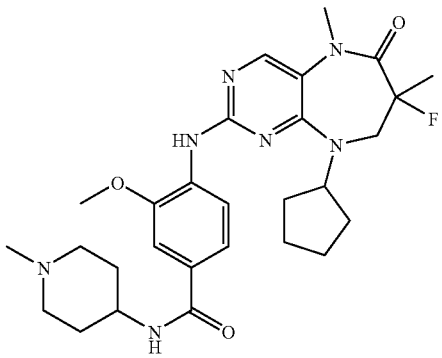

The title compound was synthesized from 4-(9-cyclopentyl-7-fluoro-5,7-dimethyl-6-oxo-6,7,8,9-tetrahydro-5H-pyrimido[4,5-b][1,4]diazepin-2-ylamino)-3-methoxybenzoic acid and 1-methylpiperidin-4-amine as described in the General procedure for amide bond synthesis using HATU. The final compound was purified by reverse phase HPLC and basified to give the free base. $^1$H NMR (400 MHz, DMSO-$d_6$) δ ppm 1.41-1.65 (m, 6H) 1.65-1.86 (m, 6H) 1.93 (d, J=3.3 Hz, 1H) 2.07 (s, 1H) 2.04 (d, J=13.1 Hz, 1H) 2.81 (d, J=5.1 Hz, 1H) 2.78 (d, J=4.6 Hz, 3H) 2.99-3.17 (m, 2H) 3.27 (s, 4H) 3.48 (d, J=11.6 Hz, 2H) 4.83 (t, J=7.8 Hz, 1H) 7.53 (dd, J=8.3, 1.8 Hz, 1H) 7.55 (s, 1H) 8.08 (d, J=8.3 Hz, 1H) 8.17 (s, 1H) 8.43 (d, J=7.3 Hz, 1H) 8.98 (br. s., 1H) 9.54 (br. s., 1H). [M+H] calc'd for $C_{28}H_{38}FN_7O_3$, 540. found 540.

Compound 88: 4-(9-Cyclopentyl-7-fluoro-5,7-dimethyl-6-oxo-6,7,8,9-tetrahydro-5H-pyrimido[4,5-b][1,4]diazepin-2-ylamino)-3-methoxy-N-(1-methylazetidin-3-yl)benzamide

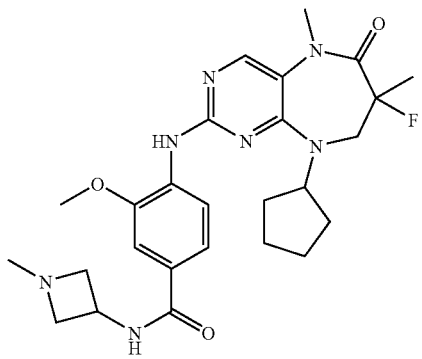

The title compound was synthesized from 4-(9-cyclopentyl-7-fluoro-5,7-dimethyl-6-oxo-6,7,8,9-tetrahydro-5H-pyrimido[4,5-b][1,4]diazepin-2-ylamino)-3-methoxybenzoic acid as described in the General procedure for amide bond synthesis using HATU and 1-methylazetidin-3-amine hydrochloride. The final compound was purified by reverse phase HPLC and basified to give the free base. $^1$H NMR (400 MHz, DMSO-$d_6$) δ ppm 1.44-1.65 (m, 5H) 1.65-1.88 (m, 4H) 1.88-2.01 (m, 1H) 2.92 (dd, J=4.7, 2.4 Hz, 3H) 3.28 (s, 3H) 3.95 (s, 3H) 4.01-4.25 (m, 2H) 4.31-4.55 (m, 2H) 4.64-4.89 (m, 2H) 7.44-7.63 (m, 2H) 8.21 (d, J=8.3 Hz, 1H) 8.18 (s, 1H) 8.97-9.09 (m, 1H) 9.78 (br. s., 1H). [M+H] calc'd for $C_{26}H_{34}FN_7O_3$, 512. found 512.

Compound 89: 4-(9-Cyclohexyl-7-fluoro-5,7-dimethyl-6-oxo-6,7,8,9-tetrahydro-5H-pyrimido[4,5-b][1,4]diazepin-2-ylamino)-3-methoxy-N-(1-methylpiperidin-4-yl)benzamide

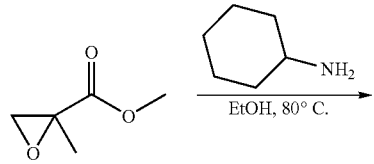

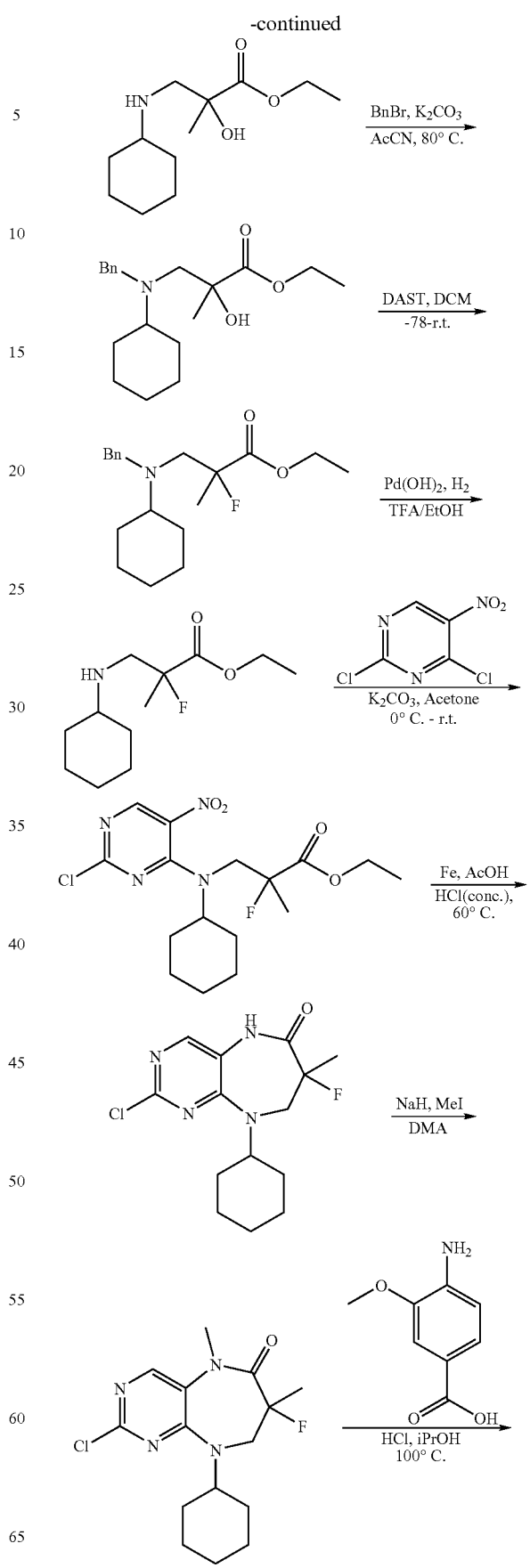

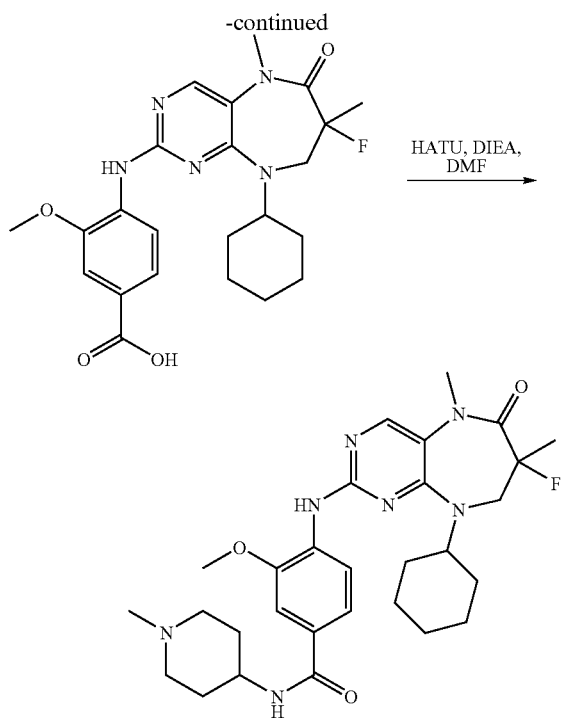

Ethyl 3-(cyclohexylamino)-2-hydroxy-2-methylpropanoate: A mixture of methyl 2-methylglycidate (3.2 mL, 30 mmol) and cyclohexylamine (5.2 mL, 45 mmol) in ethanol (50 mL) was heated at 80° C. for 24 h. The reaction mixture was then concentrated, diluted to EtOAc, washed by NaHCO$_3$, brine and water. Organic layer was dried, concentrated to give a residue which is used for next step without further purification (6.7 g, 97%). [M+H] calc'd for C$_{12}$H$_{23}$NO$_3$, 230. found 230.

Ethyl 3-(benzyl(cyclohexyl)amino)-2-hydroxy-2-methylpropanoate: To ethyl 3-(cyclohexylamino)-2-hydroxy-2-methylpropanoate (6.7 g, 29.2 mmol) in 50 ml of acetonitrile at room temperature, was added benzyl bromide (5.2 ml, 43.8 mmol) dropwise, followed by K$_2$CO$_3$ (12 g, 87.6 mmol). The reaction mixture was heated at 80° C. for 18 h. It was then diluted to EtOAc, washed by brine and water. Organic extract dried and concentrated to a residue, which was purified on silica gel column chromatographically (Hex/EtOAc=100:1 to 10:1) to give 7 g product (75%). [M+H] calc'd for C$_{19}$H$_{29}$NO$_3$, 320. found 320.

Ethyl 3-(benzyl(cyclohexyl)amino)-2-fluoro-2-methylpropanoate: To ethyl 3-(benzyl(cyclohexyl)amino)-2-hydroxy-2-methylpropanoate (7 g, 21.9 mmol) in 50 ml of dichlormethane at −78° C., was added DAST (4.3 ml, 32.8 mmol) dropwise. The reaction mixture was gradually warmed up to room temperature and stirred for 2 h. It was then diluted to dichloromethane, washed by NaHCO$_3$, brine and water. Organic extract dried and concentrated to a residue, which was purified on silica gel column chromatographically (Hex/EtOAc=40:1 to 20:1) to give 6.8 g product (97%) as light yellow liquid. [M+H] calc'd for C$_{19}$H$_{28}$FNO$_2$, 322. found 322.

Ethyl 3-(cyclohexylamino)-2-fluoro-2-methylpropanoate: A solution of ethyl 3-(benzyl(cyclohexyl)amino)-2-fluoro-2-methylpropanoate (1.6 g, 5 mmol) in ethanol (20 mL) was hydrogenated with Pd(OH)$_2$ (20%, 176 mg, 0.25 mmol) in presence of TFA (5 mmol) at atmospheric pressure for 20 h. The reaction mixture was filtered through celite. The filtrate was concentrated and diluted to EtOAc/H$_2$O, aqueous layer was basified to pH=11-12 by 1N NaOH. The organic layer was then dried and concentrated to give the product (1.1 g, 95%) as light yellow liquid. [M+H] calc'd for C$_{12}$H$_{22}$FNO$_2$, 232. found 232.

Ethyl 3-((2-chloro-5-nitropyrimidin-4-yl)(cyclohexyl)amino)-2-fluoro-2-methylpropanoate: To a solution of 2,4-dichloro-5-nitropyrimidine (970 mg, 5 mmol) in anhydrous acetone (20 ml) at 0° C., was added dropwise a solution of ethyl 3-(cyclohexylamino)-2-fluoro-2-methylpropanoate (1.1 g, 4.76 mmol) in acetone (5 mL) over 10 min. After which, potassium carbonate (1.66 g, 12 mmol) was added and the whole was stirred at rt for 18 h. After evaporation in vacuo, the residue was partitioned between ethyl acetate (200 ml) and water (200 ml). The organic layer was washed with NaHCO$_3$, brine and water, dried over Na$_2$SO$_4$ and concentrated in vacuo to give a red residue (1.9 g) which was used directly for next step. [M+H] calc'd for C$_{16}$H$_{22}$ClFN$_4$O$_4$, 389. found 389.

2-Chloro-9-cyclohexyl-7-fluoro-7-methyl-8,9-dihydro-5H-pyrimido[4,5-b][1,4]diazepin-6(7H)-one: To a suspension of ethyl 3-((2-chloro-5-nitropyrimidin-4-yl)(cyclohexyl)amino)-2-fluoro-2-methylpropanoate (1.9 g, 4.76 mmol), reduced iron (0.66 g, 12 mmol) in acetic acid (20 ml) was added dropwise concentrated hydrochloric acid (2 ml) at 0° C. The reaction mixture was stirred at 60° C. for 18 h. It was then concentrated in vacuo, diluted to EtOAc, basified with 10% NaOH solution at 0° C. The whole was filtered through celite, washed with EtOAc. The filtrate was then separated. The organic layer was dried over Na$_2$SO$_4$. The solution was concentrated in vacuo followed by precipitation from ether to afford compound X (780 mg, 52% yield) as white solid. [M+H] calc'd for C$_{14}$H$_{18}$ClFN$_4$O, 313. found 313.

2-Chloro-9-cyclohexyl-7-fluoro-5,7-dimethyl-8,9-dihydro-5H-pyrimido[4,5-b][1,4]diazepin-6(7H)-one: To a solution of 2-chloro-9-cyclohexyl-7-fluoro-7-methyl-8,9-dihydro-5H-pyrimido[4,5-b][1,4]diazepin-6(7H)-one (313 mg, 2.85 mmol) in 10 mL of DMA was added sodium hydride (60% dispersion in mineral oil, 44 mg, 1.1 mmol) at 0° C., followed by the dropwise addition of methyl iodide (0.07 mL, 1.1 mmol). The reaction mixture was warmed up to rt and stirred for 1 h. The whole was poured into ice-water, extracted with ethyl acetate. The organic layer was washed with brine and dried over Na$_2$SO$_4$. The solution was concentrated in vacuo and used for next step reaction (330 mg). [M+H] calc'd for C$_{15}$H$_{20}$ClFN$_4$O, 327. found 327.

4-(9-Cyclohexyl-7-fluoro-5,7-dimethyl-6-oxo-6,7,8,9-tetrahydro-5H-pyrimido[4,5-b][1,4]diazepin-2-ylamino)-3-methoxybenzoic acid: A mixture of 2-chloro-9-cyclohexyl-7-fluoro-5,7-dimethyl-8,9-dihydro-5H-pyrimido[4,5-b][1,4]diazepin-6(7H)-one (330 mg, 1 mmol), 4-amino-3-methoxybenzoic acid (184 mg, 1.1 mmol), isopropanol (10 ml), and concentrated hydrochloric acid (10 drops) was stirred at 100° C. for 20 h. Solid was filtered to give 146 mg product as white solid (32%). [M+H] calc'd for C$_{23}$H$_{28}$FN$_5$O$_4$, 458. found 458.

4-(9-Cyclohexyl-7-fluoro-5,7-dimethyl-6-oxo-6,7,8,9-tetrahydro-5H-pyrimido[4,5-b][1,4]diazepin-2-ylamino)-3-methoxy-N-(1-methylpiperidin-4-yl)benzamide: The title compound was synthesized using an analogous procedure to that described in connection with Compound 87 except that ethyl 3-(cyclohexylamino)-2-fluoro-2-methylpropanoate, made from commercially available starting material methyl 2-methyloxirane-2-carboxylate, was used and the final compound was purified by reverse phase HPLC and basified to give the free base. $^1$H NMR (400 MHz, DMSO-d$_6$) δ ppm 1.04-1.36 (m, 2H) 1.28-2.08 (m, 17H) 2.19 (s, 3H) 2.81 (d, J=10.6 Hz, 2H) 3.26 (s, 3H) 3.60-3.85 (m, 3H) 3.95 (s, 3H) 4.45 (m, 1H) 7.47 (d, J=8.3 Hz, 1H) 7.50 (s, 1H) 7.75 (s, 1H) 7.97-8.20 (m, 2H) 8.32 (d, J=8.3 Hz, 1H). [M+H] calc'd for $C_{29}H_{40}FN_7O_3$, 554. found 554.

Compound 90: 4-(9-Cyclohexyl-7-fluoro-5,7-dimethyl-6-oxo-6,7,8,9-tetrahydro-5H-pyrimido[4,5-b][1,4]diazepin-2-ylamino)-3-methoxy-N-(1-methylazetidin-3-yl)benzamide

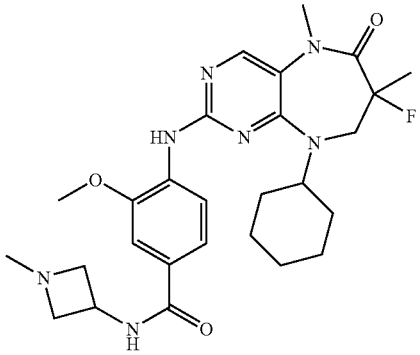

The title compound was synthesized from 4-(9-cyclohexyl-7-fluoro-5,7-dimethyl-6-oxo-6,7,8,9-tetrahydro-5H-pyrimido[4,5-b][1,4]diazepin-2-ylamino)-3-methoxybenzoic acid as described in the General procedure for amide bond synthesis using HATU and 1-methylazetidin-3-amine hydrochloride. The final compound was purified by reverse phase HPLC and basified to give the free base. $^1$H NMR (400 MHz, DMSO-d$_6$) δ ppm 1.39 (m, 2H) 1.62-2.06 (m, 14H), 2.29 (s, 1H) 2.50 (s, 3H) 3.25 (t, J=6.3 Hz, 2H) 3.47 (s, 3H) 3.80 (t, J=6.6 Hz, 2H) 3.88-4.09 (m, 2H) 4.16 (s, 3H) 4.52-4.77 (m, 1H) 7.70 (d, J=8.3 Hz, 1H) 8.00 (s, 1H). [M+H] calc'd for $C_{27}H_{36}FN_7O_3$, 526. found 526.

Compound 91: (R)-4-(9-cyclopentyl-7-ethyl-7-fluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide

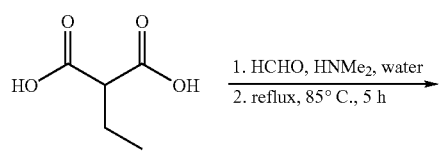

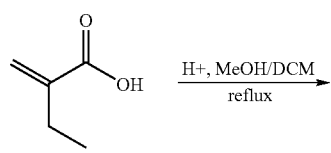

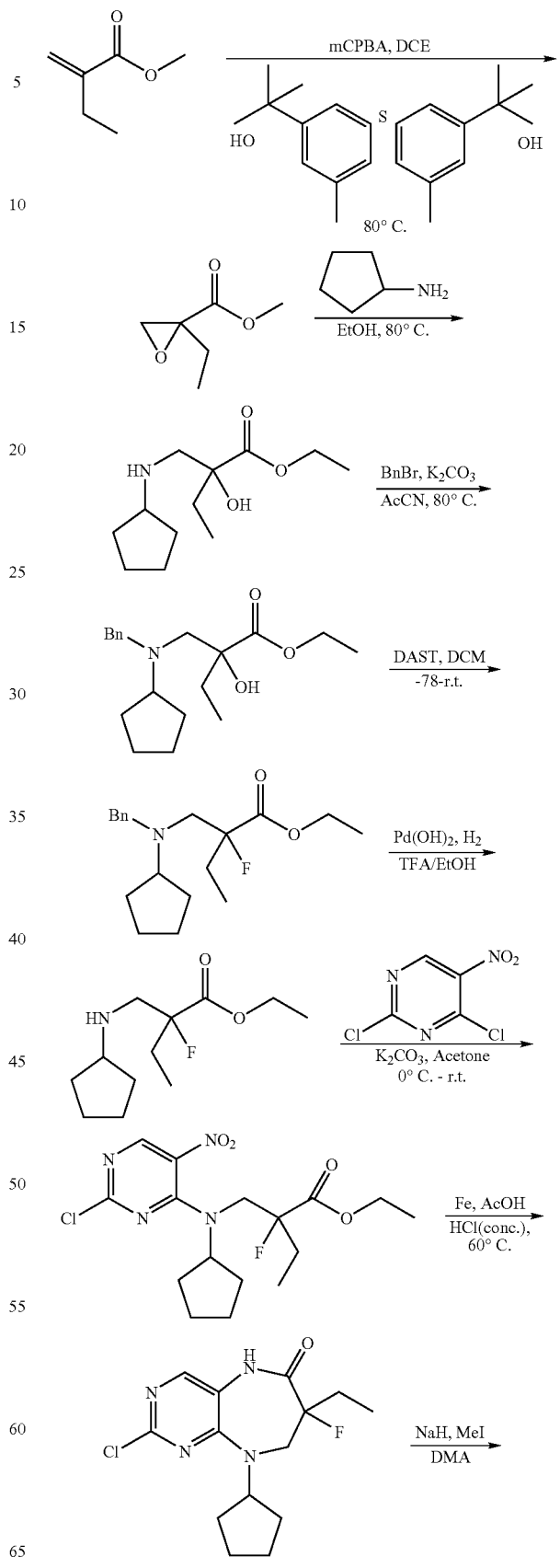

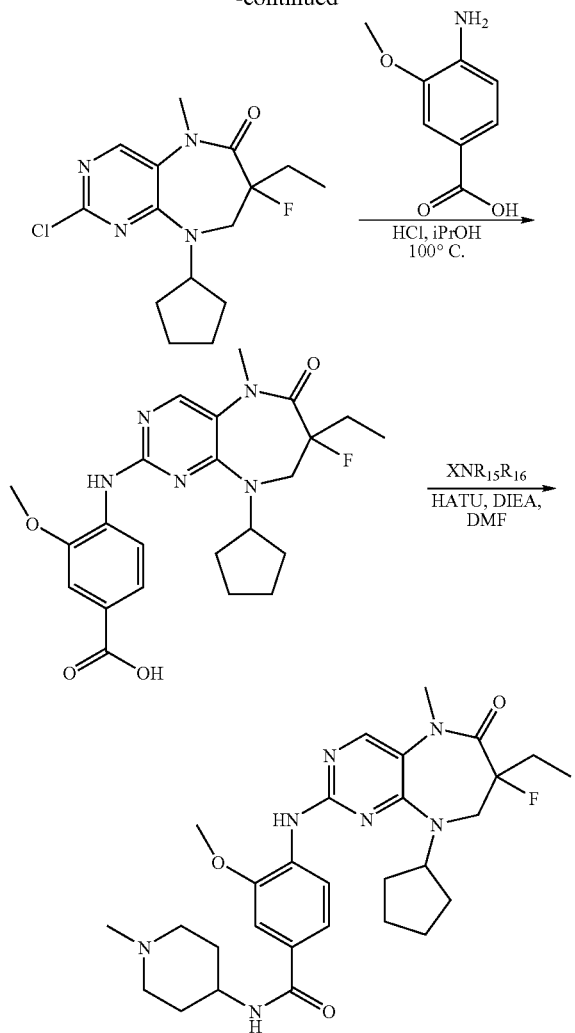

2-Methylenebutanoic acid: The ethyl malonic acid (25.8 g, 195 mmol) was dissolved in 200 mL water, and 37% formaldehyde (15 mL, 200 mmol) and diethylamine (2M in THF, 100 mL, 200 mmol) were added. The reaction mixture was stirred at room temperature for 20 h and then refluxed at 80° C. for 5 h. It was then cooled down to room temperature, acidified by concentrated HCl, extracted with dicholoromethane (3×200 mL). The organic extracts combined, dried over $Na_2SO_4$ and concentrated to give the product as clear liquid (14 g, 72%). $^1$H NMR (400 MHz, CHLOROFORM-d) δ ppm 1.12 (t, J=7.4 Hz, 3H) 2.35 (q, J=7.3 Hz, 2H) 5.66 (s, 1H) 6.30 (s, 1H).

Methyl 2-methylenebutanoate: A mixture of 2-methylenebutanoic acid (14 g, 140 mmol), methane sulfonic acid (40 drops) in dichloromethane (200 mL) and methanol (50 mL) was refluxed at 80° C. for 3 d. It was then cooled to room temperature, washed by $NaHCO_3$. Organic extract was then dried over $Na_2SO_4$, concentrated at low vacuum and low temp. (<20° C.) to give the product as clear liquid (quantitative yield). $^1$H NMR (400 MHz, CHLOROFORM-d) δ ppm 1.08 (t, J=7.3 Hz, 3H) 2.33 (q, J=7.3 Hz, 2H) 3.76 (s, 3H) 5.53 (d, J=1.5 Hz, 1H) 6.13 (d, J=1.0 Hz, 1H).

Methyl 2-ethyloxirane-2-carboxylate: A mixture of methyl 2-methylenebutanoate (140 mmol), mCPBA (77%, 67 g, 300 mmol) and 4,4'-thiobis(2-tert-butyl-6-methylphenol) (250 mg, 0.7 mmol) in 100 ml of dry 1,2-dichloroethane was refluxed at 80° C. for 2 d. It was then cooled down, solid filtered. Filtrate washed by $Na_2SO_3$, $NaHCO_3$, brine and water until clear. It was then concentrated to a light yellow liquid (7.5 g, 41%). $^1$H NMR (400 MHz, CHLOROFORM-d) δ ppm 1.02 (td, J=7.4, 1.3 Hz, 3H) 1.78 (dq, J=14.6, 7.3 Hz, 1H) 2.10 (dq, J=15.4, 7.6 Hz, 1H) 2.80 (dd, J=5.8, 1.0 Hz, 1H) 3.05 (dd, J=5.8, 1.0 Hz, 1H) 3.77 (d, J=1.5 Hz, 3H).

Ethyl 2-((cyclopentylamino)methyl)-2-hydroxybutanoate: A mixture of methyl 2-ethyloxirane-2-carboxylate (1.9 g, 15 mmol) and cyclopentylamine (2.2 mL, 22 mmol) in ethanol (50 mL) was heated at 80° C. for 3 d. The reaction mixture was then concentrated, diluted to EtOAc, washed by $NaHCO_3$, brine and water. Organic layer was dried, concentrated to give a residue which is used for next step without further purification (2.7 g, 80%). [M+H] calc'd for $C_{12}H_{23}NO_3$, 230. found 230.

Ethyl 2-((benzyl(cyclopentyl)amino)methyl)-2-hydroxybutanoate: To ethyl 2-((cyclopentylamino)methyl)-2-hydroxybutanoate (2.7 g, 12 mmol) in 50 ml of acetonitrile at room temperature, was added benzyl bromide (2.1 ml, 18 mmol) dropwise, followed by $K_2CO_3$ (5 g, 35 mmol). The reaction mixture was heated at 80° C. for 18 h. It was then diluted to EtOAc, washed by brine and water. Organic extract dried and concentrated to a residue, which was purified on silica gel column chromatographically (Hex/EtOAc=100:1 to 4:1) to give 2.9 g product (77%). [M+H] calc'd for $C_{19}H_{29}NO_3$, 320. found 320.

Ethyl 2-((benzyl(cyclopentyl)amino)methyl)-2-fluorobutanoate: To ethyl 2-((benzyl(cyclopentyl)amino)methyl)-2-hydroxybutanoate (2.9 g, 9.1 mmol) in 30 ml of dichloromethane at −78° C., was added DAST (2.4 ml, 18 mmol) dropwise. The reaction mixture was gradually warmed up to room temperature and stirred for 1 h. It was then diluted to dichloromethane, washed by $NaHCO_3$, brine and water. Organic extract dried and concentrated to a residue, which was purified on silica gel column chromatographically (Hex/EtOAc=40:1 to 20:1) to give 2.2 g product (75%) as light yellow liquid. [M+H] calc'd for $C_{19}H_{28}FNO_2$, 322. found 322.

Ethyl 2-((cyclopentylamino)methyl)-2-fluorobutanoate: A solution of ethyl 2-((benzyl(cyclopentyl)amino)methyl)-2-fluorobutanoate (2.2 g, 6.8 mmol) in ethanol (20 mL) was hydrogenated with $Pd(OH)_2$ (20%, 240 mg, 0.34 mmol) in presence of TFA (6.8 mmol) at atmospheric pressure for 20 h. The reaction mixture was filtered through celite. The filtrate was concentrated and diluted to EtOAc/$H_2O$, aqueous layer was basified to pH=11-12 by 1N NaOH. The organic layer was then dried and concentrated to give the product (1.38 g, 88%) as light yellow liquid. $^1$H NMR (400 MHz, CHLOROFORM-d) δ ppm 0.95 (t, J=7.6 Hz, 3H) 1.31 (t, J=7.1 Hz, 4H) 1.41-1.94 (m, 9H) 2.88-3.08 (m, 3H) 4.26 (qd, J=7.12, 2.40 Hz, 2H). [M+H] calc'd for $C_{12}H_{22}FNO_2$, 232. found 232.

Ethyl 2-(((2-chloro-5-nitropyrimidin-4-yl)(cyclopentyl)amino)methyl)-2-fluorobutanoate: To a solution of 2,4-dichloro-5-nitropyrimidine (1.4 g, 7.2 mmol) in anhydrous acetone (50 ml) at 0° C., was added dropwise a solution of ethyl 2-((cyclopentylamino)methyl)-2-fluorobutanoate (1.38 g, 6 mmol) in acetone (10 mL) over 10 min. After which, potassium carbonate (2.5 g, 18 mmol) was added and the whole was stirred at rt for 18 h. After evaporation in vacuo, the residue was partitioned between ethyl acetate (200 ml) and water (200 ml). The organic layer was washed with $NaHCO_3$, brine and water, dried over $Na_2SO_4$ and concentrated in vacuo to give a red residue which was used directly for next step (2.6 g). [M+H] calc'd for $C_{16}H_{22}ClFN_4O_4$, 389. found 389.

2-Chloro-9-cyclopentyl-7-ethyl-7-fluoro-8,9-dihydro-5H-pyrimido[4,5-b][1,4]diazepin-6(7H)-one: To a suspension of ethyl 2-(((2-chloro-5-nitropyrimidin-4-yl)(cyclopentyl)amino)methyl)-2-fluorobutanoate (2.6 g, 6 mmol), reduced iron (840 mg, 15 mmol) in acetic acid (20 ml) was added dropwise concentrated hydrochloric acid (2 ml) at 0°

C. The reaction mixture was stirred at 60° C. for 18 h. It was then concentrated in vacuo, diluted to EtOAc, basified with 10% NaOH solution at 0° C. The whole was filtered through celite, washed with EtOAc. The filtrate was then separated. The organic layer was dried over $Na_2SO_4$. The solution was concentrated in vacuo followed by precipitation from ether to afford the product (0.9 g, 48% yield) as white solid. $^1$H NMR (400 MHz, DMSO-$d_6$) δ ppm 0.90 (t, J=7.3 Hz, 3H) 1.53-1.91 (m, 10H) 3.53-3.69 (m, 1H) 3.78 (d, J=13.4 Hz, 1H) 5.05 (t, J=8.5 Hz, 1H) 7.96 (s, 1H) 10.31 (d, J=1.5 Hz, 1H). [M+H] calc'd for $C_{14}H_{18}ClFN_4O$, 313. found 313.

2-Chloro-9-cyclopentyl-7-ethyl-7-fluoro-5-methyl-8,9-dihydro-5H-pyrimido[4,5-b][1,4]diazepin-6(7H)-one: To a solution of 2-chloro-9-cyclopentyl-7-ethyl-7-fluoro-8,9-dihydro-5H-pyrimido[4,5-b][1,4]diazepin-6(7H)-one (890 mg, 2.85 mmol) in 10 mL of DMA was added sodium hydride (60% dispersion in mineral oil, 116 mg, 2.9 mmol) at 0° C., followed by the dropwise addition of methyl iodide (0.18 mL, 2.9 mmol). The reaction mixture was warmed up to rt and stirred for 1 h. The whole was poured into ice-water, extracted with ethyl acetate. The organic layer was washed with brine and dried over $Na_2SO_4$. The solution was concentrated in vacuo followed by precipitation from ether/EtOA to afford the product (750 mg, 80% yield) as light tan solid. $^1$H NMR (400 MHz, DMSO-$d_6$) δ ppm 0.90 (t, J=7.3 Hz, 3H) 1.55-1.98 (m, 10H) 3.28 (s, 3H) 3.70-3.93 (m, 2H) 4.74 (t, J=7.9 Hz, 1H) 8.25 (s, 1H). [M+H] calc'd for $C_{15}H_{20}ClFN_4O$, 327. found 327.

4-(9-Cyclopentyl-7-ethyl-7-fluoro-5-methyl-6-oxo-6,7,8,9-tetrahydro-5H-pyrimido[4,5-b][1,4]diazepin-2-ylamino)-3-methoxybenzoic acid: A mixture of 2-chloro-9-cyclopentyl-7-ethyl-7-fluoro-5-methyl-8,9-dihydro-5H-pyrimido[4,5-b][1,4]diazepin-6(7H)-one (630 mg, 1.93 mmol), 4-amino-3-methoxybenzoic acid (484 mg, 2.9 mmol), isopropanol (20 ml), and concentrated hydrochloric acid (10 drops) was stirred at 100° C. for 20 h. Solid was filtered to give 730 mg product as white solid (83%). $^1$H NMR (400 MHz, DMSO-$d_6$) δ ppm 0.92 (t, J=7.3 Hz, 3H) 1.56 (br. s., 3H) 1.67-1.96 (m, 6H) 3.28 (s, 3H) 3.74-3.92 (m, 3H) 3.94 (s, 3H) 4.91 (t, J=7.8 Hz, 1H) 7.21-7.43 (m, 1H) 7.47-7.69 (m, 2H) 8.13 (d, J=8.1 Hz, 1H) 8.24 (s, 1H) 9.32 (br. s., 1H). [M+H] calc'd for $C_{23}H_{28}FN_5O_4$, 458. found 458.

Compound 92: 4-(9-Cyclopentyl-7-ethyl-7-fluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide

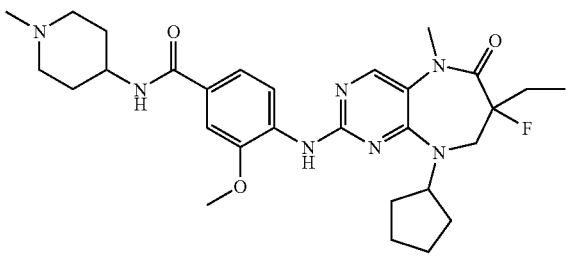

The title compound was synthesized from 4-(9-cyclopentyl-7-ethyl-7-fluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and. 1-methylpiperidin-4-amine. The final compound was purified by reverse phase HPLC and basified to give the free base. $^1$H NMR (400 MHz, DMSO-$d_6$) δ ppm 0.89 (t, J=7.3 Hz, 3H) 1.60-1.75 (m, 11H) 1.84-2.09 (m, 5H) 2.19 (s, 3H) 2.80 (d, J=11.1 Hz, 2H) 3.26 (s, 3H) 3.60-3.83 (m, 3H) 3.94 (s, 3H) 4.78 (t, J=8.1 Hz, 1H) 7.35-7.60 (m, 2H) 7.80 (s, 1H) 8.08 (d, J=7.6 Hz, 1H) 8.16 (s, 1H) 8.32 (d, J=8.3 Hz, 1H). Melting point: 149-153° C. [M+H] calc'd for $C_{29}H_{40}FN_7O_3$, 554. found 554.

Compound 93: (R) and (S)-4-(9-cyclopentyl-7-ethyl-7-fluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide

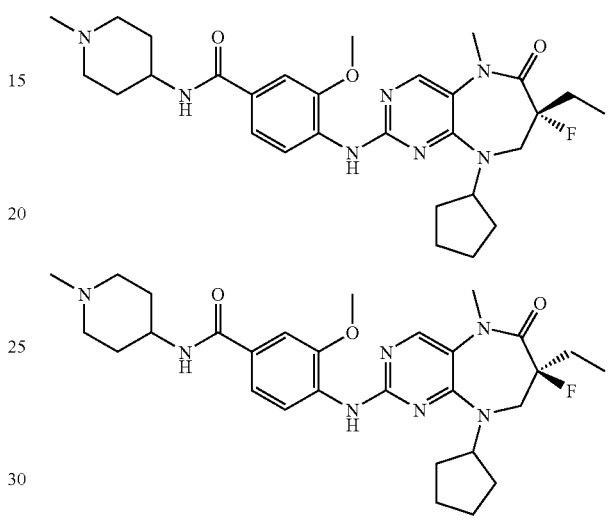

The enantiomers of 4-(9-Cyclopentyl-7-ethyl-7-fluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide were separated using SFC (ChiralPak OD-H in supercritical $CO_2$). The absolute configuration was determined using co-crystal of the title compound and PLK1 enzyme. $^1$H NMR (400 MHz, CHLOROFORM-d) δ ppm 0.99 (t, J=7.33 Hz, 3H), 1.58-1.82 (m, 9H), 1.85-2.14 (m, 5H), 2.22 (t, J=10.86 Hz, 2H), 2.35 (s, 3H), 2.90 (d, J=12.13 Hz, 2H), 3.37 (s, 3H), 3.58-3.82 (m, 2H), 3.95-4.08 (m, 4H), 4.84-4.99 (m, 1H), 5.97 (d, J=7.83 Hz, 1H), 7.24 (dd, J=8.46, 1.89 Hz, 1H), 7.43 (d, J=1.77 Hz, 1H), 7.70 (s, 1H), 7.98 (s, 1H), 8.49 (d, J=8.34 Hz, 1H) [M+H] calc'd for $C_{29}H_{40}FN_7O_3$ 554. found 554.

Compound 94: (R) and (S)-4-(9-cyclopentyl-7-ethyl-7-fluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide

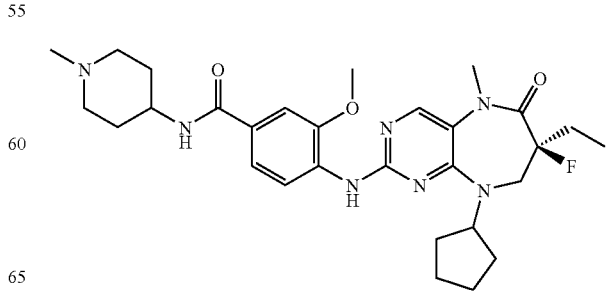

-continued

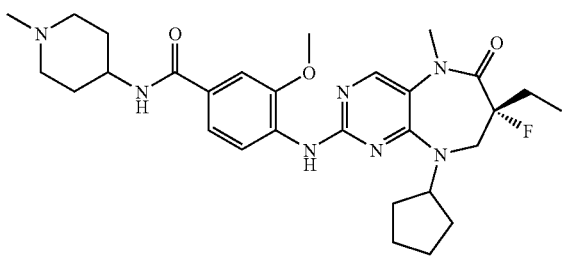

The enantiomers of 4-(9-Cyclopentyl-7-ethyl-7-fluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide were separated using SFC (ChiralPak OD-H in supercritical $CO_2$). $^1$H NMR (400 MHz, CHLOROFORM-d) δ ppm 0.99 (t, J=7.33 Hz, 3H), 1.58-1.82 (m, 9H), 1.85-2.14 (m, 5H), 2.22 (t, J=10.86 Hz, 2H), 2.35 (s, 3H), 2.90 (d, J=12.13 Hz, 2H), 3.37 (s, 3H), 3.58-3.82 (m, 2H), 3.95-4.08 (m, 4H), 4.84-4.99 (m, 1H), 5.97 (d, J=7.83 Hz, 1H), 7.24 (dd, J=8.46, 1.89 Hz, 1H), 7.43 (d, J=1.77 Hz, 1H), 7.70 (s, 1H), 7.98 (s, 1H), 8.49 (d, J=8.34 Hz, 1H) [M+H] calc'd for $C_{29}H_{40}FN_7O_3$ 554. found 554.

Compound 95: 4-(9-Cyclopentyl-7-ethyl-7-fluoro-5-methyl-6-oxo-6,7,8,9-tetrahydro-5H-pyrimido[4,5-b][1,4]diazepin-2-ylamino)-3-methoxy-N-(1-methylazetidin-3-yl)benzamide

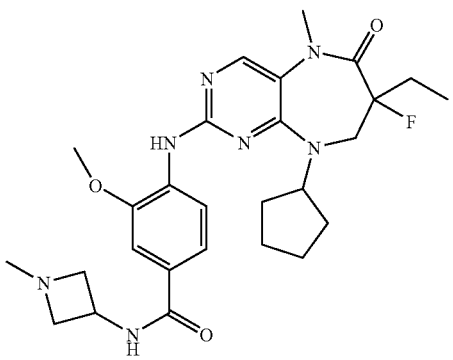

The title compound was synthesized from 4-(9-cyclopentyl-7-ethyl-7-fluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and 1-methylazetidin-3-amine hydrochloride. The final compound was purified by reverse phase HPLC and basified to give the free base. $^1$H NMR (400 MHz, DMSO-$d_6$) δ ppm 0.89 (t, J=7.3 Hz, 3H) 1.6-1.87 (m, 7H) 1.89-1.99 (m, 3H) 2.29 (s, 3H) 3.04 (t, J=7.1 Hz, 2H) 3.27 (s, 3H) 3.59 (t, J=7.2 Hz, 2H) 3.64-3.87 (m, 2H) 3.95 (s, 3H) 4.29-4.53 (m, 1H) 4.79 (t, J=8.1 Hz, 1H) 7.42-7.59 (m, 2H) 7.82 (s, 1H) 8.17 (s, 1H) 8.34 (d, J=8.3 Hz, 1H) 8.61 (d, J=6.8 Hz, 1H). [M+H] calc'd for $C_{27}H_{36}FN_7O_3$, 526. found 526.

Compound 96: 4-(9-Cyclohexyl-7-ethyl-7-fluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide

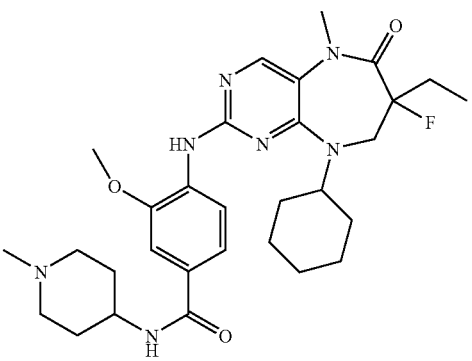

The title compound was synthesized from 4-(9-cyclohexyl-7-ethyl-7-fluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and. 1-methylpiperidin-4-amine. The final compound was purified by reverse phase HPLC and basified to give the free base. $^1$H NMR (400 MHz, DMSO-$d_6$) δ ppm 0.89 (t, J=7.4 Hz, 3H) 1.08-2.06 (m, 16H) 2.20 (s, 3H) 2.82 (d, J=11.1 Hz, 2H) 3.25 (s, 4H) 3.60-3.85 (m, 3H) 3.95 (s, 3H) 4.49 (m, 1H) 7.47 (d, J=8.3 Hz, 1H) 7.50 (s, 1H) 7.77 (s, 1H) 8.01-8.19 (m, 2H) 8.31 (d, J=8.3 Hz, 1H). [M+H] calc'd for $C_{30}H_{42}FN_7O_3$, 568. found 568.

Compound 97: 4-(9-Cyclohexyl-7-ethyl-7-fluoro-5-methyl-6-oxo-6,7,8,9-tetrahydro-5H-pyrimido[4,5-b][1,4]diazepin-2-ylamino)-3-methoxy-N-(1-methylazetidin-3-yl)benzamide

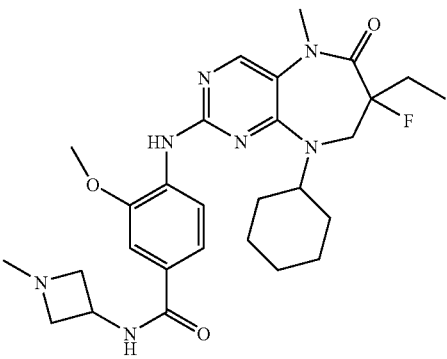

The title compound was synthesized from 4-(9-cyclohexyl-7-ethyl-7-fluoro-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and 1-methylazetidin-3-amine hydrochloride. The final compound was purified by reverse phase HPLC and basified to give the free base. $^1$H NMR (400 MHz, DMSO-$d_6$) δ ppm 0.71-0.95 (m, 1H) 0.89 (t, J=7.3 Hz, 3H) 1.07-1.92 (m, 12H) 2.29 (s, 3H) 3.03 (t, J=7.1 Hz, 2H) 3.26 (s, 3H) 3.51-3.76 (m, 1H) 3.58 (t, J=7.2 Hz, 2H) 3.76-

3.87 (m, 1H) 3.95 (s, 3H) 4.44 (m, 1H) 7.49 (d, J=8.3 Hz, 1H) 7.52 (s, 1H) 7.78 (s, 1H) 8.11 (s, 1H) 8.33 (d, J=8.6 Hz, 1H) 8.63 (d, J=6.8 Hz, 1H). [M+H] calc'd for $C_{28}H_{38}FN_7O_3$, 540. found 540.

Compound 98: 4-(9-cyclopentyl-7-fluoro-5-methyl-6-oxo-7-vinyl-6,7,8,9-tetrahydro-5H-pyrimido[4,5-b][1,4]diazepin-2-ylamino)-3-methoxybenzoic acid

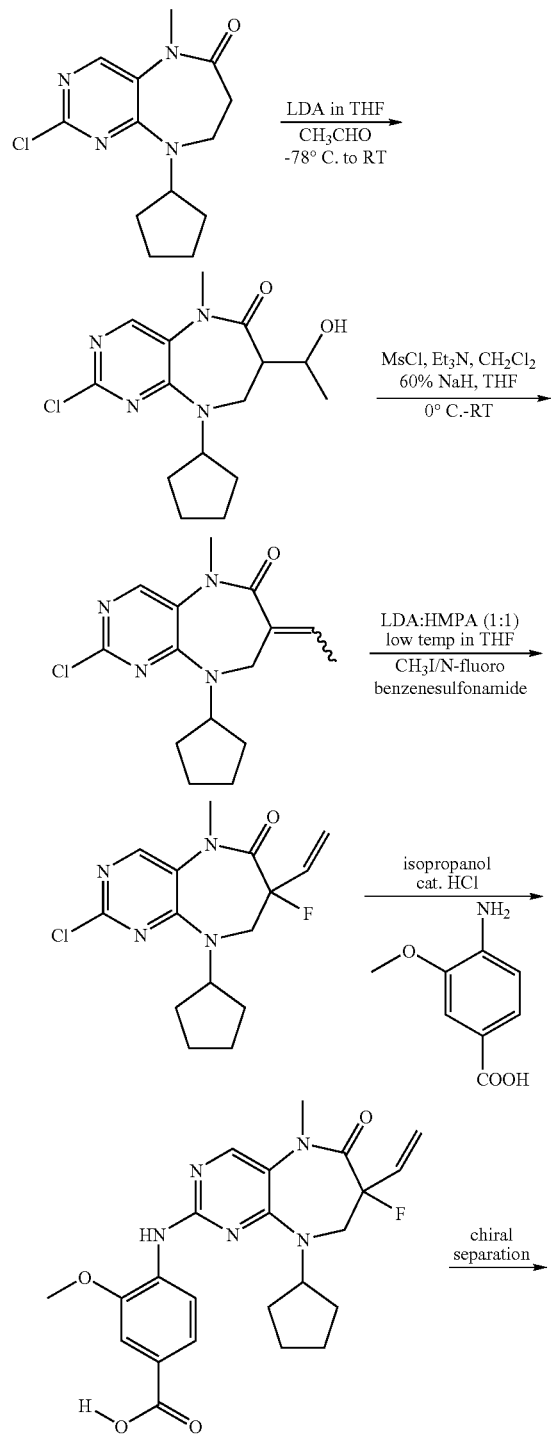

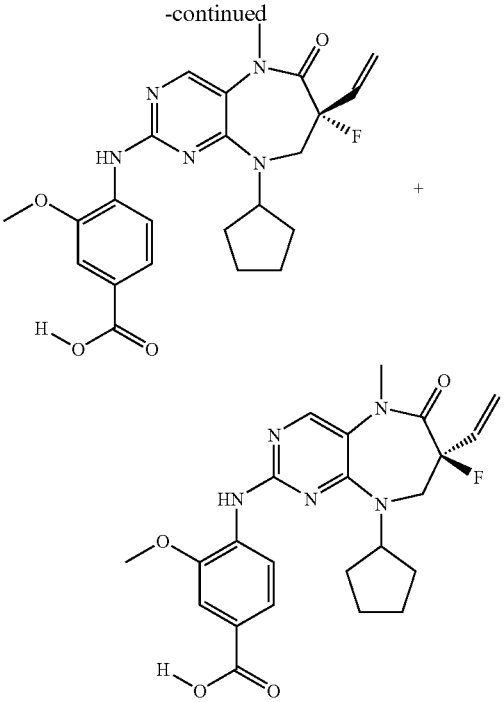

2-Chloro-9-cyclopentyl-7-(1-hydroxyethyl)-5-methyl-8,9-dihydro-5H-pyrimido[4,5-b][1,4]diazepin-6(7H)-one: In a round bottom flask, 2-chloro-9-cyclopentyl-5-methyl-8,9-dihydro-5H-pyrimido[4,5-b][1,4]diazepin-6(7H)-one (0.840 g, 3.0 mmol) was dissolved in dry tetrahydrofuran (12 mL), cooled to −78° C., then added 2.0 M lithium diisopropyl amide in tetrahydrofuran (6.0 mmol) drop wise. After 30 minutes, acetaldehyde (1.056 g, 24.0 mmol) in 6.0 mL tetrahydrofuran was added slowly drop wise to it, continued stirring for 60 minutes. After disappearing the starting material, cooled the reaction flask to −78° C., then quenched with sat. ammonium chloride solution (3 mL). At room temperature, the resultant reaction mixture was taken into ethyl acetate (50 mL), washed with 0.1 N HCl, ammonium chloride solution and finally with water, dried over sodium sulphate and evaporated. Purified the product using column chromatography with hexane:ethyl acetate mixtures to give the product (0.842 g, 86%). [M+H] calculated for $C_{15}H_{21}ClN_4O_2$, 325. found 325.

2-Chloro-9-cyclopentyl-7-ethylidene-5-methyl-8,9-dihydro-5H-pyrimido[4,5-b][1,4]diazepin-6(7H)-one: In a round bottom flask, 2-chloro-9-cyclopentyl-7-(1-hydroxyethyl)-5-methyl-8,9-dihydro-5H-pyrimido[4,5-b][1,4]diazepin-6(7H)-one (1.60 g, 4.94 mmol) was dissolved in dichloromethane (15 mL) and cooled to 0° C. Then added triethylamine (1.39 mL, 9.88 mmol) to it, after 5 minutes added methanesulfonyl chloride (0.46 mL, 5.93 mmol) drop wise, continued stirring at room temperature for 14 hrs. Then after completion, the reaction mixture was taken into dichloromethane, washed with ice cold water (50 mL), dried over sodium sulfate and evaporated. The resultant O-methane sulfonyl compound was dissolved in dry tetrahydrofuran and cooled to 0° C., and then added 60% sodium hydride in mineral oil (0.218 g, 5.47 mmol) portion wise slowly, continued at room temperature for another 30 minutes. After completing the reaction, the reaction mixture was slowly added to ice cold water (50 mL) and extracted with ethyl acetate (2×50 mL), ethyl acetate layer was dried evaporated and purified using column chromatography to yield compound 23-2 (1.38 g, 94%). $^1$H NMR (400 MHz, DMSO-$d_6$) δ ppm 1.12 (d, J=6.06 Hz, 3H) 1.42-2.10 (m, 8H) 3.18 (s, 3H) 3.42-4.05 (m, 3H) 4.75 (d, J=6.06 Hz, 1H) 4.85 (quin, J=8.39 Hz, 1H) 8.06-8.23 (m, 1H). [M+H] calculated for $C_{15}H_{19}ClN_4O$, 307. found 307.

2-Chloro-9-cyclopentyl-7-fluoro-5-methyl-7-vinyl-8,9-dihydro-5H-pyrimido[4,5-b][1,4]diazepin-6(7H)-one: 2-Chloro-9-cyclopentyl-7-ethylidene-5-methyl-8,9-dihydro-5H-pyrimido[4,5-b][1,4]diazepin-6(7H)-one (1.01 g, 3.30 mmol) in dry tetrahydrofuran (10 mL) was added to 1:1 molar 2 M lithium diisopropyl amide in tetrahydrofuran and hexamethyl phosphoramide (HMPA) (3.96 mmol each) in tetrahydrofuran (5 mL) at −78° C. After 20 minutes, N-fluorobenzene sulfonimide (2.46 mmol) was added dropwise to it. Continued the reaction at −78° C. for 30 minutes, and then elevated the temperature to 0° C. for 30 minutes. After disappearing the starting material, cooled the reaction flask to −78° C., then quenched with sat. ammonium chloride solution (6 mL). At room temperature, the resultant reaction mixture was taken into ethyl acetate (70 mL), washed with ammonium chloride solution and finally with water, dried over sodium sulphate and evaporated. Purified the product using column chromatography with hexane:ethyl acetate mixtures to give the product. $^1$H NMR (400 MHz, CHLOROFORM-d) δ ppm 1.53-2.10 (m, 8H) 3.38 (s, 3H) 3.63-3.88 (m, 2H) 4.12 (m, 1H) 4.96 (quin, J=8.59 Hz, 1H) 5.41 (d, J=11.12 Hz, 1H) 5.49 (dd, J=17.18, 2.02 Hz, 1H) 6.02 (ddd, J=17.37, 14.72, 10.86 Hz, 1H) 7.97 (s, 1H). [M+H] calculated for $C_{15}H_{18}ClFN_4O$, 325. found 325.

4-(9-Cyclopentyl-7-fluoro-5-methyl-6-oxo-7-vinyl-6,7,8,9-tetrahydro-5H-pyrimido[4,5-b][1,4]diazepin-2-ylamino)-3-methoxybenzoic acid: 2-Chloro-9-cyclopentyl-7-fluoro-5-methyl-7-vinyl-8,9-dihydro-5H-pyrimido[4,5-b][1,4]diazepin-6(7H)-one, 4-amino-3-methoxy benzoic acid (1.2 equivalent), i-PrOH and conc. HCl (30 drops) were heated to 95° C. for 18 hours. A this time the reaction was cooled to room temperature and filtered to reveal the product as a tan solid in good yield). $^1$H NMR (400 MHz, DMSO-d$_6$) δ ppm 1.51-1.75 (m, 6H) 1.85 (m, 2H) 3.29 (s, 3H) 3.73-3.97 (m, 2H) 3.93 (s, 3H) 4.94 (m, 1H) 5.40-5.54 (m, 2H) 6.05 (m, 1H) 7.48-7.65 (m, 2H) 8.09 (d, J=8.34 Hz, 1H) 8.23 (s, 1H) 9.51 (br. s., 1H). [M+H] calculated for $C_{23}H_{26}FN_5O_4$, 456. found 456.

The compound 4-(9-cyclopentyl-7-fluoro-5-methyl-6-oxo-7-vinyl-6,7,8,9-tetrahydro-5H-pyrimido[4,5-b][1,4]diazepin-2-ylamino)-3-methoxybenzoic acid was separated into its enantiomers using SFC (ChiralPak OD-H in supercritical $CO_2$). The absolute chirality was determined by co-crystallization of one of the enantiomeric components with PLK1 enzyme.

Compound 99: 4-(9-cyclopentyl-7-fluoro-5-methyl-6-oxo-7-vinyl-6,7,8,9-tetrahydro-5H-pyrimido[4,5-b][1,4]diazepin-2-ylamino)-3-methoxy-N-(1-methylpiperidin-4-yl)benzamide The title compound was synthesized from 4-(9-cyclohexyl-7-fluoro-7-vinyl-6-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and 4-amino 1-N-methyl piperidine. $^1$H NMR (400 MHz, DMSO-d$_6$) δ ppm 1.53-1.86 (m, 8H) 1.93 (t, J=10.86 Hz, 4H) 2.16 (s, 3H) 2.78 (d, J=11.12 Hz, 2H) 3.28 (s, 3H) 3.65-3.83 (m, 4H) 3.93 (s, 3H) 4.88 (m, 1H) 5.38 (d, J=11.87 Hz, 2H) 6.01 (m, 1H) 7.48 (d, J=8.0 Hz, 1H), 7.49 (br. s., 1H) 7.82 (s, 1H) 8.12 (s, 1H) 8.12 (d, J=7.83 Hz, 1H) 8.30 (d, J=8.0 Hz, 1H). [M+H] calculated for $C_{29}H_{38}FN_7O_3$, 552. found 552.

Compound 100: 4-(9-cyclopentyl-7-fluoro-5-methyl-6-oxo-7-vinyl-6,7,8,9-tetrahydro-5H-pyrimido[4,5-b][1,4]diazepin-2-ylamino)-3-methoxy-N-(1-methylazetidin-3-yl)benzamide

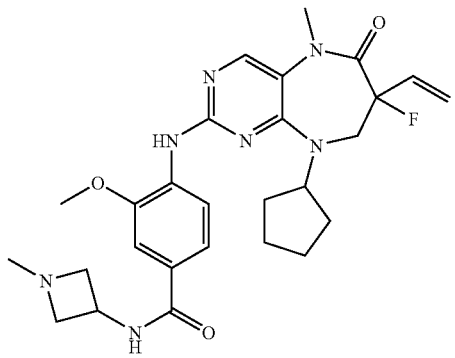

The title compound was synthesized from 4-(9-cyclohexyl-7-fluoro-7-vinyl-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and 1-methylazetidin-3-amine bis-hydrochloride. $^1$H NMR (400 MHz, DMSO-d$_6$) δ ppm 1.48-2.10 (m, 8H) 2.32 (br. s., 3H) 3.08 (t, J=6.82 Hz, 2H) 3.29 (br. s., 3H) 3.62 (t, J=6.95 Hz, 2H) 3.82 (m, 2H) 3.94 (br. s., 3H) 4.44 (m, 1H) 4.88 (m, 1H) 5.38 (d, J=12.13 Hz, 2H) 5.99 (m, 1H) 7.50 (br. s., 2H) 7.84 (br. s., 1H) 8.13 (br. s., 1H)) 8.31 (d, J=8.0 Hz, 1H) 8.65 (d, J=7.83 Hz, 1H). [M+H] calculated for $C_{27}H_{34}FN_7O_3$, 524. found 524.

Compound 101: 4-(9-cyclopentyl-7-fluoro-5-methyl-6-oxo-7-vinyl-6,7,8,9-tetrahydro-5H-pyrimido[4,5-b][1,4]diazepin-2-ylamino)-3-methoxy-N-(4-methylpiperazin-1-yl)benzamide

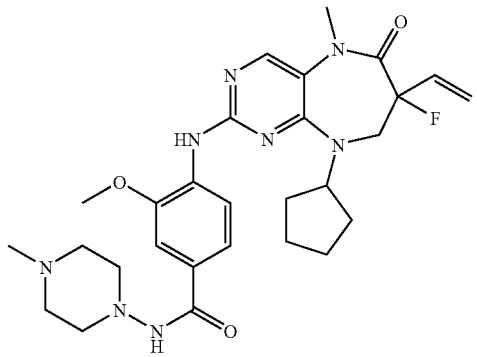

The title compound was synthesized from 4-(9-cyclohexyl-7-fluoro-7-vinyl-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and 1-amino 4-methylpiperazine. $^1$H NMR (400 MHz, DMSO-$d_6$) δ ppm 1.48-2.05 (m, 8H) 2.22 (br. s., 3H) 2.42 (m, 4H) 2.93 (t, J=4.55 Hz, 4H) 3.28 (br. s., 3H) 3.72 (m, 2H) 3.93 (br. s., 3H) 4.87 (m, 1H) 5.39 (d, 2H) 5.99 (m, 1H) 7.43 (br. s, 2H) 7.82 (s, 1H) 8.12 (br. s., 1H) 8.32 (d, J=8.0 Hz, 1H) 9.36 (s, 1H). Melting point: 253-263° C. [M+H] calculated for $C_{28}H_{37}FN_8O_3$, 553. found 553.

Compound 102: 4-(9-cyclopentyl-7-fluoro-5-methyl-6-oxo-7-vinyl-6,7,8,9-tetrahydro-5H-pyrimido[4,5-b][1,4]diazepin-2-ylamino)-3-methoxy-N—((R)-piperidin-3-yl)benzamide

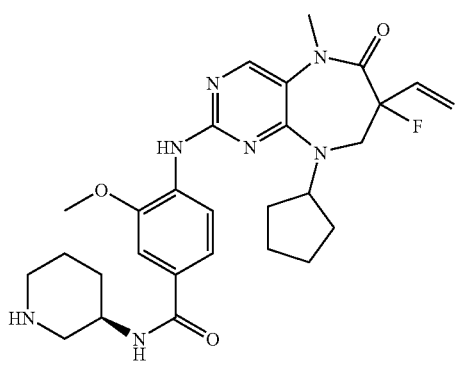

The title compound was synthesized from 4-(9-cyclohexyl-7-fluoro-7-vinyl-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and (R)-1-Boc-3-aminopiperidine. Further, after washing with water (10 ml), t-butoxycarbonyl (Boc) protection group was removed using 40% TFA in dichloromethane (6 ml) and purified the product using preparative HPLC. $^1$H NMR (400 MHz, DMSO-$d_6$) δ ppm 1.41-2.00 (m, 12H) 2.39 (t, J=6.5 Hz, 2H) 2.81 (d, J=12.38 Hz, 1H) 2.96 (d, J=12.38 Hz, 1H) 3.28 (s, 3H) 3.70-3.88 (m, 3H) 3.94 (s, 2H) 4.88 (m, 1H) 5.37 (d, 2H) 6.00 (m, 1H) 7.47 (d, J=8.0 Hz, 1H), 7.48 (br. s., 1H) 7.82 (s, 1H) 7.98 (d, J=8.0 Hz, 1H) 8.12 (s, 1H) 8.30 (d, J=8.0 Hz, 1H). Melting point: 169-172° C. [M+H] calculated for $C_{28}H_{36}FN_7O_3$, 538. found 538.

Compound 103: (R)-4-(9-cyclopentyl-7-fluoro-5-methyl-6-oxo-7-vinyl-6,7,8,9-tetrahydro-5H-pyrimido[4,5-b][1,4]diazepin-2-ylamino)-3-methoxy-N-(1-methylpiperidin-4-yl)benzamide

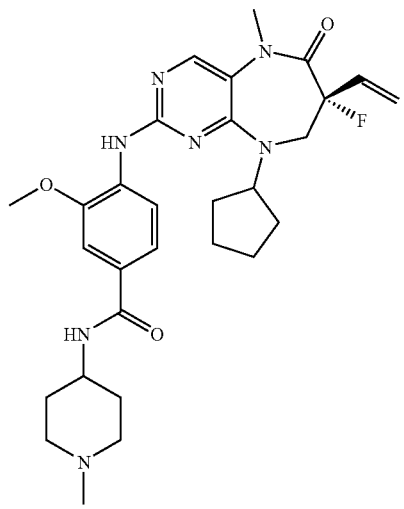

The title compound was synthesized from (R)-4-(9-cyclohexyl-7-fluoro-7-vinyl-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and 4-amino 1-N-methyl piperidine. $^1$H NMR (400 MHz, DMSO-$d_6$) δ ppm 0.79-0.93 (m, 2H) 1.18-1.31 (m, 2H) 1.50-1.80 (m, 6H) 1.83-2.00 (m, 4H) 2.17 (s, 3H) 2.71-2.95 (m, 2H) 3.29 (s, 3H) 3.67-3.87 (m, 3H) 3.94 (s, 3H) 4.89 (d, J=8.59 Hz, 1H) 5.30-5.47 (m, 2H) 6.01 (ddd, J=17.49, 12.69, 10.74 Hz, 1H) 7.41-7.54 (m, 2H) 7.82 (s, 1H) 8.12 (s, 2H) 8.30 (d, J=8.34 Hz, 1H). [M+H] calc'd for $C_{29}H_{38}FN_7O_3$, 552. found 552.

Compound 104: (S)-4-(9-cyclopentyl-7-fluoro-5-methyl-6-oxo-7-vinyl-6,7,8,9-tetrahydro-5H-pyrimido[4,5-b][1,4]diazepin-2-ylamino)-3-methoxy-N-(1-methylpiperidin-4-yl)benzamide

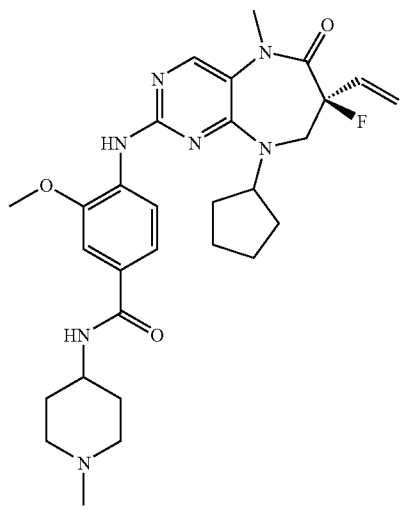

The title compound was synthesized from (S)-4-(9-cyclohexyl-7-fluoro-7-vinyl-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and 4-amino 1-N-methyl piperidine. $^1$H NMR (400 MHz, DMSO-d$_6$) δ ppm 0.79-0.93 (m, 2H) 1.18-1.31 (m, 2H) 1.50-1.80 (m, 6H) 1.83-2.00 (m, 4H) 2.17 (s, 3H) 2.71-2.95 (m, 2H) 3.29 (s, 3H) 3.67-3.87 (m, 3H) 3.94 (s, 3H) 4.89 (d, J=8.59 Hz, 1H) 5.30-5.47 (m, 2H) 6.01 (ddd, J=17.49, 12.69, 10.74 Hz, 1H) 7.41-7.54 (m, 2H) 7.82 (s, 1H) 8.12 (s, 2H) 8.30 (d, J=8.34 Hz, 1H) [M+H] calc'd for $C_{29}H_{38}FN_7O_3$, 552. found 552.

Compound 105: (R)-4-(9-cyclopentyl-7-fluoro-5-methyl-6-oxo-7-vinyl-6,7,8,9-tetrahydro-5H-pyrimido[4,5-b][1,4]diazepin-2-ylamino)-N-(1-ethylpiperidin-4-yl)-3-methoxybenzamide

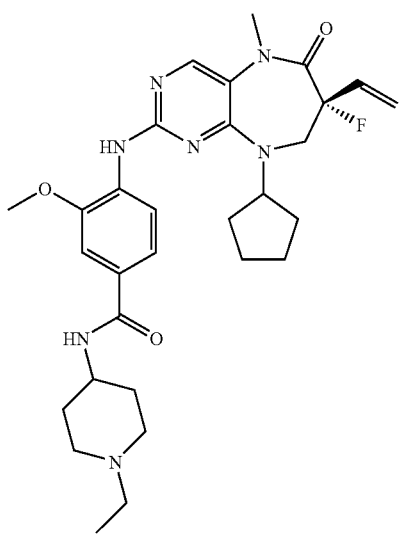

The title compound was synthesized from (R)-4-(9-cyclohexyl-7-fluoro-7-vinyl-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and 4-amino 1-N-ethyl piperidine. $^1$H NMR (400 MHz, DMSO-d$_6$) δ ppm 1.47-2.04 (m, 16H) 2.32 (q, J=7.07 Hz, 3H) 2.88 (d, J=11.62 Hz, 2H) 3.28 (s, 3H) 3.67-3.87 (m, 3H) 3.94 (s, 3H) 4.87 (d, J=8.34 Hz, 1H) 5.30-5.45 (m, 2H) 6.01 (ddd, J=17.43, 12.88, 10.86 Hz, 1H) 7.46 (d, J=1.77 Hz, 2H) 7.82 (s, 1H) 8.12 (s, 2H) 8.30 (d, J=8.08 Hz, 1H). [M+H] calc'd for $C_{30}H_{40}FN_7O_3$, 566. found 566.

Compound 106: (R)-4-(9-cyclopentyl-7-fluoro-5-methyl-6-oxo-7-vinyl-6,7,8,9-tetrahydro-5H-pyrimido[4,5-b][1,4]diazepin-2-ylamino)-N-(1-(2-hydroxyethyl)piperidin-4-yl)-3-methoxybenzamide

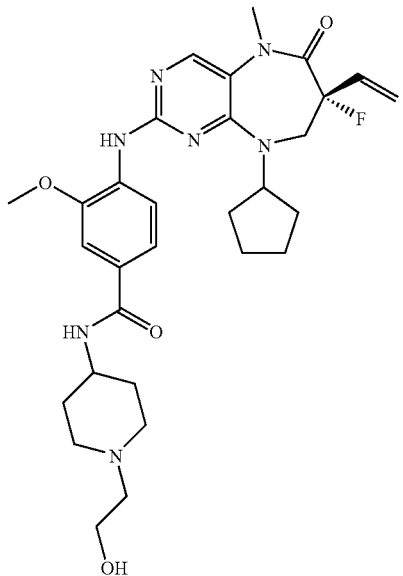

The title compound was synthesized from (R)-4-(9-cyclohexyl-7-fluoro-7-vinyl-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and 2-(4-aminopiperidin-1-yl)ethanol. $^1$H NMR (400 MHz, DMSO-d$_6$) δ ppm 1.47-2.14 (m, 15H) 2.38 (t, J=6.32 Hz, 3H) 2.89 (d, J=11.62 Hz, 2H) 3.28 (s, 3H) 3.49 (q, J=6.23 Hz, 2H) 3.67-3.85 (m, 3H) 3.94 (s, 3H) 4.37 (t, J=5.43 Hz, 1H) 4.89 (d, J=8.34 Hz, 1H) 5.28-5.48 (m, 2H) 6.01 (ddd, J=17.56, 12.76, 10.86 Hz, 1H) 7.40-7.54 (m, 2H) 7.82 (s, 1H) 8.10 (d, J=7.58 Hz, 2H) 8.30 (d, J=8.34 Hz, 1H). [M+H] calc'd for $C_{30}H_{40}FN_7O_4$, 582. found 582.

Compound 107: 4-((R)-9-cyclopentyl-7-fluoro-5-methyl-6-oxo-7-vinyl-6,7,8,9-tetrahydro-5H-pyrimido[4,5-b][1,4]diazepin-2-ylamino)-3-methoxy-N—((R)-piperidin-3-yl)benzamide

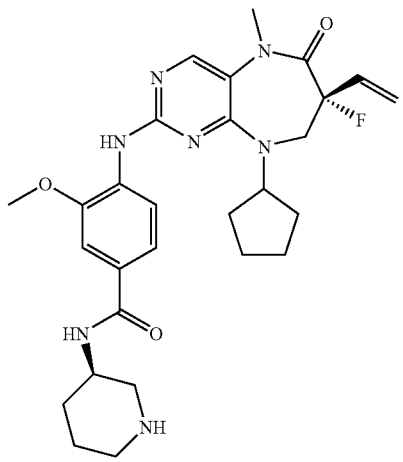

The title compound was synthesized from (R)-4-(9-cyclohexyl-7-fluoro-7-vinyl-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and (R)-1-Boc-3-aminopiperidine. Further, after washing with water (10 ml), t-butoxycarbonyl (Boc) protection group was removed using 40% TFA in dichloromethane (6 ml) and purified the product using preparative HPLC and basified using sodium bicarbonate solution to give free base. $^1$H NMR (400 MHz, DMSO-d$_6$) δ ppm 1.20-1.33 (m, 2H) 1.30-1.80 (m, 7H) 1.81-2.02 (m, 4H) 2.31-2.45 (m, 2H) 2.81 (d, J=12.63 Hz, 1H) 2.97 (d, J=8.08 Hz, 1H) 3.29 (s, 3H) 3.71-3.90 (m, 3H) 3.94 (s, 3H) 4.89 (d, J=8.59 Hz, 1H) 5.32-5.45 (m, 2H) 6.01 (ddd, J=17.56, 12.76, 10.86 Hz, 1H) 7.41-7.53 (m, 2H) 7.82 (s, 1H) 8.00 (d, J=7.83 Hz, 1H) 8.12 (s, 1H) 8.31 (d, J=8.08 Hz, 1H). [M+H] calc'd for C$_{28}$H$_{36}$FN$_7$O$_3$, 538. found 538.

Compound 108: (R)-4-(9-cyclopentyl-7-fluoro-5-methyl-6-oxo-7-vinyl-6,7,8,9-tetrahydro-5H-pyrimido[4,5-b][1,4]diazepin-2-ylamino)-N-(1-(2-(dimethylamino)acetyl)piperidin-4-yl)-3-methoxybenzamide

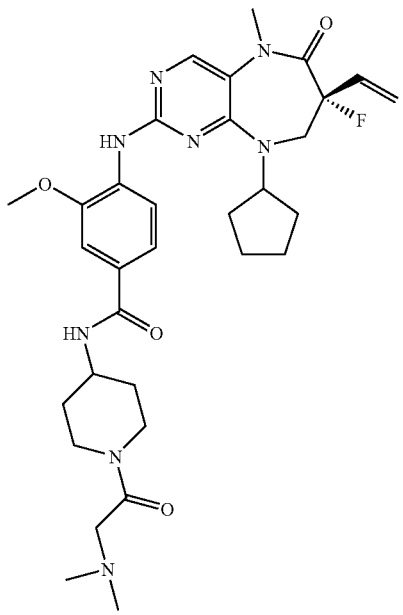

The title compound was synthesized from (R)-4-(9-cyclohexyl-7-fluoro-7-vinyl-5-methyl-6-oxo-6,7,8,9-tetrahydro-5H-pyrimido[5,4-b][1,4]diazepin-2-ylamino)-3-methoxybenzoic acid as described in the General procedure for amide bond synthesis using HATU and 1-Boc-4-aminopiperidine. Further, after washing with water (10 ml), t-butoxycarbonyl (Boc) protection group was removed using 40% TFA in dichloromethane (6 ml). The resulting product was further acylated using N,N-dimethylacetyl chloride. The title product using preparative HPLC and neutralized with bicarbonate. $^1$H NMR (400 MHz, DMSO-d$_6$) δ ppm 1.41-2.05 (m, 12H) 2.19 (s, 6H) 2.92-3.21 (m, 4H) 3.28 (s, 3H) 3.72-3.87 (m, 2H) 3.94 (s, 3H) 3.99-4.20 (m, 2H) 4.36 (d, J=15.41 Hz, 1H) 4.89 (d, J=8.34 Hz, 1H) 5.31-5.45 (m, 2H) 6.01 (ddd, J=17.49, 12.69, 10.74 Hz, 1H) 7.47 (d, J=1.77 Hz, 2H) 7.83 (s, 1H) 8.15 (d, J=7.83 Hz, 2H) 8.31 (d, J=8.08 Hz, 1H). [M+H] calc'd for C$_{32}$H$_{43}$FN$_8$O$_4$, 623. found 623.

Compound 109: (R)-4-(9-cyclopentyl-7-fluoro-5-methyl-6-oxo-7-vinyl-6,7,8,9-tetrahydro-5H-pyrimido[4,5-b][1,4]diazepin-2-ylamino)-3-methoxy-N-(4-methylpiperazin-1-yl)benzamide

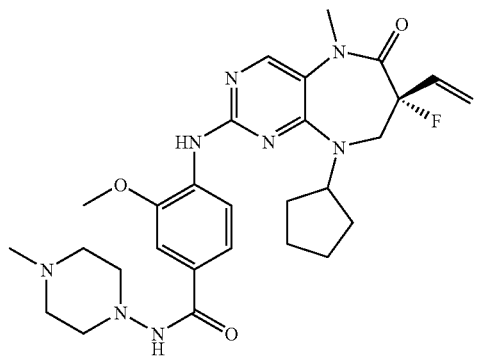

The title compound was obtained from Compound 101 after chiral separation using SFC (ChiralPak OD-H in supercritical CO$_2$). The absolute chirality was determined by co-crystallization of one of the enantiomeric components with PLK1 enzyme. $^1$H NMR (400 MHz, DMSO-d$_6$) δ ppm 1.48-2.05 (m, 8H) 2.22 (br. s., 3H) 2.42 (m, 4H) 2.93 (t, J=4.55 Hz, 4H) 3.28 (br. s., 3H) 3.72 (m, 2H) 3.93 (br. s., 3H) 4.87 (m, 1H) 5.39 (d, 2H) 5.99 (m, 1H) 7.43 (br. s., 2H) 7.82 (s, 1H) 8.12 (br. s., 1H) 8.32 (d, J=8.0 Hz, 1H) 9.36 (s, 1H). [M+H] calculated for C$_{28}$H$_{37}$FN$_8$O$_3$, 553. found 553.

Compound 110: (S)-4-(9-cyclopentyl-7-fluoro-5-methyl-6-oxo-7-vinyl-6,7,8,9-tetrahydro-5H-pyrimido[4,5-b][1,4]diazepin-2-ylamino)-3-methoxy-N-(4-methylpiperazin-1-yl)benzamide

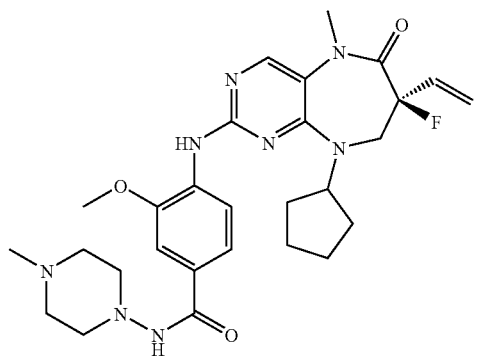

The title compound was obtained from Compound 101 after chiral separation using SFC (ChiralPak OD-H in supercritical CO$_2$). The absolute chirality was determined by co-crystallization of one of the enantiomeric components with PLK1 enzyme. $^1$H NMR (400 MHz, DMSO-d$_6$) δ ppm 1.48-2.05 (m, 8H) 2.22 (br. s., 3H) 2.42 (m, 4H) 2.93 (t, J=4.55 Hz, 4H) 3.28 (br. s., 3H) 3.72 (m, 2H) 3.93 (br. s., 3H) 4.87 (m, 1H) 5.39 (d, 2H) 5.99 (m, 1H) 7.43 (br. s., 2H) 7.82 (s, 1H) 8.12 (br. s., 1H) 8.32 (d, J=8.0 Hz, 1H) 9.36 (s, 1H). [M+H] calculated for C$_{28}$H$_{37}$FN$_8$O$_3$, 553. found 553.

Compound 111: (R)-2-(4-(4-(9-cyclopentyl-7-fluoro-5-methyl-6-oxo-7-vinyl-6,7,8,9-tetrahydro-5H-pyrimido[4,5-b][1,4]diazepin-2-ylamino)-3-methoxybenzamido) piperidin-1-yl)ethyl dihydrogen phosphate

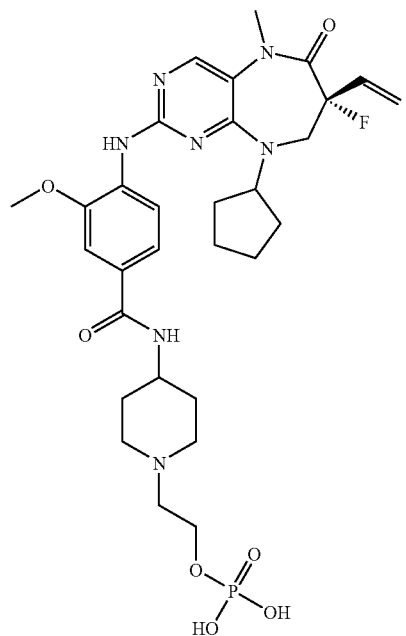

The title compound was synthesized from (R)-4-(9-cyclopentyl-7-fluoro-5-methyl-6-oxo-7-vinyl-6,7,8,9-tetrahydro-5H-pyrimido[4,5-b][1,4]diazepin-2-ylamino)-N-(1-(2-hydroxyethyl)piperidin-4-yl)-3-methoxybenzamide as described in the procedure for the preparation of compound 41. The final compound was purified by reverse phase HPLC and basified to give the free base. $^1$H NMR (400 MHz, DMSO-$d_6$) δ ppm 1.48-1.82 (m, 9H) 1.83-2.15 (m, 4H) 2.27-2.45 (m, 2H) 2.79-3.03 (m, 2H) 3.29 (s, 3H) 3.50 (d, J=4.80 Hz, 2H) 3.66-3.86 (m, 3H) 3.94 (s, 3H) 4.21 (s, 1H) 4.39 (dd, J=11.12, 5.81 Hz, 1H) 5.29-5.47 (m, 2H) 6.01 (dd, J=17.43, 1.77 Hz, 1H) 7.39-7.57 (m, 2H) 7.82 (s, 1H) 8.12 (s, 2H) 8.31 (d, J=8.08 Hz, 1H) 9.88 (s, 2H) [M+H] calc'd for $C_{30}H_{41}FN_7O_7P$ 662. found 662.

Compound 112: (R)-4-(9-cyclopentyl-7-fluoro-5-methyl-6-oxo-7-vinyl-6,7,8,9-tetrahydro-5H-pyrimido[4,5-b][1,4]diazepin-2-ylamino)-2-fluoro-5-methoxybenzoic acid a)

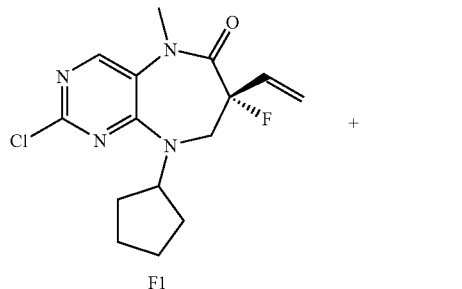

F1

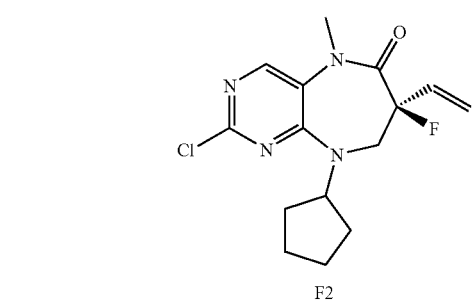

F2 b)

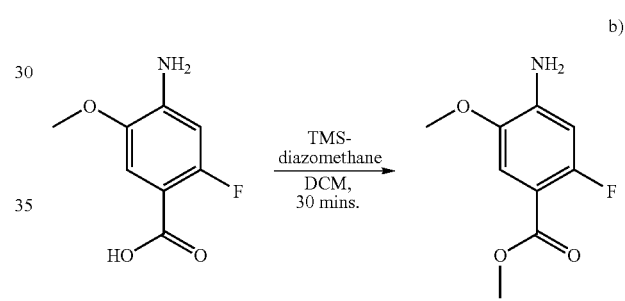

c)

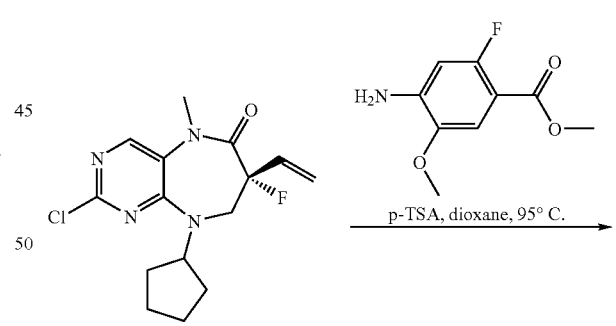

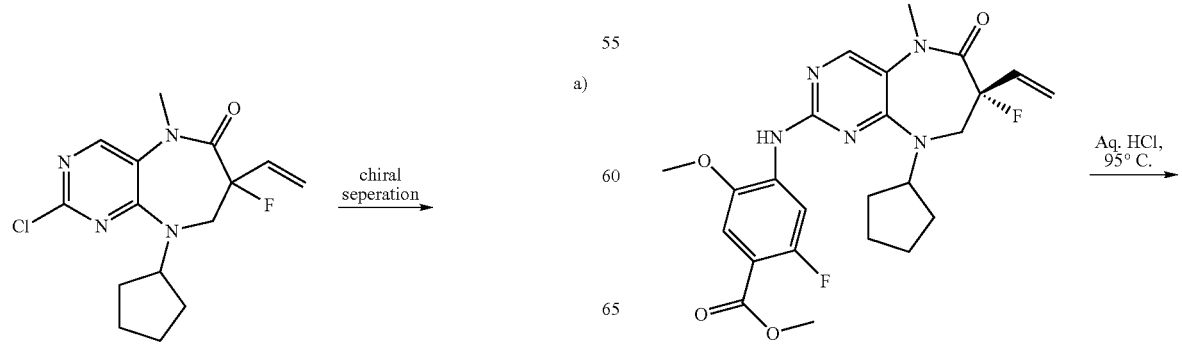

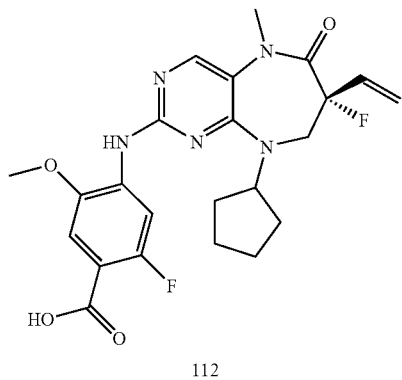

112

(R)- and (S)-2-chloro-9-cyclopentyl-7-fluoro-5-methyl-7-vinyl-8,9-dihydro-5H-pyrimido[4,5-b][1,4]diazepin-6(7H)-one: The racemic form of the title compounds was synthesized from Chloro-9-cyclopentyl-7-(1-hydroxyethyl)-5-methyl-8,9-dihydro-5H-pyrimido[4,5-b][1,4]diazepin-6(7H)-one as described in general procedure. The enantiomers were separated using SFC (CHIRAPAK AS 50 mm ID×500 mL, mobile phase: n-Hexane/2-Propanol=900/100 v/v.) Fraction 1 (F1) was (R)-2-chloro-9-cyclopentyl-7-fluoro-5-methyl-7-vinyl-8,9-dihydro-5H-pyrimido[4,5-b][1,4]diazepin-6(7H)-one. The compound 4-(9-cyclopentyl-7-fluoro-5-methyl-6-oxo-7-vinyl-6,7,8,9-tetrahydro-5H-pyrimido[4,5-b][1,4]diazepin-2-ylamino)-3-methoxybenzoic acid was separated into its enantiomers using SFC (ChiralPak OD-H in supercritical $CO_2$). The absolute chirality was determined by co-crystallization of one of the enantiomeric components after conversion to an amide with PLK1 enzyme. $^1$H NMR (400 MHz, DMSO-$d_6$) δ ppm 1.48-1.79 (m, 8H) 1.81-1.99 (m, 2H) 3.30 (s, 3H) 3.77-3.95 (m, 2H) 4.83 (quin, J=8.27 Hz, 1H) 5.32-5.52 (m, 2H) 6.01 (ddd, J=17.43, 12.38, 11.12 Hz, 1H) 8.21 (s, 1H) [M+H] calc'd for $C_{15}H_{18}ClFN_4O$ 325. found 325. Fraction 2 (F2) was (S)-2-chloro-9-cyclopentyl-7-fluoro-5-methyl-7-vinyl-8,9-dihydro-5H-pyrimido[4,5-b][1,4]diazepin-6(7H)-one). $^1$H NMR (400 MHz, DMSO-$d_6$) δ ppm 1.48-1.79 (m, 8H) 1.81-1.99 (m, 2H) 3.30 (s, 3H) 3.77-3.95 (m, 2H) 4.83 (quin, J=8.27 Hz, 1H) 5.32-5.52 (m, 2H) 6.01 (ddd, J=17.43, 12.38, 11.12 Hz, 1H) 8.21 (s, 1H) [M+H] calc'd for $C_{15}H_{18}ClFN_4O$ 325. found 325.

Methyl 4-amino-2-fluoro-5-methoxybenzoate: To an amount of 4-amino-2-fluoro-5-methoxybenzoic acid (4 g, 21.62 mmole) that was dissolved in DCM (40 ml) and MeOH (11 mL), was added TMS-diazomethane (16.2 mL, 32.43 mmole) slowly. The mixture was stirred at r.t for 30 mins. After the removal of solvent, the resulting tan solid (4.0 g, 93%) carried onto the next reaction without any purification. [M+H] calc'd for $C_9H_{10}FNO_3$, 200. found 200.

(R)-methyl 4-(9-cyclopentyl-7-fluoro-5-methyl-6-oxo-7-vinyl-6,7,8,9-tetrahydro-5H-pyrimido[4,5-b][1,4]diazepin-2-ylamino)-2-fluoro-5-methoxybenzoate: A mixture of (R)-2-chloro-9-cyclopentyl-7-fluoro-5-methyl-7-vinyl-8,9-dihydro-5H-pyrimido[4,5-b][1,4]diazepin-6(7H)-one (1.0 g, 3.086 mmol), and methyl 4-amino-2-fluoro-5-methoxybenzoate (3.07 g, 15.43 mmol) was dissolved in dioxane (20 ml), and p-toluenesulfonic acid, monohydrate (2.99 g, 15.74 mmol) was added. The mixture was stirred at 95° C. for 24-48 h. The final compound was purified by reverse phase HPLC to give 400 mg product as white solid (40%). $^1$H NMR (400 MHz, DMSO-$d_6$) δ ppm 1.48-1.82 (m, 4H) 1.93-1.98 (m, 4H) 3.29 (s, 3H) 3.51 (br. s., 2H) 3.61 (m, 3H), 3.86 (m, 3H) 3.94 (s, 3H) 4.88 (t, J=8.08 Hz, 1H) 5.30-5.47 (m, 2H) 6.01 (ddd, J=17.43, 12.63, 10.86 Hz, 1H) 7.41-7.57 (m, 1H) 7.82 (s, 1H) 8.12 (s, 1H) 8.31 (d, J=8.08 Hz, 1H). [M+H] calc'd for $C_{24}H_{27}F_2N_5O_4$, 488. found 488.

(R)-4-(9-cyclopentyl-7-fluoro-5-methyl-6-oxo-7-vinyl-6,7,8,9-tetrahydro-5H-pyrimido[4,5-b][1,4]diazepin-2-ylamino)-2-fluoro-5-methoxybenzoic acid: A mixture of (R)-methyl 4-(9-cyclopentyl-7-fluoro-5-methyl-6-oxo-7-vinyl-6,7,8,9-tetrahydro-5H-pyrimido[4,5-b][1,4]diazepin-2-ylamino)-2-fluoro-5-methoxybenzoate (400 mg, 0.821 mmol) was suspended in conc. HCl (1.0 mL) and it was stirred at 95° C. for 3-4 hrs. At this time the reaction was cooled to room temperature and filtered to reveal the product as a tan solid (295 mg, 77%). $^1$H NMR (400 MHz, DMSO-$d_6$) δ ppm 1.48-1.82 (m, 4H) 1.98-2.02 (m, 4H) 3.29 (s, 3H) 3.51 (br. s., 2H) 3.94 (s, 3H) 4.88 (t, J=8.08 Hz, 1H) 5.30-5.47 (m, 2H) 6.01 (ddd, J=17.43, 12.63, 10.86 Hz, 1H) 7.41-7.57 (m, 1H) 7.82 (s, 1H) 8.12 (s, 1H) 8.31 (d, J=8.08 Hz, 1H). [M+H] calc'd for $C_{23}H_{25}F_2N_5O_4$, 474. found 474.

Compound 113: (R)-4-(9-cyclopentyl-7-fluoro-5-methyl-6-oxo-7-vinyl-6,7,8,9-tetrahydro-5H-pyrimido[4,5-b][1,4]diazepin-2-ylamino)-2-fluoro-5-methoxy-N-(1-methylpiperidin-4-yl)benzamide

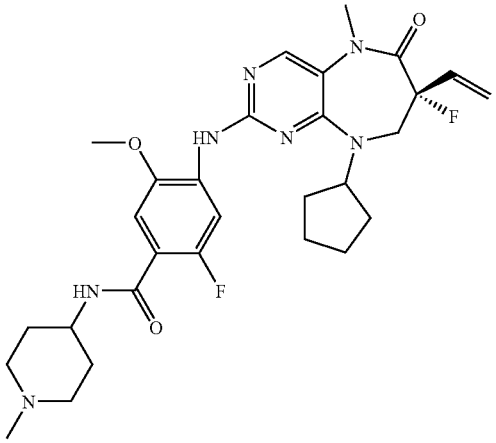

The title compound was synthesized from (R)-4-(9-cyclopentyl-7-fluoro-5-methyl-6-oxo-7-vinyl-6,7,8,9-tetrahydro-5H-pyrimido[4,5-b][1,4]diazepin-2-ylamino)-2-fluoro-5-methoxybenzoic acid as described in the general procedure for amide bond synthesis using HATU and 4-amino 1-methylpiperidine. The final compound was purified by reverse phase HPLC and basified to give the free base. $^1$H NMR (400 MHz, CHLOROFORM-d) δ ppm 1.19-1.90 (m, 8H) 2.05 (dd, J=4.29, 1.52 Hz, 4H) 2.16-2.28 (m, 2H) 2.34 (s, 3H) 2.83 (br. s., 2H) 3.39 (s, 3H) 3.69-3.89 (m, 2H) 3.96 (s, 3H) 4.00-4.10 (m, 1H) 4.97 (quin, J=8.46 Hz, 1H) 5.37 (d, J=11.12 Hz, 1H) 5.50 (dd, J=17.30, 1.89 Hz, 1H) 6.02 (ddd, J=17.30, 14.53, 10.86 Hz, 1H) 6.67 (d, J=7.07 Hz, 1H) 7.56 (d, J=7.07 Hz, 1H) 7.76 (s, 1H) 7.96 (s, 1H) 8.37 (d, J=15.16 Hz, 1H), [M+H] calc'd for $C_{29}H_{37}F_2N_7O_3$ 570. found 570.

257

Compound 114: N-1-(2-amino-2-oxoethyl)piperidin-4-yl)-4-(9-cyclopentyl-7,7-difluoro-5-methyl-6-oxo-6,7,8,9-tetrahydro-5H-pyrimido[4,5-b][1,4]diazepin-2-ylamino)-3-methoxybenzamide

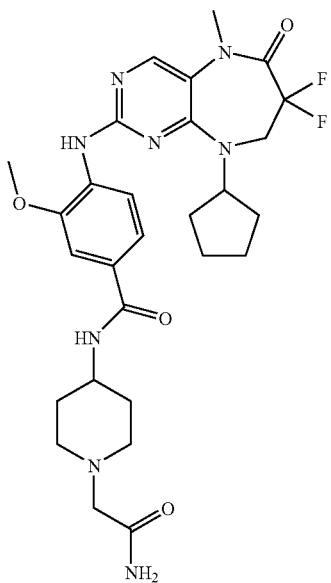

The title compound was synthesized from 4-(9-cyclohexyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for the synthesis of the compound 16 using HATU except that 2-(4-aminopiperidin-1-yl)acetamide was used. The final compound was purified by reverse phase HPLC and basified to give the free base. $^1$H NMR (400 MHz, DMSO-$d_6$) ☐ ppm 1.43-2.16 (m, 14H) 3.17 (br. s., 2H) 3.33 (s, 3H) 3.82-4.21 (m, 8H) 4.78 (t, J=8.59 Hz, 1H) 7.51 (d, J=1.52 Hz, 2H) 7.73 (s, 1H) 7.98 (s, 1H) 8.04-8.20 (m, 1H) 8.27 (s, 2H) 8.37 (d, J=7.07 Hz, 1H) 9.61 (br. s., 1H) [M+H] calc'd for $C_{28}H_{36}F_2N_8O_4$, 586. found 586.

258

Compound 115: 4-(9-cyclopentyl-7,7-difluoro-5-methyl-6-oxo-6,7,8,9-tetrahydro-5H-pyrimido[4,5-b][1,4]diazepin-2-ylamino)-N-(1-(2-(dimethylamino)-2-oxoethyl)piperidin-4-yl)-3-methoxybenzamide

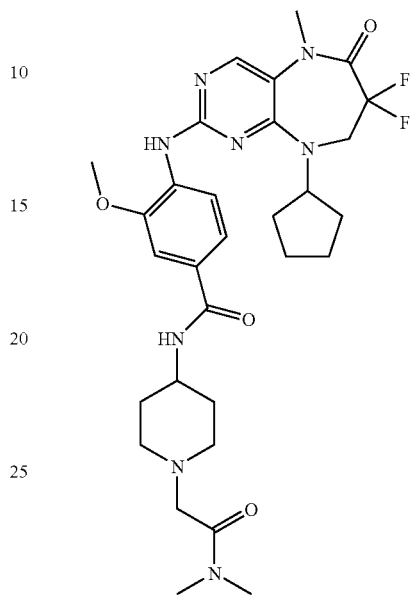

The title compound was synthesized from 4-(9-cyclohexyl-7,7-difluoro-5-methyl-6-oxo-6,7,8,9-tetrahydro-5H-pyrimido[5,4-b][1,4]diazepin-2-ylamino)-3-methoxybenzoic acid as described in the General procedure for the synthesis of the compound 16 using HATU except that 2-(4-aminopiperidin-1-yl)-N,N-dimethylacetamide was used. The final compound was purified by reverse phase HPLC and basified to give the free base. $^1$H NMR (400 MHz, DMSO-$d_6$) δ ppm 1.46-2.17 (m, 14H) 2.94 (d, J=10.61 Hz, 6H) 3.01-3.20 (m, 2H) 3.33 (s, 3H) 4.06 (t, J=13.89 Hz, 5H) 4.24 (d, J=4.55 Hz, 2H) 4.78 (t, J=7.45 Hz, 1H) 7.43-7.62 (m, 2H) 8.06 (br. s., 1H) 8.27 (s, 2H) 8.36 (d, J=7.07 Hz, 1H) 9.52 (br. s., 1H) [M+H] calc'd for $C_{30}H_{40}F_2N_8O_4$, 614. found 614.

Compound 116: 4-(9-Cyclopentyl-7,7-difluoro-5-methyl-6-oxo-6,7,8,9-tetrahydro-5H-pyrimido[4,5-b][1,4]diazepin-2-ylamino)-2-fluoro-5-methoxy-N-(1-methylpiperidin-4-yl)benzamide

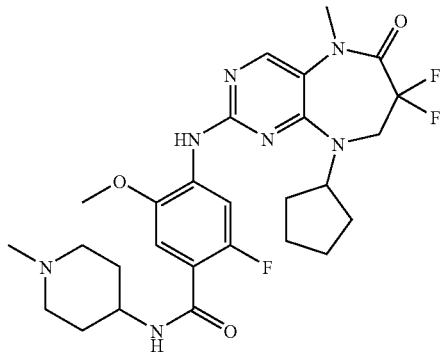

The title compound was synthesized from 4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxybenzoic acid and 1-methylpiperidin-4-amine as described in the general procedure for amide bond synthesis. The final compound was purified by reverse phase HPLC and basified to give the free base. $^1$H NMR (400 MHz, DMSO-d$_6$) δ ppm 1.60-1.73 (m, 11H), 1.88-2.21 (m, 8H) 2.78 (br. s., 2H) 3.73 (br. s., 1H) 3.91 (s, 3H) 4.08 (t, J=13.8 Hz, 2H) 4.81 (d, J=8.1 Hz, 1H) 7.18 (d, J=6.6 Hz, 1H) 7.91 (br. s., 1H) 8.04 (s, 1H) 8.24 (d, J=13.4 Hz, 1H) 8.30 (s, 1H). [M+H] calc'd for C$_{27}$H$_{34}$F$_3$N$_7$O$_3$, 562. found 562.

Compound 117: 4-(9-Cyclopentyl-7,7-difluoro-5-methyl-6-oxo-6,7,8,9-tetrahydro-5H-pyrimido[4,5-b][1,4]diazepin-2-ylamino)-2-fluoro-N-(1-(2-hydroxyethyl)piperidin-4-yl)-5-methoxybenzamide

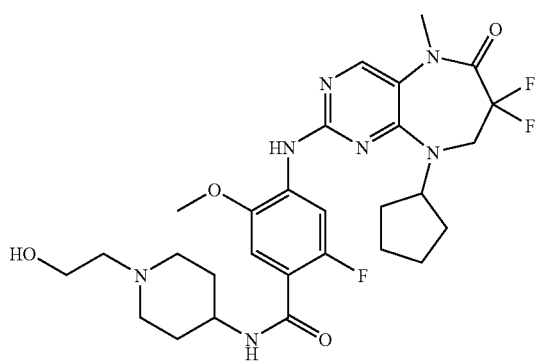

The title compound was synthesized from 4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxybenzoic acid and 2-(4-aminopiperidin-1-yl)ethanol as described in the General procedure for amide bond synthesis. The final compound was purified by reverse phase HPLC and basified to give the free base. $^1$H NMR (400 MHz, DMSO-d$_6$) δ ppm 1.40-1.86 (m, 12H) 1.88-2.10 (m, 5H) 2.33-2.42 (m, 2H) 2.84 (d, J=11.4 Hz, 2H) 3.48 (q, J=6.2 Hz, 2H) 3.73 (d, J=4.6 Hz, 1H) 4.08 (t, J=14.0 Hz, 2H) 4.37 (t, J=5.4 Hz, 1H) 4.82 (t, J=8.2 Hz, 1H) 7.18 (d, J=6.6 Hz, 1H) 7.90 (dd, J=7.7, 3.4 Hz, 1H) 8.04 (s, 1H) 8.18-8.34 (m, 2H). [M+H] calc'd for C$_{28}$H$_{36}$F$_3$N$_7$O$_4$, 592. found 592.

Compound 118: 4-(9-Cyclopentyl-7,7-difluoro-5-methyl-6-oxo-6,7,8,9-tetrahydro-5H-pyrimido[4,5-b][1,4]diazepin-2-ylamino)-N-(1-(2-(dimethylamino)acetyl)piperidin-4-yl)-2-fluoro-5-methoxybenzamide

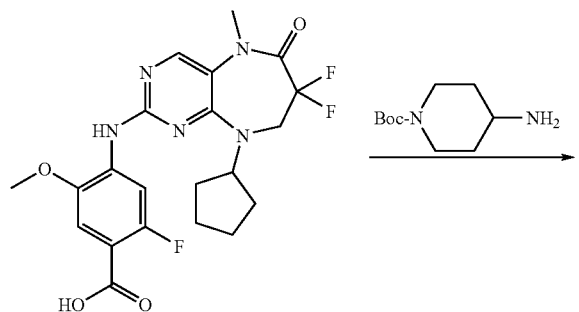

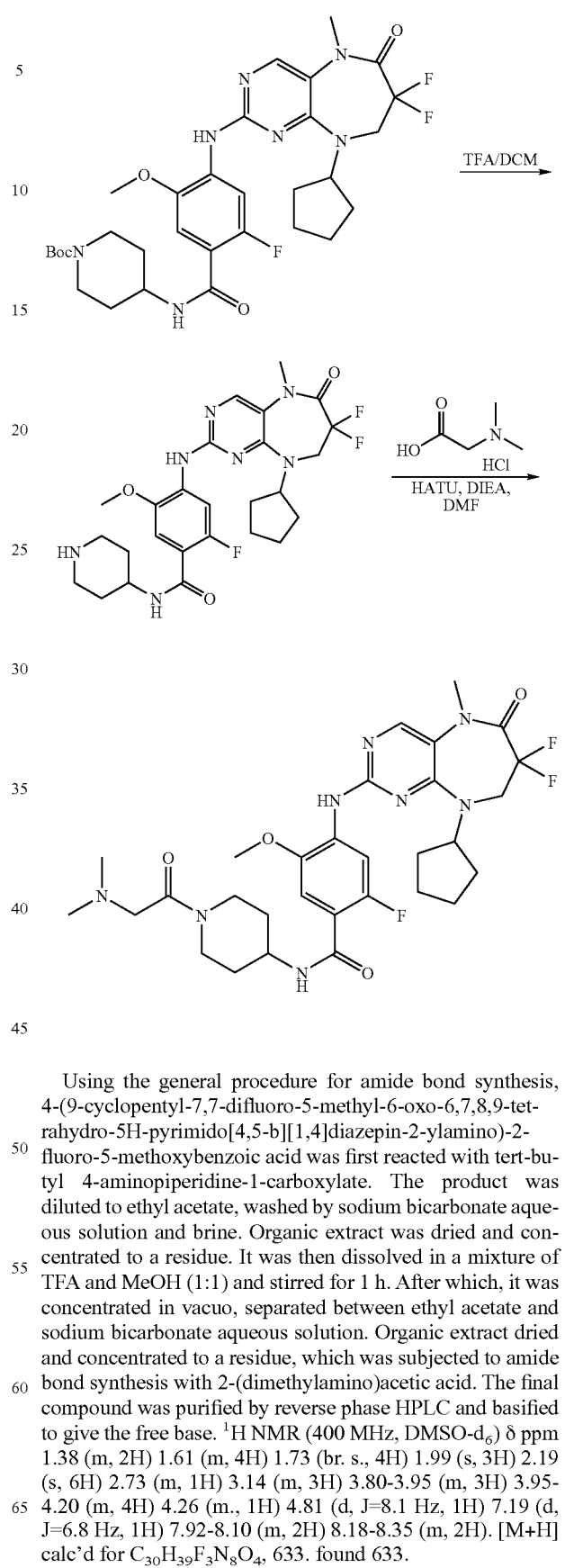

Using the general procedure for amide bond synthesis, 4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxybenzoic acid was first reacted with tert-butyl 4-aminopiperidine-1-carboxylate. The product was diluted to ethyl acetate, washed by sodium bicarbonate aqueous solution and brine. Organic extract was dried and concentrated to a residue. It was then dissolved in a mixture of TFA and MeOH (1:1) and stirred for 1 h. After which, it was concentrated in vacuo, separated between ethyl acetate and sodium bicarbonate aqueous solution. Organic extract dried and concentrated to a residue, which was subjected to amide bond synthesis with 2-(dimethylamino)acetic acid. The final compound was purified by reverse phase HPLC and basified to give the free base. $^1$H NMR (400 MHz, DMSO-d$_6$) δ ppm 1.38 (m, 2H) 1.61 (m, 4H) 1.73 (br. s., 4H) 1.99 (s, 3H) 2.19 (s, 6H) 2.73 (m, 2H) 3.14 (m, 1H) 3.80-3.95 (m, 3H) 3.95-4.20 (m, 4H) 4.26 (m., 1H) 4.81 (d, J=8.1 Hz, 1H) 7.19 (d, J=6.8 Hz, 1H) 7.92-8.10 (m, 2H) 8.18-8.35 (m, 2H). [M+H] calc'd for C$_{30}$H$_{39}$F$_3$N$_8$O$_4$, 633. found 633.

Compound 119: (R)-4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxy-N-(piperidin-3-yl)benzamide

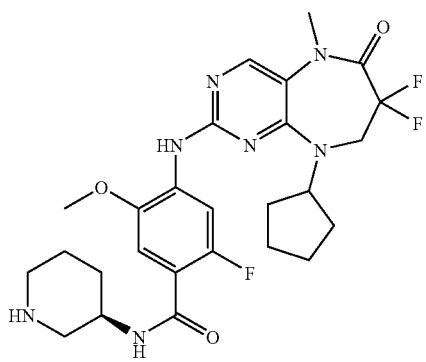

The title compound was synthesized from 4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxybenzoic acid and (R)-tert-butyl 3-aminopiperidine-1-carboxylate as described in the General procedure for amide bond synthesis. The Boc group was then deprotected using TFA. The final compound was purified by reverse phase HPLC and basified to give the free base. $^1$H NMR (400 MHz, DMSO-$d_6$) δ ppm 1.47 (m, 3H) 1.61 (m, 9H) 1.99 (s, 3H) 2.73 (m, 1H) 2.93 (m, 1H) 3.92 (s, 4H) 4.01-4.20 (t, J=14 Hz, 2H) 4.82 (m, 1H) 7.24 (d, J=6.8 Hz, 1H) 7.71-7.90 (m, 1H) 8.05 (s, 1H) 8.14-8.38 (m, 2H). [M+H] calc'd for $C_{26}H_{32}F_3N_7O_3$, 548. found 548.

Compound 120: 9-Cyclopentyl-7,7-difluoro-2-(5-fluoro-2-methoxyphenylamino)-5-methyl-8,9-dihydro-5H-pyrimido[4,5-b][1,4]diazepin-6(7H)-one

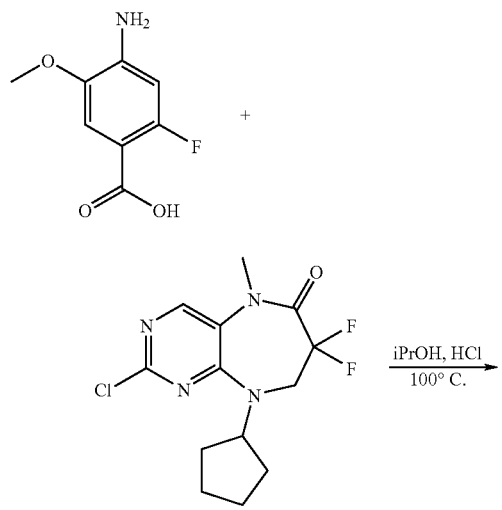

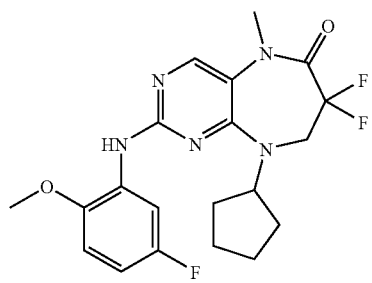

The title compound was a by-product from the reaction between the chloropyrimidine and 4-amino-2-fluoro-5-methoxybenzoic acid when heated in isopropanol solution in presence of catalytic amount of concentrated HCl at 100° C. The final compound was purified by reverse phase HPLC. $^1$H NMR (400 MHz, DMSO-$d_6$) δ ppm 1.26 (d, J=6.3 Hz, 2H) 1.57 (m, 4H) 1.70 (m, 2H) 1.92 (m, 2H) 3.80-3.93 (m, 3H) 4.05 (t, J=13.9 Hz, 2H) 4.62-4.85 (m, 1H) 6.76 (td, J=8.5, 2.8 Hz, 1H) 7.01 (dd, J=8.8, 5.3 Hz, 1H) 7.91 (s, 1H) 8.11 (dd, J=11.4, 2.8 Hz, 1H) 8.26 (s, 1H). [M+H] calc'd for $C_{20}H_{22}F_3N_5O_2$, 422. found 422.

Compound 121: 4-(9-Cyclopentyl-7,7-difluoro-5-methyl-6-oxo-6,7,8,9-tetrahydro-5H-pyrimido[4,5-b][1,4]diazepin-2-ylamino)-3-fluoro-5-methoxybenzoic acid

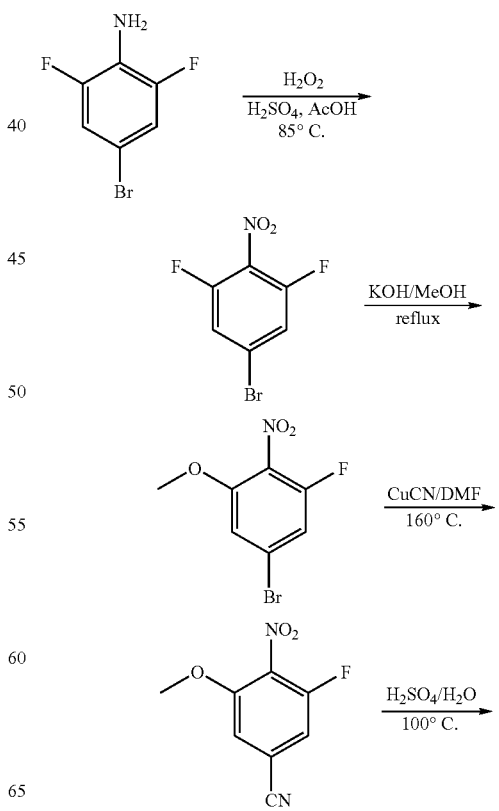

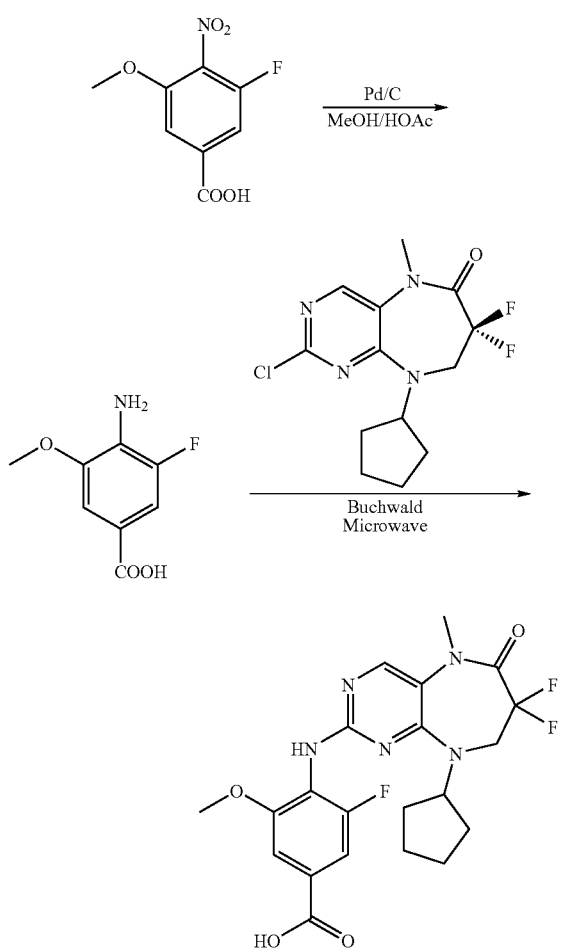

5-Bromo-1,3-difluoro-2-nitrobenzene: To a mixture of acetic acid (30 mL), 30% H₂O₂ (20 mL) and concentrated sulfuric acid (1 mL) was added 1-bromo-2,6-difluoroaniline (5 g, 24 mmol) in acetic acid (10 mL) dropwise at 85° C. The reaction mixture was heated for 1 h. It was then cooled down, diluted to water and extracted with ethyl acetate. The organic layer was dried and concentrated to a red residue, which was purified by flash column (EtOAc in Hexane 2-5%) to give the product as yellow solid (2.7 g, 47%). $^1$H NMR (400 MHz, CHLOROFORM-d) δ ppm 7.33 (m, 2H).

5-Bromo-1-fluoro-3-methoxy-2-nitrobenzene: To a solution of 5-bromo-1,3-difluoro-2-nitrobenzene (2.7 g, 11.3 mmol) in methanol (20 mL) was added potassium hydroxide (680 mg, 12 mmol). The reaction mixture was refluxed at 90° C. for 1 h. It was then concentrated, diluted to ethyl acetate and washed by water and brine. The mixture was then purified by flash column to give the product as red oil (1.8 g, 63%). $^1$H NMR (400 MHz, CHLOROFORM-d) δ ppm 3.94 (s, 3H) 7.01 (s, 1H) 7.04 (d, J=8 Hz, 1H).

3-Fluoro-5-methoxy-4-nitrobenzonitrile: A mixture of 5-bromo-1-fluoro-3-methoxy-2-nitrobenzene (1.5 g, 6 mmol), and CuCN (698 mg, 7.8 mmol) in 10 mL of DMF was heated in a sealed tube at 160° C. overnight. It was then cooled down, diluted to ethyl acetate, washed by brine and water. The organic extract was dried and concentrated to a red solid (1 g, 85%) which was used for next step without further purification. $^1$H NMR (400 MHz, CHLOROFORM-d) δ ppm 4.01 (s, 3H) 7.14 (s, 1H) 7.17 (d, J=8 Hz, 1H).

3-Fluoro-5-methoxy-4-nitrobenzoic acid. A suspension of 3-fluoro-5-methoxy-4-nitrobenzonitrile (940 mg, 4.8 mmol) in a mixture of concentrated H₂SO₄ and water (2 mL/2 mL) was heated at 100° C. overnight. The reaction mixture was then cooled down, solid filtered and dried to give the product as brown solid (770 mg, 75%).

4-Amino-3-fluoro-5-methoxybenzoic acid. A solution of 3-fluoro-5-methoxy-4-nitrobenzoic acid (obtained above), HOAc (5 mL) and MeOH (5 mL) was hydrogenated using a hydrogen balloon overnight. The solution was then filtered through celite and concentrated to a red solid (590 mg, 66%). [M+H] calc'd for C₈H₈FNO₃, 186. found 186.

4-(9-Cyclopentyl-7,7-difluoro-5-methyl-6-oxo-6,7,8,9-tetrahydro-5H-pyrimido[4,5-b][1,4]diazepin-2-ylamino)-3-fluoro-5-methoxybenzoic acid: A mixture of the chloropyrimidine (158 mg, 0.5 mmol), 4-amino-3-fluoro-5-methoxybenzoic acid (139 mg, 0.75 mmol), the catalyst Pd(OAc)₂ (12 mg, 0.05 mmol), the ligand XANTPHOS (58 mg, 0.1 mmol) and Cs₂CO₃ (652 mg, 2 mmol) were dissolved in dioxane and N,N-dimethyl acetamide (1 mL/1 mL). The reaction mixture was subjected to microwave reaction at 160° C. for 30 min. It was then poured to ice water, filtered through celite. The aqueous filtrate was acidified with HCl and extracted with ethyl acetate. The organic extract was dried and concentrated to a residue which was purified by reverse phase HPLC (68 mg, 30%). [M+H] calc'd for C₂₁H₂₂F₃N₅O₄, 466. found 466.

Compound 122: 4-(9-Cyclopentyl-7,7-difluoro-5-methyl-6-oxo-6,7,8,9-tetrahydro-5H-pyrimido[4,5-b][1,4]diazepin-2-ylamino)-3-fluoro-5-methoxy-N-(1-methylpiperidin-4-yl)benzamide

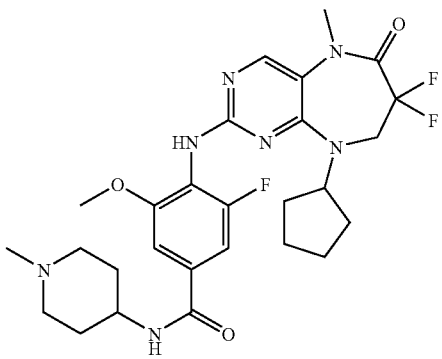

The title compound was synthesized from 4-(9-cyclopentyl-7,7-difluoro-5-methyl-6-oxo-6,7,8,9-tetrahydro-5H-pyrimido[4,5-b][1,4]diazepin-2-ylamino)-3-fluoro-5-methoxybenzoic acid and 1-methylpiperidin-4-amine as described in the General procedure for amide bond synthesis. The final compound was purified by reverse phase HPLC and basified to give the free base. $^1$H NMR (400 MHz, DMSO-d₆) δ ppm 1.33 (m, 4H) 1.58 (d, J=14.4 Hz, 6H) 1.75 (m, 2H) 1.93 (m, 2H) 1.99 (s, 1H) 2.16 (s, 3H) 2.78 (d, J=10.6 Hz, 2H) 3.29 (s, 3H) 3.83 (s, 2H) 3.89-4.01 (t, J=12 Hz, 2H) 4.32 (m, 1H) 7.24-7.48 (m, 2H) 8.10 (s, 1H) 8.26 (d, J=7.6 Hz, 1H) 8.53 (s, 1H). [M+H] calc'd for C₂₇H₃₄F₃N₇O₃, 562. found 562.

Compound 123: 4-(9-Cyclopentyl-7,7-difluoro-5-methyl-6-oxo-6,7,8,9-tetrahydro-5H-pyrimido[4,5-b][1,4]diazepin-2-ylamino)-2-fluoro-3-methoxybenzoic acid

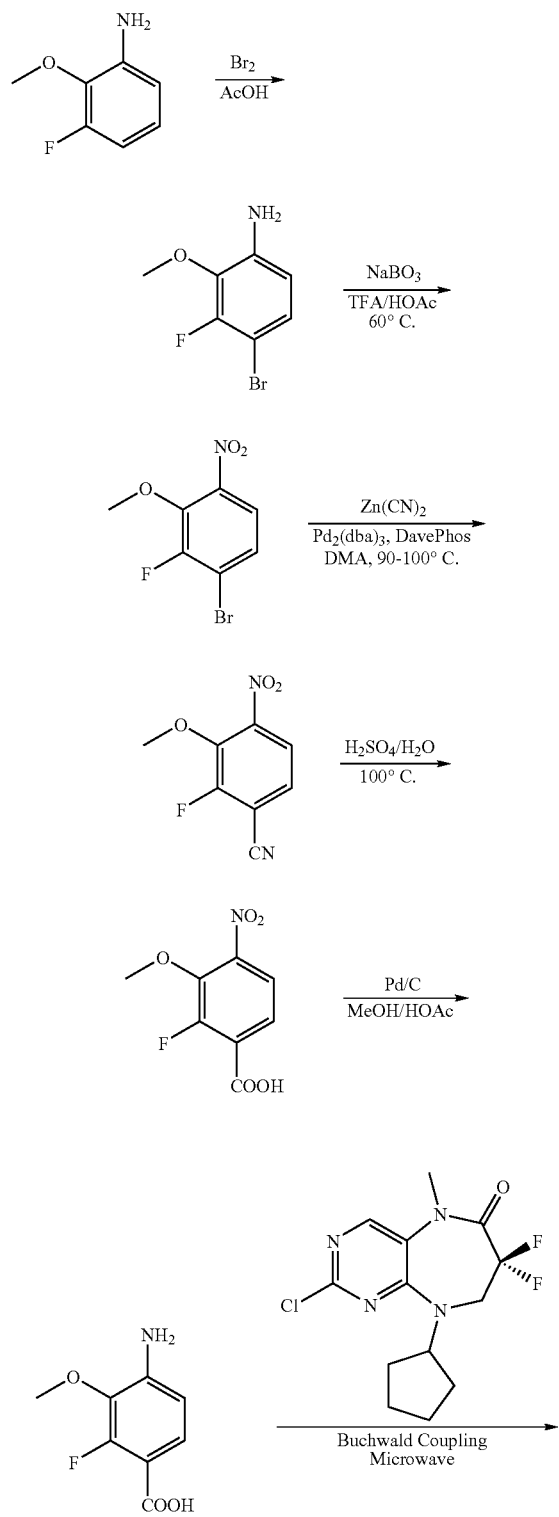

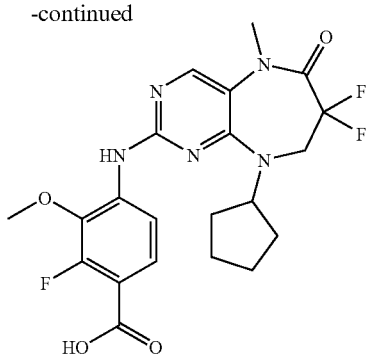

4-Bromo-3-fluoro-2-methoxyaniline: To 3-fluoro-2-methoxyaniline (2.8 g, 20 mmol) in 10 mL of acetic acid was added bromine (0.82 mL, 16 mmol) in acetic acid (10 mL) dropwise. The reaction mixture was stirred at rt. for 30 min. Solid was filtered and washed with acetic acid to give the HBr salt. It was then dissolved in water, basified by addition of KOH, extracted with ethyl acetate. The organic layer was dried and concentrated to give a white solid (2.8 g, 80%). $^1$H NMR (400 MHz, CHLOROFORM-d) δ ppm 3.93 (s, 3H) 6.42 (dd, J=8.6, 1.8 Hz, 1H) 7.01 (dd, J=8.6, 7.1 Hz, 1H). [M+H] calc'd for $C_7H_7BrFNO$, 222. found 222.

1-Bromo-2-fluoro-3-methoxy-4-nitrobenzene: To 4-bromo-3-fluoro-2-methoxyaniline (1 g, 4.5 mmol) in a mixture of TFA and acetic acid (10 mL/10 mL) was added sodium perborate tetrahydrate (3.2 g, 21 mmol). The reaction mixture was warmed up to 60° C. and heated for 24 h. It was then diluted to water, extracted with ethyl acetate. The product was obtained by flash column as a yellow solid (450 mg, 40%). $^1$H NMR (400 MHz, CHLOROFORM-d) δ ppm 4.11 (s, 3H) 7.40 (dd, J=9.0, 6.2 Hz, 1H) 7.54 (dd, J=9.0, 1.9 Hz, 1H).

2-Fluoro-3-methoxy-4-nitrobenzonitrile: A mixture of 1-Bromo-2-fluoro-3-methoxy-4-nitrobenzene (250 mg, 1 mmol) and zinc cyanide (70 mg, 0.6 mmol) were stirred in DMA (5 mL) and purged with nitrogen. The palladium catalyst, $Pd_2(dba)_3$ (92 mg, 0.1 mmol), and the ligand, Davephos (79 mg, 0.2 mmol), were added and the reaction mixture was stirred at 90° C. overnight. It was then cooled to rt., diluted to ethyl acetate, washed with brine. Organic dried, concentrated and purified by flash column (EtOAc/Hexane=1:20) to give 170 mg product (87%). $^1$H NMR (400 MHz, CHLOROFORM-d) δ ppm 4.15 (s, 3H) 7.42 (dd, J=9.0, 6.2 Hz, 1H) 7.65 (dd, J=9.0, 1.9 Hz, 1H).

4-Amino-2-fluoro-3-methoxybenzoic acid: A solution of 2-fluoro-3-methoxy-4-nitrobenzonitrile (170 mg) in $H_2SO_4$ and $H_2O$ (0.5 mL/0.5 mL) was heated at 100° C. for 18 h. After which, it was separated between ethyl acetate and water. Organic extract was dried and concentrated to give a residue, which was then dissolved in a mixture of methanol and acetic acid (2 mL/2 mL) and was hydrogenated using hydrogen balloon overnight. The solution was filtered through celite, and the filtrate concentrated to give a read solid as the product. [M+H] calc'd for $C_8H_8FNO_3$, 186. found 186.

4-(9-Cyclopentyl-7,7-difluoro-5-methyl-6-oxo-6,7,8,9-tetrahydro-5H-pyrimido[4,5-b][1,4]diazepin-2-ylamino)-2-fluoro-3-methoxybenzoic acid: A mixture of the chloropyrimidine (145 mg, 0.46 mmol), 4-amino-2-fluoro-3-methoxybenzoic acid (85 mg, 0.46 mmol), the catalyst $Pd(OAc)_2$ (11 mg, 0.05 mmol), the ligand XANTPHOS (58 mg, 0.1 mmol) and $Cs_2CO_3$ (652 mg, 2 mmol) were dissolved in dioxane and N,N-dimethyl acetamide (1.5 mL/1.5 mL). The reaction mixture was subjected to microwave reaction at 160° C. for 30 min. It was then poured to ice water, filtered through celite. The aqueous filtrate was acidified with HCl carefully and the solid was filtered, washed with water. The dark solid was then used for next step coupling without further purification. [M+H] calc'd for $C_{21}H_{22}F_3N_5O_4$, 466. found 466.

Compound 124: 4-(9-Cyclopentyl-7,7-difluoro-5-methyl-6-oxo-6,7,8,9-tetrahydro-5H-pyrimido[4,5-b][1,4]diazepin-2-ylamino)-2-fluoro-3-methoxy-N-(1-methylpiperidin-4-yl)benzamide

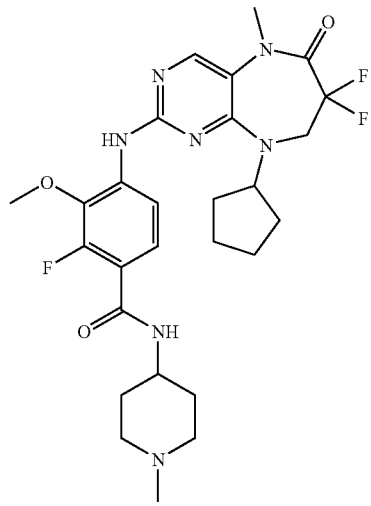

The title compound was synthesized from 4-(9-cyclopentyl-7,7-difluoro-5-methyl-6-oxo-6,7,8,9-tetrahydro-5H-pyrimido[4,5-b][1,4]diazepin-2-ylamino)-2-fluoro-3-methoxybenzoic acid and 1-methylpiperidin-4-amine as described in the General procedure for amide bond synthesis. The final compound was purified by reverse phase HPLC and basified to give the free base. $^1$H NMR (400 MHz, DMSO-d$_6$) δ ppm 1.37-1.66 (m, 7H) 1.75 (m, 4H) 1.82-2.04 (m, 4H) 2.15 (m, 3H) 2.66-2.81 (m, 2H) 3.16 (s, 1H) 3.70 (m, 1H) 3.90 (s, 3H) 4.05 (t, J=13.8 Hz, 2H) 4.77 (m, 1H) 7.24 (t, J=8.1 Hz, 1H) 7.96-8.13 (m, 2H) 8.26 (s, 1H) 8.35 (s, 1H). [M+H] calc'd for $C_{27}H_{34}F_3N_7O_3$, 562. found 562.

Compound 125: 4-(9-cyclohexyl-7,7-difluoro-5-methyl-6-oxo-6,7,8,9-tetrahydro-5H-pyrimido[4,5-b][1,4]diazepin-2-ylamino)-N-(1-isopropylazetidin-3-yl)-3-methoxybenzamide

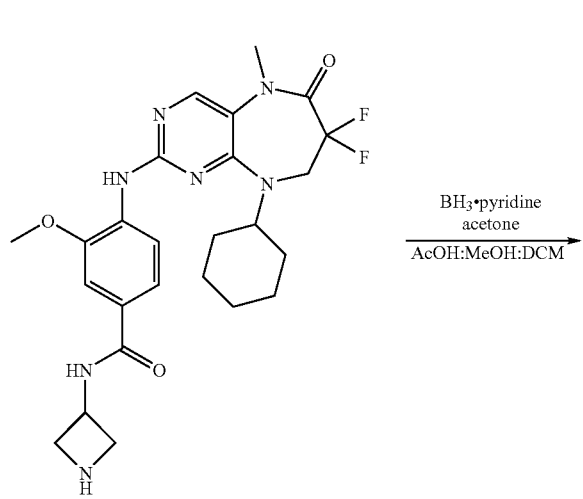

Compound 126: 4-(9-cyclohexyl-7,7-difluoro-5-methyl-6-oxo-6,7,8,9-tetrahydro-5H-pyrimido[4,5-b][1,4]diazepin-2-ylamino)-N-(1-ethylazetidin-3-yl)-3-methoxybenzamide

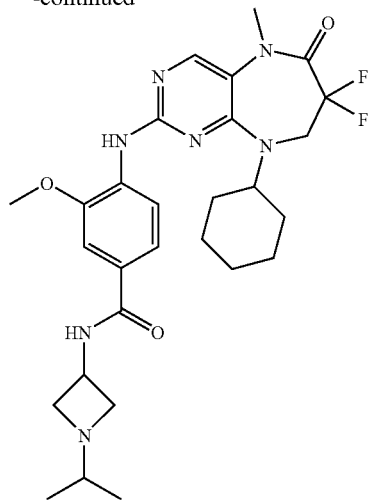

The title compound was synthesized by solubilizing N-(azetidin-3-yl)-4-(9-cyclohexyl-7,7-difluoro-5-methyl-6-oxo-6,7,8,9-tetrahydro-5H-pyrimido[4,5-b][1,4]diazepin-2-ylamino)-3-methoxybenzamide (33 mg, 0.07 mmol) in acetic acid: methanol: dichloromethane (1 mL of 1:2:2) and treatment with acetone (58 mg, 1.0 mmol), and borane-pyridine (100 μL, 0.8 mmol). The reaction was left to stir for 3 hours. The reaction solvent was removed and the final compound was purified by reverse phase HPLC and basified to give the free base (5.7 mg, 16% yield). $^1$H NMR (400 MHz, DMSO-d$_6$) δ ppm 0.87 (d, J=6.06 Hz, 6H) 1.48-1.78 (m, 8H) 1.93 (br. s., 2H) 2.24-2.36 (m, 1H) 2.94 (t, J=6.82 Hz, 2H) 3.33 (s, 3H) 3.51 (t, J=6.82 Hz, 2H) 3.94 (s, 3H) 4.05 (t, J=14.02 Hz, 2H) 4.39 (q, J=6.99 Hz, 1H) 4.70-4.83 (m, 1H) 7.49 (d, 0H) 7.51 (s, 1H) 7.98 (s, 1H) 8.26 (s, 1H) 8.29 (d, 1H) 8.61 (d, J=6.82 Hz, 1H). [M+H] calculated for $C_{28}H_{37}F_2N_7O_3$, 574. found 574.

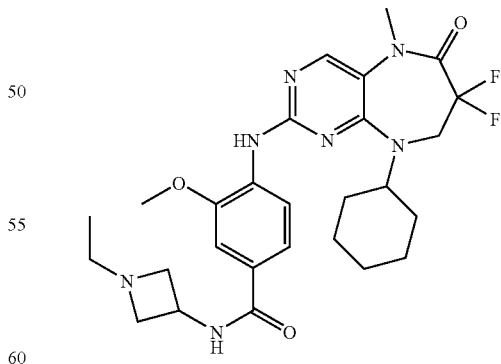

The title compound was synthesized by following the Reductive Amination Procedure for synthesizing compound 111 except that acetaldehyde was used. $^1$H NMR (400 MHz, DMSO-d$_6$) δ ppm 1.01 (t, J=7.20 Hz, 3H) 1.05-1.20 (m, 2H) 1.23-1.40 (m, 2H) 1.48-1.63 (m, 3H) 1.66-1.83 (m, 4H) 3.25 (s, 3H) 3.89 (s, 3H) 4.01 (t, J=13.26 Hz, 2H) 4.15 (br. s., 1H)

4.34-4.46 (m, 1H) 4.54-4.68 (m, 1H) 7.44 (d, J=8.34 Hz, 1H) 7.47 (s, 1H) 7.89 (s, 1H) 8.15 (s, 1H) 8.26 (d, J=8.34 Hz, 1H) 8.92 (br. s., 1H). [M+H] calculated for $C_{27}H_{35}F_2N_7O_3$, 544. found 544.

Compound 127: N-(azetidin-3-yl)-4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxybenzamide

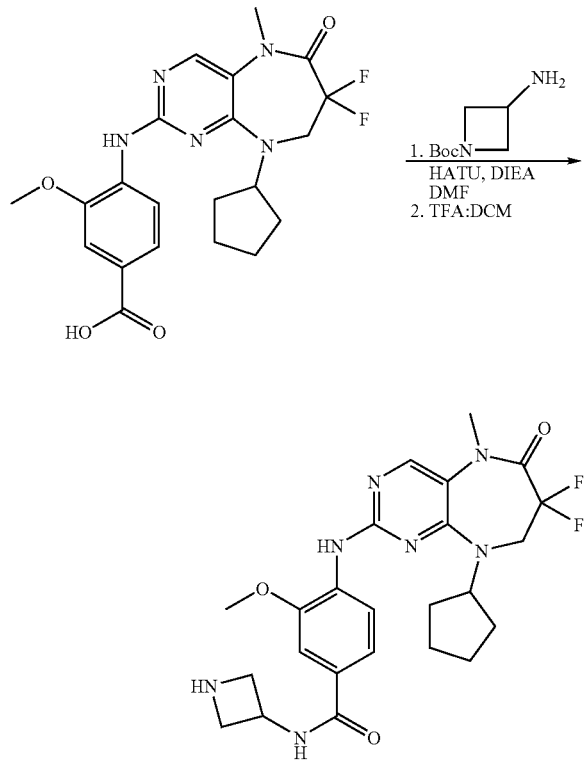

The title compound was synthesized from 4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxybenzoic acid as described in the general procedure for amide bond synthesis using HATU and 3-amino-N—Boc-azetidine. The Boc group was then removed by treatment with 1:1 trifluoroacetic acid and dichloromethane for 1 hour. At this time the solvent was removed and NaHCO₃ (sat.) and EtOAc were added to the residue. The layers were separated, the organic layer was then dried over MgSO₄, filtered, the solvent was removed and the final compound was purified by reverse phase HPLC and basified to give the free base. ¹H NMR (400 MHz, DMSO-d₆) δ ppm 1.49-1.79 (m, 6H) 1.93 (br. s., 2H) 3.52-3.66 (m, 4H) 3.94 (s, 3H) 4.05 (t, J=14.02 Hz, 2H) 4.56-4.84 (m, 2H) 7.45-7.58 (m, 2H) 7.98 (s, 1H) 8.26 (s, 1H) 8.28 (d, J=8.34 Hz, 1H) 8.75 (d, J=7.07 Hz, 1H). [M+H] calculated for $C_{24}H_{29}F_2N_7O_3$, 502. found 502.

Compound 128: 4-(9-cyclopentyl-7,7-difluoro-5-methyl-6-oxo-6,7,8,9-tetrahydro-5H-pyrimido[4,5-b][1,4]diazepin-2-ylamino)-N-(1-ethylazetidin-3-yl)-3-methoxybenzamide

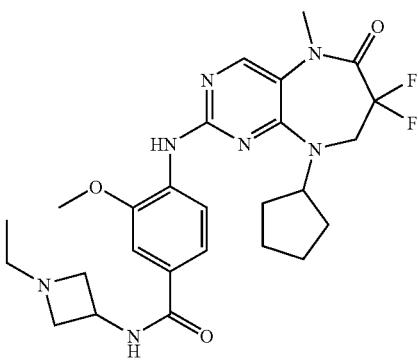

The title compound was synthesized by following the Reductive Amination Procedure using N-(azetidin-3-yl)-4-(9-cyclohexyl-7,7-difluoro-5-methyl-6-oxo-6,7,8,9-tetrahydro-5H-pyrimido[4,5-b][1,4]diazepin-2-ylamino)-3-methoxybenzamide and acetaldehyde. ¹H NMR (400 MHz, DMSO-d₆) δ ppm 0.89 (t, J=7.20 Hz, 3H) 1.49-1.76 (m, 6H) 1.93 (br. s., 2H) 2.45 (q, J=6.91 Hz, 2H) 2.98 (t, J=6.95 Hz, 1H) 3.33 (s, 3H) 3.56 (t, J=6.95 Hz, 2H) 3.94 (s, 3H) 4.05 (t, J=14.02 Hz, 2H) 4.40-4.51 (m, 1H) 4.77 (t, 1H) 7.49 (d, 0H) 7.52 (s, 1H) 7.98 (s, 1H) 8.26 (s, 1H) 8.29 (d, 1H) 8.66 (d, J=6.82 Hz, 1H). [M+H] calculated for $C_{26}H_{33}F_2N_7O_3$, 530. found 530.

Compound 129: 4-(9-cyclopentyl-7,7-difluoro-5-methyl-6-oxo-6,7,8,9-tetrahydro-5H-pyrimido[4,5-b][1,4]diazepin-2-ylamino)-N-(1-isopropylazetidin-3-yl)-3-methoxybenzamide

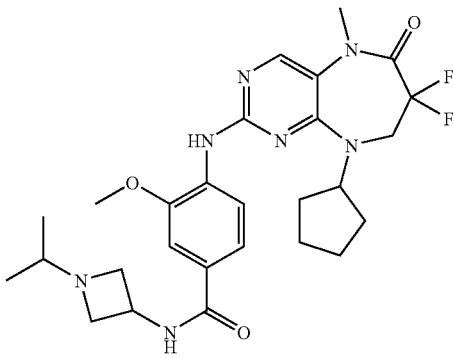

The title compound was synthesized by following the Reductive Amination Procedure using N-(azetidin-3-yl)-4-(9-cyclohexyl-7,7-difluoro-5-methyl-6-oxo-6,7,8,9-tetrahydro-5H-pyrimido[4,5-b][1,4]diazepin-2-ylamino)-3-methoxybenzamide and acetone. ¹H NMR (400 MHz, DMSO-d₆) δ ppm 0.87 (d, J=6.06 Hz, 6H) 1.48-1.78 (m, 6H) 1.93 (br. s., 2H) 2.24-2.36 (m, 1H) 2.94 (t, J=6.82 Hz, 2H) 3.33 (s, 3H) 3.51 (t, J=6.82 Hz, 2H) 3.94 (s, 3H) 4.05 (t, J=14.02 Hz, 2H) 4.39 (q, J=6.99 Hz, 1H) 4.70-4.83 (m, 1H) 7.49 (d, 0H) 7.51

(s, 1H) 7.98 (s, 1H) 8.26 (s, 1H) 8.29 (d, 1H) 8.61 (d, J=6.82 Hz, 1H). [M+H] calculated for $C_{27}H_{35}F_2N_7O_3$, 544. found 544.

Compound 130: N-(azetidin-3-yl)-4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxybenzamide

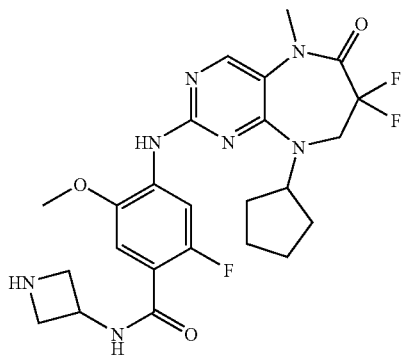

The title compound was synthesized from 4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxybenzoic acid as described in the general procedure for amide bond synthesis using HATU and 3-amino-N—Boc-azetidine. The Boc group was then removed by treatment with 1:1 trifluoroacetic acid and dichloromethane for 1 hour. At this time the solvent was removed and NaHCO$_3$ (sat.) and EtOAc were added to the residue. The layers were separated, the organic layer was then dried over MgSO$_4$, filtered, the solvent was removed and the final compound was purified by reverse phase HPLC and basified to give the free base. $^1$H NMR (400 MHz, DMSO-d$_6$) δ ppm 1.48-1.77 (m, 6H) 1.96 (br. s., 2H) 3.56 (dd, J=7.45, 4.42 Hz, 4H) 3.91 (s, 3H) 4.08 (t, J=14.02 Hz, 2H) 4.62-4.73 (m, 1H) 4.76-4.90 (m, 1H) 7.20 (d, J=6.82 Hz, 1H) 8.05 (s, 1H) 8.26 (d, J=13.39 Hz, 1H) 8.30 (s, 1H) 8.51 (d, J=3.54 Hz, 1H). [M+H] calculated for $C_{24}H_{28}F_3N_7O_3$, 520. found 520.

Compound 131: 4-(9-cyclopentyl-7,7-difluoro-5-methyl-6-oxo-6,7,8,9-tetrahydro-5H-pyrimido[4,5-b][1,4]diazepin-2-ylamino)-N-(1-ethylazetidin-3-yl)-2-fluoro-5-methoxybenzamide

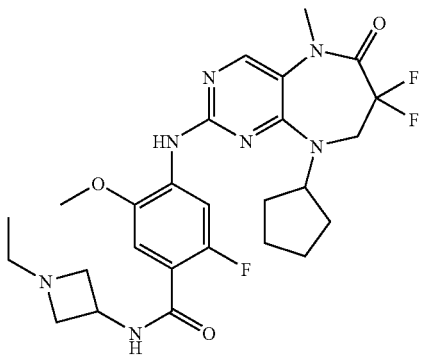

The title compound was synthesized by following the Reductive Amination Procedure using N-(azetidin-3-yl)-4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxybenzamide and acetaldehyde. $^1$H NMR (400 MHz, DMSO-d$_6$) δ ppm 0.87 (t, J=7.20 Hz, 3H) 1.61 (br. s., 6H) 1.96 (br. s., 2H) 2.40 (q, 2H) 2.88 (t, J=6.32 Hz, 2H) 3.52 (t, J=5.81 Hz, 2H) 3.91 (s, 3H) 4.08 (t, J=13.77 Hz, 2H) 4.33-4.48 (m, 1H) 4.71-4.89 (m, 1H) 7.20 (d, J=4.04 Hz, 1H) 8.05 (s, 1H) 8.26 (d, J=13.39 Hz, 1H) 8.31 (d, J=3.28 Hz, 1H) 8.43 (d, J=7.07 Hz, 1H). [M+H] calculated for $C_{26}H_{32}F_3N_7O_3$, 548. found 548.

Compound 132: 4-(9-cyclopentyl-7,7-difluoro-5-methyl-6-oxo-6,7,8,9-tetrahydro-5H-pyrimido[4,5-b][1,4]diazepin-2-ylamino)-2-fluoro-N-(1-isopropylazetidin-3-yl)-5-methoxybenzamide

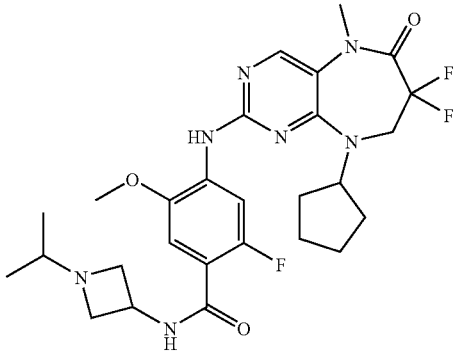

The title compound was synthesized by following the Reductive Amination Procedure using N-(azetidin-3-yl)-4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxybenzamide and acetone. $^1$H NMR (400 MHz, DMSO-d$_6$) δ ppm 0.85 (d, J=6.06 Hz, 6H) 1.44-1.80 (m, 6H) 1.95 (br. s., 2H) 2.27 (m, 6.09 Hz, 1H) 2.89 (t, J=7.33 Hz, 2H) 3.50 (t, J=7.33 Hz, 2H) 3.92 (s, 3H) 4.08 (t, J=13.89 Hz, 2H) 4.29-4.42 (m, 1H) 4.72-4.89 (m, 1H) 7.19 (d, J=6.82 Hz, 1H) 8.05 (s, 1H) 8.25 (d, J=13.39 Hz, 1H) 8.29-8.32 (m, 1H) 8.40 (d, J=7.07 Hz, 1H). [M+H] calculated for $C_{27}H_{34}F_3N_7O_3$, 562. found 562.

Compound 133: 4-(9-cyclopentyl-7,7-difluoro-5-methyl-6-oxo-6,7,8,9-tetrahydro-5H-pyrimido[4,5-b][1,4]diazepin-2-ylamino)-N-(1-cyclopentylazetidin-3-yl)-2-fluoro-5-methoxybenzamide

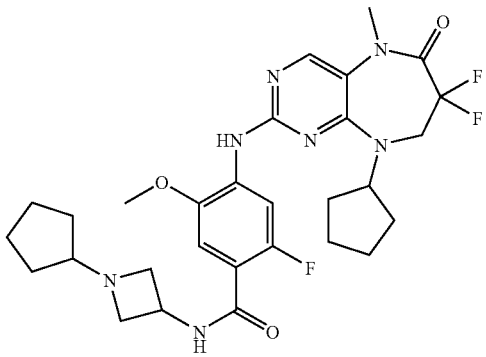

The title compound was synthesized by following the Reductive Amination Procedure using N-(azetidin-3-yl)-4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxybenzamide and cyclopentanone. $^1$H NMR (400 MHz, DMSO-d$_6$) δ ppm 1.23-1.35 (m, 2H) 1.38-1.78 (m, 11H) 1.96 (br. s., 2H) 2.67 (br. s., 1H) 2.87 (t, J=7.33 Hz, 2H) 3.49 (t, J=7.33 Hz, 2H) 3.91 (s, 3H) 4.08 (t, J=13.77 Hz, 2H) 4.33-4.44 (m, 1H) 4.78-4.88 (m, 1H) 7.19 (d, J=6.57 Hz, 1H) 8.05 (s, 1H) 8.25 (d, J=13.39 Hz, 1H) 8.30 (s, 1H) 8.41 (dd, J=6.82, 3.03 Hz, 1H). [M+H] calculated for C$_{29}$H$_{36}$F$_3$N$_7$O$_3$, 588. found 588.

Compound 134: 9-cyclopentyl-2-(4-(4-(cyclopropylmethyl)piperazine-1-carbonyl)-2-methoxyphenylamino)-7,7-difluoro-5-methyl-8,9-dihydro-5H-pyrimido[4,5-b][1,4]diazepin-6(7H)-one

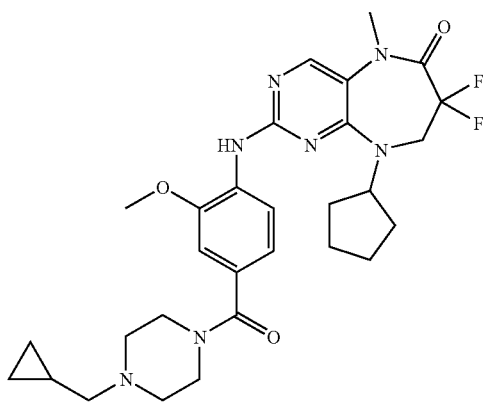

The title compound was synthesized from 4-(9-Cyclopentyl-7,7-difluoro-5-methyl-6-oxo-6,7,8,9-tetrahydro-5H-pyrimido[5,4-b][1,4]diazepin-2-ylamino)-3-methoxybenzoic acid as described in the general procedure for amide bond synthesis using HATU and 1-(cyclopropylmethyl)piperazine. $^1$H NMR (400 MHz, DMSO-d$_6$) δ ppm 0.07 (br. s., 2H) 0.47 (br. s., 2H) 1.55 (br. s., 5H) 1.68 (br. s., 2H) 1.90 (br. s., 2H) 2.21 (br. s., 1H) 2.40-2.48 (m, 3H) 3.31 (s, 4H) 3.32 (br. s., 3H) 3.88 (s, 3H) 4.03 (t, J=13.89 Hz, 2H) 4.64-4.76 (m, 1H) 6.96 (d, J=8.84 Hz, 1H) 7.04 (s, 1H) 8.00 (s, 1H) 8.15 (d, J=7.83 Hz, 1H) 8.23 (s, 1H). [M+H] calculated for C$_{29}$H$_{37}$F$_2$N$_7$O$_3$, 570. found 570.

Compound 135: 9-cyclopentyl-2-(4-(4-(cyclopropylmethyl)piperazine-1-carbonyl)-5-fluoro-2-methoxyphenylamino)-7,7-difluoro-5-methyl-8,9-dihydro-5H-pyrimido[4,5-b][1,4]diazepin-6(7H)-one

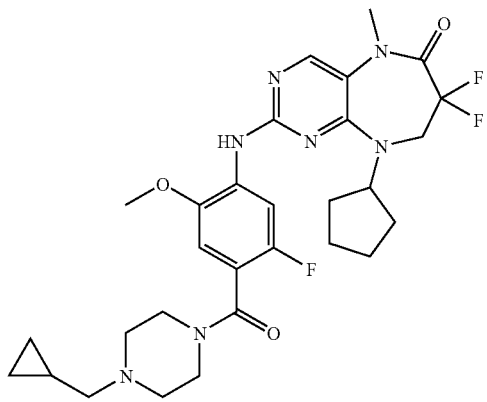

The title compound was synthesized from 4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxybenzoic acid as described in the general procedure for amide bond synthesis using HATU and 1-(cyclopropylmethyl)piperazine. $^1$H NMR (400 MHz, DMSO-d$_6$) δ ppm 0.07 (d, J=4.55 Hz, 2H) 0.45 (d, J=8.08 Hz, 2H) 0.75-0.87 (m, 1H) 1.47-1.77 (m, 6H) 1.92 (br. s., 2H) 2.20 (d, J=6.57 Hz, 2H) 2.32-2.43 (m, 2H) 3.22-3.31 (m, 2H) 3.64 (br. s., 2H) 3.88 (s, 3H) 4.06 (t, J=13.77 Hz, 3H) 4.70-4.84 (m, 1H) 6.97 (d, J=6.06 Hz, 1H) 8.04 (s, 1H) 8.16 (d, J=11.87 Hz, 1H) 8.28 (s, 1H). [M+H] calculated for C$_{29}$H$_{36}$F$_3$N$_7$O$_3$, 588. found 588.

Compound 136: 9-cyclopentyl-2-(2,2-difluorobenzo[d][1,3]dioxol-4-ylamino)-7,7-difluoro-5-methyl-8,9-dihydro-5H-pyrimido[4,5-b][1,4]diazepin-6(7H)-one

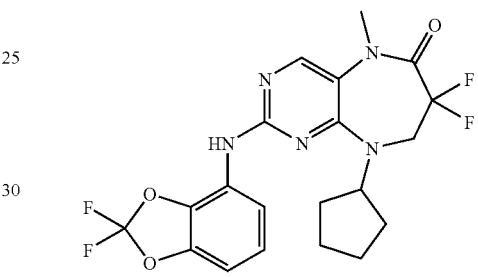

The title compound was synthesized from 2-chloro-9-cyclopentyl-7,7-difluoro-5-methyl-8,9-dihydro-5H-pyrimido[4,5-b][1,4]diazepin-6(7H)-one and 2,2-difluorobenzo[d][1,3]dioxol-4-amine using the procedure described in the general Buchwald Reaction Scheme. $^1$H NMR (400 MHz, DMSO-d$_6$) δ ppm 1.20-1.84 (m, 9H) 3.97 (t, J=14.40 Hz, 2H) 4.50-4.70 (m, 1H) 7.14 (d, J=2.27 Hz, 1H) 7.31 (dd, J=7.45, 2.15 Hz, 1H) 8.21 (s, 1H) 9.39 (s, 1H). [M+H] calculated for C$_{20}$H$_{19}$F$_4$N$_5$O$_3$, 454. found 454.

Compound 137: (4-(9-cyclopentyl-7,7-difluoro-5-methyl-6,7,8,9-tetrahydro-5H-pyrimido[4,5-b][1,4]diazepin-2-ylamino)-3-methoxyphenyl)methanol

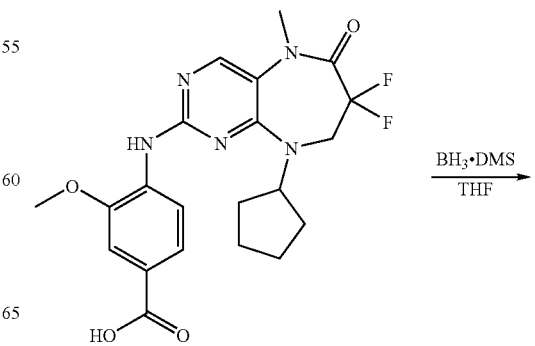

-continued

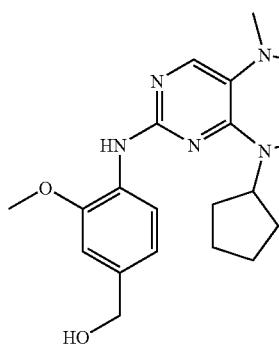

The title compound was synthesized by solubilizing 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid (0.36 mmol) in THF (20 mL), and adding borane-dimethylsulfide (2.0M, 1.8 mL, 3.6 mmol) slowly. The solution was stirred for 18 h and then heated to 50° C. for 2 hours. The reaction mixture was then washed with water (×2), brine, and the solvent evaporated. The final compound was purified by reverse phase HPLC and basified to give the free base (8.1 mg, 5% yield). 1H NMR (400 MHz, DMSO-d$_6$) δ ppm 1.37-1.96 (m, 8H) 2.82 (s, 3H) 3.48 (t, J=13.39 Hz, 2H) 3.78 (t, J=12.00 Hz, 2H) 3.86 (s, 3H) 4.43 (d, 2H) 4.84 (t, J=7.83 Hz, 1H) 5.07 (t, J=5.81 Hz, 1H) 6.82 (d, J=8.34 Hz, 1H) 6.95 (s, 1H) 7.31 (s, 1H) 7.66 (s, 1H) 8.21 (d, J=8.08 Hz, 1H). [M+H] calculated for $C_{21}H_{27}F_2N_5O_2$, 420. found 420.

Compound 138: 4-(9-cyclopentyl-7,7-difluoro-5-methyl-6,7,8,9-tetrahydro-5H-pyrimido[4,5-b][1,4]diazepin-2-ylamino)-3-methoxy-N-(1-methylpiperidin-4-yl)benzamide

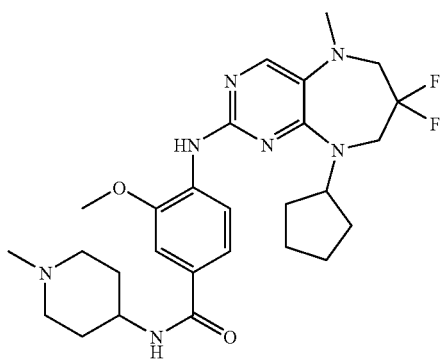

The title compound was synthesized by first following the general Ring Amide Reduction procedure using isopropyl 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoate to yield isopropyl 4-(9-cyclopentyl-7,7-difluoro-5-methyl-6,7,8,9-tetrahydro-5H-pyrimido[4,5-b][1,4]diazepin-2-ylamino)-3-methoxybenzoate. This ester was then saponified by treating with 4N HCl and MeOH (10:1) and heating 100° C. overnight. The solvent was evaporated and the title amide formed as described in the general procedure for amide bond synthesis using HATU and 4-amino-N-methylpiperidine. 1H NMR (400 MHz, DMSO-d$_6$) δ ppm 1.51-1.97 (m, 8H) 2.16 (s, 3H) 2.78 (d, J=10.61 Hz, 2H) 2.83 (s, 3H) 3.31 (br. s., 10H) 3.50 (t, J=13.52 Hz, 2H) 3.81 (t, J=12.13 Hz, 2H) 3.93 (s, 3H) 4.72-4.93 (m, 1H) 7.46 (s, 1H) 7.52 (s, 1H) 7.70 (s, 1H) 8.06 (d, J=7.83 Hz, 1H) 8.39 (d, J=8.34 Hz, 1H). [M+H] calculated for $C_{27}H_{37}F_2N_7O_2$, 530. found 530.

Compound 139: 3-(cyclopentyl(2-(2-methoxy-4-(1-methylpiperidin-4-ylcarbamoyl)phenylamino)-5-(methylamino)pyrimidin-4-yl)amino)-2,2-difluoropropanoic acid

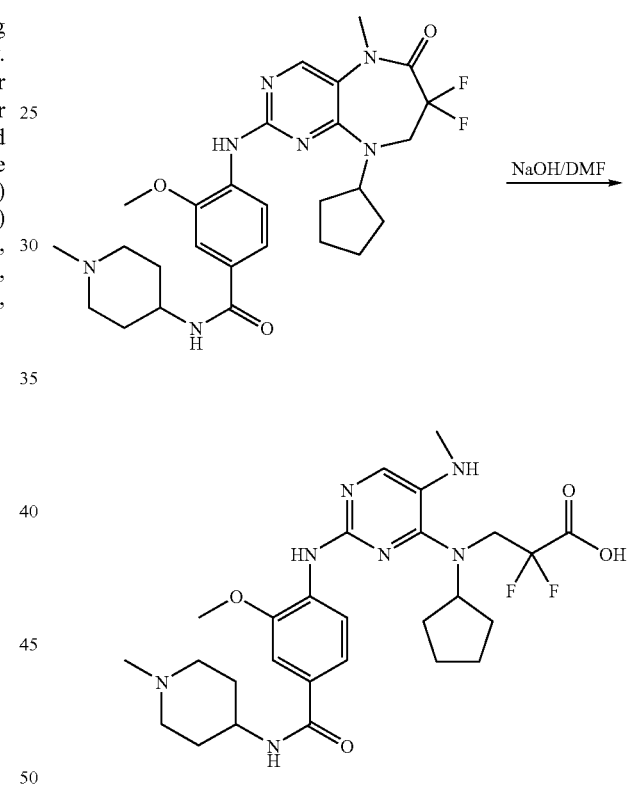

To a mixture of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide (543 mg, 1 mmol) in 10 ml of DMF, was added 1N NaOH (5 ml) dropwise. The reaction mixture was stirred at rt. for 1 h and then subjected to reverse phase HPLC purification using basic column. The final compound was obtained by lyophilization first and then dried in the vacuum oven at 60° C. for 3 d (380 mg, 68%). 1H NMR (400 MHz, DMSO-d$_6$) δ ppm 1.47-1.99 (m, 12H) 2.54 (d, J=2.8 Hz, 2H) 2.64-2.79 (m, 5H) 3.00 (d, J=4.6 Hz, 2H) 3.85-4.10 (m, 6H) 4.20 (d, J=7.3 Hz, 1H) 7.42 (s, 2H) 7.48 (d, J=8.3 Hz, 1H) 7.61-7.80 (m, 1H) 8.23 (br. s., 1H) 8.42 (d, J=8.3 Hz, 1H). [M+H] calc'd for $C_{27}H_{37}F_2N_7O_4$, 562. found 562.

Compound 140: 3-(cyclopentyl(2-(5-fluoro-2-methoxy-4-(1-methylpiperidin-4-ylcarbamoyl)phenylamino)-5-(methylamino)pyrimidin-4-yl)amino)-2,2-difluoropropanoic acid

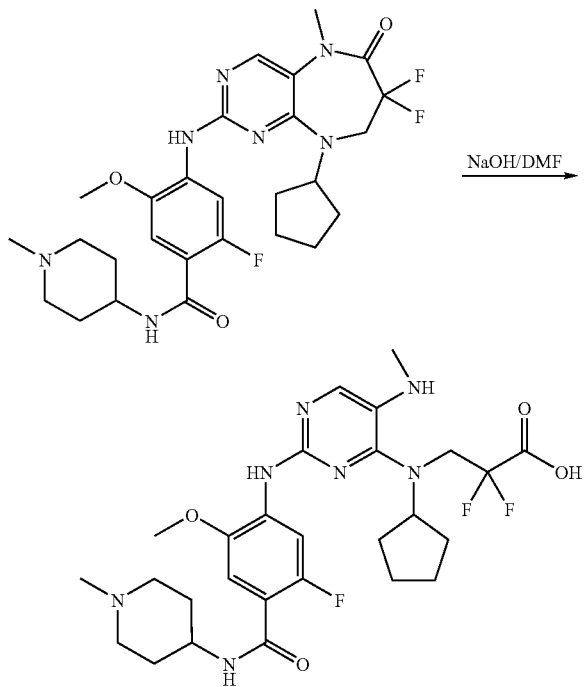

To a mixture of compound 116 (300 mg, 0.53 mmol) in 2 ml of DMF, was added 1N NaOH (1 ml) dropwise. The reaction mixture was stirred at rt. for 1 h and then subjected to reverse phase HPLC purification using basic column (Gemini 5μ C18 column, mobile phase A: H$_2$O; B: 20% H$_2$O in CH$_3$CN which contains 10 μM NH$_4$HCO$_3$). The final compound was directly lyophilized and then dried in the vacuum oven at 60° C. for 3 days to give 234 mg white solid (76%). $^1$H NMR (400 MHz, DMSO-d$_6$) δ ppm 1.48-1.98 (m, 12H) 2.60-2.81 (m, 6H) 3.03 (m, 2H) 3.79-4.08 (s&m, 6H) 4.16 (m, 1H) 7.14 (d, J=6.8 Hz, 1H) 7.52 (s, 1H) 7.71 (s, 1H) 8.03 (br. s., 1H) 8.34-8.38 (d, J=16 Hz, 1H) 9.81 (br. s., 1H). [M+H] calc'd for C$_{27}$H$_{36}$F$_3$N$_7$O$_4$, 580. found 580.

Compound 141: 4-(9-Cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide

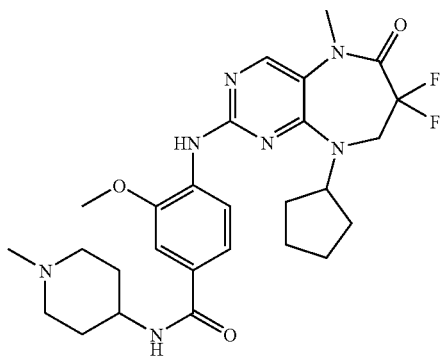

Methyl 3-amino-2,2-difluoropropanoate-HCl salt: In a round bottom flask, 3-amino-2,2-difluoropropanoic acid (500 mg, 4 mmol) was solubilized in MeOH (10 mL). At 0° C., SOCl$_2$ (1 mL) was added dropwise. The reaction mixture was then stirred at room temperature overnight. Evaporation of the reaction mixture gave a white solid to be the product as HCl salt (570 mg, 81%). $^1$H NMR (400 MHz, DMSO-d$_6$) δ ppm 3.63 (t, J=16 Hz, 2H) 3.87 (s, 3H) 9.07 (br. s., 2H).

Methyl 3-(cyclopentylamino)-2,2-difluoropropanoate: To a round bottom flask was added methyl 3-amino-2,2-difluoropropanoate (570 mg, 3.24 mmol), THF (20 mL), cyclopentanone (0.433 mL, 4.87 mmol), and HOAc (1 mL). To this mixture was added sodium triacetoxyborohydride (1.06 g, 5 mmol) portionwise. The reaction was left to stir overnight. It was then added slowly to a stirring solution of ice, NaHCO$_3$ (sat.), and EtOAc. The aqueous layer was further extracted with EtOAc, the organic extracts combined, dried over MgSO$_4$, filtered and concentrated to yield the desired product as clear syrup (400 mg, 60%). $^1$H NMR (400 MHz, DMSO-d$_6$) δ ppm 1.30 (td, J=13, 6 Hz, 2H) 1.43 (d, J=8 Hz, 1H) 1.47-1.70 (m, 4H) 1.77 (dt, J=12, 6 Hz, 2H) 3.12 (t, J=6 Hz, 1H) 3.19 (t, J=14 Hz, 2H) 3.88 (s, 3H).

Methyl 3-((2-chloro-5-nitropyrimidin-4-yl)(cyclopentyl)amino)-2,2-difluoropropanoate: Compound methyl 3-(cyclopentylamino)-2,2-difluoropropanoate (400 mg, 2 mmol) was solubilized in acetone (20 mL, dry). The solution was cooled in an ice water bath under a nitrogen atmosphere and K$_2$CO$_3$ (552 mg, 4 mmol) added. To this, a solution of 2,4-dichloro-5-nitropyrimidine (407 mg, 2.1 mmol) in acetone (5 mL, dry) was added dropwise. The reaction mixture was warmed up to room temperature and stirred for 4 hr. After that, it was diluted with EtOAc and washed by brine and water. The organic extracts were dried over MgSO$_4$, filtered and concentrated to yield the desired product which was used directly for next step without further purification. [M+H] calc'd for C$_{13}$H$_{15}$ClF$_2$N$_4$O$_4$, 365. found 365.

2-Chloro-9-cyclopentyl-7,7-difluoro-8,9-dihydro-5H-pyrimido[5,4-b][1,4]diazepin-6(7H)-one: Above obtained compound, methyl 3-((2-chloro-5-nitropyrimidin-4-yl)(cyclopentyl)amino)-2,2-difluoropropanoate, was dissolved in AcOH (10 mL). Iron powder (224 mg, 4 mmol) was added followed by the slow addition of HCl (1.5 mL, conc.). The reaction mixture was left to stir at 60° C. for 1 hr. The reaction was then cooled, the stir bar and unreacted iron removed by filtration through paper, and the solvent volume reduced by about 75% on a rotovap. The mixture was then diluted with ice water and EtOAc. Aqueous layer basified by careful addition of sat. NaHCO$_3$. The organic extracts combined, dried over MgSO$_4$, filtered and concentrated to yield a brown syrup (550 mg) which was used directly for next step without further purification. [M+H] calc'd for C$_{12}$H$_{13}$ClF$_2$N$_4$O, 303. found 303.

2-Chloro-9-cyclopentyl-7,7-difluoro-5-methyl-8,9-dihydro-5H-pyrimido[5,4-b][1,4]diazepin-6(7H)-one: 2-Chloro-9-cyclopentyl-7,7-difluoro-8,9-dihydro-5H-pyrimido[5,4-b][1,4]diazepin-6(7H)-one (550 mg, 1.82 mmol) was dissolved in DMA (10 mL) and cooled in an ice bath. Sodium hydride (80 mg of 60% in mineral oil, 2 mmol) was added slowly and left to stir for 10 minutes. Methyl iodide (0.125 mL, 2 mmol) was then added and the reaction mixture was warmed up to room temperature. After 30 minutes the reaction was deemed complete by LCMS, poured into ice water, the solution extracted with EtOAc. The organic layer washed with brine and water, dried over MgSO$_4$, and concentrated to give a brown residue which was used directly for next step. [M+H] calc'd for C$_{13}$H$_{15}$ClF$_2$N$_4$O, 317. found 317.

4-(9-Cyclopentyl-7,7-difluoro-5-methyl-6-oxo-6,7,8,9-tetrahydro-5H-pyrimido[5,4-b][1,4]diazepin-2-ylamino)-3-methoxybenzoic acid: 2-Chloro-9-cyclopentyl-7,7-difluoro-5-methyl-8,9-dihydro-5H-pyrimido[5,4-b][1,4]diazepin-6(7H)-one (obtained above), 4-amino-3-methoxy benzoic acid (334 mg, 2 mmol), i-PrOH (10 mL) and conc. HCl (10 drops) were heated to 100° C. overnight. The reaction mixture was then cooled to room temperature, concentrated and redissolved in MeOH, treated with NaOH and refluxed for 1 hr. After which, it was concentrated, acidified with HCl and filtered to get the product as a tan solid (300 mg). [M+H] calc'd for $C_{21}H_{23}F_2N_5O_4$, 448. found 448.

The title compound was synthesized from 4-(9-cyclopentyl-7,7-difluoro-5-methyl-6-oxo-6,7,8,9-tetrahydro-5H-pyrimido[5,4-b][1,4]diazepin-2-ylamino)-3-methoxybenzoic acid (obtained above, 300 mg) as described in the general procedure for amide bond synthesis using HATU and 1-methylpiperidin-4-amine. The final compound was purified by reverse phase HPLC and basified to give the free base (40 mg). $^1$H NMR (400 MHz, DMSO-$d_6$) δ ppm 1.59-2.01 (m, 16H) 2.17 (s, 3H) 2.78 (d, J=11 Hz, 2H) 3.28 (s, 1H) 3.33 (s, 3H) 3.73 (m., 1H) 3.94 (s, 3H) 4.04 (t, J=14 Hz, 2H) 4.76 (m, 1H) 7.47 (s, 1H) 7.50 (s, 1H) 7.95 (s, 1H) 8.09 (d, J=8 Hz, 1H) 8.26 (d, J=8 Hz, 1H) 8.26 (s, 1H). [M+H] calc'd for $C_{27}H_{35}F_2N_7O_3$, 544. found 544.

Compound 142: 4-(9-Cyclopentyl-7,7-difluoro-5-methyl-6-oxo-6,7,8,9-tetrahydro-5H-pyrimido[4,5-b][1,4]diazepin-2-ylamino)-2-fluoro-5-methoxy-N-(1-methylpiperidin-4-yl)benzamide

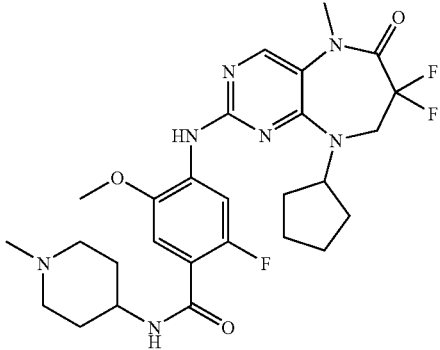

2-Fluoro-5-methoxy-4-nitrobenzoic acid: To a solution of methyl-2,5-difluoro-4-nitrobenzoate (1 g, 4.6 mmol) in methanol (10 mL) was added sodium methoxide (95%, 393 mg, 6.9 mmol). The reaction mixture was stirred at room temperature overnight. It was then concentrated, acidified with HCl. Solid was filtered and dried to give the product as light yellow powder (728 mg, 70%). $^1$H NMR (400 MHz, DMSO-$d_6$) δ ppm 3.95 (s, 3H) 7.66 (d, J=4 Hz, 1H) 8.01 (d, J=8 Hz, 1H).

4-Amino-2-fluoro-5-methoxybenzoic acid: A solution of ethyl 2-fluoro-5-methoxy-4-nitrobenzoic acid (217 mg, 1 mmol), HOAc (cat.) and MeOH (10 mL) was hydrogenated using H-cube hydrogenator. The solution was then concentrated and dried to give the product which can be used for next step without further purification. $^1$H NMR (400 MHz, DMSO-$d_6$) δ ppm 3.76 (s, 3H) 5.88 (br s, 2H) 6.36 (d, J=16 Hz, 1H) 7.13 (d, J=8 Hz, 1H) 12.32 (br s, 1H).

4-(9-Cyclopentyl-7,7-difluoro-5-methyl-6-oxo-6,7,8,9-tetrahydro-5H-pyrimido[4,5-b][1,4]diazepin-2-ylamino)-2-fluoro-5-methoxybenzoic acid: 2-Chloro-9-cyclopentyl-7,7-difluoro-5-methyl-8,9-dihydro-5H-pyrimido[5,4-b][1,4]diazepin-6(7H)-one (158 mg, 0.5 mmol), 4-amino-2-fluoro-5-methoxy benzoic acid (obtained above), i-PrOH (5 mL) and conc. HCl (10 drops) were heated to 100° C. overnight. The reaction mixture was then cooled to room temperature. The reaction mixture contains desired product plus lots of decarboxylation byproduct, which were separated by RP-HPLC to give the product as a white solid (12 mg). [M+H] calc'd for $C_{21}H_{22}F_3N_5O_4$, 466. found 466.

The title compound was synthesized from 4-(9-cyclopentyl-7,7-difluoro-5-methyl-6-oxo-6,7,8,9-tetrahydro-5H-pyrimido[5,4-b][1,4]diazepin-2-ylamino)-2-fluoro-5-methoxybenzoic acid (obtained above, 12 mg) as described in the general procedure for amide bond synthesis using HATU and 1-methylpiperidin-4-amine. The final compound was purified by reverse phase HPLC and basified to give the free base (8 mg, 55%). $^1$H NMR (400 MHz, DMSO-$d_6$) δ ppm 1.60-1.73 (m, 11H), 1.88-2.21 (m, 8H) 2.78 (br. s., 2H) 3.73 (br. s., 1H) 3.91 (s, 3H) 4.08 (t, J=14 Hz, 2H) 4.81 (d, J=8 Hz, 1H) 7.18 (d, J=7 Hz, 1H) 7.91 (br. s., 1H) 8.04 (s, 1H) 8.24 (d, J=13 Hz, 1H) 8.30 (s, 1H). [M+H] calc'd for $C_{27}H_{34}F_3N_7O_3$, 562. found 562.

Compound 143: 9-Cyclopentyl-2-(2,5-difluorophenylamino)-7,7-difluoro-5-methyl-8,9-dihydro-5H-pyrimido[4,5-b][1,4]diazepin-6(7H)-one

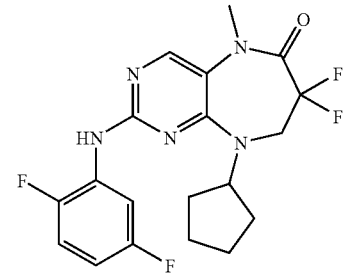

2-Chloro-9-cyclopentyl-7,7-difluoro-5-methyl-8,9-dihydro-5H-pyrimido[5,4-b][1,4]diazepin-6(7H)-one (50 mg, 0.16 mmol), 2,5-difluoroaniline (31 mg, 0.24 mmol), i-PrOH (2 mL) and conc. HCl (5 drops) were heated to 100° C. overnight to give the title compound. The final compound was purified by reverse phase HPLC and basified to give the free base (20 mg, 31%). $^1$H NMR (400 MHz, DMSO-$d_6$) δ ppm 1.23-1.85 (m, 11H) 4.02 (t, J=14 Hz, 2H) 4.68 (d, J=8 Hz, 1H) 6.88 (t, J=8 Hz, 1H) 7.26 (td, J=10, 6 Hz, 1H) 7.74-7.96 (m, 1H) 8.24 (s, 1H) 9.04 (br. s., 1H). [M+H] calc'd for $C_{19}H_{19}F_4N_5O$, 410. found 410.

Compound 144: 9-Cyclopentyl-7,7-difluoro-2-(3-fluorophenylamino)-5-methyl-8,9-dihydro-5H-pyrimido[4,5-b][1,4]diazepin-6(7H)-one

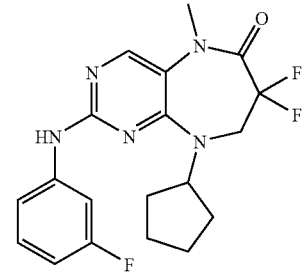

2-Chloro-9-cyclopentyl-7,7-difluoro-5-methyl-8,9-dihydro-5H-pyrimido[5,4-b][1,4]diazepin-6(7H)-one (100 mg, 0.32 mmol), 3-fluoroaniline (54 mg, 0.48 mmol), i-PrOH (2 mL) and conc. HCl (5 drops) were heated to 100° C. overnight to give the title compound. The final compound was purified by reverse phase HPLC and basified to give the free base (50 mg, 40%). $^1$H NMR (400 MHz, DMSO-$d_6$) δ ppm 1.58-1.96 (m, 8H) 4.04 (t, J=14 Hz, 2H) 4.78 (m, 1H) 6.59-6.87 (m, 1H) 7.16-7.33 (m, 1H) 7.38 (d, J=8 Hz, 1H) 7.79 (d, J=12 Hz, 1H) 8.26 (s, 1H) 9.66 (br. s., 1H). [M+H] calc'd for $C_{19}H_{20}F_3N_5O$, 392. found 392.

Compound 145: 9-Cyclopentyl-7,7-difluoro-2-(5-fluoro-2-methylphenylamino)-5-methyl-8,9-dihydro-5H-pyrimido[4,5-b][1,4]diazepin-6(7H)-one

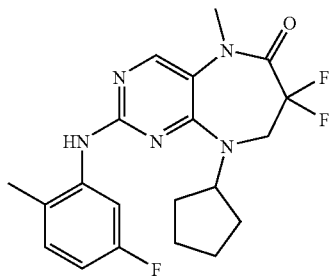

2-Chloro-9-cyclopentyl-7,7-difluoro-5-methyl-8,9-dihydro-5H-pyrimido[5,4-b][1,4]diazepin-6(7H)-one (100 mg, 0.32 mmol), 5-fluoro-2-methylaniline (60 mg, 0.48 mmol), i-PrOH (2 mL) and conc. HCl (5 drops) were heated to 100° C. overnight to give the title compound. The final compound was purified by reverse phase HPLC and basified to give the free base (50 mg, 39%). $^1$H NMR (400 MHz, DMSO-$d_6$) δ ppm 1.40-1.96 (m, 9H) 2.22 (s, 3H) 3.99 (t, J=14 Hz, 2H) 4.62 (t, J=8 Hz, 1H) 6.81 (td, J=8, 3 Hz, 1H) 7.19 (t, J=8 Hz, 1H) 7.58 (dd, J=12, 3 Hz, 1H) 8.20 (s, 1H) 8.57 (s, 1H). [M+H] calc'd for $C_{20}H_{22}F_3N_5O$, 406. found 406.

Compound 146: 4-(9-Cyclopentyl-7,7-difluoro-5-methyl-6-oxo-6,7,8,9-tetrahydro-5H-pyrimido[4,5-b][1,4]diazepin-2-ylamino)-2-methyl-N-(1-methylpiperidin-4-yl)benzamide

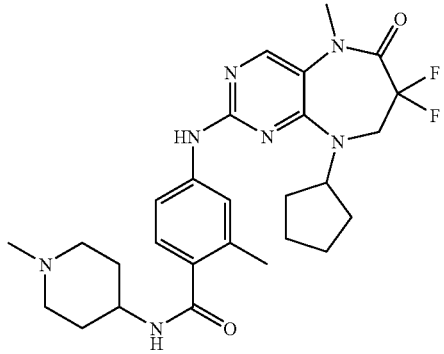

The title compound was synthesized from 4-(9-cyclopentyl-7,7-difluoro-5-methyl-6-oxo-6,7,8,9-tetrahydro-5H-pyrimido[4,5-b][1,4]diazepin-2-ylamino)-2-methylbenzoic acid as described in the general procedure for amide bond synthesis using HATU and 1-methylpiperidin-4-amine. The final compound was purified by reverse phase HPLC and basified to give the free base. $^1$H NMR (400 MHz, DMSO-$d_6$) δ ppm 1.36-1.77 (m, 11H) 1.98 (m, 4H) 2.16 (s, 3H) 2.31 (s, 3H) 2.75 (d, J=11 Hz, 2H) 3.17 (br. s., 2H) 3.67 (d, J=7 Hz, 1H) 4.03 (t, J=14 Hz, 3H) 4.81 (m, 1H) 7.22 (d, J=8 Hz, 1H) 7.46 (d, J=8 Hz, 1H) 7.68 (br. s., 1H) 7.99 (d, J=8 Hz, 1H) 8.25 (s, 1H) 9.51 (br. s., 1H). [M+H] calc'd for $C_{27}H_{35}F_2N_7O_2$, 528. found 528.

Compound 147: 4-(9-Cyclopentyl-7,7-difluoro-5-methyl-6-oxo-6,7,8,9-tetrahydro-5H-pyrimido[4,5-b][1,4]diazepin-2-ylamino)-2-methoxy-N-(1-methylpiperidin-4-yl)benzamide

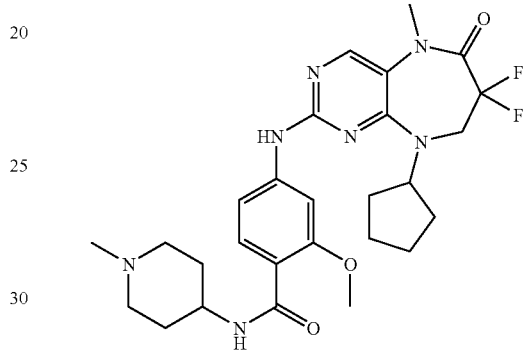

The title compound was synthesized from 4-(9-cyclopentyl-7,7-difluoro-5-methyl-6-oxo-6,7,8,9-tetrahydro-5H-pyrimido[4,5-b][1,4]diazepin-2-ylamino)-2-methoxybenzoic acid as described in the general procedure for amide bond synthesis using HATU and 1-methylpiperidin-4-amine. The final compound was purified by reverse phase HPLC. $^1$H NMR (400 MHz, DMSO-$d_6$) δ ppm 1.48-2.22 (m, 14H) 2.66-2.88 (m, 2H) 3.05 (m, 2H) 3.33 (s, 3H) 3.46 (d, J=11 Hz, 2H) 3.86 (s, 3H) 4.05 (t, J=14 Hz, 3H) 4.81 (m, 1H) 7.49 (m, 2H) 7.64 (m, 1H) 7.93 (d, J=7 Hz, 1H) 8.28 (s, 1H) 9.69 (s, 1H). [M+H] calc'd for $C_{27}H_{35}F_2N_7O_3$, 544. found 544.

Compound 148: 5-(9-Cyclopentyl-7,7-difluoro-5-methyl-6-oxo-6,7,8,9-tetrahydro-5H-pyrimido[4,5-b][1,4]diazepin-2-ylamino)-N-(1-methylpiperidin-4-yl)picolinamide

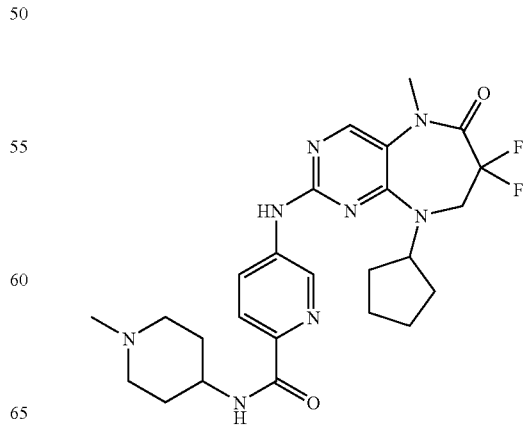

The title compound was synthesized from 5-(9-cyclopentyl-7,7-difluoro-5-methyl-6-oxo-6,7,8,9-tetrahydro-5H-pyrimido[4,5-b][1,4]diazepin-2-ylamino)picolinic acid as described in the general procedure for amide bond synthesis using HATU and 1-methylpiperidin-4-amine. The final compound was purified by reverse phase HPLC. $^1$H NMR (400 MHz, DMSO-$d_6$) δ ppm 1.44-2.04 (m, 13H) 2.77 (d, J=5 Hz, 2H) 3.01-3.22 (m, 2H) 3.34 (s, 3H) 3.47 (d, J=11 Hz, 2H) 4.08 (m, 3H) 4.80 (m, 1H) 7.85-8.02 (m, 1H) 8.30 (s, 1H) 8.44 (dd, J=9, 2 Hz, 1H) 8.69 (d, J=8 Hz, 1H) 8.80-8.92 (m, 1H) 9.85-10.01 (m, 1H). [M+H] calc'd for $C_{25}H_{32}F_2N_8O_2$, 516. found 516.

Compound 149: 4-(9-cyclopentyl-7,7-difluoro-5-methyl-6-oxo-6,7,8,9-tetrahydro-5H-pyrimido[5,4-b][1,4]diazepin-2-ylamino)-3-methoxy-N-(4-((4-methylpiperazin-1-yl)methyl)phenyl)benzamide

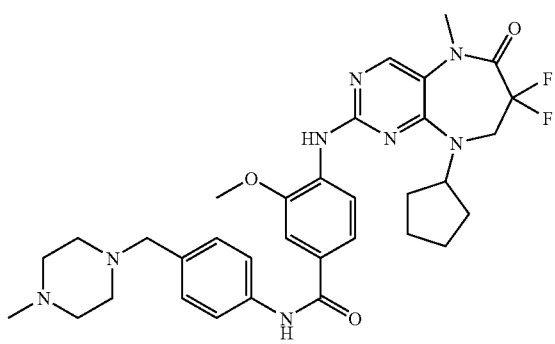

In a dry round bottom flask, 4-(9-cyclopentyl-7,7-difluoro-5-methyl-6-oxo-6,7,8,9-tetrahydro-5H-pyrimido[5,4-b][1,4]diazepin-2-ylamino)-3-methoxybenzoic acid (89.4 mg, 0.2 mmol), 4-((4-methylpiperazin-1-yl)methyl)aniline hydrochloride (66.7 mg, 0.24 mmol) were dissolved in dry N,N-dimethylformamide (3.0 mL). Then added diisopropylethylamine (107 μL, 0.6 mmol) and finally HATU (114 mg, 0.3 mmol) to the reaction, continued at room temperature for 2 hours. After completion, purified the product using reverse phase HPLC using water-acetonitrile solvent system. Pure fractions were mixed and evaporated to a minimal amount then basified with sat.NaHCO$_3$ solution and extracted into EtOAc ((2×100 mL), combined organic layer was washed with sat. brine solution, dried over Na$_2$SO$_4$ and evaporated to get the pure product 72 mg (57% yield). $^1$H NMR (400 MHz, DMSO-$d_6$) δ ppm 1.51-1.80 (m, 6H) 1.97 (br. s., 2H) 2.15 (s, 3H) 2.34 (br. s., 8H) 3.42 (s, 2H) 3.93 (s, 3H) 4.07 (t, J=12 Hz, 2H) 4.80 (t, J=8.21 Hz, 1H) 7.26 (d, J=8.59 Hz, 2H) 7.51-7.67 (m, 2H) 7.70 (m, J=8.59 Hz, 2H) 8.05 (s, 1H) 8.29 (s, 1H) 8.37 (d, J=8.34 Hz, 1H) 10.09 (s, 1H). [M+H] calc'd for $C_{33}H_{40}F_2N_8O_3$, 635. found 635.

Compound 150A: 4-(9-cyclopentyl-7,7-difluoro-5-methyl-6-oxo-6,7,8,9-tetrahydro-5H-pyrimido[5,4-b][1,4]diazepin-2-ylamino)-N-(3-fluoro-4-(4-methylpiperazin-1-yl)phenyl)-3-methoxybenzamide

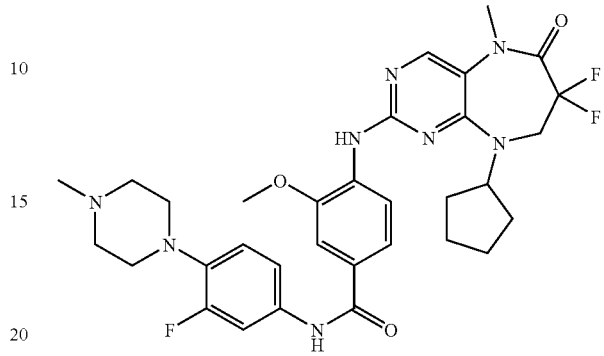

The title compound was prepared in a manner analogous to the compound 149 from 4-(9-cyclopentyl-7,7-difluoro-5-methyl-6-oxo-6,7,8,9-tetrahydro-5H-pyrimido[5,4-b][1,4]diazepin-2-ylamino)-3-methoxybenzoic acid and 3-fluoro-4-(4-methylpiperazin-1-yl)aniline with yield 52.4 mg (41%). $^1$H NMR (400 MHz, DMSO-$d_6$) δ ppm 1.60 (br. s., 6H) 1.99 (s, 2H) 2.22 (s, 3H) 2.40-2.51 (m, 4H) 2.98 (br. s., 4H) 3.97 (s, 3H) 4.22 (t, 2H) 4.79 (m, 1H) 7.03 (t, J=9.35 Hz, 1H) 7.45 (dd, J=8.72, 1.64 Hz, 1H) 7.54-7.78 (m, 3H) 8.04 (s, 1H) 8.28 (s, 1H) 8.36 (d, J=8.34 Hz, 1H) 10.11 (s, 1H). [M+H] calc'd for $C_{32}H_{37}F_2N_8O_3$, 639. found 639.

Compound 150B 4-(9-cyclopentyl-7,7-difluoro-5-methyl-6-oxo-6,7,8,9-tetrahydro-5H-pyrimido[5,4-b][1,4]diazepin-2-ylamino)-3-methoxy-N-(4-(4-methylpiperazin-1-yl)-3-(trifluoromethyl)phenyl)benzamide

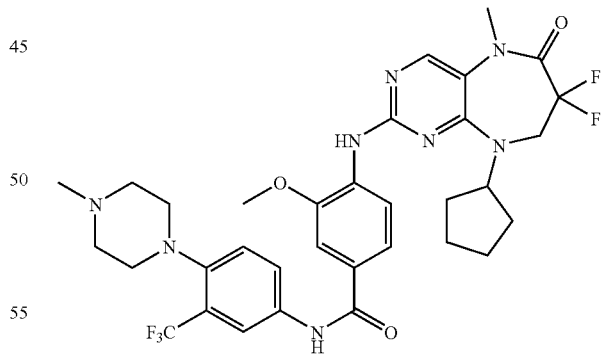

The title compound was prepared in a manner analogous to compound 149 from 4-(9-cyclopentyl-7,7-difluoro-5-methyl-6-oxo-6,7,8,9-tetrahydro-5H-pyrimido[5,4-b][1,4]diazepin-2-ylamino)-3-methoxybenzoic acid and 4-(4-methylpiperazin-1-yl)-3-(trifluoromethyl)aniline with yield 46 mg (34%). $^1$H NMR (400 MHz, DMSO-$d_6$) δ ppm 1.43-1.72 (m, 6H) 1.99 (br. s., 2H) 2.23 (s, 3H) 2.47 (br.s., 4H) 2.85 (t, J=4.29 Hz, 4H) 3.99 (s, 3H) 4.07 (t, J=12 Hz, 2H) 4.80 (t, J=7.96 Hz, 1H) 7.46-7.73 (m, 3H) 7.97-8.10 (m, 2H) 8.14 (d, J=2.53 Hz, 1H) 8.29 (s, 1H) 8.38 (d, J=8.34 Hz, 1H) 10.31 (s, 1H). [M+H] calc'd for $C_{33}H_{37}F_5N_8O_3$, 689. found 689.

Compound 151: 4-(9-cyclopentyl-7,7-difluoro-5-methyl-6-oxo-6,7,8,9-tetrahydro-5H-pyrimido[5,4-b][1,4]diazepin-2-ylamino)-3-methoxy-N-(3-(4-methylpiperazin-1-yl)phenyl)benzamide

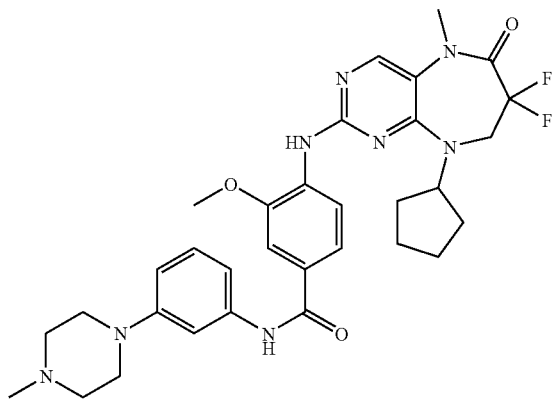

The title compound was prepared in a manner analogous to compound 149 from 4-(9-cyclopentyl-7,7-difluoro-5-methyl-6-oxo-6,7,8,9-tetrahydro-5H-pyrimido[5,4-b][1,4]diazepin-2-ylamino)-3-methoxybenzoic acid and 3-(4-methylpiperazin-1-yl)aniline with yield 35 mg (28%). $^1$H NMR (400 MHz, DMSO-$d_6$) δ ppm 1.43-1.72 (m, 6H) 1.98 (br. s., 2H) 2.22 (s, 2H) 2.35-2.50 (m, 4H) 2.97-3.23 (m, 4H) 3.98 (s, 3H) 4.06 (t, J=12 Hz, 2H) 4.79 (m, 1H) 6.55-6.79 (m, 1H) 7.12-7.26 (m, 2H) 7.40 (s, 1H) 7.52-7.72 (m, 2H) 8.03 (s, 1H) 8.28 (s, 1H) 8.35 (d, J=8.34 Hz, 1H) 9.94 (s, 1H). [M+H] calc'd for $C_{32}H_{38}F_2N_8O_3$, 621. found 621.

Compound 152: 4-(9-cyclopentyl-7,7-difluoro-5-methyl-6-oxo-6,7,8,9-tetrahydro-5H-pyrimido[5,4-b][1,4]diazepin-2-ylamino)-2-fluoro-5-methoxy-N-(4-((4-methylpiperazin-1-yl)methyl)phenyl)benzamide

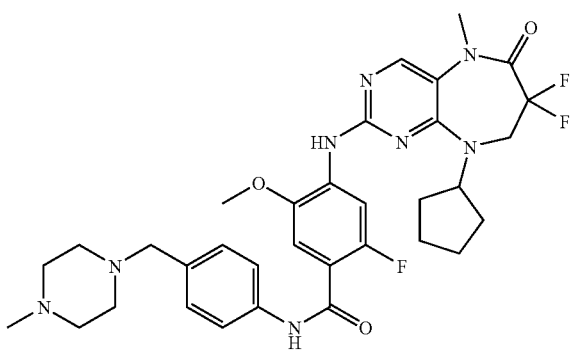

The title compound was prepared in a manner analogous to compound 149 from 4-(9-cyclopentyl-7,7-difluoro-5-methyl-6-oxo-6,7,8,9-tetrahydro-5H-pyrimido[5,4-b][1,4]diazepin-2-ylamino)-2-fluoro-5-methoxybenzoic acid and 4-((4-methylpiperazin-1-yl)methyl)aniline hydrochloride with yield 48 mg (37%). $^1$H NMR (400 MHz, DMSO-$d_6$) δ ppm 1.62 (br. s., 4H) 1.73 (br. s., 2H) 1.98 (m, 2H) 2.14 (s, 3H) 2.17-2.45 (m, 8H) 3.40 (s, 2H) 3.94 (s, 3H) 4.09 (t, J=12 Hz, 2H) 4.84 (t, J=8.08 Hz, 1H) 7.16-7.37 (m, 3H) 7.66 (d, J=8.34 Hz, 2H) 8.10 (s, 1H) 8.19-8.39 (m, 2H) 10.13 (s, 1H). [M+H] calc'd for $C_{33}H_{39}F_3N_8O_3$, 653. found 653.

Compound 153: 4-(9-cyclopentyl-7,7-difluoro-5-methyl-6-oxo-6,7,8,9-tetrahydro-5H-pyrimido[5,4-b][1,4]diazepin-2-ylamino)-2-fluoro-5-methoxy-N-(3-((4-methylpiperazin-1-yl)methyl)phenyl)benzamide

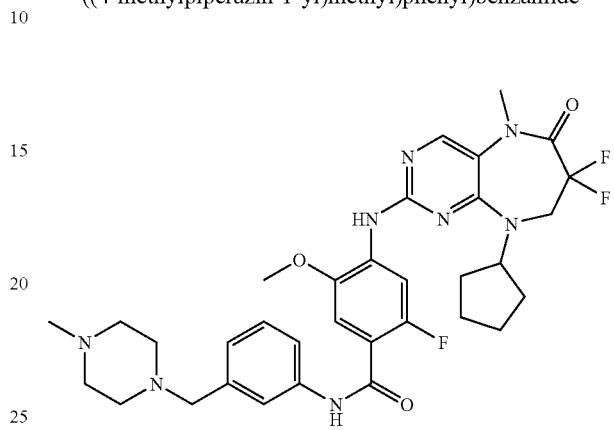

The title compound was prepared in a manner analogous to compound 149 from 4-(9-cyclopentyl-7,7-difluoro-5-methyl-6-oxo-6,7,8,9-tetrahydro-5H-pyrimido[5,4-b][1,4]diazepin-2-ylamino)-2-fluoro-5-methoxybenzoic acid and 3-((4-methylpiperazin-1-yl)methyl)aniline hydrochloride with yield 43 mg (33%). $^1$H NMR (400 MHz, DMSO-$d_6$) δ ppm 1.62 (br. s., 6H) 1.99 (br. s., 2H) 2.14 (s, 3H) 2.33 (br. s., 8H) 3.43 (s, 2H) 3.94 (s, 3H) 4.09 (t, J=13.89 Hz, 2H) 4.84 (br. s., 1H) 7.01 (d, J=7.58 Hz, 1H) 7.20-7.35 (m, 2H) 7.61 (br. s., 1H) 7.67 (br. s., 1H) 8.10 (s, 1H) 8.23-8.40 (m, 2H) 10.14 (s, 1H). [M+H] calc'd for $C_{33}H_{39}F_3N_8O_3$, 653. found 653.

Compound 154: 4-(9-cyclopentyl-7,7-difluoro-5-methyl-6-oxo-6,7,8,9-tetrahydro-5H-pyrimido[5,4-b][1,4]diazepin-2-ylamino)-2-fluoro-N-(3-fluoro-4-(4-methylpiperazin-1-yl)phenyl)-5-methoxybenzamide

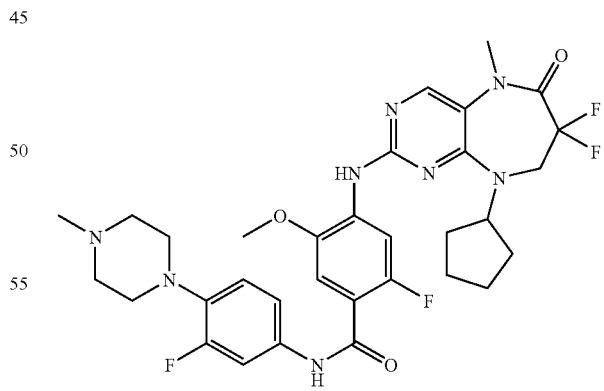

The title compound was prepared in a manner analogous to compound 149 from 4-(9-cyclopentyl-7,7-difluoro-5-methyl-6-oxo-6,7,8,9-tetrahydro-5H-pyrimido[5,4-b][1,4]diazepin-2-ylamino)-2-fluoro-5-methoxybenzoic and 3-fluoro-4-(4-methylpiperazin-1-yl)aniline with yield 70 mg (53%). $^1$H NMR (400 MHz, DMSO-$d_6$) δ ppm 1.42-1.73 (m, 6H) 1.86-2.06 (m, 2H) 2.22 (s, 3H) 2.35-2.49 (m, 4H) 2.97

(br. s., 4H) 3.94 (s, 3H) 4.09 (t, J=13.89 Hz, 2H) 4.82 (t, J=7.83 Hz, 1H) 7.01 (t, J=9.35 Hz, 1H) 7.26 (d, J=6.82 Hz, 1H) 7.32-7.45 (m, 1H) 7.63 (dd, J=15.03, 1.89 Hz, 1H) 8.10 (s, 1H) 8.19-8.46 (m, 2H) 10.16 (s, 1H). [M+H] calc'd for $C_{32}H_{36}F_4N_8O_3$, 657. found 657.

Compound 155: 4-(9-cyclopentyl-7,7-difluoro-5-methyl-6-oxo-6,7,8,9-tetrahydro-5H-pyrimido[5,4-b][1,4]diazepin-2-ylamino)-2-fluoro-5-methoxy-N-(4-(4-methylpiperazin-1-yl)phenyl)benzamide

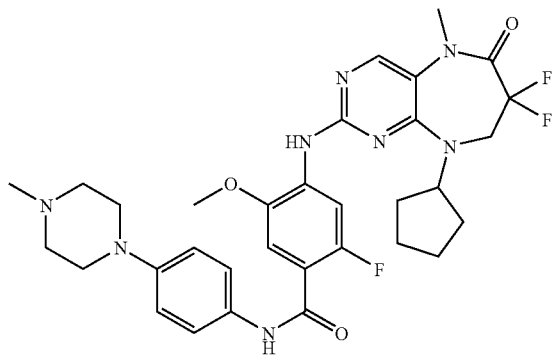

The title compound was prepared in a manner analogous to compound 149 from 4-(9-cyclopentyl-7,7-difluoro-5-methyl-6-oxo-6,7,8,9-tetrahydro-5H-pyrimido[5,4-b][1,4]diazepin-2-ylamino)-2-fluoro-5-methoxybenzoic acid and 4-(4-methylpiperazin-1-yl)aniline with yield 82 mg (53%). $^1$H NMR (400 MHz, DMSO-$d_6$) δ ppm 1.61 (br. s., 4H) 1.73 (br. s., 2H) 1.99 (br. s., 2H) 2.22 (s, 3H) 2.45 (br. s., 4H) 3.09 (br. s., 4H) 3.94 (s, 3H) 4.08 (t, J=13.89 Hz, 2H) 4.84 (br. s., 1H) 6.91 (d, J=8.84 Hz, 2H) 7.26 (d, J=6.32 Hz, 1H) 7.56 (d, J=8.59 Hz, 2H) 8.08 (s, 1H) 8.18-8.41 (m, 2H) 9.91 (br. s., 1H). [M+H] calc'd for $C_{32}H_{37}F_3N_8O_3$, 639. found 639.

Compound 156: N-(azetidin-3-yl)-4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxybenzamide

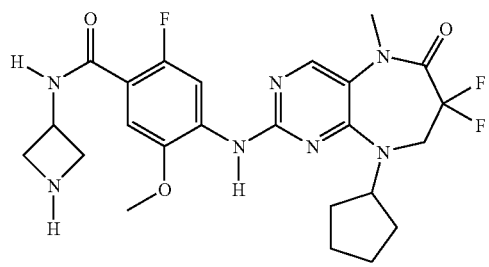

To a solution of 4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxybenzoic acid (1 g, 2.2 mmol) in DMF (4 mL) was added tert-butyl 3-aminoazetidine-1-carboxylate (413 mg, 2.4 mmol), HATU (1.43 g, 3.75 mmol), and DIEA (973 µL, 5.5 mmol). The reaction mixture was stirred for 1 h. It was then poured into 100 mL of rapidly stirring water. A dark brown solid forms and was filtered, washed with water and dried to give 884 mg of the Boc protected intermediate. This solid was treated with TFA in DCM (10 mL 1:1) for 30 minutes. The solvent was then removed, and the residue partitioned between ethyl acetate and sodium bicarbonate (sat. aq.). The layers were separated and the aqueous layer was further extracted with a portion of DCM with 3% MeOH. The organic layers were combined, dried over MgSO$_4$, filtered and concentrated to yield a brown tar (568 mg, 50% yield) which was used crude in subsequent reactions. $^1$H NMR (400 MHz, DMSO-$d_6$) δ ppm 1.48-1.77 (m, 6H) 1.96 (br. s., 2H) 3.56 (dd, J=7.45, 4.42 Hz, 3H) 3.91 (s, 2H) 4.08 (t, J=14.02 Hz, 2H) 4.62-4.73 (m, 1H) 4.76-4.90 (m, 1H) 7.20 (d, J=6.82 Hz, 1H) 8.05 (s, 1H) 8.26 (d, J=13.39 Hz, 1H) 8.30 (s, 1H) 8.51 (d, J=3.54 Hz, 1H). [M+H] calc'd for $C_{24}H_{28}F_3N_7O_3$, 520. found 520.

Compound 157: 4-(9-cyclopentyl-7,7-difluoro-5-methyl-6-oxo-6,7,8,9-tetrahydro-5H-pyrimido[4,5-b][1,4]diazepin-2-ylamino)-2-fluoro-N-(1-isopropylazetidin-3-yl)-5-methoxybenzamide

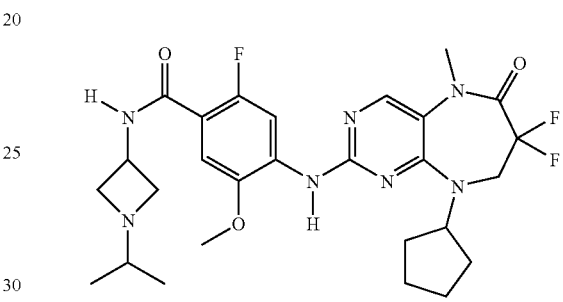

To a solution of N-(azetidin-3-yl)-4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxybenzamide (100 mg, 0.19 mmol) in AcOH:DCM:MeOH (2.5 mL, 1:2:2) was added acetone (100 µL, 1.36 mmol), borane-pyridine complex (100 µL, 0.8 mmol), and left to stir for 3 h. The solvent was then removed and the product purified by reverse phase HPLC, free based, and lyophilized to yield a white solid (3.3 mg, 3%). $^1$H NMR (400 MHz, DMSO-$d_6$) δ ppm 0.85 (d, J=6.06 Hz, 4H) 1.05 (d, J=6.57 Hz, 2H) 1.44-1.80 (m, 6H) 1.95 (br. s., 2H) 2.27 (dt, J=12.32, 6.09 Hz, 1H) 2.89 (t, J=7.33 Hz, 2H) 3.50 (t, J=7.33 Hz, 1H) 3.92 (s, 3H) 4.08 (t, J=13.89 Hz, 2H) 4.29-4.42 (m, 1H) 4.72-4.89 (m, 1H) 7.19 (d, J=6.82 Hz, 1H) 8.05 (s, 1H) 8.25 (d, J=13.39 Hz, 1H) 8.29-8.32 (m, 1H) 8.40 (d, J=7.07 Hz, 1H). [M+H] calc'd for $C_{27}H_{34}F_3N_7O_3$, 562. found 562.

Compound 158: 4-(9-cyclopentyl-7,7-difluoro-5-methyl-6-oxo-6,7,8,9-tetrahydro-5H-pyrimido[4,5-b][1,4]diazepin-2-ylamino)-N-(1-cyclopentylazetidin-3-yl)-2-fluoro-5-methoxybenzamide

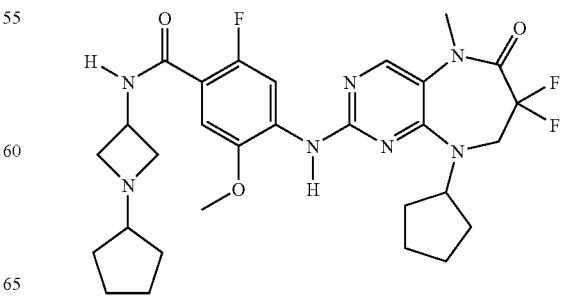

To a solution of N-(azetidin-3-yl)-4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxybenzamide (100 mg, 0.19 mmol) in AcOH:DCM:MeOH (2.5 mL, 1:2:2) was added cyclopentanone (100 µL, 1.09 mmol), borane-pyridine complex (100 µL, 0.8 mmol), and left to stir for 3 h. The solvent was then removed and the product purified by reverse phase HPLC, free based, and lyophilized to yield a white solid (5.0 mg, 9%). $^1$H NMR (400 MHz, DMSO-$d_6$) δ ppm 1.23-1.35 (m, 2H) 1.38-1.78 (m, 11H) 1.96 (br. s., 2H) 2.67 (br. s., 1H) 2.87 (t, J=7.33 Hz, 2H) 3.49 (t, J=7.33 Hz, 2H) 3.91 (s, 3H) 4.08 (t, J=13.77 Hz, 2H) 4.33-4.44 (m, 1H) 4.78-4.88 (m, 1H) 7.19 (d, J=6.57 Hz, 1H) 8.05 (s, 1H) 8.25 (d, J=13.39 Hz, 1H) 8.30 (s, 1H) 8.41 (dd, J=6.82, 3.03 Hz, 1H). [M+H] calc'd for $C_{29}H_{36}F_3N_7O_3$, 588. found 588.

Compound 159: N-(azetidin-3-yl)-4-(9-cyclopentyl-7,7-difluoro-5-methyl-6-oxo-6,7,8,9-tetrahydro-5H-pyrimido[4,5-b][1,4]diazepin-2-ylamino)-3-methoxybenzamide

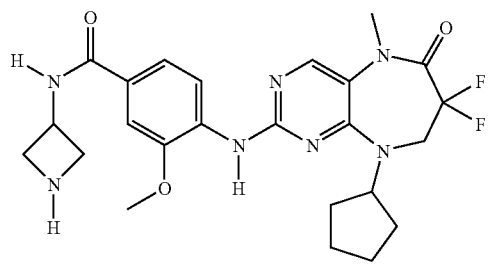

To a solution of 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid (100 mg, 0.22 mmol) in DMF (1 mL) was added tert-butyl 3-aminoazetidine-1-carboxylate (41.3 mg, 0.24 mmol), HATU (125 mg, 0.33 mmol), and DIEA (80 µL, 0.44 mmol). The reaction mixture was stirred for 1 h. It was then poured into 100 mL of rapidly stirring water. A peach solid forms and was filtered, washed with water and dried. This solid was treated with TFA in DCM (3 mL 1:1) for 30 minutes. The solvent was then removed, and the product purified by reverse phase HPLC, free based and lyophilized to yield a white solid (37.4 mg, 34% yield). $^1$H NMR (400 MHz, DMSO-$d_6$) δ ppm 1.49-1.79 (m, 6H) 1.93 (br. s., 2H) 3.52-3.66 (m, 4H) 3.94 (s, 3H) 4.05 (t, J=14.02 Hz, 2H) 4.56-4.84 (m, 2H) 7.45-7.58 (m, 2H) 7.98 (s, 1H) 8.26 (s, 1H) 8.28 (d, J=8.34 Hz, 1H) 8.75 (d, J=7.07 Hz, 1H). [M+H] calc'd for $C_{24}H_{29}F_2N_7O_3$, 502. found 502.

Compound 160: 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-(methylsulfonyl)azetidin-3-yl)benzamide

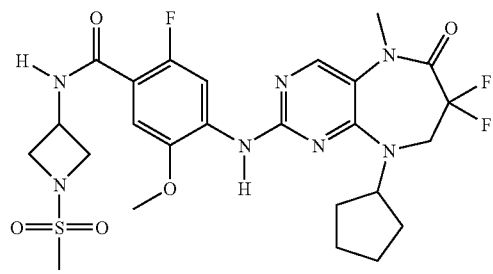

To a solution of N-(azetidin-3-yl)-4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxybenzamide (100 mg, 0.19 mmol) in DCM (2.5 mL, 1:2:2) was added DIEA (50 µL, 0.285 mmol), followed by methanesulfonyl chloride (23 µL, 0.21 mmol). After stirring overnight the solvent was removed and the product purified by reverse phase HPLC, free based, and lyophilized to yield a white solid (9.3 mg, 9%). $^1$H NMR (400 MHz, DMSO-$d_6$) δ ppm 1.54-1.79 (m, 6H) 1.96 (br. s., 2H) 3.05 (s, 3H) 3.92 (s, 3H) 3.94 (d, J=1.77 Hz, 2H) 4.03-4.15 (m, 4H) 4.61-4.72 (m, 1H) 4.76-4.87 (m, 1H) 7.24 (d, J=6.57 Hz, 1H) 8.08 (s, 1H) 8.27 (d, 1H) 8.31 (s, 1H) 8.73 (d, J=3.79 Hz, 1H). [M+H] calc'd for $C_{25}H_{30}F_3N_7O_5S$, 598. found 598.

Compound 161: 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-(piperidin-4-yl)azetidin-3-yl)benzamide

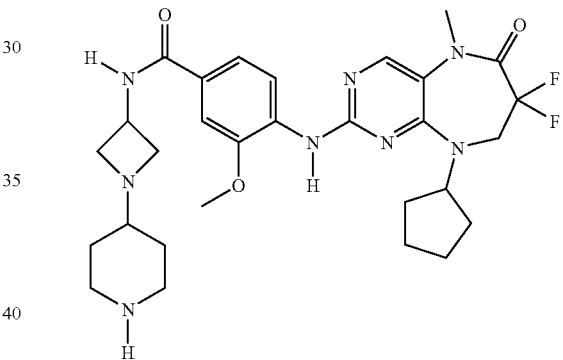

To a solution of 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid (100 mg, 0.22 mmol) in DMF (1 mL) was added tert-butyl 4-(3-aminoazetidin-1-yl)piperidine-1-carboxylate (72 mg, 0.25 mmol), HATU (125 mg, 0.33 mmol), and DIEA (80 µL, 0.44 mmol). The reaction mixture was stirred for 1 h. It was then poured into 100 mL of rapidly stirring water. A white solid forms and was filtered, washed with water and dried. This solid was treated with TFA in DCM (3 mL 1:1) for 2 days. The solvent was then removed, and the product purified by reverse phase HPLC, free based and lyophilized to yield a white solid (17.8 mg, 14% yield $^1$H NMR (400 MHz, DMSO-$d_6$) δ ppm 1.02 (br. s., 2H) 1.50-1.79 (m, 9H) 1.93 (br. s., 2H) 2.07 (br. s., 1H) 2.35-2.44 (m, 2H) 2.85-3.00 (m, 4H) 3.52 (t, J=7.20 Hz, 2H) 3.94 (s, 3H) 4.05 (t, J=14.02 Hz, 2H) 4.37-4.50 (m, 1H) 4.68-4.84 (m, 1H) 7.47-7.52 (m, 2H) 7.98 (s, 1H) 8.26 (s, 1H) 8.29 (d, 1H) 8.61 (d, J=6.57 Hz, 1H). [M+H] calc'd for $C_{29}H_{38}F_2N_8O_3$, 585. found 585.

Compound 162: 4-(9-cyclopentyl-7,7-difluoro-5-methyl-6-oxo-6,7,8,9-tetrahydro-5H-pyrimido[4,5-b][1,4]diazepin-2-ylamino)-N-(1-(1-(cyclopropylmethyl)piperidin-4-yl)azetidin-3-yl)-3-methoxybenzamide

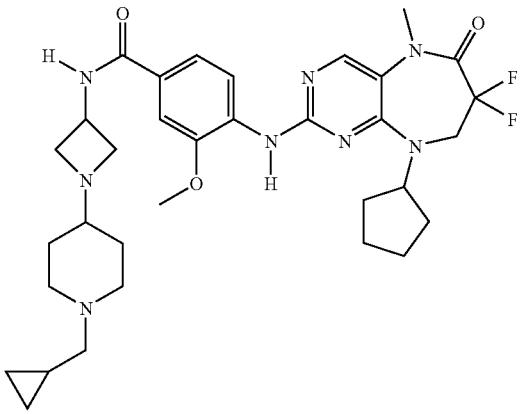

To a solution of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-(piperidin-4-yl)azetidin-3-yl)benzamide (13 mg, 0.023 mmol) in MeOH (2.5 mL) was added AcOH (0.03 mL), cyclopropane aldehyde (3 µL, 0.034 mmol), borane-pyridine complex (10 µL, 0.08 mmol), and left to stir overnight. The solvent was then removed and the product purified by reverse phase HPLC, free based, and lyophilized to yield a white solid (6.4 mg, 44%). $^1$H NMR (400 MHz, DMSO-$d_6$) δ ppm −0.03-0.14 (m, 3H) 0.34-0.51 (m, 2H) 0.80 (s, 1H) 1.17 (d, J=2.53 Hz, 2H) 1.60 (br. s., 6H) 1.71 (br. s., 2H) 1.94 (br. s., 5H) 2.13 (d, J=6.32 Hz, 2H) 2.82 (br. s., 2H) 2.96 (t, J=7.20 Hz, 2H) 3.52 (t, J=7.20 Hz, 2H) 3.92 (s, 1H) 4.05 (t, J=14.02 Hz, 2H) 4.38-4.50 (m, 1H) 4.70-4.82 (m, 1H) 7.41-7.58 (m, 2H) 7.98 (s, 1H) 8.22-8.33 (m, 2H) 8.61 (d, J=6.57 Hz, 1H). [M+H] calc'd for $C_{33}H_{44}F_2N_8O_3$, 638. found 638.

Compound 163: 4-(7,7-difluoro-9-isopropyl-5-methyl-6-oxo-6,7,8,9-tetrahydro-5H-pyrimido[4,5-b][1,4]diazepin-2-ylamino)-3-methoxy-N-(1-methylpiperidin-4-yl)benzamide

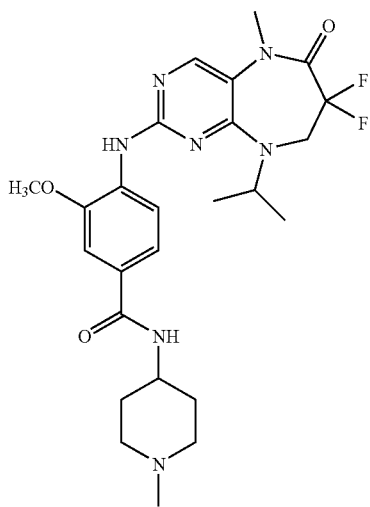

Ethyl 2,2-difluoro-3-(isopropylamino)propanoate: Ethyl 3-(dibenzylamino)-2,2-difluoropropanoate (5.00 g, 15.0 mmol) was dissolved in EtOH (25 mL) and trifluoroacetic acid was added (1.15 mL, 15.5 mmol). To this mixture, Pd(OH)$_2$/C (20%, 250 mg) was added, and the reaction mixture was hydrogenated at 60 psi overnight. The mixture was filtered through a pad of Celite, the Celite pad was washed with ethanol and the filtrate was concentrated in vacuo. The residue was dissolved in THF (65 mL) and to the solution was added acetone (0.872 g, 15.0 mmol) and sodium acetate (1.23 g, 15.0 mmol). The reaction mixture was cooled to 0° C. and NaBH(OAc)$_3$ (4.77 g, 22.5 mmol) was added in portions over 5 min. The mixture was stirred vigorously at room temperature overnight and then was poured into a cold (0° C.) brine solution (100 mL). The pH was adjusted to 12.5 with NaOH (50%) and the mixture was extracted with ethyl acetate (3×50 mL). The combined organic extract were dried (MgSO$_4$) and concentrated in vacuo to afford the title compound as a clear light yellow oil (1.54 g, 54%). $^1$H NMR (400 MHz, CHLOROFORM-d) δ ppm 1.04 (d, J=6.32 Hz, 6H) 1.36 (t, J=7.20 Hz, 3H) 2.73-2.94 (m, 1H) 3.20 (t, J=13.52 Hz, 2H) 4.34 (q, J=7.24 Hz, 2H)

Ethyl 3-((2-chloro-5-nitropyrimidin-4-yl)(isopropyl)amino)-2,2-difluoropropanoate: Ethyl 2,2-difluoro-3-(isopropylamino)propanoate (1.50 g, 7.68 mmol) was dissolved in acetone and K$_2$CO$_3$ (2.12 g, 15.3 mmol) was added. The solution was purged with nitrogen gas and cooled to 0° C. A solution of 2,4-dichloro-5-nitropyrimidine (1.64 g, 8.45 mmol) in acetone (10 mL) was added dropwise at 0° C. over 1 h. The reaction mixture was allowed to slowly warm to room temperature and stirred overnight. It was diluted with dichloromethane (50 mL) and filtered thru a celite plug. The filtrate was concentrated in vacuo and the residue purified by flash column chromatography on silica gel (120 g SiO$_2$, hexanes:ethyl acetate 10:1-3:1) to afford the title compound as a yellow oil (1.96 g, 72%). $^1$H NMR (400 MHz, CHLOROFORM-d) δ ppm 1.29 (d, J=6.82 Hz, 6H) 1.34 (t, J=7.20 Hz, 3H) 3.63-3.75 (m, 1H) 4.24 (t, J=13.14 Hz, 2H) 4.34 (q, J=7.07 Hz, 2H) 8.74 (s, 1H).

2-chloro-7,7-difluoro-9-isopropyl-8,9-dihydro-5H-pyrimido[4,5-b][1,4]diazepin-6(7H)-one: Ethyl 3-((2-chloro-5-nitropyrimidin-4-yl)(isopropyl)amino)-2,2-difluoropropanoate (1.90 g, 5.39 mmol) was dissolved in HOAc (10 mL) and HCl (conc, 3.1 mL). Iron (0.610 g, 10.9 mmol) was added and the rm was stirred at rt for 3 h and at 60° C. overnight. The mixture was diluted with water and extracted with ethyl acetate. The combined organic extracts were dried, filtered and concentrated in vacuo. The residue was purified using flash column chromatography on silica gel (40 g SiO$_2$, hexanes:ethyl acetate 2:1-1:1) to afford the title compounds as a light yellow solid (0.809 g, 54%). $^1$H NMR (400 MHz, CHLOROFORM-d) δ ppm 1.27 (d, J=6.82 Hz, 6H) 3.42 (s, 3H) 3.89 (t, J=12.38 Hz, 2H) 4.97-5.10 (m, 1H) 8.06 (s, 1H).

2-chloro-7,7-difluoro-9-isopropyl-5-methyl-8,9-dihydro-5H-pyrimido[4,5-b][1,4]diazepin-6(7H)-one: 2-chloro-7,7-difluoro-9-isopropyl-8,9-dihydro-5H-pyrimido[4,5-b][1,4]diazepin-6(7H)-one (0.800 g, 2.89 mmol) was dissolved in DMA (7 mL) and cooled to 0° C. under nitrogen. NaH (140 mg, 3.50 mmol) was added, the mixture was stirred for 20 min and MeI (0.23 mL, 3.61 mmol) was added dropwise. The reaction mixture was stirred at room temperature for 1 h and quenched with water (25 mL). The pH was adjusted to 1 (aq. HCl) and the mixture was extracted with ethyl acetate (4×20 mL). The comb organic extracts were concentrated in vacuo, dissolved in dichloromethane/trifluoroacetic acid (5:1, 6 ml) and concentrated in vacuo. The residue was purified by flash column chromatography on silica gel (80 g SiO$_2$, hexanes: ethyl acetate 1:1) to afford the title compound as a yellow solid (0.753 g, 90%).

2-chloro-7,7-difluoro-9-isopropyl-5-methyl-8,9-dihydro-5H-pyrimido[4,5-b][1,4]diazepin-6(7H)-one (100 mg, 0.344 mmol) and 4-amino-3-methoxy-N-(1-methylpiperidin-4-yl)benzamide (95.0 mg, 0.361 mmol) were suspended in water (2 mL) and sulfuric acid (118 mg, 1.20 mmol) was added. The reaction mixture was stirred in a closed vial at 100° C. for 18 h, cooled, diluted with water (8 mL) and brought to pH=7 using solid Na$_2$CO$_3$. The resulting mixture was diluted with ethanol (0.5 mL) and stirred for 5 min. The precipitate was filtered and dried in air for 20-30 min. I was then suspended in ethanol (~10 mL), treated with solid sodium bicarbonate (350 mg) and stirred vigorously for 1 h. The insoluble salts were filtered off and filtrate was concentrated in vacuo. The residue was crystallized from ethanol-water (1:10; 11 mL) and dried in vacuum to afford the title compound as a white solid (115 mg, 65%). $^1$H NMR (400 MHz, DMSO-d$_6$) δ ppm 1.25 (d, J=6.82 Hz, 6H) 1.52-1.65 (m, 2H) 1.70-1.80 (m, 2H) 1.87-1.97 (m, 2H) 2.17 (s, 3H) 2.78 (d, J=11.62 Hz, 2H) 3.32 (s, 3H) 3.64-3.82 (m, 1H) 3.94 (s, 3H) 4.04 (t, J=13.52 Hz, 2H) 4.88 (spt, 1H) 7.46-7.54 (m, 2H) 7.88 (s, 1H) 8.11 (d, J=7.83 Hz, 1H) 8.22 (s, 1H) 8.30 (d, J=8.34 Hz, 1H); [M+H] calc'd for C$_{25}$H$_{33}$F$_2$N$_7$O$_3$, 518. found 518.

Compound 164: 4-(7,7-difluoro-9-isopropyl-5-methyl-6-oxo-6,7,8,9-tetrahydro-5H-pyrimido[4,5-b][1,4]diazepin-2-ylamino)-2-fluoro-5-methoxy-N-(1-methylpiperidin-4-yl)benzamide

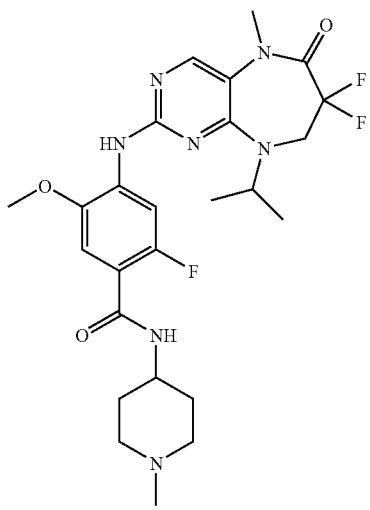

2-chloro-7,7-difluoro-9-isopropyl-5-methyl-8,9-dihydro-5H-pyrimido[4,5-b][1,4]diazepin-6(7H)-one (100 mg, 0.344 mmol) and 4-amino-2-fluoro-5-methoxy-N-(1-methylpiperidin-4-yl)benzamide (100 mg, 0.355 mmol) were suspended in water (2 mL) and sulfuric acid (118 mg, 1.20 mmol) was added. The reaction mixture was stirred in a closed vial at 100° C. for 18 h, cooled, diluted with water (5 mL) and brought to pH=7 using solid sodium carbonate. The resulting mixture was diluted with ethanol (0.5 mL) and stirred for 5 min. The precipitate was filtered, washed with water (5 mL) and dried in air for 20-30 min. It was then suspended in ethanol (~10 mL), treated with solid sodium bicarbonate (130 mg) and stirred vigorously for 45 min. The insoluble salts were filtered off and filtrate was concentrated in vacuo. The residue was crystallized from ethanol-water (1:7; 8 mL) and dried in vacuum to afford the title compound as a white solid (65 mg, 35%). $^1$H NMR (400 MHz, DMSO-d$_6$) δ ppm 1.26 (d, J=6.82 Hz, 6H) 1.49-1.62 (m, 2H) 1.77 (br. d., 2H) 1.95 (app. t, J=11.2 Hz, 2H) 2.15 (s, 3H) 2.73 (br. d., J=11.12 Hz, 2H) 3.33 (s, 3H) 3.71 (m, J=7.83 Hz, 1H) 3.91 (s, 3H) 4.07 (t, J=13.52 Hz, 2H) 4.90 (m, 1H) 7.19 (d, J=6.57 Hz, 1H) 7.88 (dd, J=7.33, 3.03 Hz, 1H) 7.97 (s, 1H) 8.20-8.32 (m, 2H); [M+H] calc'd for C$_{25}$H$_{32}$F$_3$N$_7$O$_3$, 536. found 536.

Compound 165: N-((1r,4r)-4-(4-(cyclopropylmethyl)piperazin-1-yl)cyclohexyl)-4-(7,7-difluoro-9-isopropyl-5-methyl-6-oxo-6,7,8,9-tetrahydro-5H-pyrimido[4,5-b][1,4]diazepin-2-ylamino)-2-fluoro-5-methoxybenzamide

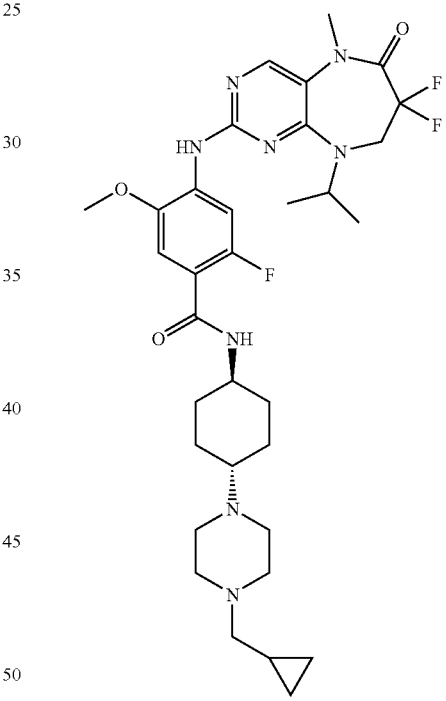

The title compound was prepared using Buchwald reaction from 2-chloro-7,7-difluoro-9-isopropyl-5-methyl-8,9-dihydro-5H-pyrimido[5,4-b][1,4]diazepin-6(7H)-one (573 mg, 1.98 mmole) and 4-amino-N-((1r,4r)-4-(4-(cyclopropylmethyl)piperazin-1-yl)cyclohexyl)-2-fluoro-5-methoxybenzamide (958 mg, 2.372 mmole) and the final product was purified by reverse phase HPLC and basified to give the free base. $^1$H NMR (400 MHz, CHLOROFORM-d) δ ppm 0.53 (br. s, 2H) 0.88 (br. s., 2H) 1.34 (d, J=6.82 Hz, 8H) 1.57 (s, 6H) 1.98 (br. s., 2H) 2.19 (br. s., 6H) 2.67 (br. s., 6H) 3.41 (s, 3H) 3.80-4.10 (m, 4H) 4.88-5.09 (m, 1H) 6.60 (dd, J=15.16, 7.83 Hz, 1H) 7.56 (d, J=7.07 Hz, 1H) 7.78 (s, 1H) 8.04 (s, 1H) 8.37 (d, J=15.16 Hz, 1H). [M+H] calc'd for C$_{33}$H$_{45}$F$_3$N$_8$O$_3$, 659. found 659.

Compound 166: 4-(9-Cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide

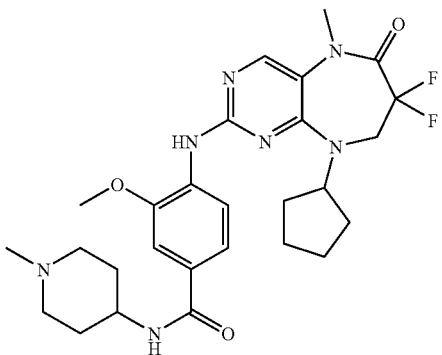

Ethyl 3-(dibenzylamino)-2,2-difluoropropanoate (241 g, 0.72 mol) was dissolved in EtOH (1 L) and then 20% Pd(OH)$_2$/C (24 g) and trifluoroacetic acid (60 mL, 0.78 mol) were added. The vessel was repeatedly purged with hydrogen three times and then left under hydrogen (60 psi, 413 kP) and shaken overnight. The mixture was filtered through a pad of Celite®, washed with ethanol and the filtrate was concentrated without heating to give 200 g of compound ethyl 3-amino-2,2-difluoropropanoate which contained a little bit of ethanol.

To a solution of ethyl 3-amino-2,2-difluoropropanoate (401 g, 1.5 mol), cyclopentanone (140 mL, 1.575 mol) and sodium acetate (123 g, 1.5 mol) in THF (6.5 L) was added NaBH(OAc)$_3$ (477 g, 2.25 mol) portionwise over a period of 40 min in ice bath. The resulting mixture was stirred vigorously at room temperature overnight. The mixture was added slowly to a stirring solution of ice (3300 mL), saturated aqueous sodium bicarbonate (3300 mL) and ethyl acetate (3300 mL) cooled in ice-salt bath over a period of 30 min. At this time the layers were separated and the pH of aqueous phase was further adjusted to 11 by addition of 25% aqueous NaOH while cooling in the bath. The aqueous phase was extracted with ethyl acetate (3.5 L×2) and all organic layers were combined, washed with cold saturated NaHCO$_3$ (1.5 L×2), brine (1.5 L), dried over MgSO$_4$, filtered and concentrated to give 280 g of ethyl 3-(cyclopentylamino)-2,2-difluoropropanoate.

To a 12 L three-necked flask were charged with ethyl 3-(cyclopentylamino)-2,2-difluoropropanoate (268 g, 1.21 mol) and acetone (2.7 L) and the solution was cooled in ice-salt bath. Then potassium carbonate (337 g, 2.44 mol) was added followed by addition of a solution of 2,4-dichloro-5-nitropyrimidine (260 g, 1.34 mol) in acetone (1.3 L) over a period of 1 h. The resulting mixture was allowed to warm to room temperature slowly and stirred overnight which was monitored by LC-MS. The solvent was removed on rotavapor and the resulting residue was redissloved in water (2 L) and ethyl acetate (2 L). After separation, the aqueous phase was extracted with ethyl acetate (2 L×2) and all organic extracts were combined, washed with water (2 L), brine (2 L), dried over MgSO$_4$ and concentrated. The resulting solid was purified by column chromatography (eluting with hexanes/ethyl acetate=20/1, 15/1 then 10/1) to give 289 g of compound ethyl 3-((2-chloro-5-nitropyrimidin-4-yl)(cyclopentyl)amino)-2,2-difluoropropanoate.

To a solution of ethyl 3-((2-chloro-5-nitropyrimidin-4-yl)(cyclopentyl)amino)-2,2-difluoropropanoate (289 g, 0.763 mol) in acetic acid (1.75 L) in ice bath was added iron powder (86 g, 1.53 mol) followed by addition of conc. HCl (435 mL) over a period of 30 min. The resulting mixture was continued to stir in ice bath for 10 min and then transferred to heating mantle and heated to 60° C. which was monitored by LC-MS. After 5 h, the mixture was concentrated by about 75% and the residue was poured into 3.5 L of ice water and 3.5 L of ethyl acetate. After separation, the aqueous phase was extracted with ethyl acetate (4 L×2) and all organic extracts were combined, washed with saturated sodium bicarbonate (2.5 L), brine (2.5 L), dried over anhydrous sodium sulfate and concentrated. The resulting residue was triturated with ethyl acetate (420 mL) and diethyl ether (3 L) to give 169 g of compound 2-chloro-9-cyclopentyl-7,7-difluoro-8,9-dihydro-5H-pyrimido[4,5-b][1,4]diazepin-6(7H)-one.

2-Chloro-9-cyclopentyl-7,7-difluoro-8,9-dihydro-5H-pyrimido[4,5-b][1,4]diazepin-6(7H)-one (100 g, 0.33 mol) was dissolved in DMA (700 mL) and cooled in ice bath under nitrogen. NaH (14.35 g, 60% in mineral oil, 0.363 mol) was added portionwise over a period of 20 min and the resulting mixture was continued to stir in ice bath for 10 min. Then iodomethane (21 mL, 0.363 mol) was added over a period of 10 min in ice bath and the mixture was stirred in ice bath for 10 min and then allowed to warm to room temperature and stirred for 1 h. The mixture was poured into ice water (2.5 L) and the resulting solid was filtered, washed with water, dried to give 98 g of 2-chloro-9-cyclopentyl-7,7-difluoro-5-methyl-8,9-dihydro-5H-pyrimido[4,5-b][1,4]diazepin-6(7H)-one.

A mixture of 2-chloro-9-cyclopentyl-7,7-difluoro-5-methyl-8,9-dihydro-5H-pyrimido[4,5-b][1,4]diazepin-6(7H)-one (98 g, 0.31 mol), 3-methoxy-4-aminobenzoic acid (57 g, 0.341 mol) in i-PrOH (1.05 L) and conc. HCl (30 mL) was heated to reflux for a day. The mixture was cooled to room temperature and the solid was filtered, washed with isopropanol and dried to give 96.5 g of 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid.

A mixture of 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid (96.5 g, 0.216 mol), N-methyl-4-aminopiperidine (29.3 g, 0.259 mol), HOBt (35 g, 0.259 mol), diisopropylethylamine (45 mL, 0.259 mol) in anhydrous DMF (2.6 L) was cooled in ice bath under nitrogen. EDCI (49.8 g, 0.259 mol) was added and the resulting mixture was allowed to warm to room temperature and stirred overnight. The mixture was poured into ice water (8 L) and ethyl acetate (3 L) and separated. The aqueous phase was extracted with ethyl acetate (4 L×2) and all organic extracts were combined, washed with water, brine, dried over MgSO$_4$ and concentrated. The resulting solid was triturated with diethyl ether to give 47 g of the title compound. DSC peak at 241.42° C.

Compound 167: 4-(9-Cyclopentyl-7,7-difluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide

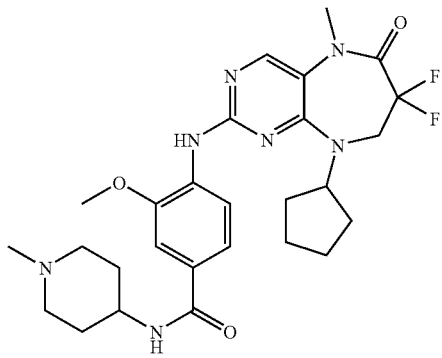

2-Chloro-9-cyclopentyl-7,7-difluoro-8,9-dihydro-5H-pyrimido[4,5-b][1,4]diazepin-6(7H)-one (3598 g, 11.89 mol) was dissolved in NMP (11.108 kg) and cooled to about −3° C. A 1 M solution of NaAHMDS (11.919 kg, 1.1 eq.) was added over a period of 80 minutes maintaining the temperature below 4° C. Iodomethane (1.858 kg) was added over a period of 10 minutes maintaining the temperature below 35° C. The addition funnel was washed with THF. The temperature was adjusted to 20 to 25° C. and the reaction mixture was stirred for 3 hours. A 1 M solution of NaHMDS (1.2 kg) was added at 23° C. followed by iodomethane (0.188 kg). The addition funnel was washed with THF. The temperature was adjusted to 20 to 25° C. and the reaction mixture was stirred overnight. The temperature was adjusted to 10° C., concentrated aqueous hydrochloric acid (6.42 L), the THF was removed by distillation at reduced pressure, the temperature was adjusted to 20° C., and water (53.31 kg) was slowly added over about 60 minutes maintaining the temperature at about 23 to 25° C. The temperature was adjusted to about 10° followed by stirring overnight. The reaction mixture was filtered, the filter cake was washed with isopropyl alcohol/water (1:1, 2×2 L), and dried in by a stream of nitrogen. The filter cake was dissolved in isopropyl alcohol (4.17 kg) at 76° C., water (20.70 kg) was slowly added over about 85 minutes maintaining the temperature at about 73 to 76° C., after 20 minutes cooled to about 11° over about 3 hours and stir overnight. Collect the solid by filtration, rinse with isopropyl alcohol/water (1:1, 2×1.7 L), and dry under a stream of nitrogen, followed by drying in an oven for 4 days to give 2-chloro-9-cyclopentyl-7,7-difluoro-5-methyl-8,9-dihydro-5H-pyrimido[4,5-b][1,4]diazepin-6(7H)-one.

A mixture of 2-chloro-9-cyclopentyl-7,7-difluoro-5-methyl-8,9-dihydro-5H-pyrimido[4,5-b][1,4]diazepin-6(7H)-one (2.542 kg, 8.05 mol), 3-methoxy-4-aminobenzoic acid (1.50 kg) in t-butyl alcohol (23 L) and heat to about 53° C. Add conc. HCl (951 g) over about 10 minutes, heat to 80° C. and stir for 60 hours. The temperature was adjusted to 15° C. and stirred for 40 hours to give a solid which was collected by filtration, rinsed with isopropyl alcohol/water (1:1, 2×2.5 L) and dried under a stream of nitrogen for about 1.5 hours, then in a vacuum oven at 40° C. for 4 days to give 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid.

A mixture of 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid (5.125 kg, 6.51 mol), dichloromethane (12 kg), and NMP (0.058 L, 0.09 eq.) was adjusted to 18° C. Thionyl chloride (1.868 kg, 2.4 eq.) was added over about 10 minutes, and each reaction was stirred at about 18 to 19° C. for 17.5 hours. The temperature was adjusted to 25° C. and the reaction was stirred for 7 hours, adjusted to 18 to 20° C. and stirred for overnight, then 2 days. The dichloromethane was removed by distillation at reduced pressure, toluene (6.2 kg) was added and the distillation continued. About 6 L of dichloromethane were removed. Toluene (6.18 L) was added, the temperature was adjusted to about 20 to 25° C., and a suspension was stirred overnight. The solid was collected by filtration, rinsed with toluente (2×2.12 kg), dried for 3.5 hours in a stream of nitrogen, and then in a vacuum oven at 40° C. for 2 days to give 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid.

Combine 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid (3.108 kg, 6.17 mol) and acetonitrile (14.56 kg) and adjust the temperature to about 0° C. Add N-methyl-4-aminopiperidine (0.775 k, 1.1 eq.). Diisopropylethylamine (1.595 kg) was added aver about 29 minutes at temperature of about 6 to 12° C., the temperature was adjusted to about 20 to 25° C. and the reaction mixture was stirred overnight. The solid was collected by filtration, rinsed with acetonitrile (4.47 kg) and dried under at stream of nitrogen for 1 hour, then in a vacuum oven at 40° C. for 2 days to give the title compound.

The title compound (3.35 kg), ethyl alcohol (10.65 kg), and aqueous 2N hydrochloric acid solution were combined at about 20° C. and filtered. Aqueous 2N sodium hydroxide was added and the reaction mixture was stirred at about 20 to 25° C. overnight. Crystals (0.5 g) similar to the ones obtained in Compound 166 were added and the stirring continued for 24 hours. Water (5.39 kg) was added and the suspension stirred for 4 hours, filtered, rinsed with water (1.7 kg) and ethyl alcohol (1.7 kg), dried with a stream of nitrogen, and then in a vacuum oven at 40° C. for 3.8 days to give the title compound. DSC peak at 242.12° C.

Compound 168: 4-(9-Cyclopentyl-7,7-difluoro-5-methyl-6-oxo-6,7,8,9-tetrahydro-5H-pyrimido[4,5-b][1,4]diazepin-2-ylamino)-2-fluoro-5-methoxy-N-(1-methylpiperidin-4-yl)benzamide

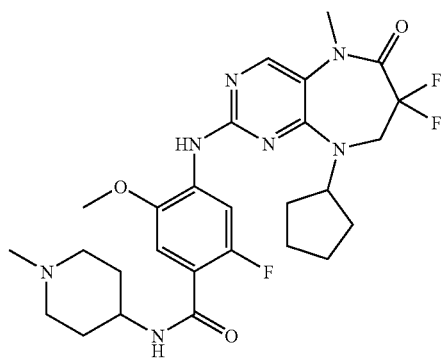

2-Fluoro-5-methoxy-4-nitrobenzoic acid: To a solution of 2,5-difluoro-4-nitrobenzoic acid (55 g, 291 mmol) in methanol (800 mL) at 80° C. was added a methanolic solution of potassium hydroxide (48.9 g, 873 mmol in 175 mL MeOH, pre-heated at 80° C. to dissolve) dropwise in a period of 2 h using an addition funnel. The reaction mixture was continuously stirred for 1 h after addition was completed. It was then concentrated, acidified with HCl to pH=1-2. The reaction mixture was then vigorously stirred overnight. Fine powder was filtered, washed with more water and dried to give the product as light yellow powder (55.4 g, 90%). $^1$H NMR (400 MHz, DMSO-d$_6$) δ ppm 3.95 (s, 3H) 7.66 (d, J=4 Hz, 1H) 8.01 (d, J=8 Hz, 1H). [M+H] calc'd for $C_8H_6FNO_5$, 216. found 216.

2-Fluoro-5-methoxy-N-(1-methylpiperidin-4-yl)-4-nitrobenzamide: To a mixture of 2-fluoro-5-methoxy-4-nitrobenzoic acid (53.8 g, 250 mmol), 1-methylpiperidin-4-amine (31.4 g, 275 mmol), DIEA (134 mL, 750 mmol) in 1 L of DCM at 0° C. was added HATU (114 g, 300 mmol) in four batches. The reaction mixture was stirred at room temp. for 16 h. After which, it was concentrated and diluted to IL of a mixture of MeOH in water (5%). The suspension was stirred vigorously for 2 h until seen a suspension of fine powder. The solid was filtered, washed with more water and dried to give 55 g of light yellow product. The filtrate was extracted with EtOAc, concentrated and re-suspended in water (5% of MeOH) and repeating the same procedure as above, after which another batch of solid was obtained (total 67 g, 86%). $^1$H NMR (400 MHz, DMSO-d$_6$) δ ppm 1.53 (m, 2H) 1.81 (m, 2H) 2.04 (m, 2H) 2.19 (s, 3H) 2.77 (d, J=8 Hz, 2H) 3.73 (m, 1H) 3.94 (s, 3H) 7.42 (d, J=5.6 Hz, 1H) 7.98 (d, J=8.8 Hz, 1H) 8.51 (d, J=7.6 Hz, 1H). [M+H] calc'd for $C_{14}H_{18}FN_3O_4$, 312. found 312.

4-Amino-2-fluoro-5-methoxy-N-(1-methylpiperidin-4-yl)benzamide: To a solution of 2-fluoro-5-methoxy-N-(1-methylpiperidin-4-yl)-4-nitrobenzamide (55 g, 177 mmol) in EtOH (450 mL) was added 10% Pd/C (11 g), followed by 4.4 mL of concentrated HCl. The reaction mixture was hydrogenated using a hydrogen balloon for 22 h. The solution was filtered through celite and concentrated to a minimum volume, after which solid was filtered, washed with ether. The filtrate concentrated again and triturated with EtOH and repeated several times to get out more products. The solid was combined and further dried to give total 50 g of product as light yellow powder (>98%). $^1$H NMR (400 MHz, DMSO-d$_6$) δ 1.64-2.02 (m, 4H) 2.61 (s, 3H) 2.90 (t, J=11.0 Hz, 2H) 3.24 (m, 2H) 3.72-3.81 (m, 3H) 3.84-4.03 (m, 1H) 5.60 (s, 2H) 6.29-6.50 (m, 1H) 7.01 (d, J=6.8 Hz, 1H) 7.69 (dd, J=7.3, 4.8 Hz, 1H). [M+H] calc'd for $C_{14}H_{20}FN_3O_2$, 282. found 282.

4-(9-Cyclopentyl-7,7-difluoro-5-methyl-6-oxo-6,7,8,9-tetrahydro-5H-pyrimido[4,5-b][1,4]diazepin-2-ylamino)-2-fluoro-5-methoxy-N-(1-methylpiperidin-4-yl)benzamide: A mixture of 2-chloro-9-cyclopentyl-7,7-difluoro-5-methyl-8,9-dihydro-5H-pyrimido[4,5-b][1,4]diazepin-6(7H)-one (25 g, 79.1 mmol), 4-amino-2-fluoro-5-methoxy-N-(1-methylpiperidin-4-yl)benzamide (23.3 g, 83 mmol), isopropanol (197 ml), and concentrated hydrochloric acid (8 mL) was stirred in an oil bath of 100° C. (temp. inside the flask was 83° C.) for 3 days (lots of precipitate appeared after first day of stirring). The reaction mixture was cooled down and the white solid was filtered and washed with more iPrOH, finally dried to give 40 g tan solid as HCl salt.

Above obtained HCl salt (40 g) was dissolved in 1 L of MeOH with an effective stirring bar. It was cooled to 0° C., sodium bicarbonate solid (28.1 g, 0.33 mol) was added slowly. The reaction mixture was then stirred at r.t for 4 h. After which, it was filtered through a pad of celite. The filtrate concentrated in vacuo to 500 mL in volume, and 500 mL of water was charged into the flask. The mixture was then kept on rotavaping at 20° C. Lots of pinkish precipitate appeared. Until around 100 mL of MeOH left, 500 mL more of water was added to the flask. The whole was filtered, solid washed with more water (500 mL) and dried to give 35 g of product as light pinkish solid (>99% pure by LC).

To a 500 mL round bottom flask, was added 60 g of the free base and EtOH (200 ml). It was heated at 85° C. for 0.5 h. It was then cooled down, solid filtered and washed with more EtOH (200 mL). When dried, around 48 g of off-white solid was obtained (filtrate contained color and some impurities). The solid was then completely dissolved in 4 L of MeOH, filtered on the paper. The filtrate was concentrated to a solid. It was then dissolved in 200 mL of EtOH. The suspension was then heated at 60° C. with effective stirring for 24 h. The slurry was then cooled down gradually to room temperature, filtered. The solid was washed with more EtOH (200 mL), dried in a vacuum oven (60° C.) for 3 days. Finally, 44 g of product as white solid was obtained (73% recovery). The combined filtrate (contained mostly product) was concentrated and set aside for further purification by prep-HPLC. $^1$H NMR (400 MHz, DMSO-d$_6$) δ ppm 1.47-1.82 (m, 10H) 1.90-2.04 (m, 4H) 2.16 (s, 3H) 2.74 (d, J=11.6 Hz, 2H) 3.63-3.77 (m, 1H) 3.92 (s, 3H) 4.09 (t, J=13.9 Hz, 2H) 4.82 (m, 1H) 7.19 (d, J=6.8 Hz, 1H) 7.91 (dd, J=7.7, 3.4 Hz, 1H) 8.04 (d, J=1.3 Hz, 1H) 8.25 (d, J=13.4 Hz, 1H) 8.31 (s, 1H). Melting point 194.5-195.5° C. [M+H] calc'd for $C_{27}H_{34}F_3N_7O_3$, 562. found 562.

In addition to the foregoing, the above reaction schemes and variations thereof have been used to prepare the following compounds:

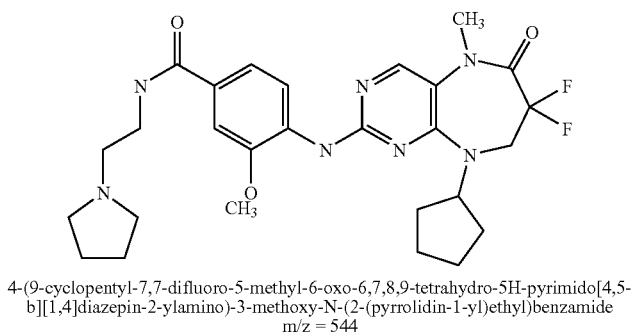

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(2-(pyrrolidin-1-yl)ethyl)benzamide
m/z = 544

-continued

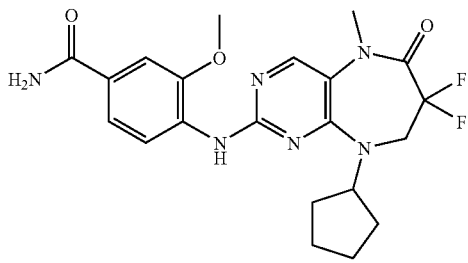

4-(9-cyclopentyl-7,7-difluoro-5-methyl-6-oxo-6,7,8,9-tetrahydro-5H-pyrimido[4,5-b][1,4]diazepin-2-ylamino)-3-methoxybenzamide
m/z = 447

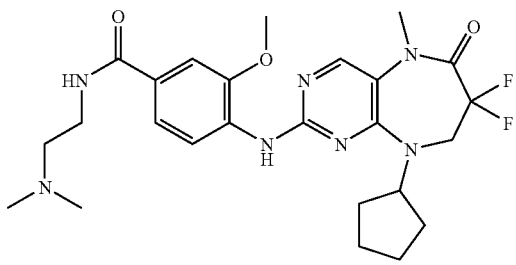

4-(9-cyclopentyl-7,7-difluoro-5-methyl-6-oxo-6,7,8,9-tetrahydro-5H-pyrimido[4,5-b][1,4]diazepin-2-ylamino)-N-(2-(dimethylamino)ethyl)-3-methoxybenzamide
m/z = 517

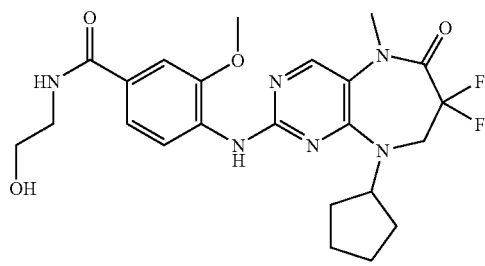

4-(9-cyclopentyl-7,7-difluoro-5-methyl-6-oxo-6,7,8,9-tetrahydro-5H-pyrimido[4,5-b][1,4]diazepin-2-ylamino)-N-(2-hydroxyethyl)-3-methoxybenzamide
m/z = 491

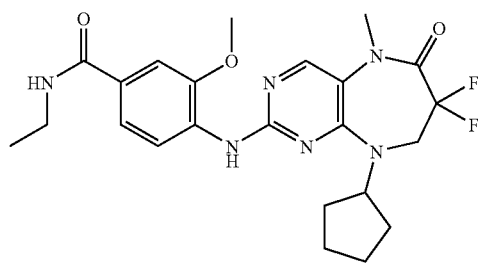

4-(9-cyclopentyl-7,7-difluoro-5-methyl-6-oxo-6,7,8,9-tetrahydro-5H-pyrimido[4,5-b][1,4]diazepin-2-ylamino)-N-ethyl-3-methoxybenzamide
m/z = 475

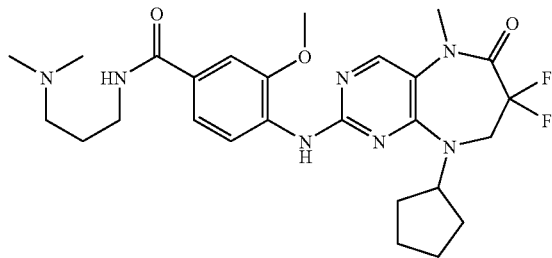

4-(9-cyclopentyl-7,7-difluoro-5-methyl-6-oxo-6,7,8,9-tetrahydro-5H-pyrimido[4,5-b][1,4]diazepin-2-ylamino)-N-(3-(dimethylamino)propyl)-3-methoxybenzamide
m/z = 532

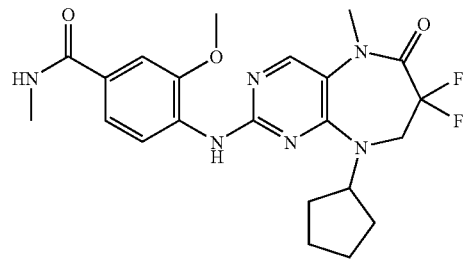

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-methylbenzamide
m/z = 461

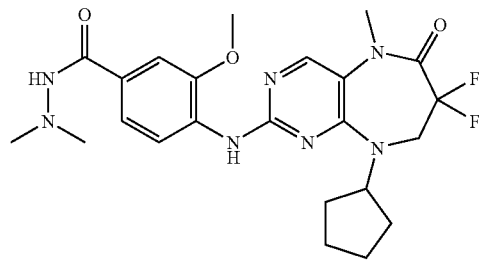

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N',N'-dimethylbenzohydrazide
m/z = 490

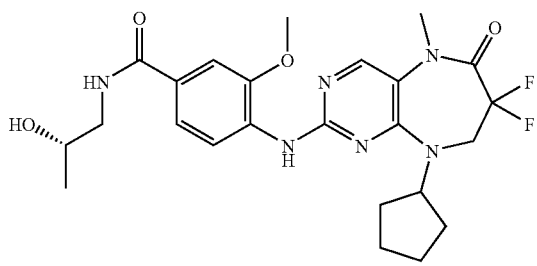

(S)-4-(9-cyclopentyl-7,7-difluoro-5-methyl-6-oxo-6,7,8,9-tetrahydro-5H-pyrimido[4,5-b][1,4]diazepin-2-ylamino)-N-(2-hydroxypropyl)-3-methoxybenzamide
m/z = 505

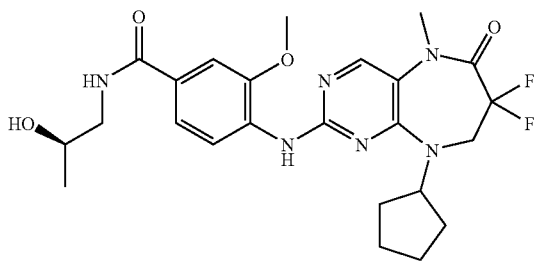

(R)-4-(9-cyclopentyl-7,7-difluoro-5-methyl-6-oxo-6,7,8,9-tetrahydro-5H-pyrimido[4,5-b][1,4]diazepin-2-ylamino)-N-(2-hydroxypropyl)-3-methoxybenzamide
m/z = 505

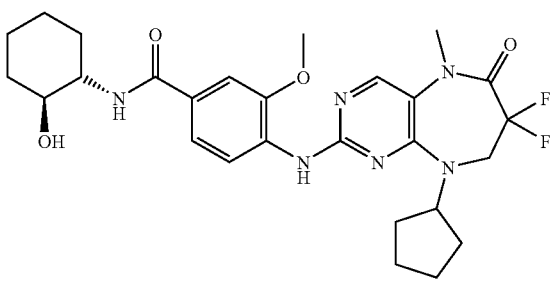

4-(9-cyclopentyl-7,7-difluoro-5-methyl-6-oxo-6,7,8,9-tetrahydro-5H-pyrimido[4,5-b][1,4]diazepin-2-ylamino)-N-((1S,2S)-2-hydroxycyclohexyl)-3-methoxybenzamide
m/z = 545

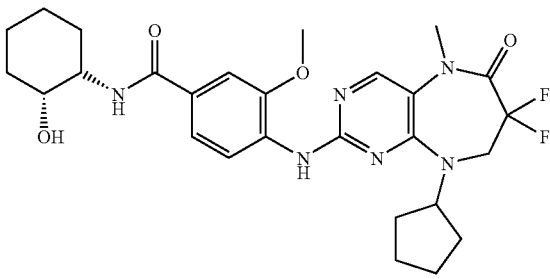

4-(9-cyclopentyl-7,7-difluoro-5-methyl-6-oxo-6,7,8,9-tetrahydro-5H-pyrimido[4,5-b][1,4]diazepin-2-ylamino)-N-((1S,2RS)-2-hydroxycyclohexyl)-3-methoxybenzamide
m/z = 545

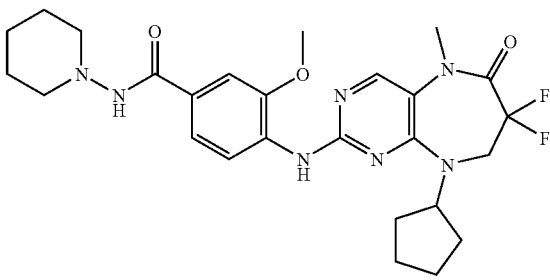

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(piperidin-1-yl)benzamide
m/z = 530

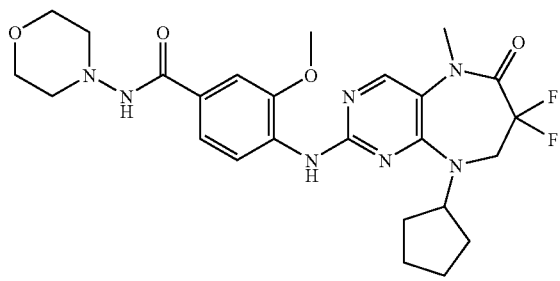

4-(9-cyclopentyl-7,7-difluoro-5-methyl-6-oxo-6,7,8,9-tetrahydro-5H-pyrimido[4,5-b][1,4]diazepin-2-ylamino)-3-methyoxy-N-morpholinobenzamide
m/z = 531

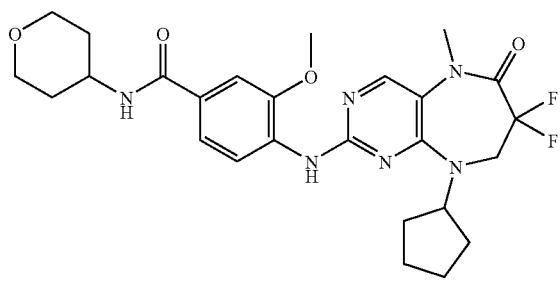

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(tetrahydro-2H-pyran-4-yl)benzamide
m/z = 532

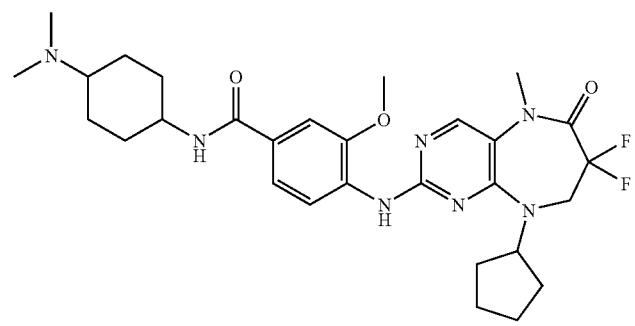

4-(9-cyclopentyl-7,7-difluoro-5-methyl-6-oxo-6,7,8,9-tetrahydro-5H-pyrimido[4,5-b][1,4]diazepin-2-ylamino)-N-(4-(dimethylamino)cyclohexyl)-3-methoxybenzamide
m/z = 572

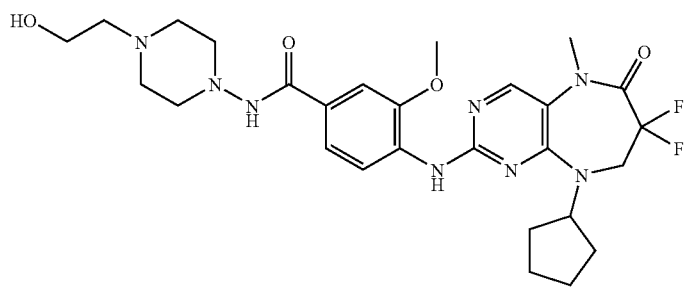

4-(9-cyclopentyl-7,7-difluoro-5-methyl-6-oxo-6,7,8,9-tetrahydro-5H-pyrimido[4,5-b][1,4]diazepin-2-ylamino)-N-(4-(2-hydroxyethyl)piperizin-1-yl)-3-methoxybenzamide
m/z = 575

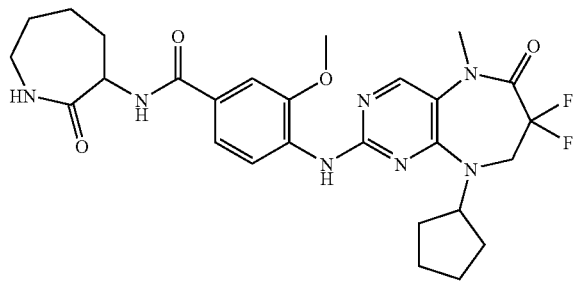

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(2-oxoazepan-3-yl)benzamide
m/z = 558

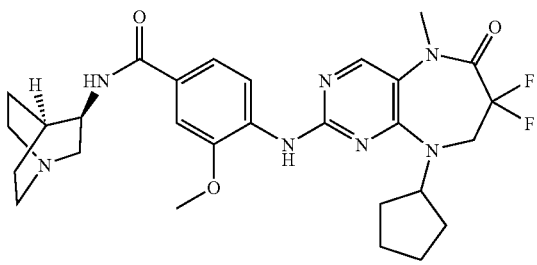

(R)-4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(quinuclidin-3-yl)benzamide
m/z = 556

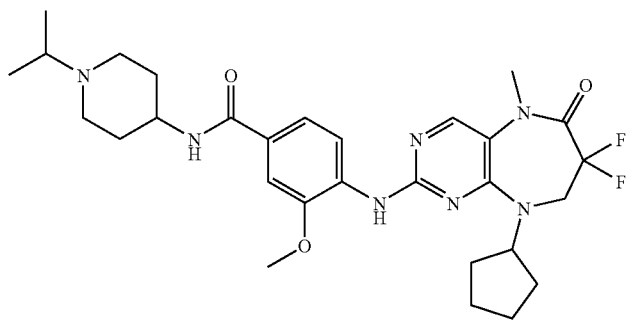

4-(9-cyclopentyl-7,7-difluoro-5-methyl-6-oxo-6,7,8,9-tetrahydro-5H-pyrimido[4,5-b][1,4]diazepin-2-ylamino)-N-(1-isopropylpiperidin-4-yl)-3-methoxybenzamide
m/z = 572

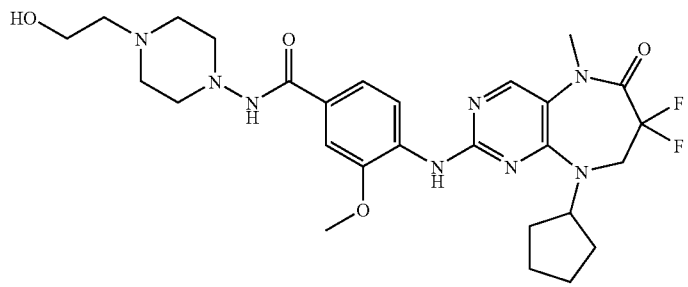

4-(9-cyclopentyl-7,7-difluoro-5-methyl-6-oxo-6,7,8,9-tetrahydro-5H-pyrimido[4,5-b][1,4]diazepin-2-ylamino)-N-(4-(2-hydroxyethyl)piperazin-1-yl)-3-methoxybenzamide
m/z = 574

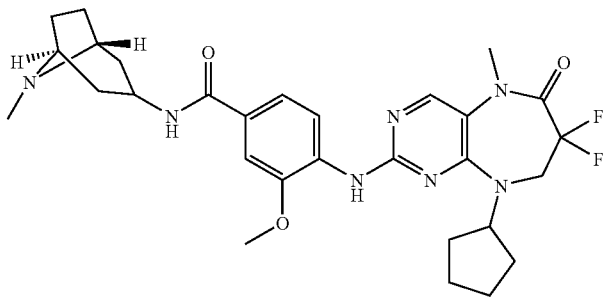

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-((1R,5S)-8-methyl-8-azabicyclo[3.2.1]octan-3-yl)benzamide
m/z = 570

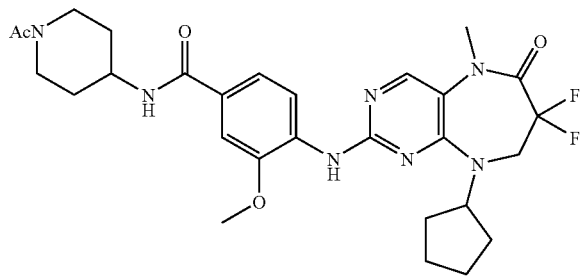

N-(1-acetylpiperidin-4-yl)-4-(9-cyclopentyl-7,7-difluoro-5-methyl-6-oxo-6,7,8,9-tetrahydro-5H-pyrimido[4,5-b][1,4]diazepin-2-ylamino)-3-methoxybenzamide
m/z = 572

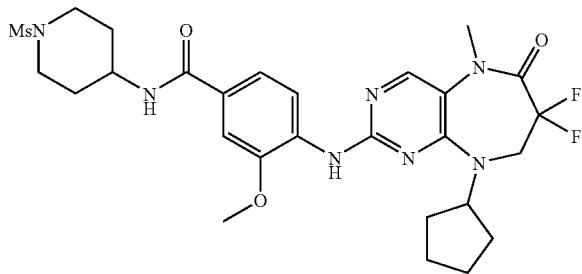

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-(methylsulfonyl)piperidin-4-yl)benzamide
m/z = 608

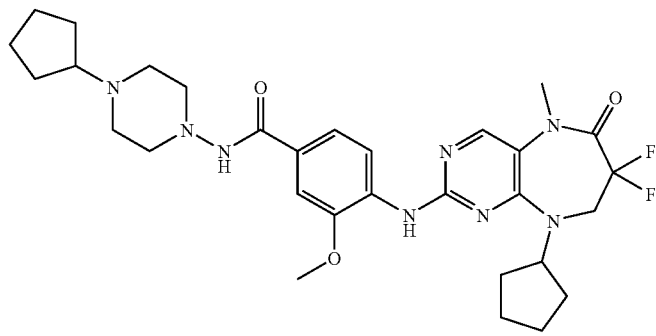

4-(9-cyclopentyl-7,7-difluoro-5-methyl-6-oxo-6,7,8,9-tetrahydro-5H-pyrimido[4,5-b][1,4]diazepin-2-ylamino)-N-(4-cyclopentylpiperazin-1-yl)-3-methoxybenzamide
m/z = 599

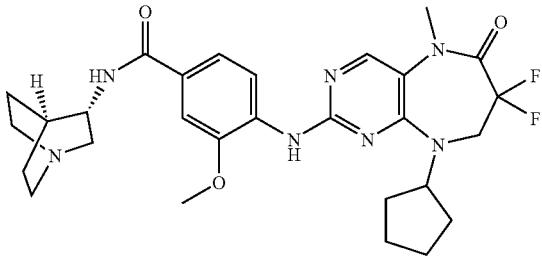

(S)-4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(quinuclidin-3-yl)benzamide
m/z = 556

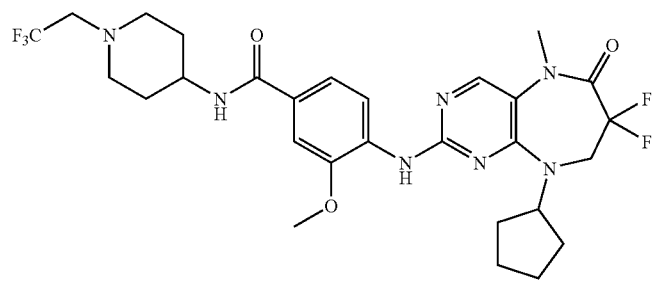

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-(2,2,2-trifluoroethyl)piperidin-4-yl)benzamide
m/z = 612

Further, the following compounds can be prepared using variations of the procedure described in connection with Scheme 15.

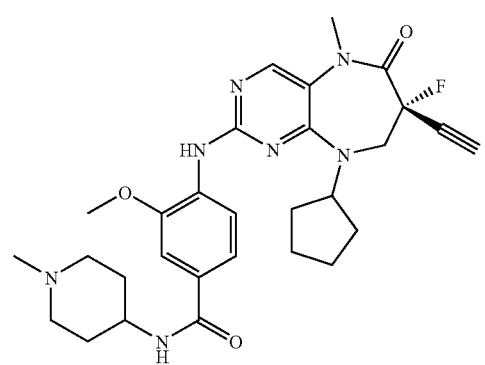

(R)-4-(9-cyclopentyl-7-ethynyl-7-fluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide

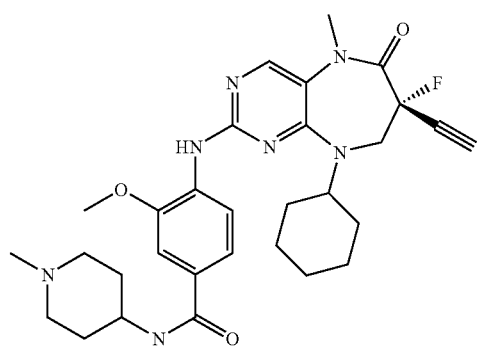

(R)-4-(9-cyclohexyl-7-ethynyl-7-fluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide 315
-continued

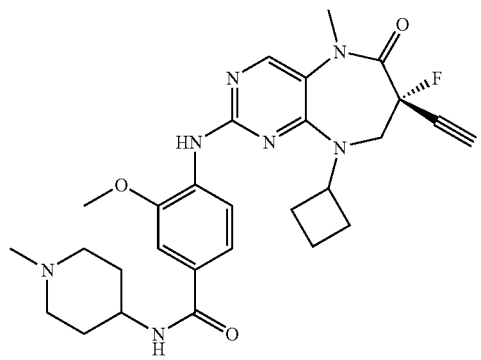

(R)-4-(9-cyclopentyl-7-ethynyl-7-fluoro-5-methyl-6-oxo-6,7,8,9-
tetrahydro-5H-pyrimido[4,5-b][1,4]diazepin-2-ylamino)-3-methoxy-N-(1-
methylpiperidin-4-yl)benzamide

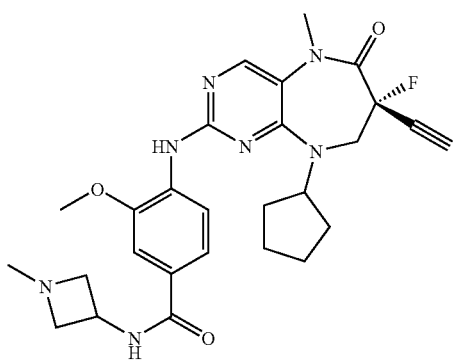

(R)-4-(9-cyclopentyl-7-ethynyl-7-fluoro-5-methyl-6-oxo-6,7,8,9-
tetrahydro-5H-pyrimido[4,5-b][1,4]diazepin-2-ylamino)-3-methoxy-N-(1-
methylazetidin-3-yl)benzamide

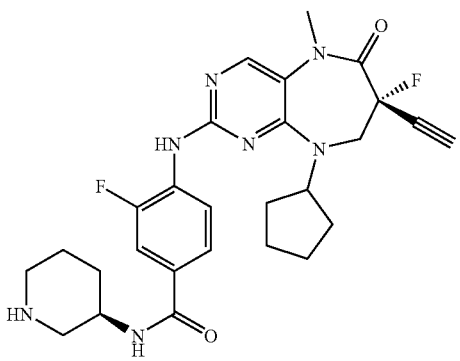

4-((R)-9-cyclopentyl-7-ethynyl-7-fluoro-5-methyl-6-oxo-6,7,8,9-
tetrahydro-5H-pyrimido[4,5-b][1,4]diazepin-2-ylamino)-3-fluoro-N-((R)-
piperidin-3-yl)benzamide 316
-continued

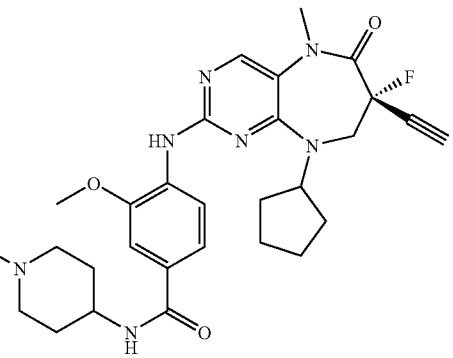

(R)-4-(9-cyclopentyl-7-ethynyl-7-fluoro-5-methyl-6-oxo-6,7,8,9-
tetrahydro-5H-pyrimido[4,5-b][1,4]diazepin-2-ylamino)-N-(1-(2-
hydroxyethyl)piperidin-4-yl)-3-methoxybenzamide

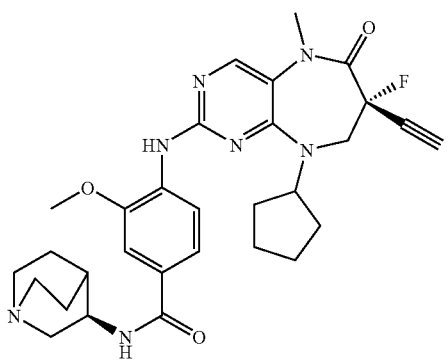

4-((R)-9-cyclopentyl-7-ethynyl-7-fluoro-5-methyl-6-oxo-6,7,8,9-
tetrahydro-5H-pyrimido[4,5-b][1,4]diazepin-2-ylamino)-3-methoxy-N-
((R)-quinuclidin-3-yl)benzamide

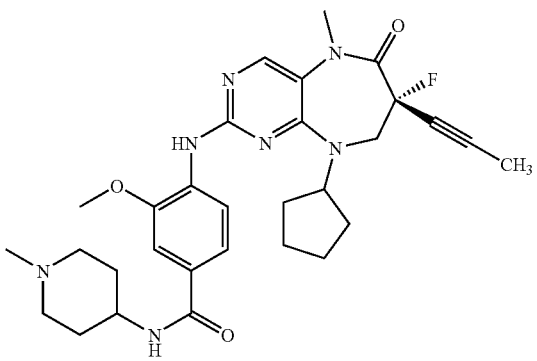

(R)-4-(9-cyclopentyl-7-fluoro-5-methyl-6-oxo-7-(prop-1-ynyl)-6,7,8,9-
tetrahydro-5H-pyrimido[4,5-b][1,4]diazepin-2-ylamino)-3-methoxy-N-(1-
methylpiperidin-4-yl)benzamide

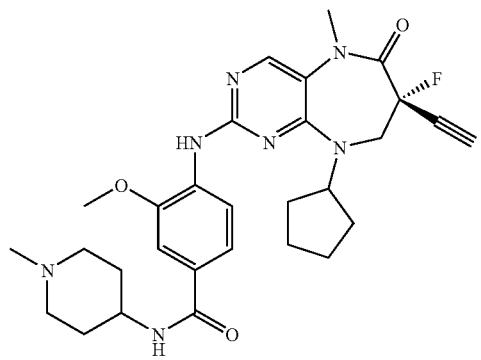

(S)-4-(9-cyclopentyl-7-ethynyl-7-fluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide

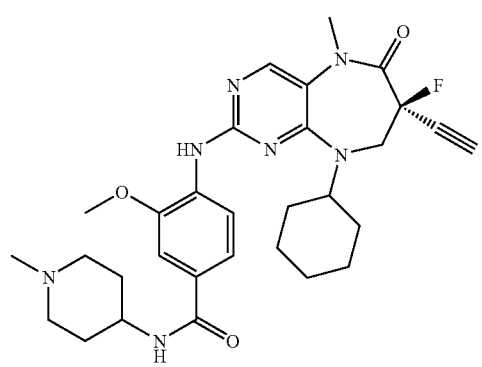

(S)-4-(9-cyclohexyl-7-ethynyl-7-fluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide

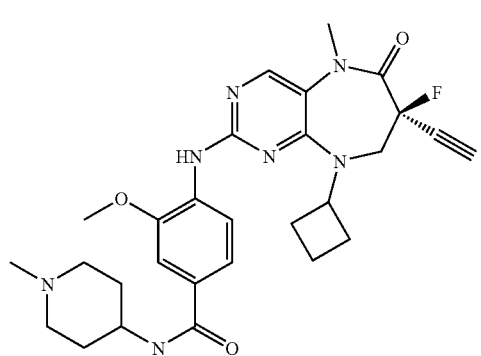

(S)-4-(9-cyclobutyl-7-ethynyl-7-fluoro-5-methyl-6-oxo-6,7,8,9-tetrahydro-5H-pyrimido[4,5-b][1,4]diazepin-2-ylamino)-3-methoxy-N-(1-methylpiperidin-4-yl)benzamide

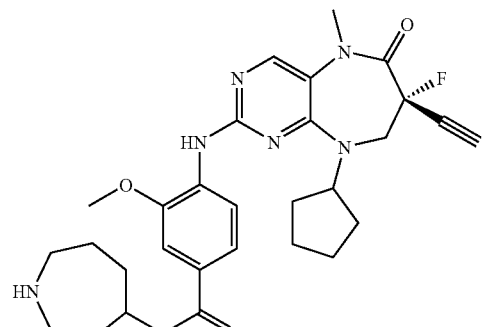

N-(azepan-4-yl)-4-((R)-9-cyclopentyl-7-ethynyl-7-fluoro-5-methyl-6-oxo-6,7,8,9-tetrahydro-5H-pyrimido[4,5-b][1,4]diazepin-2-ylamino)-3-methoxybenzamide In addition, the following compounds can be prepared using variations of the procedure described in connection with Scheme 16.

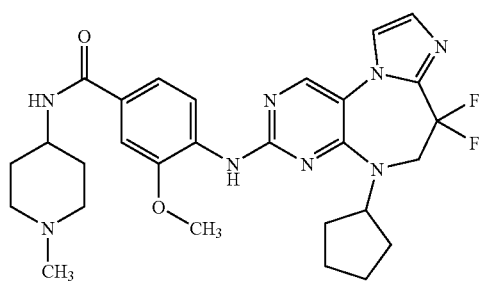

4-(5-cyclopentyl-7,7-difluoro-6,7-dihydro-5H-imidazo[1,2-d]pyrimido[4,5-b][1,4]diazepin-3-ylamino)-3-methoxy-N-(1-methylpiperidin-4-yl)benzamide

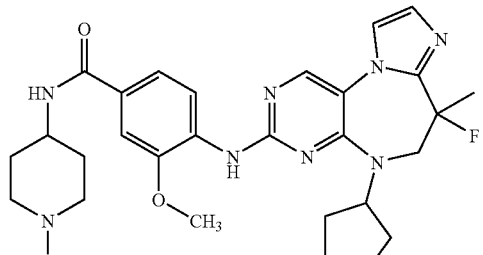

4-(5-cyclopentyl-7-fluoro-7-methyl-6,7-dihydro-5H-imidazo[1,2-d]pyrimido[4,5-b][1,4]diazepin-3-ylamino)-3-methoxy-N-(1-methylpiperidin-4-yl)benzamide

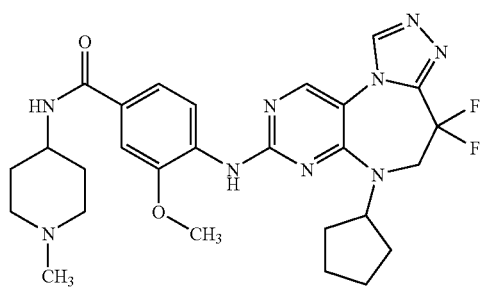

4-(6-cyclopentyl-4,4-difluoro-5,6-dihydro-4H-pyrimido[4,5-b][1,2,4]triazolo[4,3-b][1,4]diazepin-8-ylamino)-3-methoxy-N-(1-methylpiperidin-4-yl)benzamide

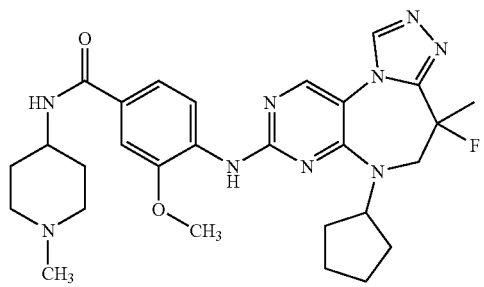

4-(6-cyclopentyl-4-fluoro-4-methyl-5,6-dihydro-4H-pyrimido[4,5-b][1,2,4]triazolo[4,3-d][1,4]diazepin-8-ylamino)-3-methoxy-N-(1-methylpiperidin-4-yl)benzamide

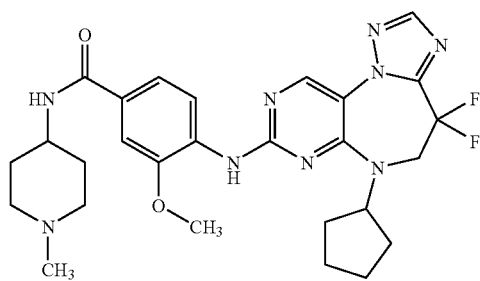

4-(6-cyclopentyl-4,4-difluoro-5,6-dihydro-4H-pyrimido[4,5-b][1,2,4]triazolo[1,5-d][1,4]diazepin-8-ylamino)-3-methoxy-N-(1-methylpiperidin-4-yl)benzamide

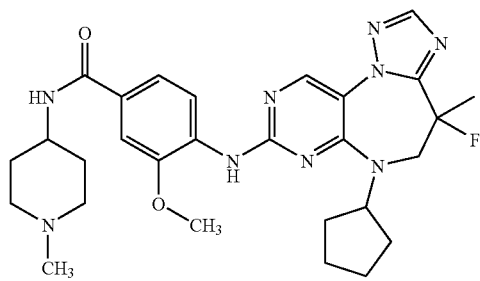

4-(6-cyclopentyl-4-fluoro-4-methyl-5,6-dihydro-4H-pyrimido[4,5-b][1,2,4]triazolo[1,5-d][1,4]diazepin-8-ylamino)-3-methoxy-N-(1-methylpiperidin-4-yl)benzamide

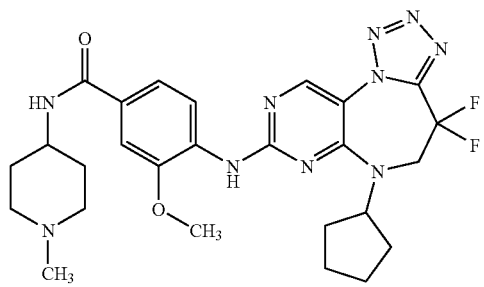

4-(6-cyclopentyl-4,4-difluoro-5,6-dihydro-4H-pyrimido[4,5-b]tetrazolo[1,5-d][1,4]diazepin-8-ylamino)-3-methoxy-N-(1-methylpiperidin-4-yl)benzamide

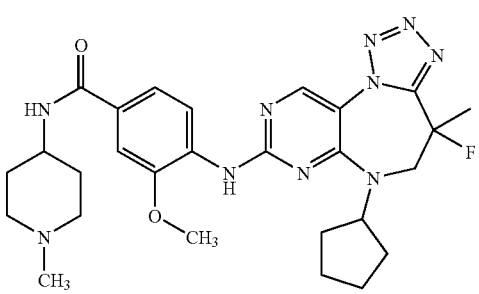

4-(6-cyclopentyl-4-fluoro-4-methyl-5,6-dihydro-4H-pyrimido[4,5-b]tetrazolo[1,5-d][1,4]diazepin-8-ylamino)-3-methoxy-N-(1-methylpiperidin-4-yl)benzamide

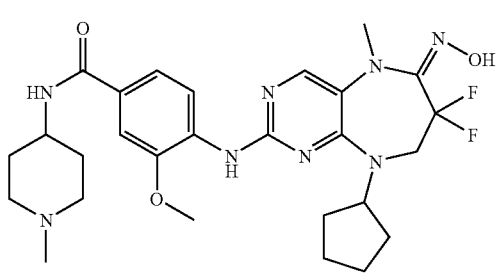

4-(9-cyclopentyl-7,7-difluoro-6-(hydroxyimino)-5-methyl-6,7,8,9-tetrahydro-5H-pyrimido[5,4-b][1,4]diazepin-2-ylamino)-3-methoxy-N-(1-methylpiperidin-4-yl)benzamide

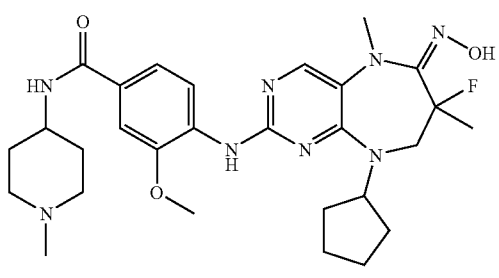

4-(9-cyclopentyl-7-fluoro-6-(hydroxyimino)-5,7-dimethyl-6,7,8,9-tetrahydro-5H-pyrimido[5,4-b][1,4]diazepin-2-ylamino)-3-methoxy-N-(1-methylpiperidin-4-yl)benzamide

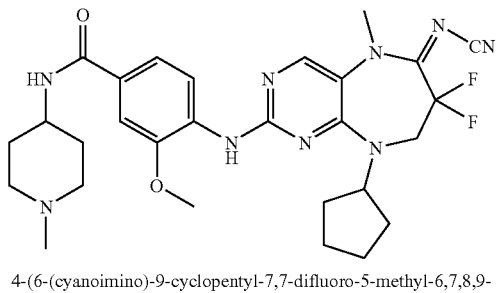

4-(6-(cyanoimino)-9-cyclopentyl-7,7-difluoro-5-methyl-6,7,8,9-tetrahydro-5H-pyrimido[5,4-b][1,4]diazepin-2-ylamino)-3-methoxy-N-(1-methylpiperidin-4-yl)benzamide

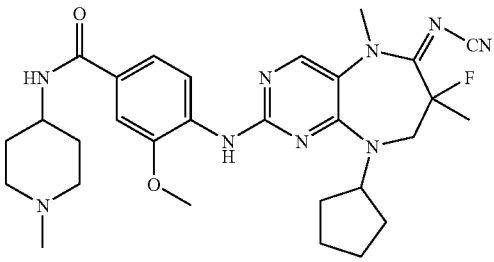

4-(6-(cyanoimino)-9-cyclopentyl-7-fluoro-5,7-dimethyl-6,7,8,9-tetrahydro-5H-pyrimido[5,4-b][1,4]diazepin-2-ylamino)-3-methoxy-N-(1-methylpiperidin-4-yl)benzamide

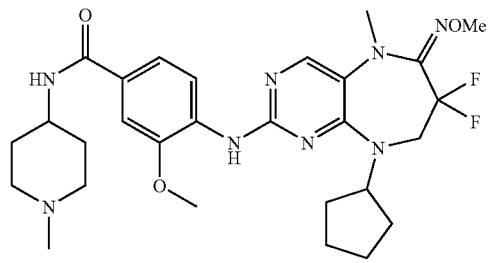

4-(9-cyclopentyl-7,7-difluoro-6-(methoxyimino)-5-methyl-6,7,8,9-tetrahydro-5H-pyrimido[5,4-b][1,4]diazepin-2-ylamino)-3-methoxy-N-(1-methylpiperidin-4-yl)benzamide

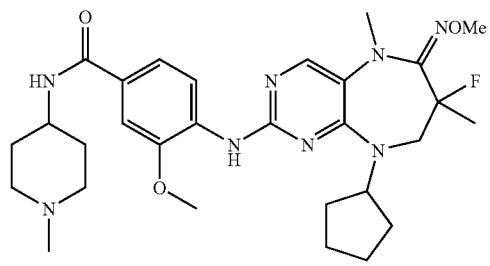

4-(9-cyclopentyl-7-fluoro-6-(methoxyimino)-5,7-dimethyl-6,7,8,9-tetrahydro-5H-pyrimido[5,4-b][1,4]diazepin-2-ylamino)-3-methoxy-N-(1-methylpiperidin-4-yl)benzamide

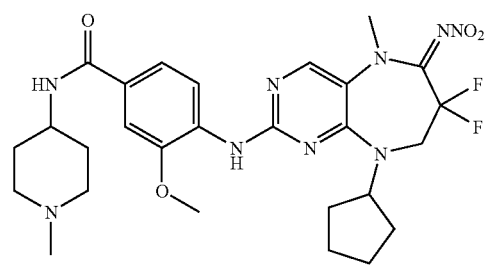

4-(9-cyclopentyl-7,7-difluoro-5-methyl-6-(nitroimino)-6,7,8,9-tetrahydro-5H-pyrimido[5,4-b][1,4]diazepin-2-ylamino)-3-methoxy-N-(1-methylpiperidin-4-yl)benzamide

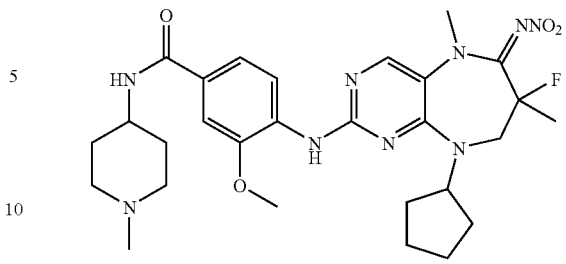

4-(9-cyclopentyl-7-fluoro-5,7-dimethyl-6-(nitroimino)-6,7,8,9-tetrahydro-5H-pyrimido[5,4-b][1,4]diazepin-2-ylamino)-3-methoxy-N-(1-methylpiperidin-4-yl)benzamide Biological Testing PLK Activity The activity of compounds as PLK inhibitors may be assayed in vitro, in vivo or in a cell line. Provided below is an in vitro enzymatic activity assay for activity against PLK1.

Purified PLK1 may be obtained as follows. cDNA encoding human PLK1 (SEQ ID No. 1, Accession Number: NM_005030) was isolated by polymerase chain reaction (PCR) with primers (SEQ ID Nos. 2 and 3) and cloned into pcDNA4/His-Max-TOPO (Invitrogen, USA) according to the manufacturer's manual. PCR was performed using the vector as a template. In the PCR, primers containing sequences encoding a FLAG-tag (DYKDDDDK) in the amino-terminal region (SEQ ID No. 4) and vector sequence (SEQ ID No. 5) were used. After XbaI and XhoI digestion of the PCR product, the fragment was subcloned into pFAST-BAC1 (Invitrogen, USA). Recombinant baculoviruses were prepared according to the procedure of the Bac-to-Bac baculovirus expression system (Invitrogen, USA). Sf21 cells were purchased from Invitrogen and grown in Sf-900 II SFM medium containing 10% fetal bovine serum, 50 μg/mL gentamicin and 0.1% pluronic F-68 (Invitrogen, USA) at 28° C. For preparation of PLK1 enzyme, Sf21 cells were infected with recombinant baculoviruses and cultured at 28° C. for 72 h. Cells were lysed and FLAG-tagged PLK1 protein (SEQ ID No. 6) was purified by affinity chromatography using anti-FLAG M2 affinity gel (Sigma, USA).

It should be noted that a variety of other expression systems and hosts are also suitable for the expression of PLK1, as would be readily appreciated by one of skill in the art.

The inhibition of PLK1 by the compounds was determined with the following assay that measures the phosphorylation of alpha casein by recombinant PLK1. Kinase reactions were performed at room temperature for 40 min in the kinase reaction buffer (25 mmol/L HEPES, pH 7.5, 10 mmol/L magnesium acetate, 1 mmol/L dithiothreitol) containing 50 ng PLK1 enzyme, 0.1 μCi [γ-$^{32}$P]ATP, 500 nmol/L ATP and 3 μg alpha casein (MP Biomedicals Inc., USA) in a final volume of 50 μL. The incubation was terminated by the addition of 10% trichloroacetic acid (Wako, Japan). Phosphorylated proteins were filtrated in GF/C filter plates (Packard, USA) with a Cell harvester (Packard, USA) and washed out free [γ-$^{32}$P]-ATP with 250 mmol/L phosphoric acid. Then, the plates were air dried for 60 min at 45° C., followed by the addition of 20 μL of MicroScint-O (Packard, USA). The radioactivity was counted by a Top-count scintillation counter (Packard, USA). The IC$_{50}$ values for test compounds were calculated by Prism 3.02 (GraphPad Software, USA).

The cell culture and proliferation assay may be carried out as follows: the HT29 human colorectal adenocarcinoma cell line (ATCC, USA) was maintained in Dulbecco's Modified Eagle's Medium (Invitrogen, USA) supplemented with 10% fetal bovine serum (JRH, USA). The cell proliferation assay was carried out with the Cell Titer-Glo luminescent cell viability assay (Promega, USA) according to the manufacture's instruction after the 72 hr treatment of the cells in the presence of the compounds. The cell viability was shown as a percentage of DMSO treated cells. The $IC_{50}$ values for the compounds were calculated by Prism 4 (GraphPad Software, USA).

For analysis of the cell cycle distribution and the phosphorylation of histone H3, the cells were harvested and fixed with ice-cold 70% ethanol after the 48 hr treatment of the cells in the presence of the compounds. The cells were washed twice with PBS containing 2% FCS (JRH), then incubated with Alexa Flour 647-conjugated anti-phospho-histone H3 antibody (Cell signaling, USA) and RNase (Invitrogen) for 30 min at room temperature. After washing twice with PBS containing 2% FCS, the cells were counterstained with propidium iodide. The cell cycle distribution and phosphorylation of histone H3 were analyzed using the FACSCalibur system (BD Bioscience, San Jose, Calif., USA,).

The activity of compounds as PLK inhibitors can be assessed in vivo using BALB/cA Jcl-nu/nu mice bearing the HCT116 or the HT29 cells inoculated subcutaneously in axillary area. The growth retardation may be determined, for example, by caliper measurements of the tumor volume.

$pIC_{50}$ values may be calculated by non-linear curve fitting of the compound concentrations and fluorescence intensities to the standard $pIC_{50}$ equation. $pIC_{50}$ values for the cell proliferative assay of select compounds of the present invention are given in Table 1.

TABLE 1

| Compound | $pIC_{50}$ (PLK1) |
|---|---|
| 2 | <8.7 |
| 3 | ≧8.7 |
| 4 | ≧8.7 |
| 5 | ≧8.7 |
| 7 | <8.7 |
| 8 | ≧8.7 |
| 9 | ≧8.7 |
| 10 | ≧8.7 |
| 11 | ≧8.7 |
| 12 | <8.7 |
| 14 | ≧8.7 |
| 15 | ≧8.7 |
| 17 | <8.7 |
| 18 | <8.7 |
| 19 | <8.7 |
| 20 | <8.7 |
| 21 | <8.7 |
| 22 | ≧8.7 |
| 23 | ≧8.7 |
| 24 | <8.7 |
| 25 | <8.7 |
| 26 | <8.7 |
| 27 | ≧8.7 |
| 28 | <8.7 |
| 29 | <8.7 |
| 30 | <8.7 |
| 31 | ≧8.7 |
| 33 | ≧8.7 |
| 34 | ≧8.7 |
| 35 | ≧8.7 |
| 36 | ≧8.7 |
| 37 | <8.7 |
| 38 | ≧8.7 |
| 39 | <8.7 |
| 40 | ≧8.7 |
| 41 | ≧8.7 |
| 42 | ≧8.7 |
| 43 | ≧8.7 |
| 44 | ≧8.7 |
| 45 | ≧8.7 |
| 46 | <8.7 |
| 47 | ≧8.7 |
| 48 | ≧8.7 |
| 49 | ≧8.7 |
| 50 | ≧8.7 |
| 51 | ≧8.7 |
| 52 | <8.7 |
| 54 | <8.7 |
| 56 | <8.7 |
| 57 | <8.7 |
| 58 | ≧8.7 |
| 60 | ≧8.7 |
| 61 | ≧8.7 |
| 62 | ≧8.7 |
| 63 | ≧8.7 |
| 64 | ≧8.7 |
| 65 | ≧8.7 |
| 66 | ≧8.7 |
| 67 | ≧8.7 |
| 69 | ≧8.7 |
| 70 | ≧8.7 |
| 71 | ≧8.7 |
| 72 | ≧8.7 |
| 73 | ≧8.7 |
| 74 | ≧8.7 |
| 75 | ≧8.7 |
| 76 | ≧8.7 |
| 77 | ≧8.7 |
| 78 | ≧8.7 |
| 79 | ≧8.7 |
| 80 | ≧8.7 |
| 81 | ≧8.7 |
| 83 | ≧8.7 |
| 84 | ≧8.7 |
| 85 | <8.7 |
| 87 | ≧8.7 |
| 88 | ≧8.7 |
| 89 | ≧8.7 |
| 90 | ≧8.7 |
| 92 | <8.7 |
| 95 | ≧8.7 |
| 96 | <8.7 |
| 97 | <8.7 |
| 99 | ≧8.7 |
| 100 | ≧8.7 |
| 101 | <8.7 |
| 102 | ≧8.7 |
| 103 | <8.7 |
| 104 | <8.7 |
| 105 | ≧8.7 |
| 106 | <8.7 |
| 107 | <8.7 |
| 109 | ≧8.7 |
| 110 | <8.7 |
| 111 | ≧8.7 |
| 113 | ≧8.7 |
| 114 | <8.7 |
| 115 | <8.7 |
| 116 | ≧8.7 |
| 117 | ≧8.7 |
| 118 | <8.7 |
| 119 | <8.7 |
| 120 | <8.7 |
| 122 | <8.7 |
| 123 | <8.7 |
| 124 | <8.7 |
| 125 | ≧8.7 |
| 126 | <8.7 |
| 127 | ≧8.7 |
| 128 | ≧8.7 |
| 129 | ≧8.7 |
| 130 | ≧8.7 |

TABLE 1-continued

| Compound | pIC$_{50}$ (PLK1) |
|---|---|
| 131 | ≧8.7 |
| 132 | ≧8.7 |
| 133 | ≧8.7 |
| 134 | <8.7 |
| 135 | <8.7 |
| 136 | <8.7 |
| 137 | <8.7 |
| 138 | <8.7 |
| 139 | <8.7 |

Drug Resistance

P-glycoprotein (PgP, MDR1) overexpression has been shown to be correlated with resistance to anti-cancer agents such as taxanes and anthracyclines. Accordingly, development of compounds that are not susceptible to PgP may be capable of overcoming drug-resistance in cancer (Nat Rev Drug Discov., 2006 March; 5(3): 219-34).

To assess whether compounds are susceptible to PgP, in vitro growth inhibitory assays were performed using MES-SA and its derivative MES-SA/Dx5, which are known to be anthracycline resistant cell lines that overexpress PgP (Anti-cancer Res., 2005 January-February; 25(1A): 383-9). Cells were seeded at 1000 cells/well in McCoy's 5A medium (Invitrogen) with 10% FCS in 96-well plates (Falcon). After 24 hours, compounds were added to the cell culture medium at the final concentrations of 1000, 300, 100, 30, 10, 3, 1, 0.3 and 0.1 nM. Cell viability was quantified using CellTiter-Glo kits (Promega) after three days of incubation. The IC$_{50}$ of each compound was calculated using GraphPad software (Prism). The IC$_{50}$ values for select examples are shown in Table 2. The data is reported as the ratio of the IC$_{50}$ value for the MES-SA/Dx5 assay to the IC$_{50}$ value for the MES-SA assay.

TABLE 2

| Compound No. | IC$_{50}$ (MES-SA/Dx5; nM)/ IC$_{50}$ (MES-SA; nM) |
|---|---|
| 3 | 31.9 |
| 10 | >15.1 |
| 116 | 1.9 |
| 117 | 12.5 |
| 113 | 2.5 |
| 131 | 2.5 |

It will be apparent to those skilled in the art that various modifications and variations can be made in the compounds, compositions, kits, and methods of the present invention without departing from the spirit or scope of the invention. Thus, it is intended that the present invention cover the modifications and variations of this invention provided they come within the scope of the appended claims and their equivalents.

What is claimed is:

1. The compound 4-(9-Cyclopentyl-7,7-difluoro-5-methyl-6-oxo-6,7,8,9-tetrahydro-5H-pyrimido[4,5-b][1,4]diazepin-2-ylamino)-2-fluoro-5-methoxy-N-(1-methylpiperidin-4-yl)benzamide or a pharmaceutically acceptable salt thereof.

2. A pharmaceutical composition comprising a compound of claim 1 and a pharmaceutically acceptable excipient.

* * * * *

SEQUENCE LISTING

```
<160> NUMBER OF SEQ ID NOS: 6

<210> SEQ ID NO 1
<211> LENGTH: 1809
<212> TYPE: DNA
<213> ORGANISM: Homo sapiens

<400> SEQUENCE: 1
atgagtgctg cagtgactgc agggaagctg gcacgggcac cggccgaccc tgggaaagcc      60
ggggtccccg gagttgcagc tcccggagct ccggcggcgg ctccaccggc gaaagagatc     120
ccggaggtcc tagtggaccc acgcagccgg cggcgctatg tgcggggccg cttttgggc     180 aagggcggct tgccaagtg cttcgagatc tcggacgcgg acaccaagga ggtgttcgcg     240
ggcaagattg tgcctaagtc tctgctgctc aagccgcacc agagggagaa gatgtccatg     300
gaaatatcca ttcaccgcag cctcgcccac cagcacgtcg taggattcca cggcttttc     360 gaggacaacg acttcgtgtt cgtggtgttg gagctctgcc gccggaggtc tctcctggag     420
ctgcacaaga ggaggaaagc cctgactgag cctgaggccc gatactacct acggcaaatt     480
gtgcttggct gccagtacct gcaccgaaac cgagttattc atcgagacct caagctgggc     540 aacctttcc tgaatgaaga tctggaggtg aaaatagggg atttttggact ggcaaccaaa     600 gtcgaatatg acggggagag gaagaagacc ctgtgtggga ctcctaatta catagctccc     660
gaggtgctga gcaagaaagg gcacagttc gaggtggatg tgtggtccat tgggtgtatc     720
atgtatacct tgttagtggg caaaccacct tttgagactt cttgcctaaa agagacctac     780
ctccggatca agaagaatga atacagtatt cccaagcaca tcaacccgt ggccgcctcc     840 ctcatccaga gatgcttca gacagatccc actgccccgc caaccattaa cgagctgctt     900
aatgacgagt tcttactc tggctatatc cctgccgtc tccccatcac ctgcctgacc     960
attccaccaa ggttttcgat tgctcccagc agcctggacc cagcaaccg gaagcccctc    1020
```

-continued

```
acagtcctca ataaaggctt ggagaacccc ctgcctgagc gtccccggga aaaagaagaa    1080
ccagtggttc gagagacagg tgaggtggtc gactgccacc tcagtgacat gctgcagcag    1140
ctgcacagtg tcaatgcctc caagccctcg gagcgtgggc tggtcaggca agaggaggct    1200
gaggatcctg cctgcatccc catcttctgg gtcagcaagt gggtggacta ttcggacaag    1260
tacggccttg ggtatcagct ctgtgataac agcgtggggg tgctcttcaa tgactcaaca    1320
cgcctcatcc tctacaatga tggtgacagc ctgcagtaca tagagcgtga cggcactgag    1380
tcctacctca ccgtgagttc ccatcccaac tccttgatga agaagatcac cctccttaaa    1440
tatttccgca attacatgag cgagcacttg ctgaaggcag gtgccaacat cacgccgcgc    1500
gaaggtgatg agctcgcccg gctgccctac ctacggacct ggttccgcac ccgcagcgcc    1560
atcatcctgc acctcagcaa cggcagcgtg cagatcaact tcttccagga tcacaccaag    1620
ctcatcttgt gcccactgat ggcagccgtg acctacatcg acgagaagcg ggacttccgc    1680
acataccgcc tgagtctcct ggaggagtac ggctgctgca aggagctggc cagccggctc    1740
cgctacgccc gcactatggt ggacaagctg ctgagctcac gctcggccag caaccgtctc    1800
aaggcctcc                                                             1809
```

<210> SEQ ID NO 2
<211> LENGTH: 27
<212> TYPE: DNA
<213> ORGANISM: Artificial
<220> FEATURE:
<223> OTHER INFORMATION: DNA sequence endoding PCR Primer
<220> FEATURE:
<221> NAME/KEY: misc_feature
<222> LOCATION: (1)..(27)
<223> OTHER INFORMATION: DNA sequence endoding PCR Primer

<400> SEQUENCE: 2

```
agtgctgcag tgactgcagg gaagctg                                            27
```

<210> SEQ ID NO 3
<211> LENGTH: 29
<212> TYPE: DNA
<213> ORGANISM: Artificial
<220> FEATURE:
<223> OTHER INFORMATION: Synthetic Primer
<220> FEATURE:
<221> NAME/KEY: misc_feature
<222> LOCATION: (1)..(29)
<223> OTHER INFORMATION: DNA sequence endoding PCR Primer

<400> SEQUENCE: 3

```
ttaggaggcc ttgagacggt tgctggccg                                          29
```

<210> SEQ ID NO 4
<211> LENGTH: 69
<212> TYPE: DNA
<213> ORGANISM: Artificial
<220> FEATURE:
<223> OTHER INFORMATION: Synthetic Primer
<220> FEATURE:
<221> NAME/KEY: misc_feature
<222> LOCATION: (1)..(69)
<223> OTHER INFORMATION: DAN sequence endoding PCT Primer

<400> SEQUENCE: 4

```
aaatctagag ccaccatgga ctacaaggac gacgatgaca agagtgctgc agtgactgca    60
gggaagctg                                                              69
```

<210> SEQ ID NO 5
<211> LENGTH: 27
<212> TYPE: DNA
<213> ORGANISM: Artificial
<220> FEATURE:
<223> OTHER INFORMATION: Synthetic Primer
<220> FEATURE:
<221> NAME/KEY: misc_feature
<222> LOCATION: (1)..(27)
<223> OTHER INFORMATION: DNA sequence endoding PCT Primer

<400> SEQUENCE: 5
tggcaactag aaggcacagt cgaggct                                             27

<210> SEQ ID NO 6
<211> LENGTH: 611
<212> TYPE: PRT
<213> ORGANISM: Artificial
<220> FEATURE:
<223> OTHER INFORMATION: Protein Sequence encoding FLAG-tagged PLK1
<220> FEATURE:
<221> NAME/KEY: MISC_FEATURE
<222> LOCATION: (1)..(9)
<223> OTHER INFORMATION: FLAG-tag
<220> FEATURE:
<221> NAME/KEY: MISC_FEATURE
<222> LOCATION: (10)..(611)
<223> OTHER INFORMATION: Human PLK1

<400> SEQUENCE: 6

Met Asp Tyr Lys Asp Asp Asp Asp Lys Ser Ala Ala Val Thr Ala Gly
1               5                   10                  15

Lys Leu Ala Arg Ala Pro Ala Asp Pro Gly Lys Ala Gly Val Pro Gly
            20                  25                  30

Val Ala Ala Pro Gly Ala Pro Ala Ala Pro Pro Ala Lys Glu Ile Pro
        35                  40                  45

Pro Glu Val Leu Val Asp Pro Arg Ser Arg Arg Arg Tyr Val Arg Gly
    50                  55                  60

Arg Phe Leu Gly Lys Gly Gly Phe Ala Lys Cys Phe Glu Ile Ser Asp
65                  70                  75                  80

Ala Asp Thr Lys Glu Val Phe Ala Gly Lys Ile Val Pro Lys Ser Leu
                85                  90                  95

Leu Leu Lys Pro His Gln Arg Glu Lys Met Ser Met Glu Ile Ser Ile
            100                 105                 110

His Arg Ser Leu Ala His Gln His Val Val Gly Phe His Gly Phe Phe
        115                 120                 125

Glu Asp Asn Asp Phe Val Phe Val Val Leu Glu Leu Cys Arg Arg Arg
    130                 135                 140

Ser Leu Leu Glu Leu His Lys Arg Arg Lys Ala Leu Thr Glu Pro Glu
145                 150                 155                 160

Ala Arg Tyr Tyr Leu Arg Gln Ile Val Leu Gly Cys Gln Tyr Leu His
                165                 170                 175

Arg Asn Arg Val Ile His Arg Asp Leu Lys Leu Gly Asn Leu Phe Leu
            180                 185                 190

Asn Glu Asp Leu Glu Val Lys Ile Gly Asp Phe Gly Leu Ala Thr Lys
        195                 200                 205

Val Glu Tyr Asp Gly Glu Arg Lys Lys Thr Leu Cys Gly Thr Pro Asn
    210                 215                 220

Tyr Ile Ala Pro Glu Val Leu Ser Lys Lys Gly His Ser Phe Glu Val
225                 230                 235                 240

Asp Val Trp Ser Ile Gly Cys Ile Met Tyr Thr Leu Leu Val Gly Lys
                245                 250                 255

-continued

```
Pro Pro Phe Glu Thr Ser Cys Leu Lys Glu Thr Tyr Leu Arg Ile Lys
            260                 265                 270
Lys Asn Glu Tyr Ser Ile Pro Lys His Ile Asn Pro Val Ala Ala Ser
            275                 280                 285
Leu Ile Gln Lys Met Leu Gln Thr Asp Pro Thr Ala Arg Pro Thr Ile
            290                 295                 300
Asn Glu Leu Leu Asn Asp Glu Phe Phe Thr Ser Gly Tyr Ile Pro Ala
305                 310                 315                 320
Arg Leu Pro Ile Thr Cys Leu Thr Ile Pro Pro Arg Phe Ser Ile Ala
                325                 330                 335
Pro Ser Ser Leu Asp Pro Ser Asn Arg Lys Pro Leu Thr Val Leu Asn
                340                 345                 350
Lys Gly Leu Glu Asn Pro Leu Pro Glu Arg Pro Arg Glu Lys Glu Glu
                355                 360                 365
Pro Val Val Arg Glu Thr Gly Glu Val Val Asp Cys His Leu Ser Asp
            370                 375                 380
Met Leu Gln Gln Leu His Ser Val Asn Ala Ser Lys Pro Ser Glu Arg
385                 390                 395                 400
Gly Leu Val Arg Gln Glu Glu Ala Glu Asp Pro Ala Cys Ile Pro Ile
                405                 410                 415
Phe Trp Val Ser Lys Trp Val Asp Tyr Ser Asp Lys Tyr Gly Leu Gly
            420                 425                 430
Tyr Gln Leu Cys Asp Asn Ser Val Gly Val Leu Phe Asn Asp Ser Thr
            435                 440                 445
Arg Leu Ile Leu Tyr Asn Asp Gly Asp Ser Leu Gln Tyr Ile Glu Arg
            450                 455                 460
Asp Gly Thr Glu Ser Tyr Leu Thr Val Ser Ser His Pro Asn Ser Leu
465                 470                 475                 480
Met Lys Lys Ile Thr Leu Leu Lys Tyr Phe Arg Asn Tyr Met Ser Glu
                485                 490                 495
His Leu Leu Lys Ala Gly Ala Asn Ile Thr Pro Arg Glu Gly Asp Glu
                500                 505                 510
Leu Ala Arg Leu Pro Tyr Leu Arg Thr Trp Phe Arg Thr Arg Ser Ala
                515                 520                 525
Ile Ile Leu His Leu Ser Asn Gly Ser Val Gln Ile Asn Phe Phe Gln
                530                 535                 540
Asp His Thr Lys Leu Ile Leu Cys Pro Leu Met Ala Ala Val Thr Tyr
545                 550                 555                 560
Ile Asp Glu Lys Arg Asp Phe Arg Thr Tyr Arg Leu Ser Leu Leu Glu
                565                 570                 575
Glu Tyr Gly Cys Cys Lys Glu Leu Ala Ser Arg Leu Arg Tyr Ala Arg
            580                 585                 590
Thr Met Val Asp Lys Leu Leu Ser Ser Arg Ser Ala Ser Asn Arg Leu
            595                 600                 605
Lys Ala Ser
610
```